United States Patent
Kato

US009260390B2

(10) Patent No.: US 9,260,390 B2
(45) Date of Patent: Feb. 16, 2016

(54) AROMATIC AMINE DERIVATIVES AND ORGANIC ELECTROLUMINESCENT ELEMENTS USING SAME

(75) Inventor: Tomoki Kato, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 6 days.

(21) Appl. No.: 13/399,412

(22) Filed: Feb. 17, 2012

(65) Prior Publication Data
US 2012/0146014 A1 Jun. 14, 2012

Related U.S. Application Data

(63) Continuation of application No. PCT/JP2010/063425, filed on Aug. 6, 2010.

(30) Foreign Application Priority Data

Aug. 19, 2009 (JP) .................................. 2009-190398

(51) Int. Cl.
| | |
|---|---|
| *H01L 51/54* | (2006.01) |
| *C07D 405/12* | (2006.01) |
| *C07D 403/12* | (2006.01) |
| *C07D 409/12* | (2006.01) |
| *C07D 209/86* | (2006.01) |
| *C07D 307/91* | (2006.01) |
| *C07D 333/76* | (2006.01) |
| *C09K 11/06* | (2006.01) |
| *H01L 51/00* | (2006.01) |
| *H05B 33/14* | (2006.01) |
| *H01L 51/50* | (2006.01) |

(52) U.S. Cl.
CPC ............ *C07D 209/86* (2013.01); *C07D 307/91* (2013.01); *C07D 333/76* (2013.01); *C09K 11/06* (2013.01); *H01L 51/006* (2013.01); *H01L 51/0061* (2013.01); *H01L 51/0072* (2013.01); *H01L 51/0073* (2013.01); *H05B 33/14* (2013.01); *C09K 2211/1011* (2013.01); *H01L 51/5012* (2013.01)

(58) Field of Classification Search
CPC .. C07D 209/86; C07D 307/91; C07D 333/76; C09K 11/06; C09K 2211/1011; H01L 51/006; H01L 51/0061; H01L 51/0072; H01L 51/0073; H01L 51/5012; H05B 33/14
See application file for complete search history.

(56) References Cited

U.S. PATENT DOCUMENTS

| | | | |
|---|---|---|---|
| 6,517,957 B1 | 2/2003 | Senoo et al. | |
| 6,858,325 B2 | 2/2005 | Senoo et al. | |
| 7,425,654 B2 | 9/2008 | Kawamura et al. | |
| 7,998,596 B2 * | 8/2011 | Yabunouchi et al. | ......... 428/690 |
| 7,998,597 B2 | 8/2011 | Saitoh et al. | |
| 8,022,253 B2 | 9/2011 | Hosokawa et al. | |
| 8,129,038 B2 * | 3/2012 | Yabunouchi et al. | ......... 428/690 |
| 8,367,222 B2 | 2/2013 | Arakane et al. | |
| 8,932,735 B2 | 1/2015 | Mizuki et al. | |
| 8,940,412 B2 | 1/2015 | Takashima et al. | |
| 9,087,997 B2 * | 7/2015 | Yabunouchi | ......... C07D 307/91 |
| 9,145,363 B2 * | 9/2015 | Yabunouchi | ......... C07D 209/86 |
| 2003/0157364 A1 * | 8/2003 | Senoo et al. | ................... 428/690 |
| 2003/0219625 A1 * | 11/2003 | Wolk et al. | .................... 428/690 |
| 2005/0221124 A1 | 10/2005 | Hwang et al. | |
| 2006/0110623 A1 | 5/2006 | Funahashi et al. | |
| 2007/0278938 A1 * | 12/2007 | Yabunouchi et al. | ......... 313/504 |
| 2008/0014464 A1 | 1/2008 | Kawamura et al. | |
| 2009/0066235 A1 | 3/2009 | Yabunouchi et al. | |
| 2009/0115320 A1 | 5/2009 | Kawamura et al. | |
| 2009/0160323 A1 | 6/2009 | Nomura et al. | |
| 2009/0167161 A1 | 7/2009 | Yabunouchi et al. | |
| 2010/0001636 A1 | 1/2010 | Yabunouchi et al. | |
| 2010/0001638 A1 | 1/2010 | Kawakami et al. | |
| 2010/0025669 A1 | 2/2010 | Hwang et al. | |
| 2010/0032658 A1 | 2/2010 | Lee et al. | |
| 2010/0133519 A1 * | 6/2010 | Chen et al. | ...................... 257/40 |
| 2011/0297924 A1 | 12/2011 | Yabunouchi et al. | |

FOREIGN PATENT DOCUMENTS

| | | |
|---|---|---|
| EP | 2 145 936 | 1/2010 |
| EP | 2 149 555 | 2/2010 |
| JP | 11 35532 | 2/1999 |
| JP | 2005 112765 | 4/2005 |
| JP | 2005 290000 | 10/2005 |
| JP | 2006 151844 | 6/2006 |
| JP | 2008285460 A | 11/2008 |
| WO | 2009 020095 | 2/2009 |
| WO | 2009 072587 | 6/2009 |
| WO | 2009 084268 | 7/2009 |
| WO | 2009 099060 | 8/2009 |
| WO | 2009 145016 | 12/2009 |
| WO | 2010 021524 | 2/2010 |
| WO | 2010 041872 | 4/2010 |
| WO | 2010 061824 | 6/2010 |

OTHER PUBLICATIONS

International Search Report Issued Sep. 14, 2010 in PCT/JP10/63425 Filed Aug. 6, 2010.
U.S. Appl. No. 13/509,681, filed May 14, 2012, Kato.
U.S. Appl. No. 13/435,965, filed Mar. 30, 2012, Kato.
Office Action issued Oct. 6, 2013 in corresponding Korean Patent Application No. KR2012-7004106, 7 pp.
U.S. Appl. No. 13/979,075, filed Jul. 17, 2013, Kato.
Japanese Office Action issued Jun. 17, 2014 in JP Application No. 2011-527638, with no English translation, 6 pp.

\* cited by examiner

*Primary Examiner* — Dawn L. Garrett
(74) *Attorney, Agent, or Firm* — Oblon, McClelland, Maier & Neustadt, L.L.P.

(57) ABSTRACT

Provided are an organic EL device material that reduce the driving voltage of an organic EL device and increase the lifetime of the device as compared with a conventional organic EL device material. Also provided are organic electroluminescence devices containing the organic EL device material.

18 Claims, No Drawings

AROMATIC AMINE DERIVATIVES AND ORGANIC ELECTROLUMINESCENT ELEMENTS USING SAME

TECHNICAL FIELD

The present invention relates to an aromatic amine derivative and an organic electroluminescence (organic EL) device using the same.

BACKGROUND ART

An organic EL device is a spontaneous light emitting device which utilizes such a principle that a fluorescent substance emits light by virtue of recombination energy of holes injected from an anode and electrons injected from a cathode by an application of an electric field. Since an organic EL device of the laminate type capable of being driven under low electric voltage has been reported by C. W. Tang et al. of Eastman Kodak Company (see Non Patent Literature 1), many studies have been conducted for an organic EL device using an organic material as a constituent material.

Tang et al. discloses an organic EL device having a laminate structure in which tris(8-quinolinolato)aluminum is used in a light emitting layer and a triphenyldiamine derivative is used in a hole transporting layer. Advantages of adopting the laminate structure in the organic EL device include: (i) injection efficiency of holes into the light emitting layer can be increased; (ii) efficiency of forming excitons which are formed through recombination in the light emitting layer can be increased by blocking electrons injected from the cathode toward the light emitting layer in the hole transporting (injecting) layer; and (iii) excitons formed in the light emitting layer can be easily enclosed in the light emitting layer. In order to increase the efficiency of recombination of injected holes and electrons in the organic EL device having such laminate structure, there have been made refinements of the device structure and a method of forming the device, and studies on a material itself for each layer.

In general, when an organic EL device is driven or stored in an environment of high temperature, there occur adverse affects such as a change in luminescent color, a decrease in luminous efficiency, an increase in driving voltage, and a decrease in lifetime of light emission.

In order to prevent such adverse effects, there have been reported, as hole transporting material, aromatic amine derivatives each having a carbazole skeleton (see Patent Literatures 1 to 3), an aromatic amine derivative having a dibenzofuran skeleton or a dibenzothiophene skeleton and a fluorene skeleton (see Patent Literature 4), and the like.

CITATION LIST

Patent Literature

[PTL 1] WO 07/148,660 A1
[PTL 2] WO 08/062,636 A1
[PTL 3] US 2007-0215889 A1
[PTL 4] JP 2005-290000 A

Non Patent Literature

[NPL 1] C. W. Tang, S. A. Vanslyke, "Applied Physics Letters," Vol. 51, p. 913, 1987

SUMMARY OF INVENTION

Technical Problem

However, the aromatic amine derivatives disclosed in Patent Literatures 1 to 4 are still susceptible to improvement because it cannot be said that a reduction in the driving voltage of a device and the lifetime of the device are satisfactory.

In view of the foregoing, an object of the present invention is to provide an organic EL device material capable of reducing the driving voltage of an organic EL device and increasing the lifetime of the device as compared with a conventional organic EL device material, and an organic EL device using the material.

Solution to Problem

The inventors of the present invention have made extensive studies to achieve the object, and as a result, have found the following. When an aromatic amine derivative having a fluorene skeleton and a carbazole skeleton, a dibenzofuran skeleton, or a dibenzothiophene skeleton is used as a material for an organic EL device, in particular, a hole transporting material, an additional reduction in the driving voltage of the organic EL device is achieved because of its high charge mobility. In addition, the stability of a thin film is improved, and hence additional lengthening of the lifetime of the organic EL device is achieved.

That is, the present invention relates to the following items (1) and (2).

(1) An aromatic amine derivative represented by the following formula (I):

[Chem. 1]

$$Ar^c - N(Ar^a) - Ar^b \quad (I)$$

in the formula (I), $Ar^a$ is represented by the following formula (II):

[Chem. 2]

$$(II)$$

(structure with $L^a$, $R^1$, $R^2$, $(R^3)_o$, $(R^3)_p$ on a fluorene skeleton)

in the formula (II):
$L^a$ represents a single bond, or a substituted or unsubstituted arylene group having 6 to 50 ring carbon atoms;
$R^1$ and $R^2$ each represent a linear or branched alkyl group having 1 to 50 carbon atoms, or an aryl group having 6 to 50 ring carbon atoms;
$R^3$ and $R^4$ each independently represent a linear or branched alkyl group having 1 to 50 carbon atoms, a linear or branched alkenyl group having 3 to 50 carbon atoms, a cycloalkyl group having 3 to 50 ring carbon atoms, an aryl group having 6 to 50 ring carbon atoms, a heteroaryl group having 5 to 50 ring atoms, a triarylalkyl group having aryl groups each having 6 to 50 ring carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a halogen atom, or a cyano group, and a plurality of $R^3$'s or $R^4$'s adjacent to each other, or $R^3$ and $R^4$ may be bonded to each other to form a ring; and o represents an integer of 0 to 3 and p represents an integer of 0 to 4;

in the formula (I), $Ar^b$ is represented by the following formula (III):

[Chem. 3]

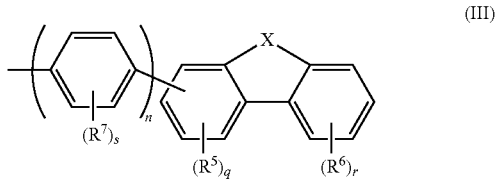

(III)

in the formula (III):

X represents $NR^a$, an oxygen atom, or a sulfur atom, and $R^a$ represents a substituted or unsubstituted aryl group having 6 to 50 ring carbon atoms, or a triarylalkyl group having substituted or unsubstituted aryl groups each having 6 to 50 ring carbon atoms;

$R^5$, $R^6$, and $R^7$ each independently represent a linear or branched alkyl group having 1 to 50 carbon atoms, a linear or branched alkenyl group having 3 to 50 carbon atoms, a cycloalkyl group having 3 to 50 ring carbon atoms, an aryl group having 6 to 50 ring carbon atoms, a heteroaryl group having 6 to 50 ring atoms, a triarylalkyl group having aryl groups each having 6 to 50 ring carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a halogen atom, or a cyano group, and a plurality of $R^5$'s, $R^6$'s, or $R^7$'s adjacent to each other, or $R^5$ and $R^6$ may be bonded to each other to form a ring;

n represents an integer of 2 to 4 when X represents $NR^a$, and represents an integer of 0 to 4 when X represents an oxygen atom or a sulfur atom;

when n represents an integer of 2 to 4, $R^7$'s on different benzene rings may be identical to or different from each other, and respective $R^7$'s present on benzene rings adjacent to each other may be bonded to each other to form a ring; and q represents an integer of 0 to 3, r and s each independently represent an integer of 0 to 4, and when n represents an integer of 2 to 4, s's that specify the numbers of $R^7$'s on different benzene rings may have the same value or may have different values; and in the formula (I), $Ar^c$ represents a substituted or unsubstituted aryl group having 6 to 50 ring carbon atoms, or is represented by the formula (III).

(2) An organic electroluminescence device, including one or more organic thin-film layers including at least a light emitting layer, the organic thin-film layers being interposed between an anode and a cathode, in which at least one layer of the organic thin-film layers contains the aromatic amine derivative according to the above-mentioned item (1).

Advantageous Effects of Invention

When the aromatic amine derivative of the present invention is used as a material for an organic EL device, the driving voltage of the organic EL device can be reduced because of its high charge mobility. In addition, the stability of a thin film is improved, and hence the lifetime of the organic EL device is additionally lengthened.

DESCRIPTION OF EMBODIMENTS

An aromatic amine derivative of the present invention is an aromatic monoamine derivative represented by the following formula (I).

[Chem. 4]

(I)

In the formula (I), $Ar^a$ is represented by the following formula (II).

[Chem. 5]

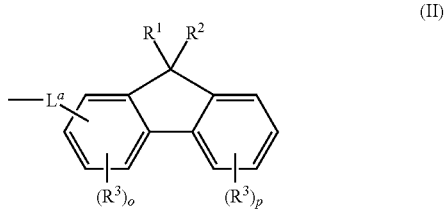

(II)

In the formula (II), $L^a$ represents a single bond, or a substituted or unsubstituted arylene group having 6 to 50 ring carbon atoms. Examples of the arylene group include a phenylene group, a biphenylene group, a terphenylene group, a naphthylene group, an acenaphthylenylene group, an anthranylene group, a phenanthrenylene group, a pyrenylene group, a naphthacenylene group, a quaterphenylene group, a pentacenylene group, a perylenylene group, a coronylene group, a fluorenylene group, a 9,9-dimethylfluorenylene group, an acenaphthofluorenylene group, an s-indacenylene group, an as-indacenylene group, and a chrycenylene group. The arylene group is preferably an arylene group having 6 to 24 ring carbon atoms, more preferably a phenylene group, a biphenylene group, a terphenylene group, a phenanthrenylene group, a quaterphenylene group, or a fluorenylene group, still more preferably a phenylene group, a biphenylene group, a terphenylene group, or a quaterphenylene group, particularly preferably a p-phenylene group, a p-biphenylene group, a p-terphenylene group, or a p-quaterphenylene group. When a benzene ring is bonded at a para position, the driving voltage of a device is reduced. This is probably because a charge mobility is increased by the expansion of a conjugated system. When the benzene ring is bonded at a meta position, the luminous efficiency of the device is improved. This is probably because the energy gap of a hole transporting layer increases.

In addition, the arylene group represented by La may have a substituent, and examples of the substituent include: alkyl groups each having 1 to 10 (preferably 1 to 6) carbon atoms such as a methyl group, an ethyl group, an n-propyl group, an isopropyl group, an n-butyl group, an isobutyl group, an s-butyl group, a t-butyl group, various pentyl groups, and various hexyl groups; cycloalkyl groups each having 3 to 10 (preferably 5 to 7) ring carbon atoms such as a cyclopropyl group, a cyclopentyl group, a cyclohexyl group, a cyclooctyl group, and a cyclodecyl group; trialkylsilyl groups each having alkyl groups each having 1 to 10 (preferably 1 to 6) carbon atoms such as a trimethylsilyl group and a triethylsilyl group; triarylsilyl groups each having aryl groups each having 6 to 20 (preferably 6 to 10) ring carbon atoms such as a triphenylsilyl group; alkylarylsilyl groups each having an alkyl group having 1 to 10 (preferably 1 to 6) carbon atoms and an aryl group having 6 to 20 (preferably 6 to 10) ring carbon atoms; halogen atoms such as a fluorine atom, a chlorine atom, a bromine atom, and an iodine atom; and a cyano group (hereinafter, these groups are referred to as "substituents A").

$L^a$ represents preferably a single bond or a phenylene group, more preferably a single bond. When $L^a$ represents a single bond, the fluorene skeleton is directly bonded to the nitrogen atom. Accordingly, it is conceivable that an ionization potential reduces, and holes are accumulated at an interface between the hole transporting layer and a light emitting layer to promote the injection of electrons. Thus, the driving voltage of the organic EL device is additionally reduced.

In the formula (II), $R^1$ and $R^2$ each represent a linear or branched alkyl group having 1 to 50 carbon atoms, or an aryl group having 6 to 50 ring carbon atoms.

Examples of the alkyl group represented by each of $R^1$ and $R^2$ include a methyl group, an ethyl group, an n-propyl group, an isopropyl group, an n-butyl group, an isobutyl group, an s-butyl group, a t-butyl group, various pentyl groups (the term "various" means that a linear group and all kinds of branched groups are included, and the same holds true for the following), various hexyl groups, various heptyl groups, various octyl groups, various nonyl groups, various decyl groups, various undecyl groups, and various dodecyl groups. When the alkyl chain of the alkyl group is elongated, the aromatic amine derivative of the present invention can be suitably used in the production of the organic EL device by an application method because its solubility is improved. The alkyl group suitable for the application method is preferably an alkyl group having 1 to 20 carbon atoms, more preferably an alkyl group having 1 to 10 carbon atoms, still more preferably an alkyl group having 1 to 8 carbon atoms. In addition, when the alkyl group has 5 or less carbon atoms, the aromatic amine derivative of the present invention can be suitably used in the production of the organic EL device by a deposition method because its molecular weight can be suppressed. The alkyl group suitable for the deposition method is preferably an alkyl group having 1 to 5 carbon atoms, more preferably an alkyl group having 1 to 3 carbon atoms, still more preferably a methyl group.

Examples of the aryl group represented by each of $R^1$ and $R^2$ include a phenyl group, a naphthylphenyl group, a biphenylyl group, a terphenylyl group, a biphenylenyl group, a naphthyl group, a phenylnaphthyl group, an acenaphthylenyl group, an anthryl group, a benzanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a pentacenyl group, a picenyl group, a pentaphenyl group, pyrenyl group, a chrysenyl group, a benzochrysenyl group, an s-indacenyl group, an as-indacenyl group, fluoranthenyl group, and perylenyl group. The aryl group is preferably an aryl group having 6 to 20 ring carbon atoms, more preferably and aryl group having 6 to 14 ring carbon atoms, more preferably an aryl group having 6 to 10 ring carbon atoms, still more preferably a phenyl group.

Of those, a methyl group or a phenyl group is preferred as each of $R^1$ and $R^2$. In particular, in the case where $R^1$ and $R^2$ each represent an alkyl group having 1 to 10 carbon atoms, the molecular weight becomes small as compared with that in the case where $R^1$ and $R^2$ each represent an aryl group. Accordingly, a deposition temperature is easily adjusted to fall within a proper range, and hence the thermal decomposition of the material can be prevented. Accordingly, $R^1$ and $R^2$ each more preferably represent a methyl group.

In the formula (II), $R^3$ and $R^4$ each independently represent a linear or branched alkyl group having 1 to 50 carbon atoms, a linear or branched alkenyl group having 3 to 50 carbon atoms, a cycloalkyl group having 3 to 50 ring carbon atoms, an aryl group having 6 to 50 ring carbon atoms, a heteroaryl group having 5 to 50 ring atoms, a triarylalkyl group having aryl groups each having 6 to 50 ring carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a halogen atom, or a cyano group.

Examples of the alkyl group and the aryl group each represented by each of $R^3$ and $R^4$ include the same examples as those of $R^1$ and $R^2$, and preferred examples thereof are also the same. It should be noted that the alkyl group may be substituted with a hydroxyl group and the aryl group may be substituted with an alkyl group having 1 to 10 (preferably 1 to 5) carbon atoms or a cycloalkyl group having 3 to 10 ring carbon atoms.

Examples of the alkenyl group represented by each of $R^3$ and $R^4$ include groups each obtained by making at least one carbon-carbon bond in a group having 2 to 50 carbon atoms out of the alkyl groups represented by $R^3$ and $R^4$ a double bond.

Examples of the cycloalkyl group represented by each of $R^3$ and $R^4$ include a cyclopropyl group, a cyclopentyl group, a cyclohexyl group, a cyclooctyl group, a cyclodecyl group, a cylopentylmethyl group, a cylohexylmethyl group, a cyclohexylethyl group, a 1-adamantyl group, a 2-adamantyl group, a 1-norbornyl group, and a 2-norbornyl group. Of those, a cycloalkyl group having 3 to 20 ring carbon atoms is preferred, a cycloalkyl group having 3 to 10 ring carbon atoms is more preferred, a cycloalkyl group having 3 to 6 ring carbon atoms is still more preferred, and a cyclopentyl group or a cyclohexyl group is still further more preferred. The cycloalkyl group may be substituted with a halogen atom such as a fluorine atom, a chlorine atom, a bromine atom, or an iodine atom (preferably a fluorine atom).

Examples of the heteroaryl group represented by each of $R^3$ and $R^4$ include groups each obtained by substituting at least one carbon atom in the aryl group represented by each of $R^3$ and $R^4$ with a nitrogen atom or an oxygen atom. The heteroaryl group may be substituted with an alkyl group having 1 to 10 (preferably 1 to 5) carbon atoms or a cycloalkyl group having 3 to 10 ring carbon atoms.

Examples of the aryl groups and the alkyl group in the triarylalkyl group represented by each of $R^3$ and $R^4$ include the same examples as those of the aryl group and the alkyl group each represented by each of $R^3$ and $R^4$. Preferred examples thereof are also the same, and examples of the substituent which any such group may have also include the same examples. The triarylalkyl group is preferably a triphenylmethyl group or a trinaphthylmethyl group, more preferably a triphenylmethyl group. The three aryl groups with which the alkyl group is substituted may be identical to or different from one another.

Examples of the alkyl groups in the trialkylsilyl group represented by each of $R^3$ and $R^4$ include the same examples as those of the alkyl group represented by each of $R^3$ and $R^4$. Preferred examples thereof are also the same, and examples of the substituent which any such group may have also include the same examples. The three alkyl groups with which the silyl group is substituted may be identical to or different from one another.

Examples of the aryl groups in the triarylsilyl group represented by each of $R^3$ and $R^4$ include the same examples as those of the aryl group represented by each of $R^3$ and $R^4$. Preferred examples thereof are also the same, and examples of the substituent which any such group may have also include the same examples. Of those, a triphenylsilyl group or a trinaphthylsilyl group is preferred as the triarylsilyl group, and a triphenylsilyl group is more preferred. The three aryl groups with which the silyl group is substituted may be identical to or different from one another.

Examples of the alkyl group and the aryl group in the alkylarylsilyl group represented by each of $R^3$ and $R^4$ include the same examples as those of the alkyl group and the aryl group each represented by each of $R^3$ and $R^4$. Examples of the alkylarylsilyl group include a monoalkyldiarylsilyl group and a dialkylmonoarylsilyl group.

Examples of the halogen atom represented by each of $R^3$ and $R^4$ include a fluorine atom, a chlorine atom, a bromine atom, and an iodine atom.

In addition, a plurality of $R^3$'s or $R^4$'s adjacent to each other, or $R^3$ and $R^4$ may be bonded to each other to form a ring. The ring is preferably formed of two $R^3$'s or $R^4$'s adjacent to each other, and examples of the ring include a benzene ring and a naphthalene ring.

Of those, an aryl group having 6 to 50 ring carbon atoms, a triarylalkyl group having aryl groups each having 6 to 50 ring carbon atoms, or a triarylsilyl group having aryl groups each having 6 to 50 ring carbon atoms is preferred as each of $R^3$ and $R^4$, and a phenyl group, a triphenylmethyl group, or a triphenylsilyl group is more preferred. In addition, a plurality of $R^3$'s or $R^4$'s adjacent to each other are preferably bonded to each other to form a ring (more preferably a benzene ring).

When a plurality of $R^3$'s or $R^4$'s adjacent to each other, or $R^3$ and $R^4$ are bonded to each other to form a ring, specific examples of the structure of $Ar^a$ include, but not particularly limited to, the following structures.

[Chem. 6]

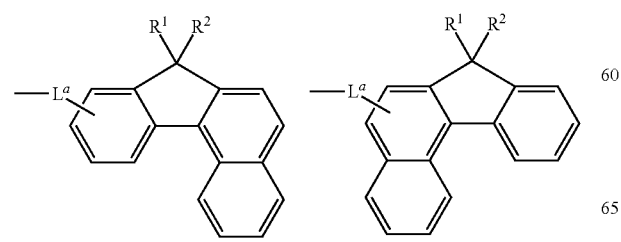

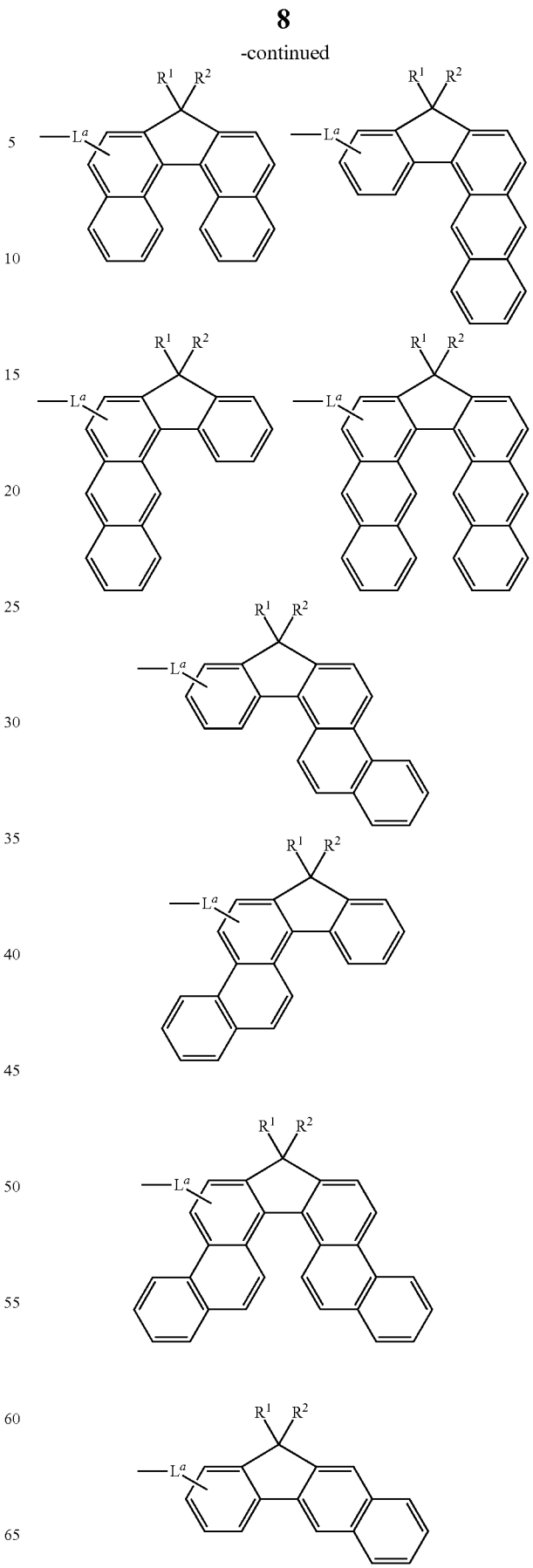

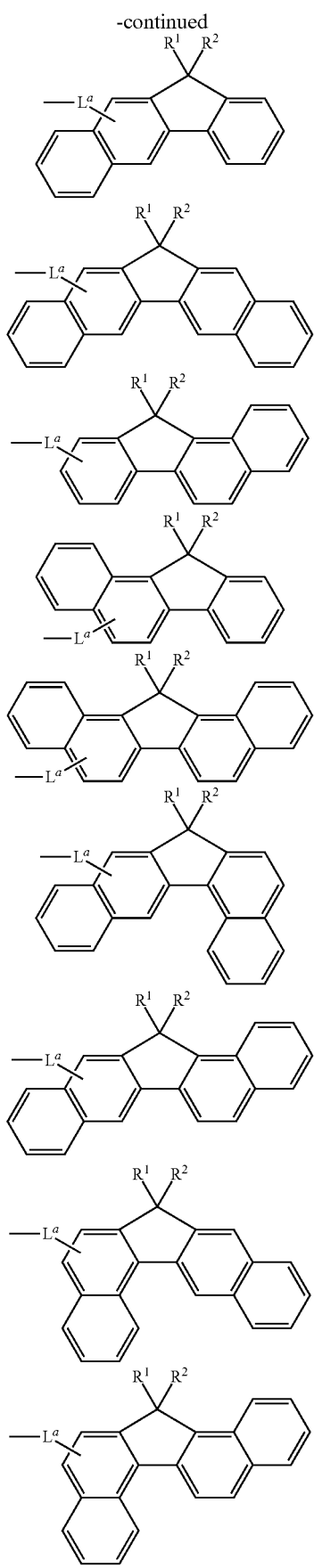

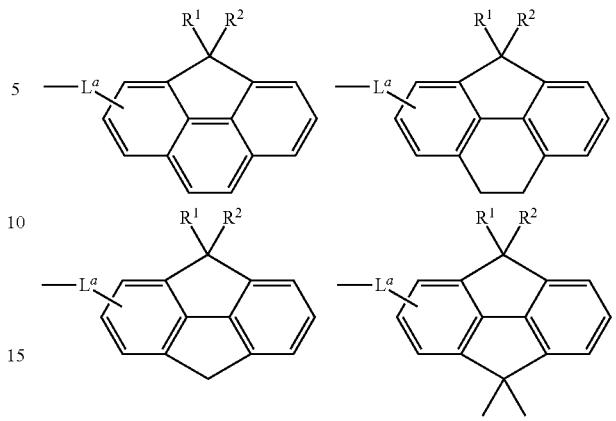

In the formula (II), o represents an integer of 0 to 3, preferably 0 or 1, more preferably 0, and p represents an integer of 0 to 4, preferably 0 or 1.

It should be noted that when there exist a plurality of $R^3$'s or $R^4$'s, the plurality of $R^3$'s or $R^4$'s may be identical to or different from each other. When $R^3$ and $R^4$ are placed at the 2- and 7-positions of the fluorene ring in the formula (II), such an effect that a site having a high electron density and rich in reactivity is protected may be exerted. Accordingly, the material becomes electrochemically stable, and hence the lifetime of the device is lengthened.

Of the formulae (II), the following formula (II') in which the bonding position of $L^a$ is limited is preferred from the viewpoints of an additionally high charge mobility and an additional reduction in the driving voltage of the organic EL device.

[Chem. 7]

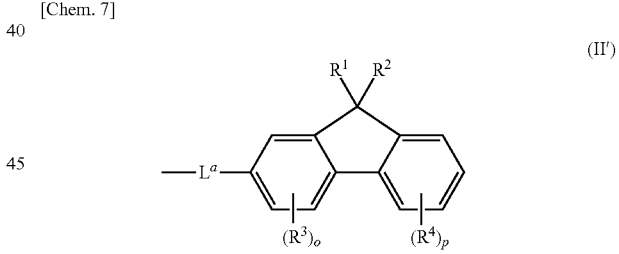

(II')

In the formula (II'), $L^a$, $R^1$, $R^2$, $R^3$, $R^4$, o, and p are as defined in the foregoing.

Here, specific examples of $Ar^a$ are shown below. However, $Ar^a$ is not particularly limited to these examples. It should be noted that a wave dash represents a bonding site.

[Chem. 8]

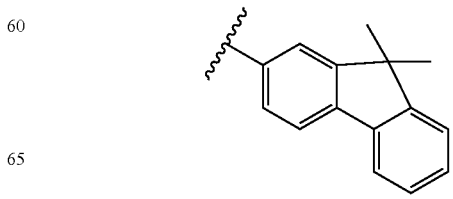

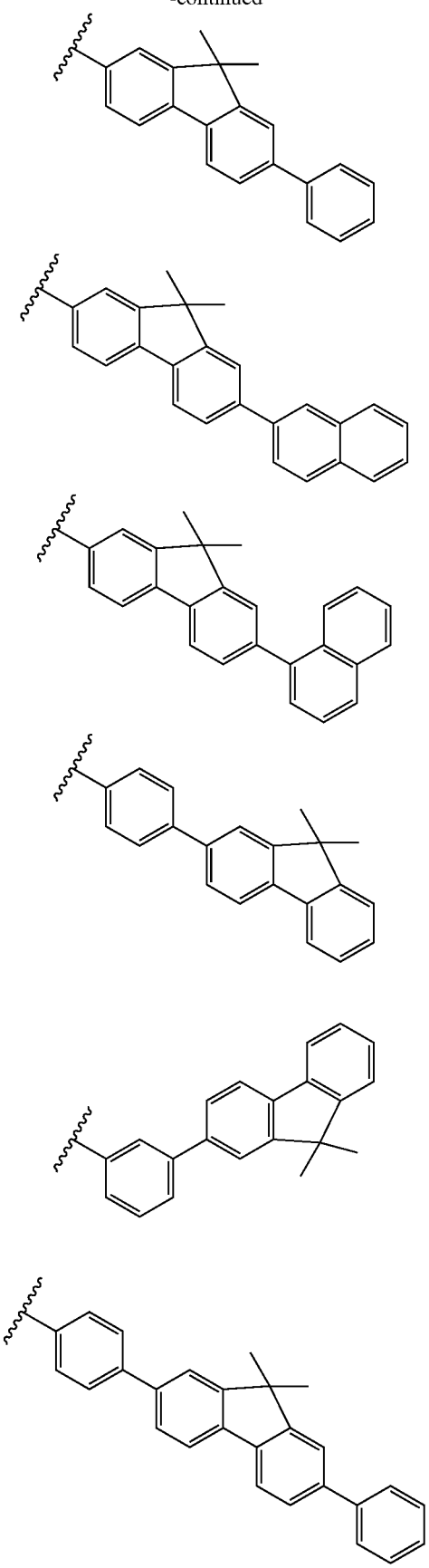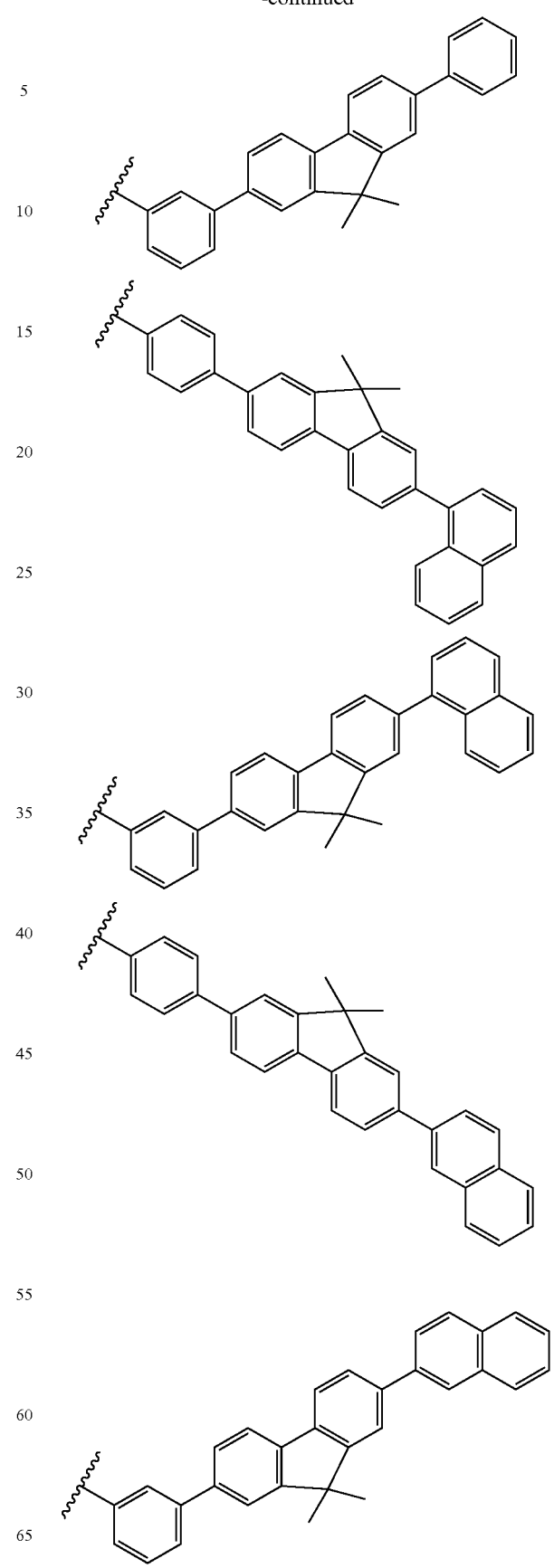

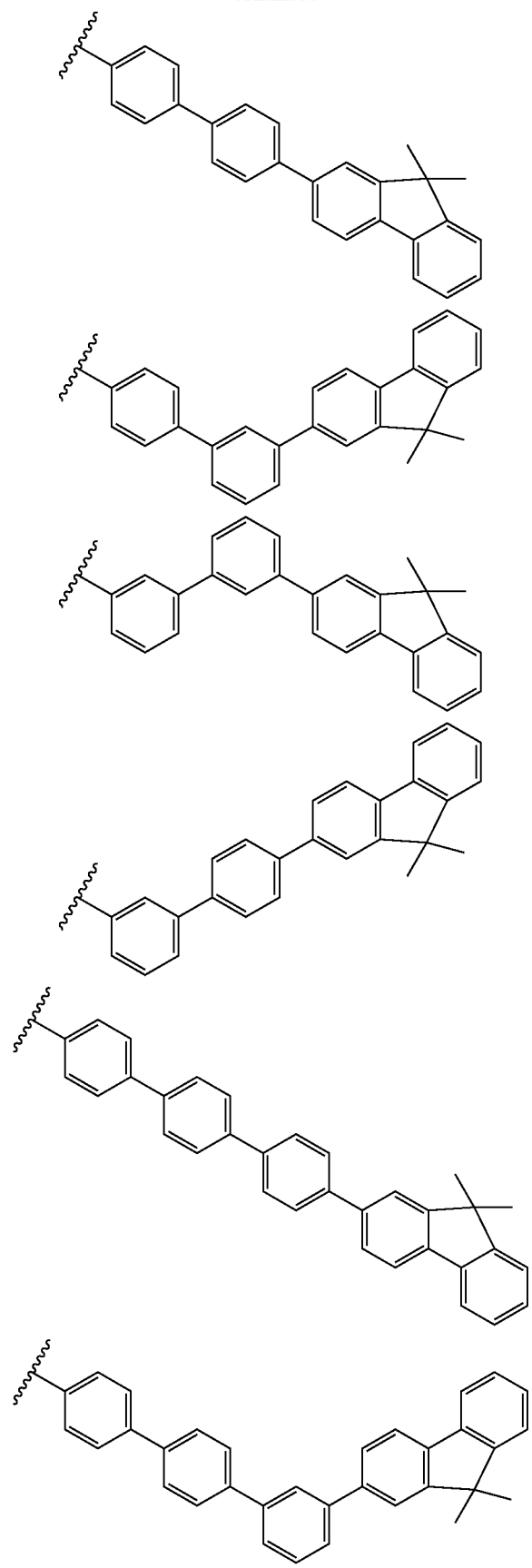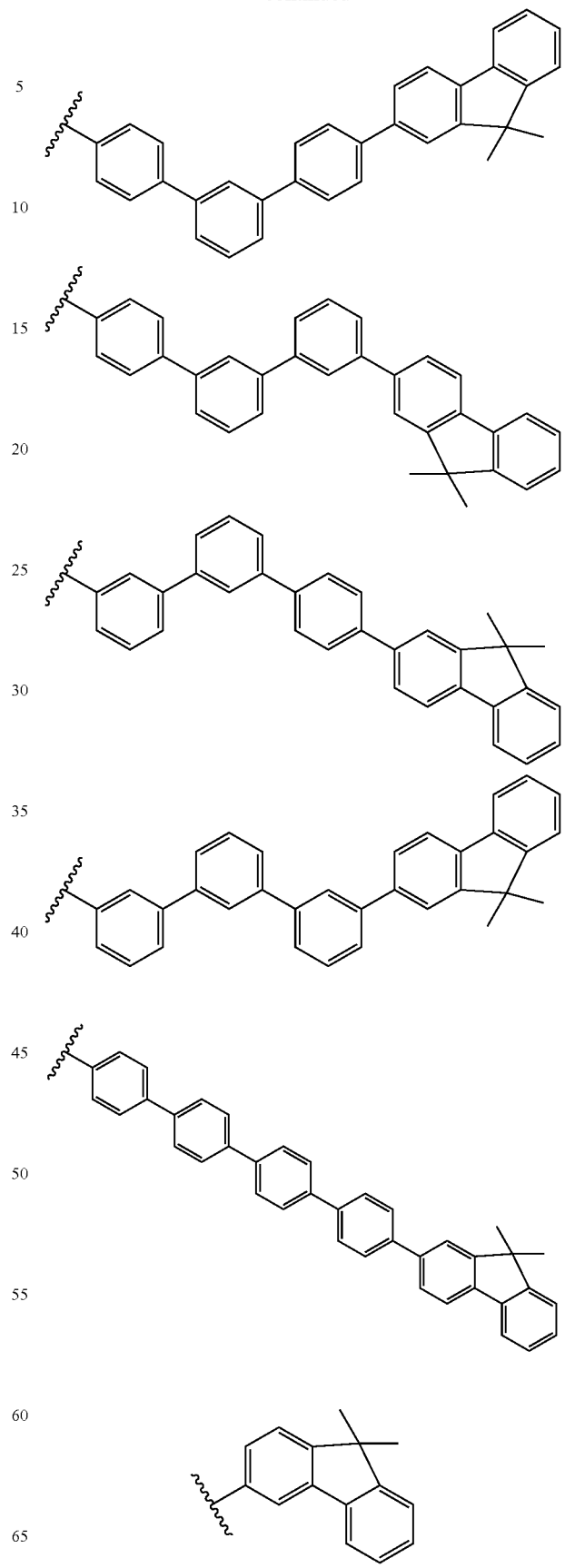

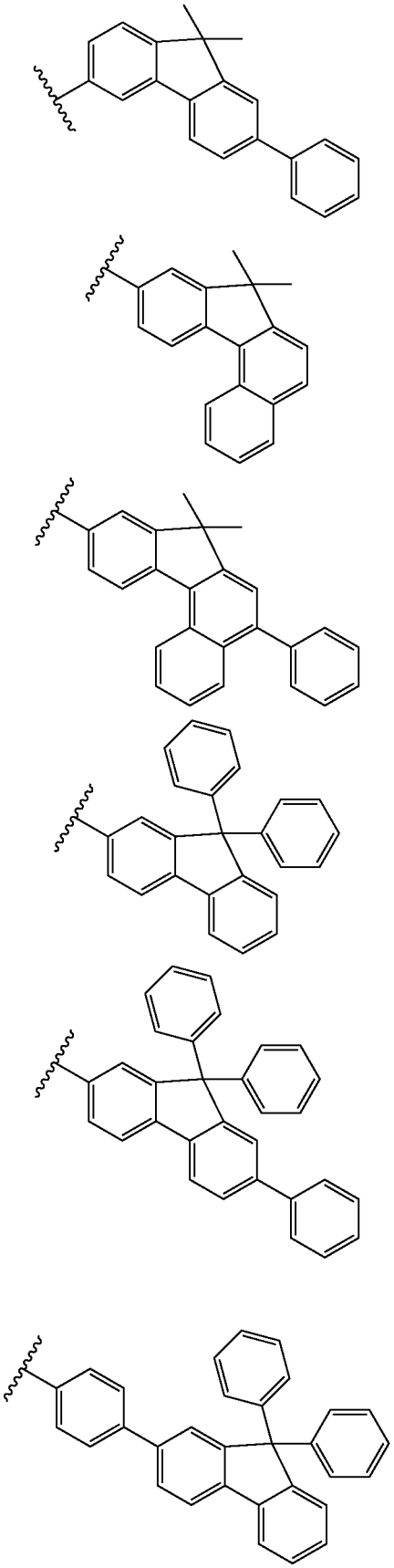
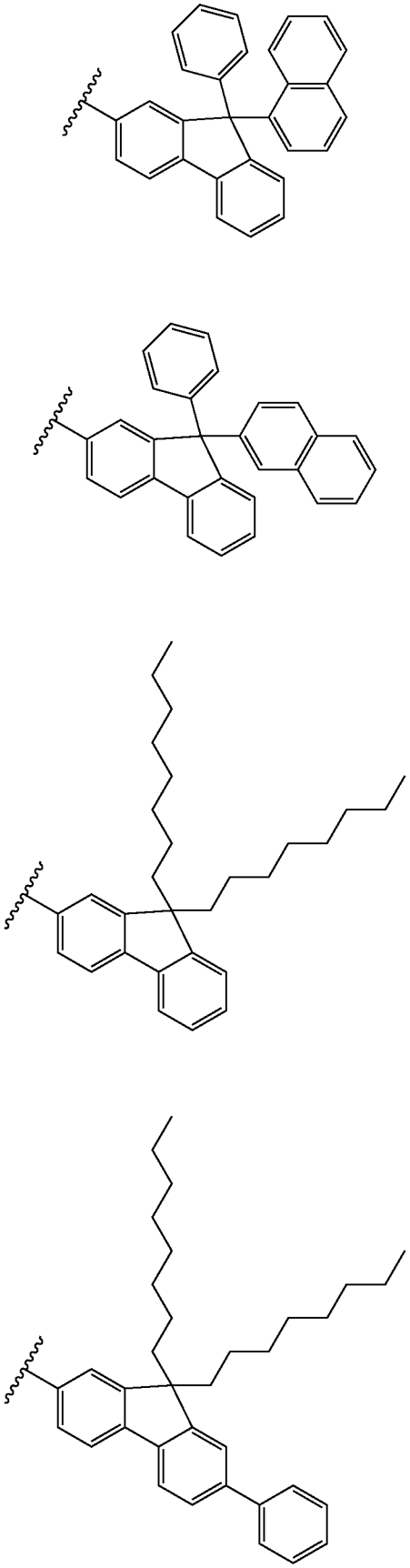

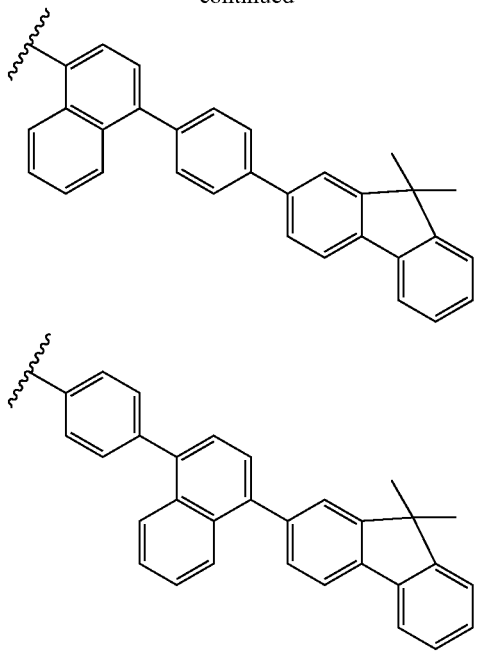

In addition, $Ar^b$ in the formula (I) is represented by the following formula (III).

[Chem. 9]

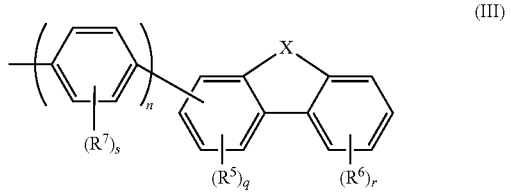
(III)

X represents $NR^a$, an oxygen atom, or a sulfur atom. $R^a$ in $NR^a$ represents a substituted or unsubstituted aryl group having 6 to 50 ring carbon atoms, or a triarylalkyl group having substituted or unsubstituted aryl groups each having 6 to 50 ring carbon atoms. When X represents $NR^a$, an oxygen atom, or a sulfur atom, the charge mobility is increased, and hence the voltage is reduced. In particular, when X represents $NR^a$, the driving voltage of the organic EL device is additionally reduced, and when X represents an oxygen atom or a sulfur atom (especially an oxygen atom), resistance to reduction is improved, and hence the lifetime of the organic EL device is additionally lengthened.

Examples of the aryl group represented by $R^a$ include the same examples as those of $R^1$ and $R^2$, and the aryl group is preferably an aryl group having 6 to 20 ring carbon atoms, more preferably an aryl group having 6 to 14 ring carbon atoms, still more preferably a phenyl group or a naphthyl group. The aryl group may have a substituent, and examples of the substituent include the substituents A. Of those, a triarylsilyl group is preferred and a triphenylsilyl group is more preferred.

Examples of the aryl groups in the triarylalkyl group include the same examples as those of $R^1$ and $R^2$, and preferred examples thereof are also the same. Examples of the triarylalkyl group include a triphenylmethyl group and a 2-triphenylethyl group. Of those, a triphenylmethyl group is preferred.

In the formula (III), $R^5$, $R^6$, and $R^7$ each independently represent a linear or branched alkyl group having 1 to 50 carbon atoms, a linear or branched alkenyl group having 3 to 50 carbon atoms, a cycloalkyl group having 3 to 50 ring carbon atoms, an aryl group having 6 to 50 ring carbon atoms, a heteroaryl group having 6 to 50 ring atoms, a triarylalkyl group having aryl groups each having 6 to 50 ring carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a halogen atom, or a cyano group.

Examples of each of the alkyl group, the alkenyl group, the cycloalkyl group, the aryl group, the heteroaryl group, the triarylalkyl group, the trialkylsilyl group, the triarylsilyl group, the alkylarylsilyl group, and the halogen atom include the same examples as those of $R^3$ and $R^4$, and preferred examples thereof are also the same. Further, examples of the substituent which each of the groups may have are the same.

In addition, a plurality of $R^5$'s, $R^6$'s, or $R^7$'s adjacent to each other, or $R^5$ and $R^6$ may be bonded to each other to form a ring. The ring is preferably formed of two $R^5$'s or $R^6$'s adjacent to each other, and examples of the ring include a benzene ring and a naphthalene ring.

Of those, an aryl group having 6 to 50 ring carbon atoms is preferred as each of $R^5$ and $R^6$, an aryl group having 6 to 20 ring carbon atoms is more preferred, an aryl group having 6 to 10 ring carbon atoms is still more preferred, and a phenyl group is still further more preferred. In addition, a plurality of $R^5$'s or $R^6$'s adjacent to each other are preferably bonded to each other to form a ring (more preferably a benzene ring). In addition, as for $R^7$, a plurality of $R^7$'s adjacent to each other on the same benzene ring are preferably bonded to each other to form a ring (more preferably a benzene ring).

It should be noted that when a plurality of $R^5$'s or $R^6$'s adjacent to each other, or $R^5$ and $R^6$ are bonded to each other to form a ring, specific examples of the structure of $Ar^b$ include, but not particularly limited to, the following structures (in the formulae, $R^7$, X, n, and s are as defined in the foregoing).

[Chem. 10]

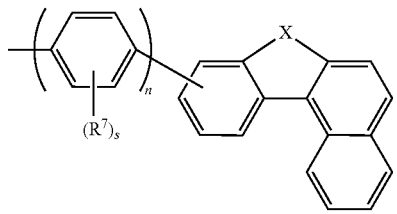

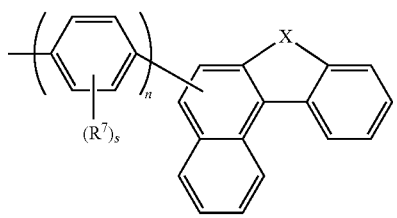

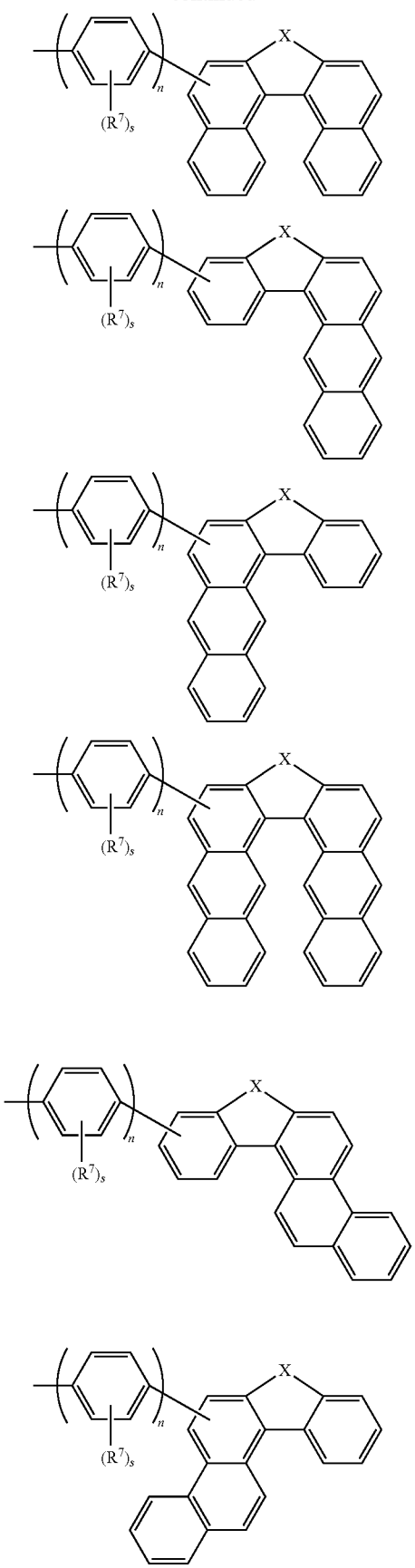
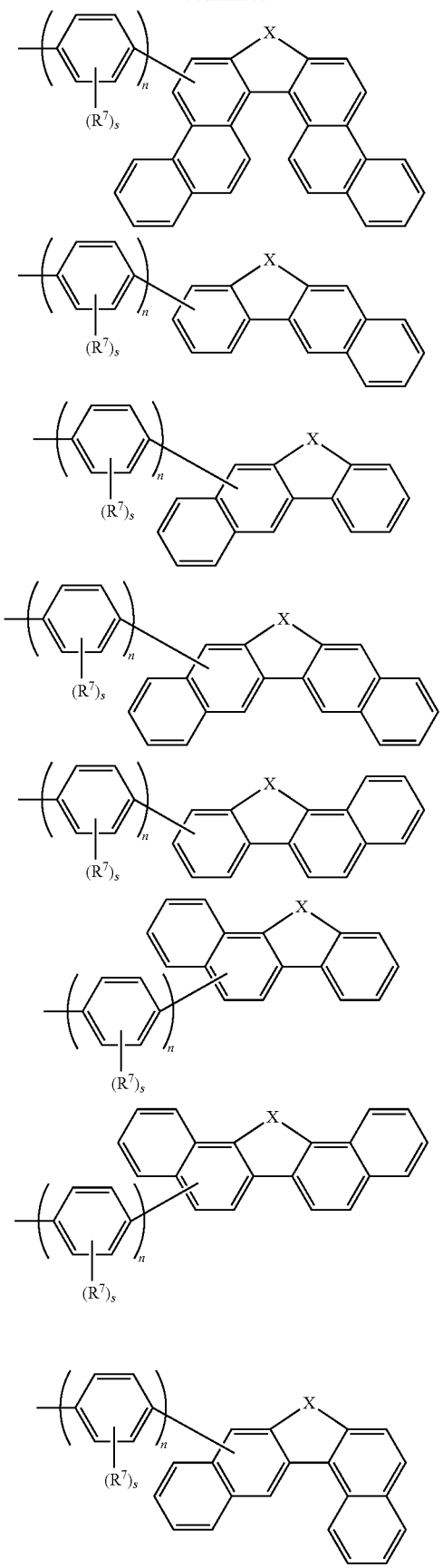

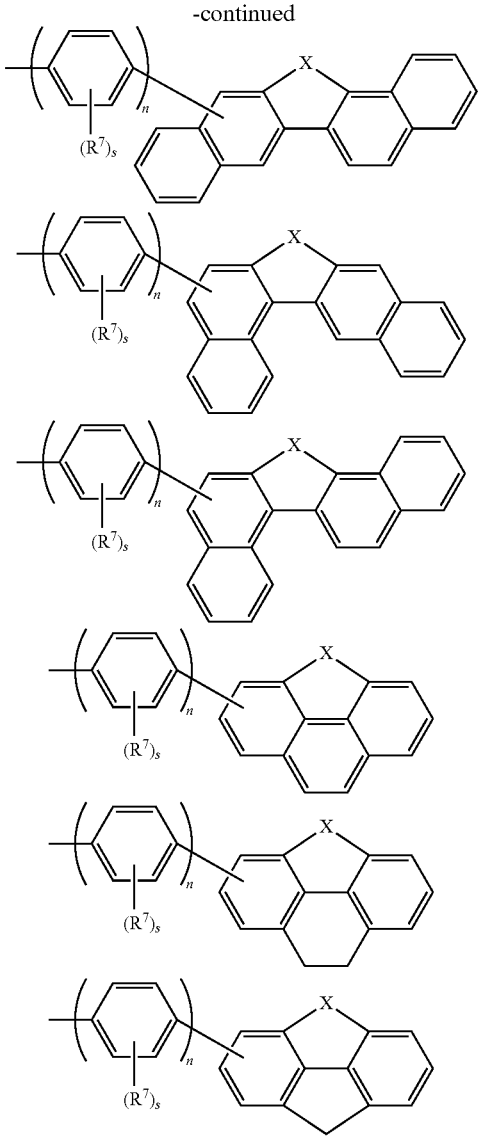

is protected is exerted. Accordingly, the material may become electrochemically stable, and hence the lifetime of the organic EL device is lengthened.

Here, the following linking group in the formula (III) is referred to as "linking group B."

[Chem. 11]

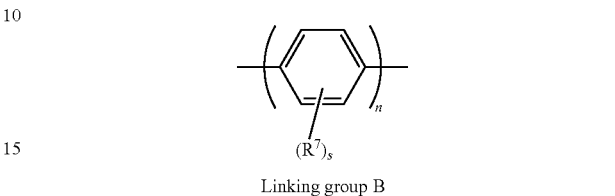

Linking group B (In the formula, $R^7$, n, and s are as defined in the foregoing.)

When $R^7$'s present on benzene rings adjacent to each other in the linking group B or $R^7$'s present on the same benzene ring are bonded to each other to form a ring, specific examples of the structure of the linking group B include, but not particularly limited to, the following structures.

[Chem. 12]

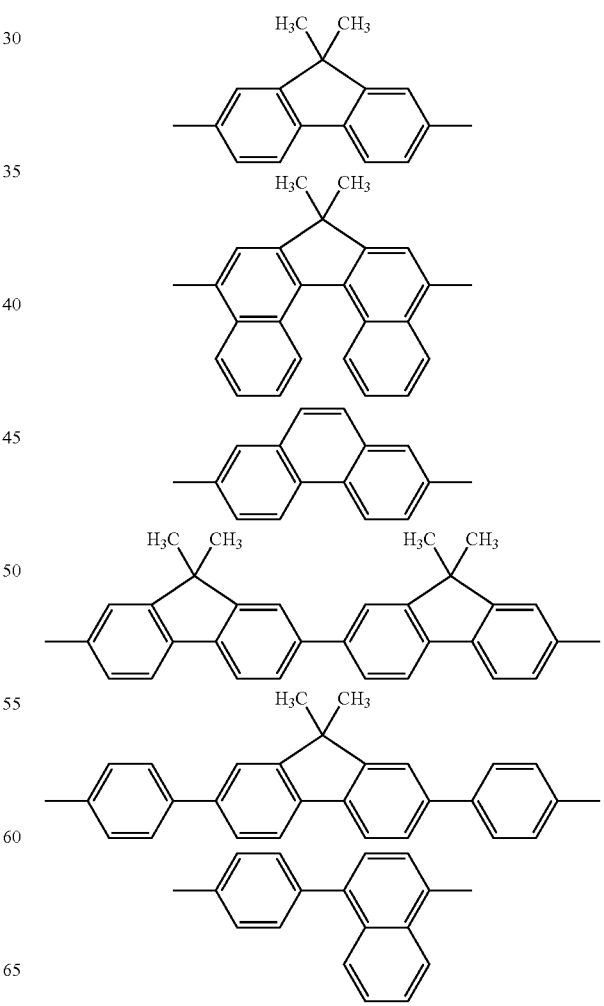

In the formula (III), n represents an integer of 2 to 4 when X represents $NR^a$, and represents an integer of 0 to 4 when X represents an oxygen atom or a sulfur atom.

When n represents an integer of 2 to 4, $R^7$'s on different benzene rings may be identical to or different from each other. In addition, respective $R^7$'s present on benzene rings adjacent to each other may be bonded to each other to form a ring, or as described in the foregoing, $R^7$'s on the same benzene ring may be bonded to each other to form a ring.

q represents an integer of 0 to 3, and r and s each independently represent an integer of 0 to 4. When q represents 2 or 3, a plurality of $R^5$'s may be identical to or different from each other. In addition, when r represents an integer of 2 to 4, a plurality of $R^6$'s may be identical to or different from each other.

When n represents an integer of 2 to 4, s's that specify the numbers of $R^7$'s on different benzene rings may have the same value or may have different values.

When $R^5$ and $R^6$ are placed preferably at the 3- and 6-positions, or 1- and 8-positions, of the heterocycle in the formula (III), more preferably at the 3- and 6-positions, such an effect that a site having a high electron density and rich in reactivity

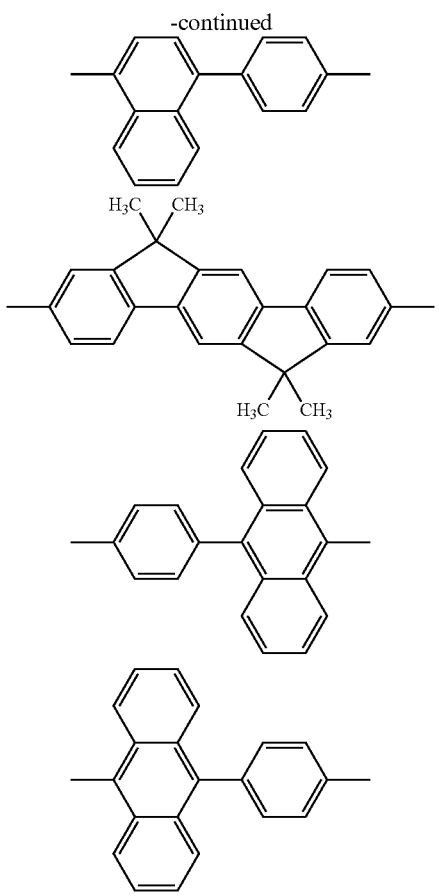

When $R^7$'s in the linking group B are bonded to each other to form a ring, in other words, when the linking group B has no crosslink, the aromatic amine derivative of the present invention has such an effect that an increase in the electron density of the compound is suppressed and its ionization potential is increased as compared with a conventional aromatic amine derivative.

As described later, when the linking group B is bonded to a para position with respect to X, such effect that an increase in the electron density of the compound is suppressed and its ionization potential is increased is additionally enhanced.

In addition, when abenzene ring is bonded at the para position, the driving voltage of the organic EL device is reduced. This is probably because the charge mobility is increased by the expansion of a conjugated system.

Of the formulae (III), the following formula (III') in which the bonding position of the linking group B is limited is preferred from the viewpoints of the suppression of an increase in the electron density of the compound, the increase of the ionization potential, and an additional reduction in the driving voltage of the organic EL device.

[Chem. 13]

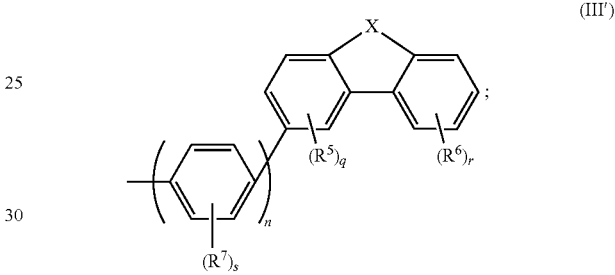

(III')

In the formula (III'), X, $R^5$, $R^6$, $R^7$, n, q, r, and s are as defined in the foregoing.

Further, $Ar^b$ is more preferably represented by any one of the following formulae (III-1) to (III-6) out of the formulae (III) from the viewpoint of an additional reduction in the driving voltage of the organic EL device.

[Chem. 14]

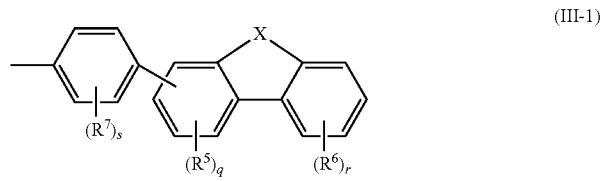

(III-1)

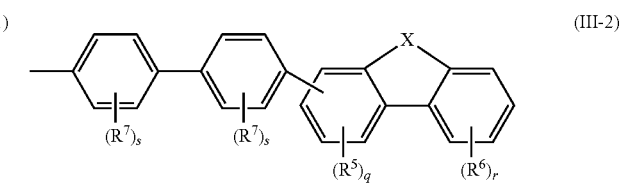

(III-2)

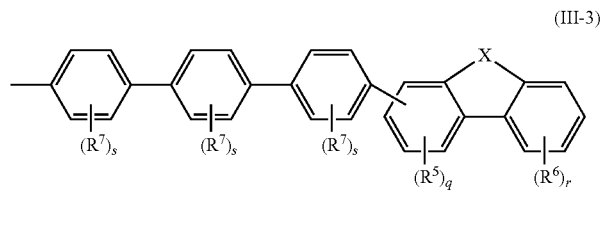

(III-3)

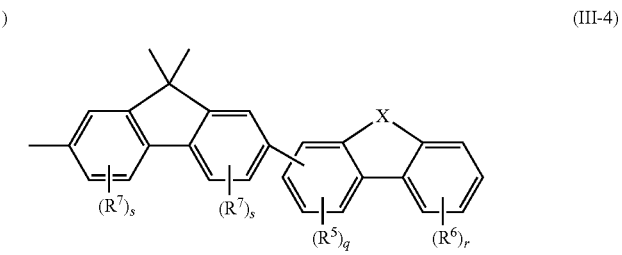

(III-4)

-continued

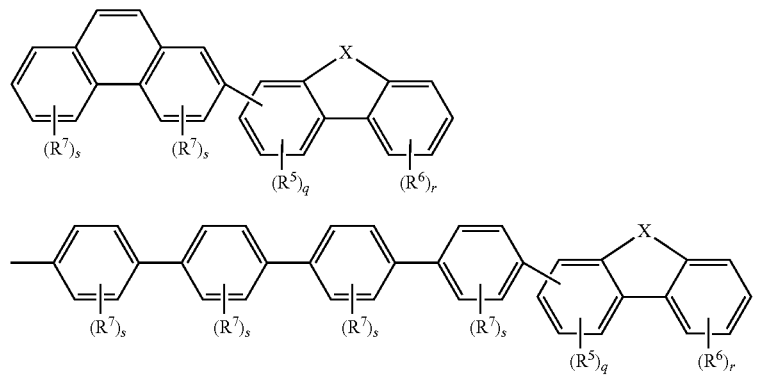

(III-5)

(III-6)

In the formulae (III-1) to (III-6), $R^5$, $R^6$, $R^7$, X, q, r, and s are as defined in the foregoing, and $R^7$'s or s's described in plurality may be identical to or different from each other.

$Ar^b$ is still more preferably represented by any one of the formulae (III-2), (III-3), and (III-6) out of the formulae (III-1) to (III-6).

Here, specific examples of $Ar^b$ are shown below. However, $Ar^b$ is not particularly limited to these examples. It should be noted that a wave dash represents a bonding site.

[Chem. 15]

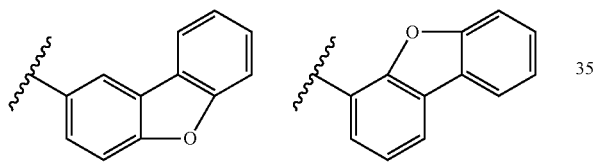

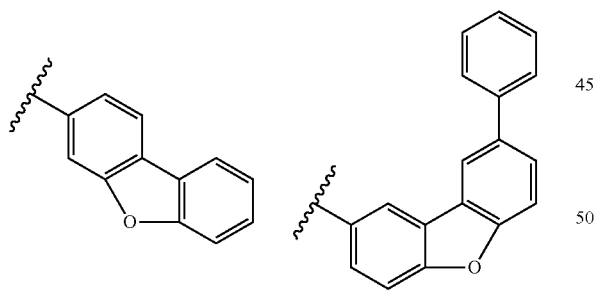

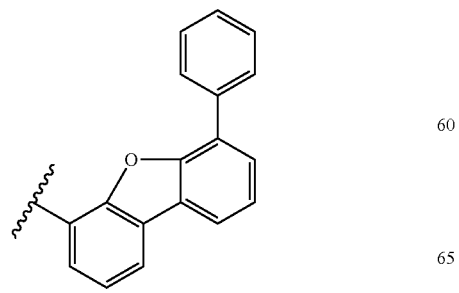

-continued

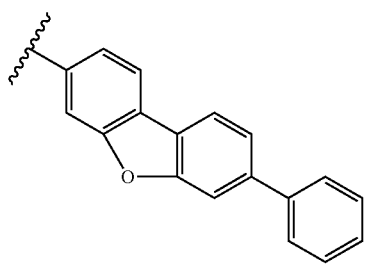

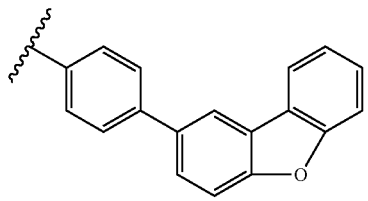

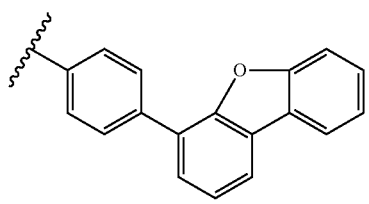

-continued
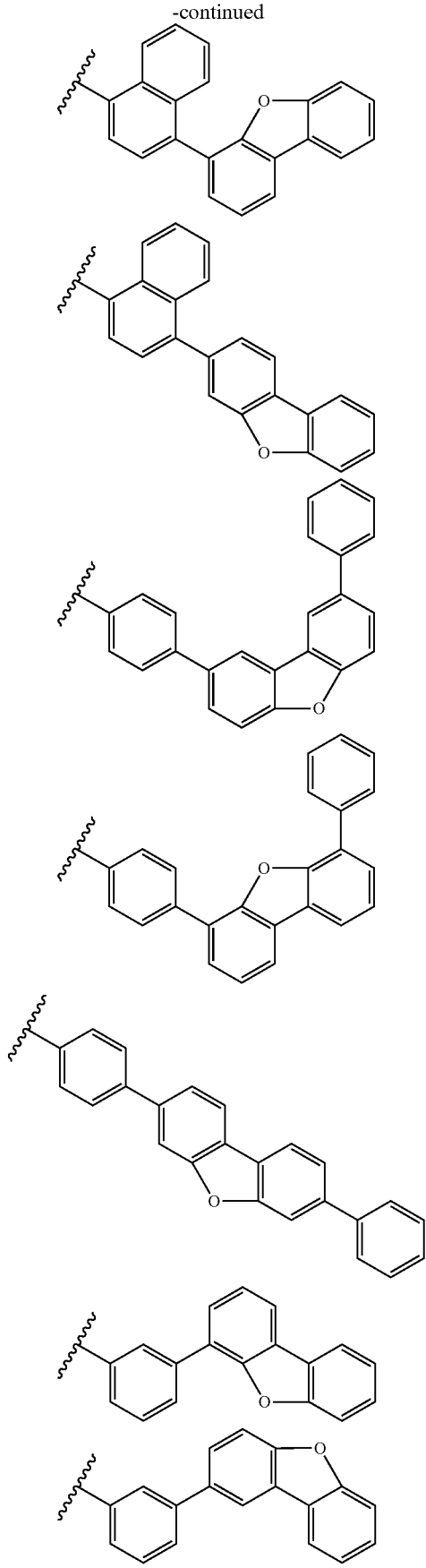
-continued
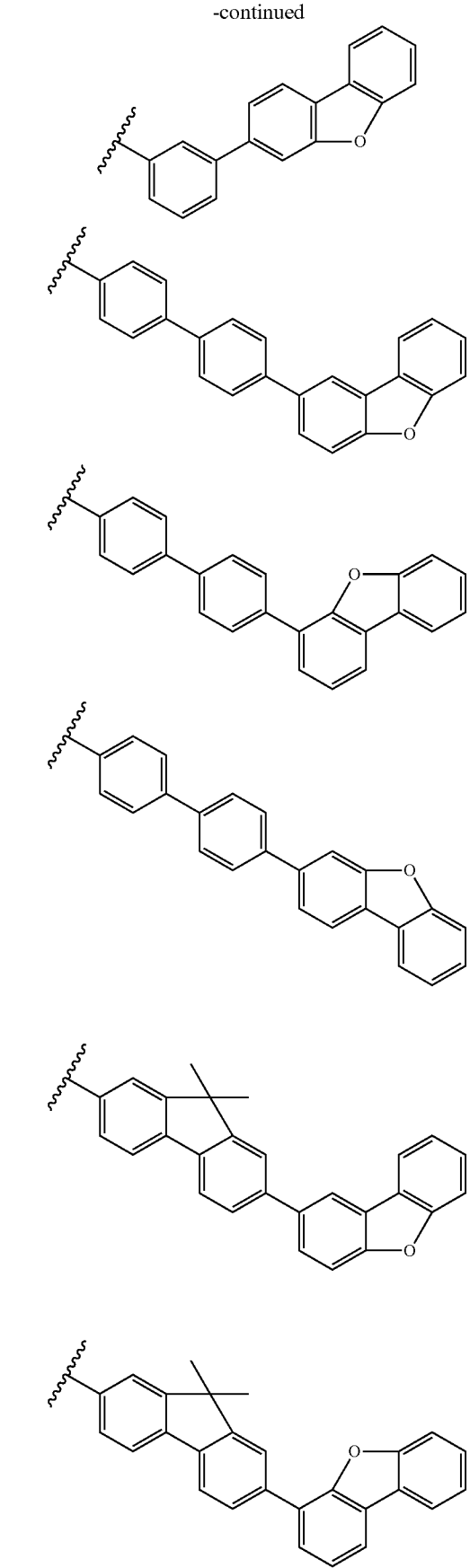

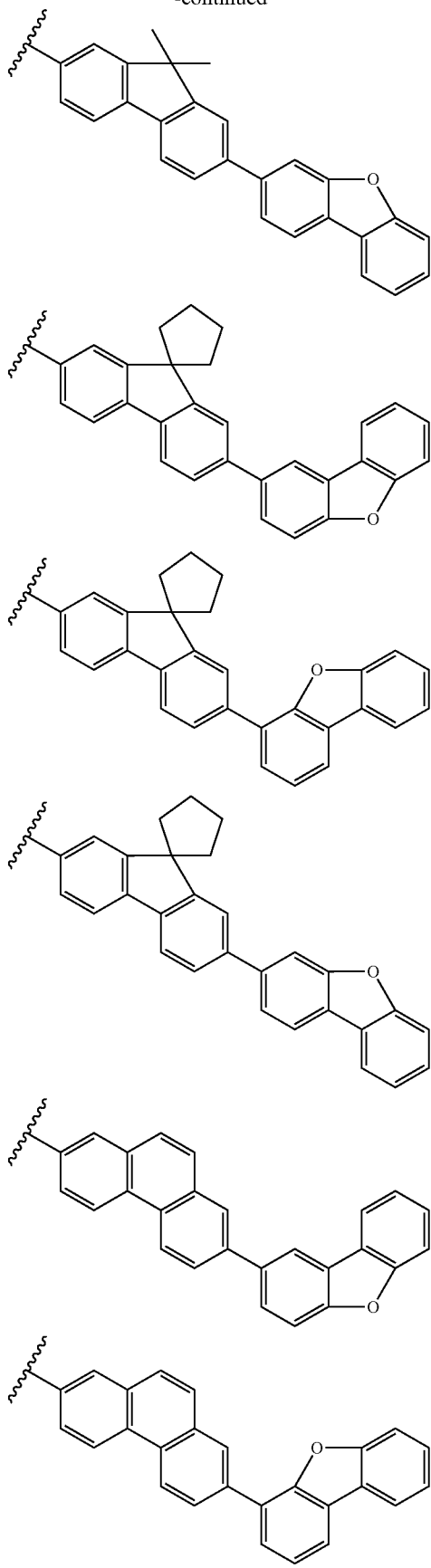

-continued
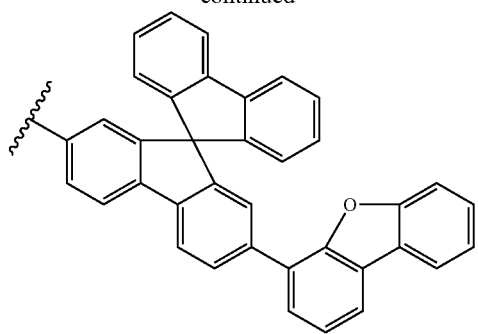
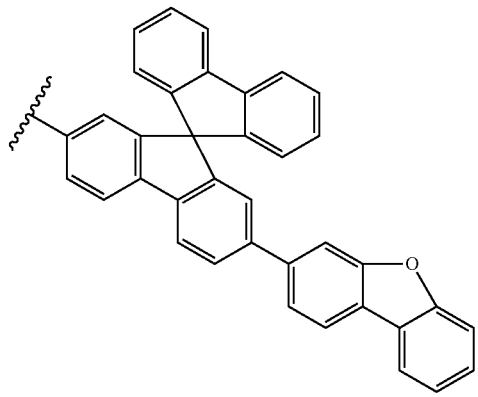
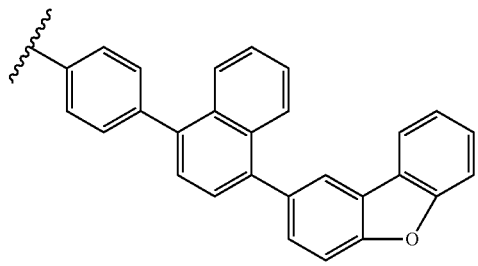
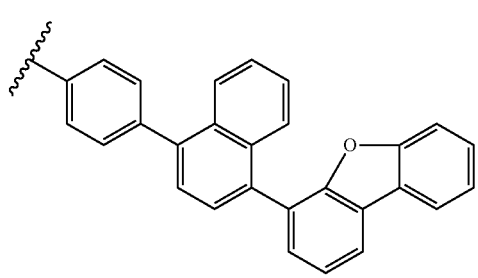
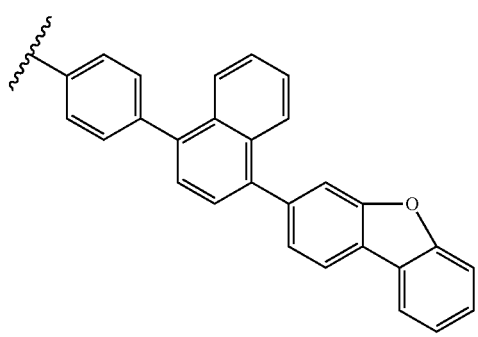
-continued
[Chem. 16]
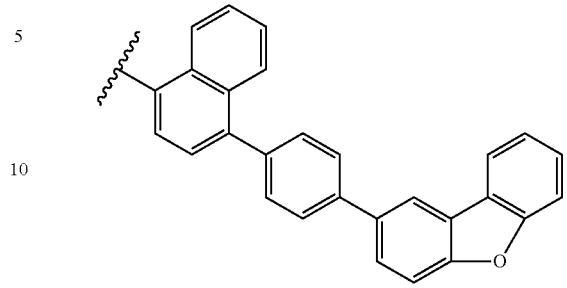
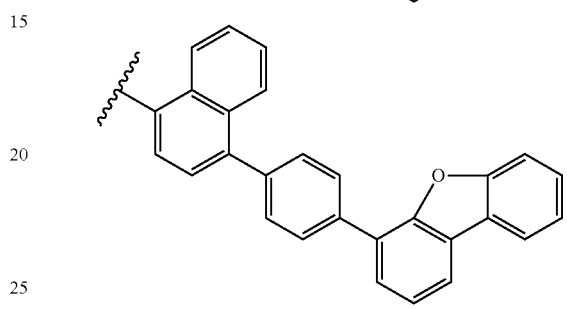
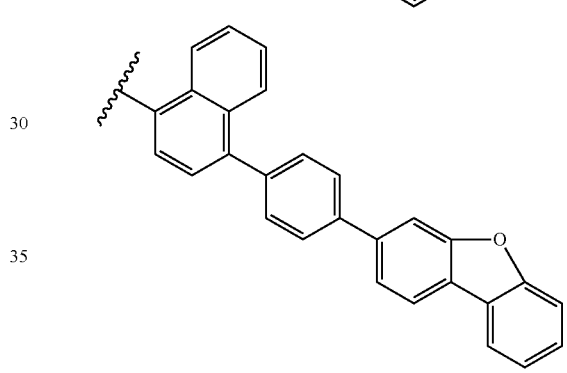
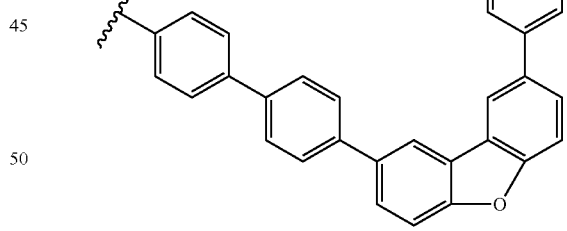
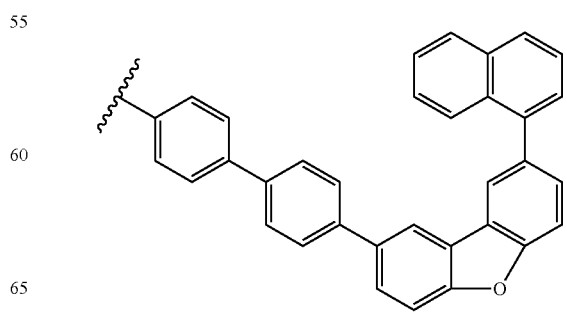

33
-continued
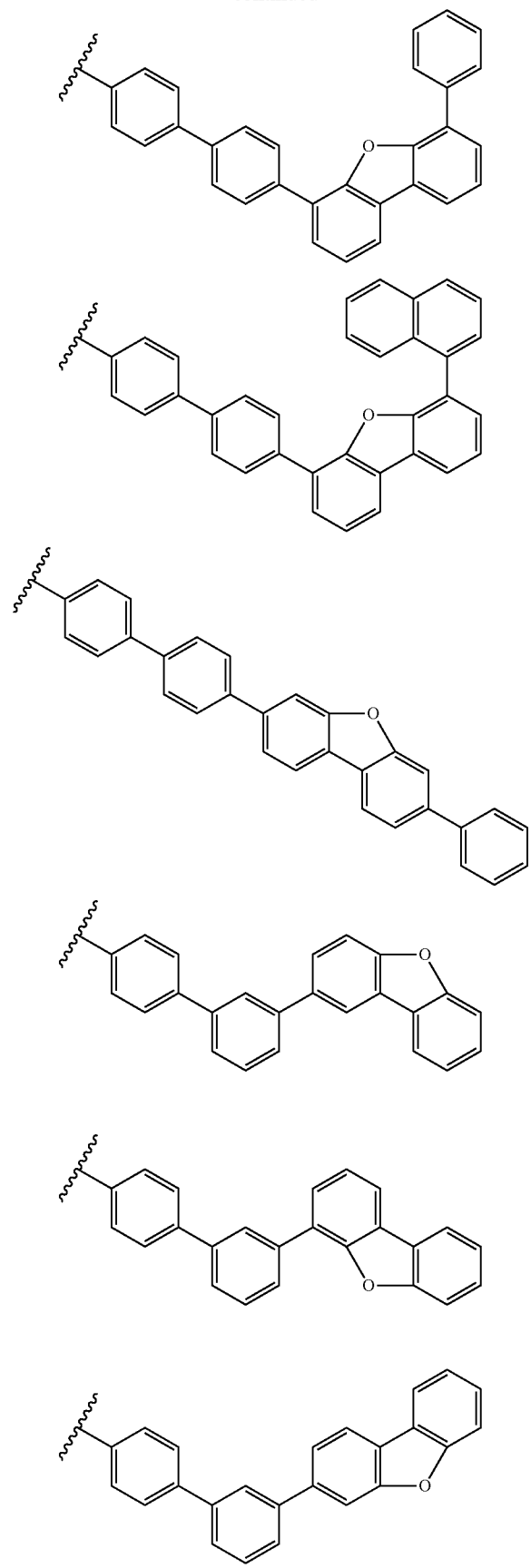
34
-continued
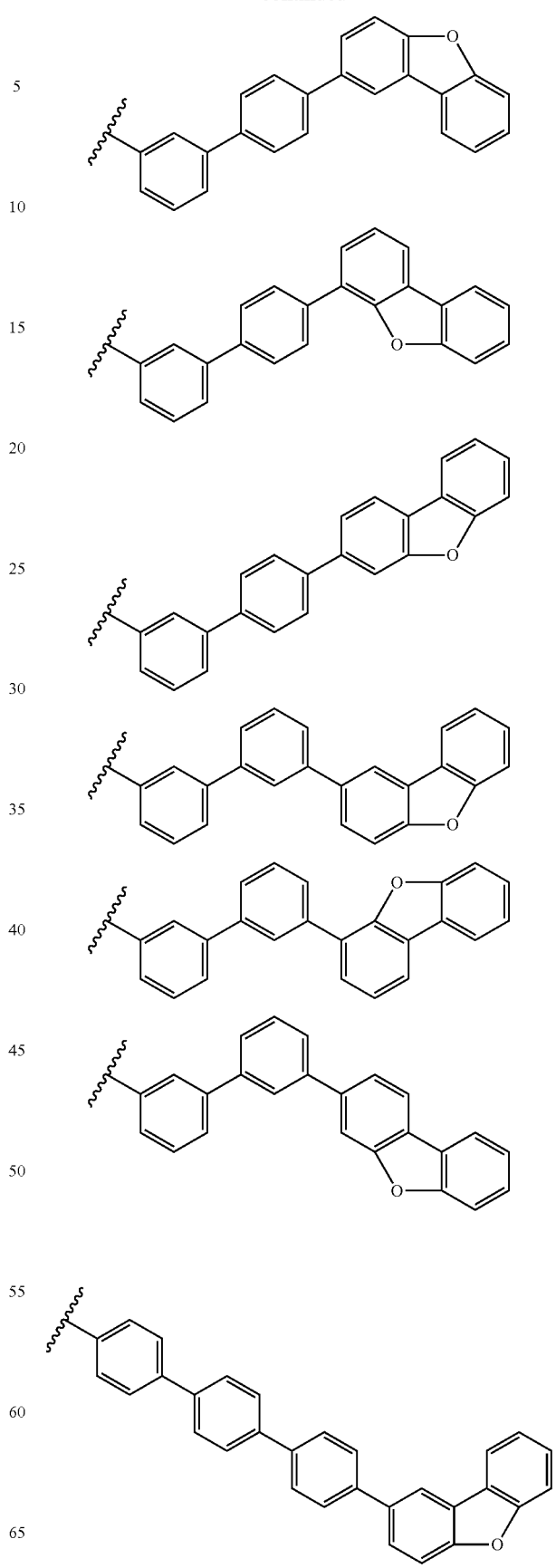

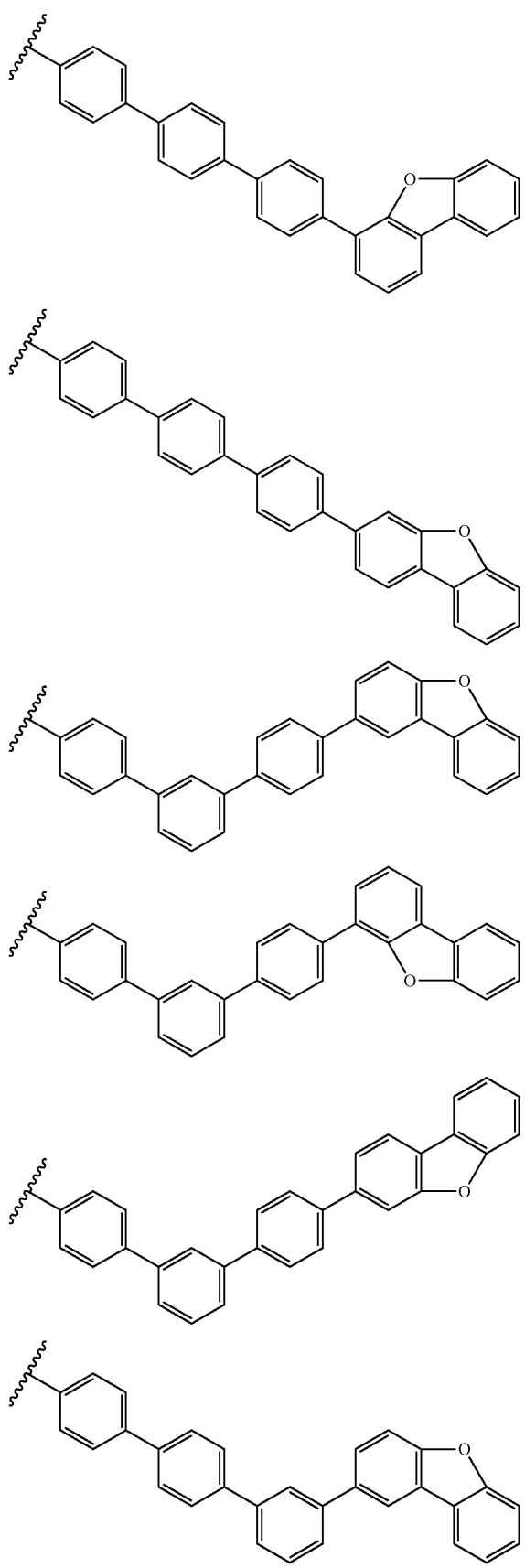
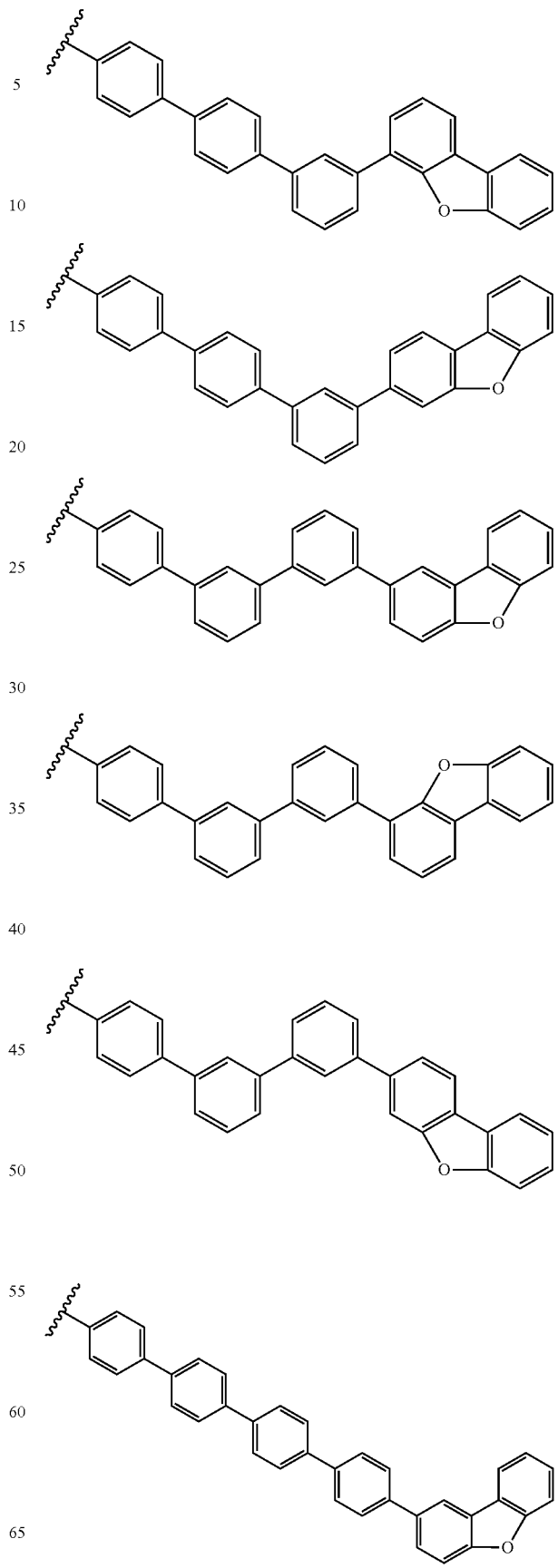

37
-continued
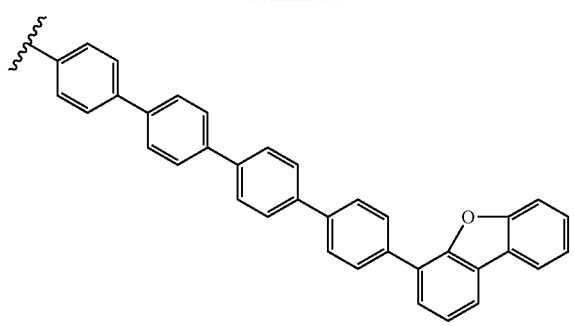
[Chem. 17]
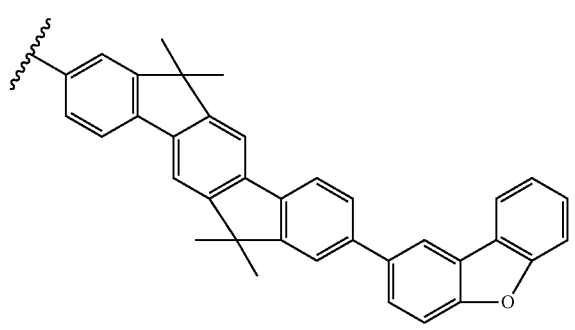
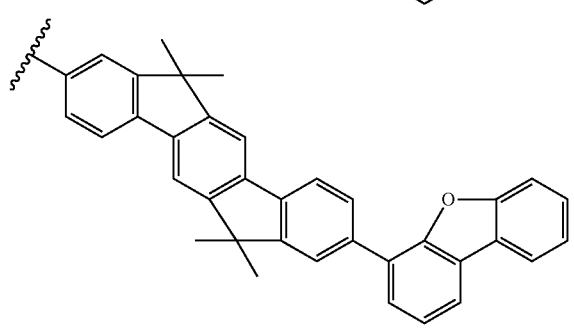
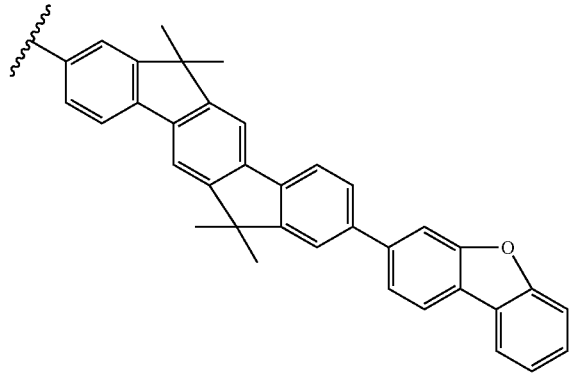
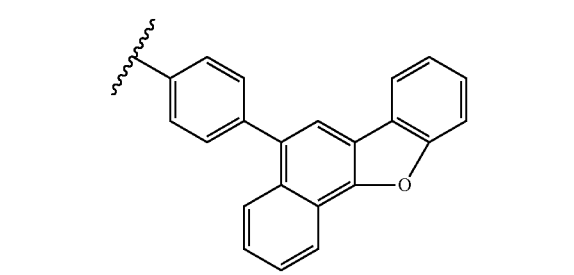
38
-continued
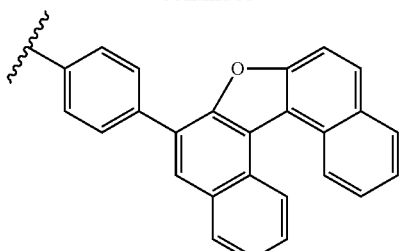
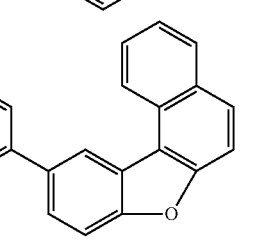
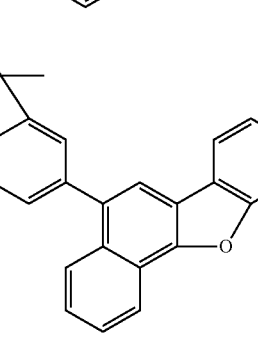
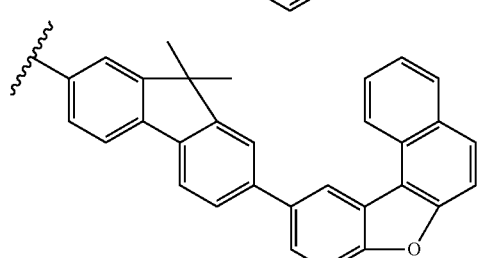
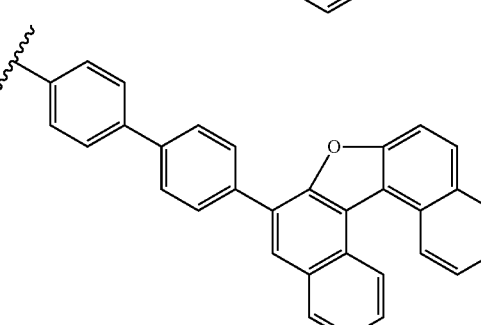
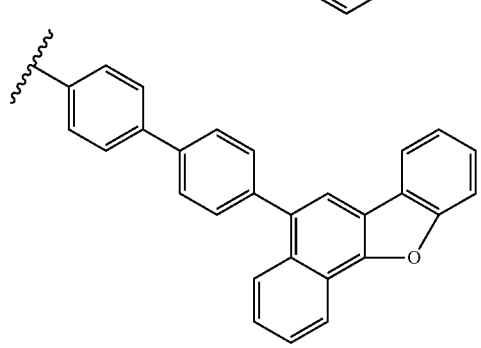

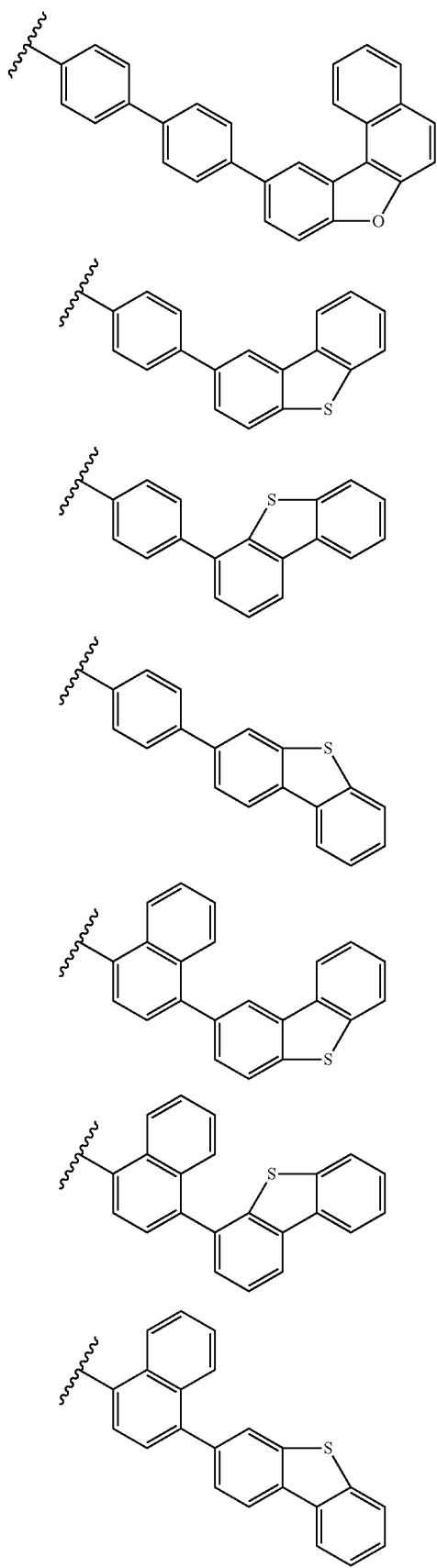
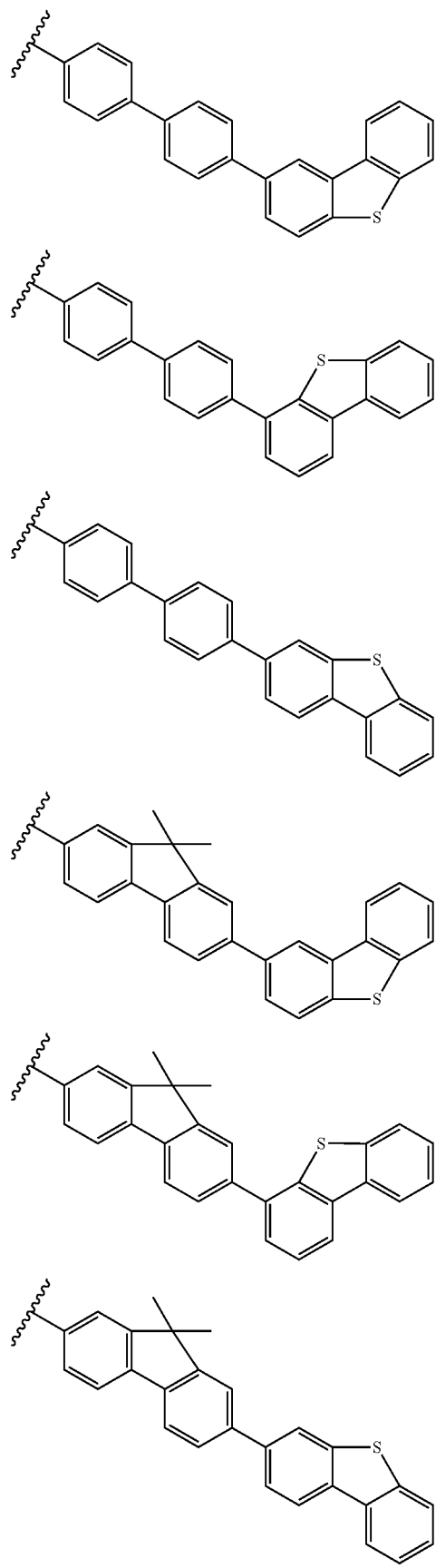

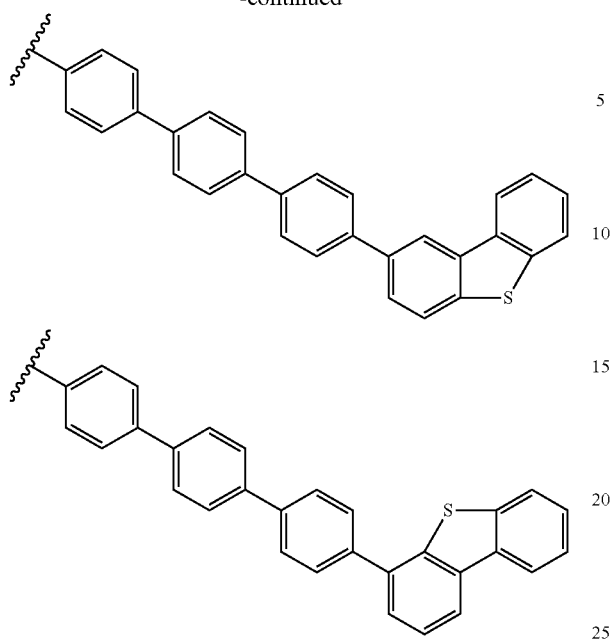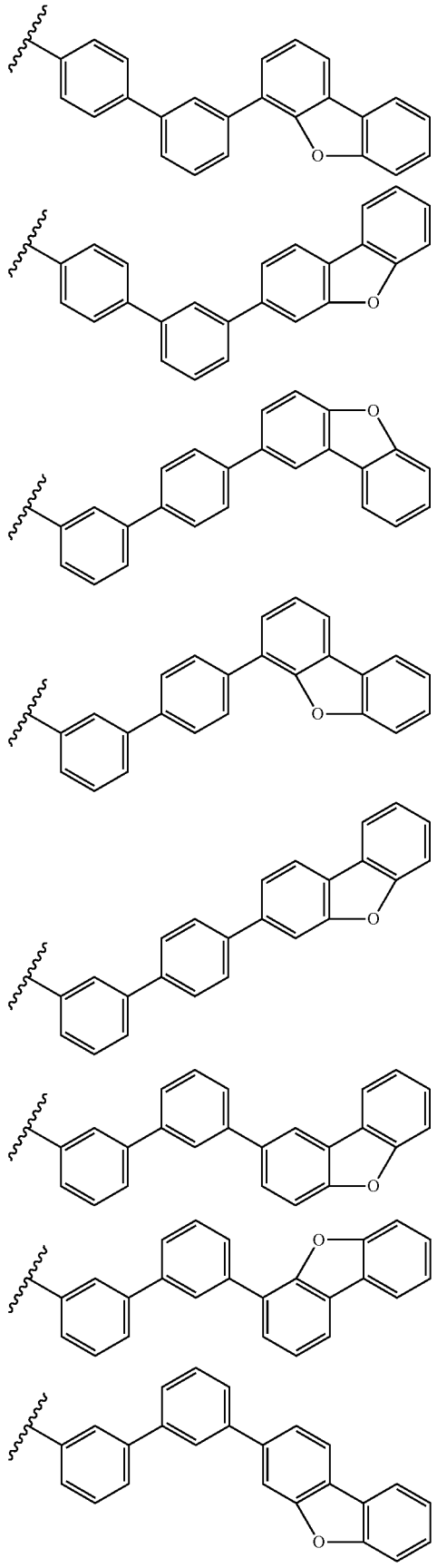

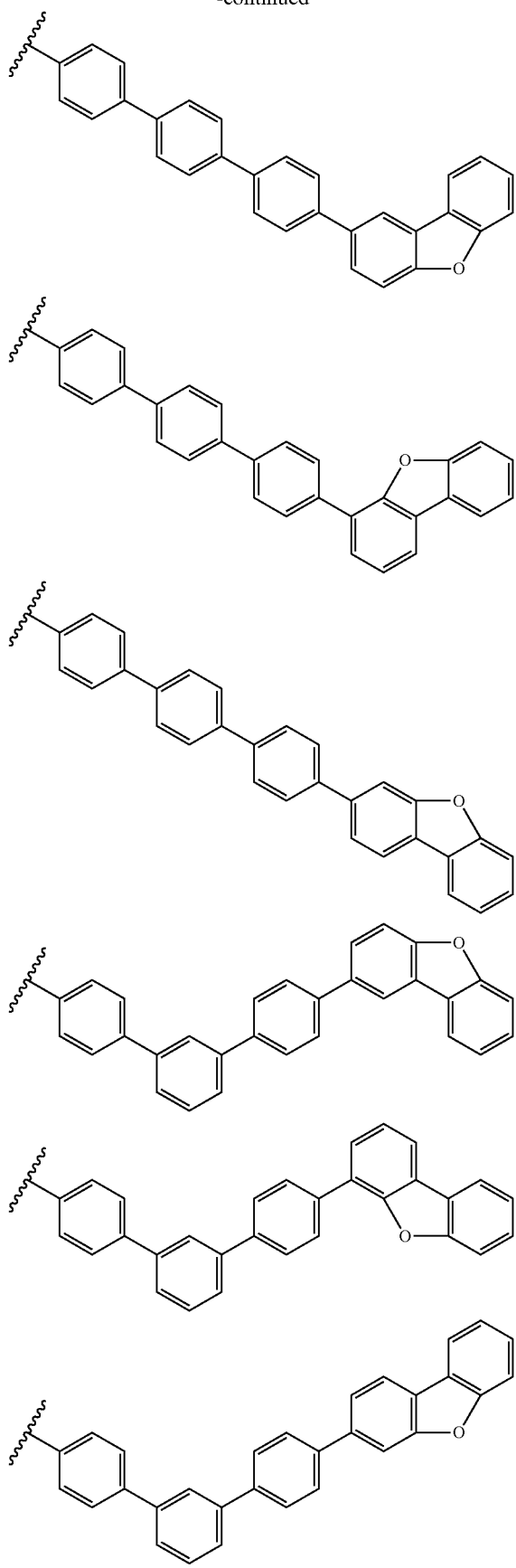
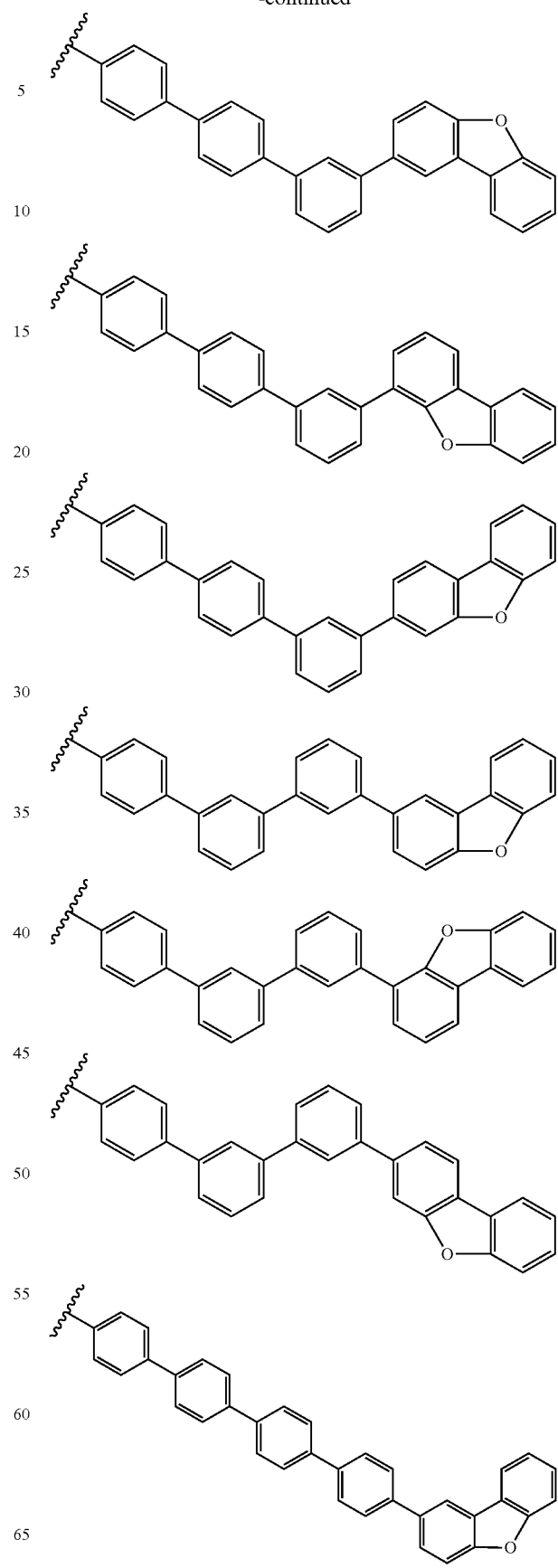

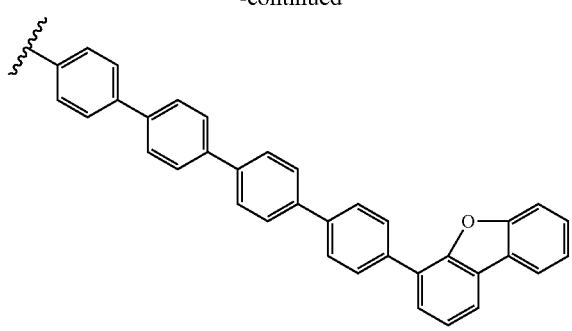
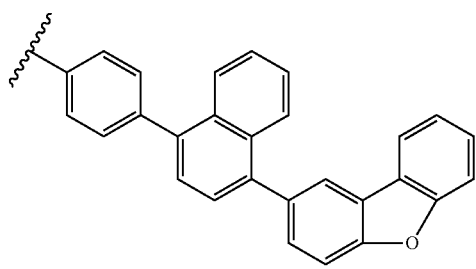
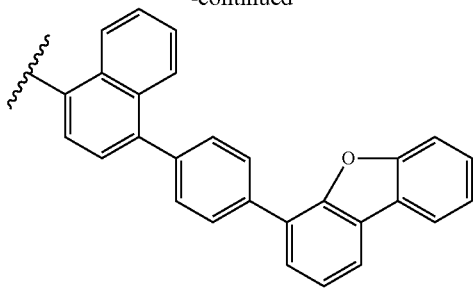
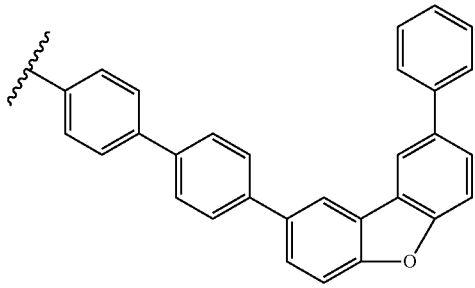
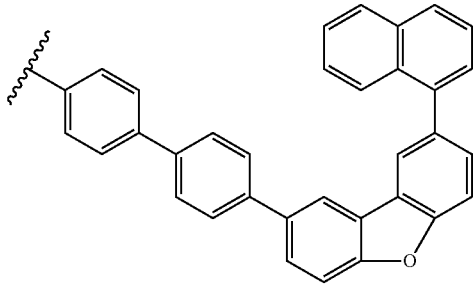
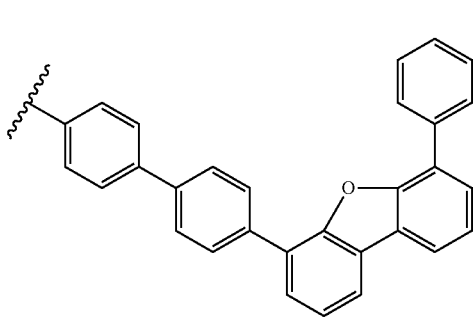

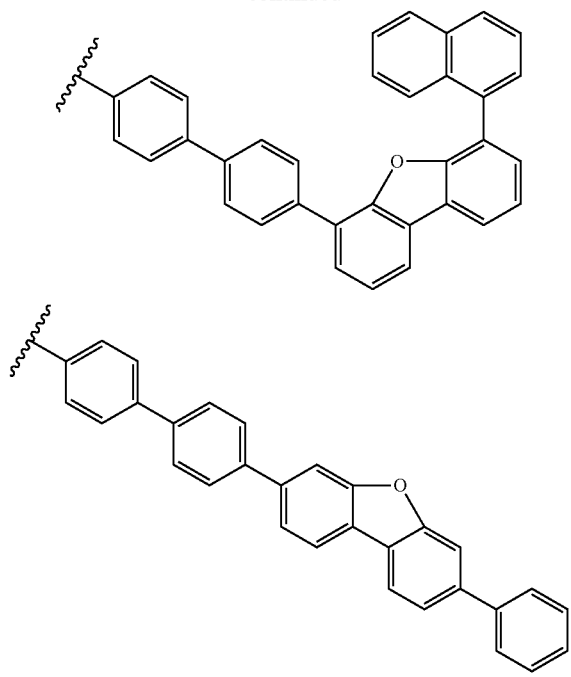
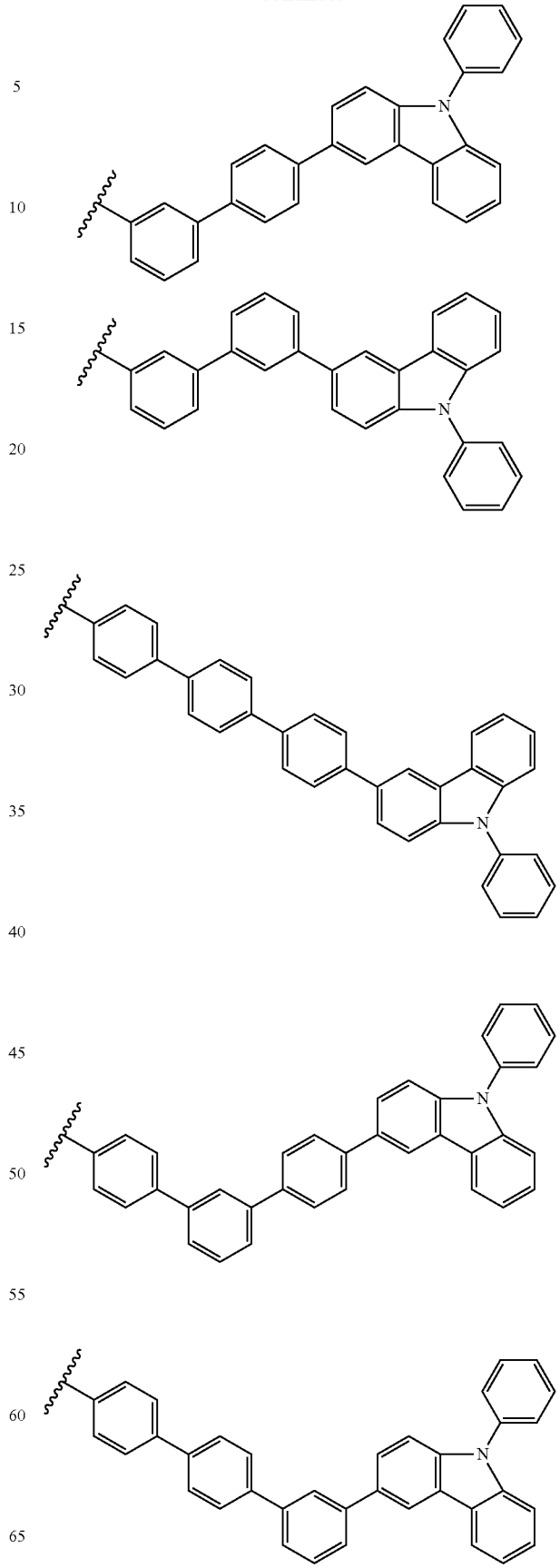

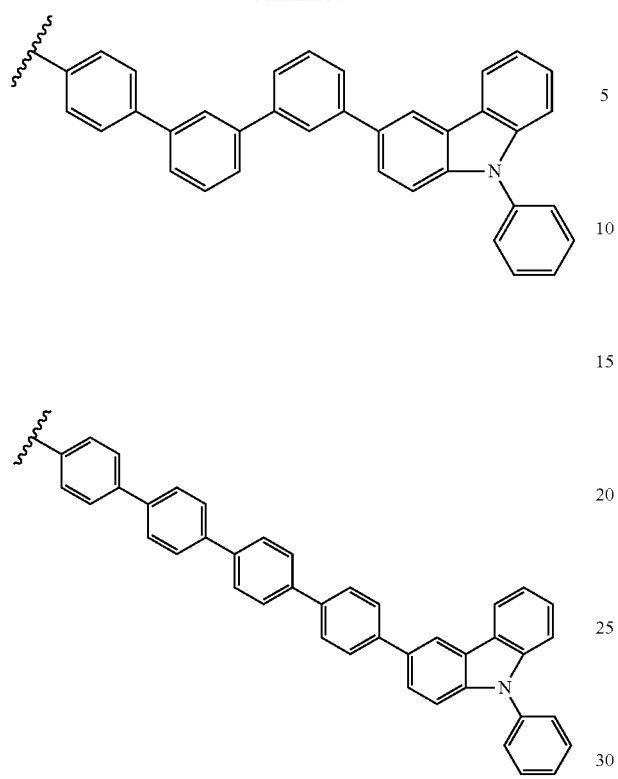
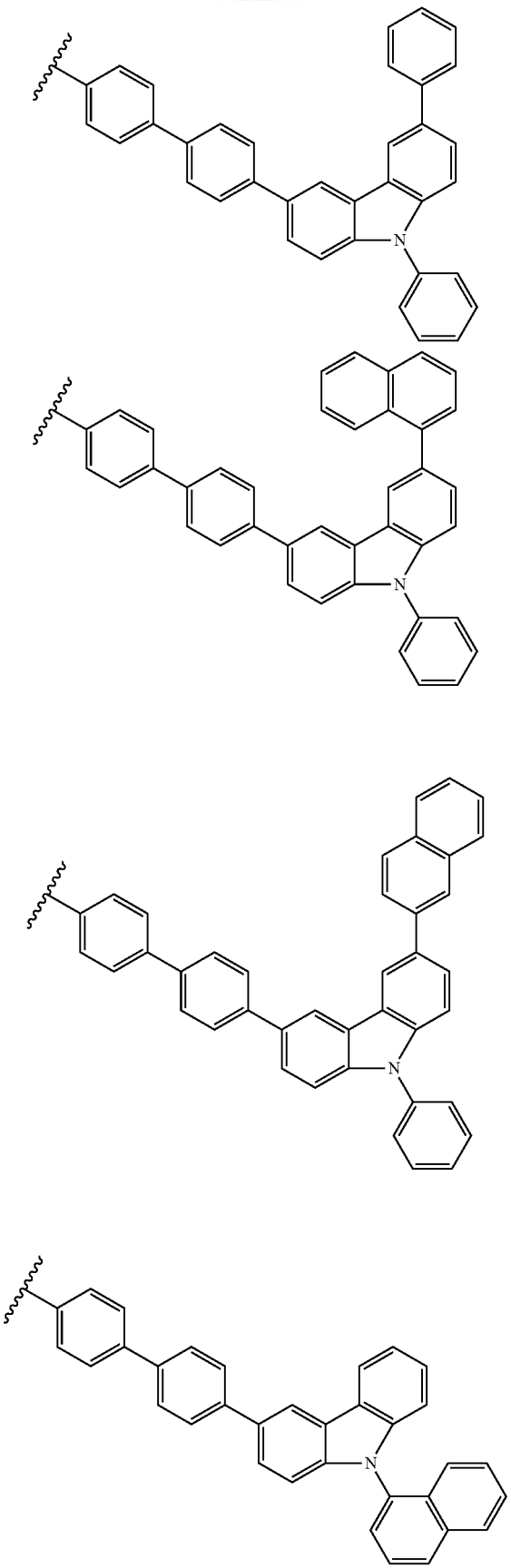

-continued

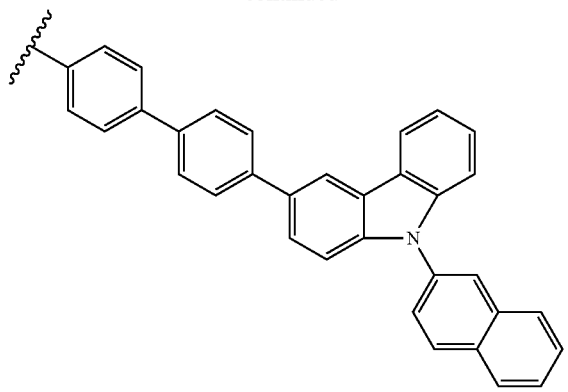

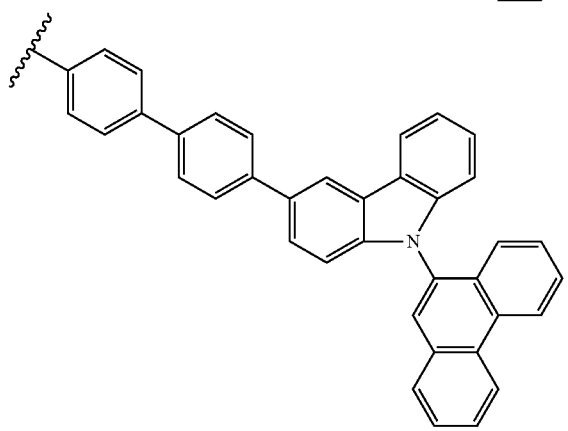

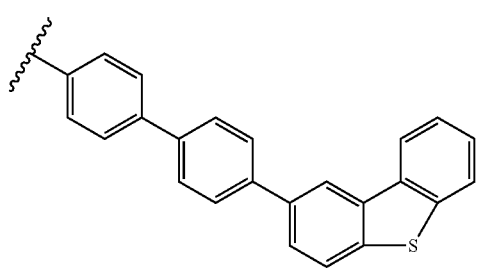

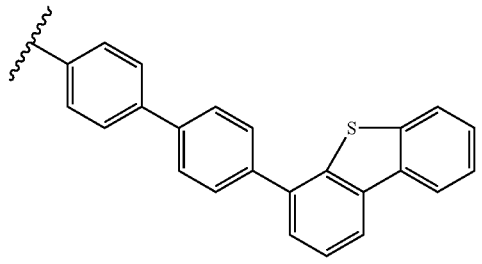

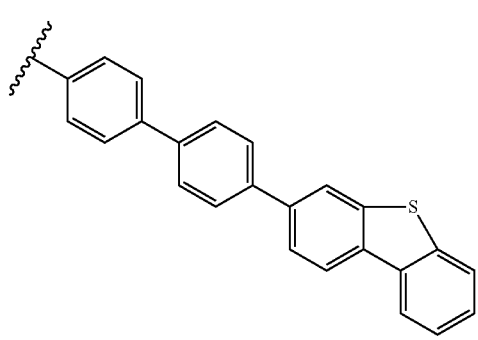

-continued

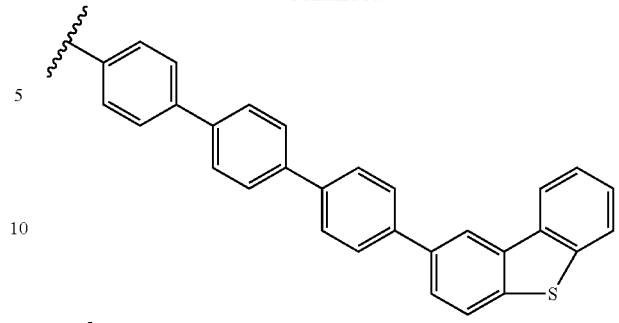

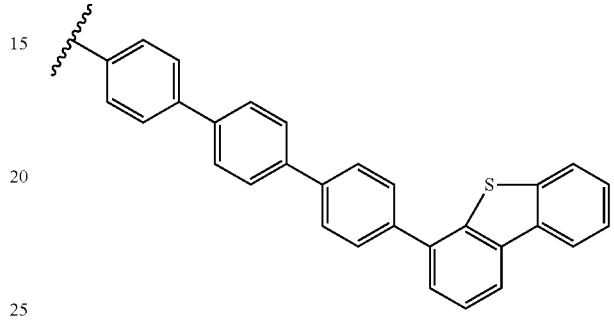

In addition, in the formula (I), $Ar^c$ represents a substituted or unsubstituted aryl group having 6 to 50 ring carbon atoms, or is represented by the formula (III) (the formula (III') and the formulae (III-1) to (III-6) are included, and the same holds true for the following).

Examples of the aryl group represented by $Ar^c$ include the same examples as those of $R^1$ and $R^2$, and a group represented by the formula (II) (the formula (II') is included and the same holds true for the following). Preferred examples of the aryl group include a phenyl group, a naphthylphenyl group, a biphenylyl group, a terphenylyl group, a biphenylenyl group, a naphthyl group, a phenylnaphthyl group, an acenaphthylenyl group, an anthryl group, a benzanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a pentacenyl group, a picenyl group, a pentaphenyl group, a pyrenyl group, a chrysenyl group, a benzochrysenyl group, an s-indacenyl group, an as-indacenyl group, a fluoranthenyl group, a perylenyl group, and the group represented by the formula (II).

The aryl group may have a substituent, and the substituent is a group selected from the group consisting of a linear or branched alkyl group having 1 to 50 carbon atoms (preferably 1 to 10 carbon atoms, more preferably 1 to 5 carbon atoms), a cycloalkyl group having 3 to 50 carbon atoms (preferably 3 to 6 carbon atoms, more preferably 5 or 6 carbon atoms), a trialkylsilyl group having alkyl groups each having 1 to 50 carbon atoms (preferably 1 to 10 carbon atoms, more preferably 1 to 5 carbon atoms), a triarylsilyl group having aryl groups each having 6 to 50 ring carbon atoms (preferably 6 to 24 ring carbon atoms, more preferably 6 to 12 ring carbon atoms), an alkylarylsilyl group having an alkyl group having 1 to 50 carbon atoms (preferably 1 to 10 carbon atoms, more preferably 1 to 5 carbon atoms) and an aryl group having 6 to 50 ring carbon atoms (preferably 6 to 24 ring carbon atoms, more preferably 6 to 12 ring carbon atoms), a triarylalkyl group having aryl groups each having 6 to 50 ring carbon atoms (preferably 6 to 24 ring carbon atoms, more preferably 6 to 12 ring carbon atoms), an aryl group having 6 to 50 ring carbon atoms (preferably 6 to 24 ring carbon atoms, more preferably 6 to 12 ring carbon atoms), a heteroaryl group having 5 to 50 ring atoms (preferably 5 to 24 ring atoms, more preferably 5 to 12 ring atoms), halogen atoms such as a fluorine atom, a chlorine atom, a bromine atom, and an iodine atom, and a cyano group.

It is also preferred that $Ar^c$ be a group represented by the following formula (IV).

[Chem. 20]

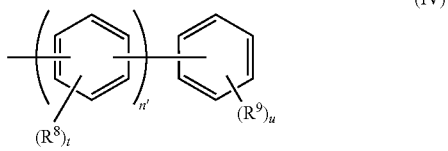

(IV)

In the formula (IV), $R^8$ and $R^9$ each represent a halogen atom, a linear or branched alkyl group having 1 to 50 carbon atoms, a linear or branched alkenyl group having 1 to 50 carbon atoms, an aryl group having 6 to 50 ring carbon atoms, or a heteroaryl group having 5 to 50 ring atoms.

Examples of the halogen atom, the alkyl group, the alkenyl group, the aryl group, and the heteroaryl group include the same examples as those of $R^3$ and $R^4$. Preferred examples thereof are also the same, and examples of the substituent which any such group may have also include the same examples. The alkyl group may be substituted with a hydroxyl group.

A plurality of $R^8$'s or $R^9$'s adjacent to each other, or $R^8$ and $R^9$ may be bonded to each other to form a ring. Further, an oxygen atom or a nitrogen atom may be present in the ring. A group thus formed can be represented by, for example, the formula (II) or the formula (III) (provided that the case where X represents a sulfur atom is excluded here), and in this case, $Ar^c$ may be identical to or different from $Ar^a$ and $Ar^b$. When $Ar^c$ represents a group different from $Ar^a$ and $Ar^b$, the molecular symmetry of the aromatic amine derivative can be reduced by a group having steric hindrance. Accordingly, an intermolecular interaction is small, crystallization is suppressed, and a yield upon production of the organic EL device can be increased.

n' represents an integer of 0 to 3. n' preferably represents 2 or 3 because of the following reason. The steric hindrance of the aromatic amine derivative is raised, and hence the intermolecular interaction is reduced and a suppressing effect on the crystallization is enhanced.

t represents an integer of 0 to 4 and u represents an integer of 0 to 5.

It should be noted that when a plurality of $R^8$'s are present on the same benzene ring or on different benzene rings, the plurality of $R^8$'s may be identical to or different from each other. In addition, when a plurality of $R^9$'s are present on the same benzene ring, the plurality of $R^9$'s may be identical to or different from each other.

The case where $Ar^c$ represents a substituted or unsubstituted aryl group having 6 to 50 ring carbon atoms, especially the case where $Ar^c$ is represented by an aryl group having 18 to 50 ring carbon atoms is preferred from the following viewpoint. As steric bulkiness is raised to reduce the intermolecular interaction, the crystallization of the material is suppressed and the stability of a thin film is improved, and as a result, the lifetime of the organic EL device is additionally lengthened. In addition, when $Ar^c$ is represented by the formula (II), $Ar^c$ is preferably represented by the formula (II') from the viewpoints of an additionally high charge mobility and an additional reduction in the driving voltage of the organic EL device.

When $Ar^c$ is represented by the formula (III), $Ar^c$ may be identical to or different from $Ar^b$. In addition, when $Ar^c$ is represented by the formula (III), $Ar^c$ is preferably represented by the formula (III') from the viewpoints of an additionally high charge mobility and an additional reduction in the driving voltage of the organic EL device.

Here, specific examples of $Ar^c$ are shown below. However, $Ar^c$ is not particularly limited to these examples. It should be noted that D in an exemplified compound represents a deuterium atom.

[Chem. 21]

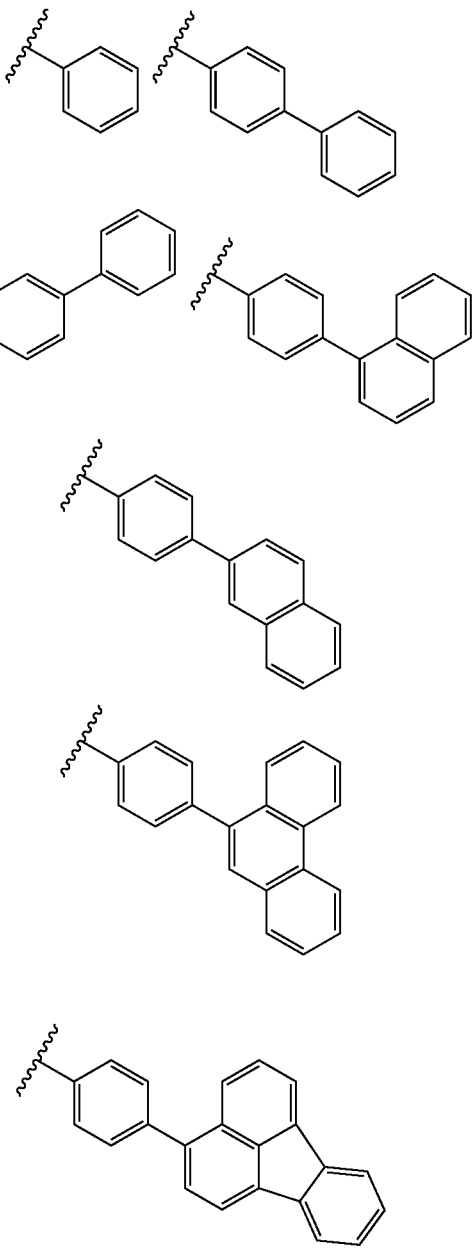

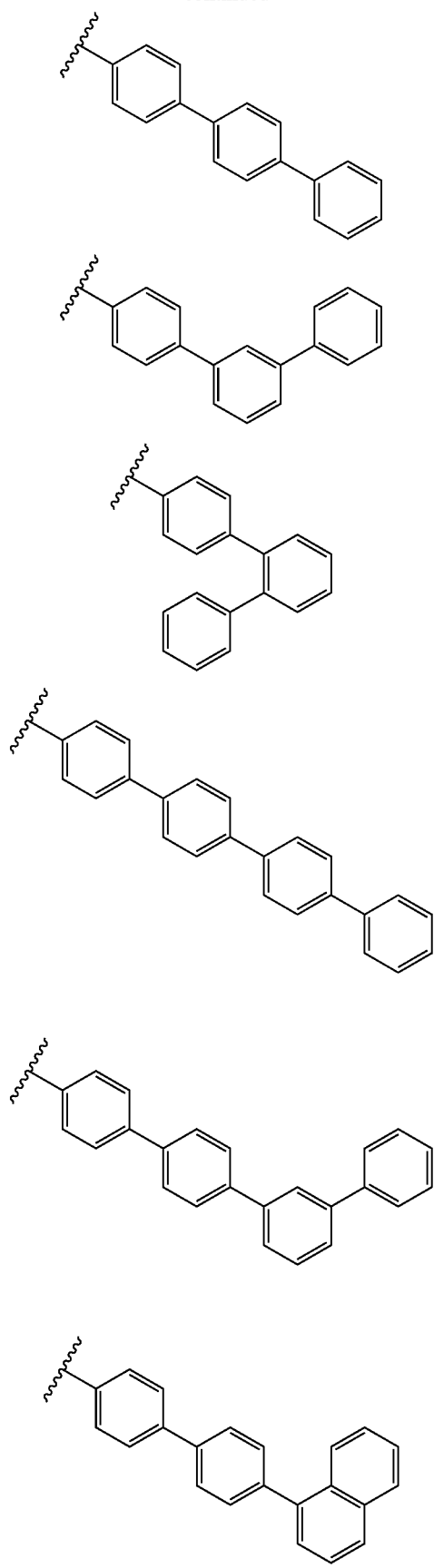
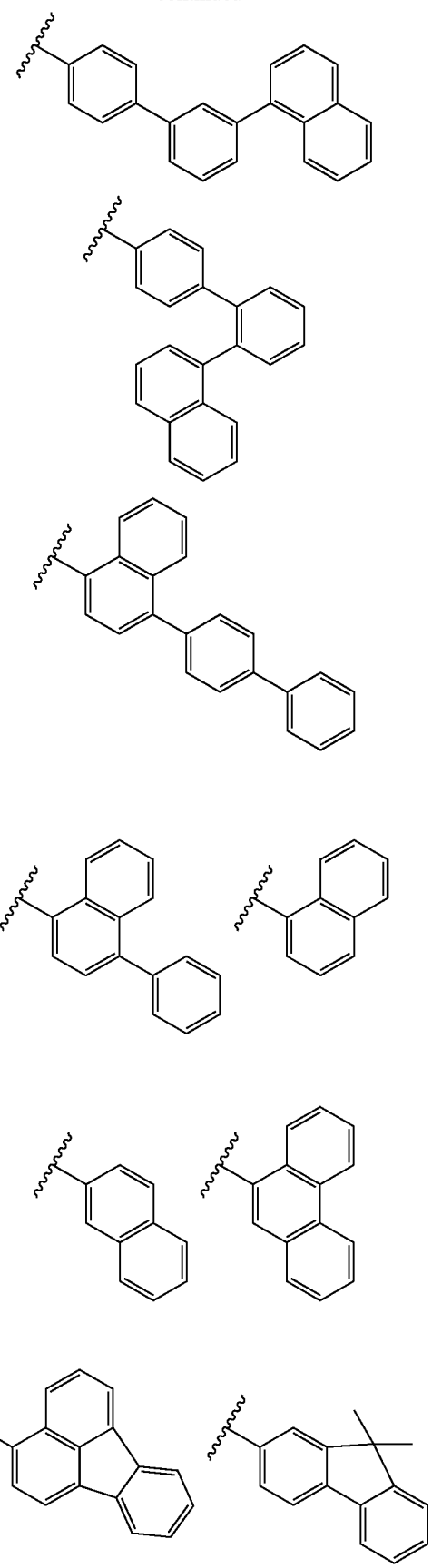

57
-continued
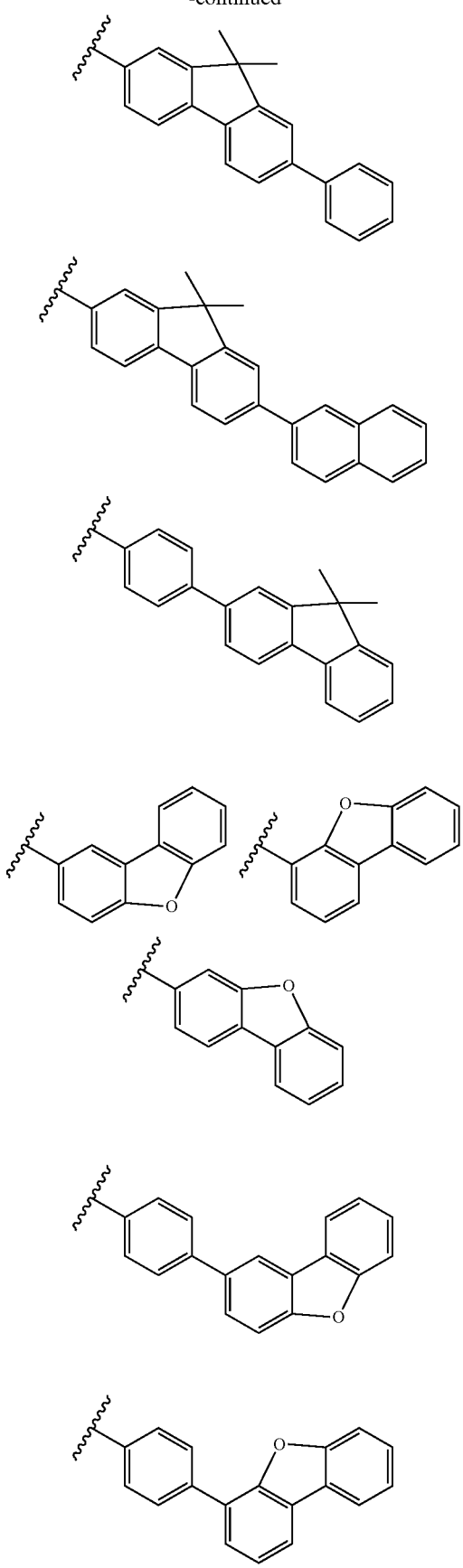
58
-continued
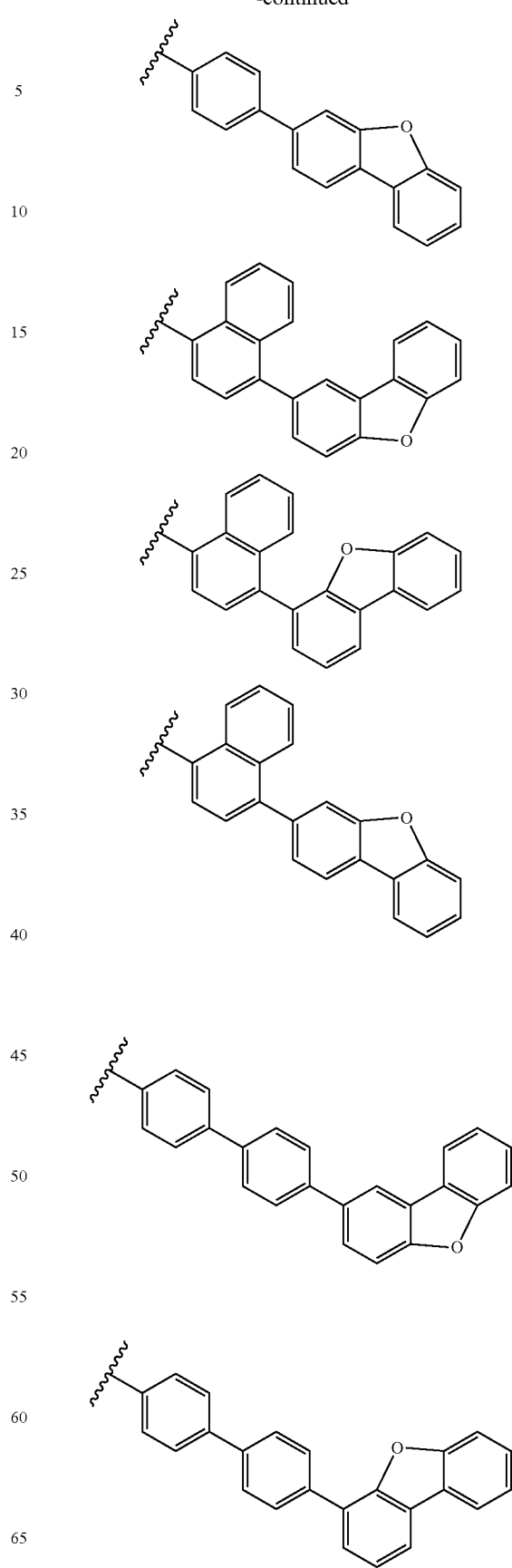

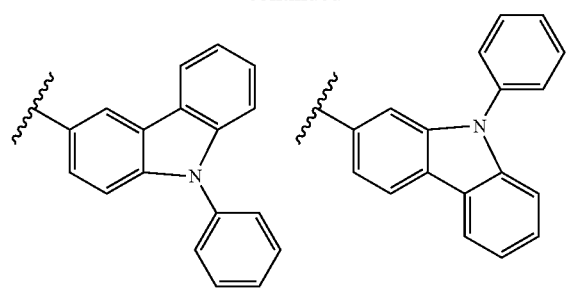
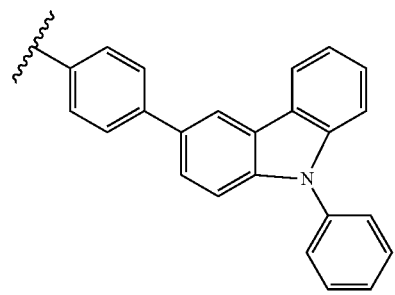
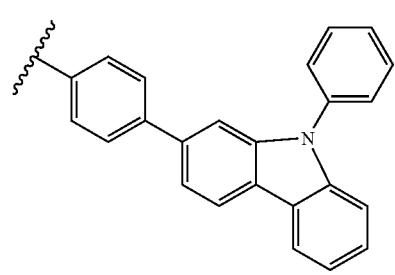
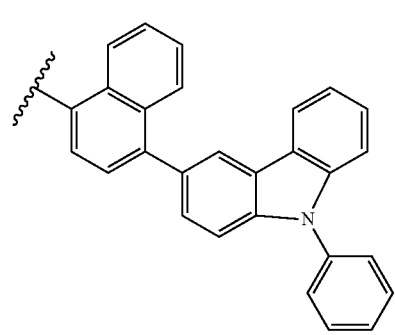
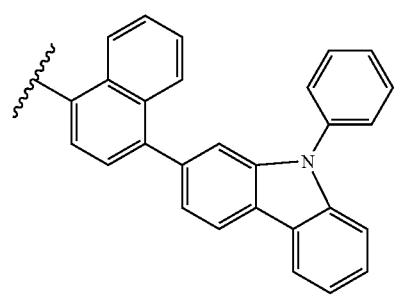
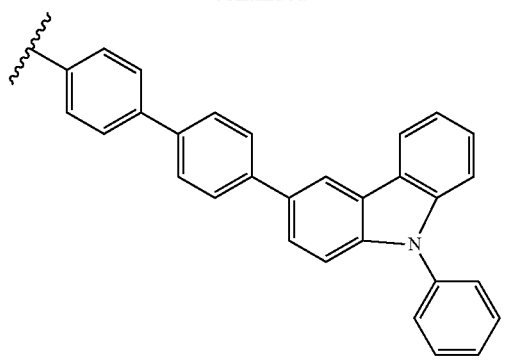
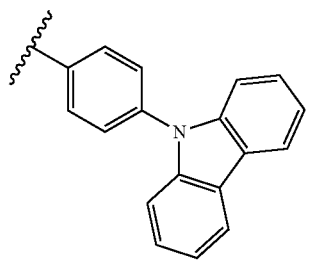
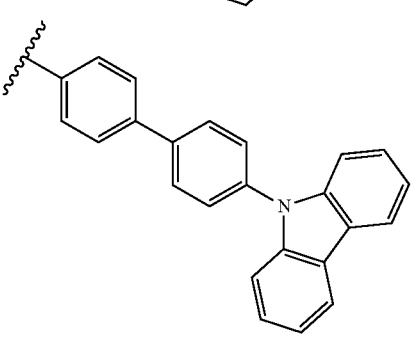
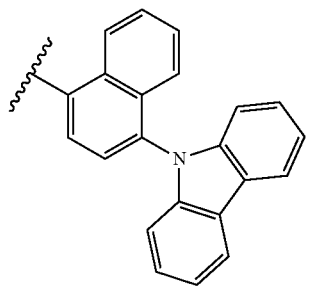
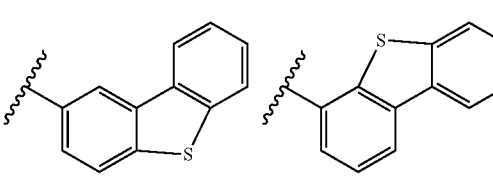
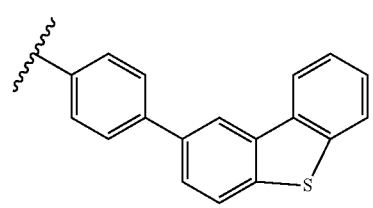

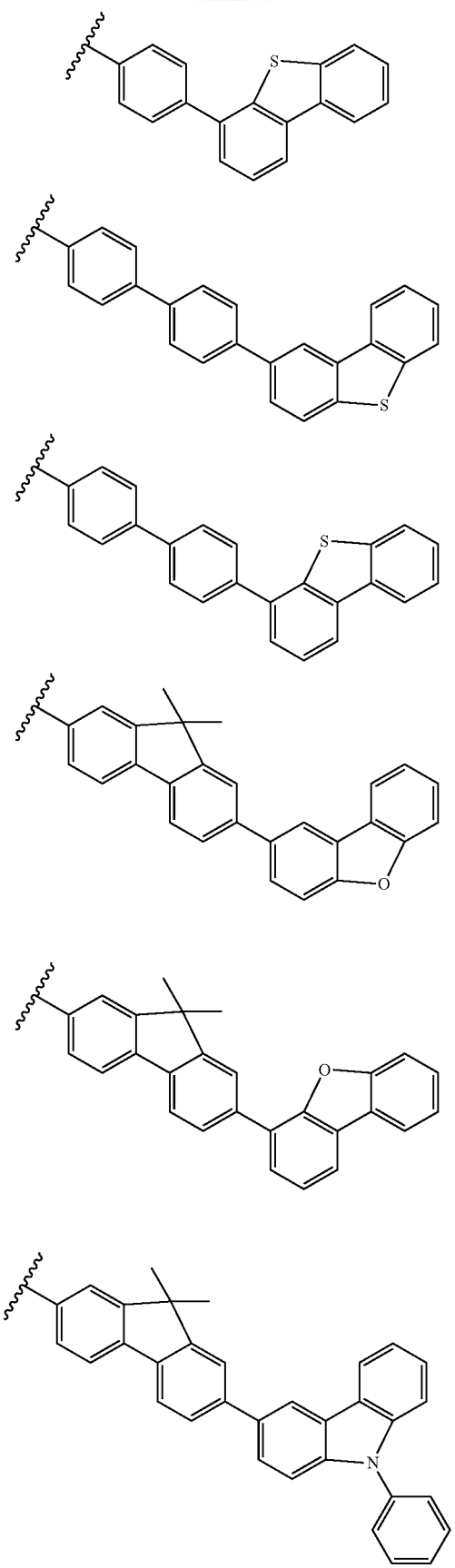

When Ar$^c$ represents an aryl group, preferably a biphenyl group, a terphenyl group, a quaterphenyl group, a naphthyl group, an anthracene group, a fluorene group, or a phenanthrene group, more preferably a terphenyl group or a quaterphenyl group, the following effect can be expected. As the intermolecular interaction is reduced by the raised steric hindrance of the aromatic amine derivative, the crystallization is suppressed, the stability of the thin film is additionally improved, and the lifetime of the organic EL device is additionally lengthened.

In particular, in the case where Ar$^c$ represents a terphenyl group or a quaterphenyl group, when benzene rings for constructing the terphenyl group or the quaterphenyl group are bonded to one another at the irrespective para positions, such a chemical structure that a conjugated system is bonded and expanded is established, and hence an increasing effect on the charge mobility can be expected. On the other hand, when the benzene rings for constructing the terphenyl group or the quaterphenyl group are bonded to one another at their respective meta positions, the steric hindrance is additionally raised to reduce the intermolecular interaction, and hence the suppressing effect on the crystallization can be additionally expected.

In addition, in the case where Ar$^c$ represents a heteroaryl group, preferably a dibenzofuran group, a carbazole group, or a dibenzothiophene group, more preferably a dibenzofuran group, an additional lengthening effect on the lifetime of the organic EL device can be expected.

It should be noted that Ar$^c$ and Ar$^a$, and Ar$^c$ and Ar$^b$ are preferably not of the same structure because the symmetry of the aromatic amine derivative reduces, the stability of the thin film is improved, and the lifetime of the organic EL device is additionally lengthened. On the other hand, when Ar$^c$ and Ar$^a$ or Ar$^c$ and Ar$^b$ represent groups of the same kind, their bonding positions are preferably caused to differ from each other (in the case of, for example, a dibenzofuranyl group, a 2-dibenzofuranyl group and a 4-dibenzofuranyl group are prepared) because the symmetry of the aromatic amine derivative reduces, the stability of the thin film is improved, and the lifetime of the organic EL device is additionally lengthened.

Next, specific examples of the aromatic amine derivative of the present invention represented by the formula (I) are shown below. However, the derivative is not particularly limited to these examples.

[Chem. 22]
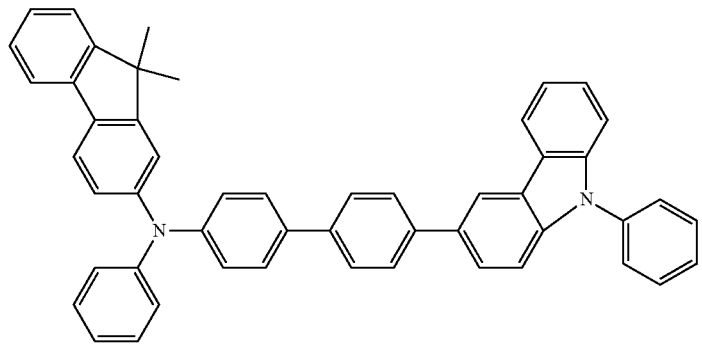
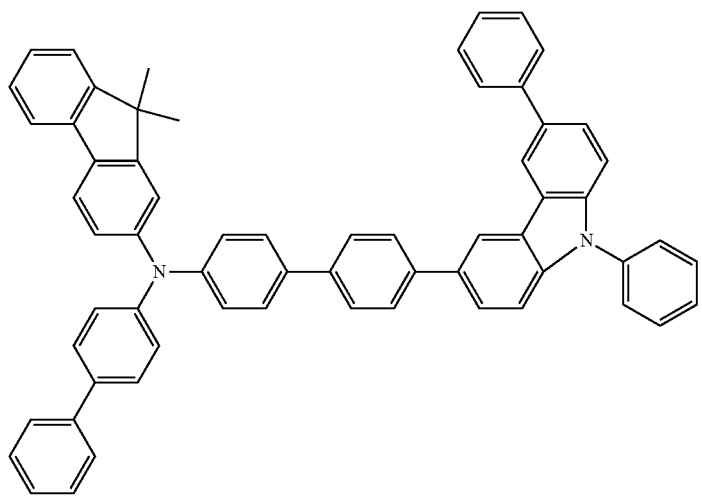
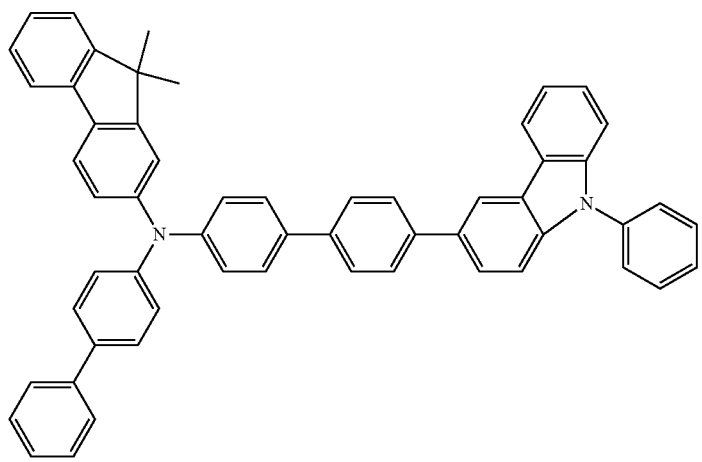

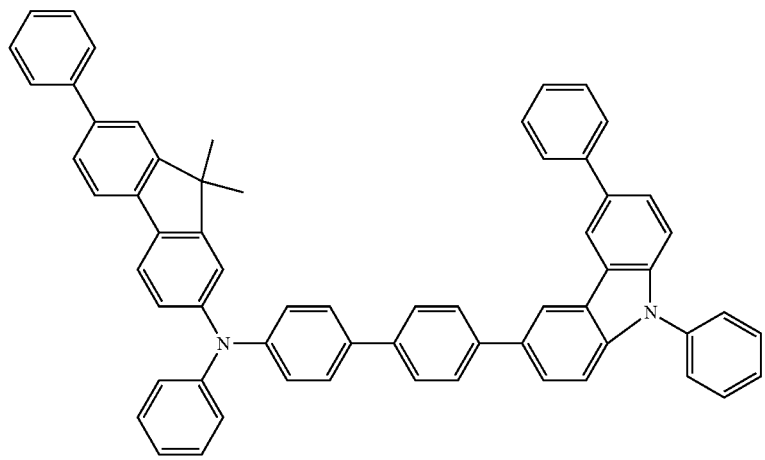
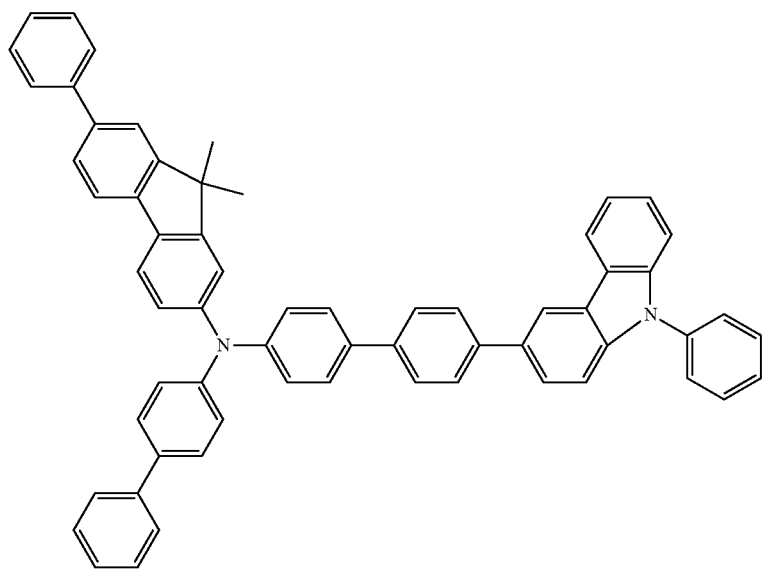
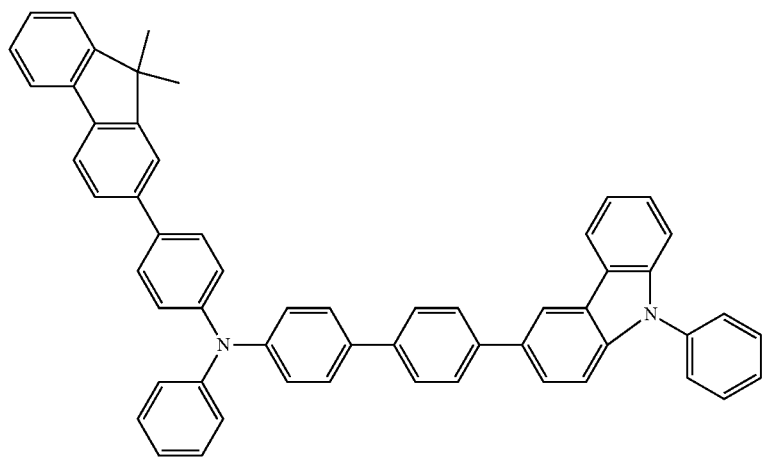

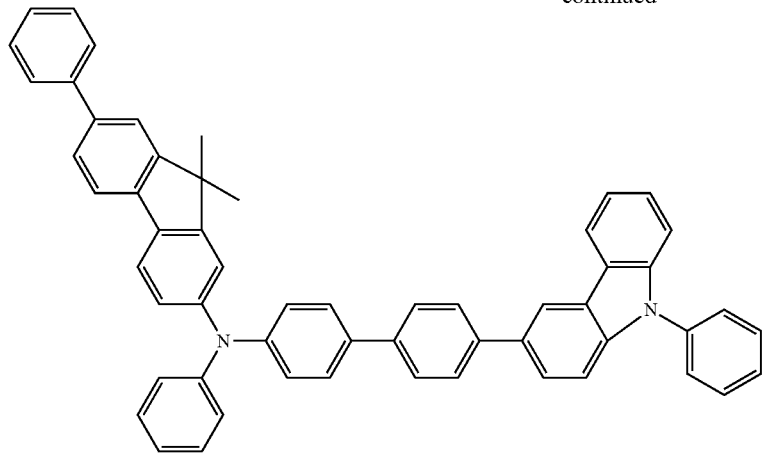
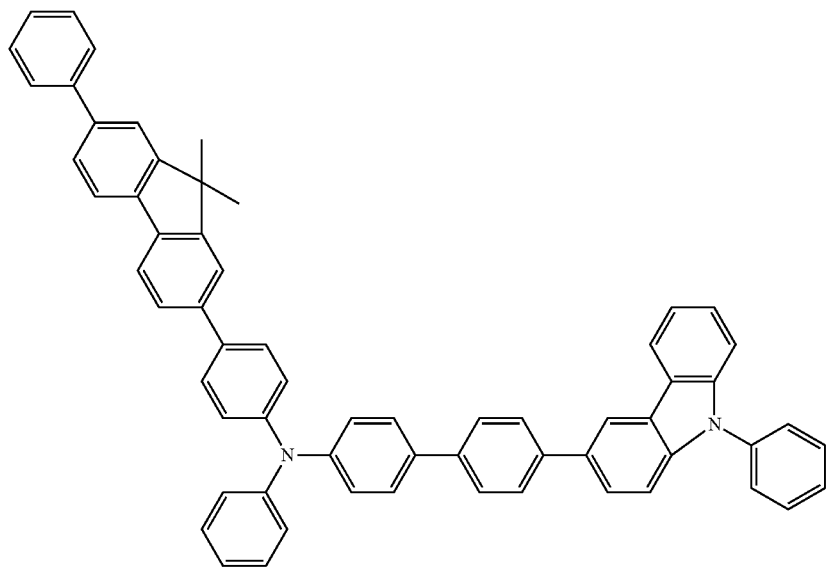
[Chem. 23]
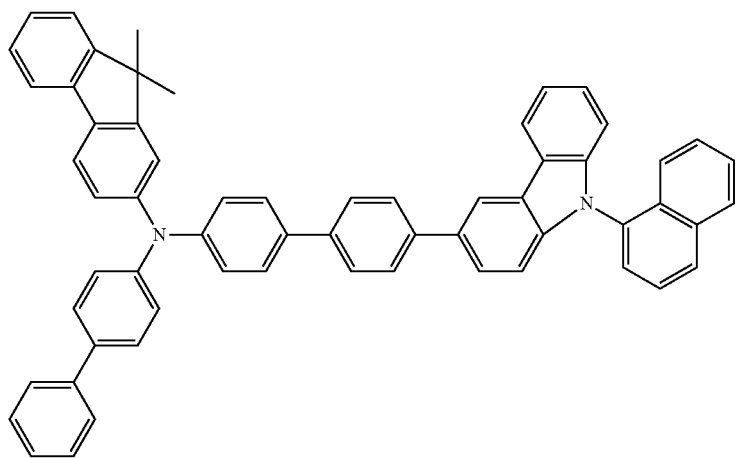

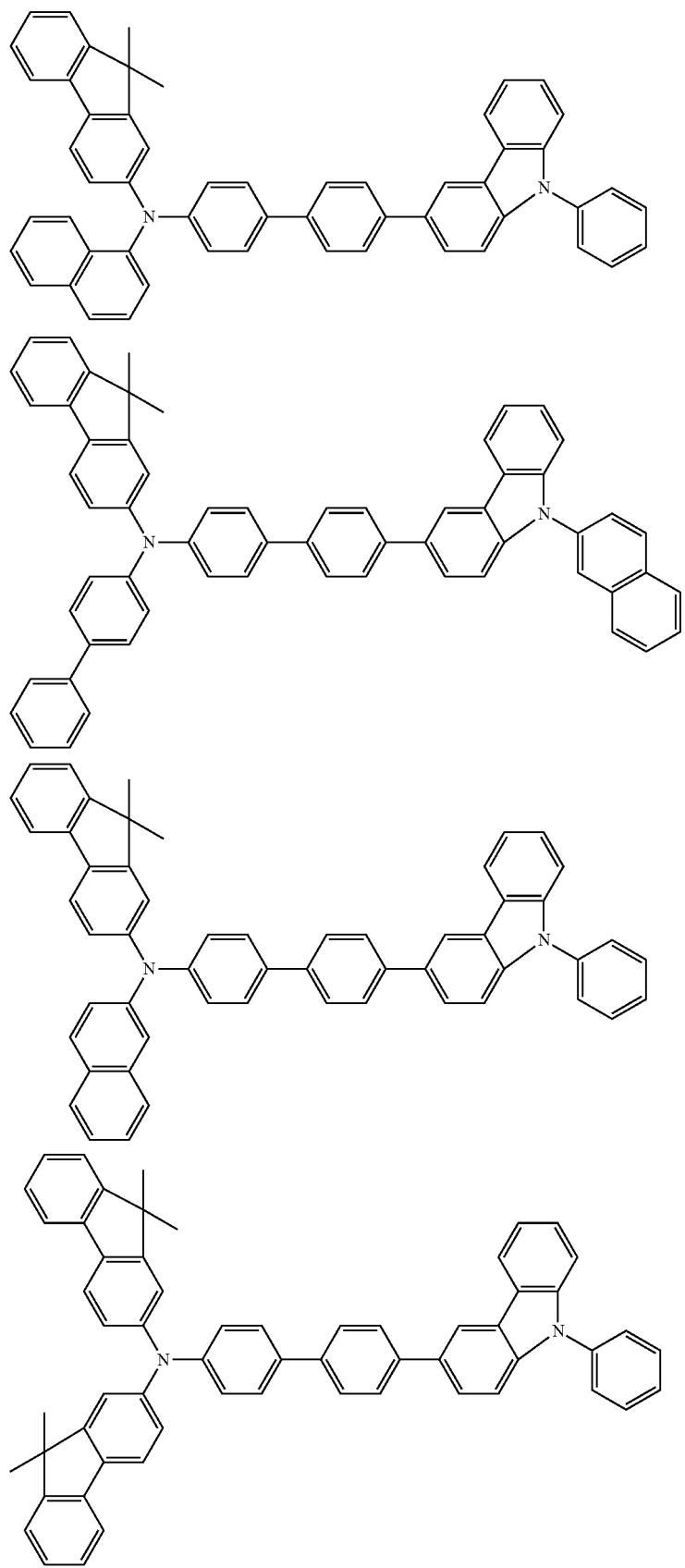

-continued
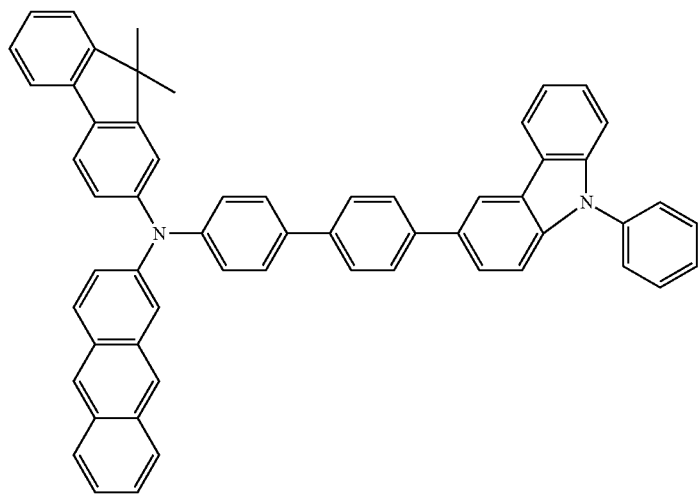
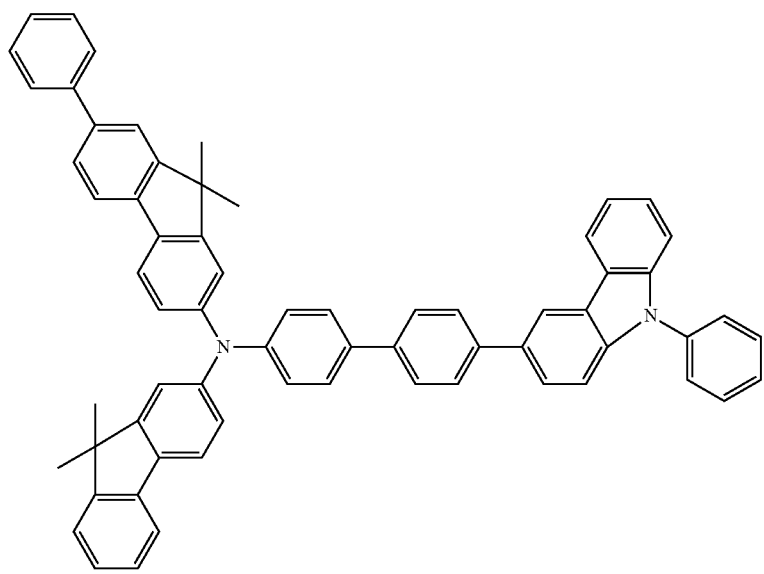
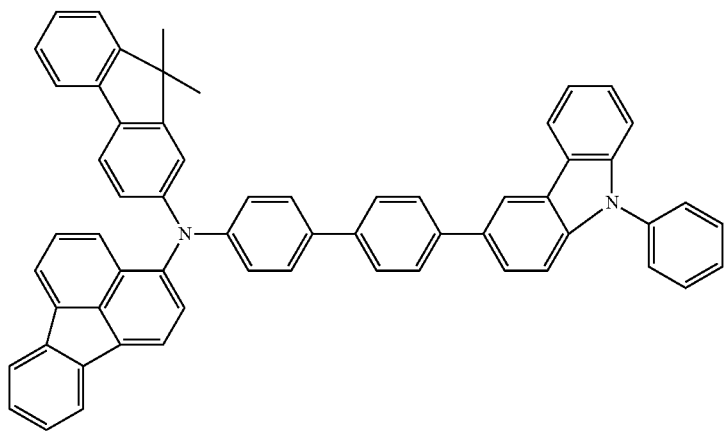

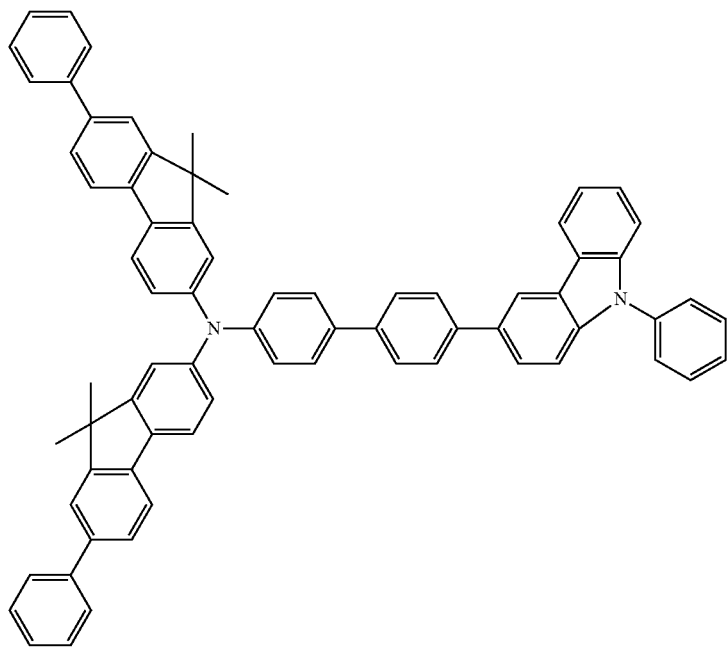
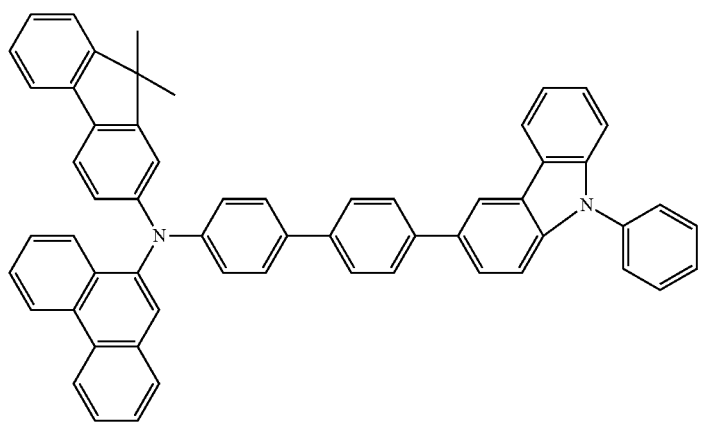
[Chem. 24]
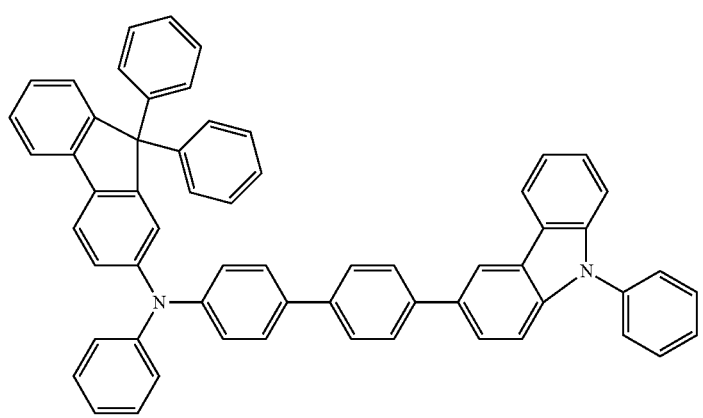

-continued
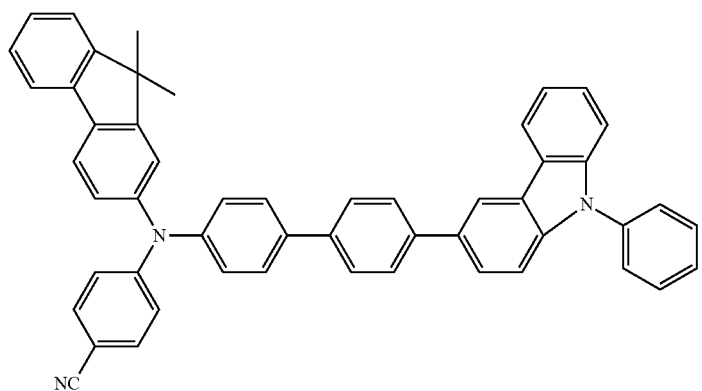
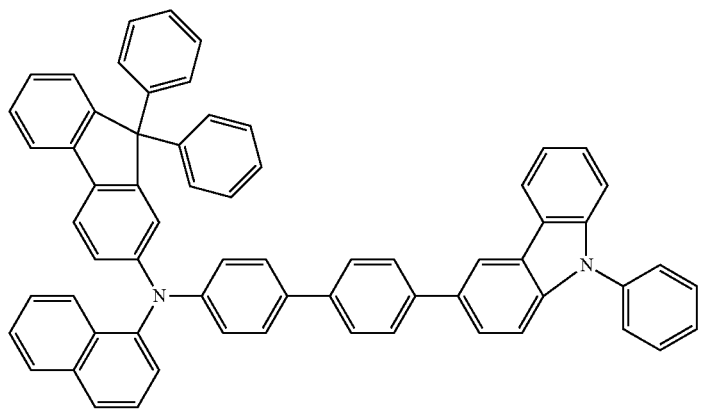
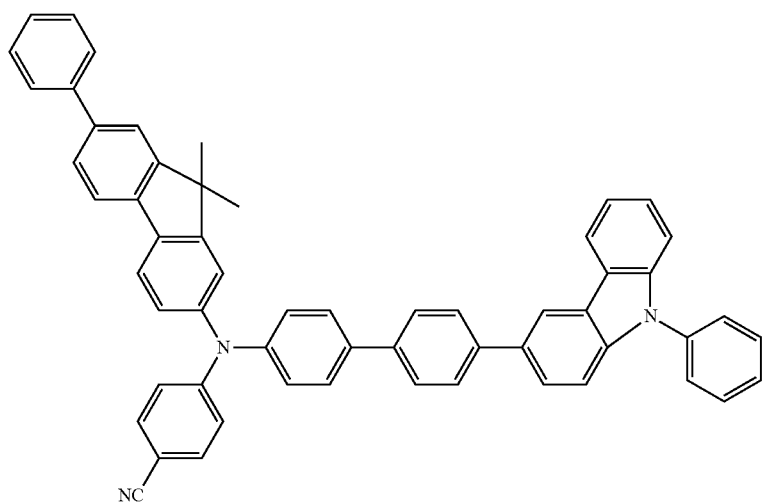

-continued
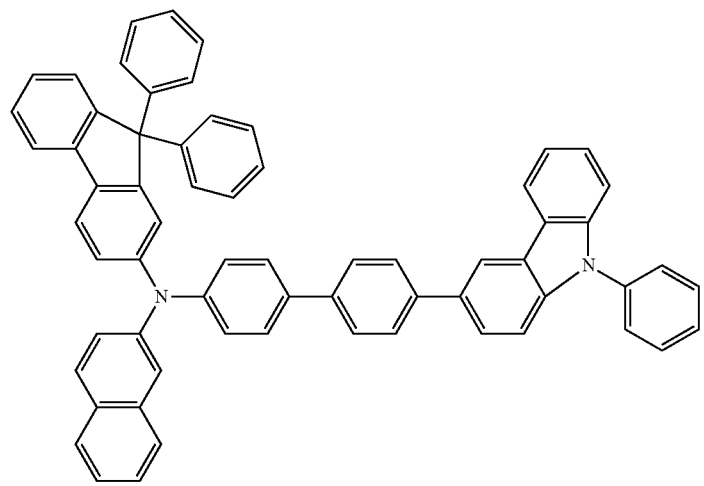
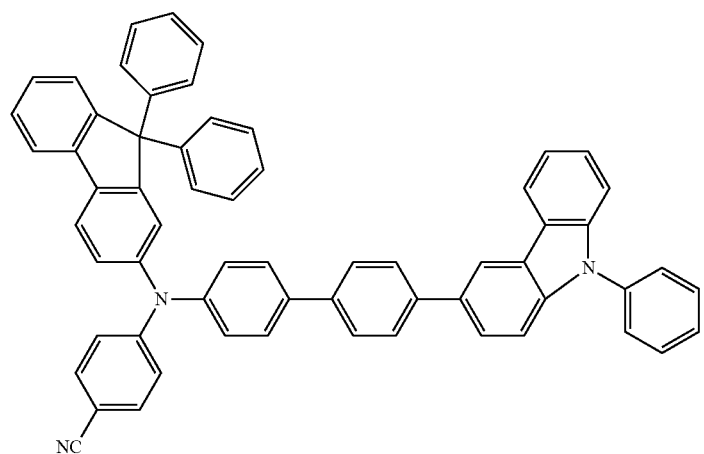
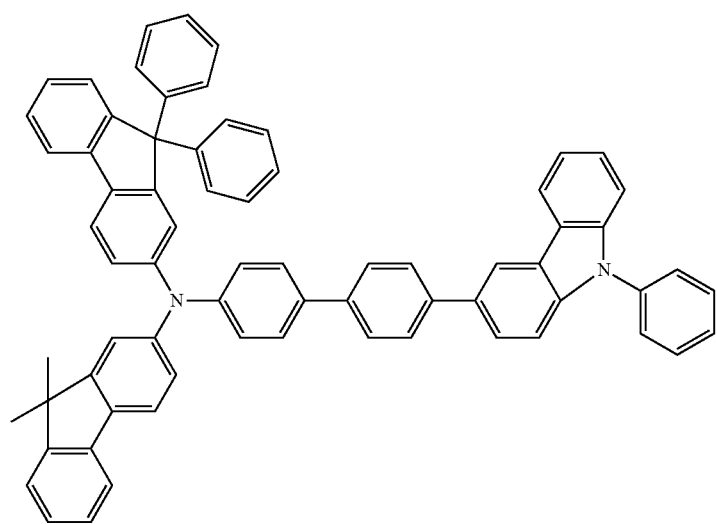

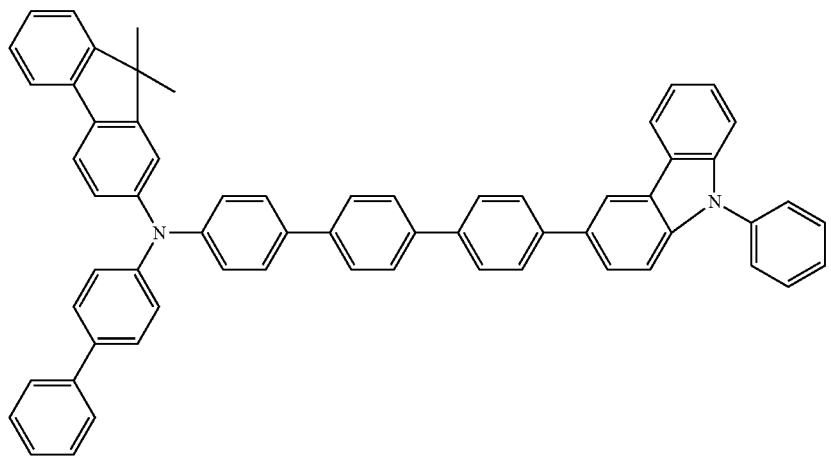
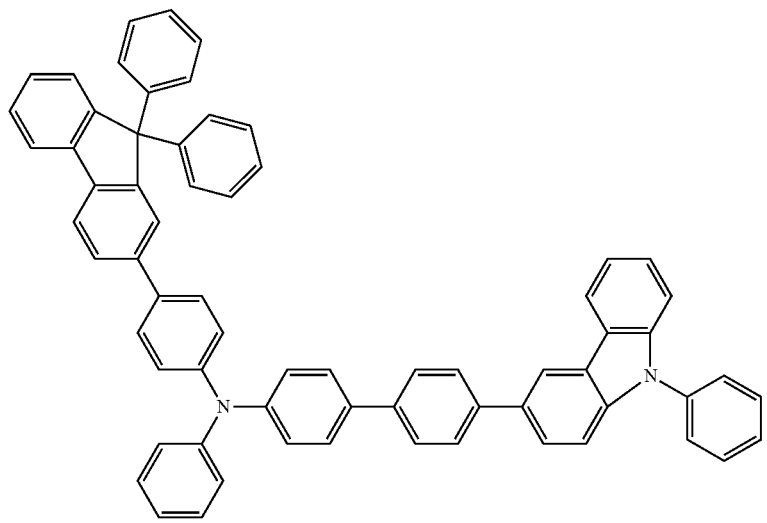
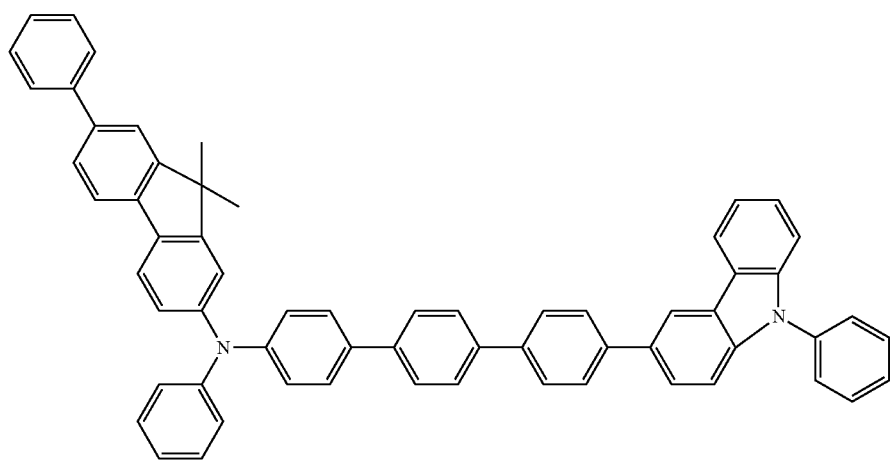

-continued
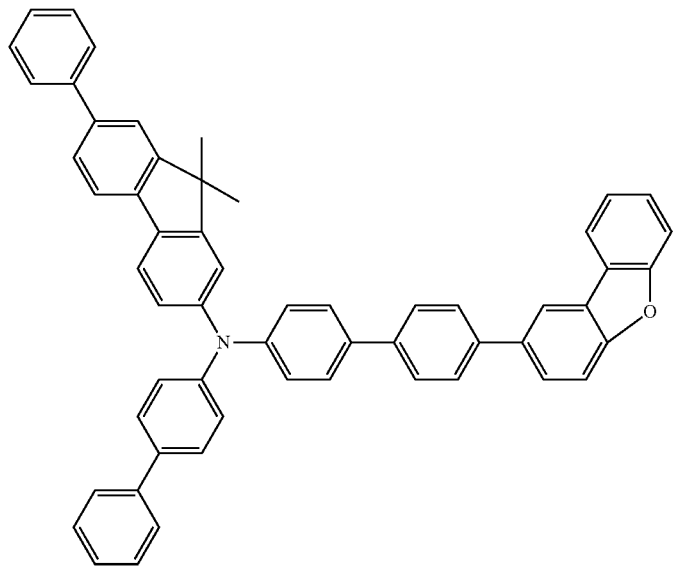
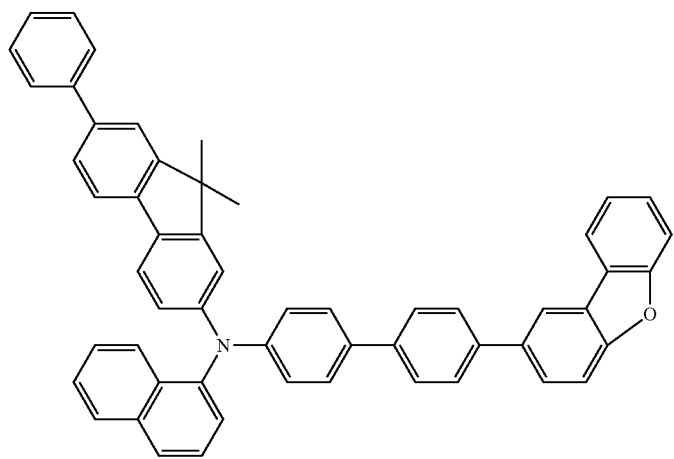
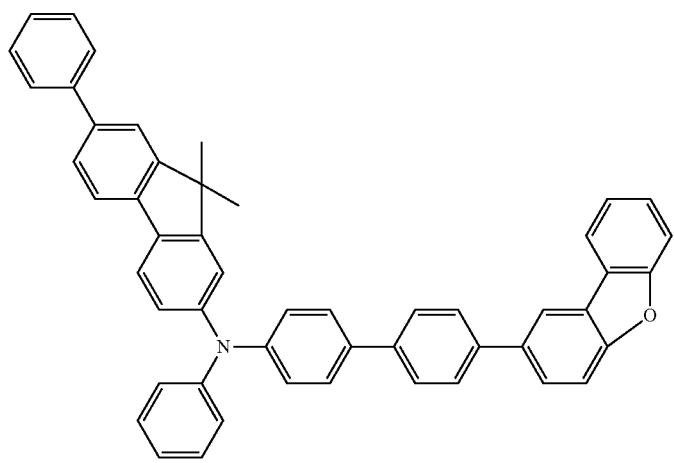

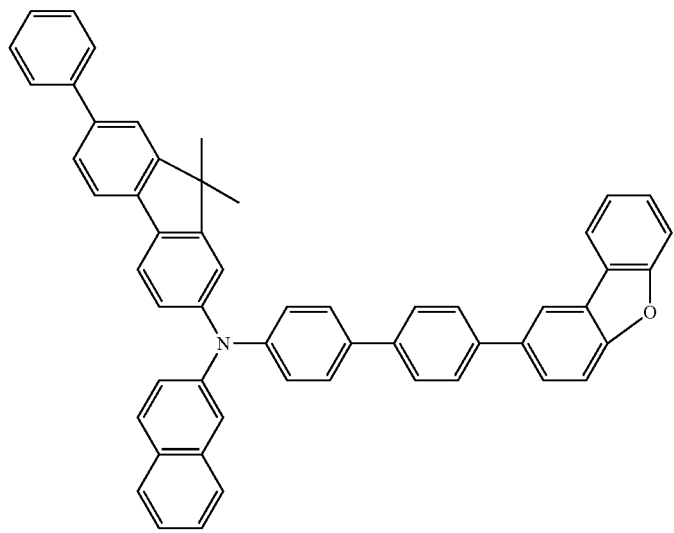
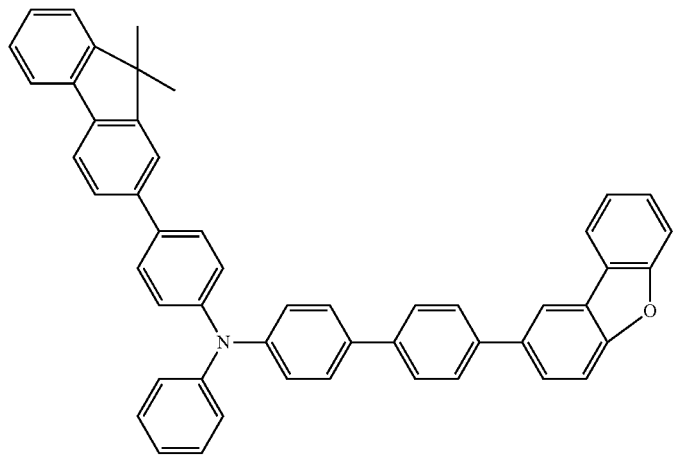
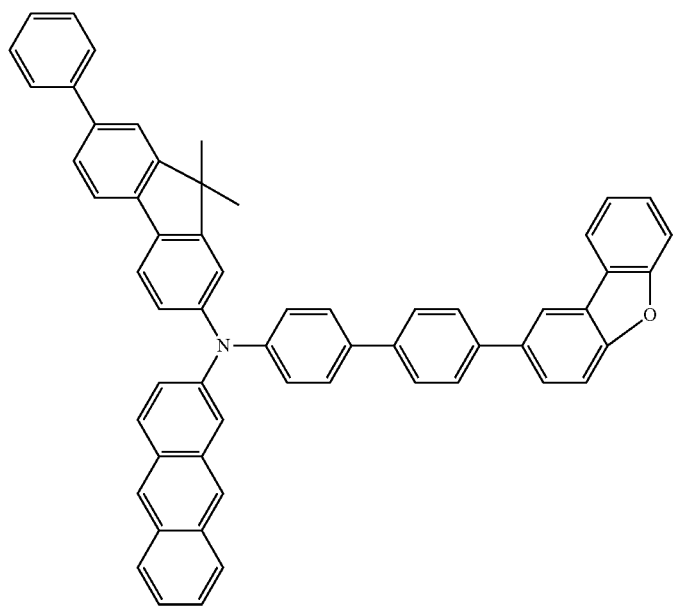

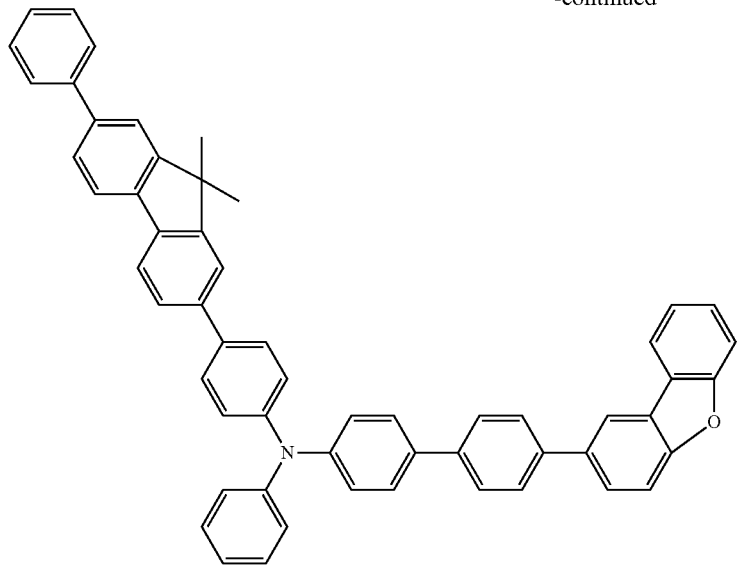
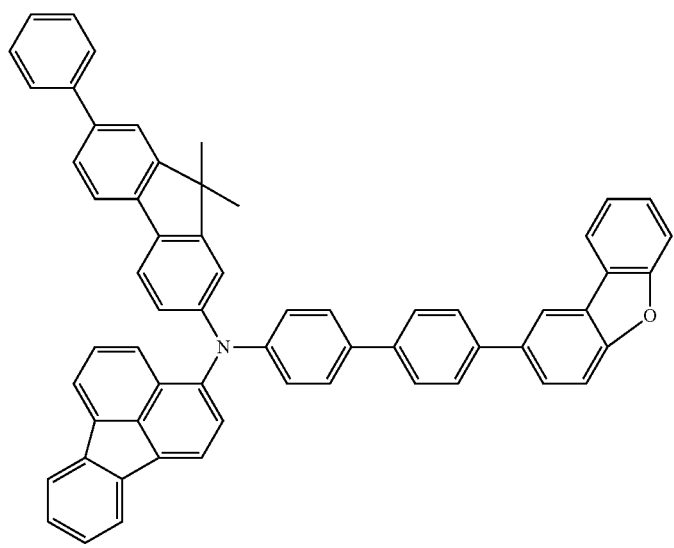
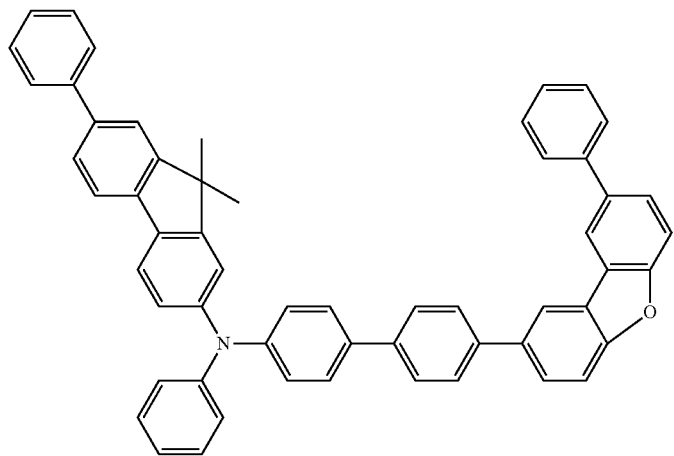

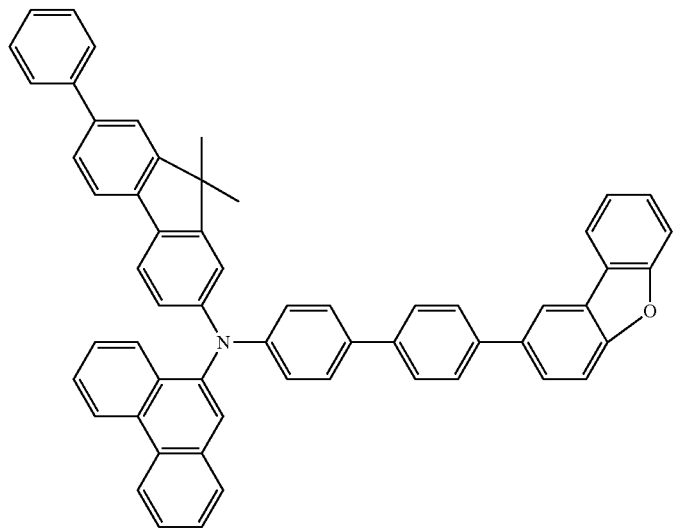
[Chem. 26]
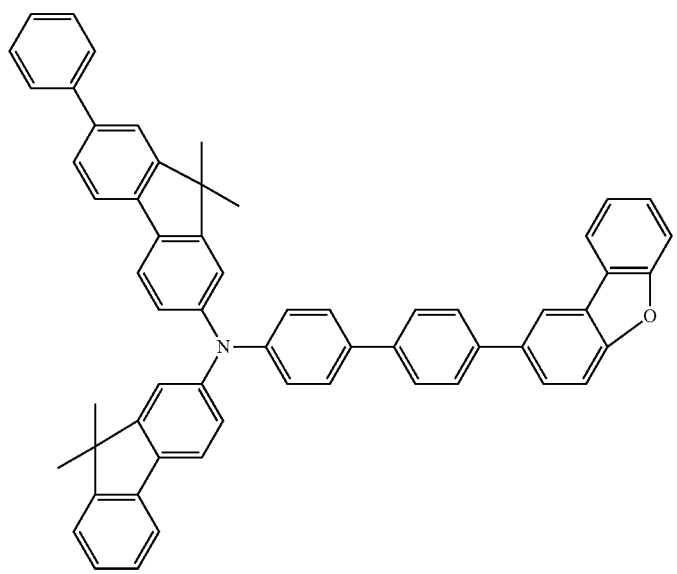
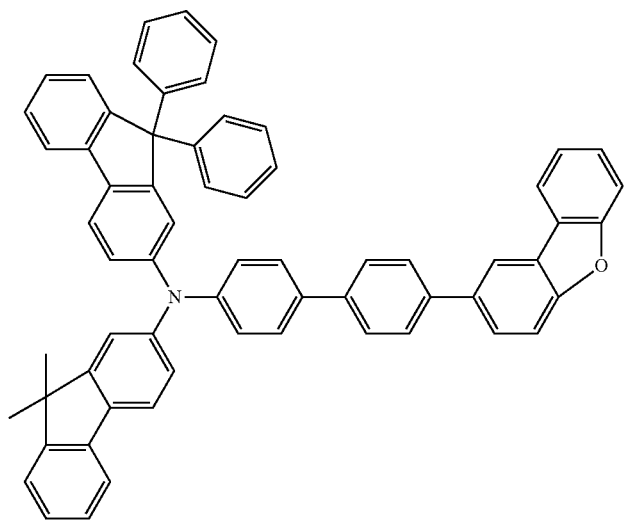

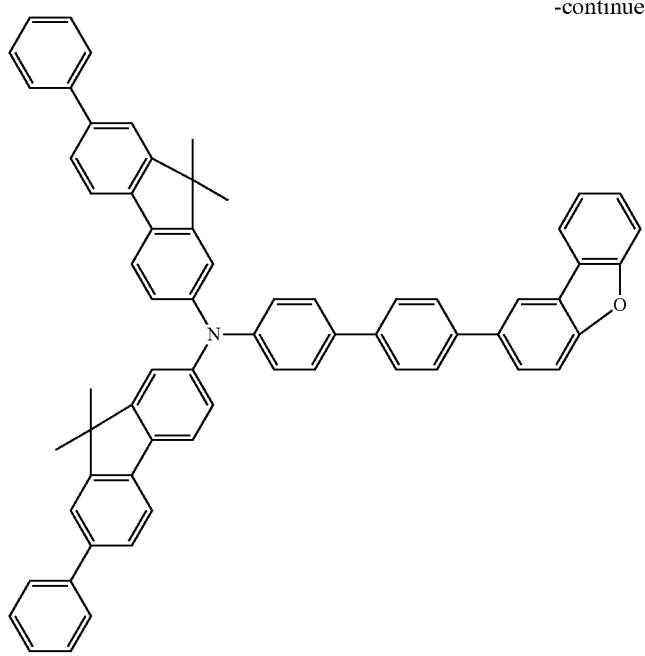
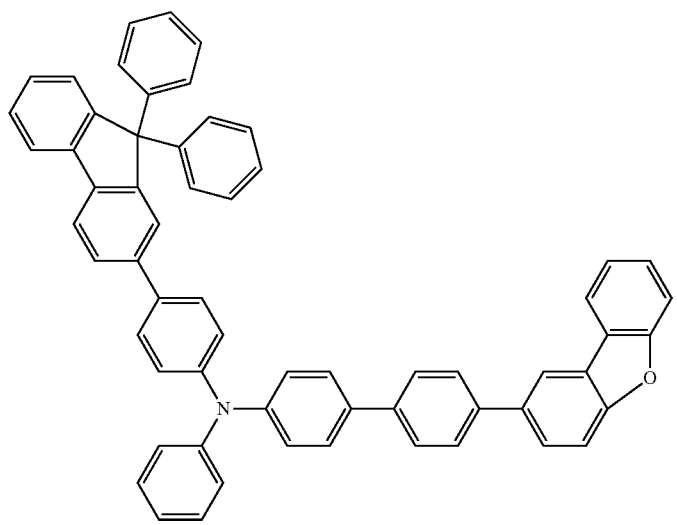
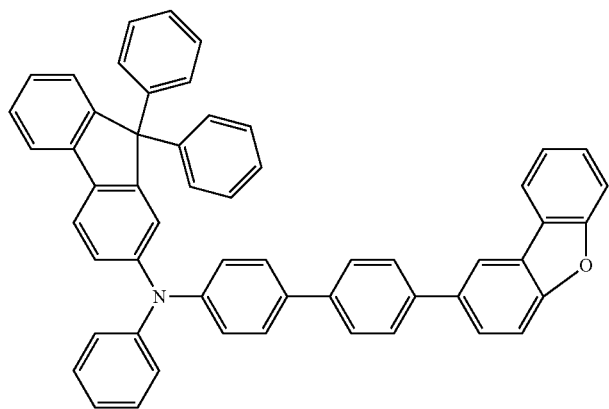

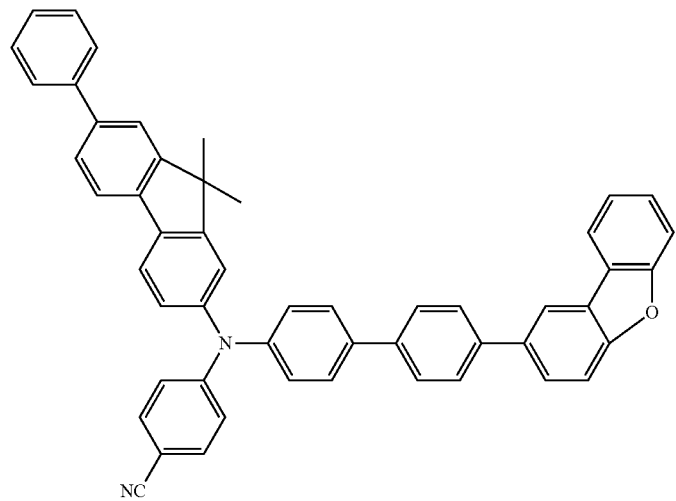
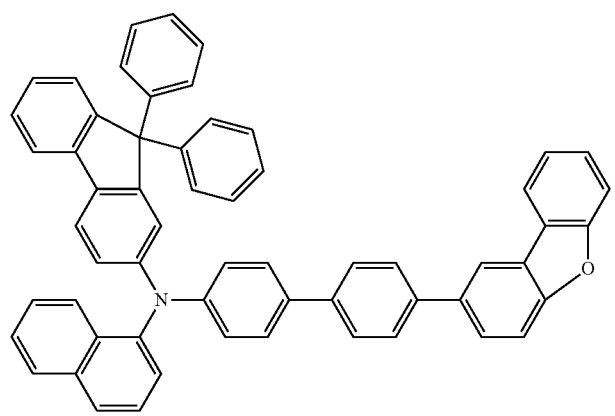
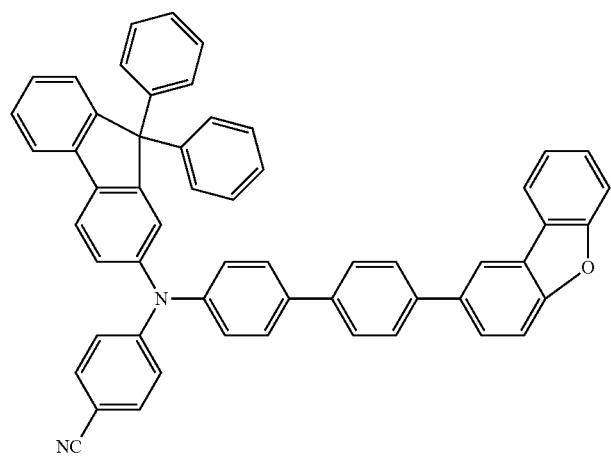

-continued
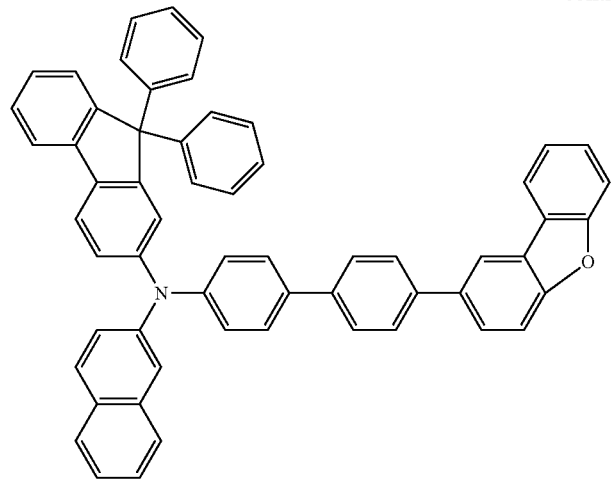
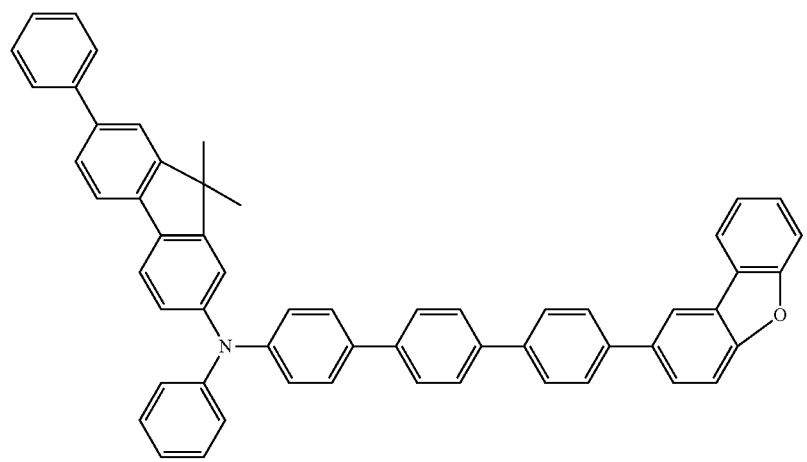
[Chem. 27]
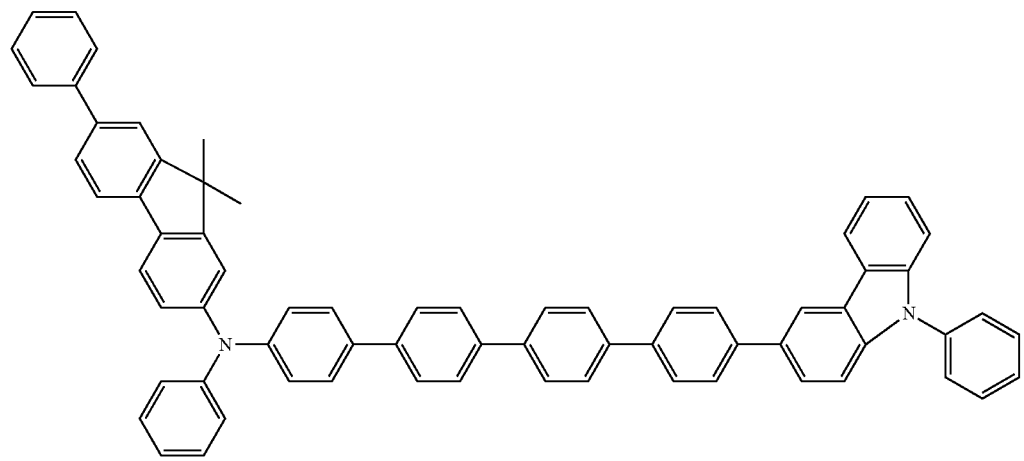

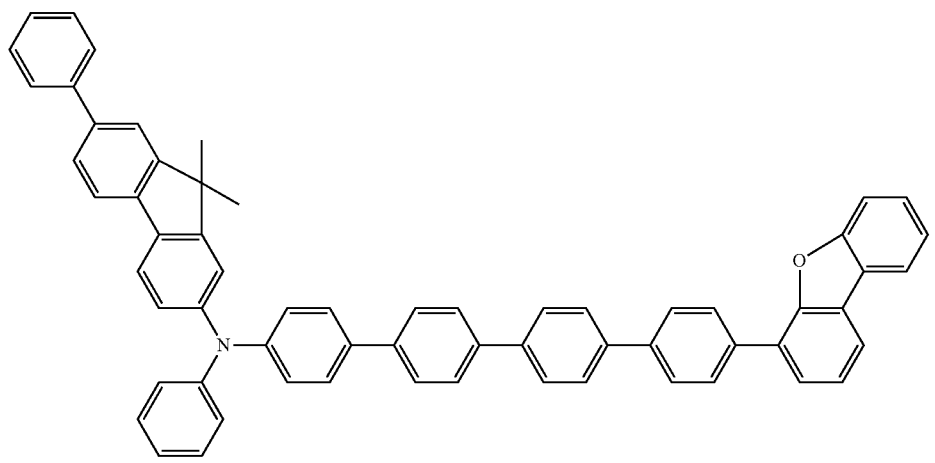
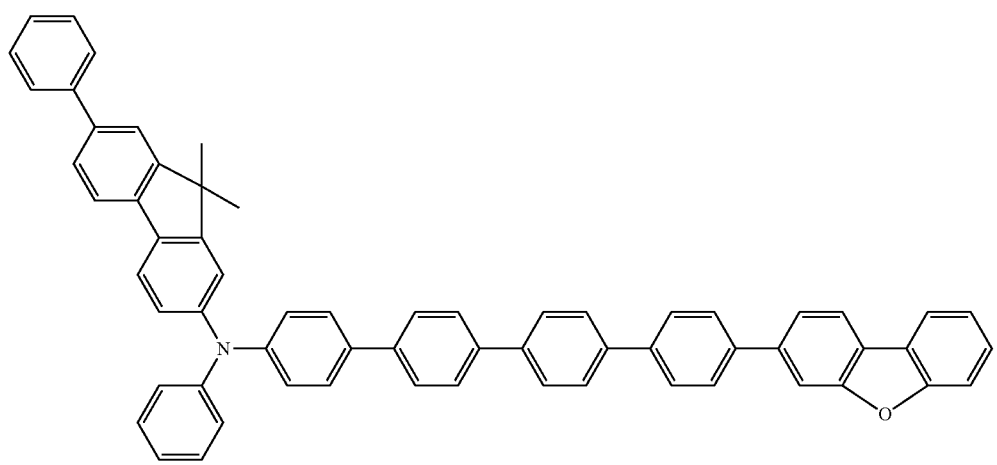

[Chem. 28]
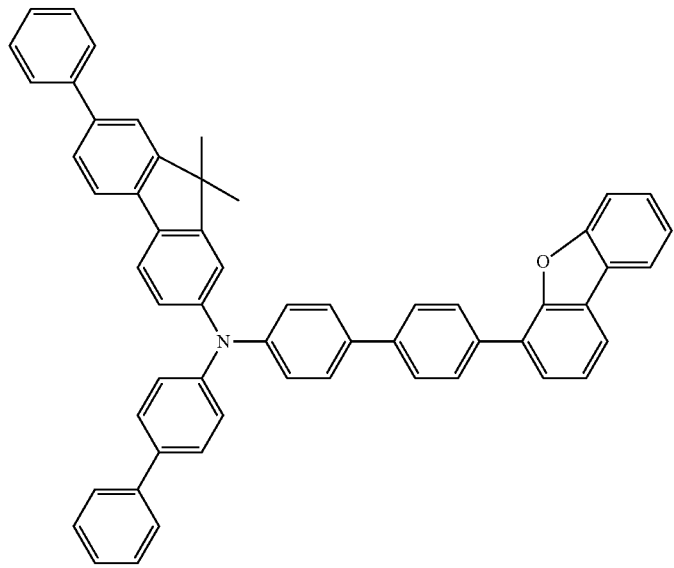
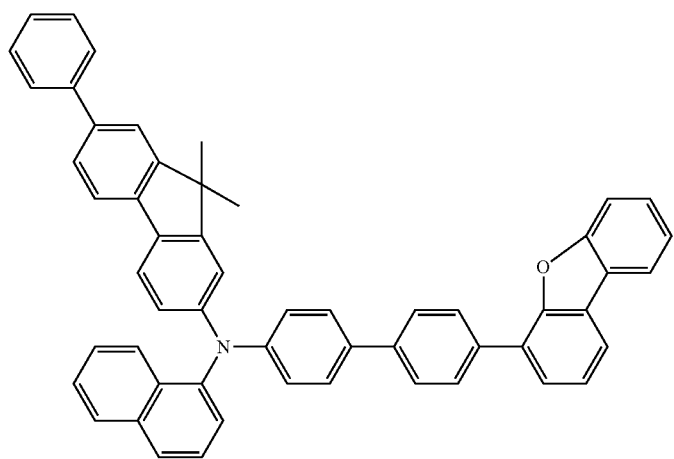
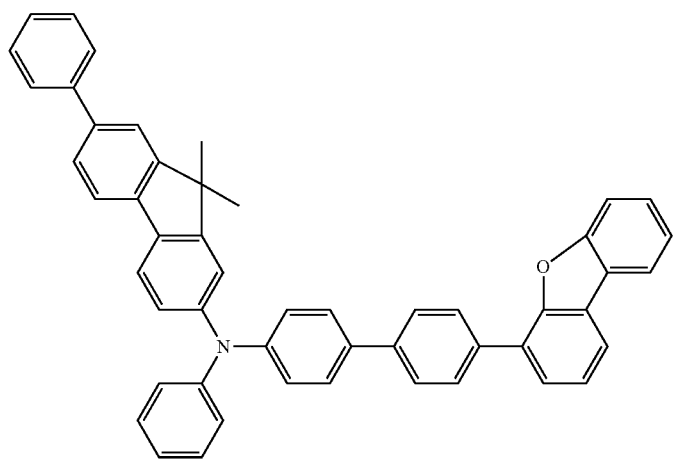

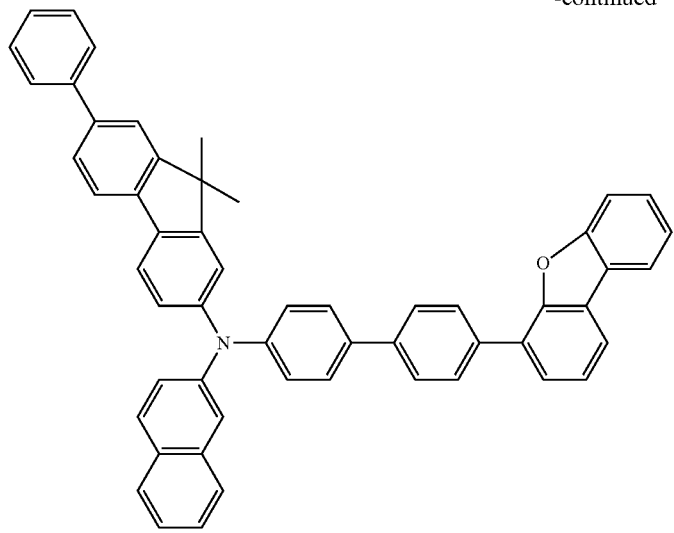
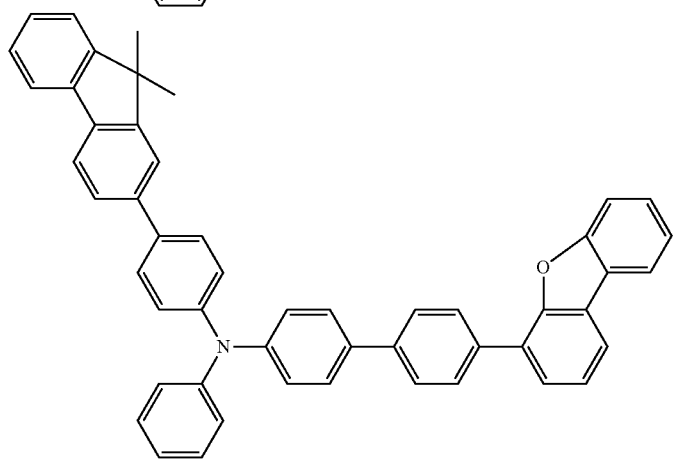
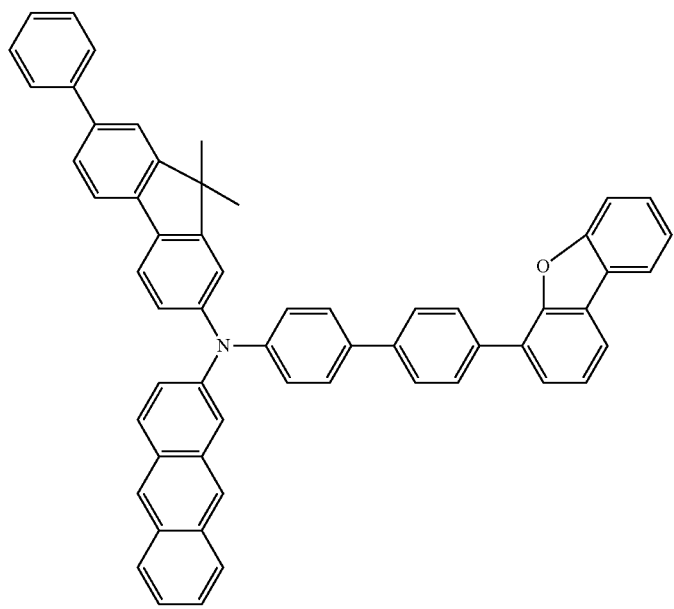

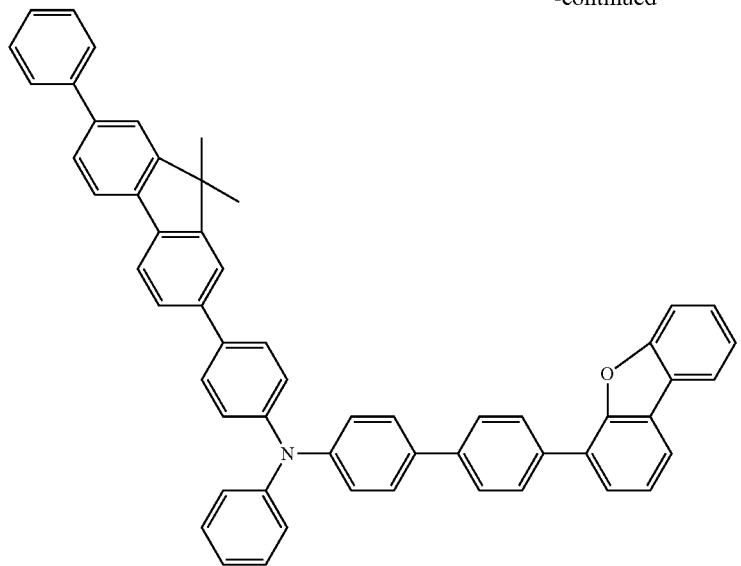
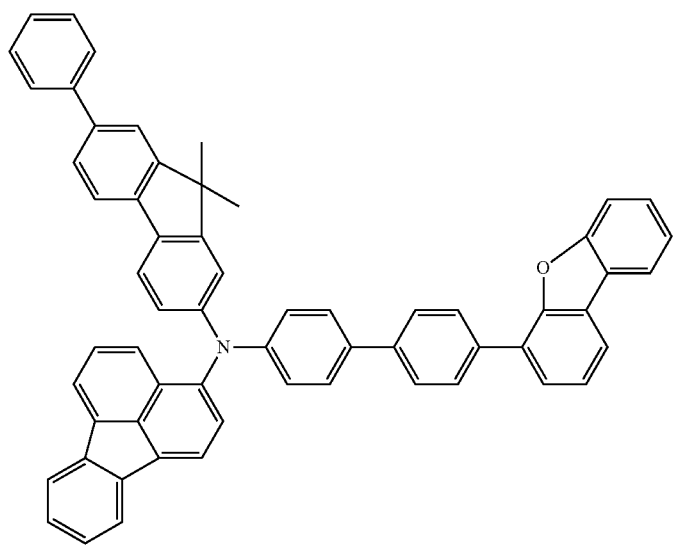
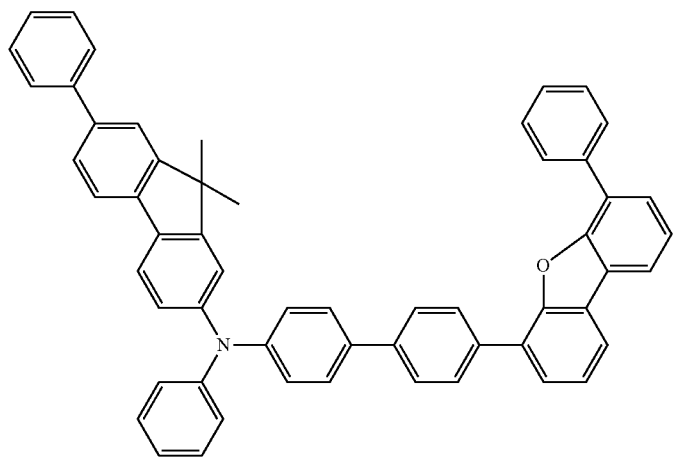

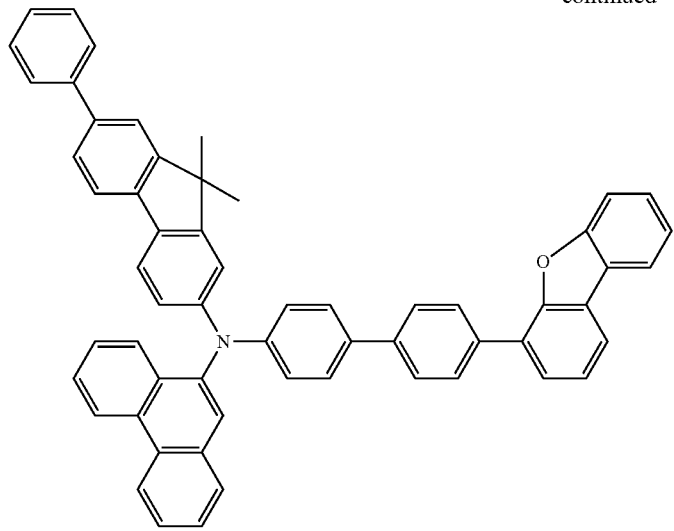
[Chem. 29]
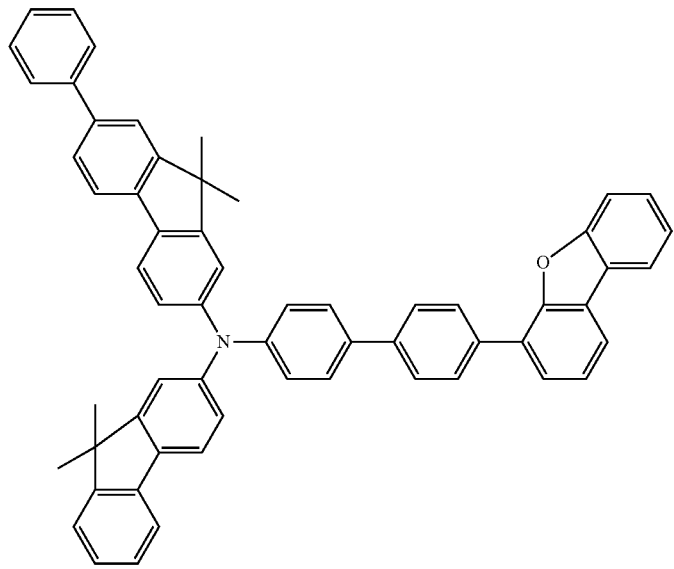
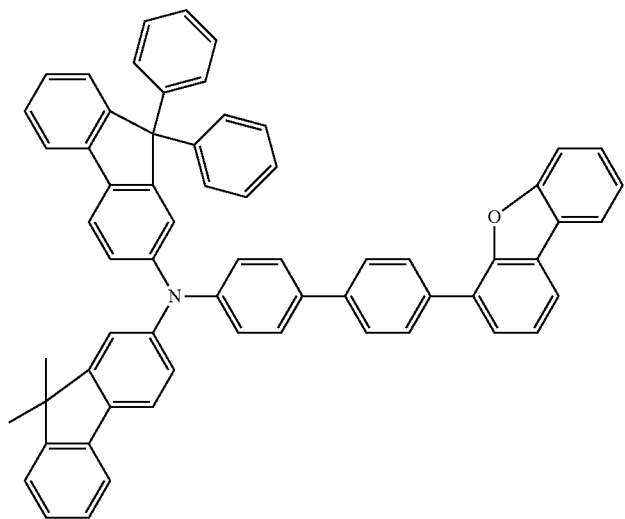

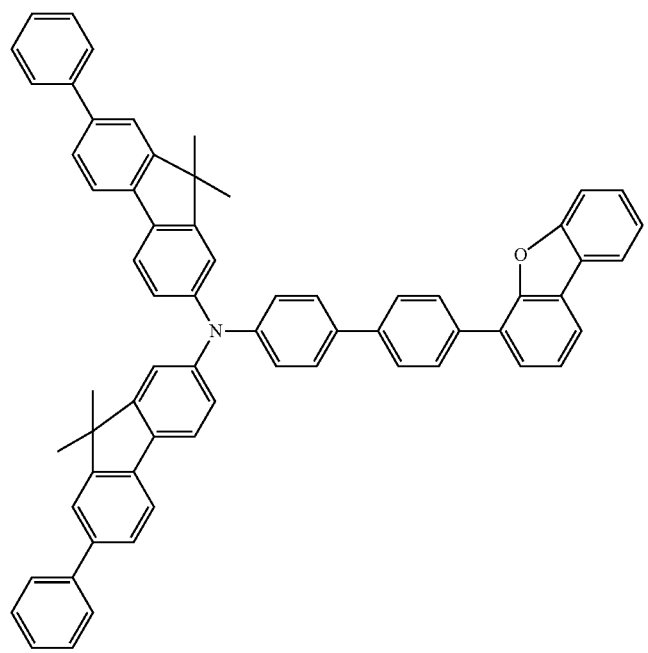
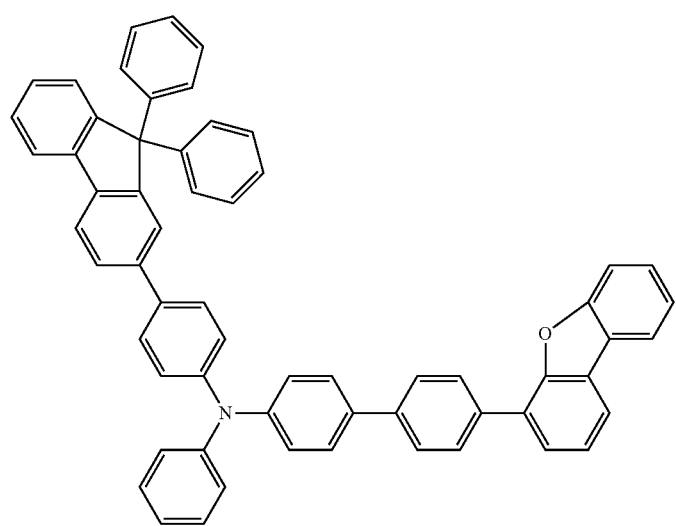
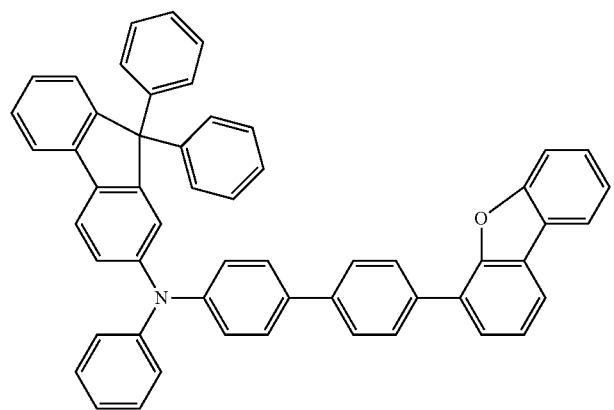

-continued
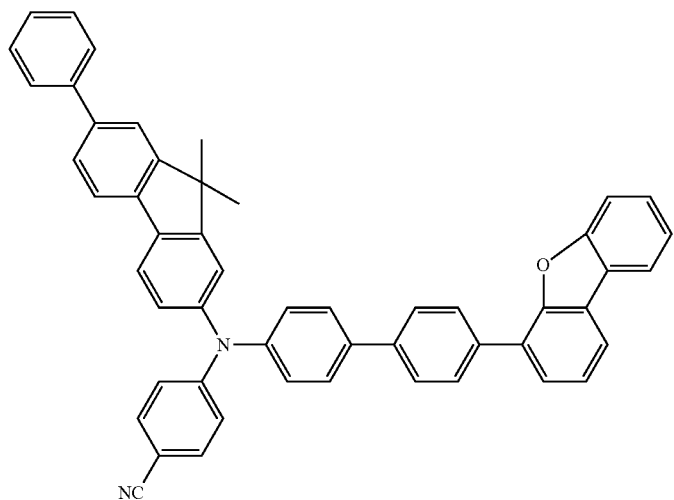
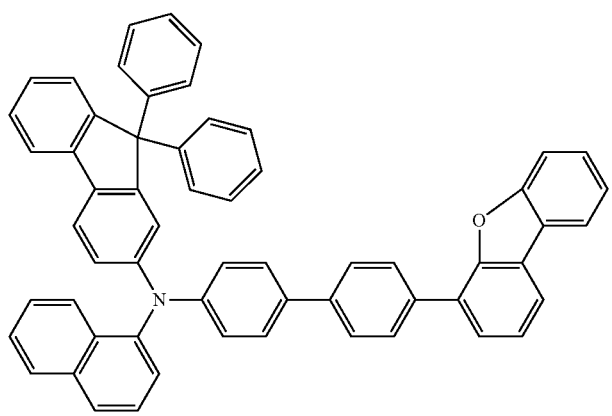
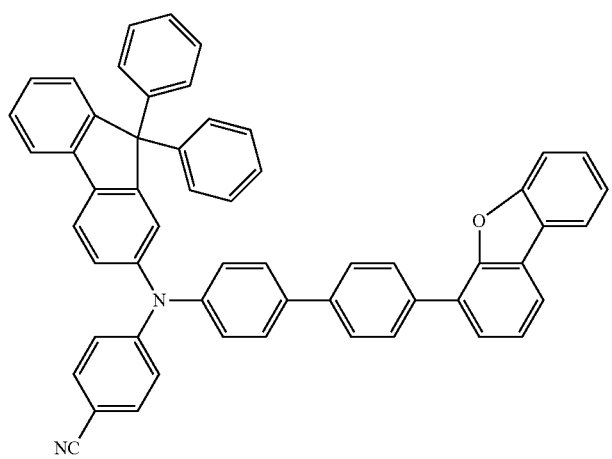

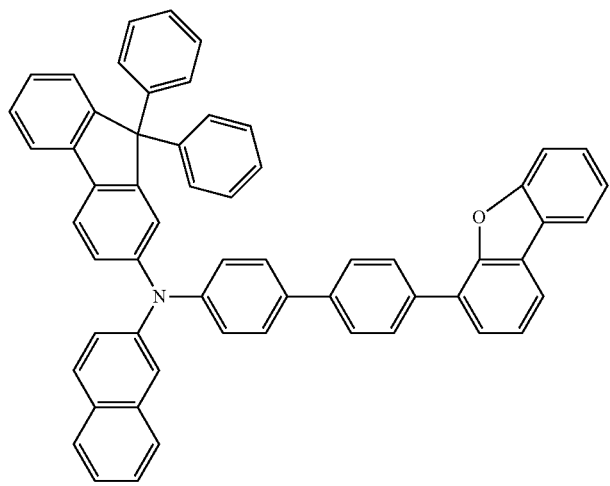
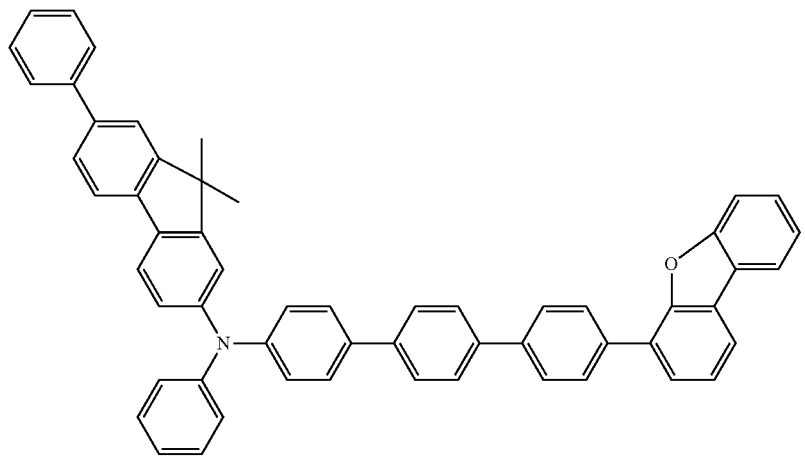
[Chem. 30]
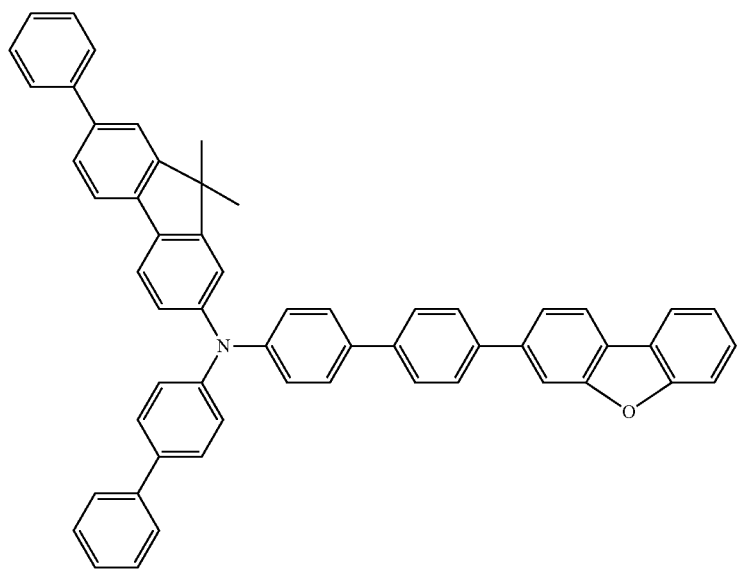

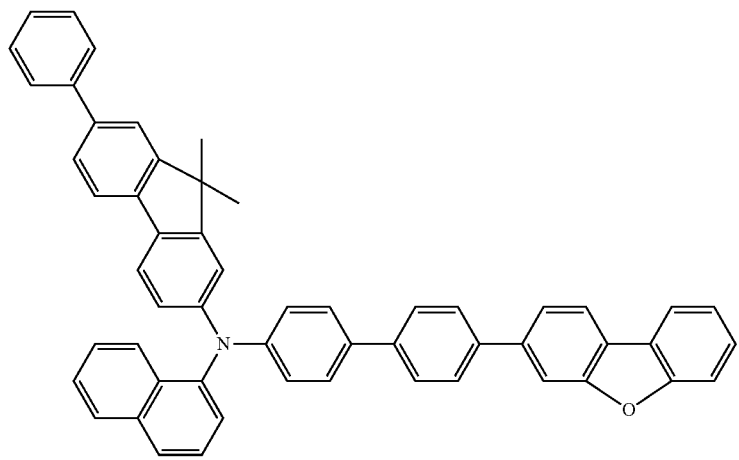
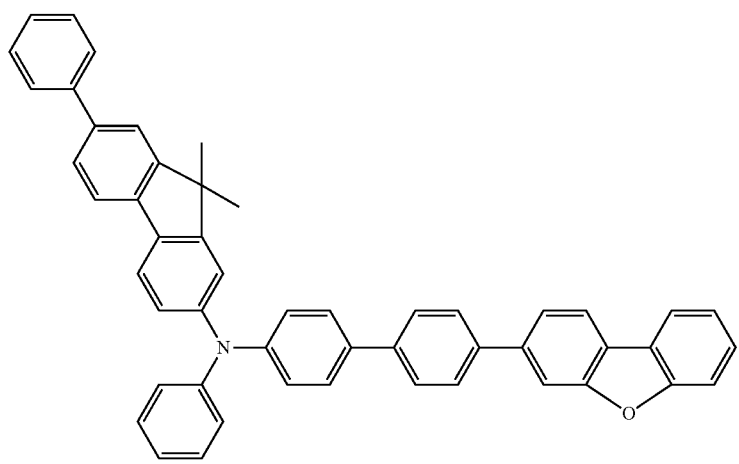
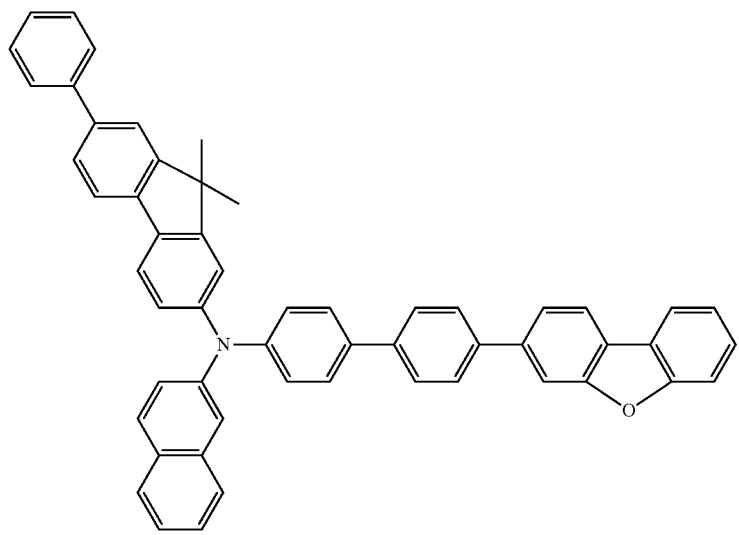

-continued
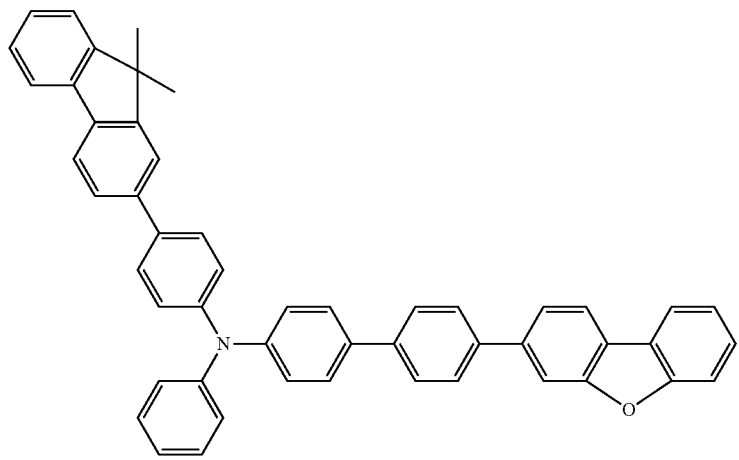
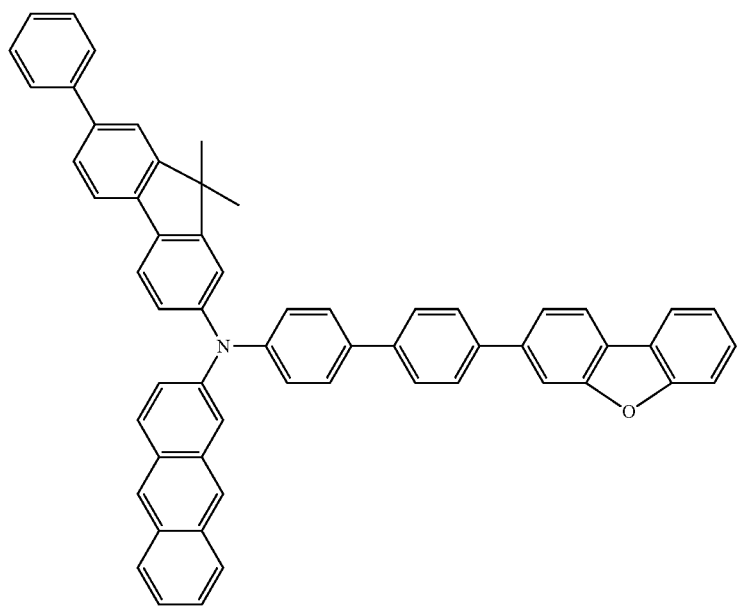
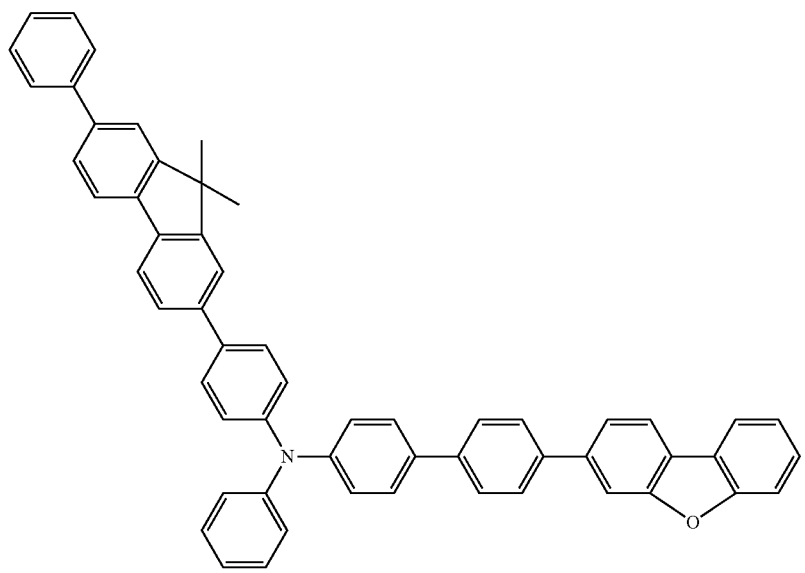

-continued
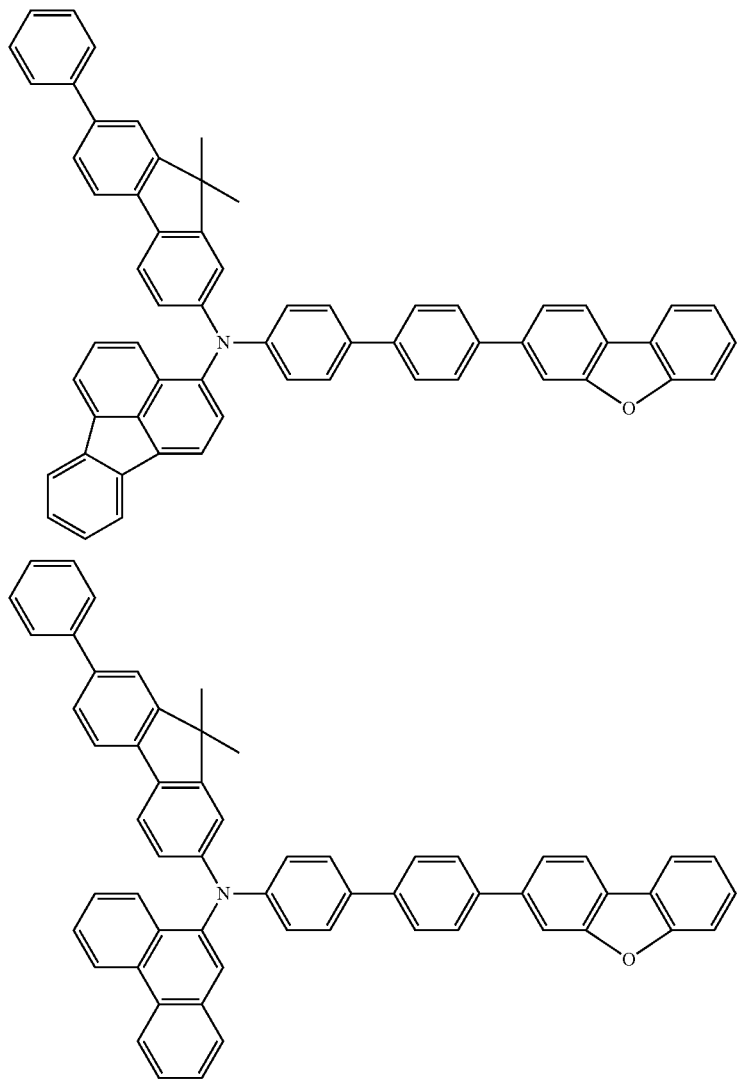
[Chem. 31]
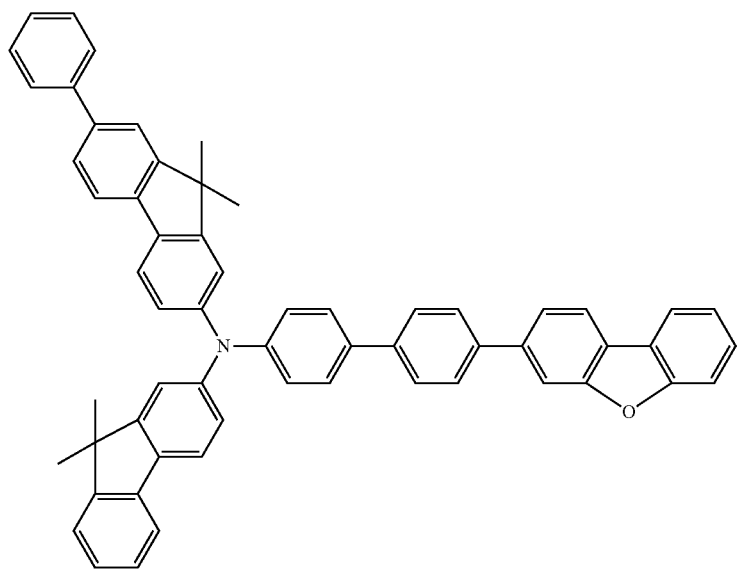

-continued
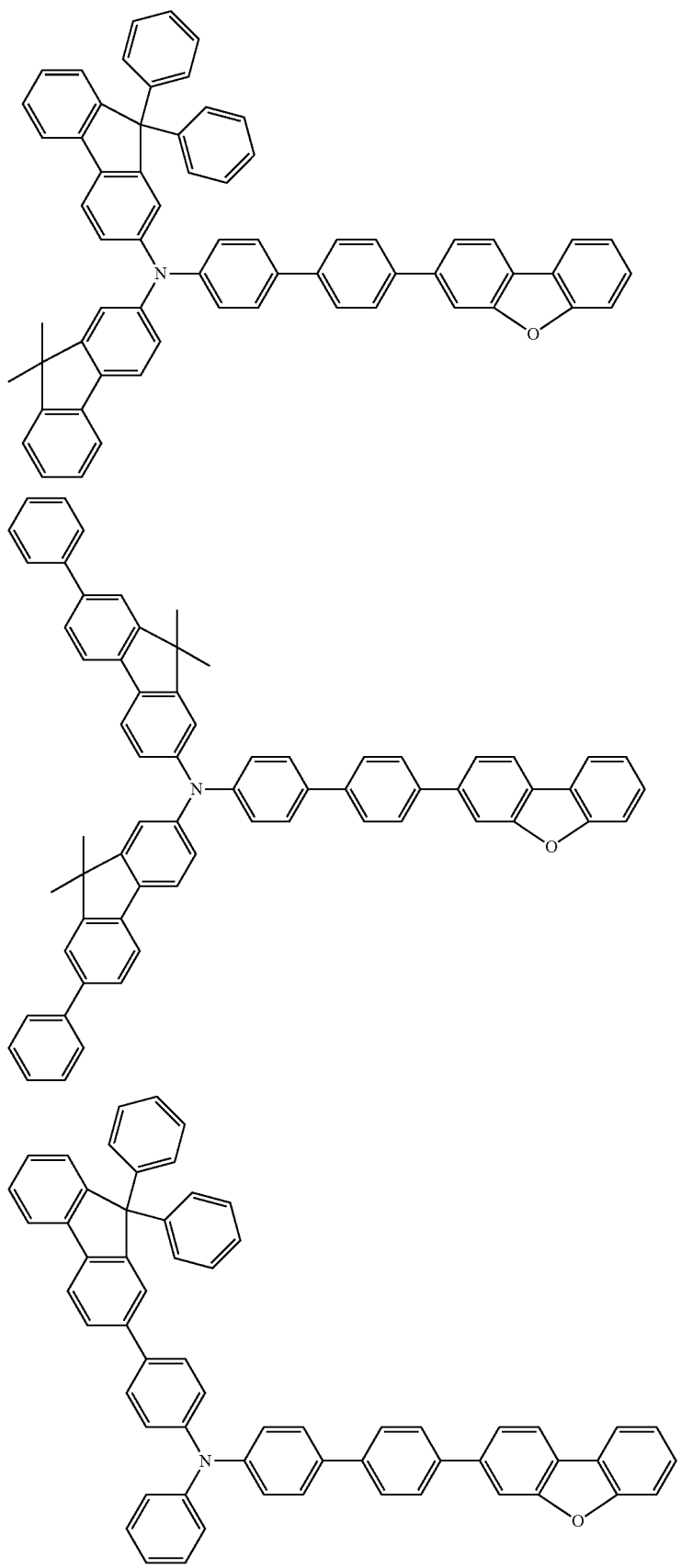

-continued
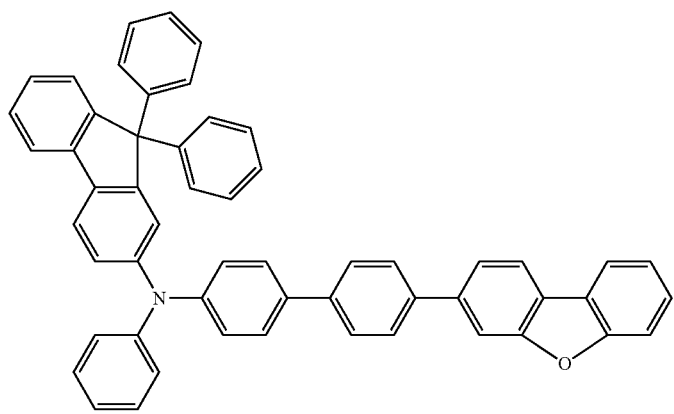
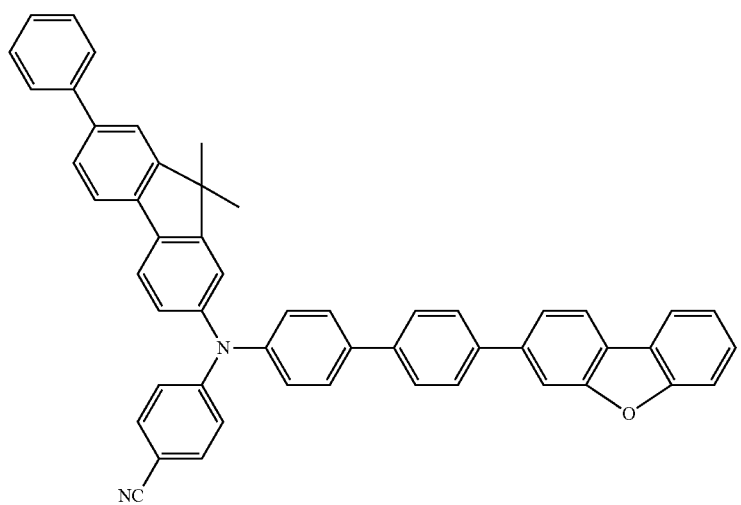
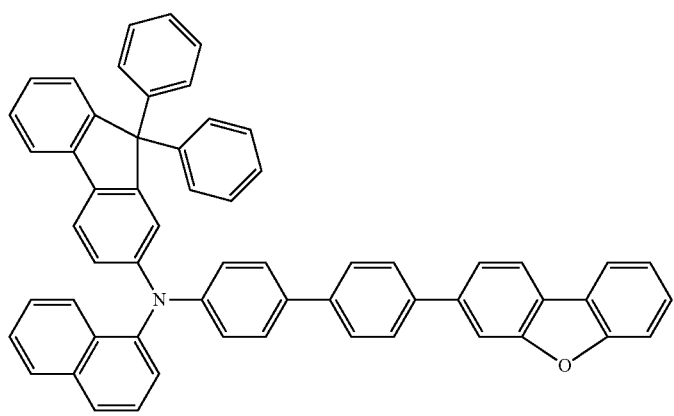

-continued
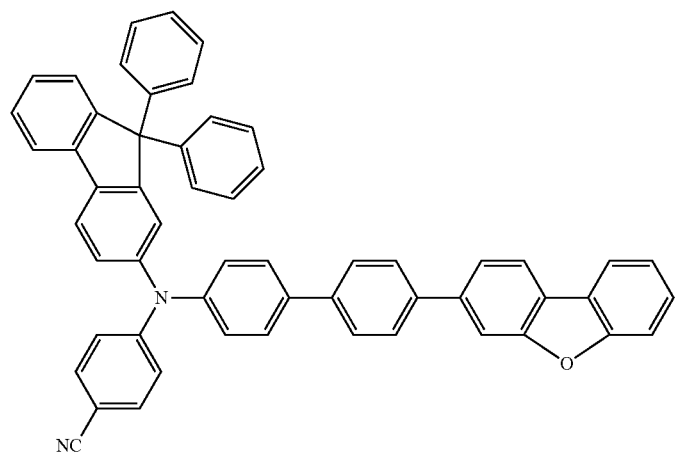
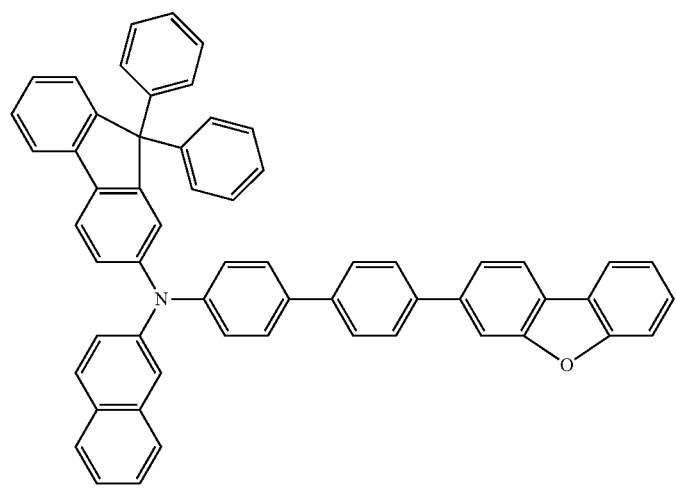
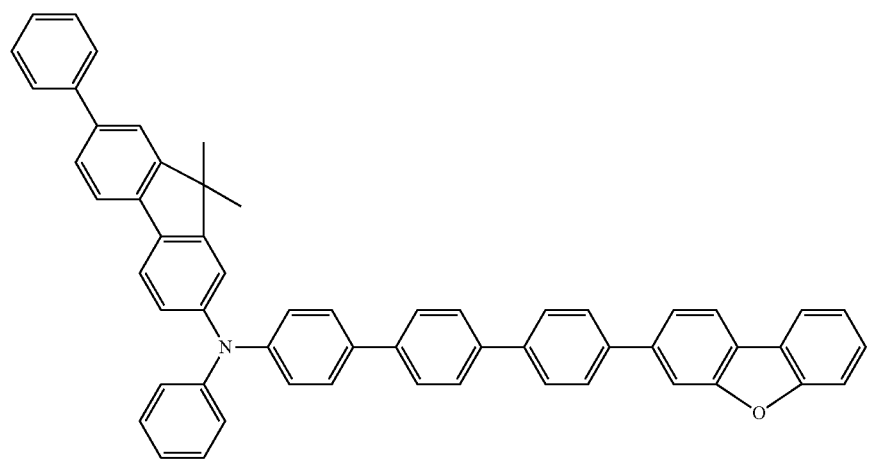

[Chem. 32]
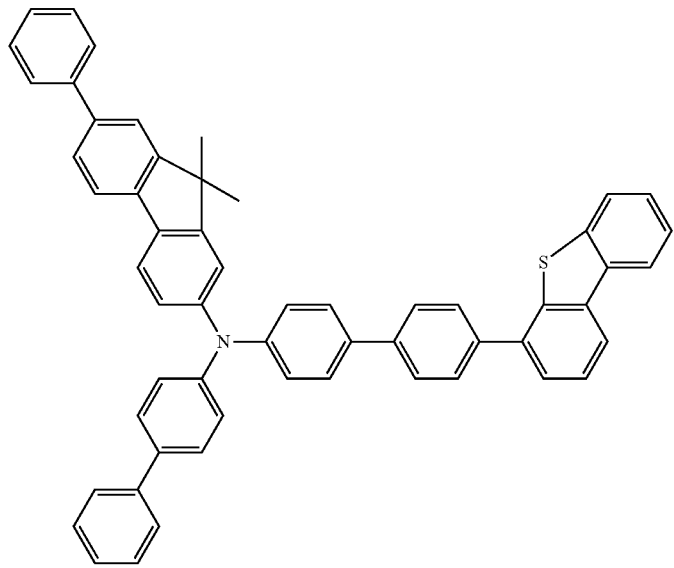
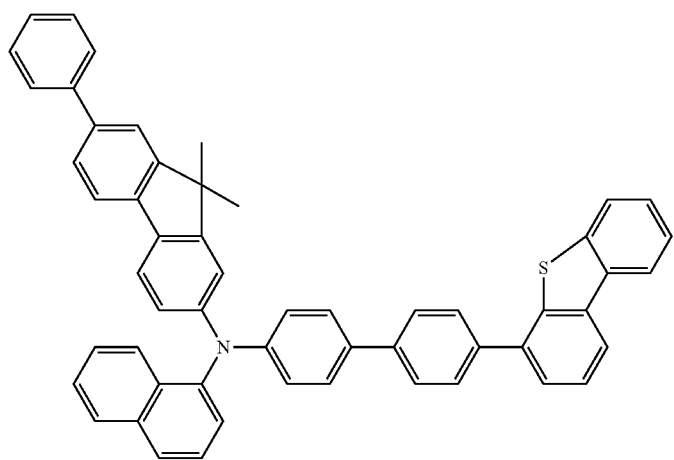
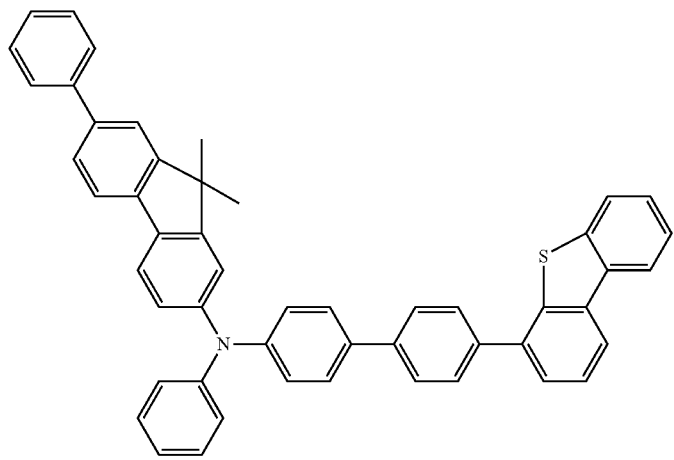

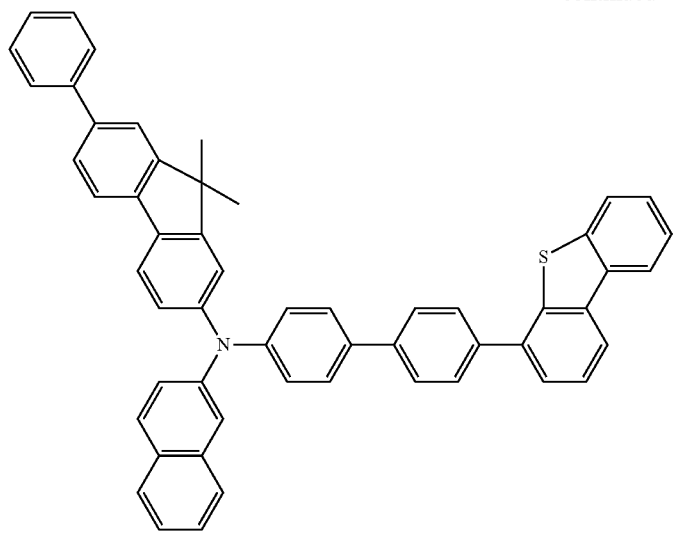
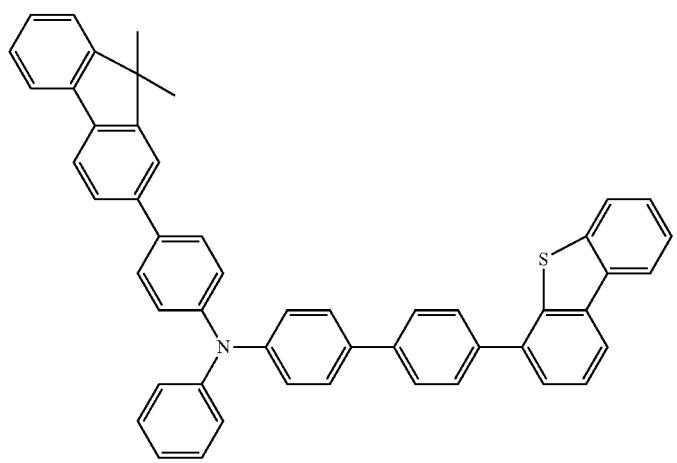
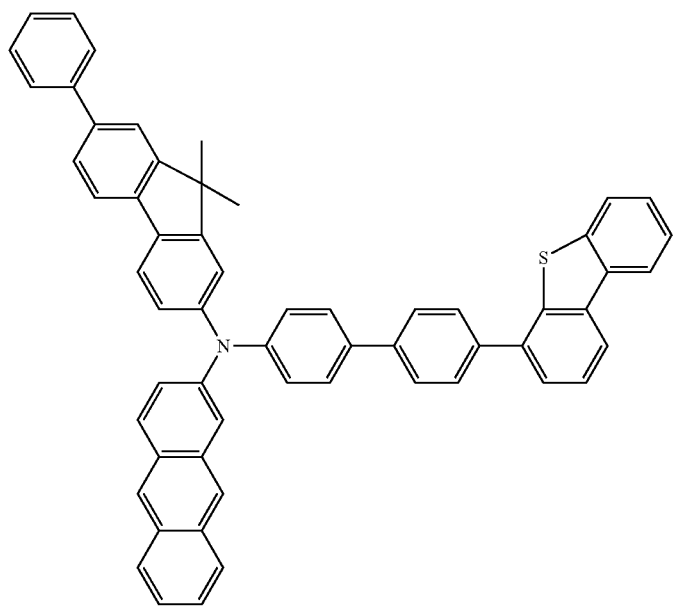

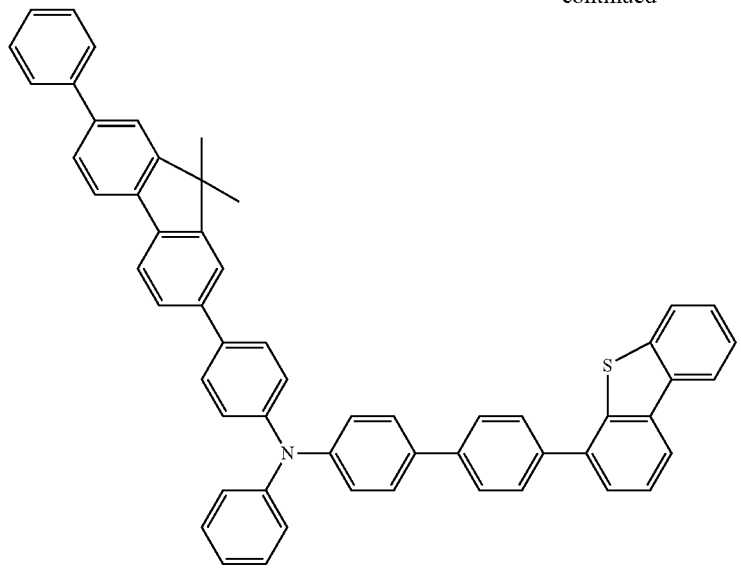
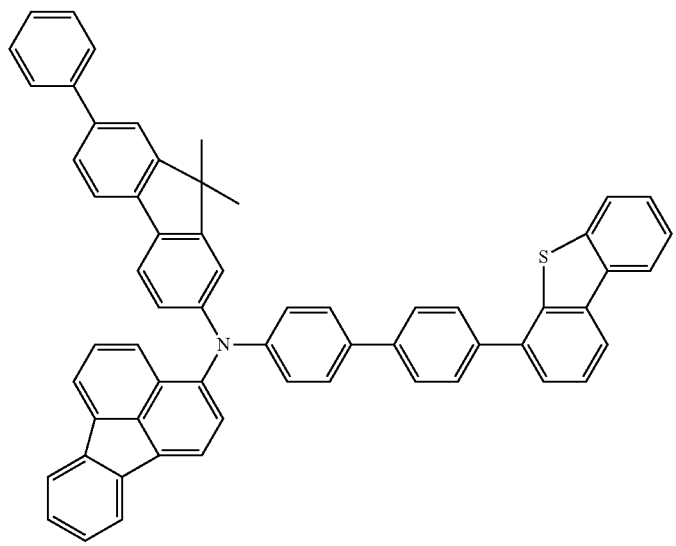
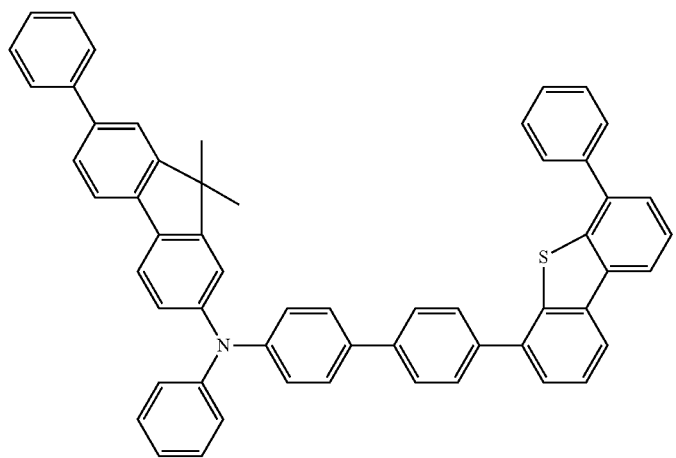

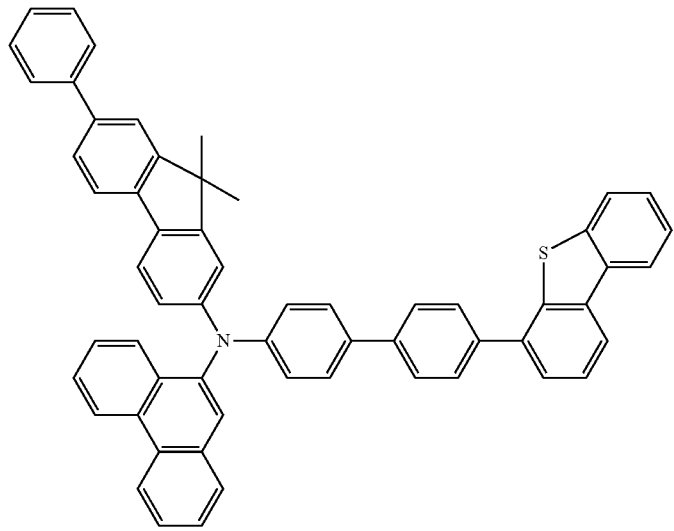
[Chem. 33]
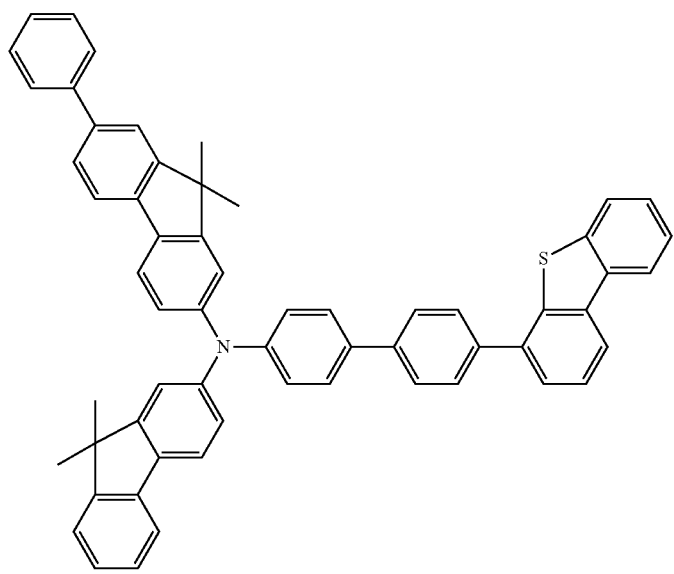
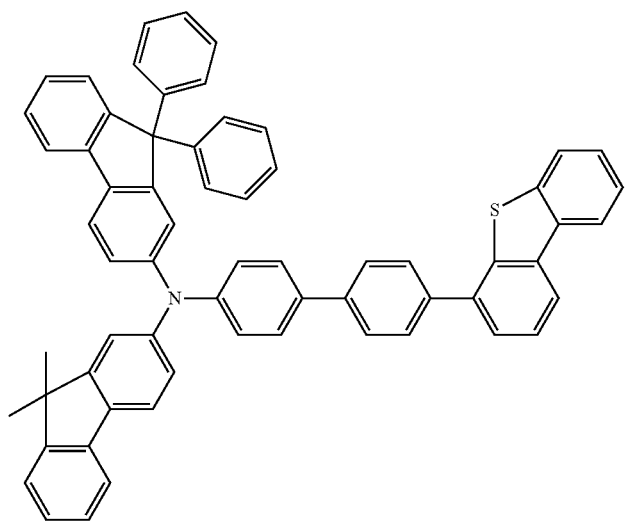

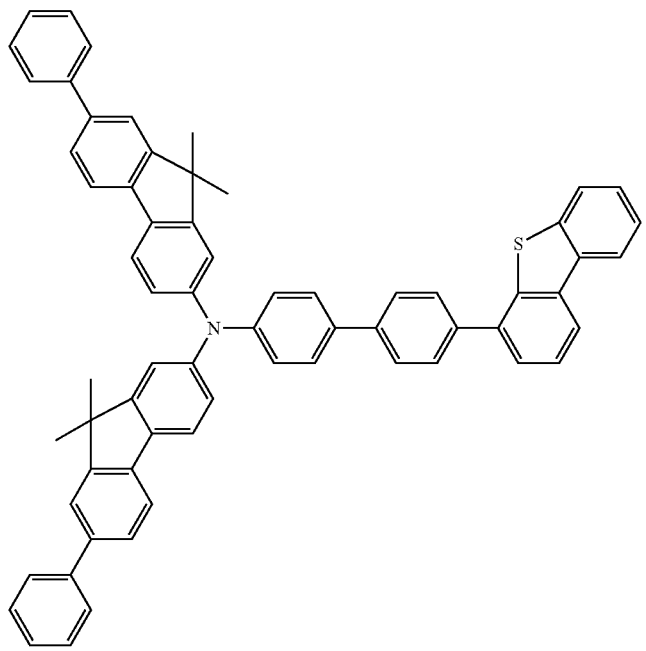
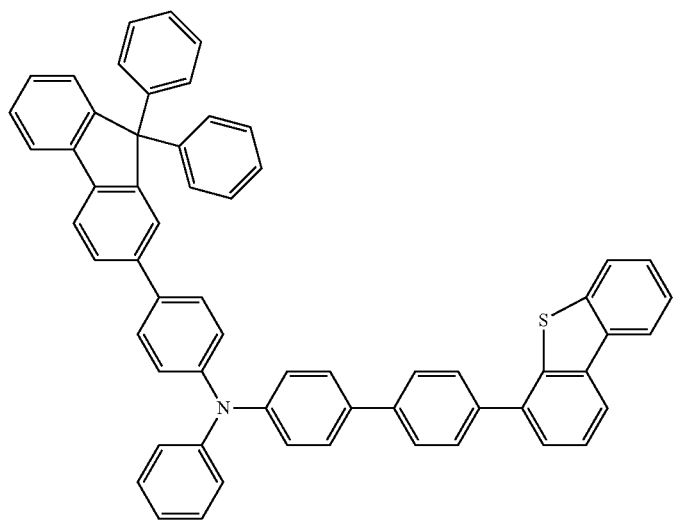
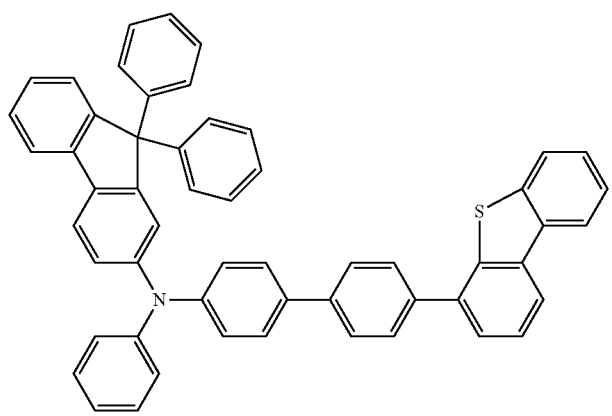

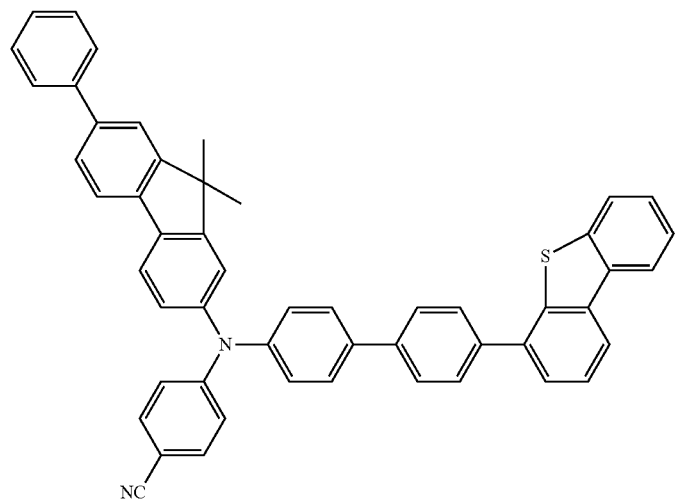
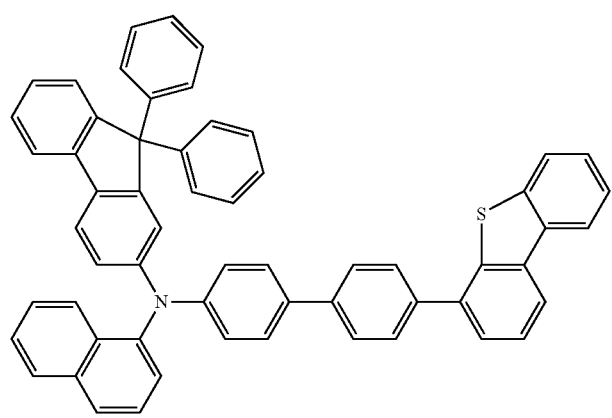
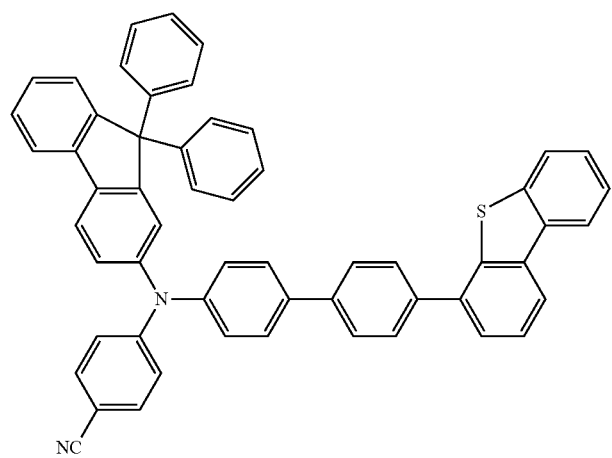

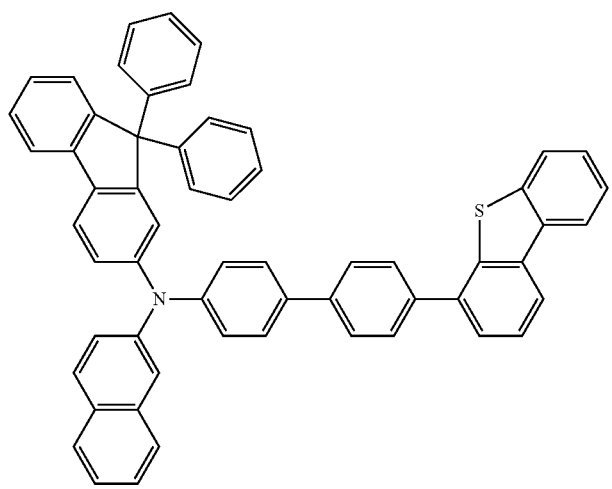
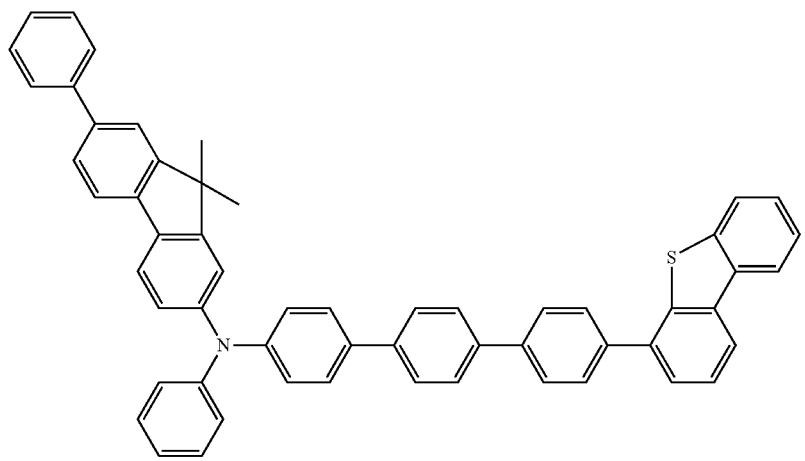
[Chem. 34]
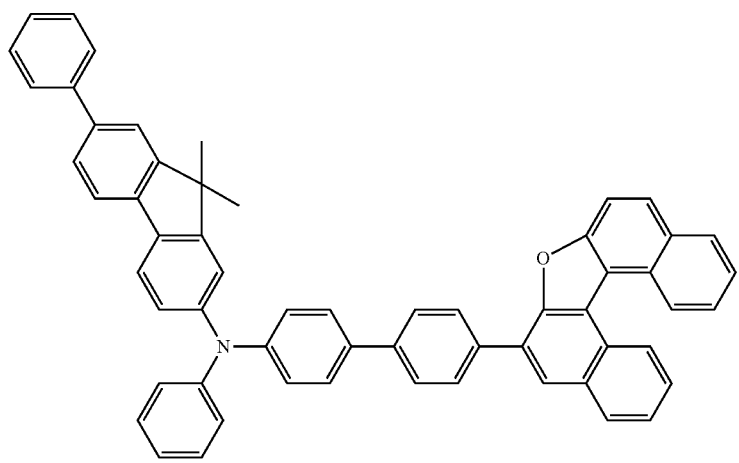

-continued
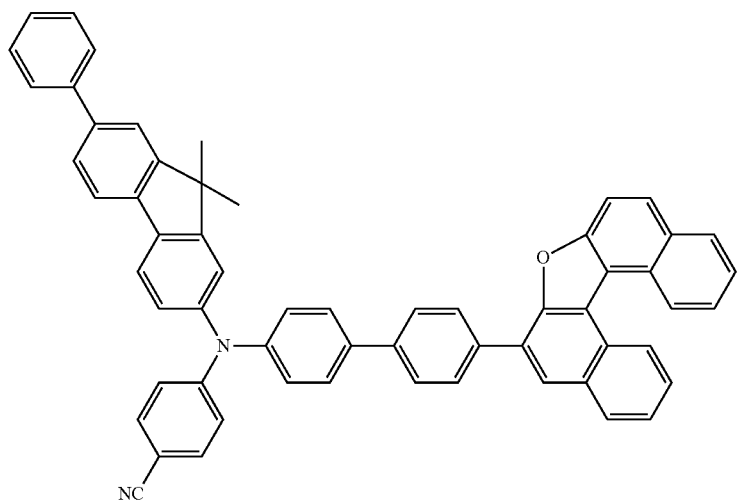
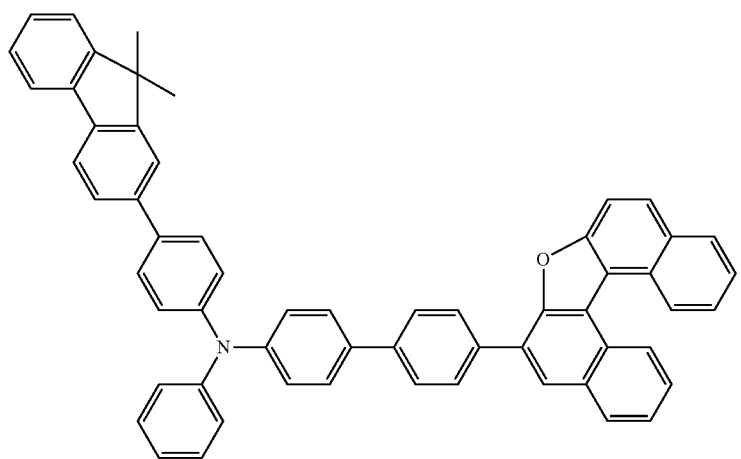
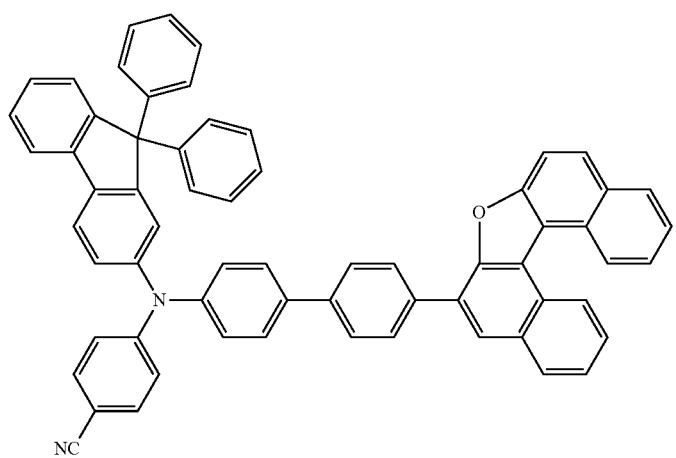

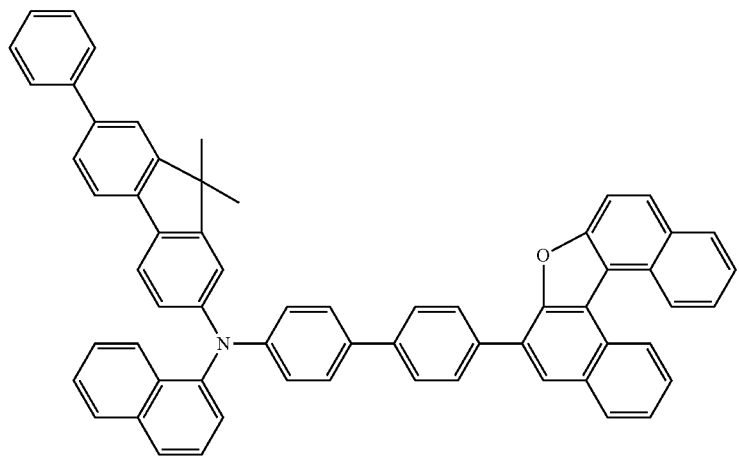
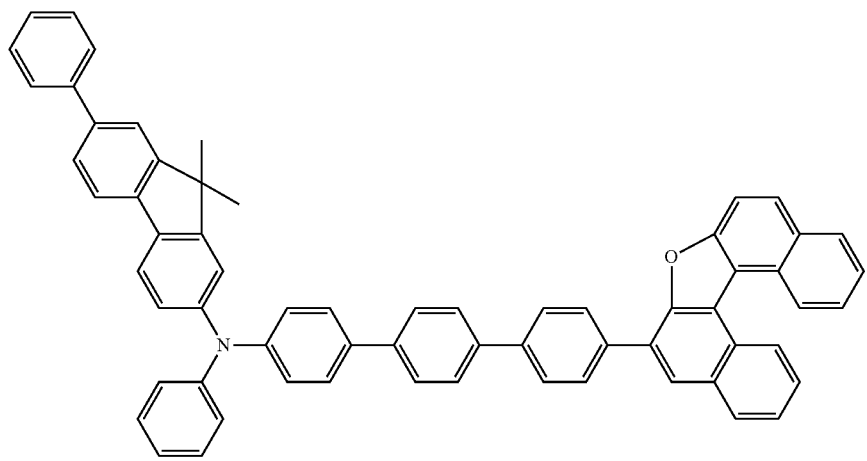
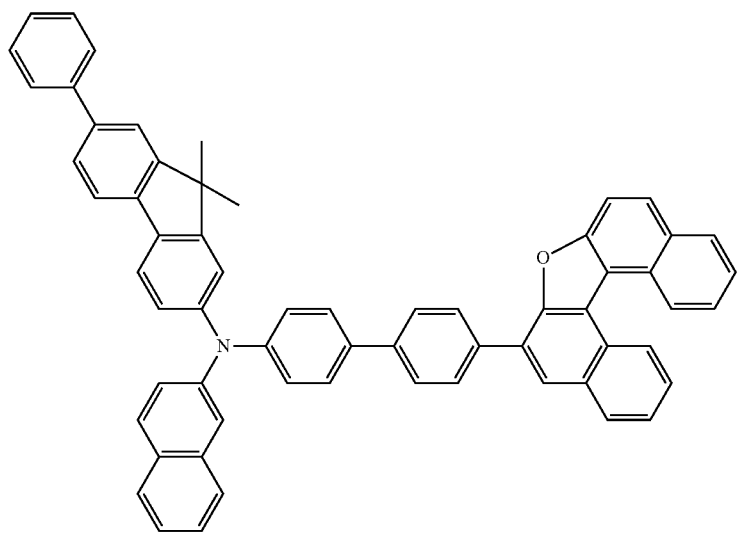

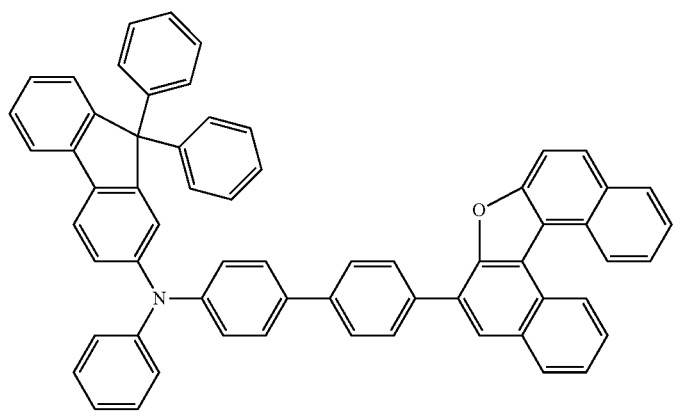
[Chem. 35]
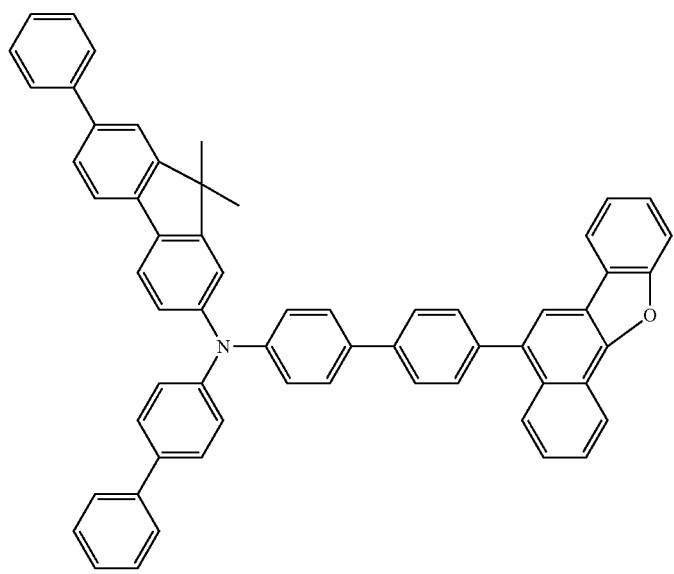
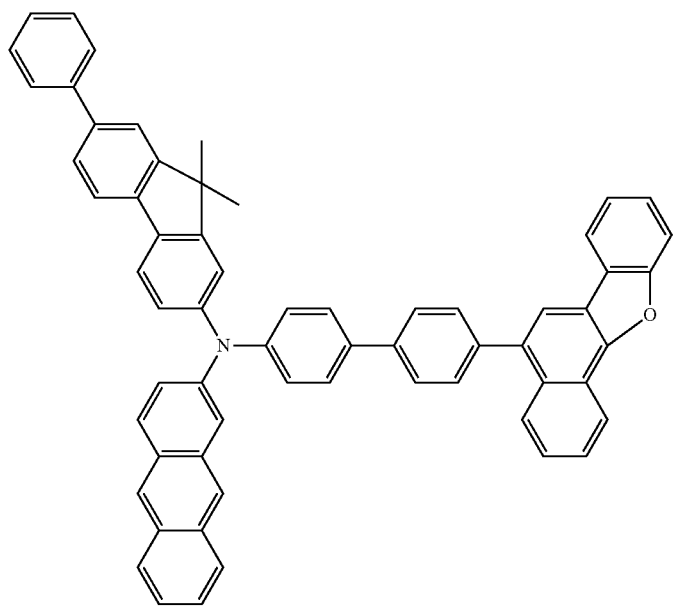

-continued
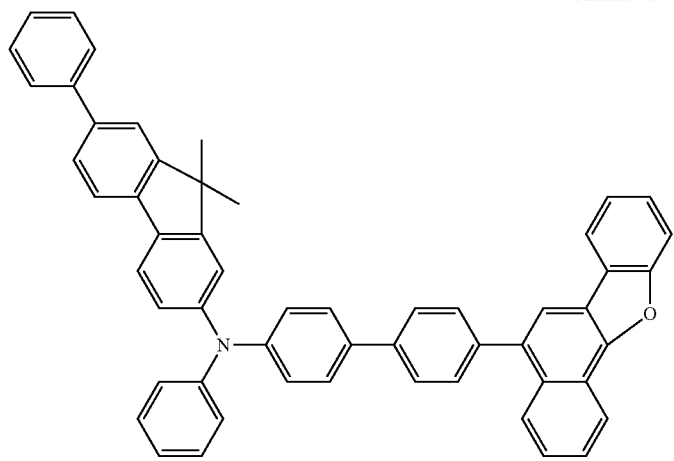
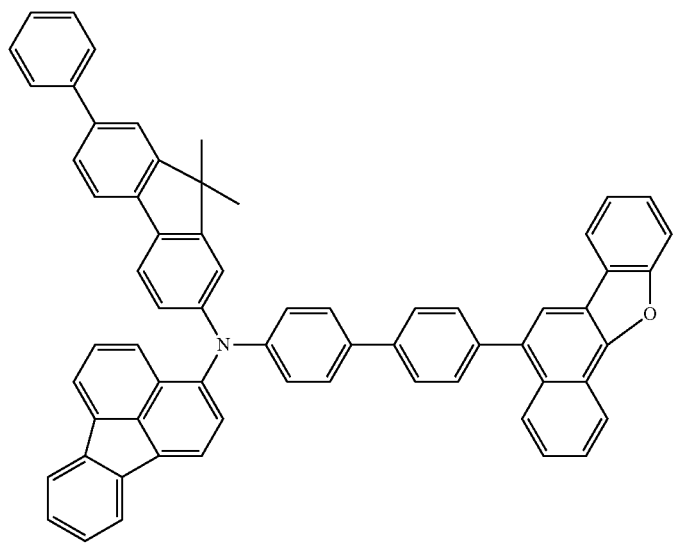
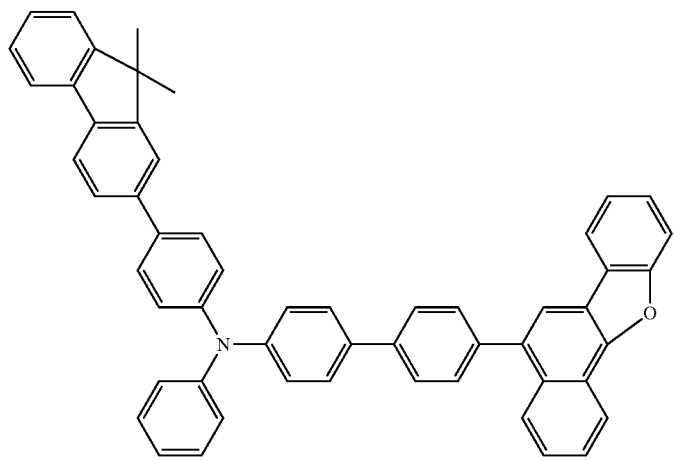

-continued
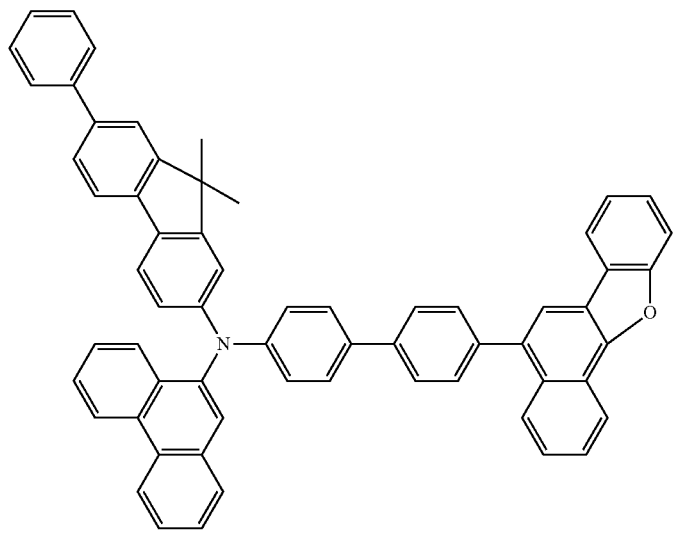
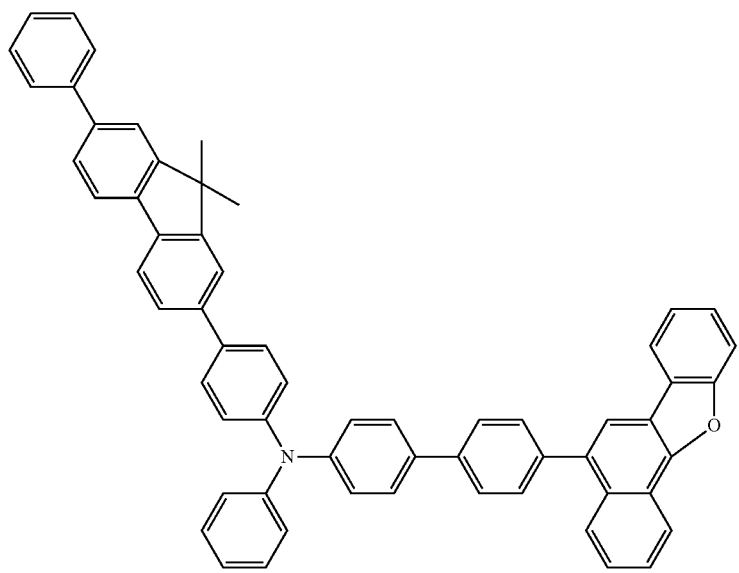
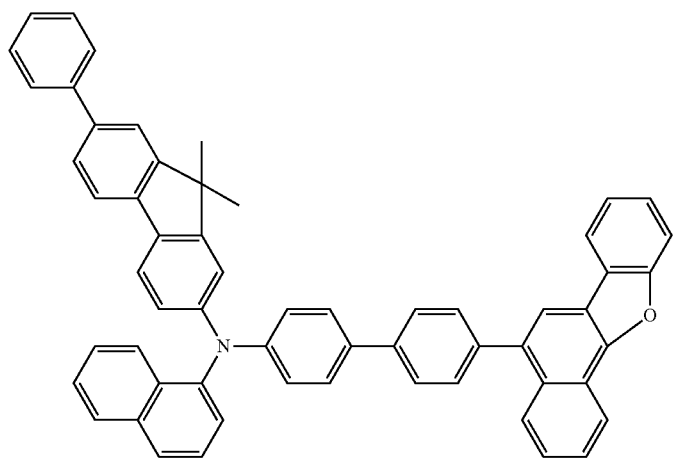

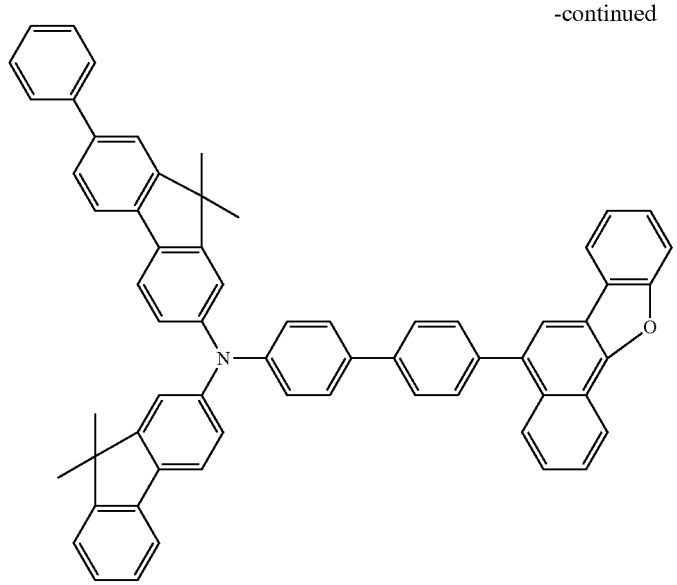
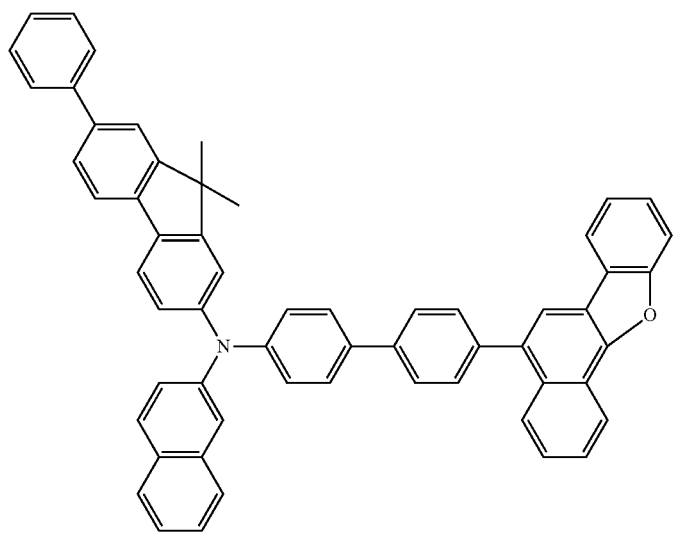
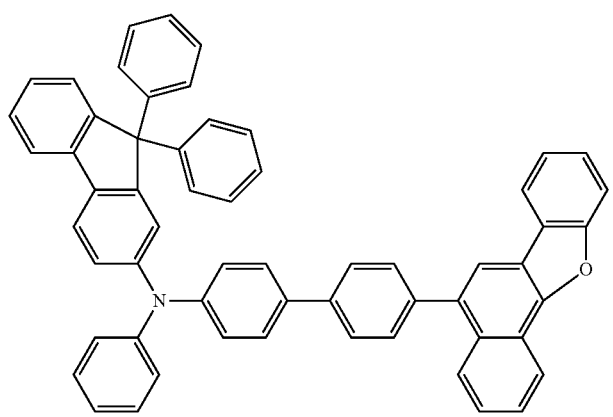

[Chem. 36]
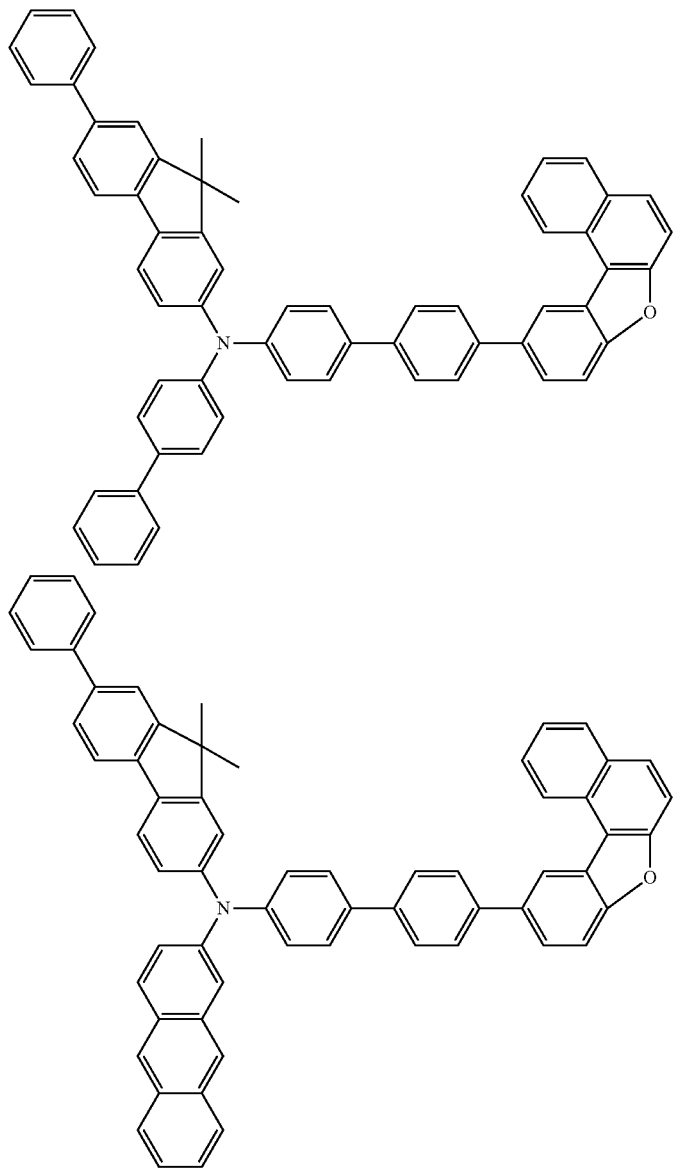
-continued
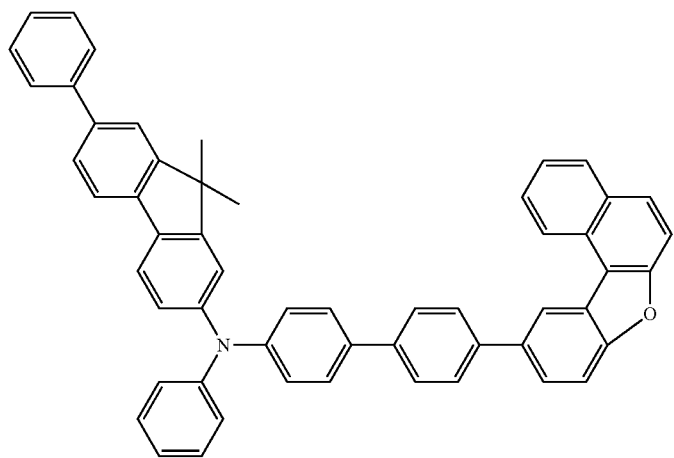

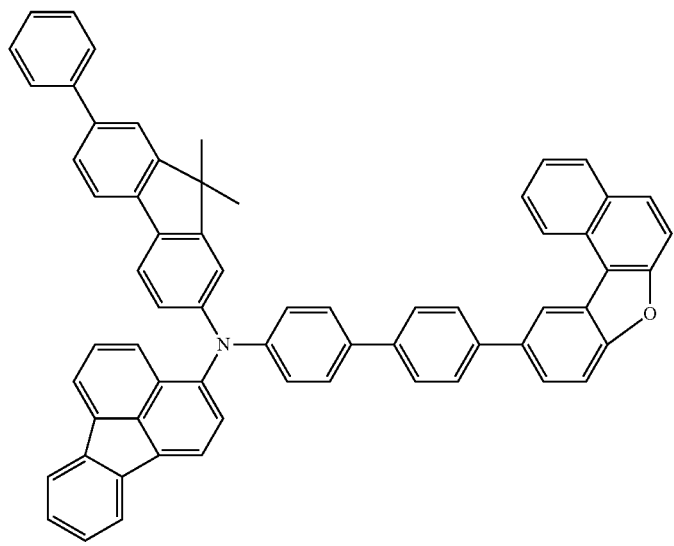
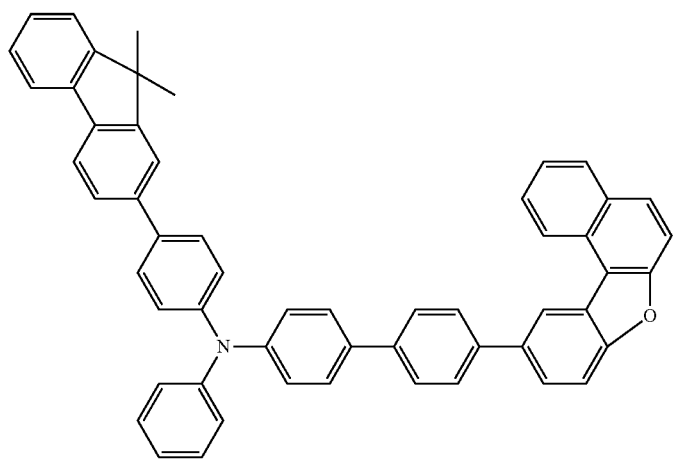
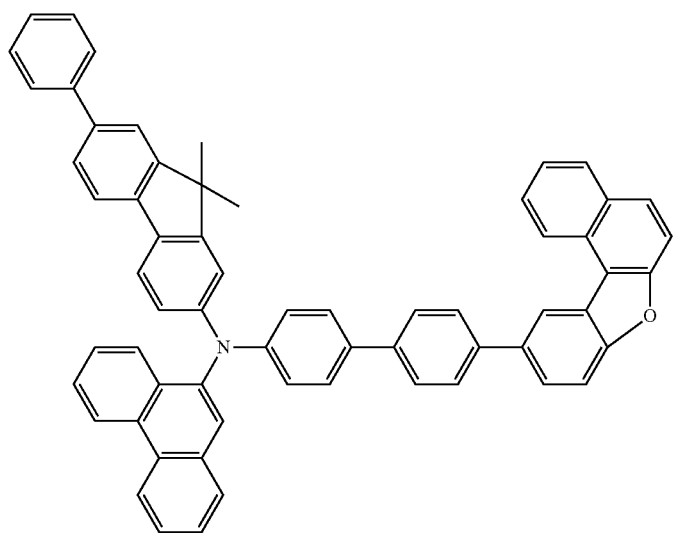

-continued
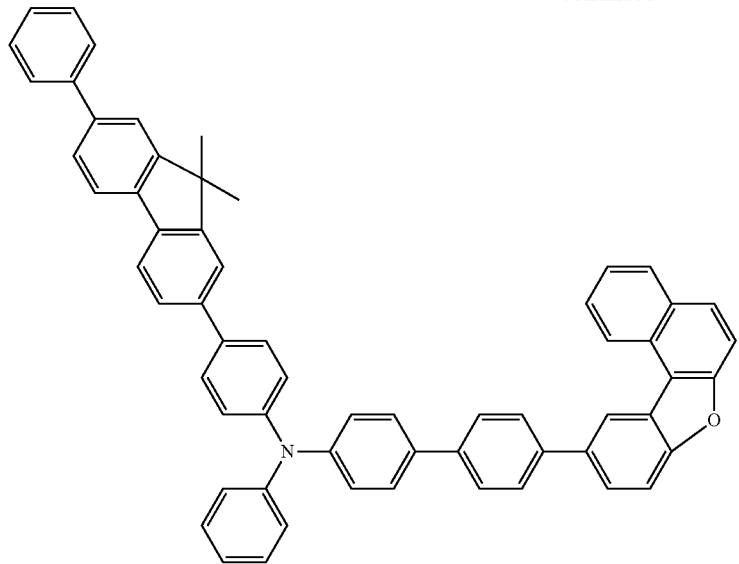
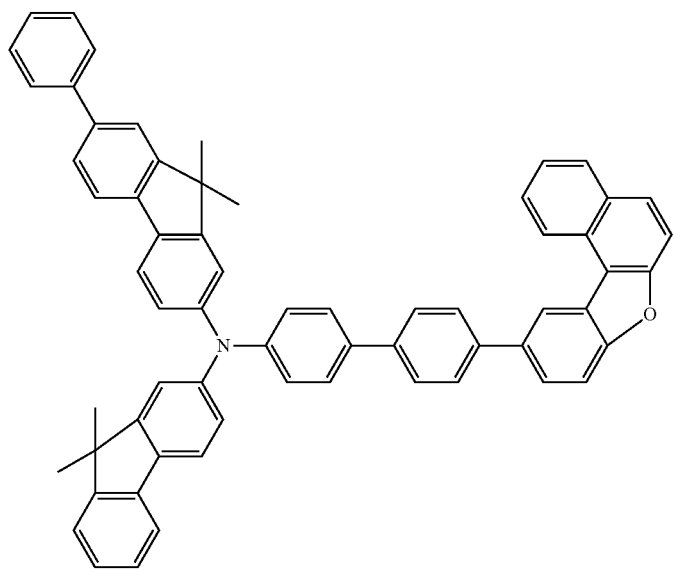
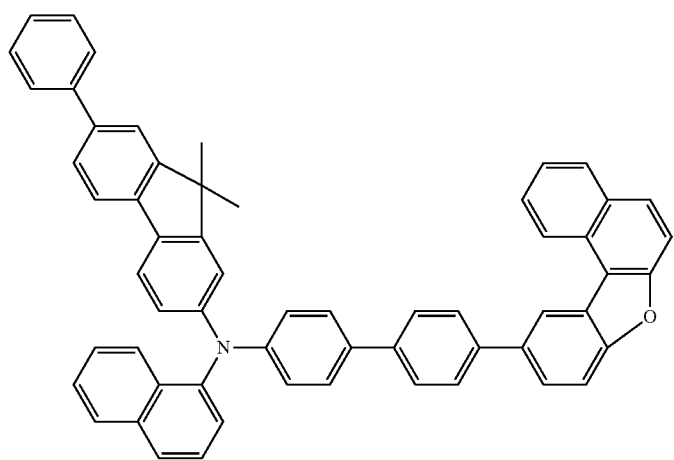

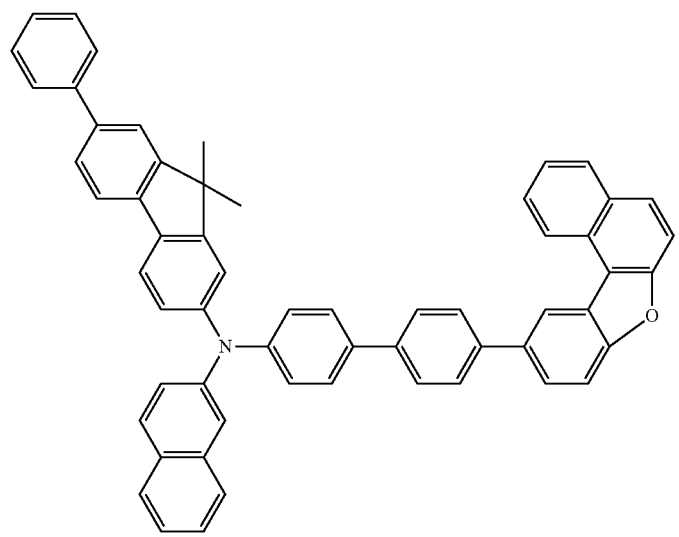
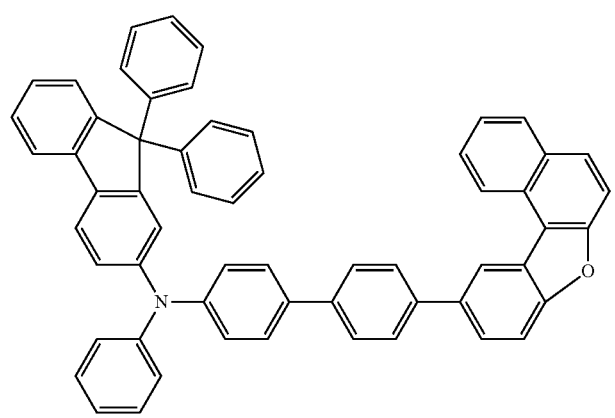
[Chem. 37]
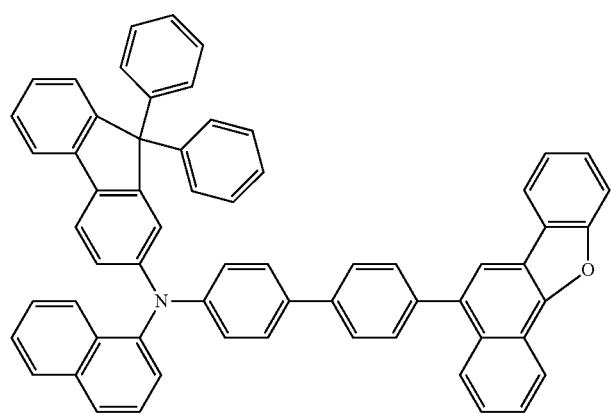

-continued
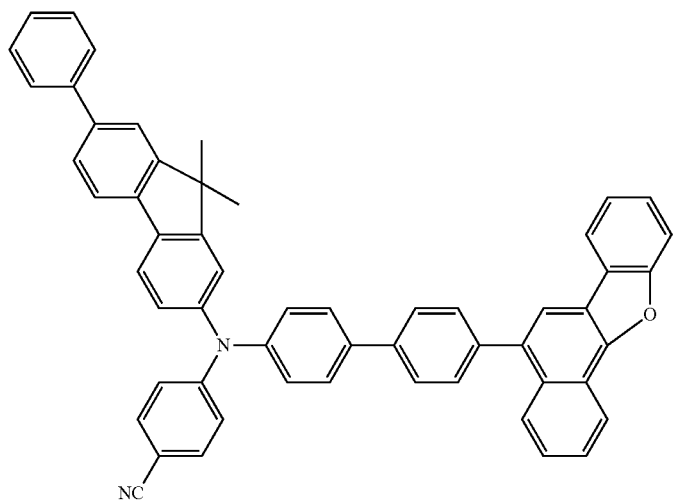
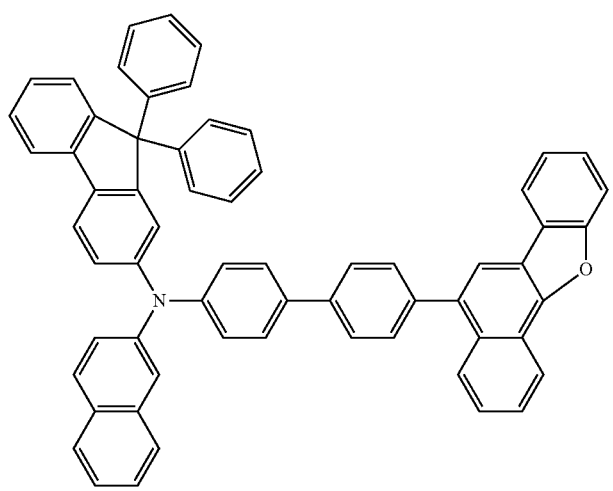
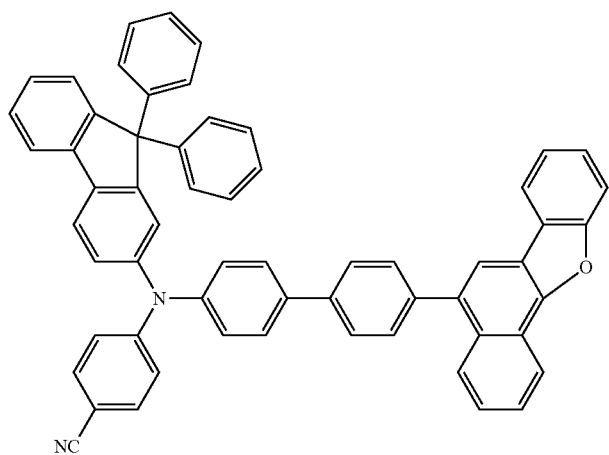

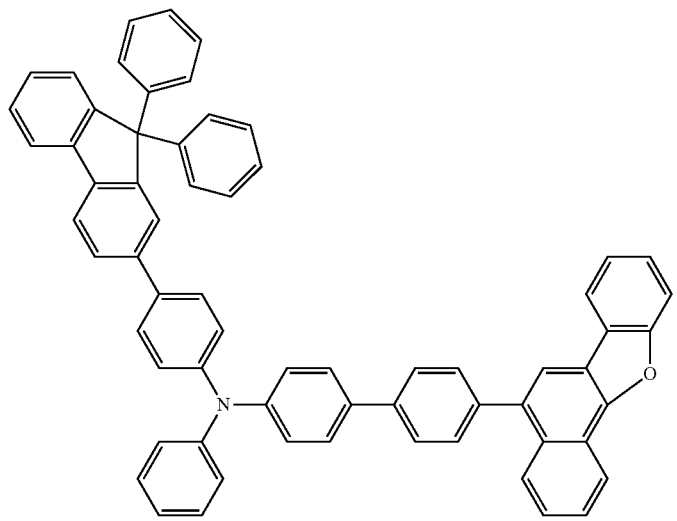
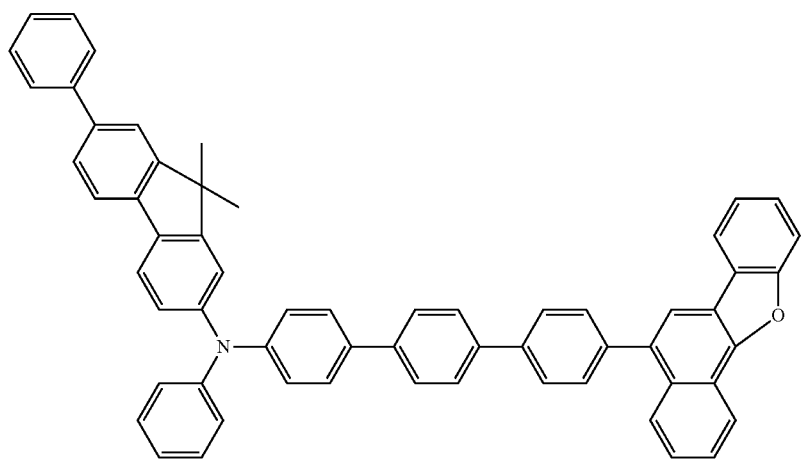
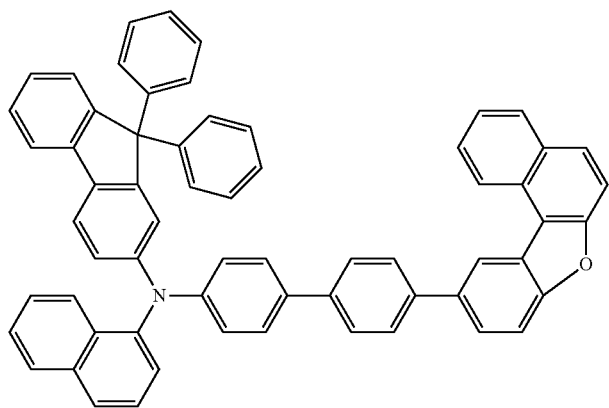

-continued
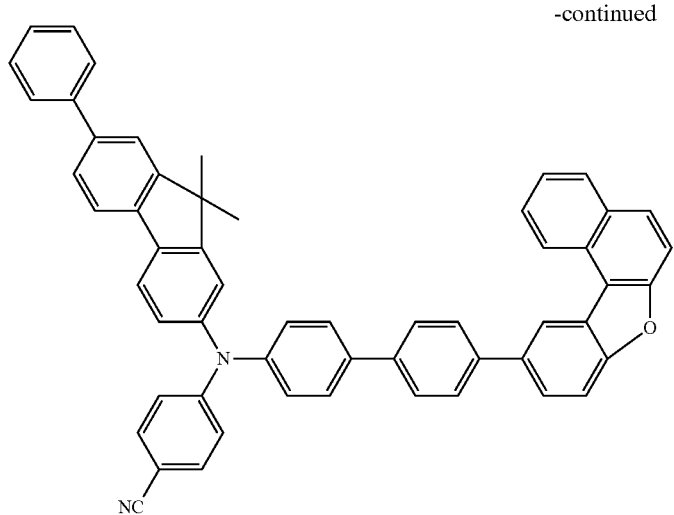
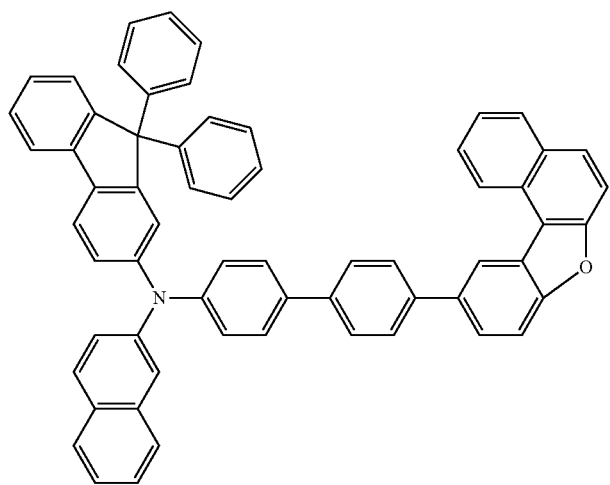
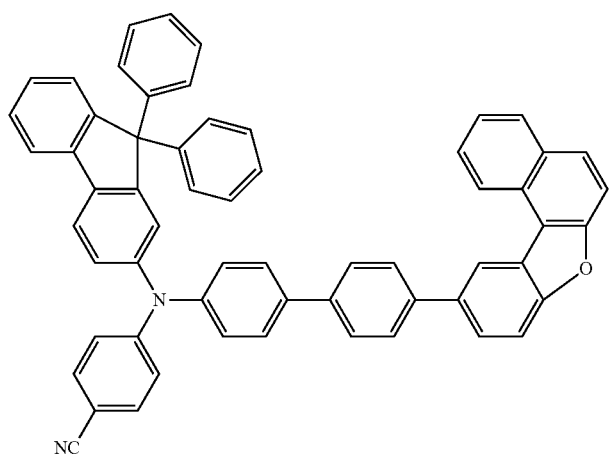

-continued
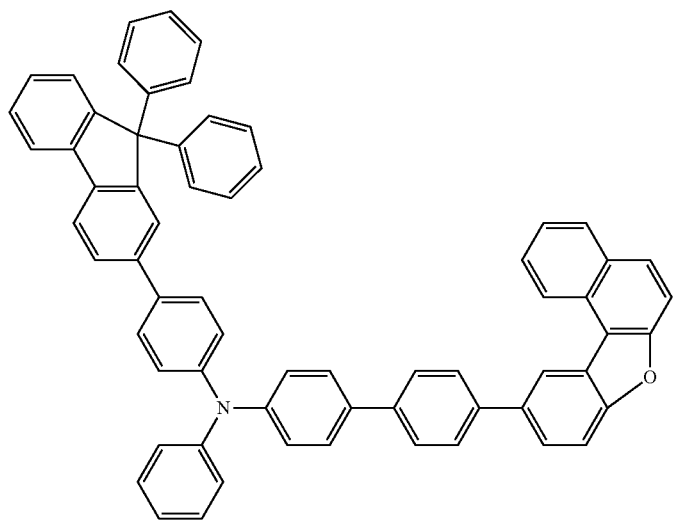
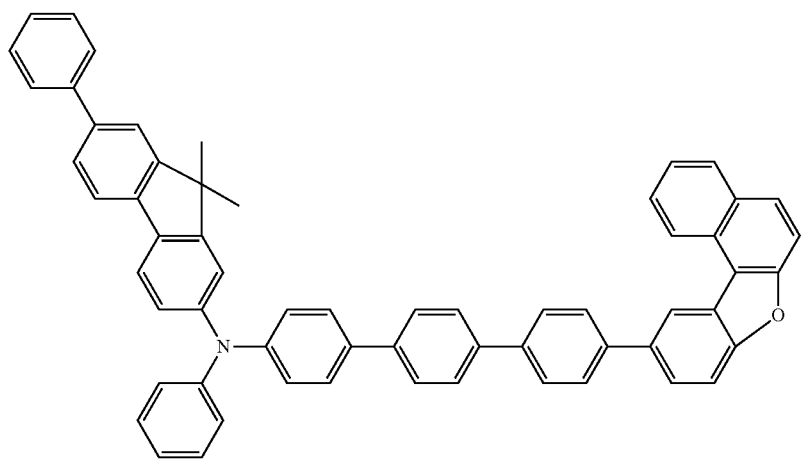
[Chem. 38]
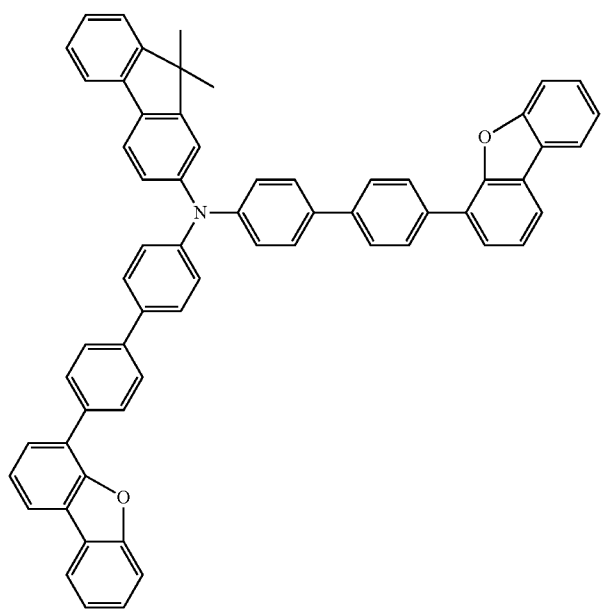

-continued
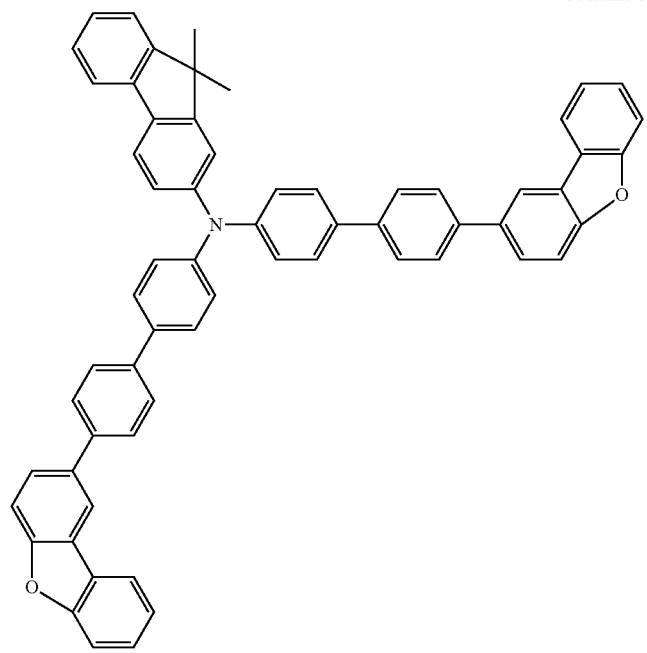
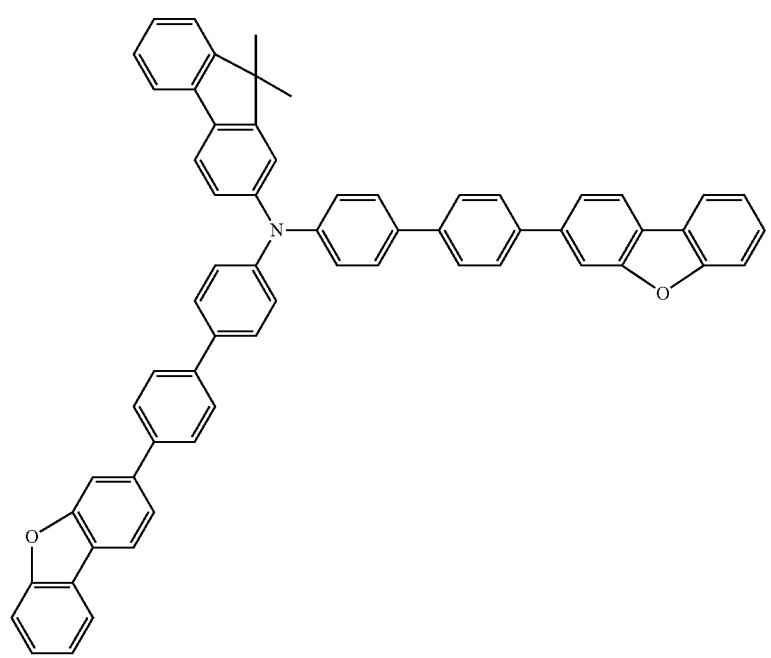

-continued
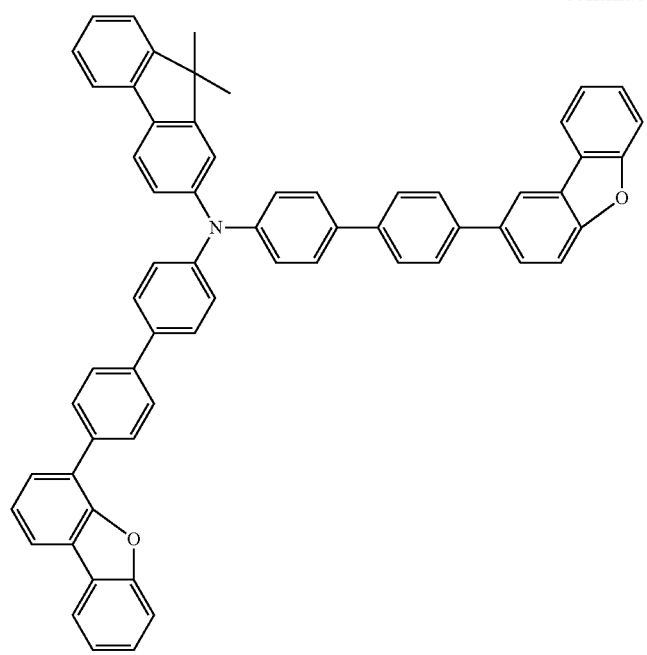
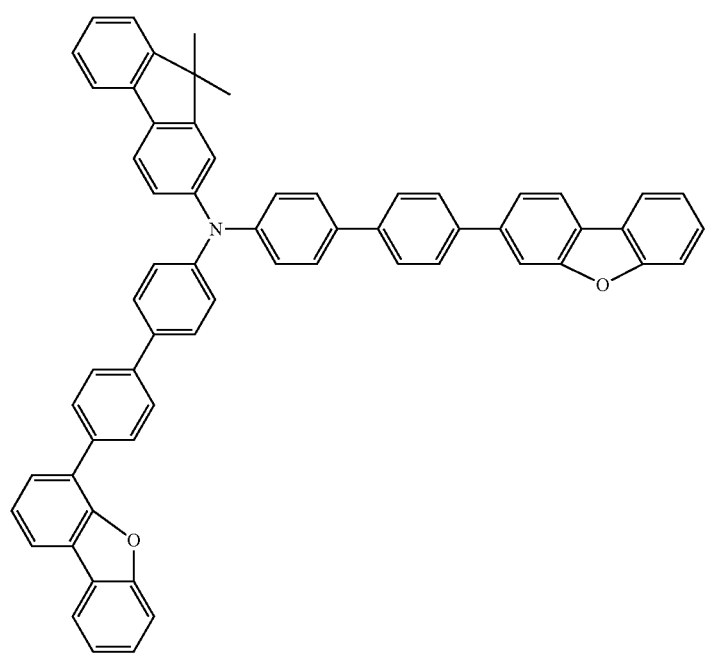

-continued
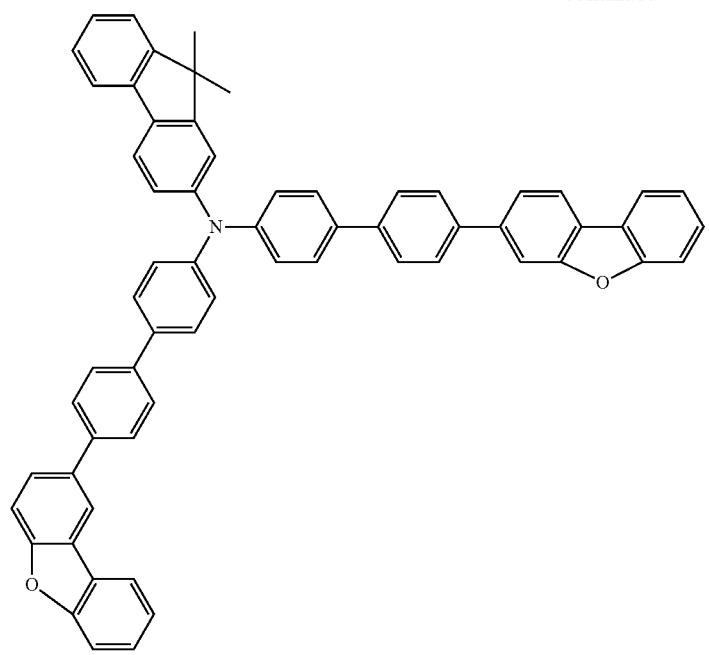
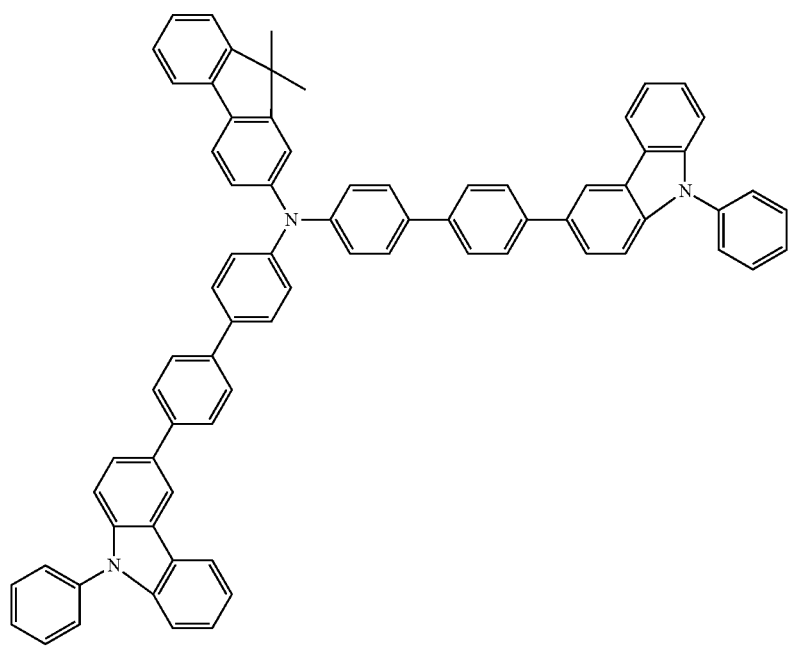

-continued
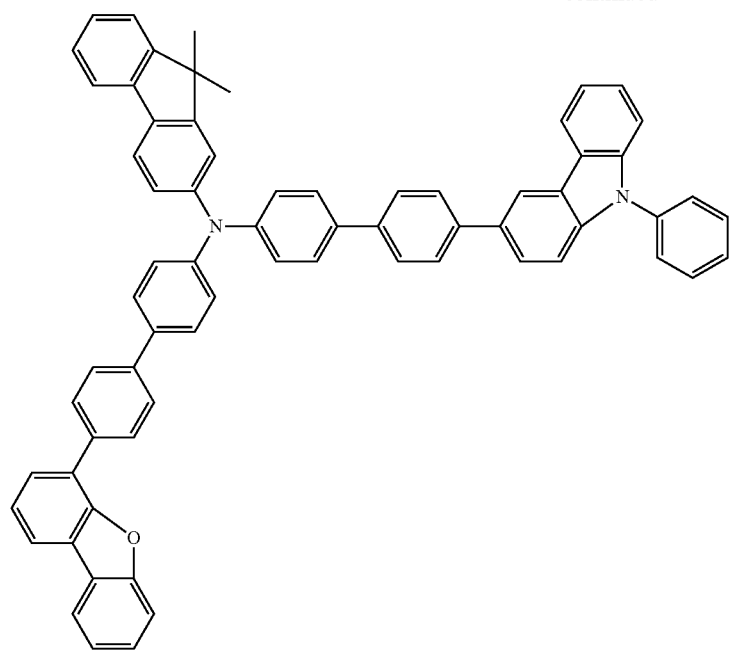
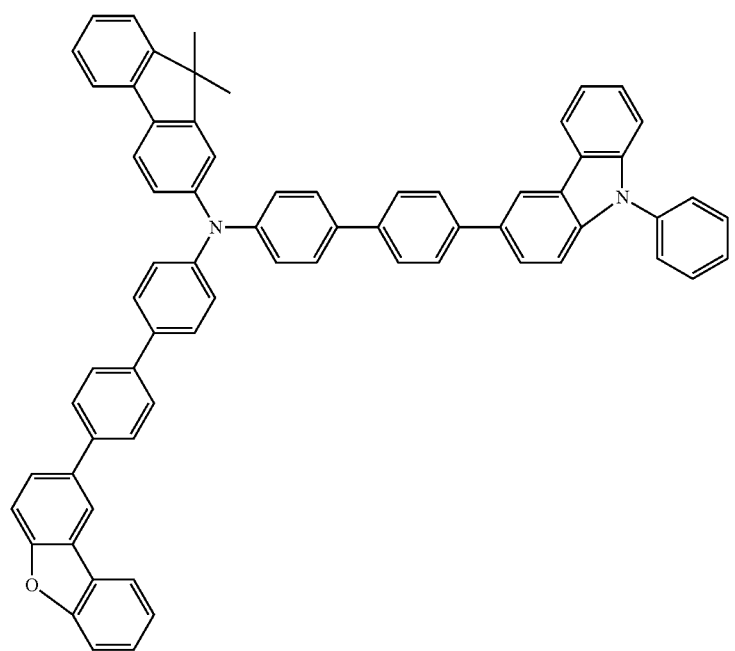

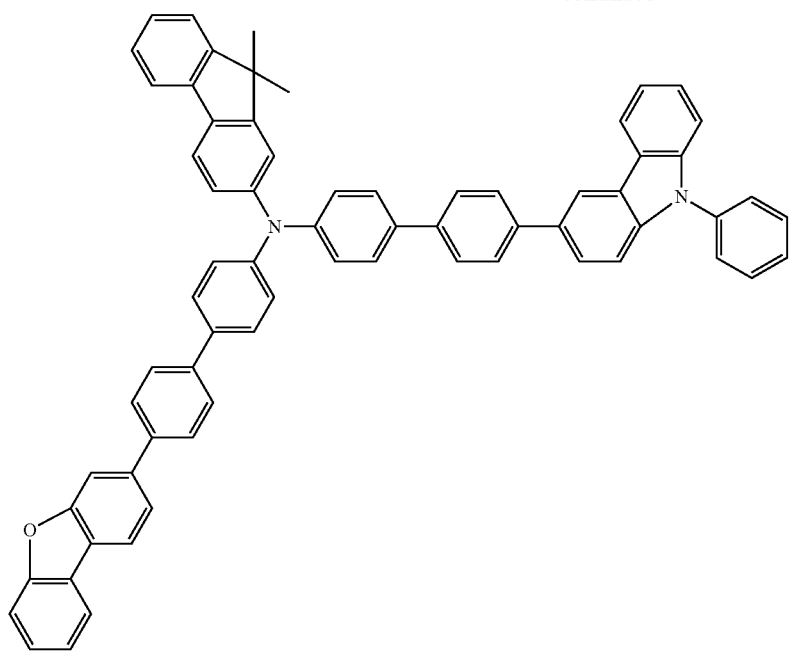
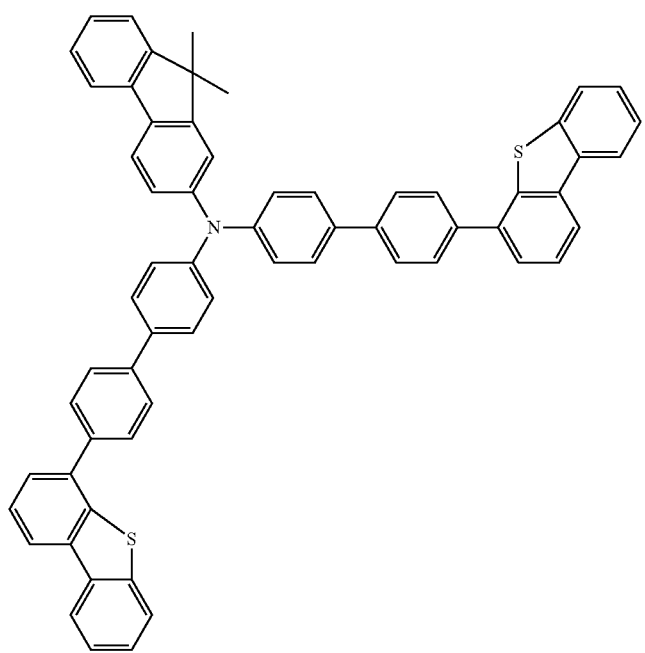

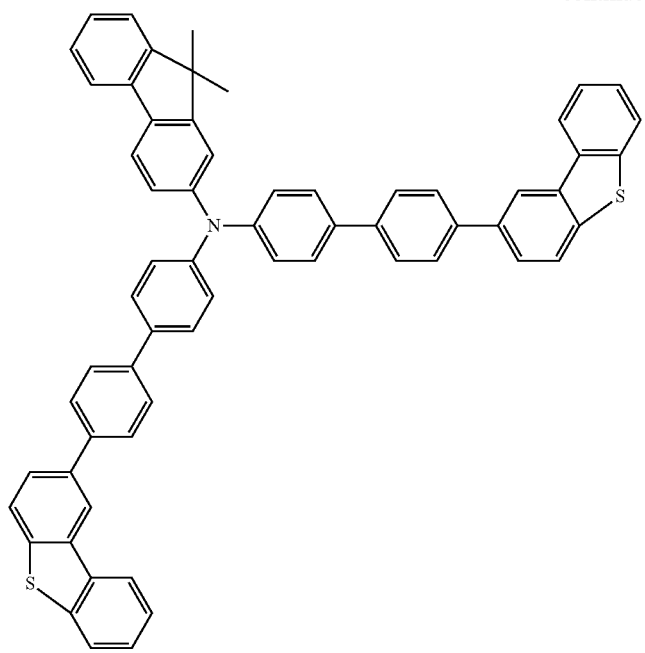
[Chem. 39]
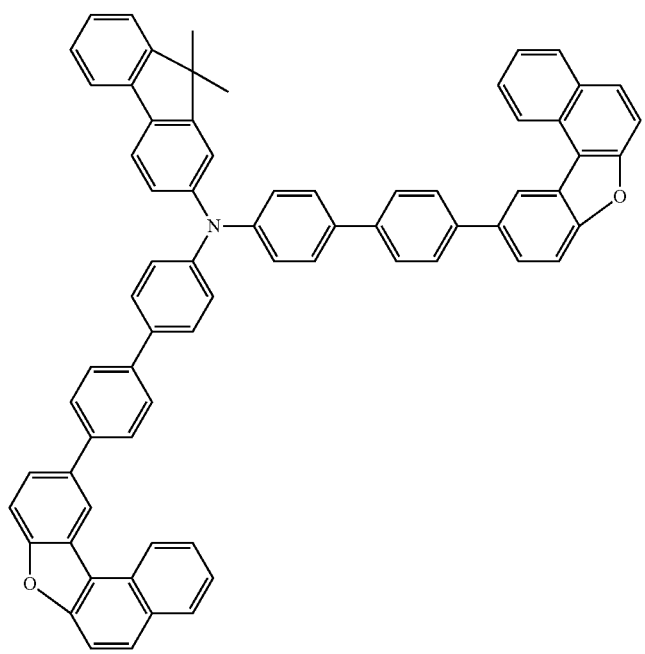

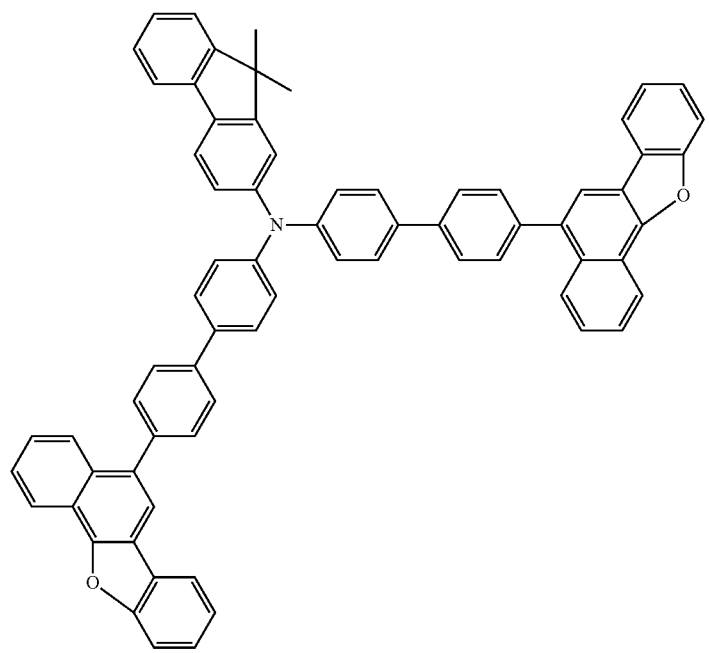
[Chem. 40]
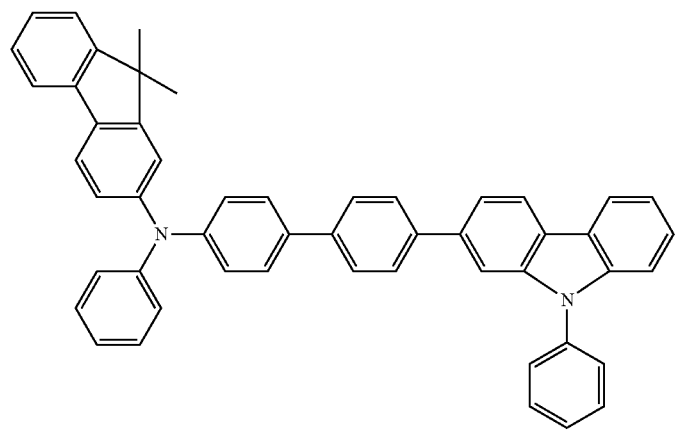
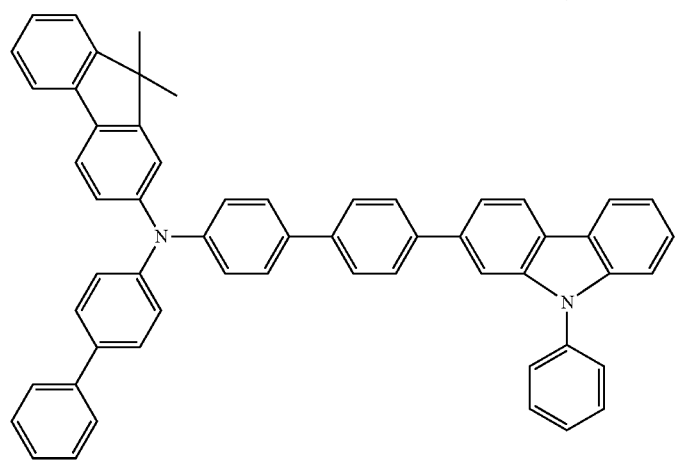

-continued
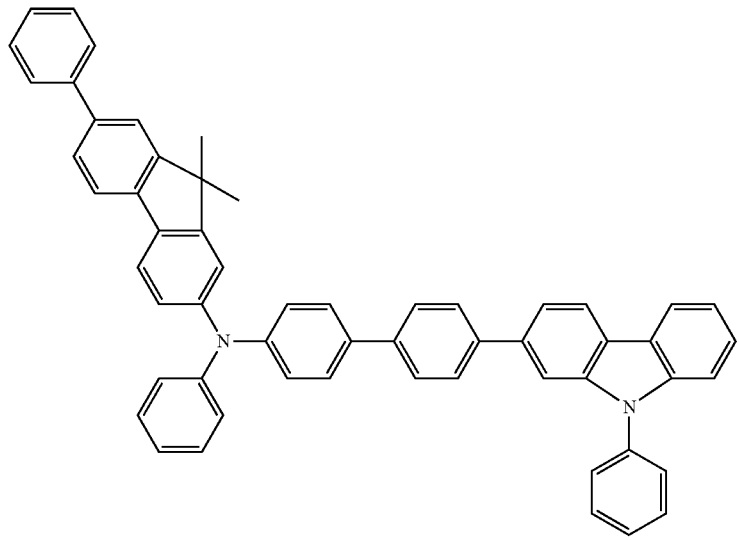
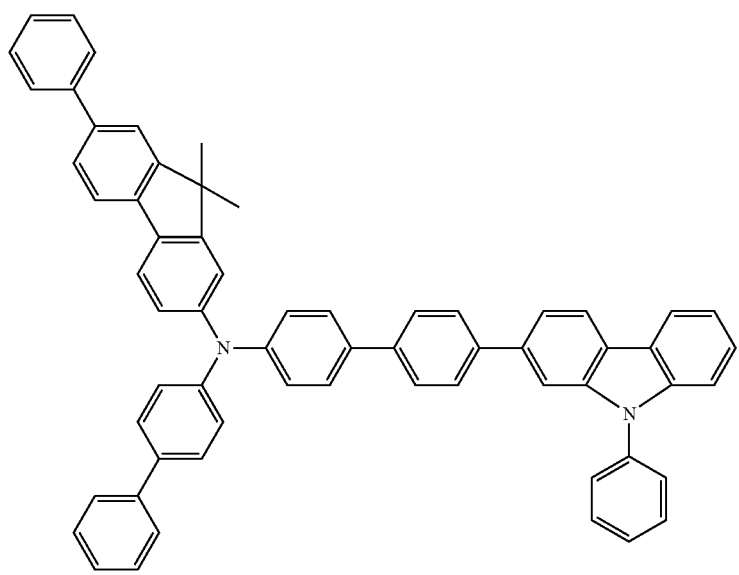
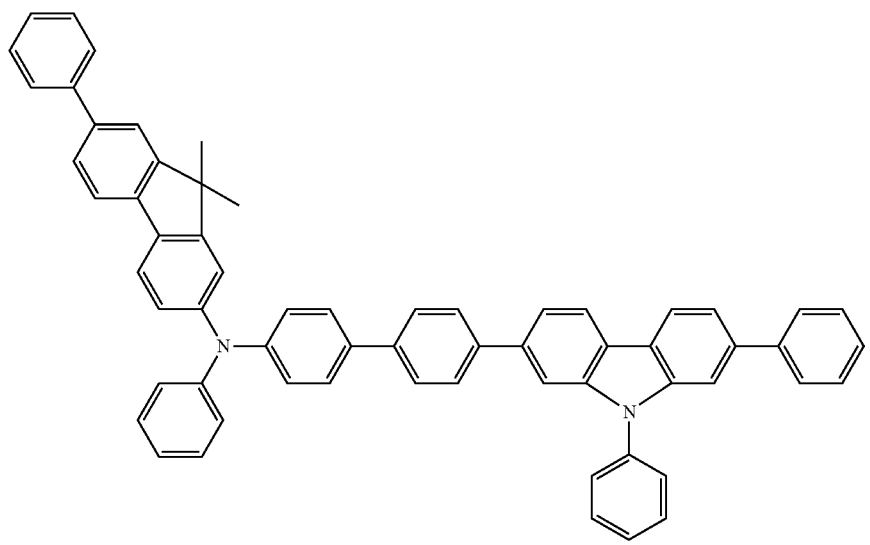

-continued
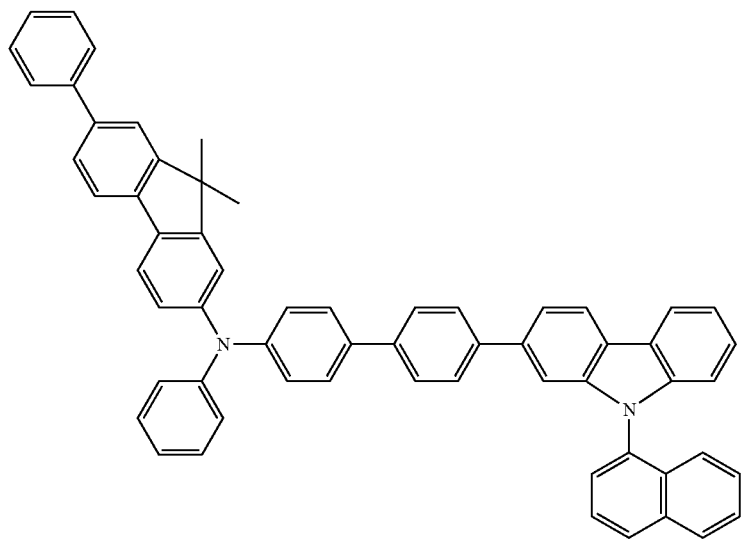
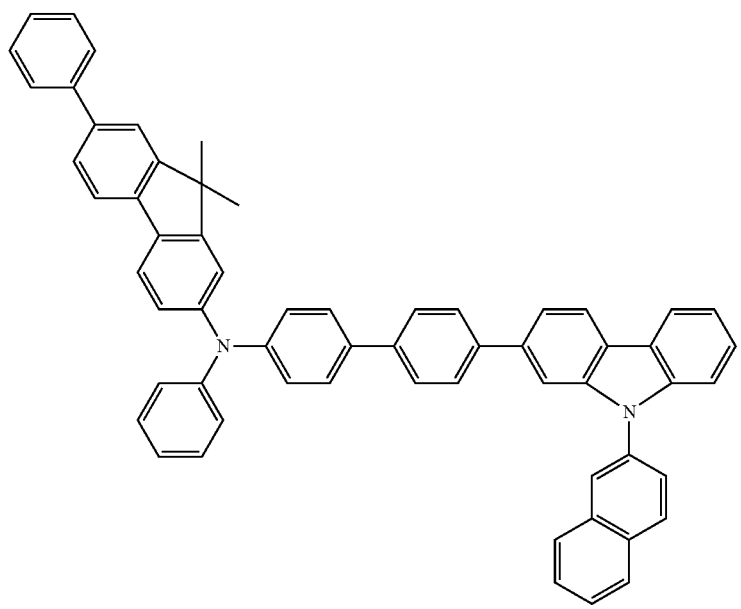
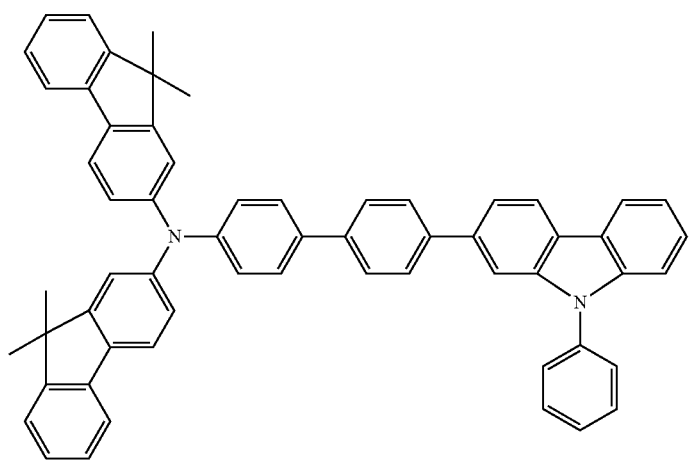

-continued
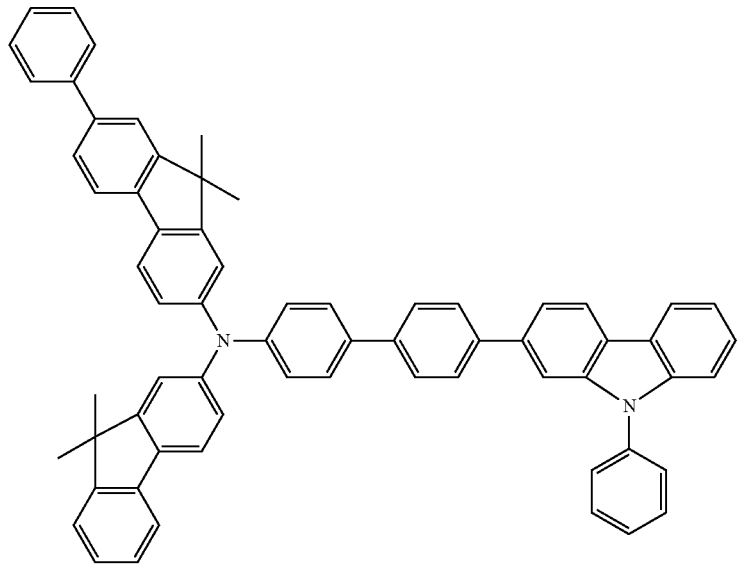
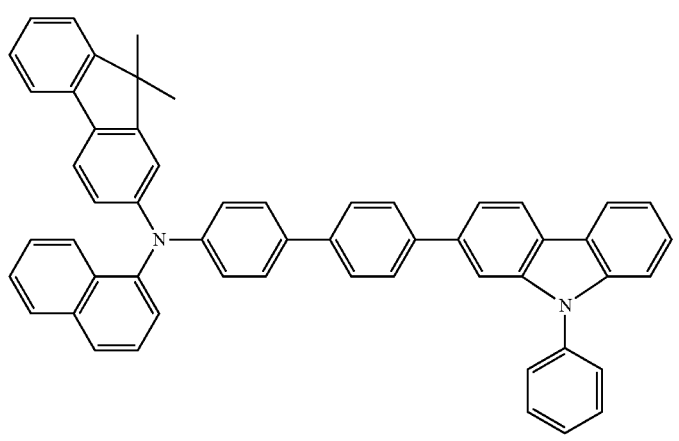
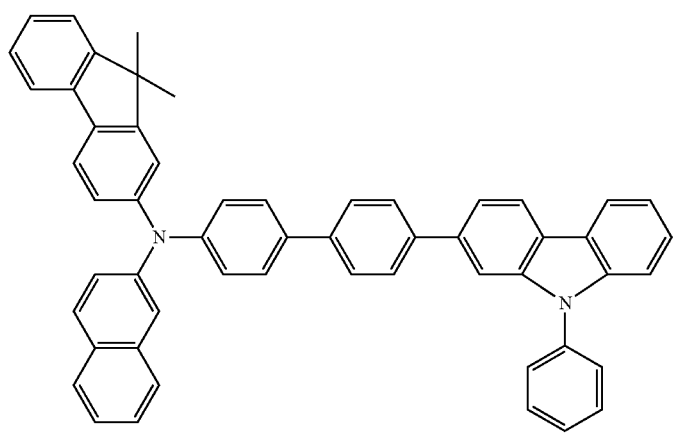

-continued
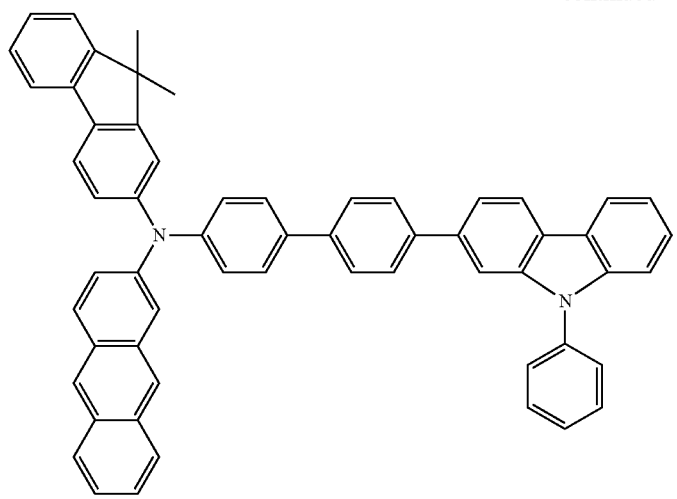
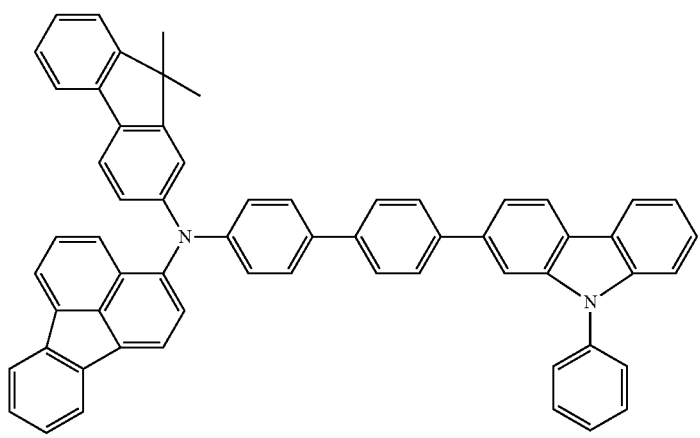
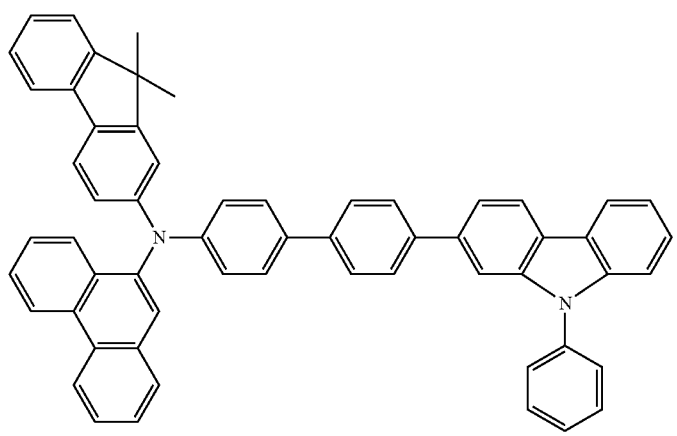

[Chem. 41]
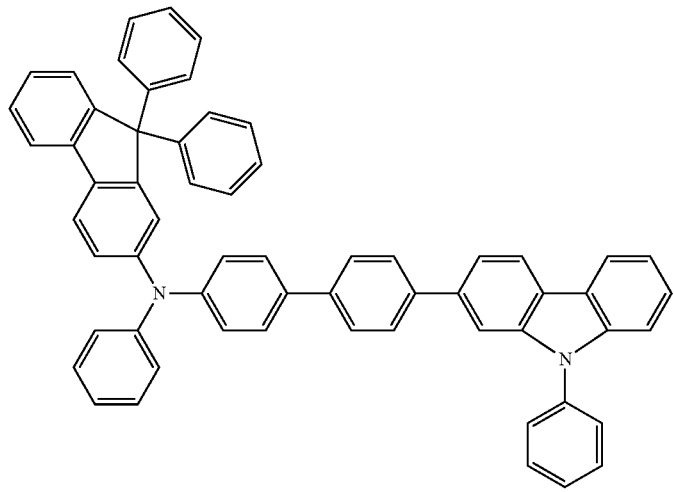
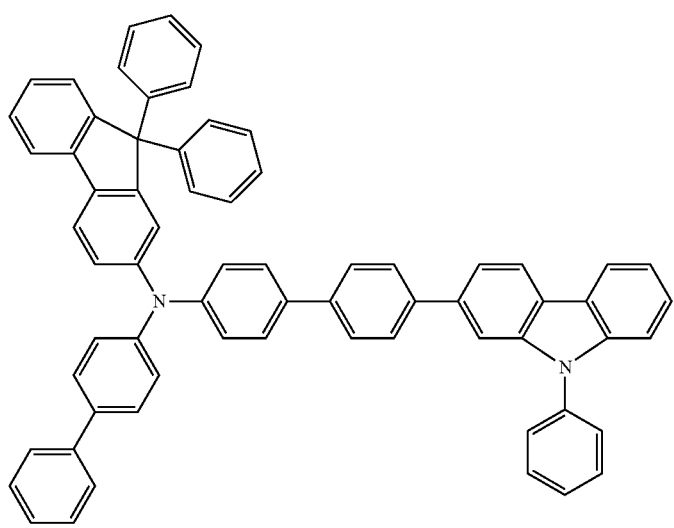
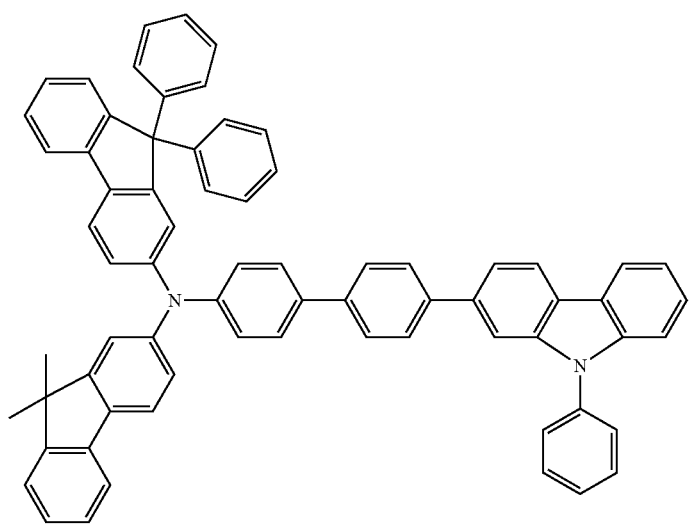

-continued
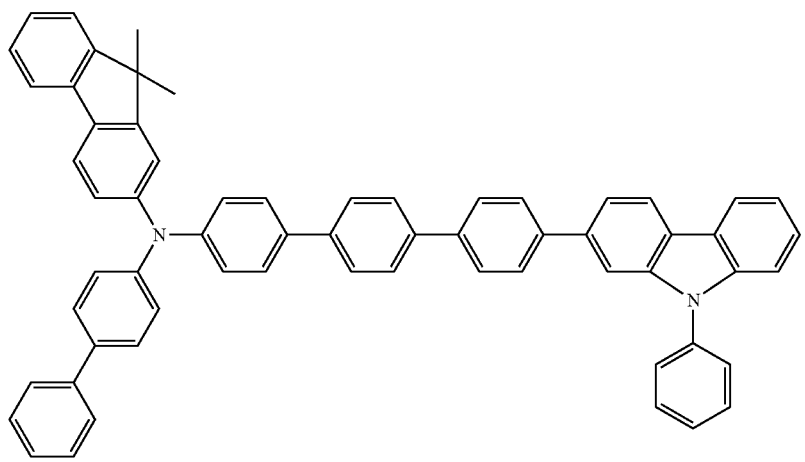
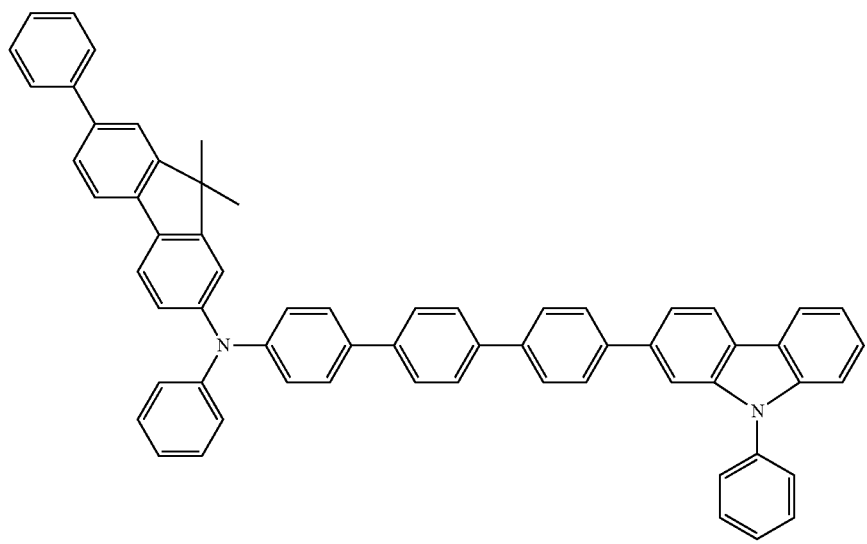
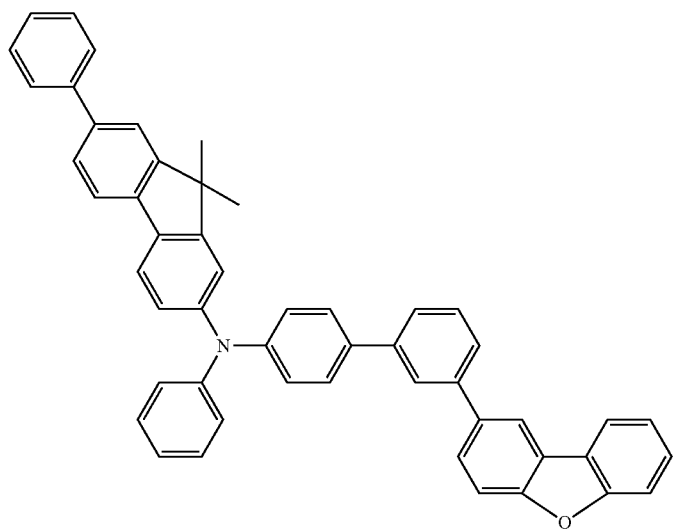

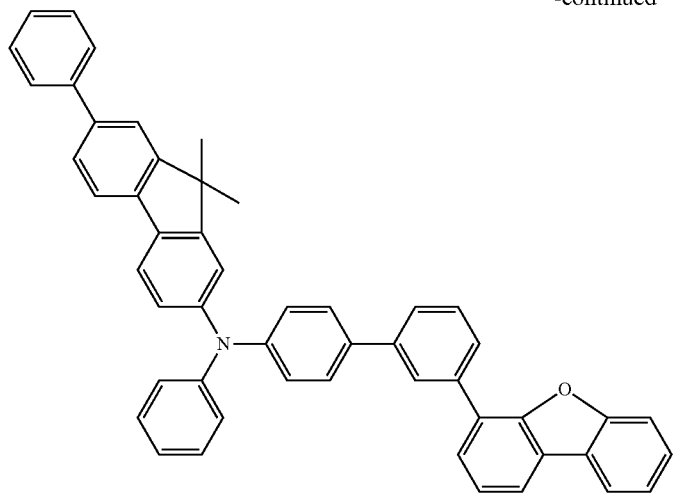
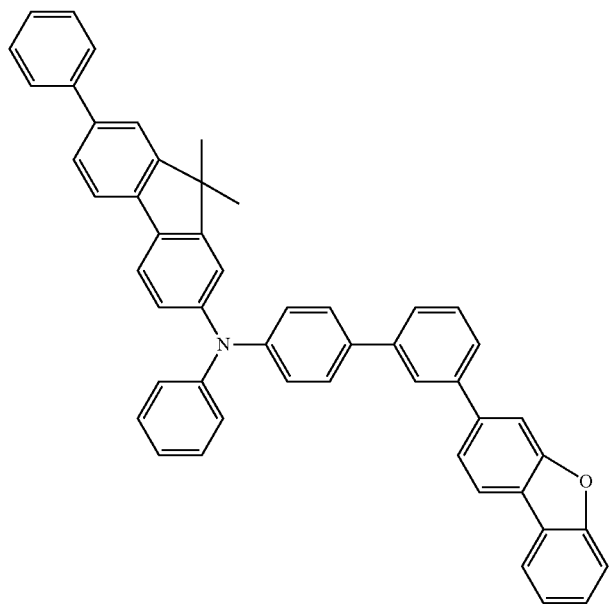
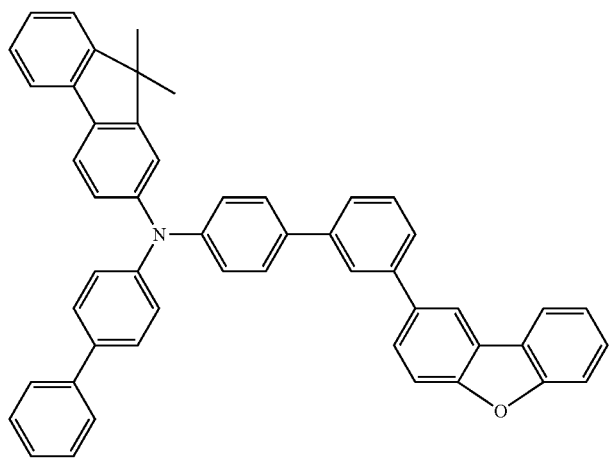

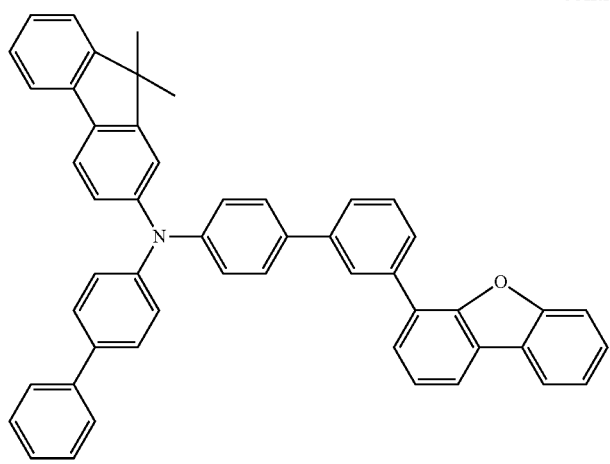
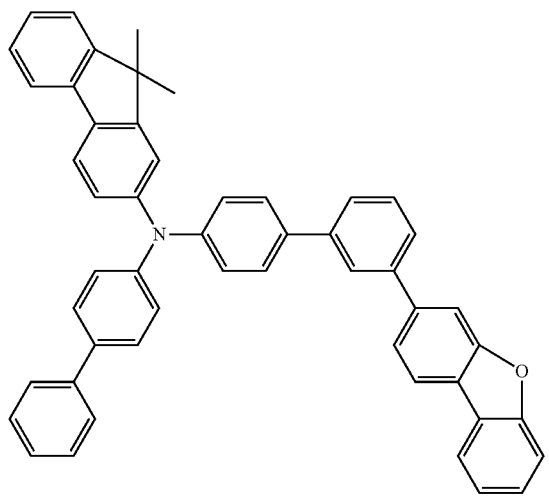
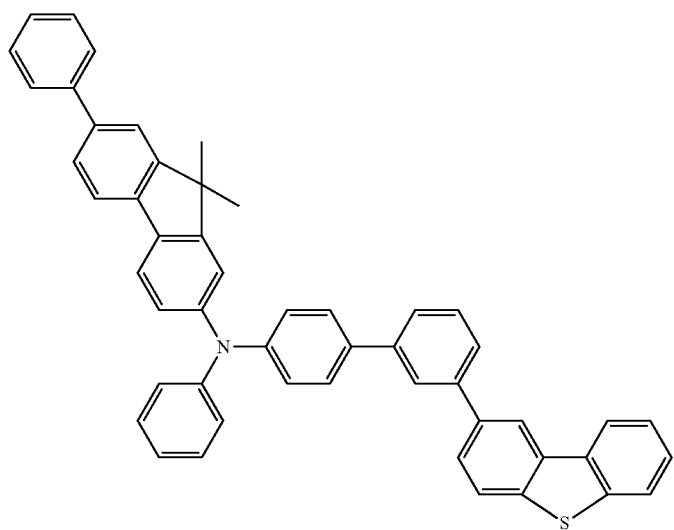

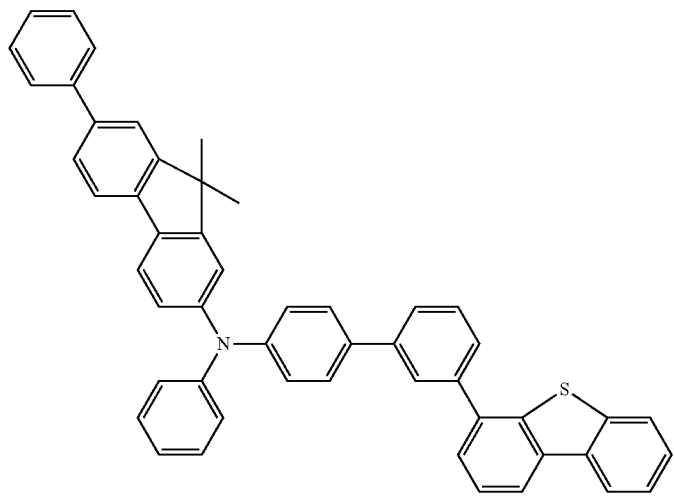
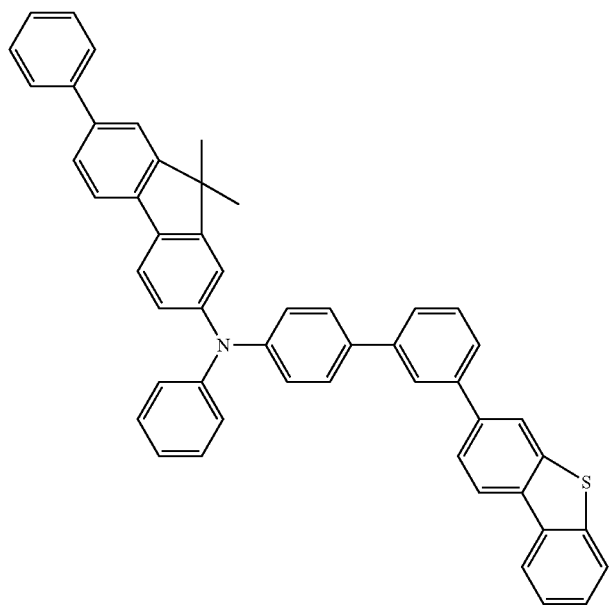

[Chem. 42]
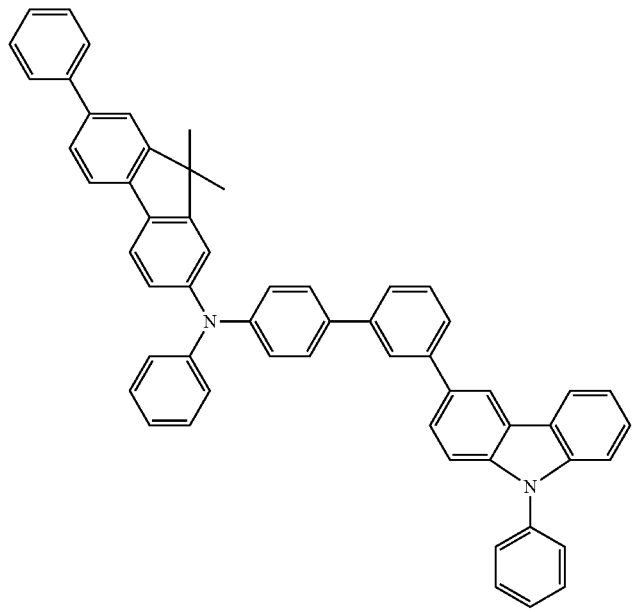
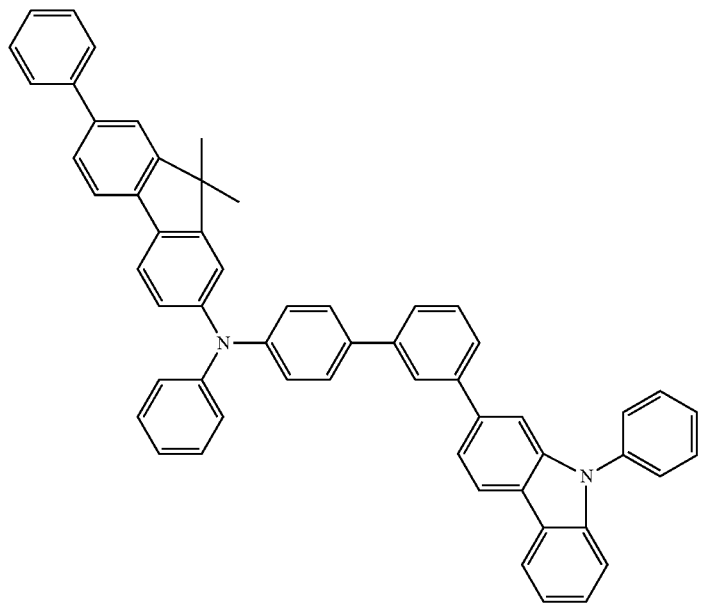

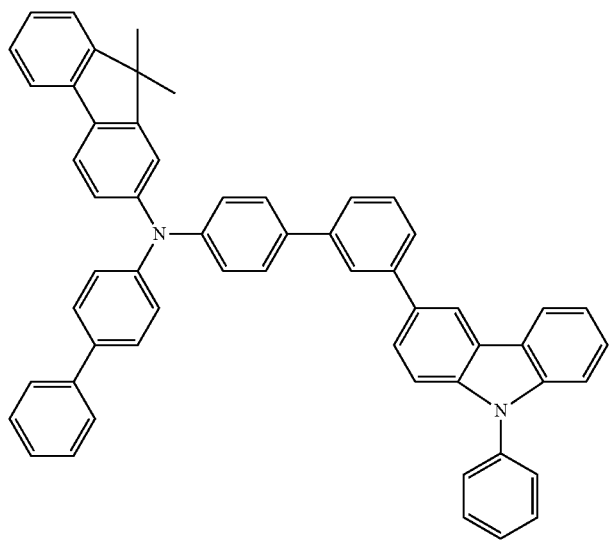
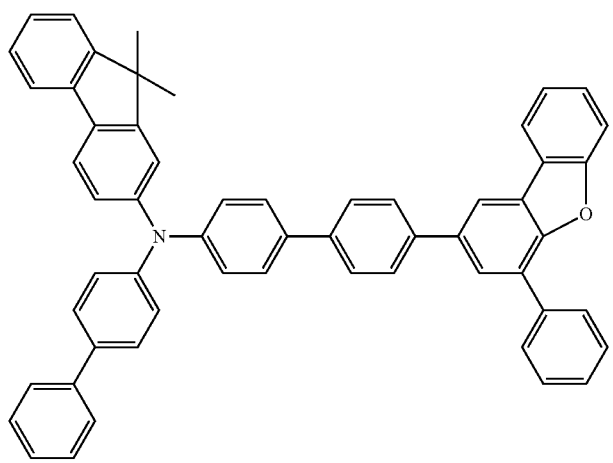
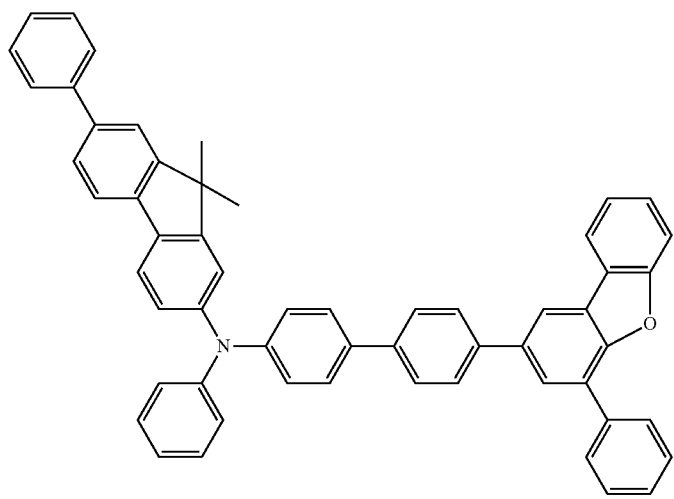

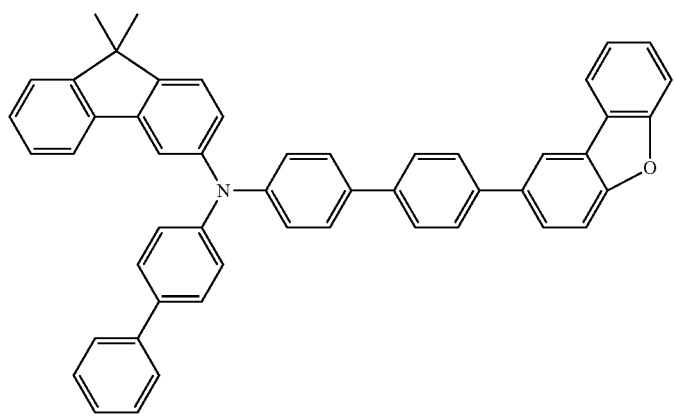
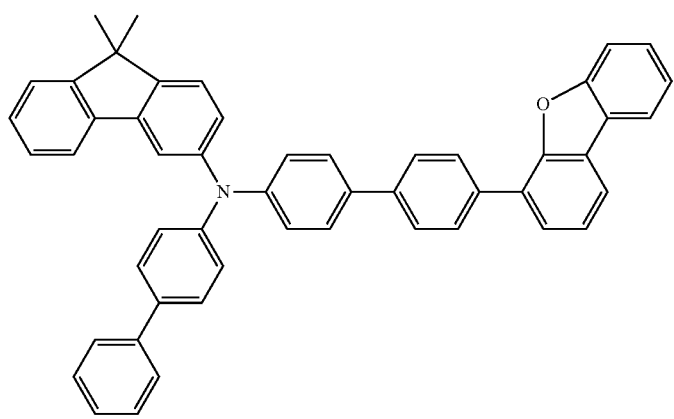
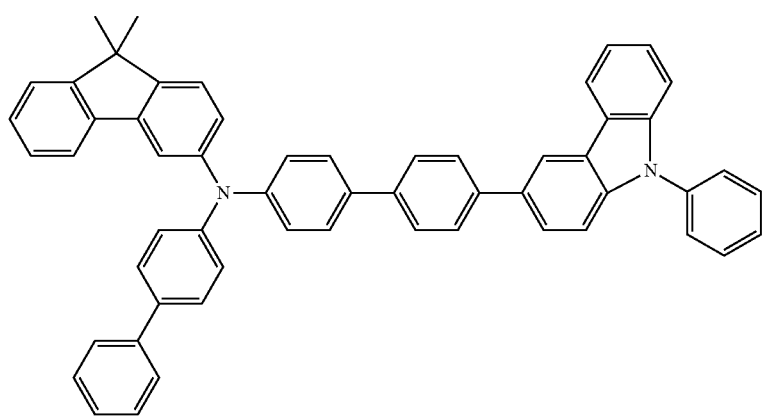

[Chem. 43]
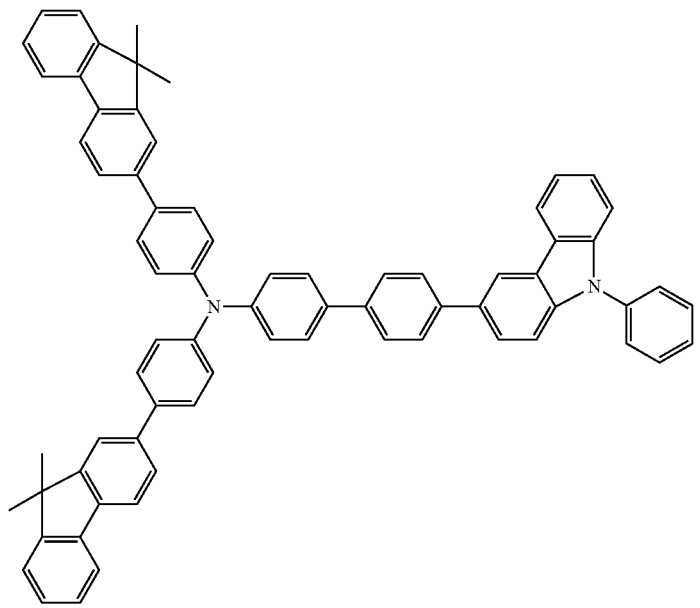
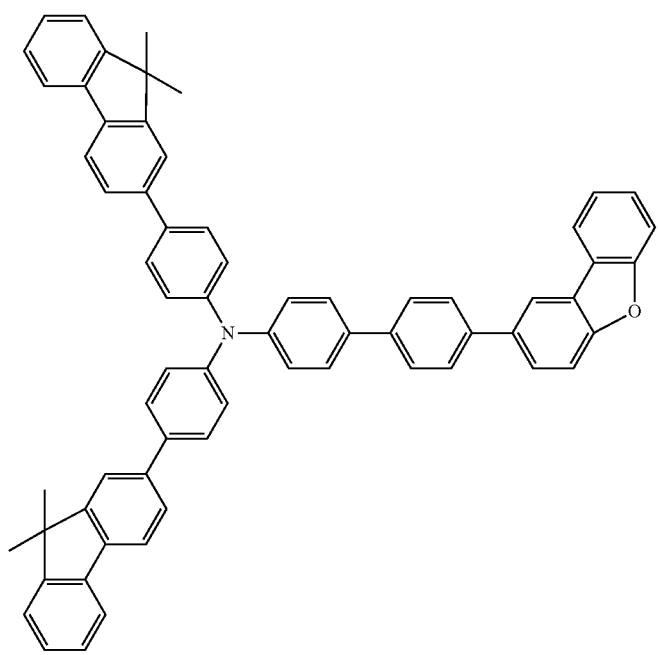

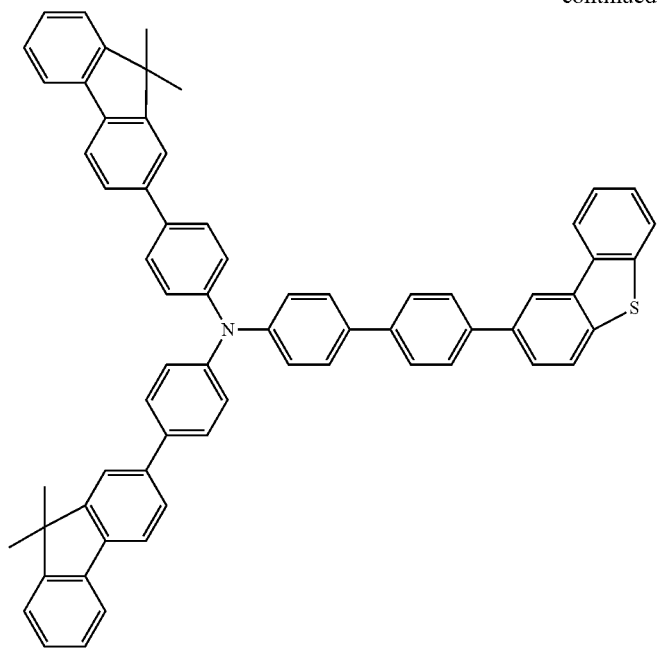
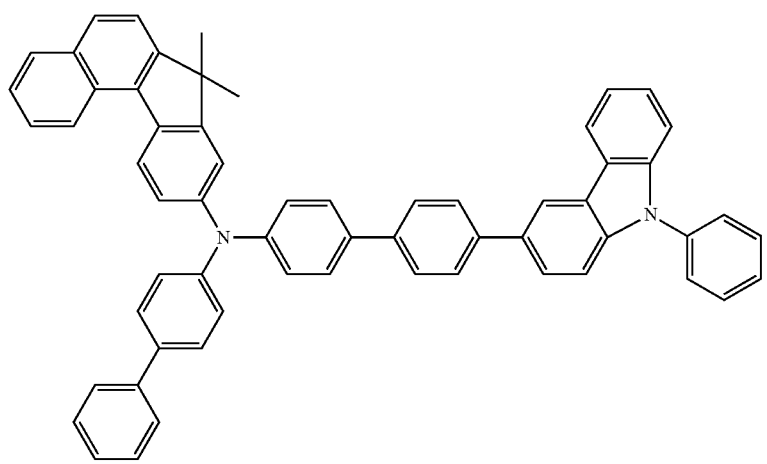
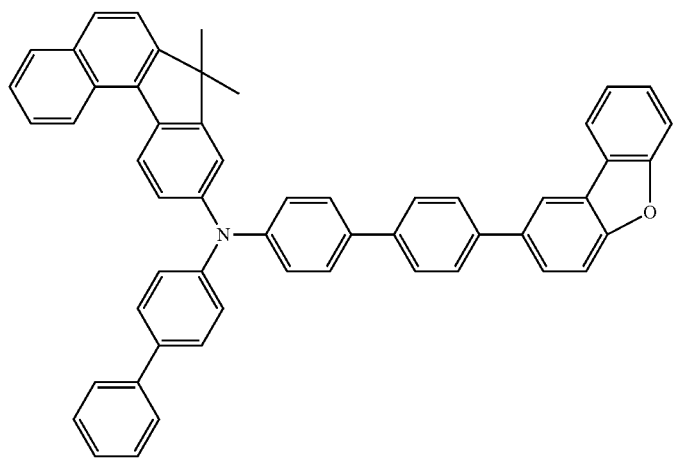

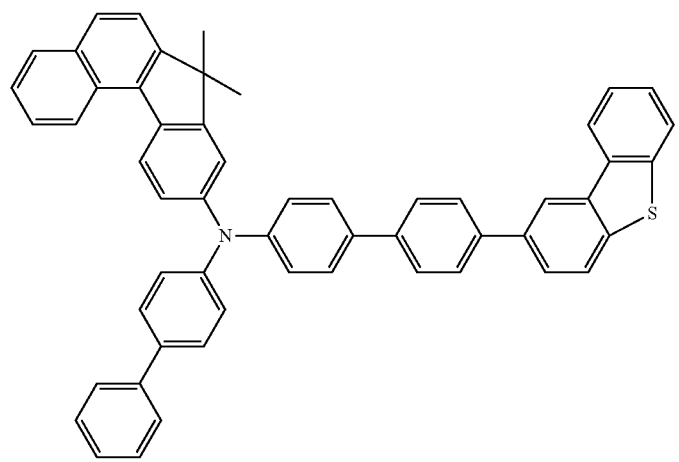
[Chem. 44]
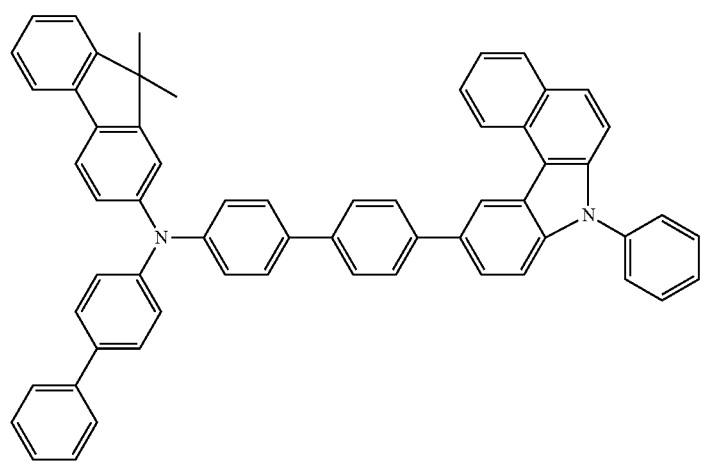
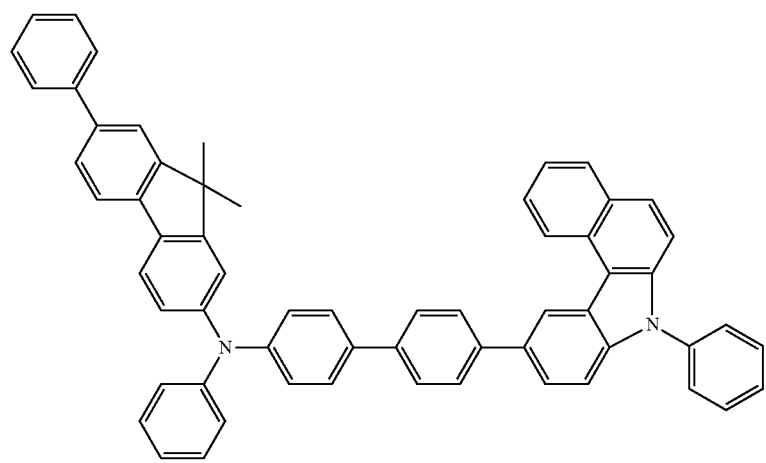

-continued
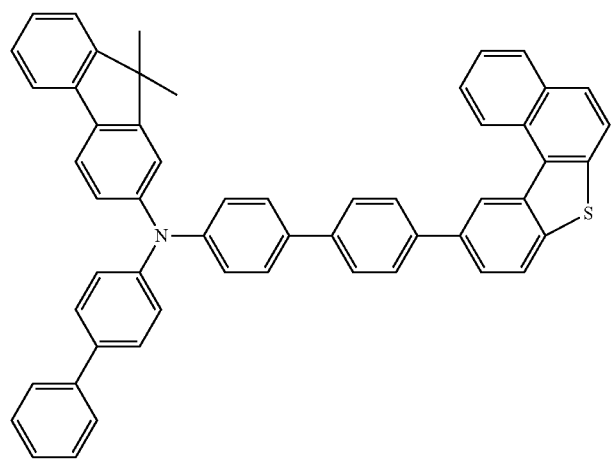
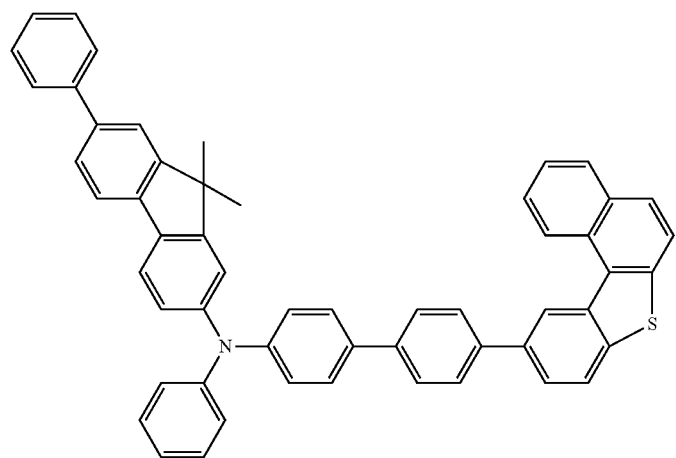
[Chem. 45]
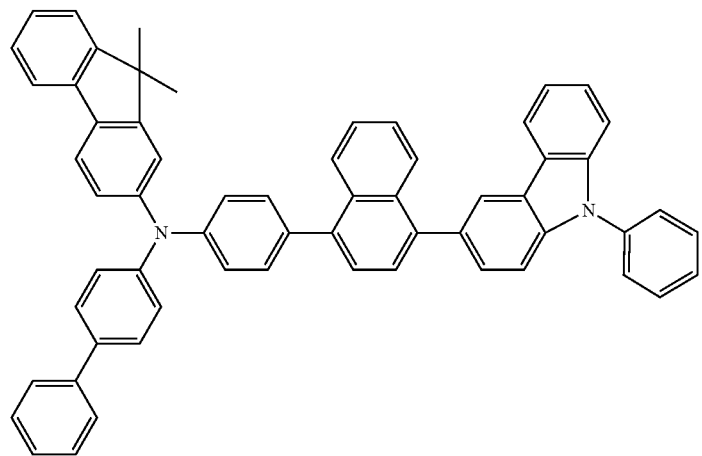

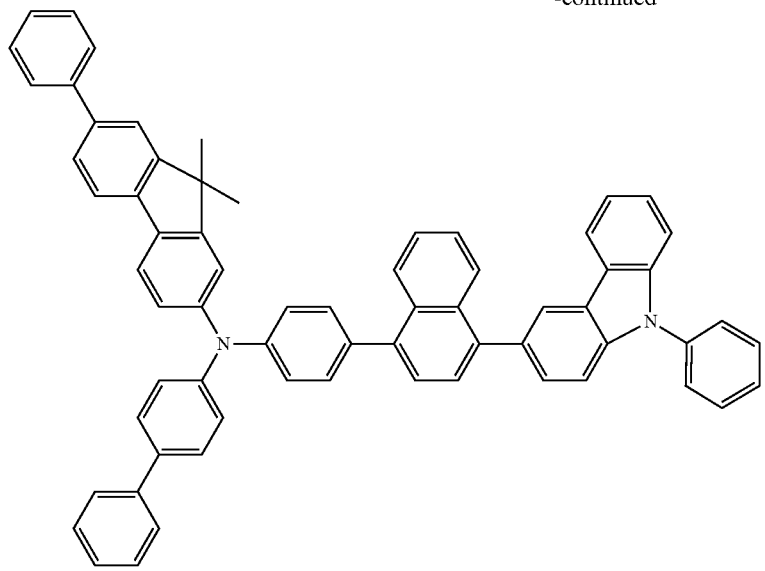
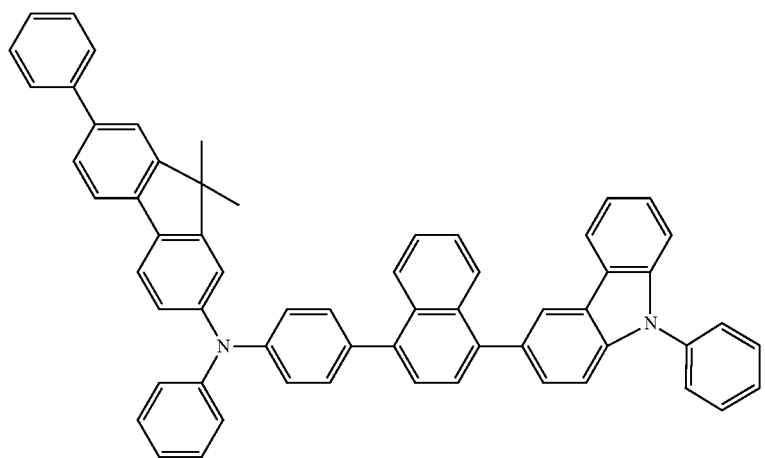
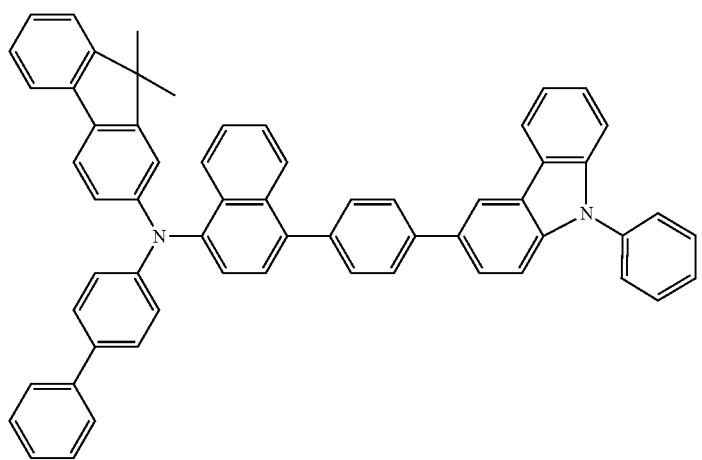

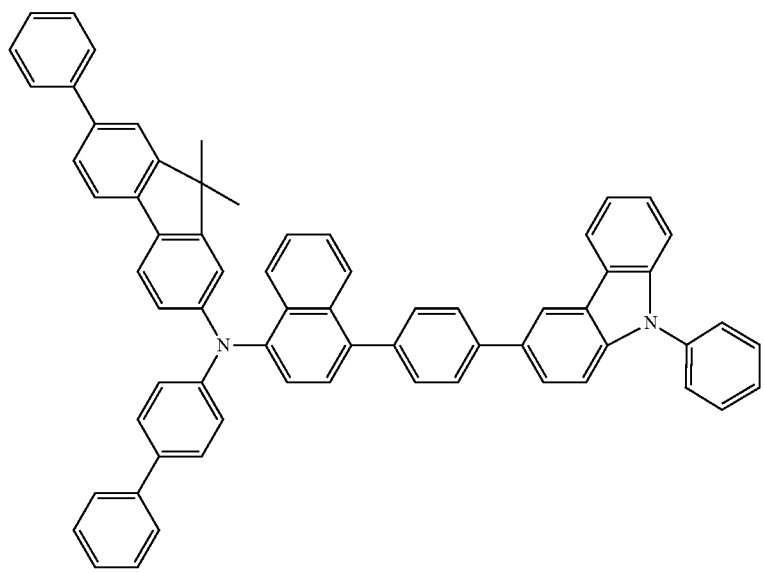
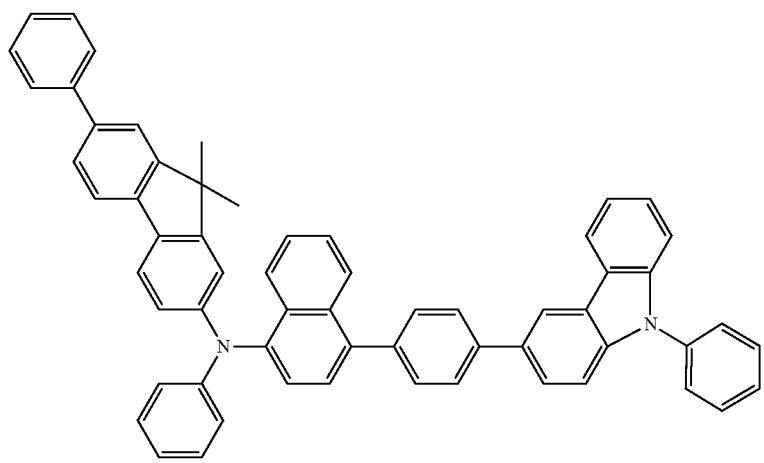
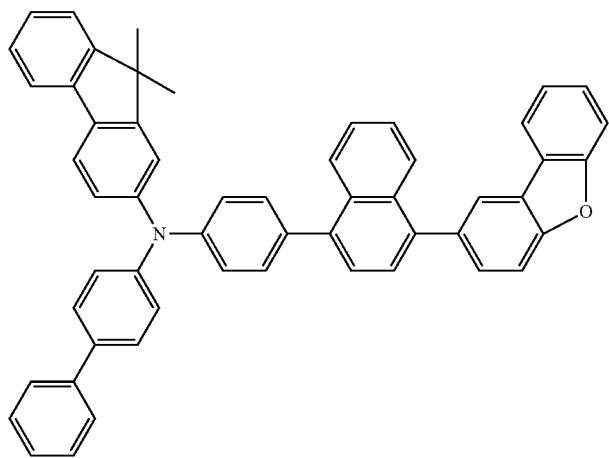

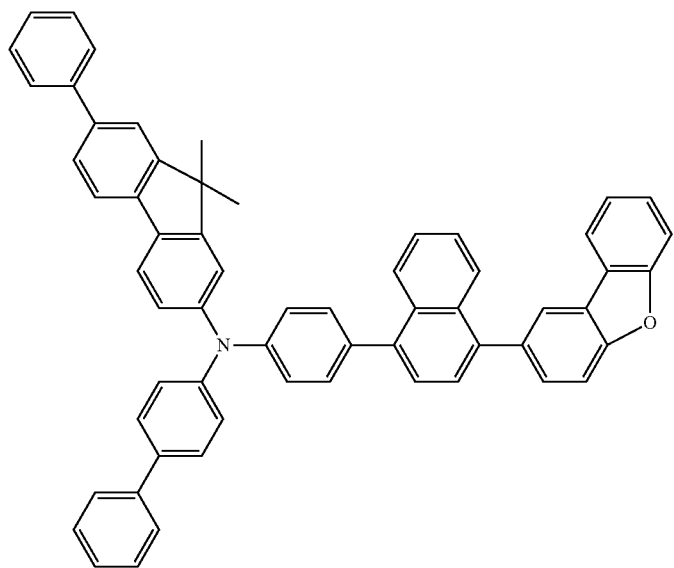
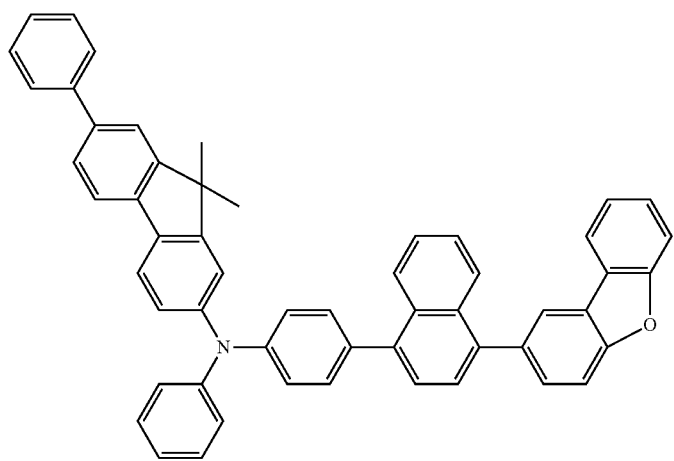
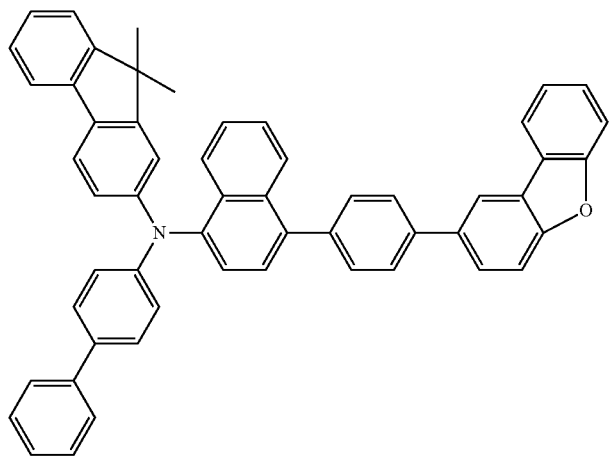

-continued
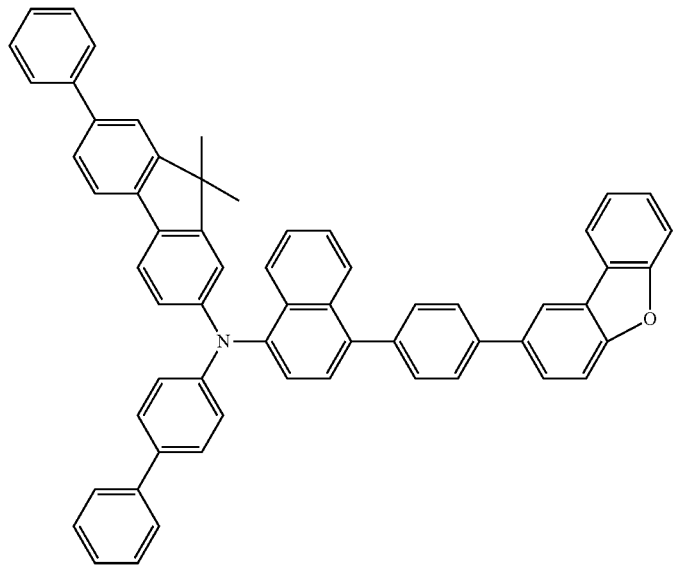
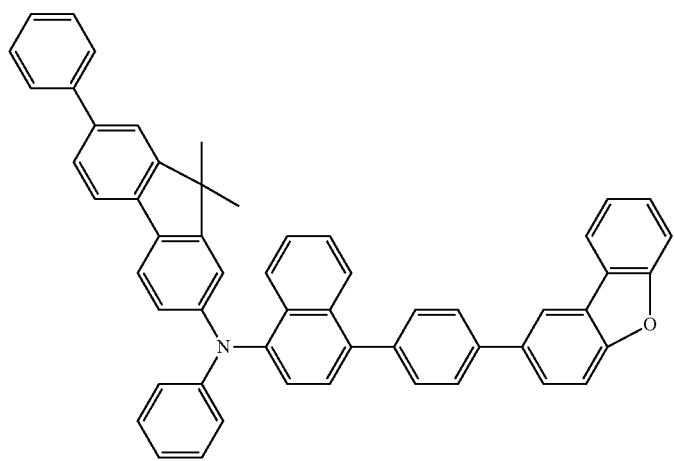
[Chem. 46]
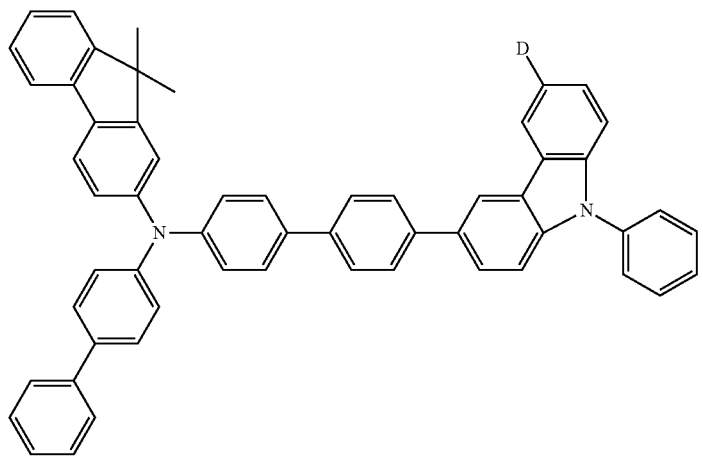

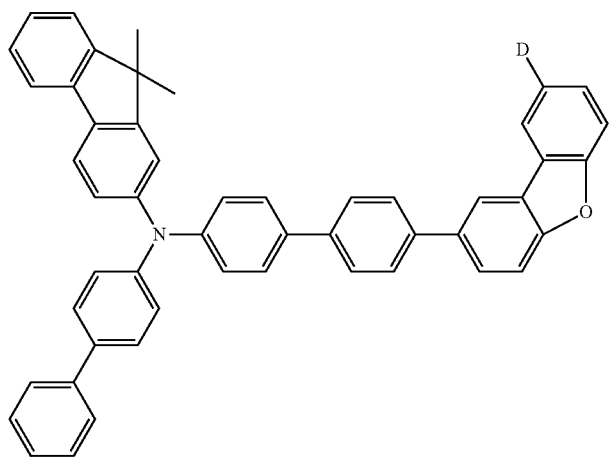
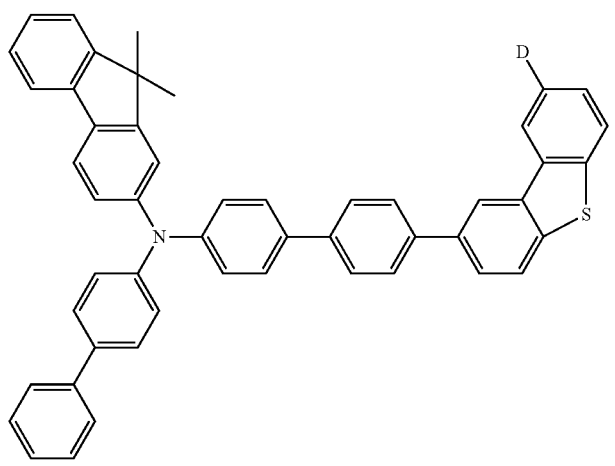
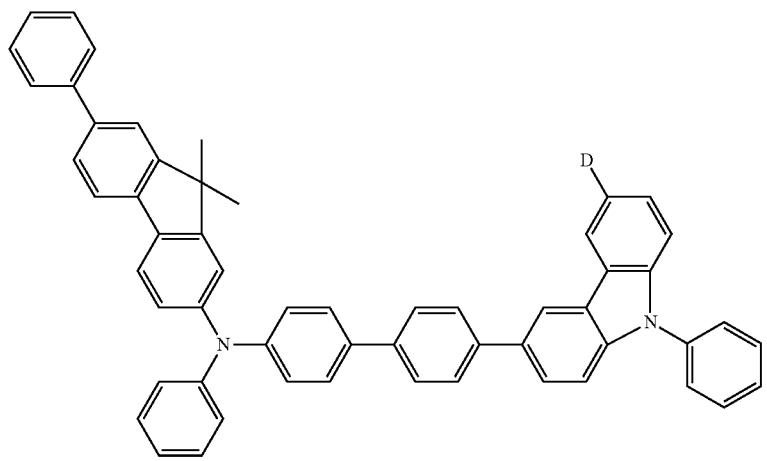

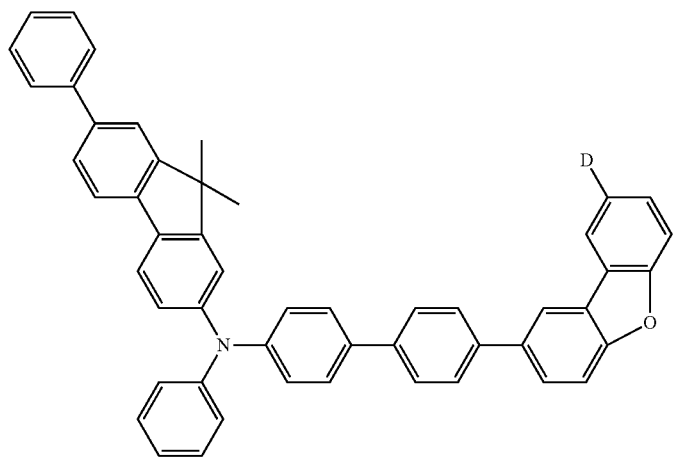
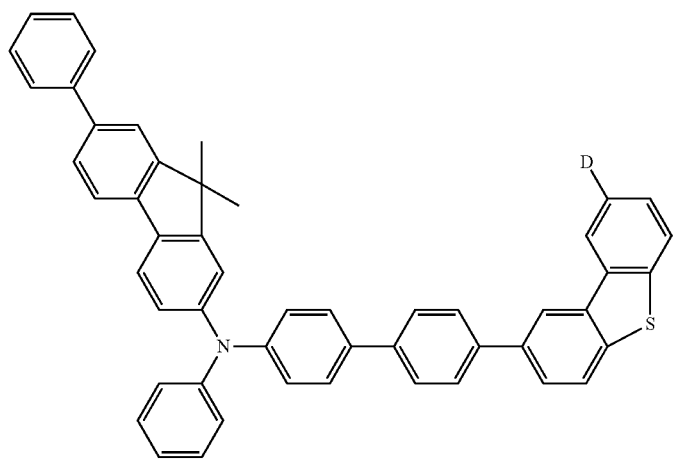
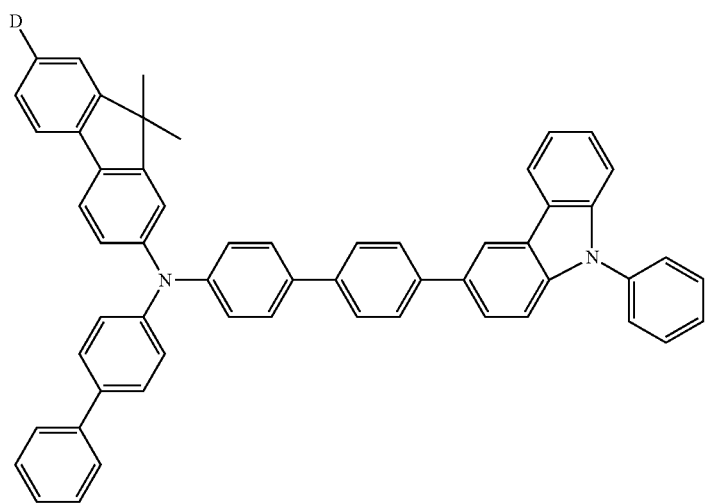

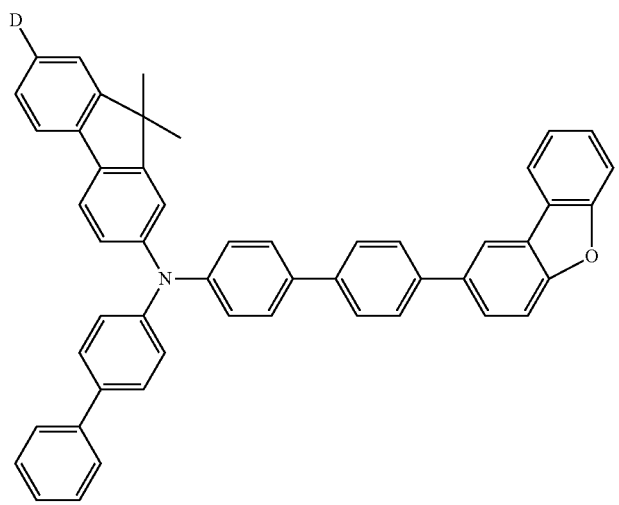
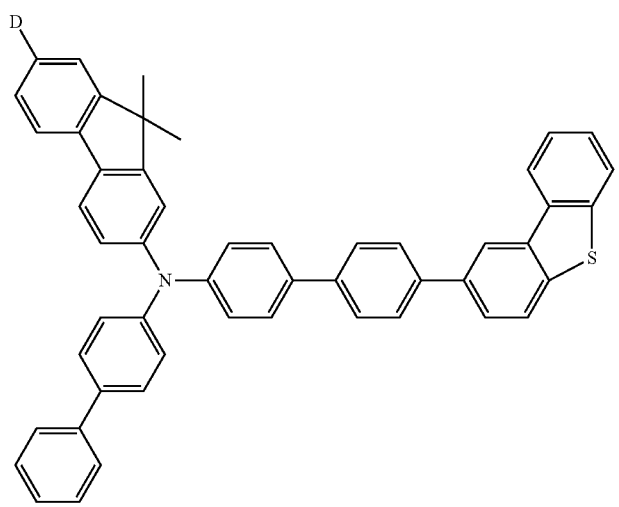
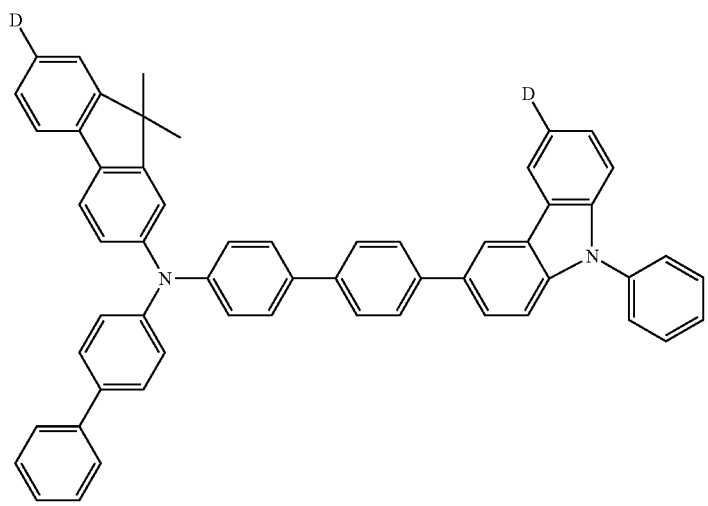

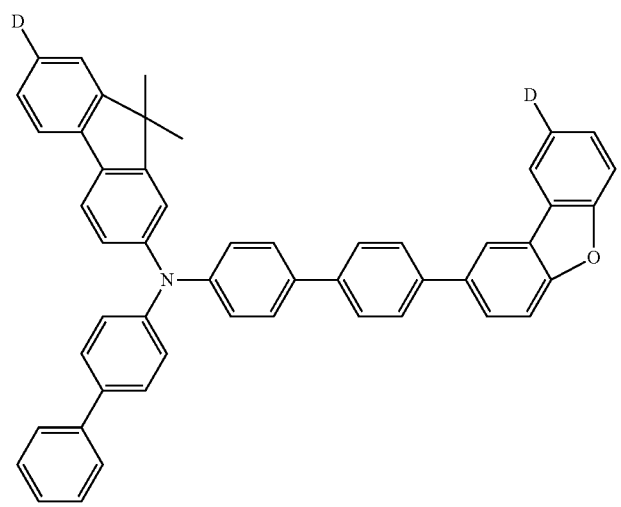
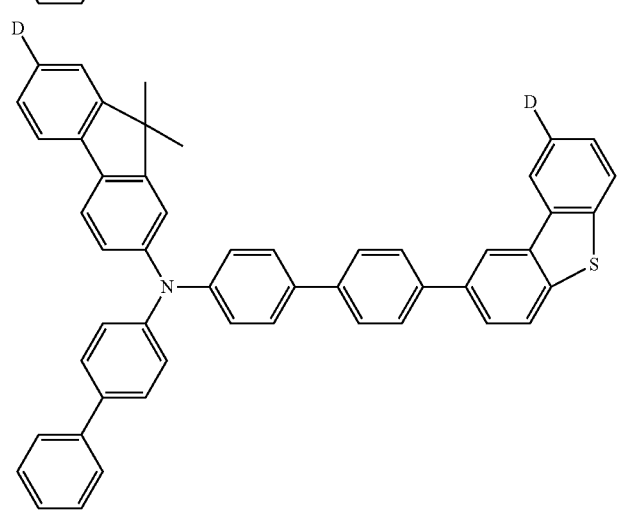
[Chem. 47]
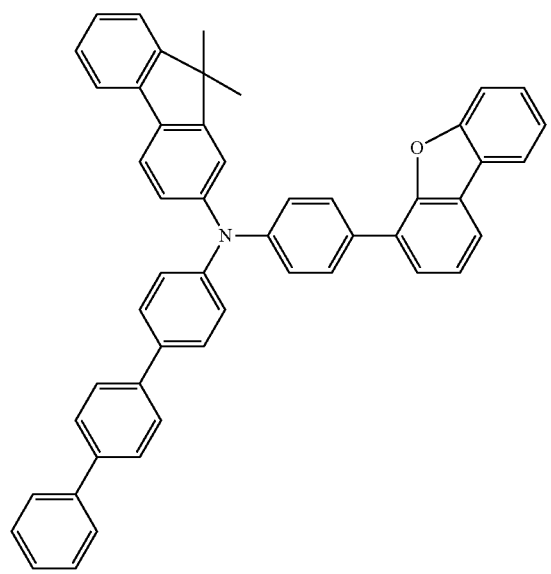
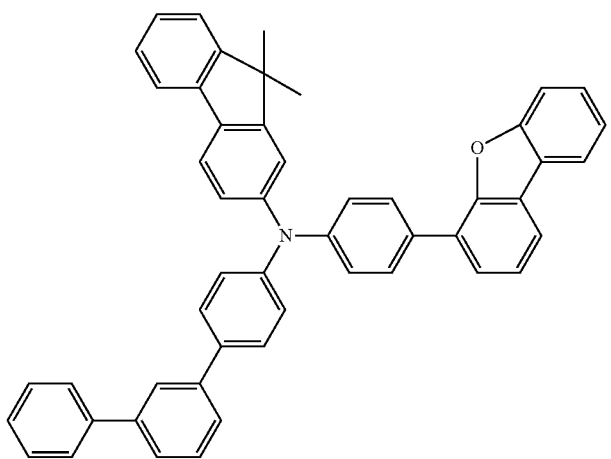

-continued
227
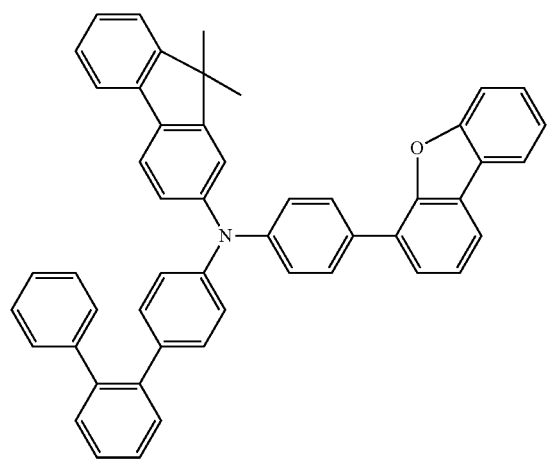
228
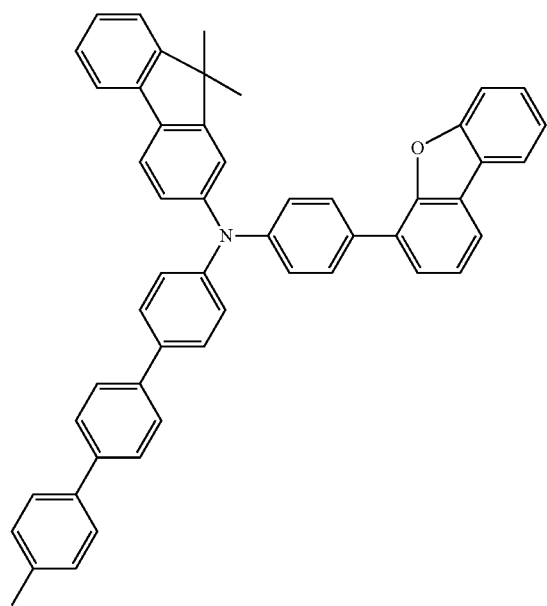
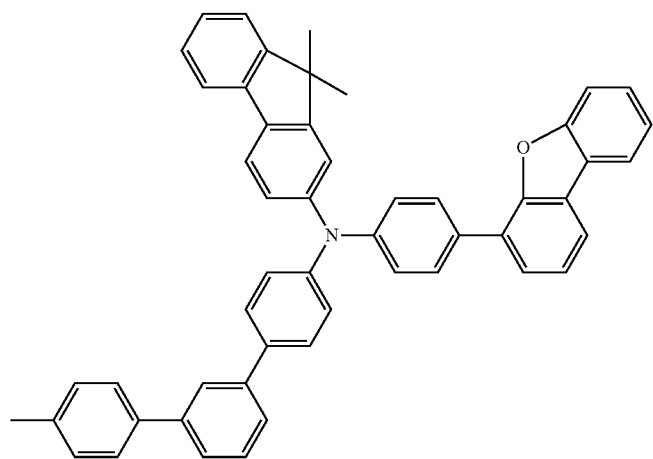
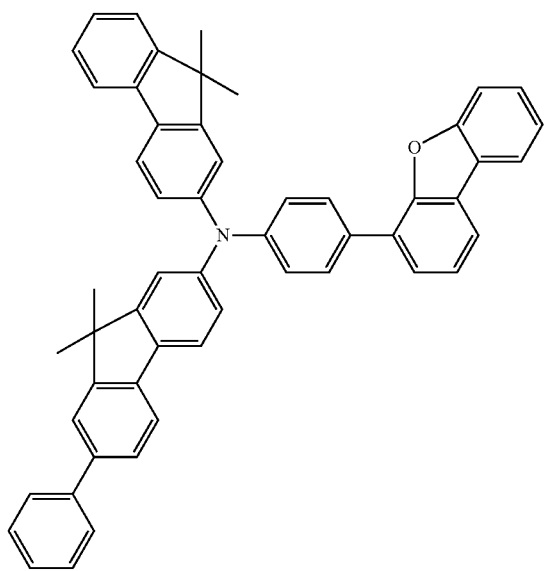

-continued
229
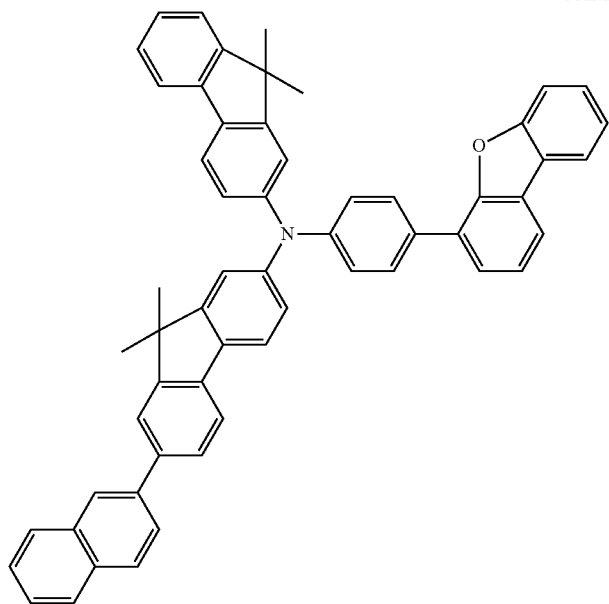
230
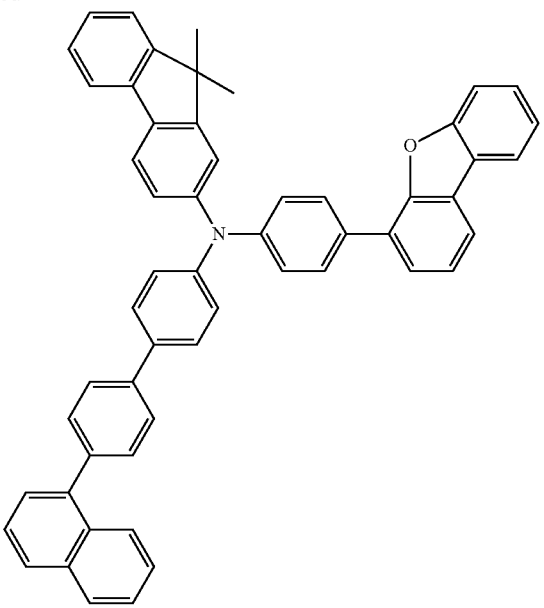
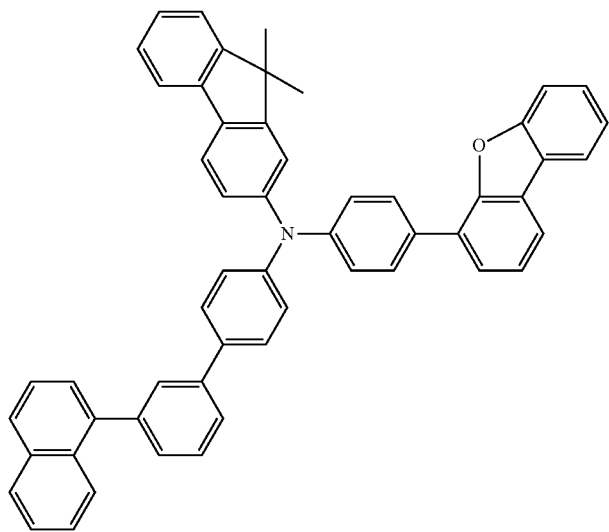
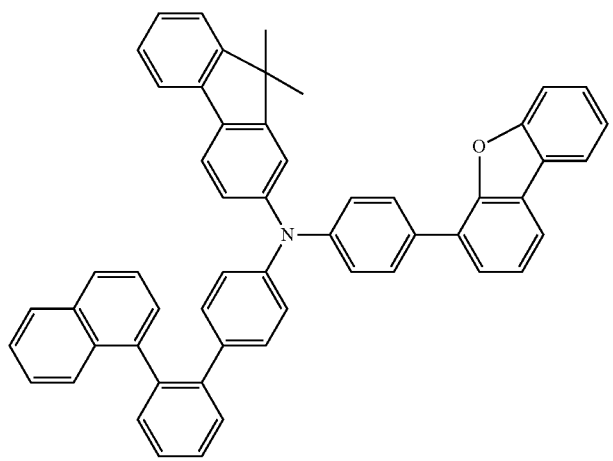

[Chem. 48]
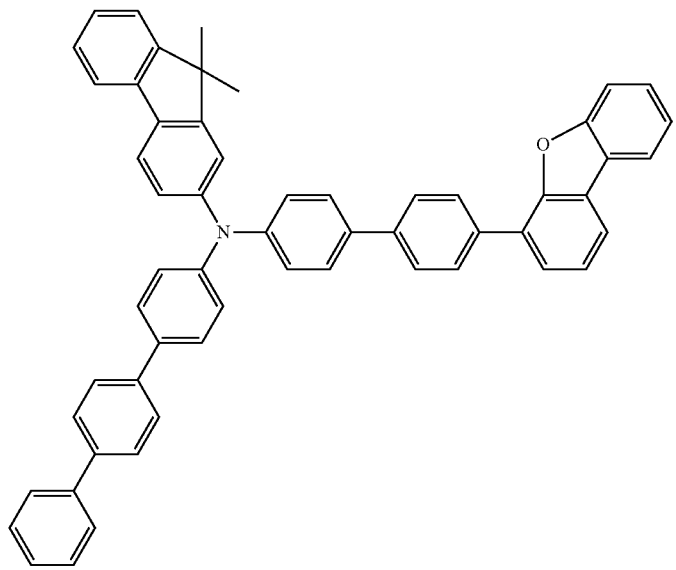
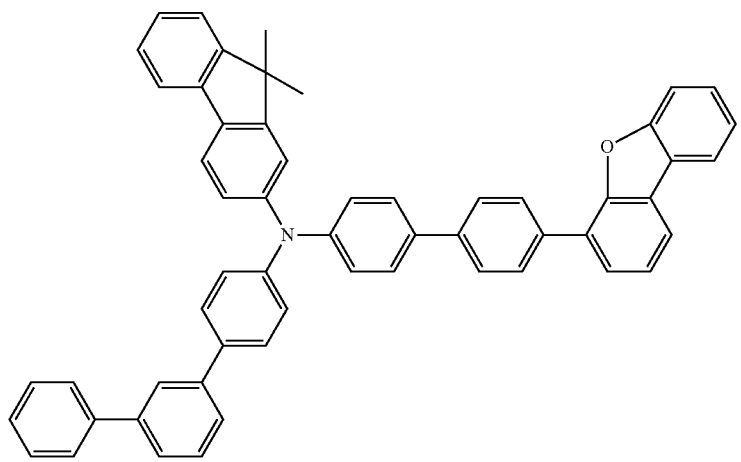
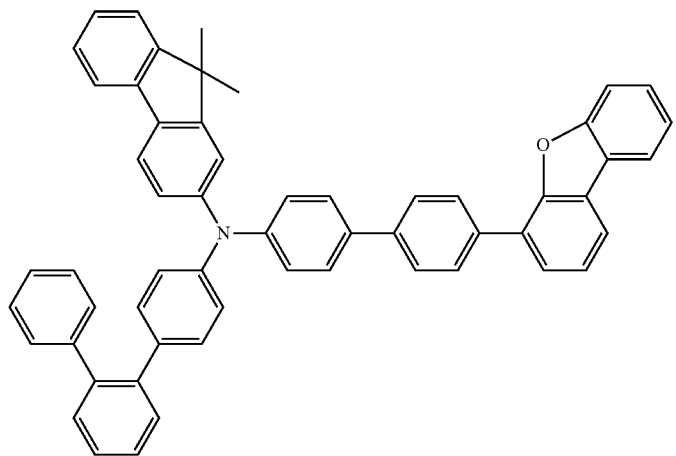

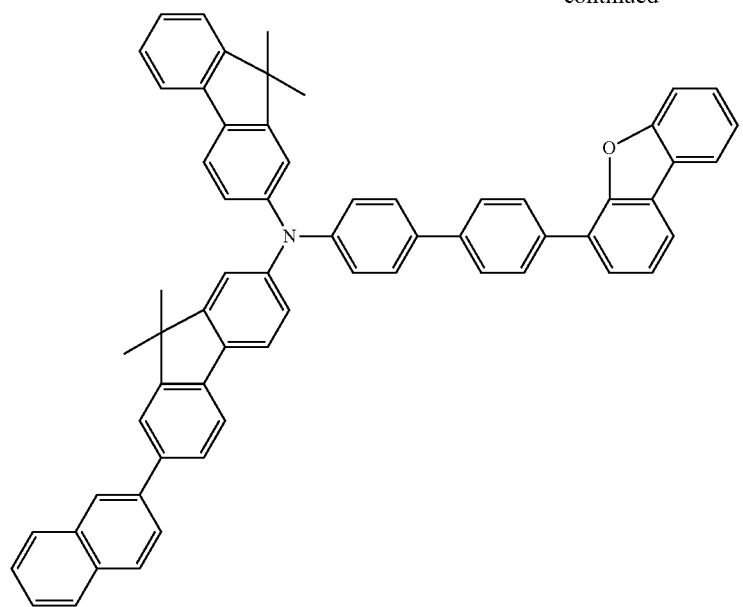
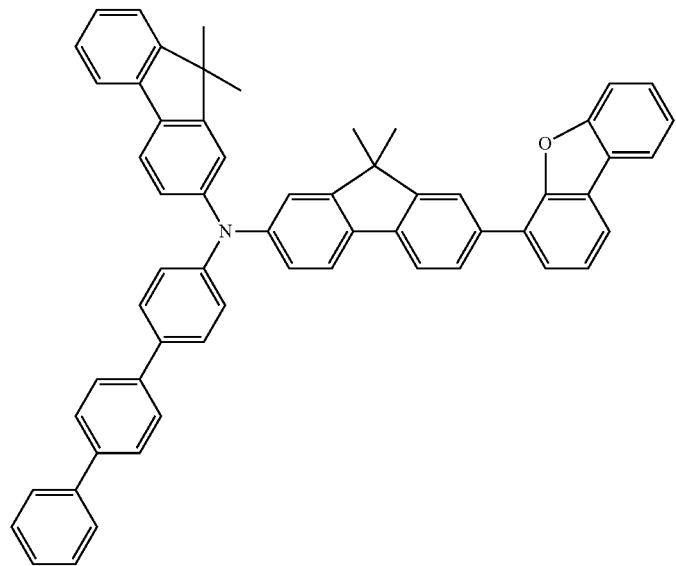
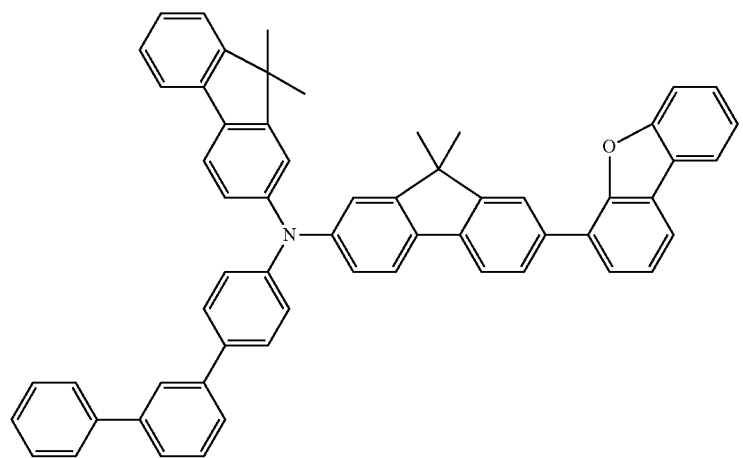

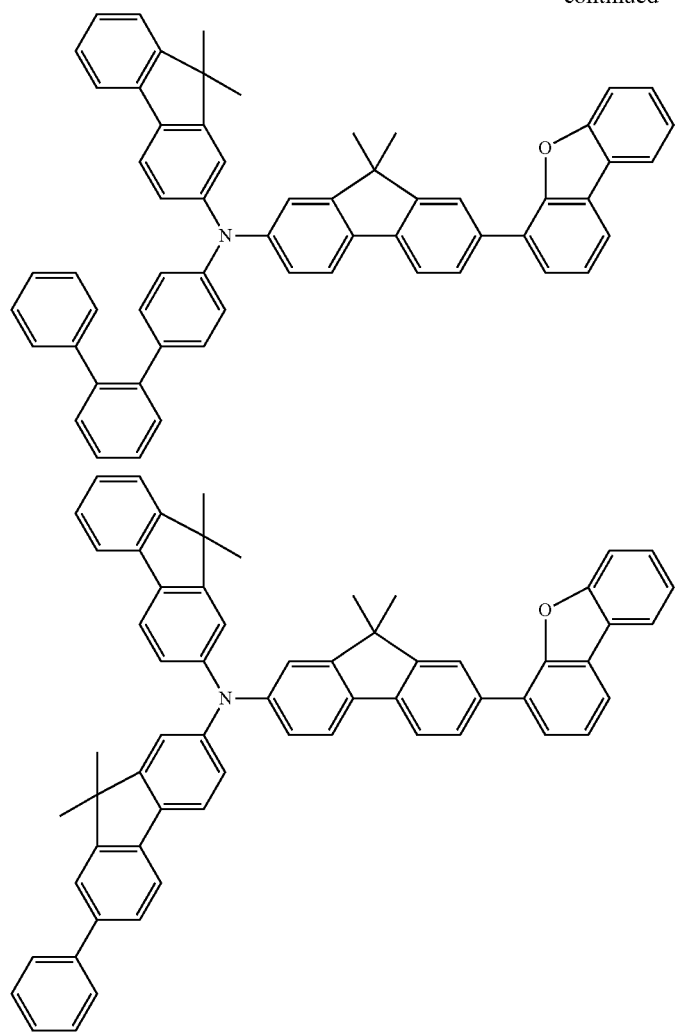
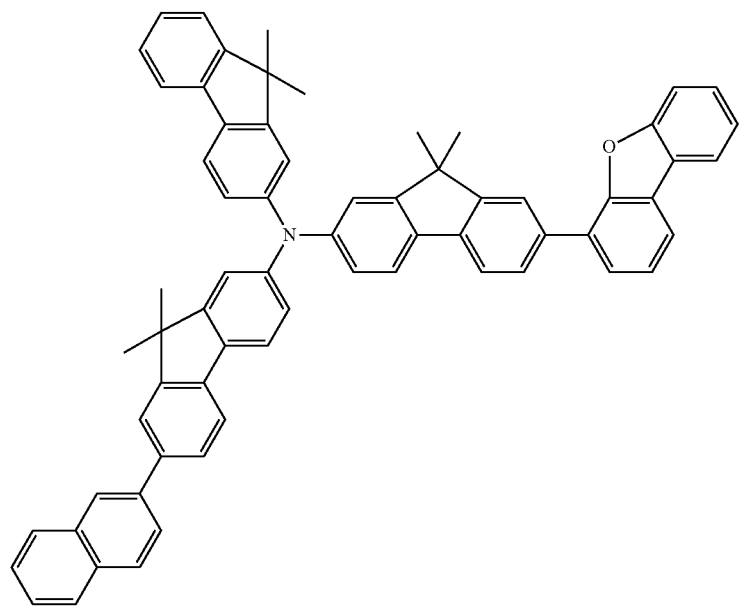

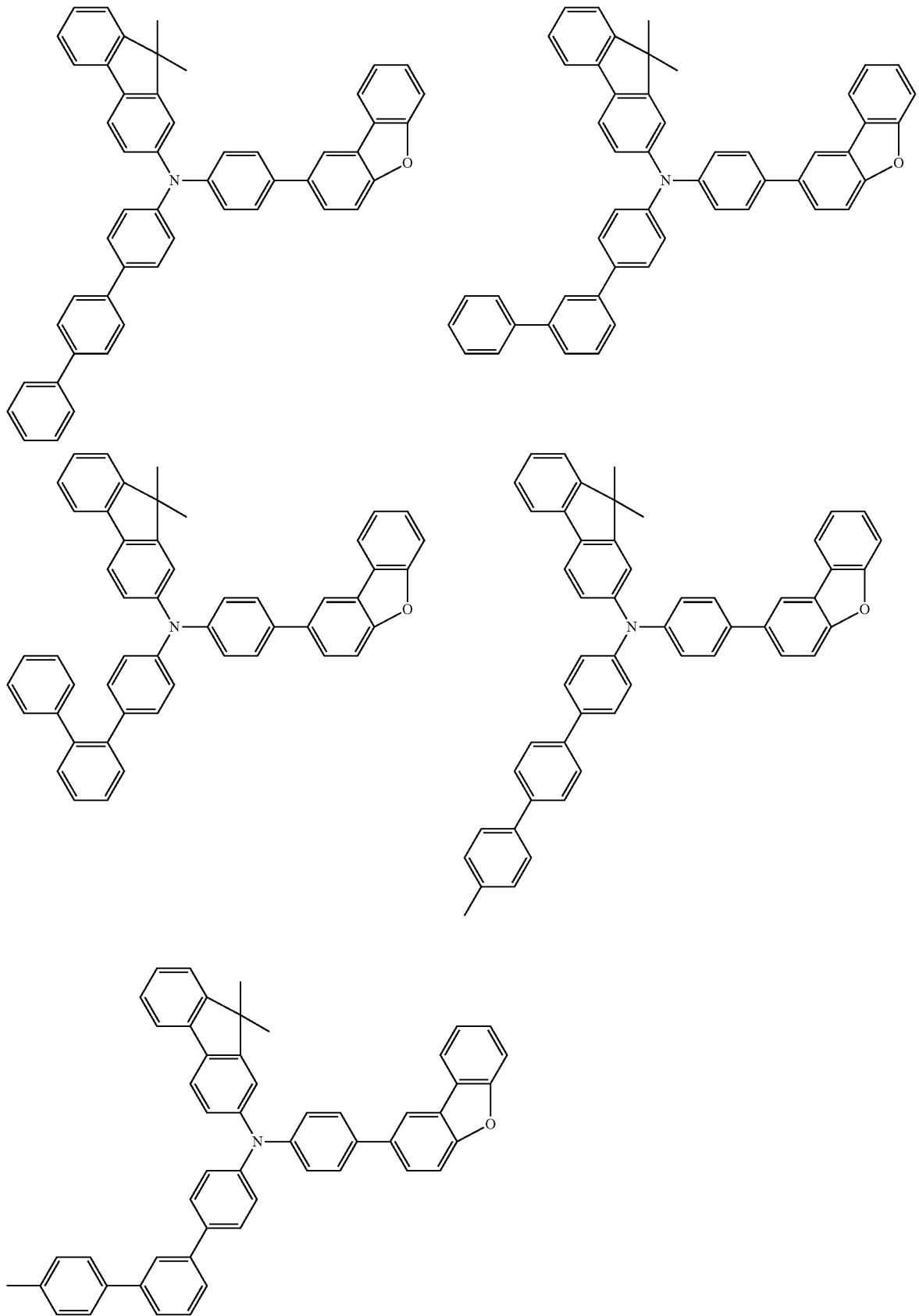

-continued
239
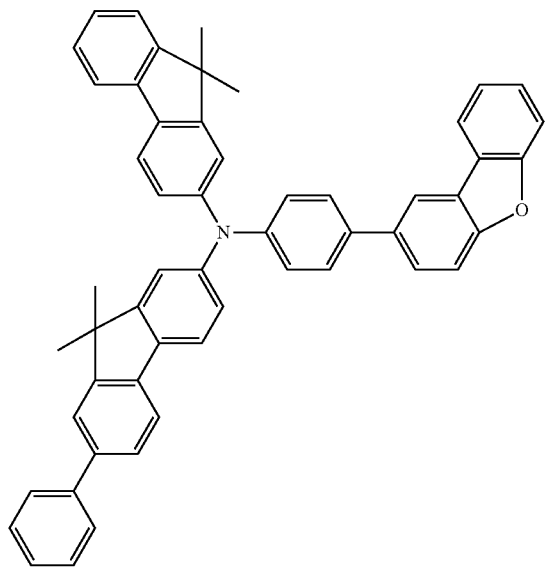
240
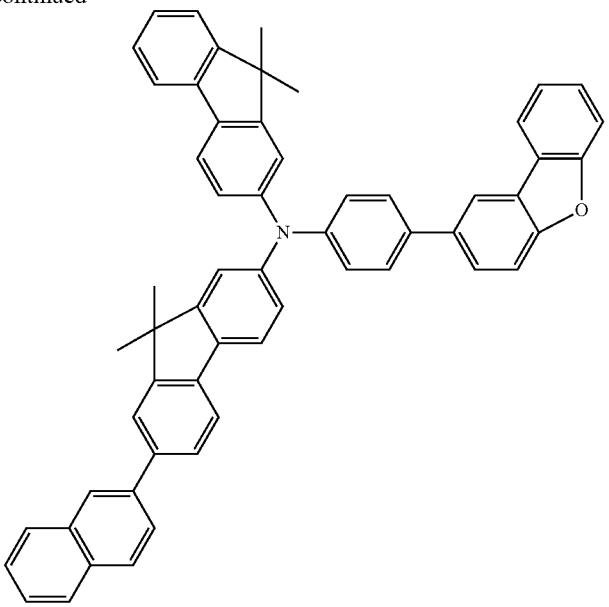
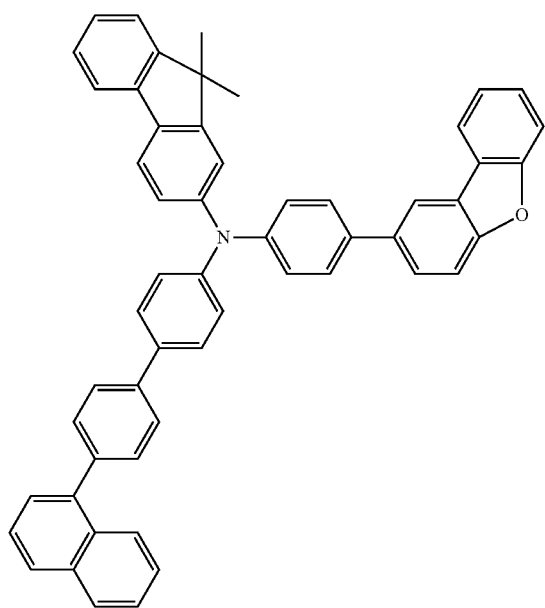
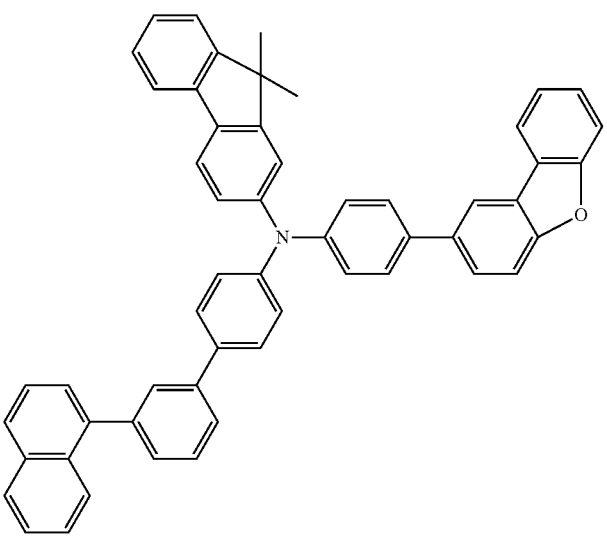
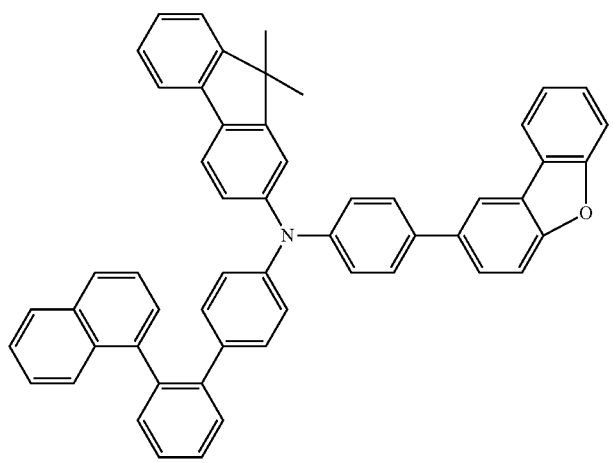

[Chem. 50]
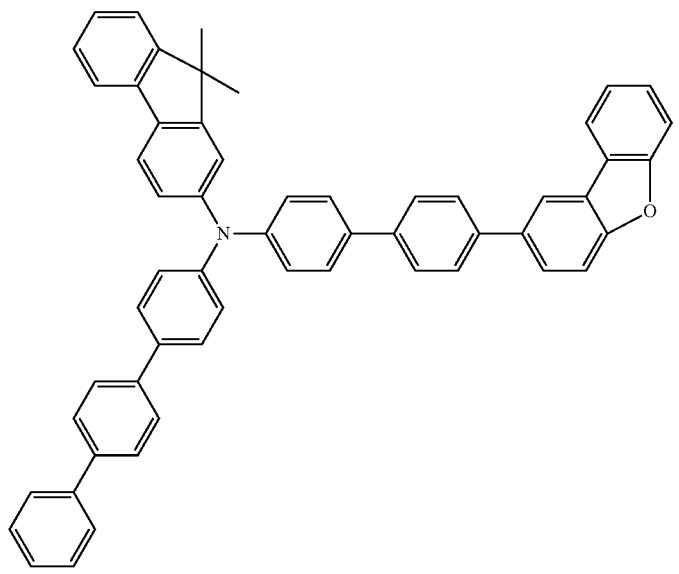
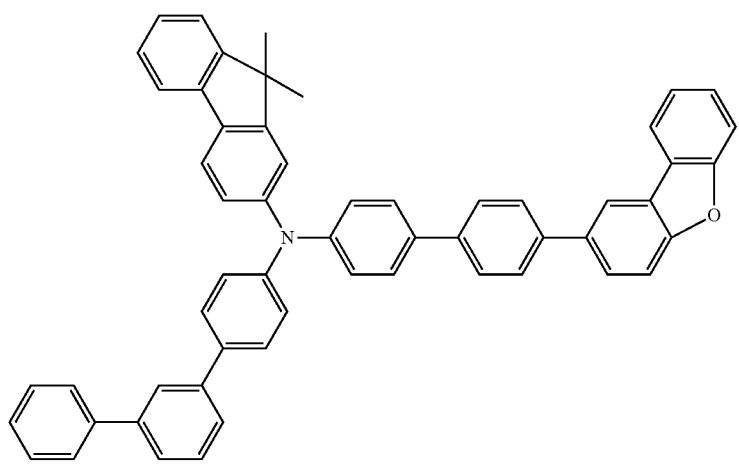
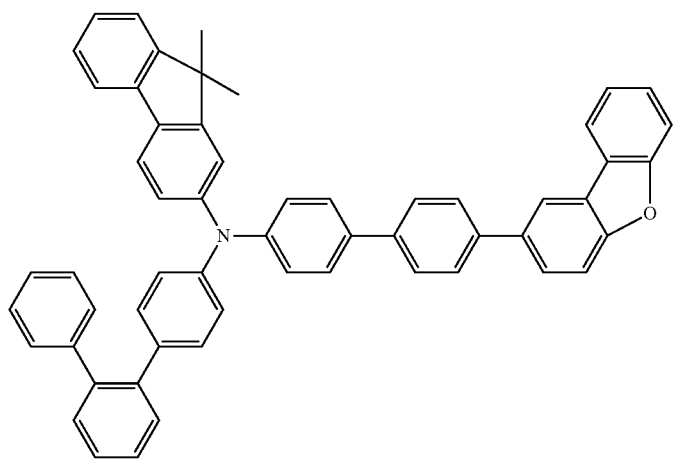

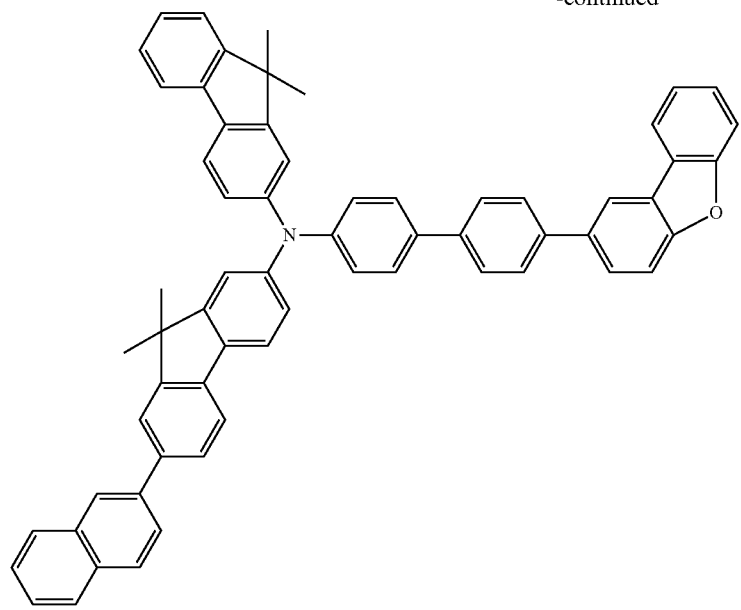
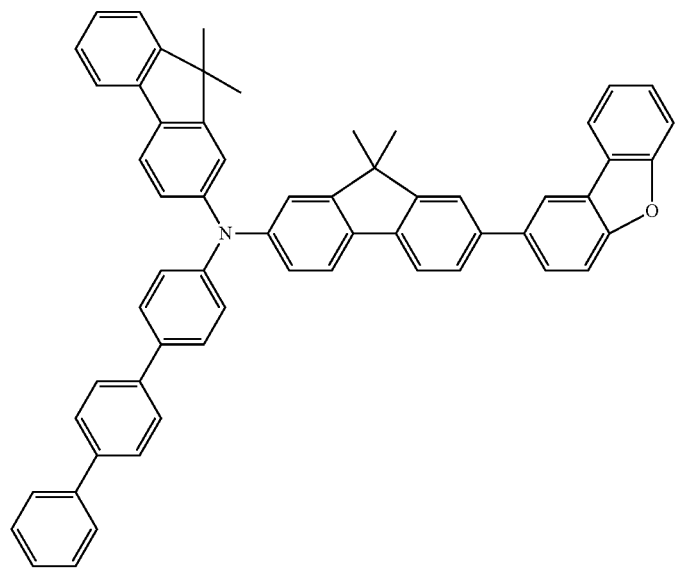
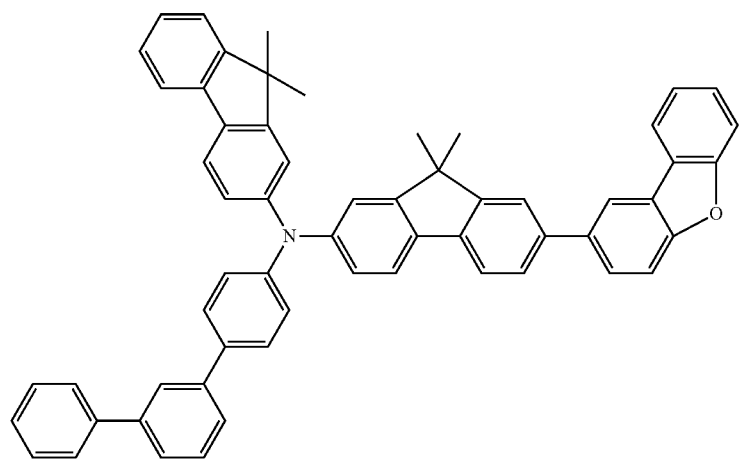

-continued
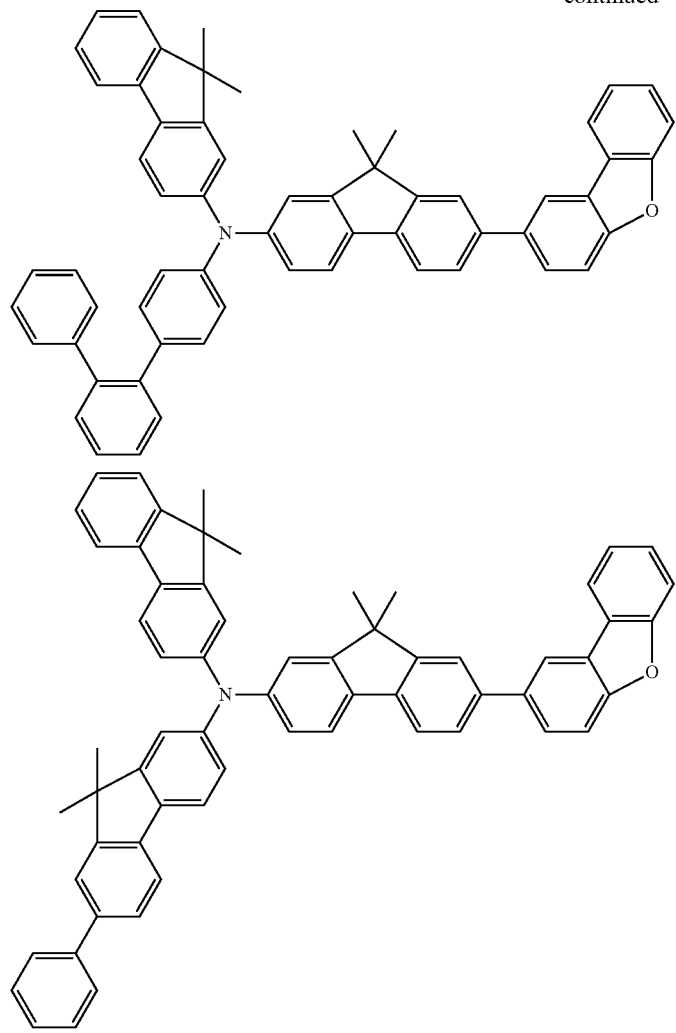
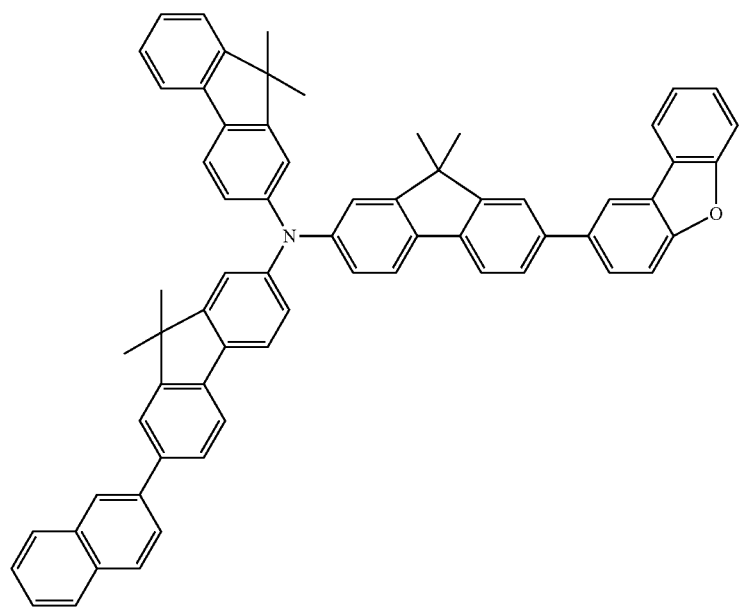

[Chem. 51]
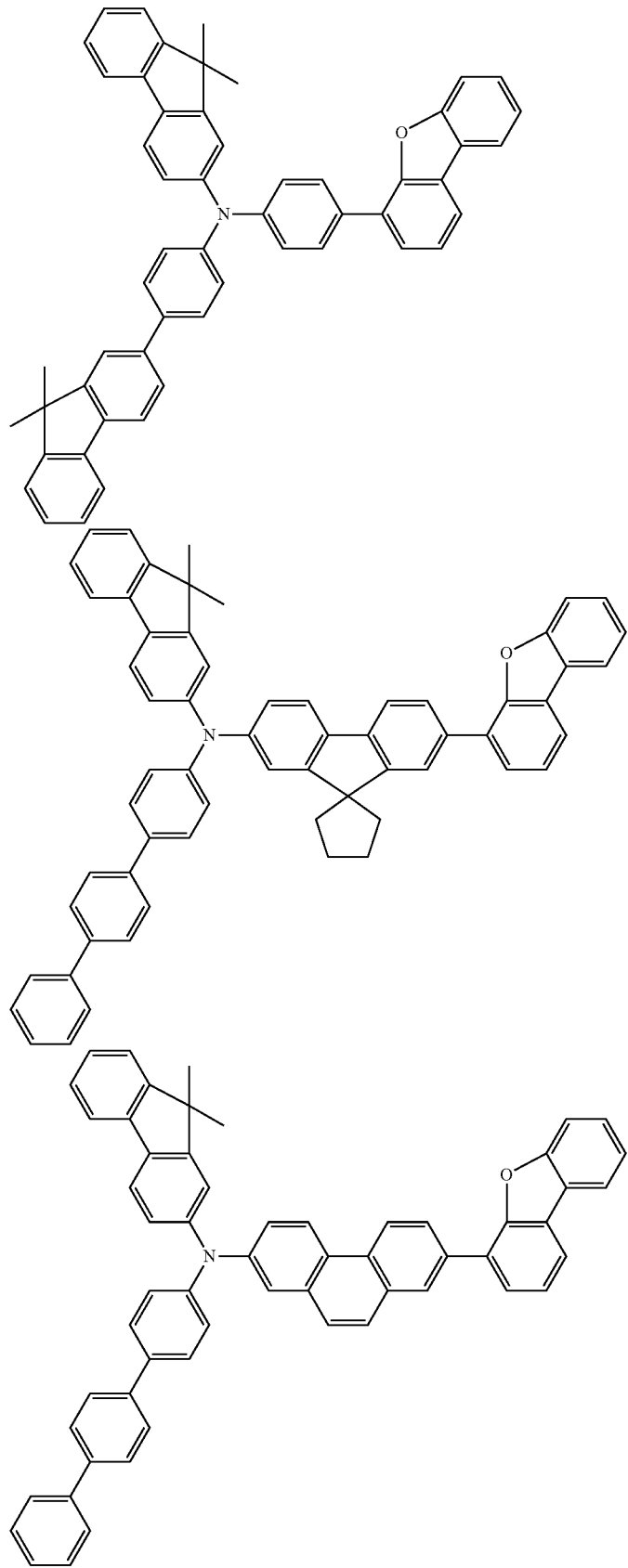

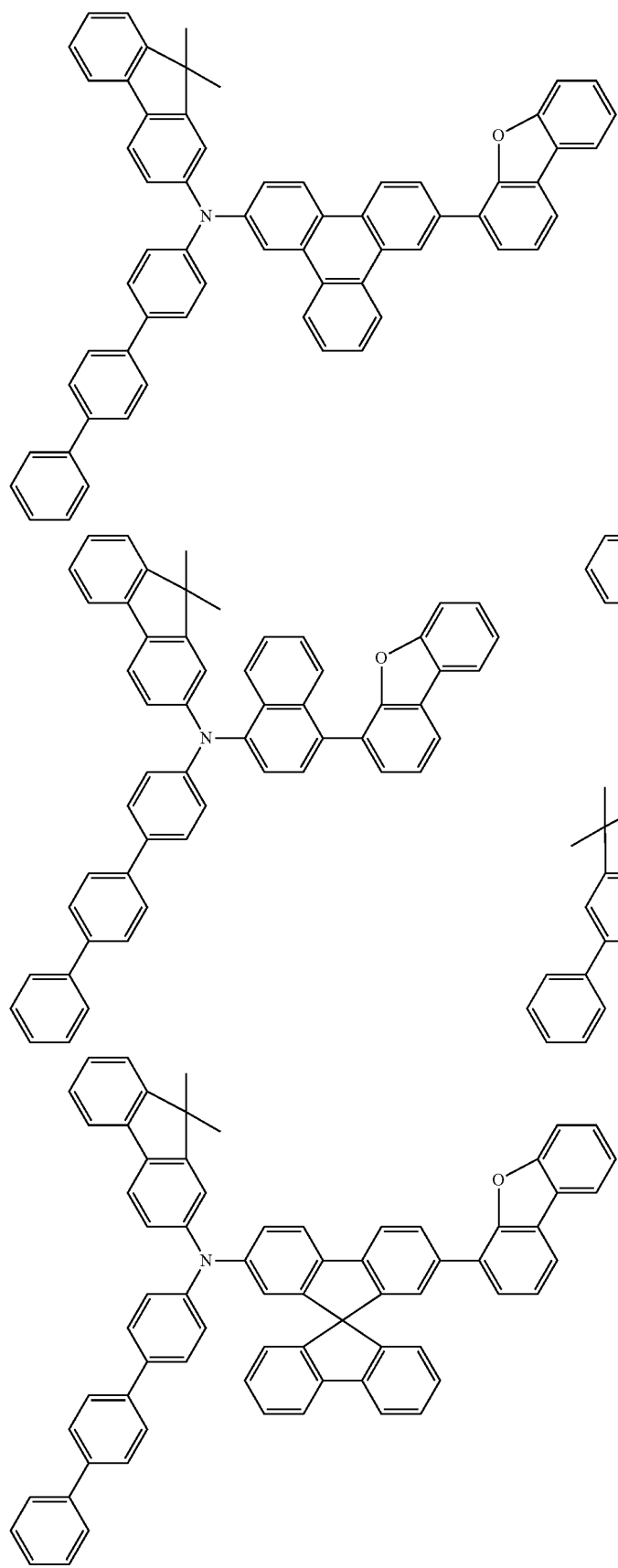

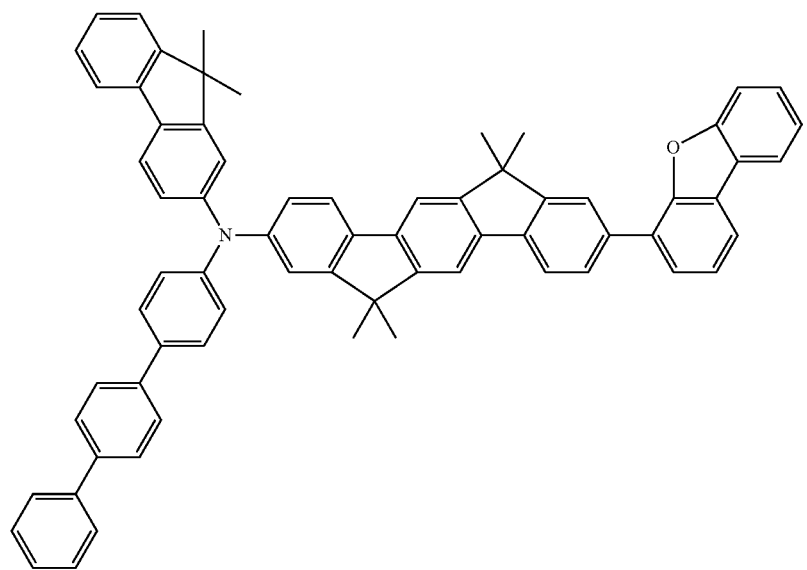
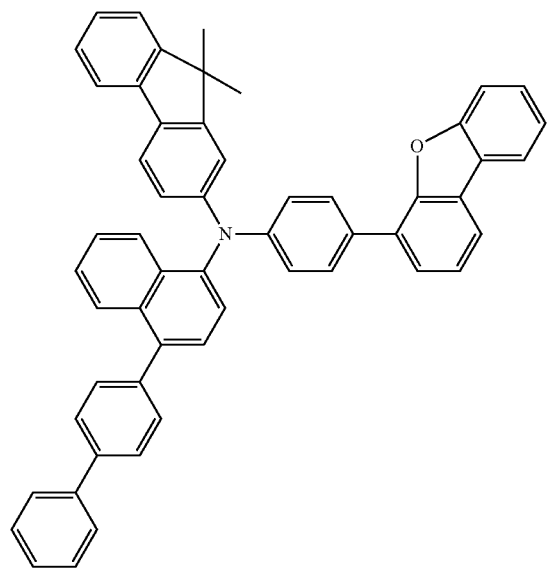
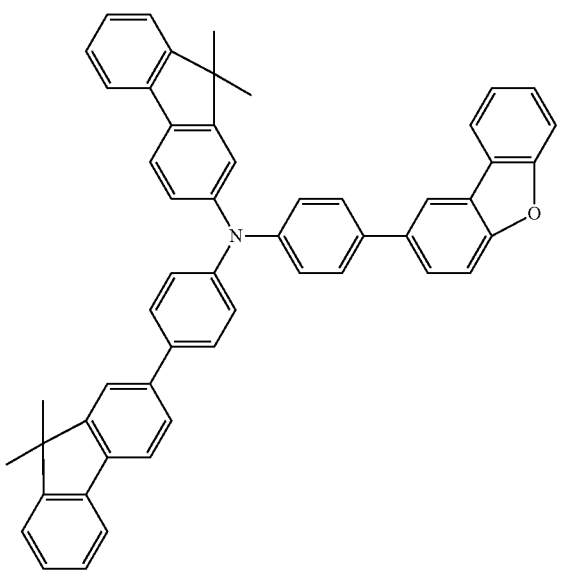
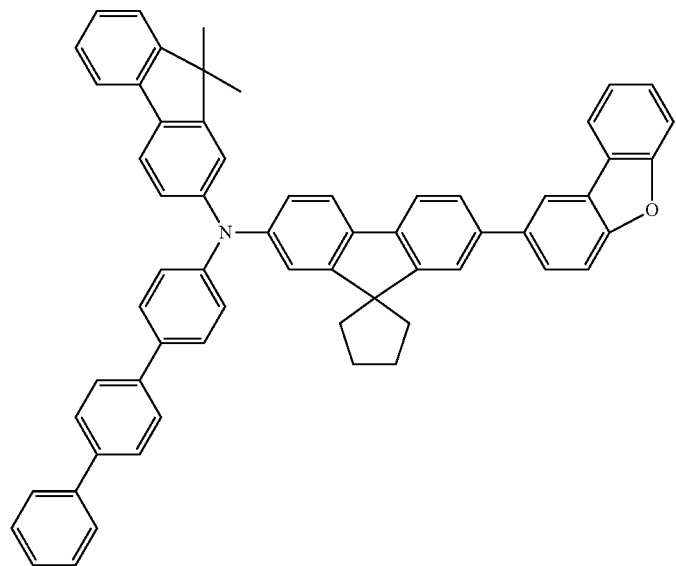

-continued
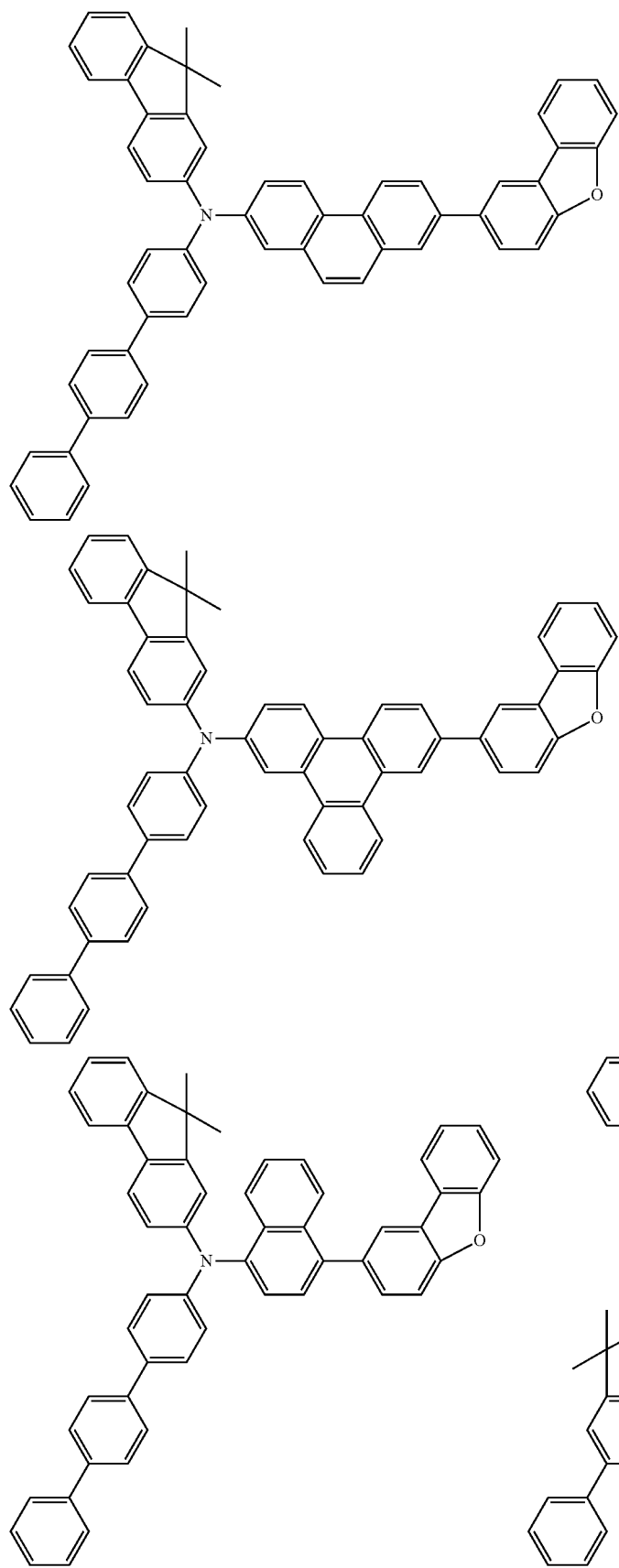
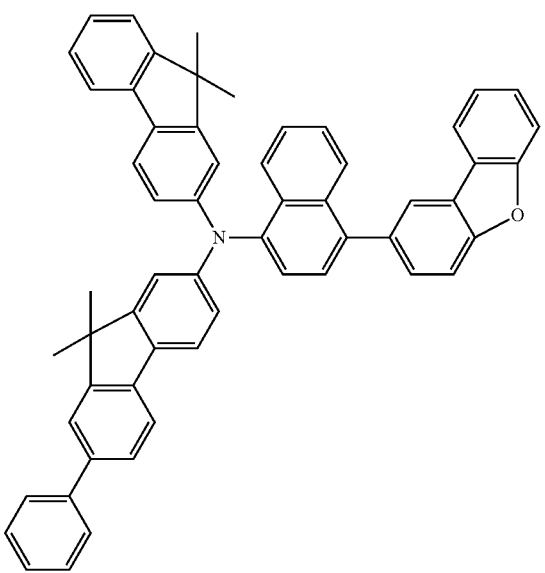

[Chem. 52]
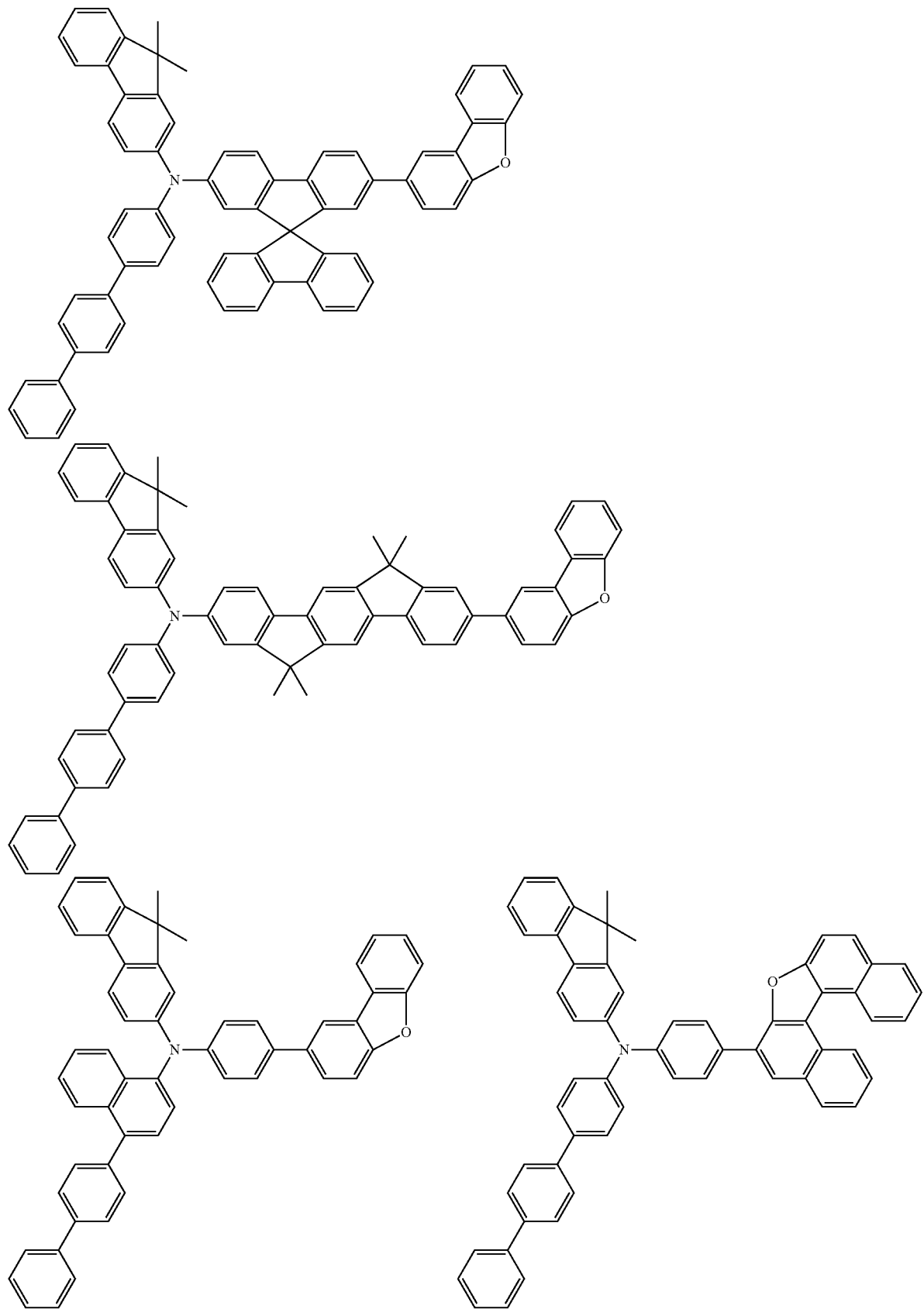

257 258
-continued
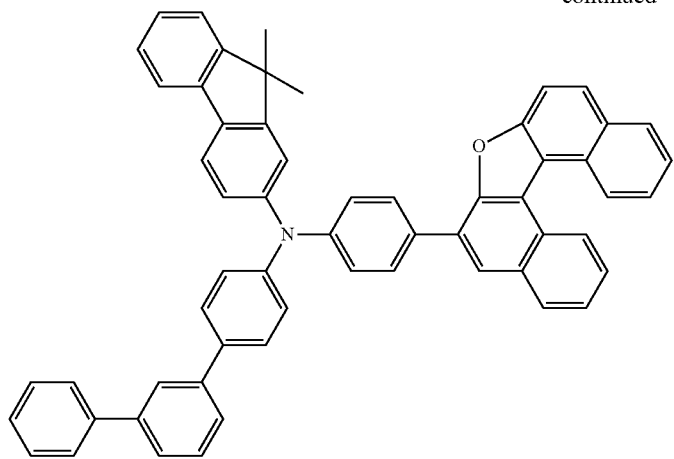
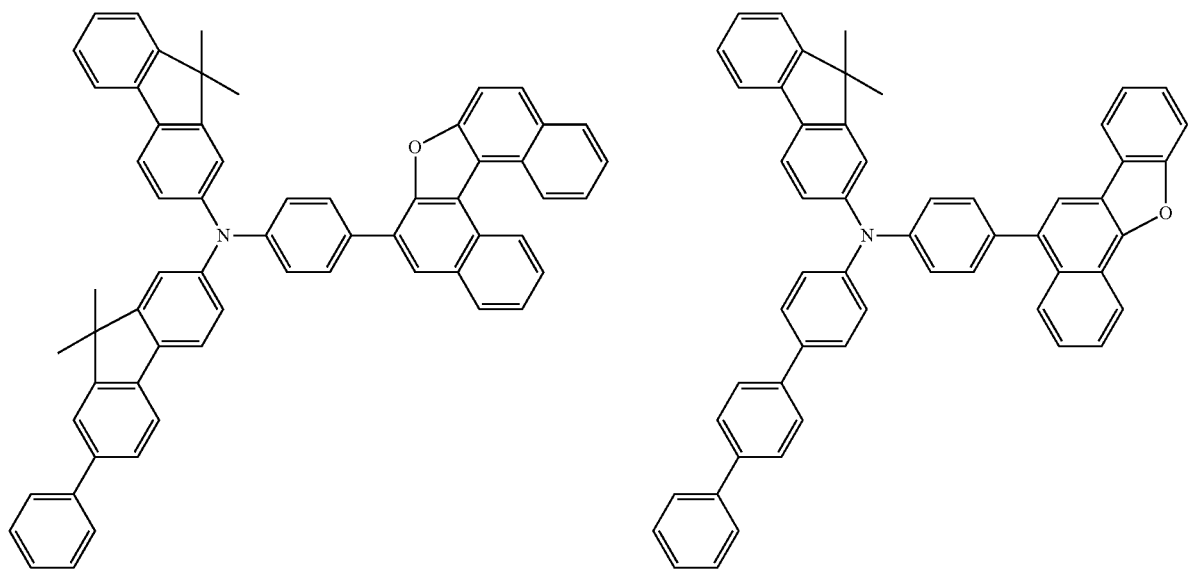
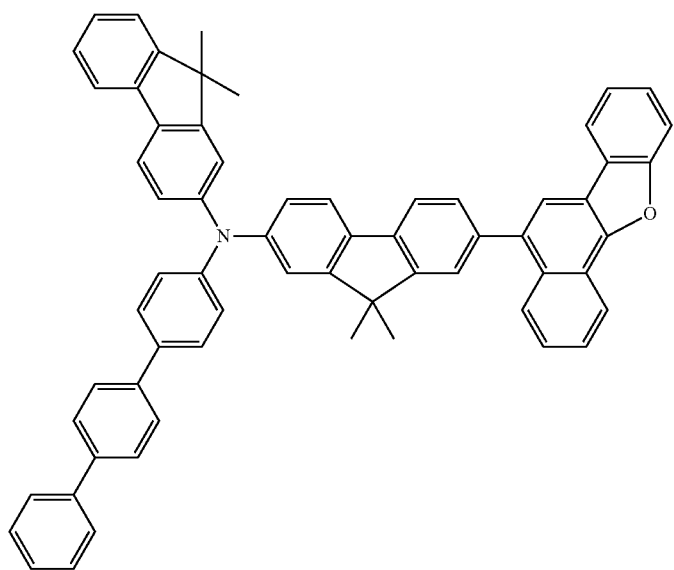

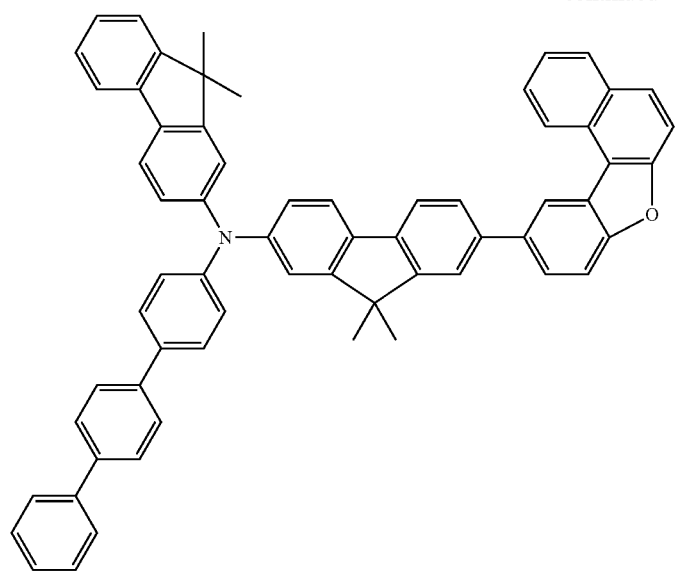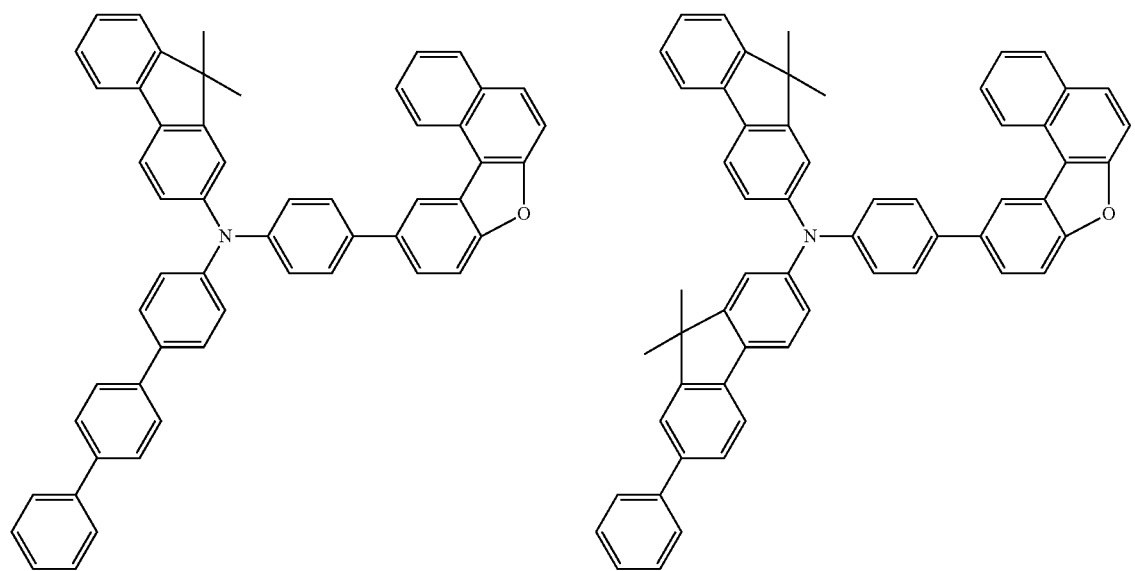

[Chem. 53]
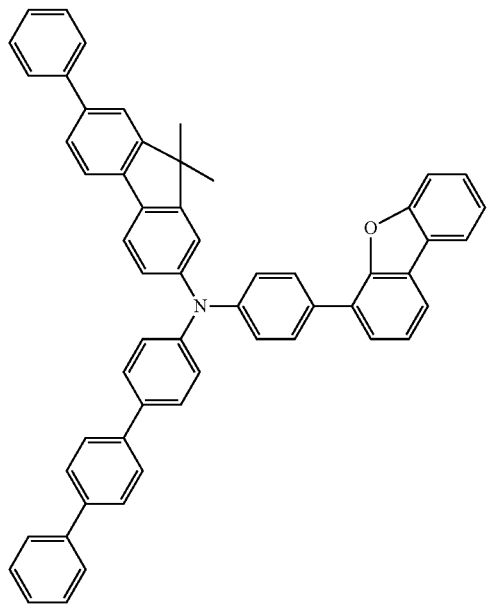
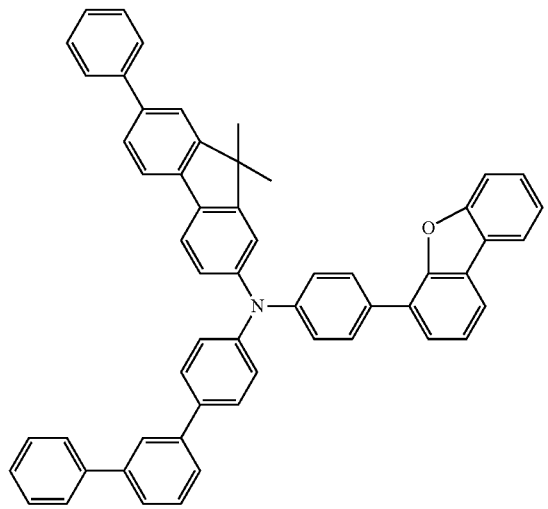
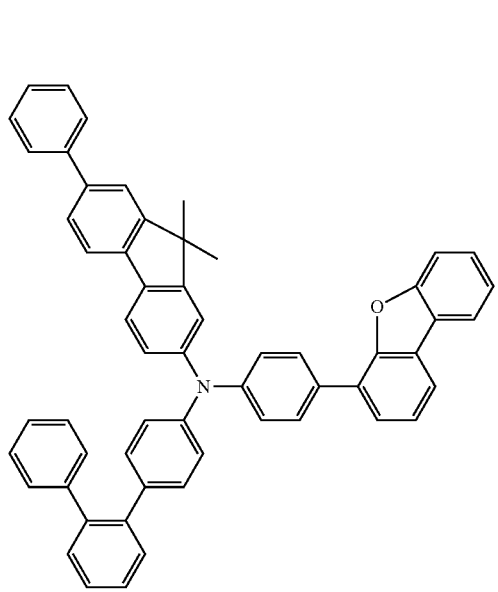
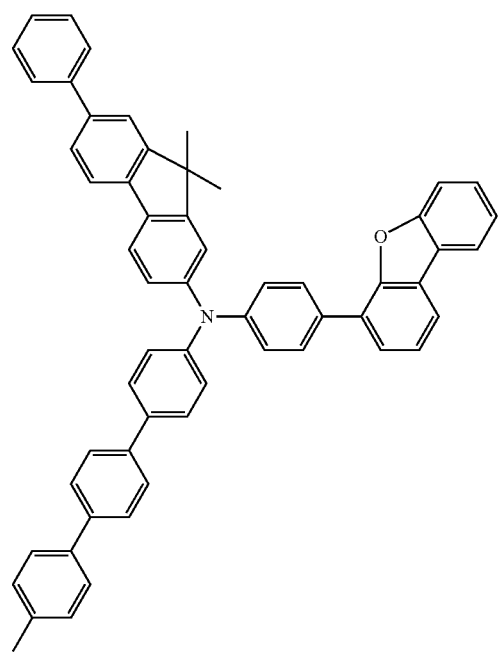

263
264
-continued
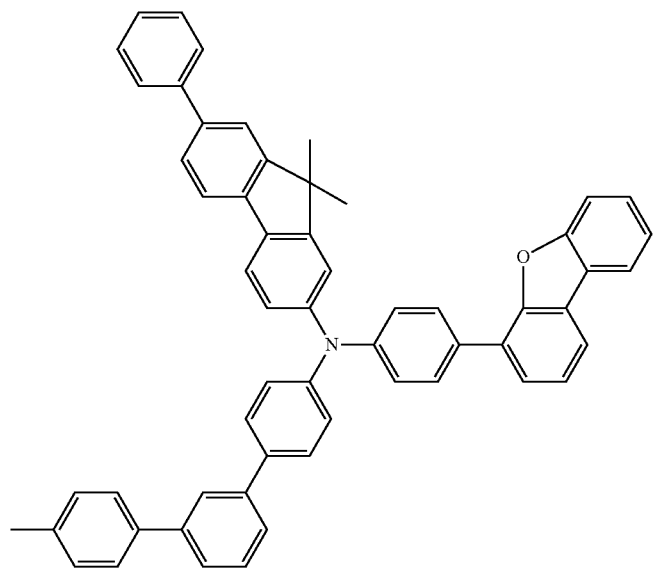
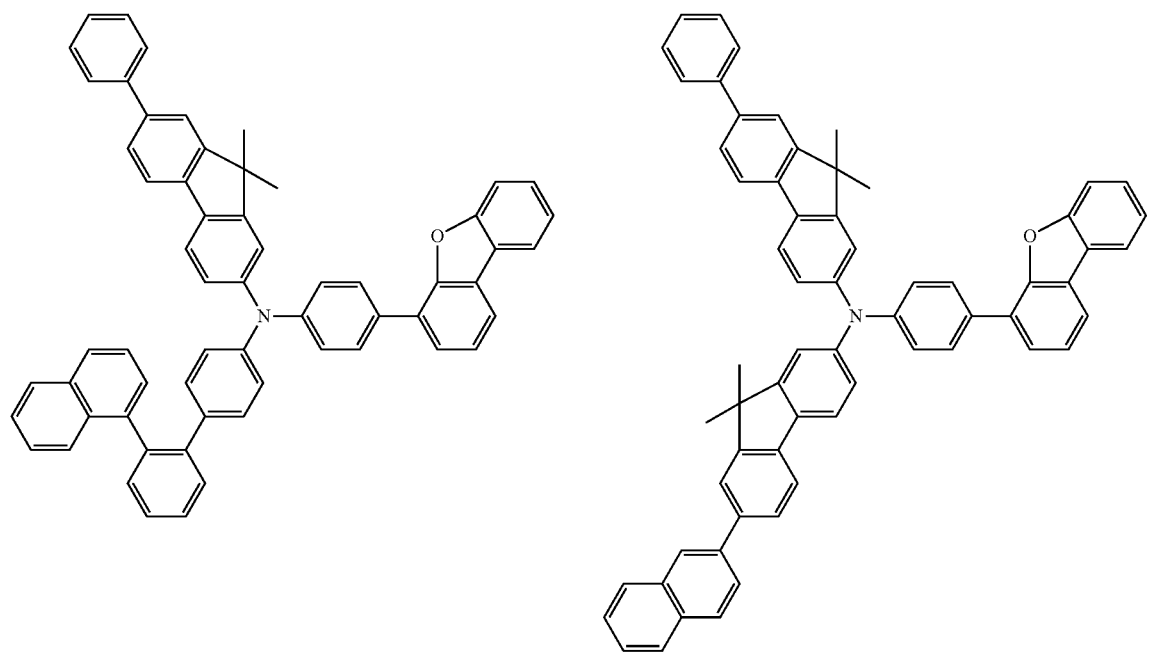

265
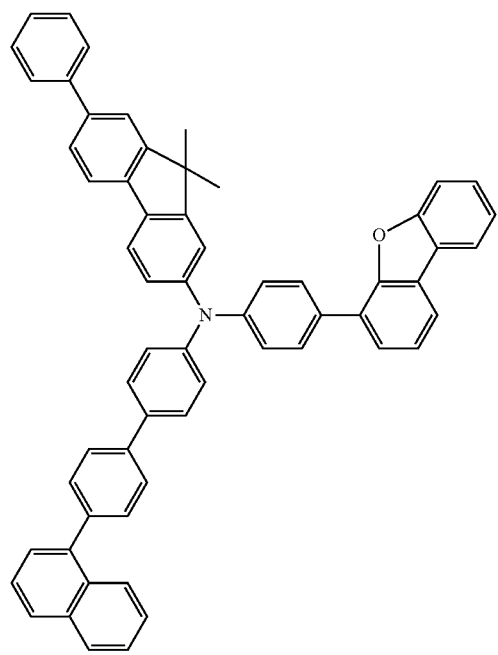
-continued
266
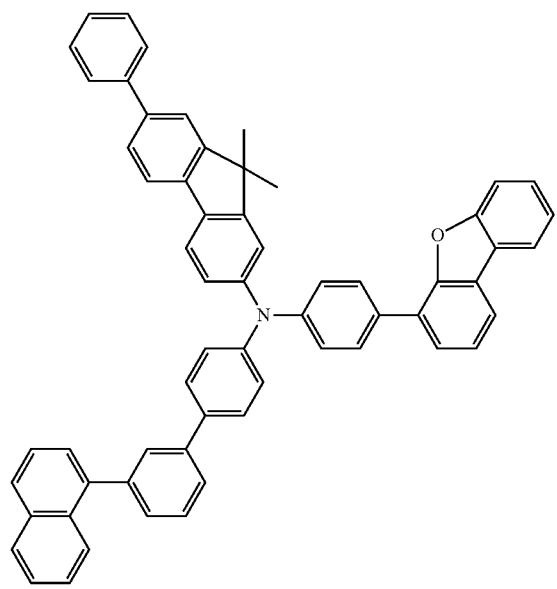
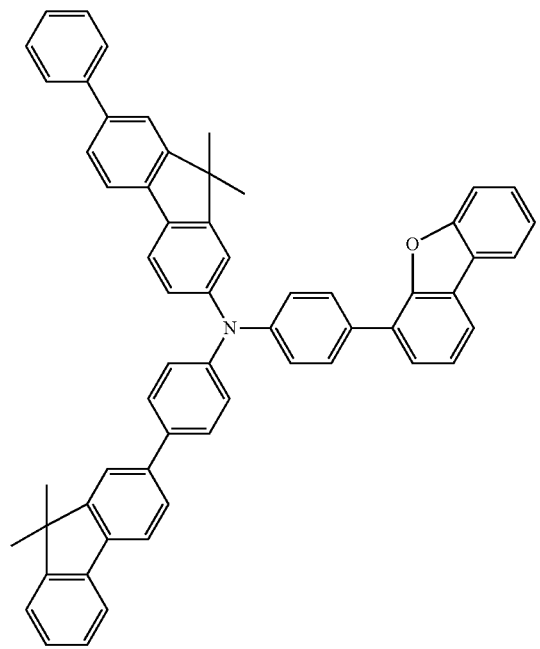
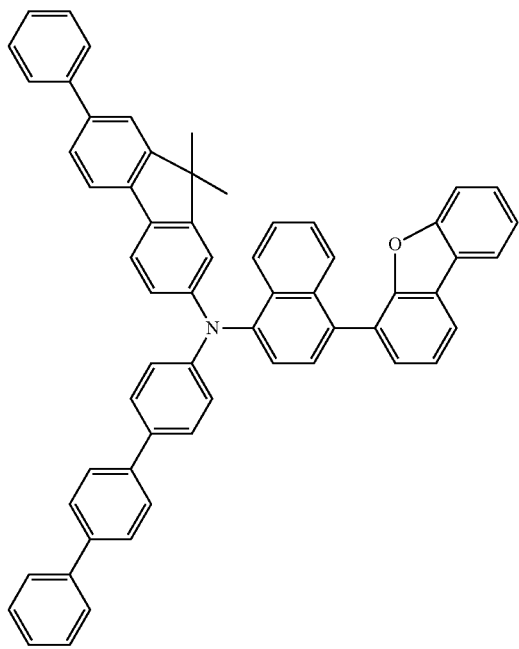

-continued
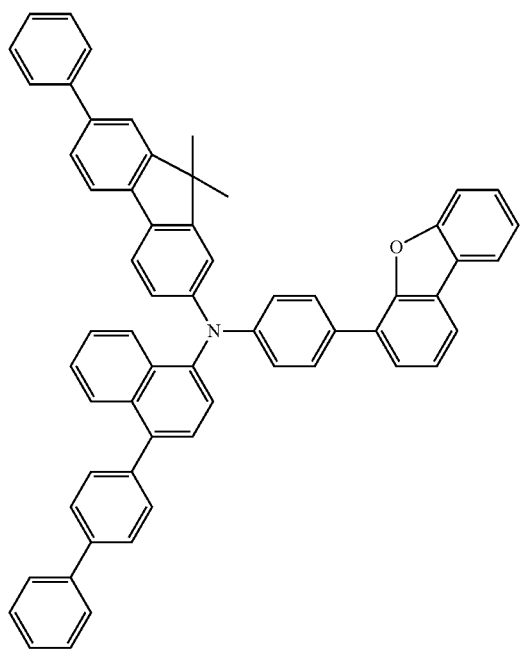
[Chem. 54]
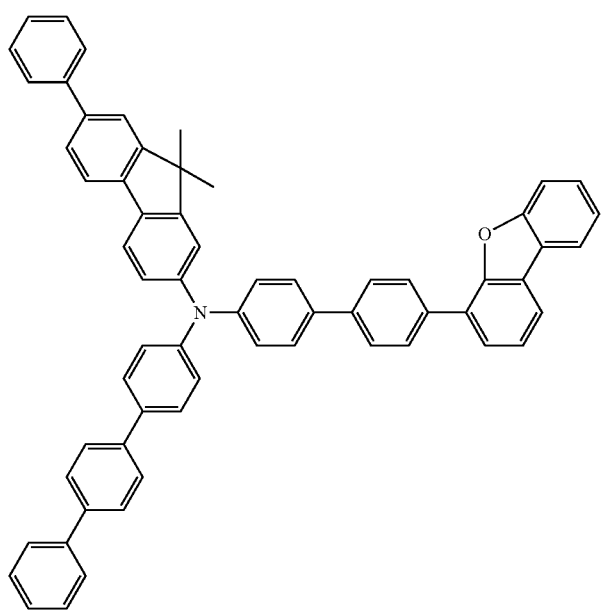

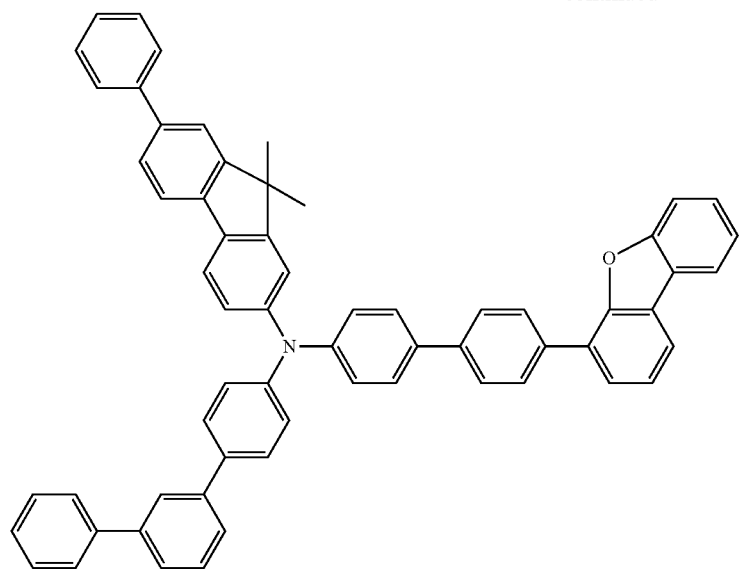
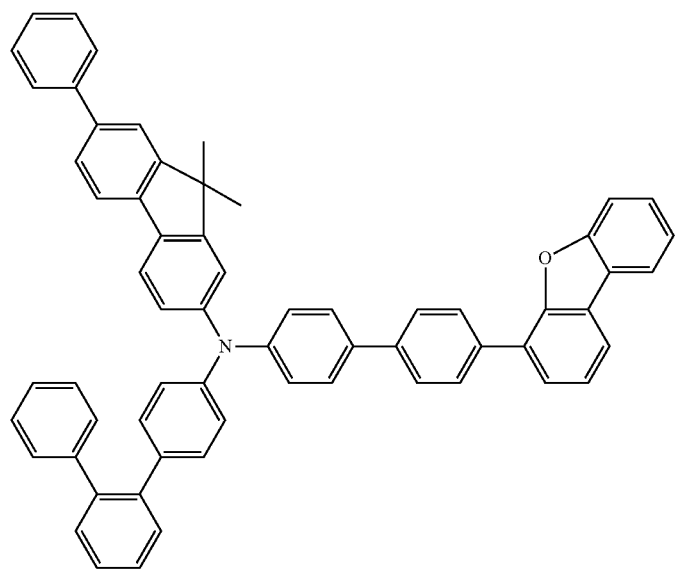

-continued
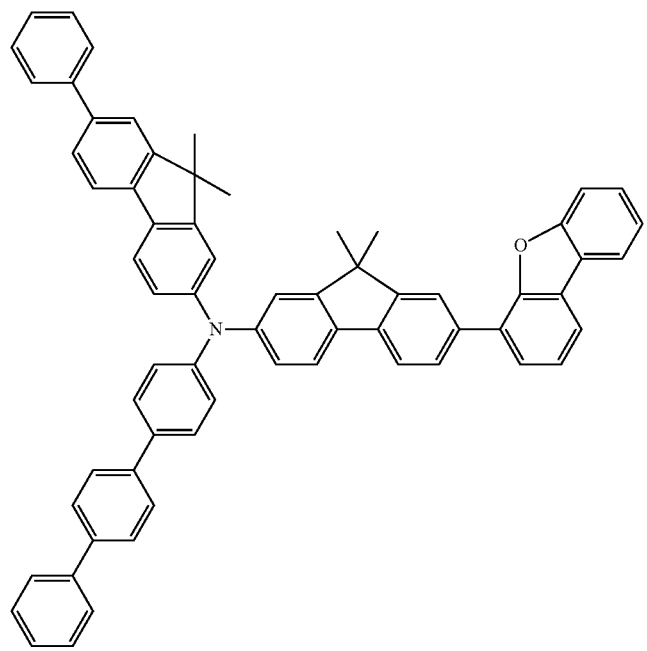
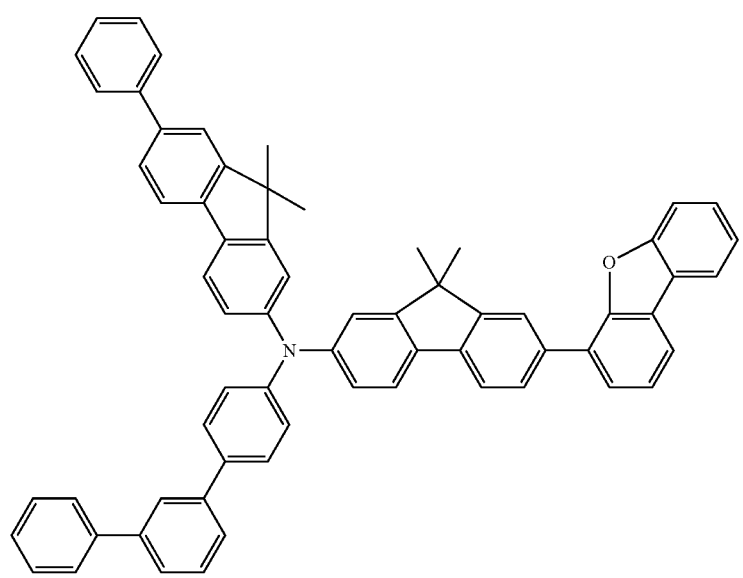

-continued
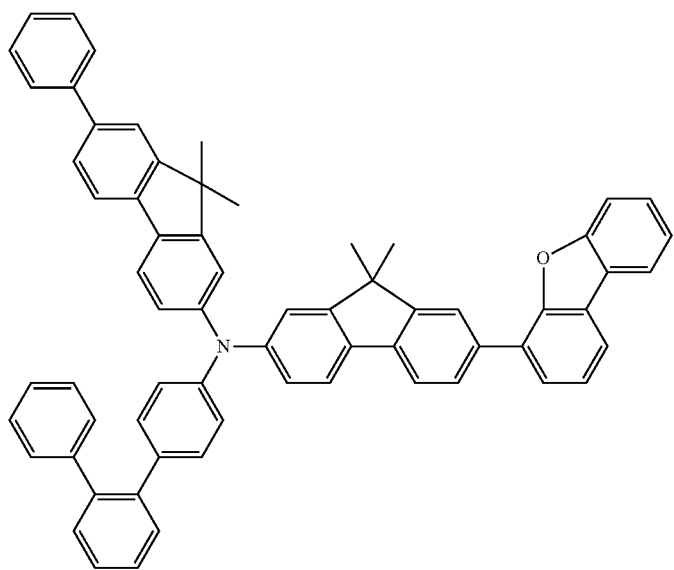
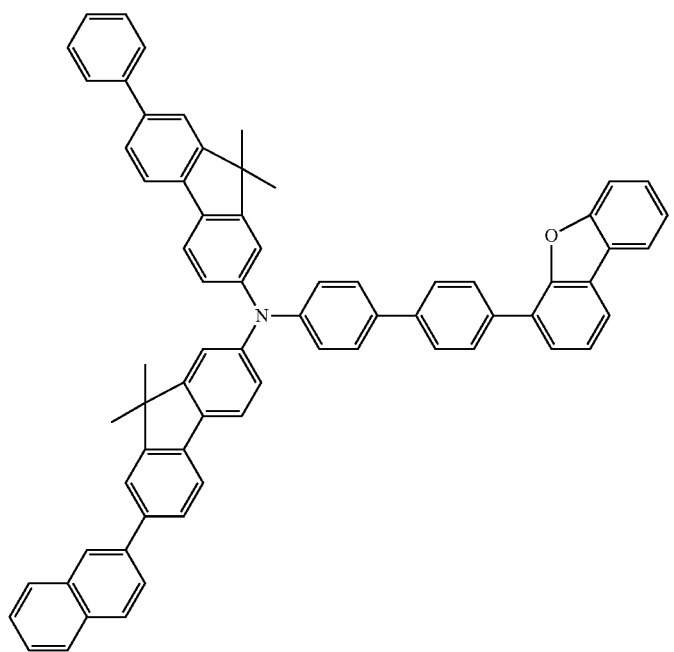

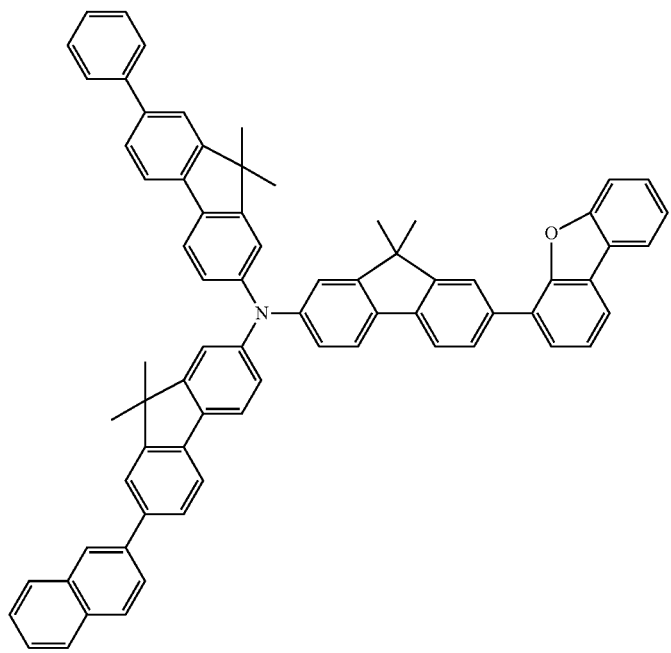
[Chem. 55]
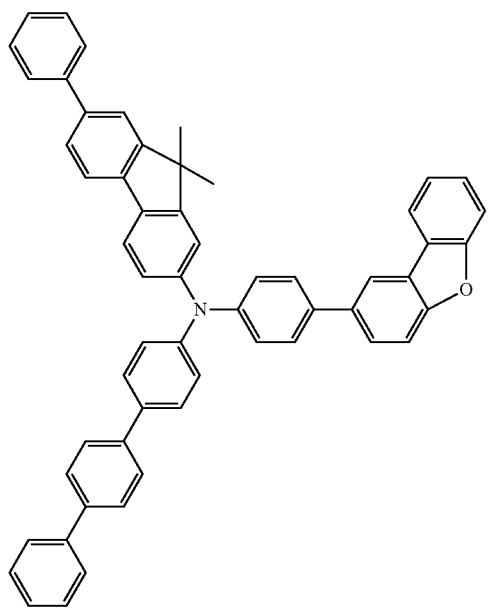
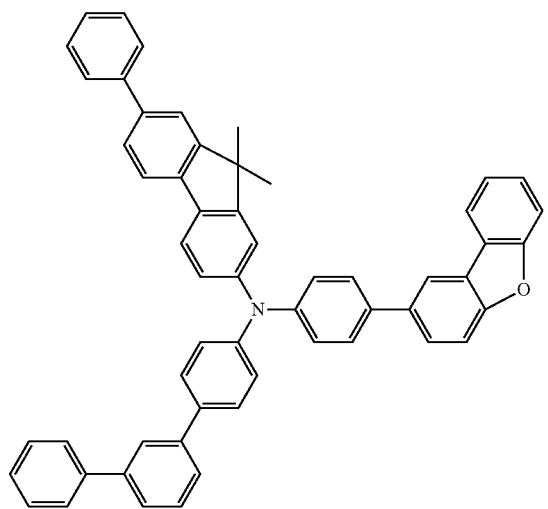

277
278
-continued
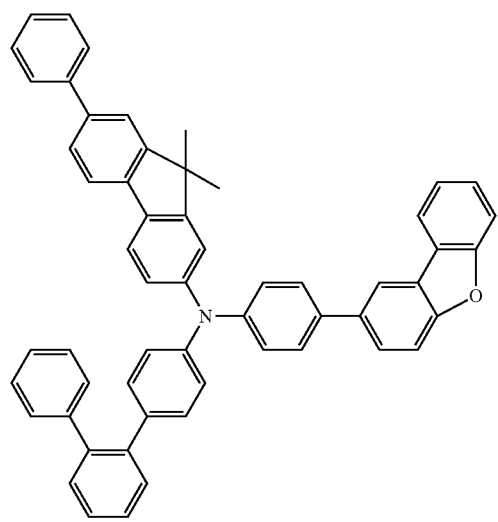
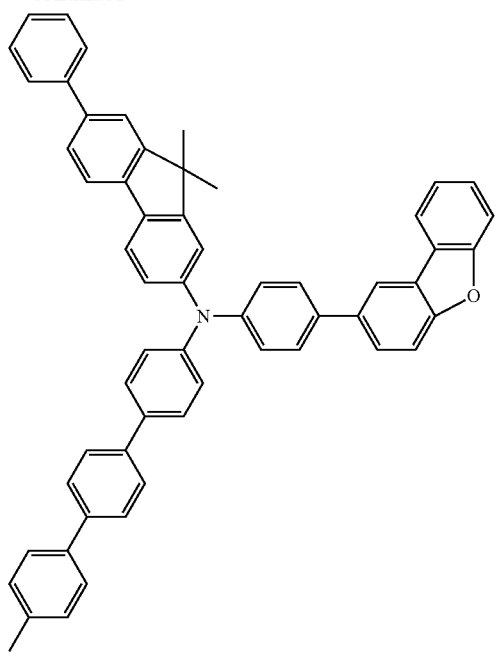
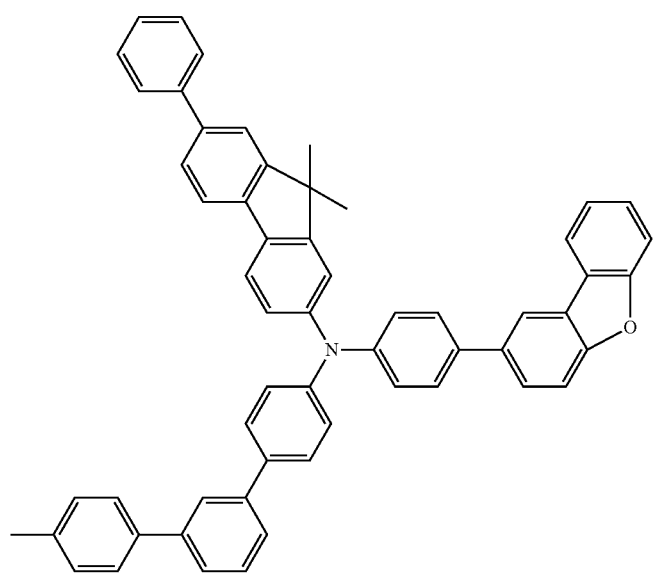

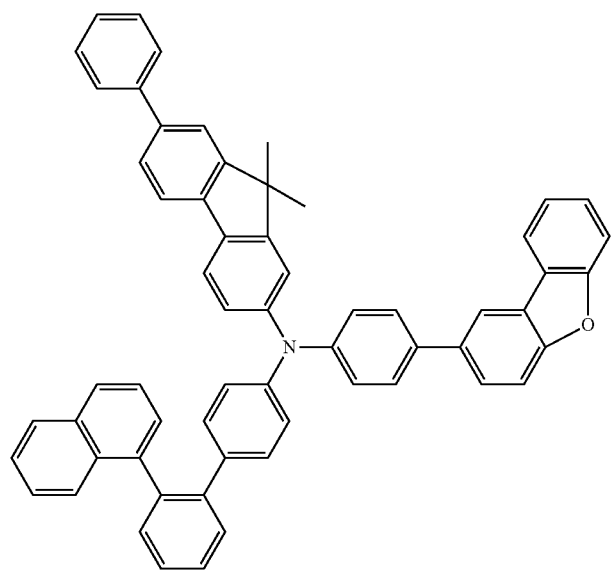
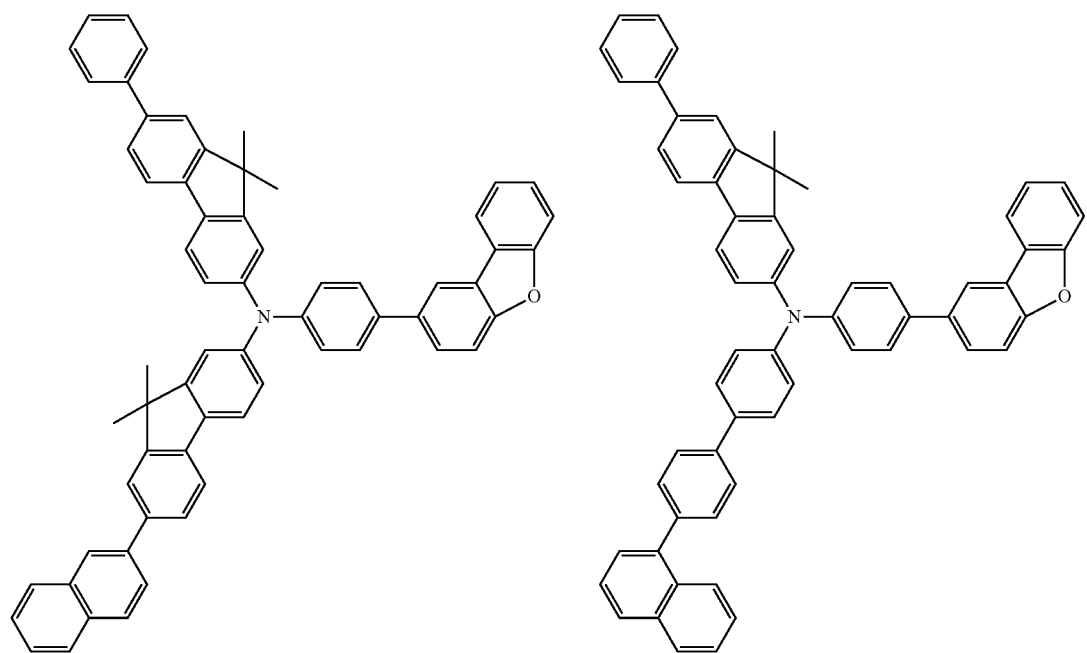

-continued
281
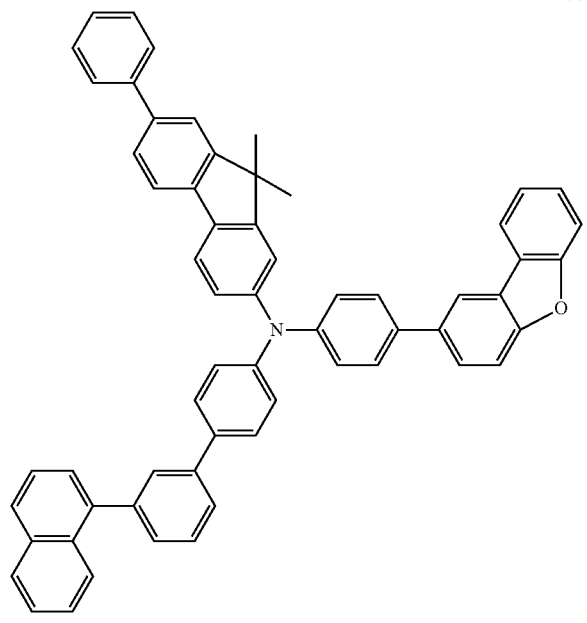
282
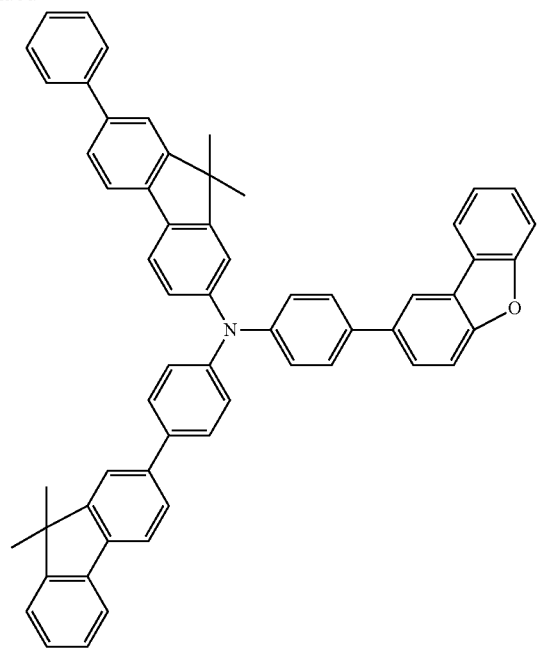
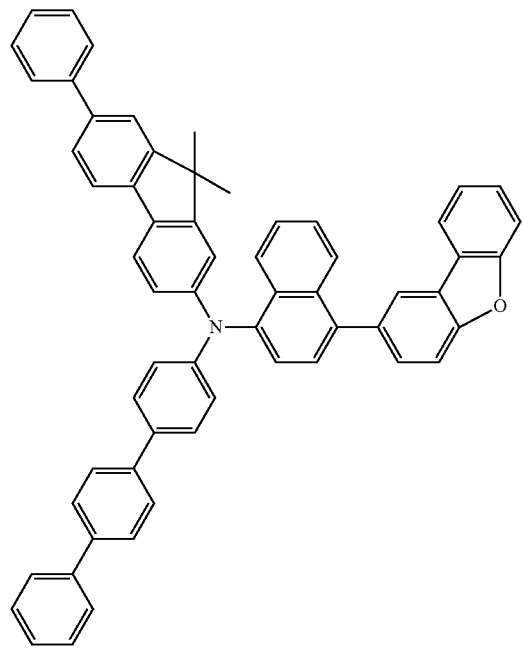
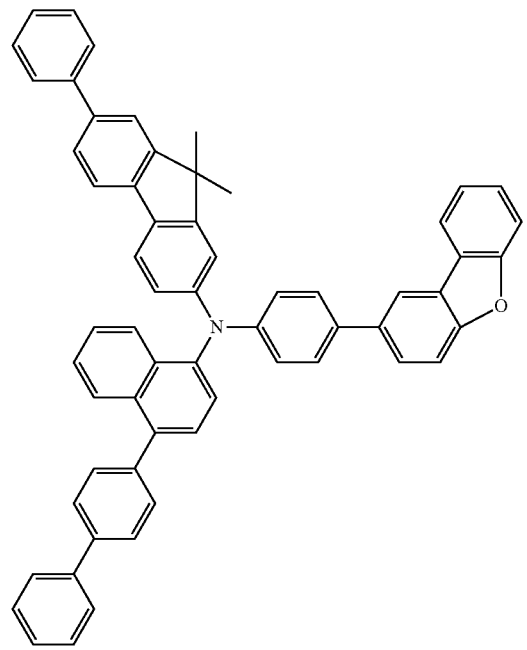

[Chem. 56]
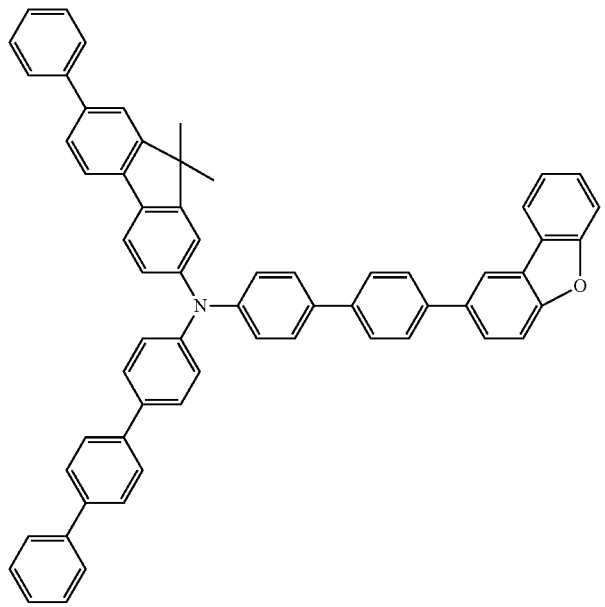
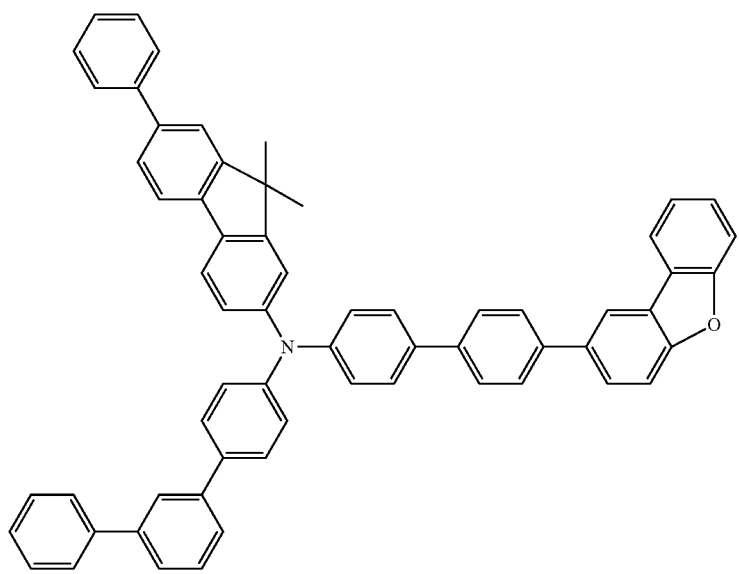

-continued
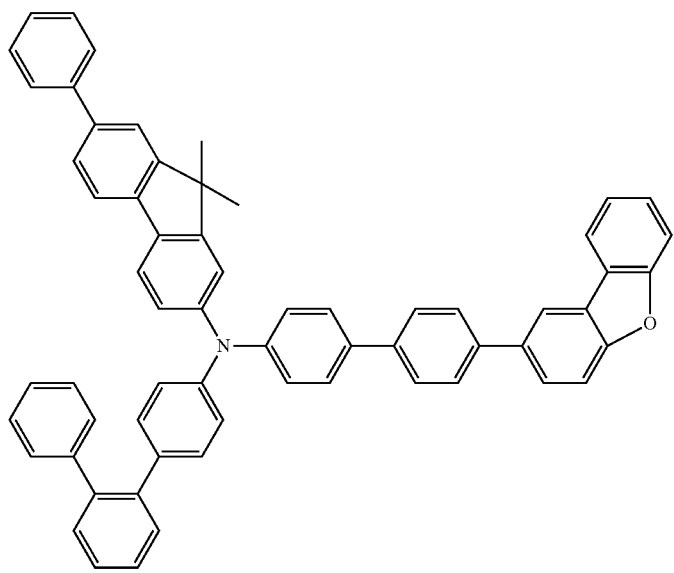
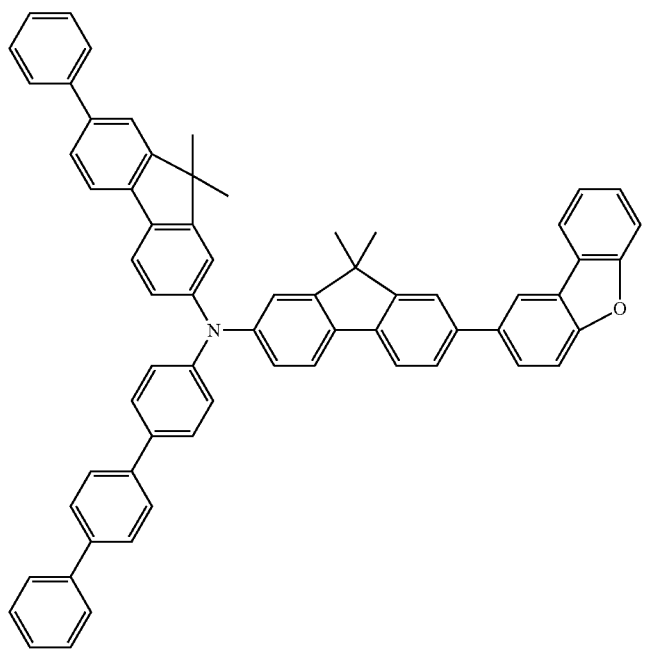

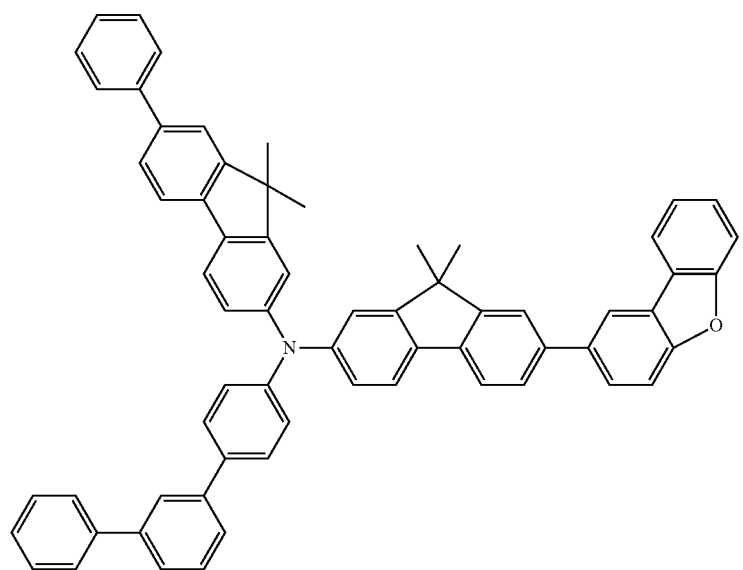
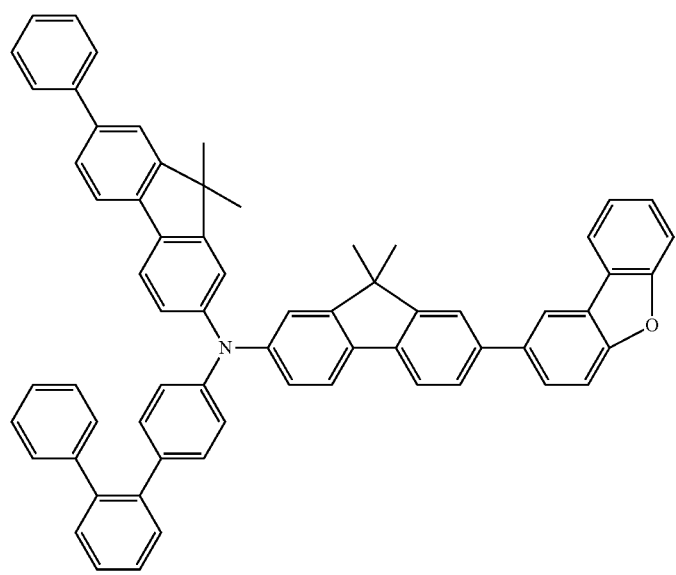

-continued
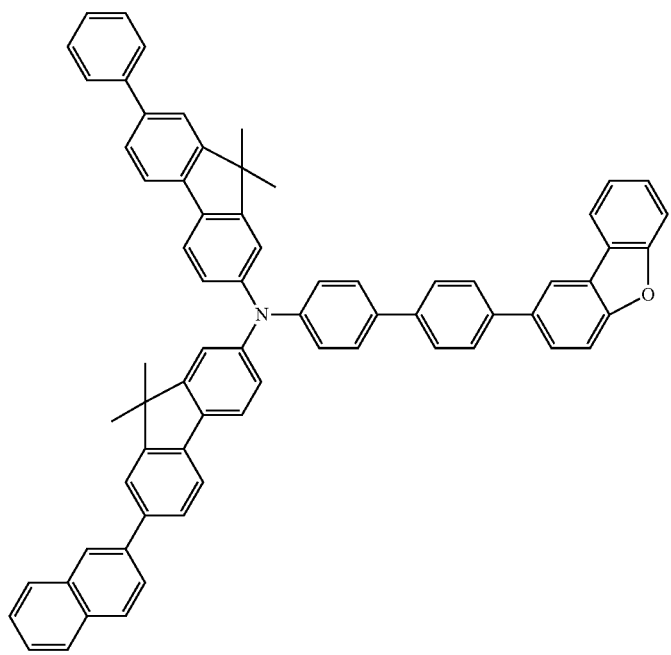
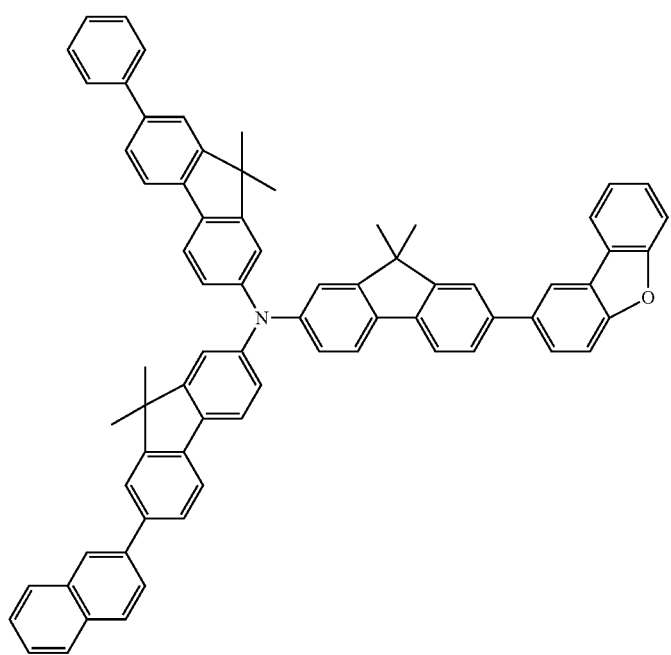

[Chem. 57]
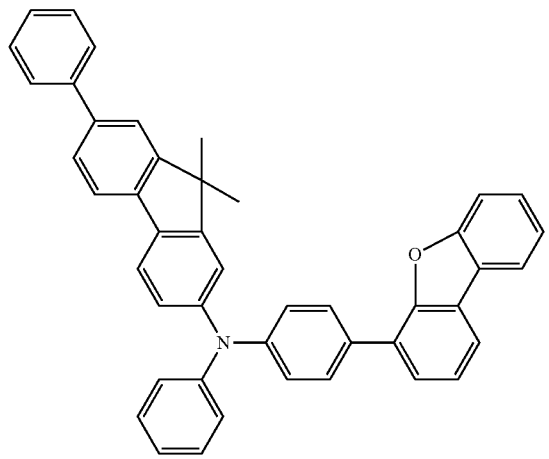
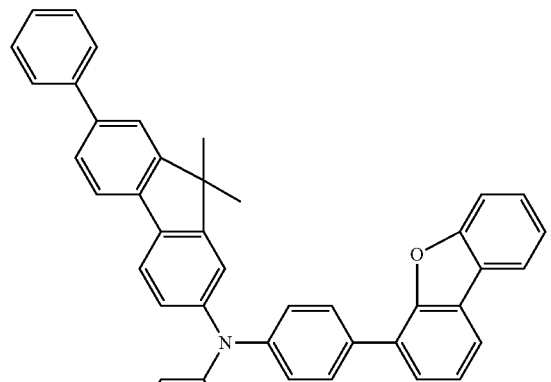
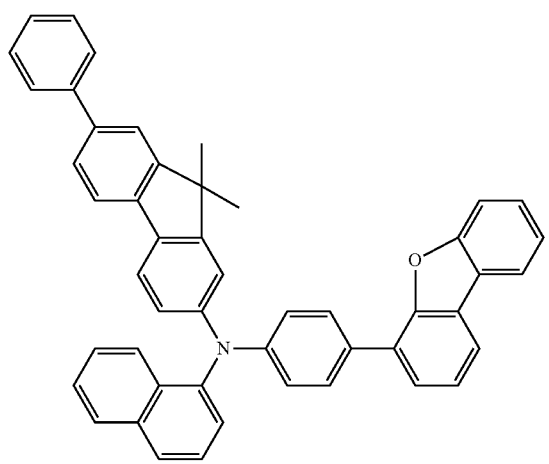
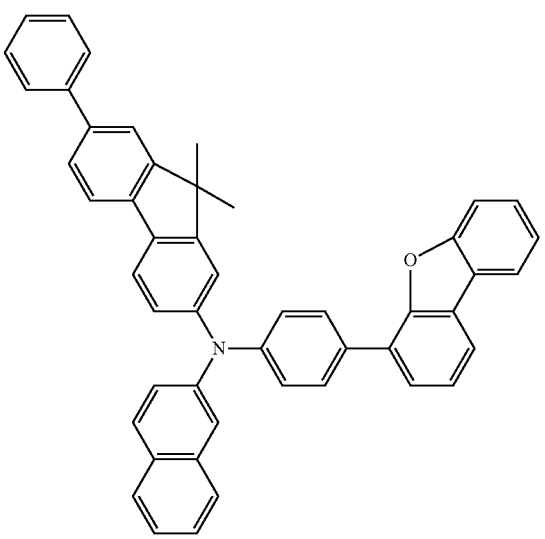
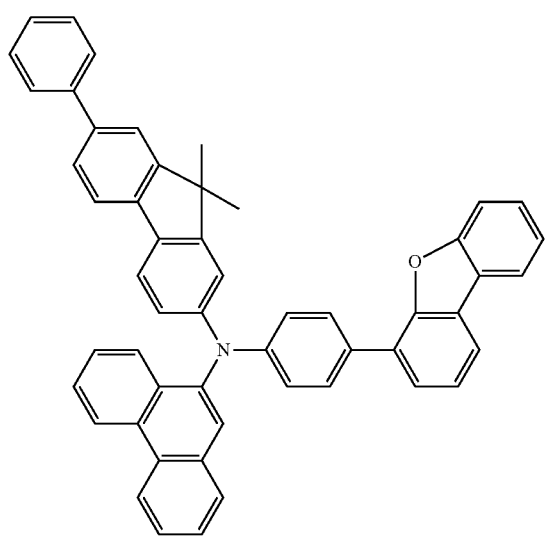
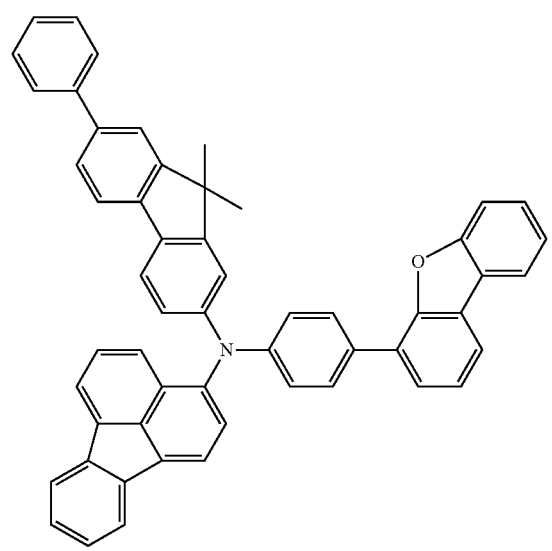

293
294
-continued
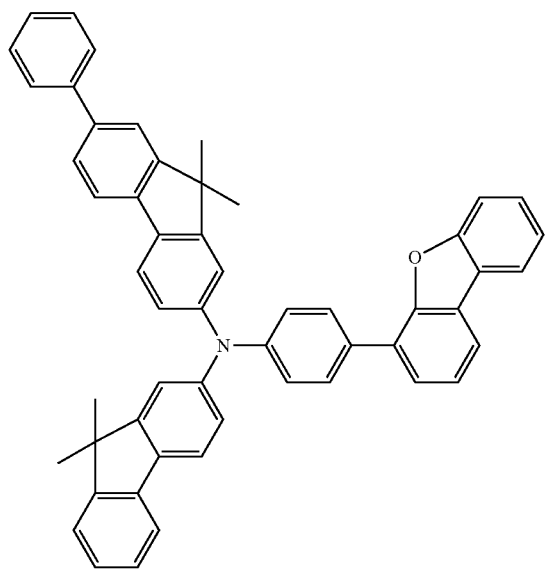
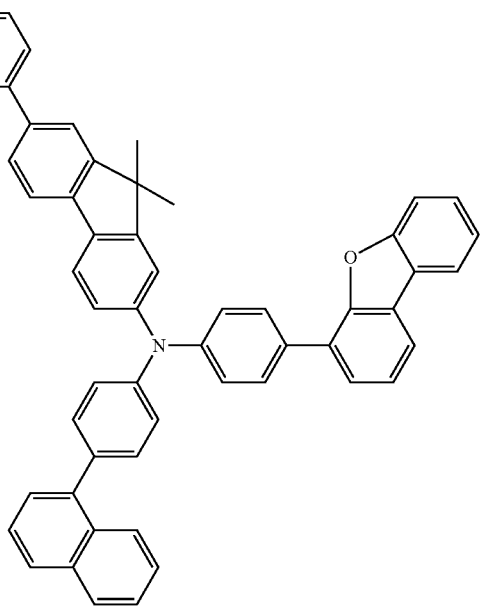
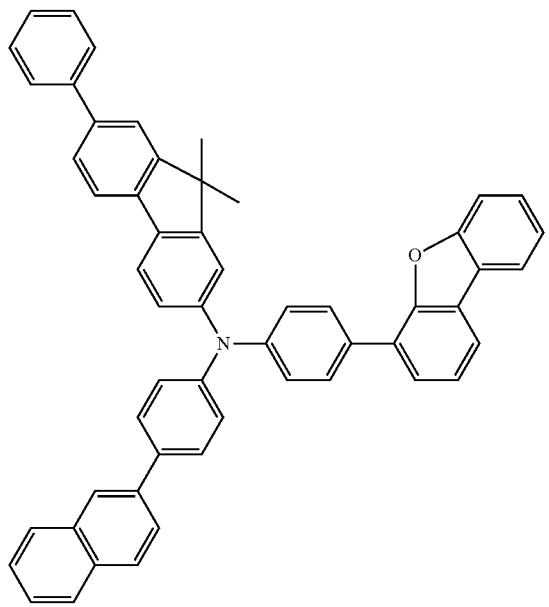
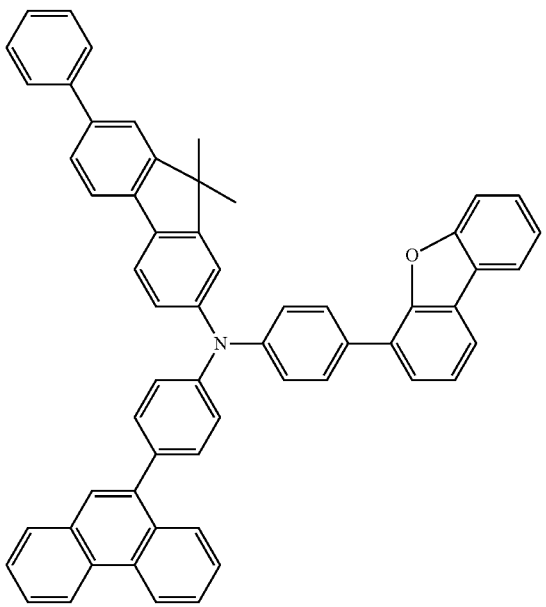

295
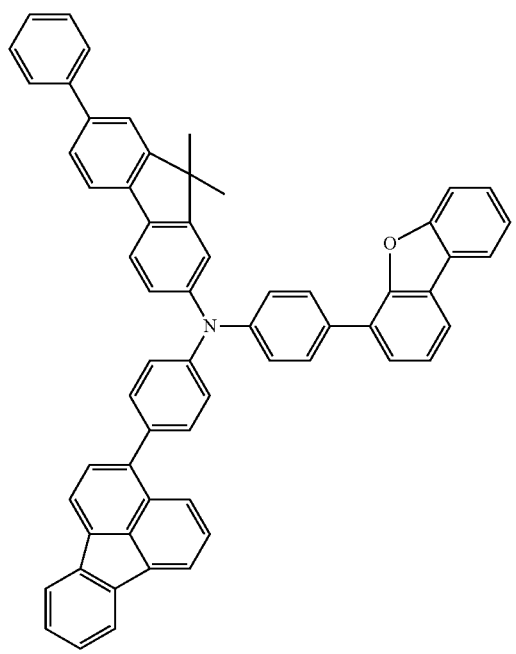
296
-continued
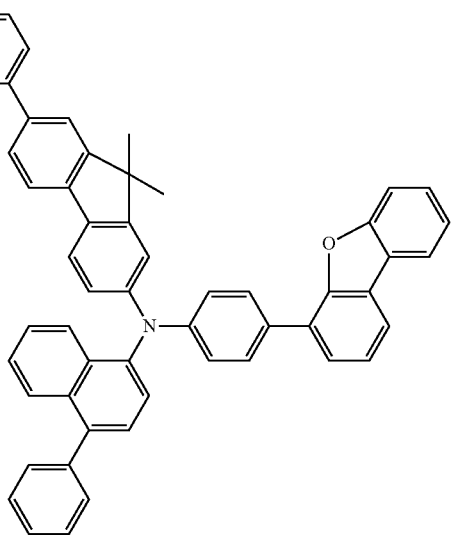
[Chem. 58]
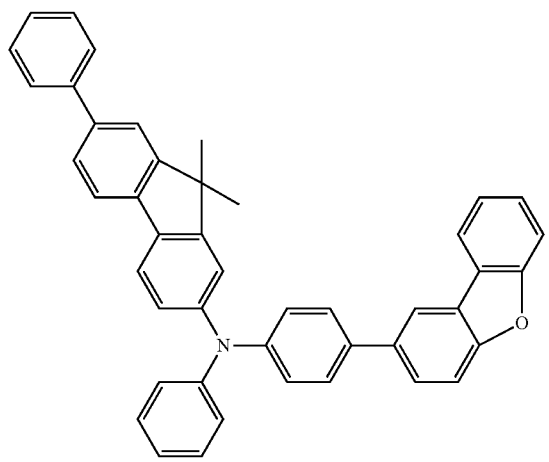
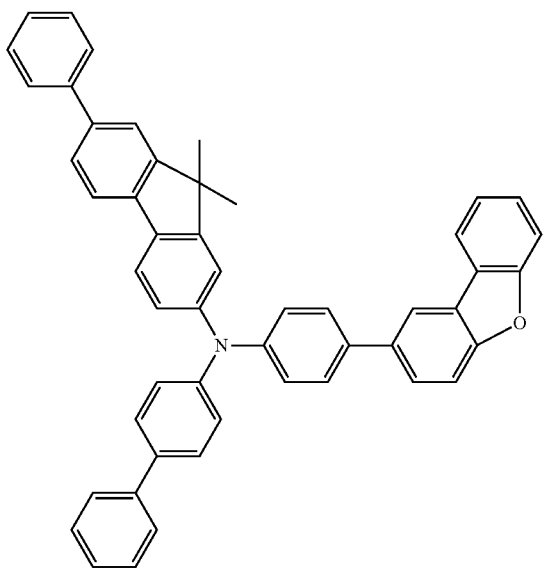

297
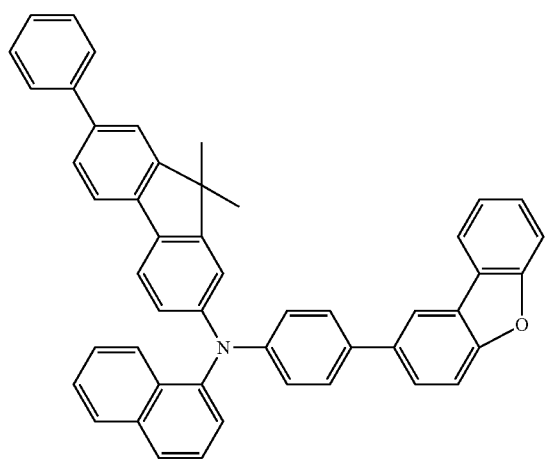
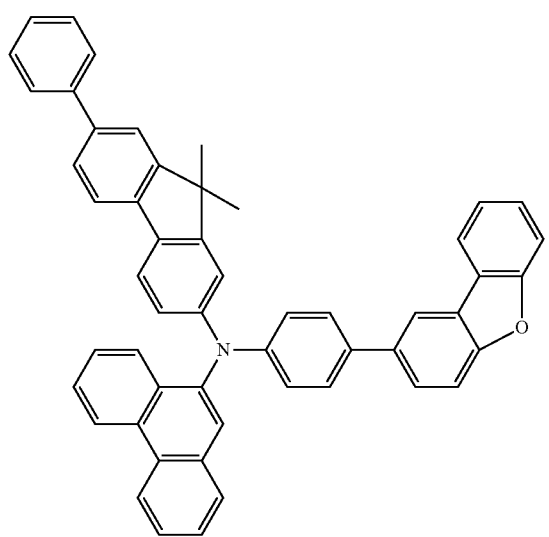
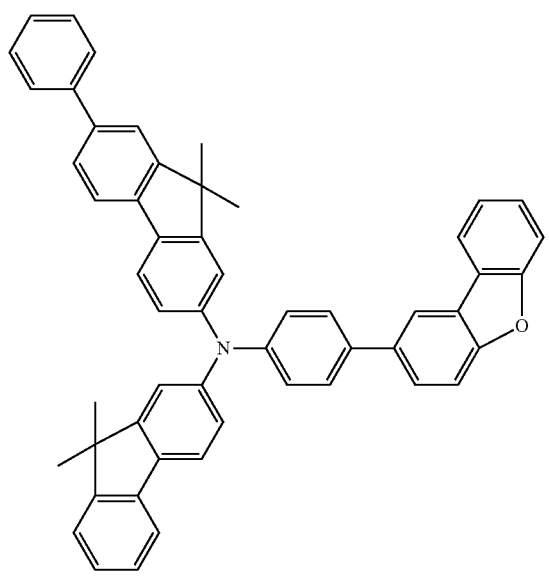
-continued
298
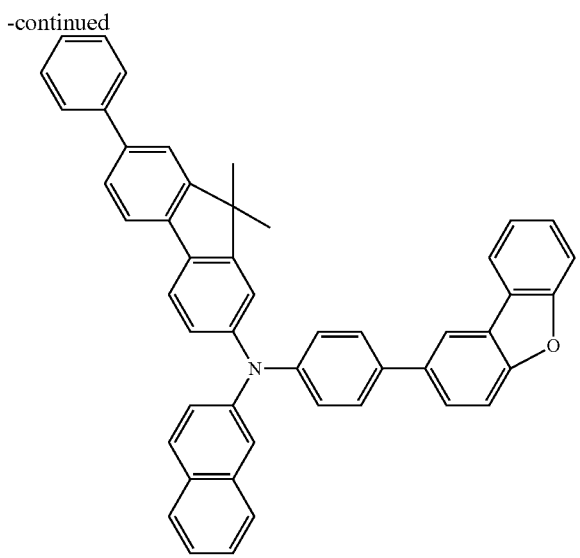
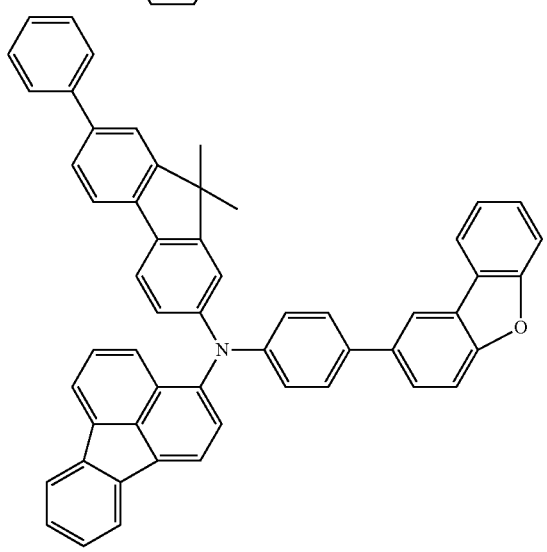
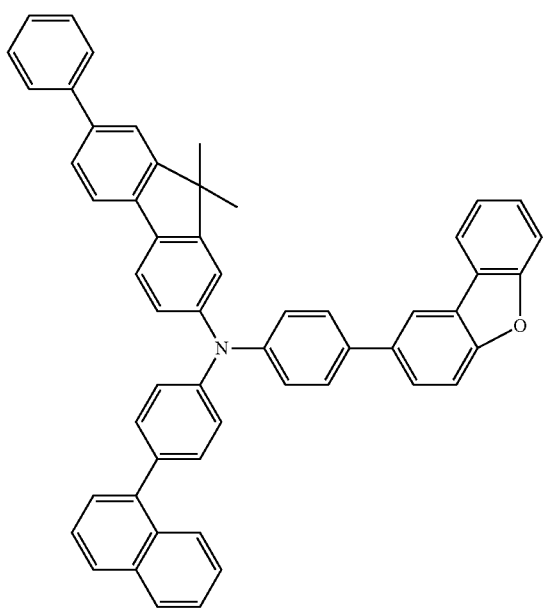

299
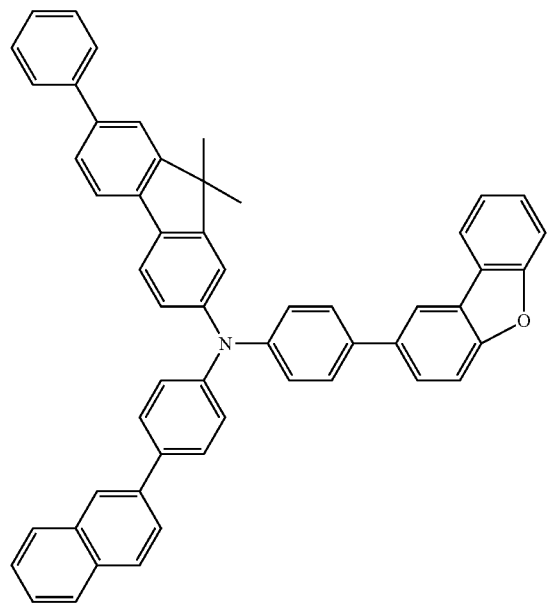
300
-continued
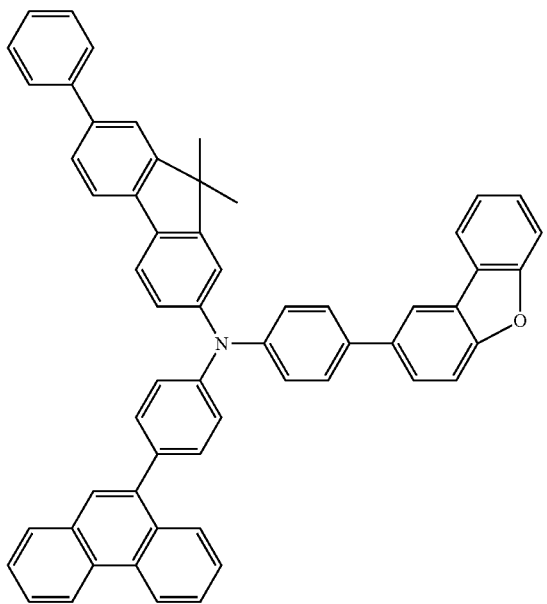
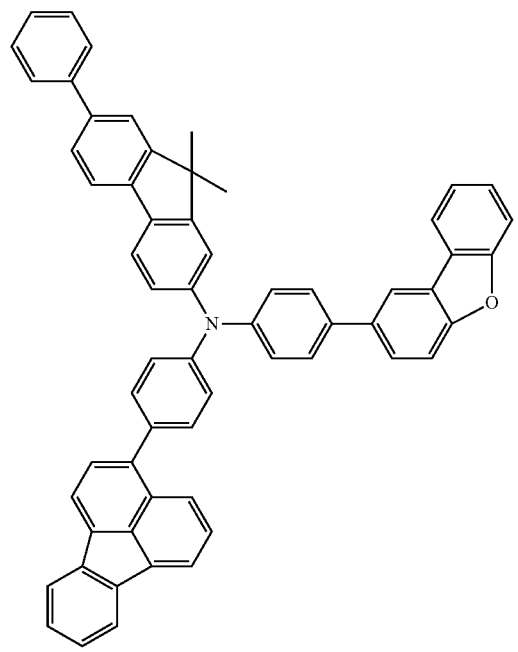
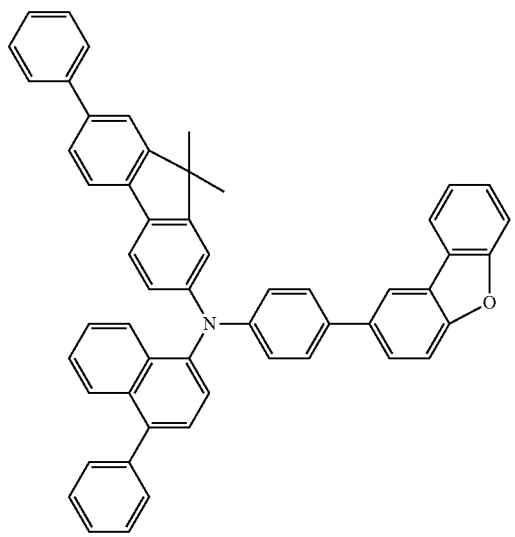

-continued
[Chem. 59]
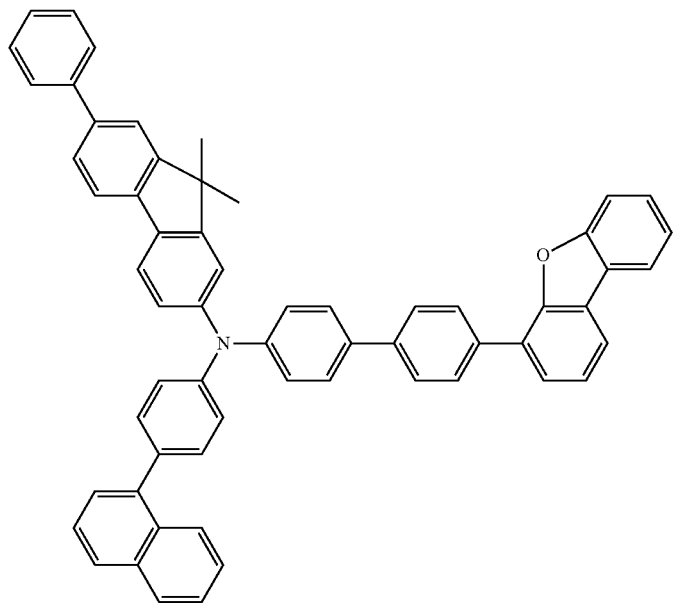
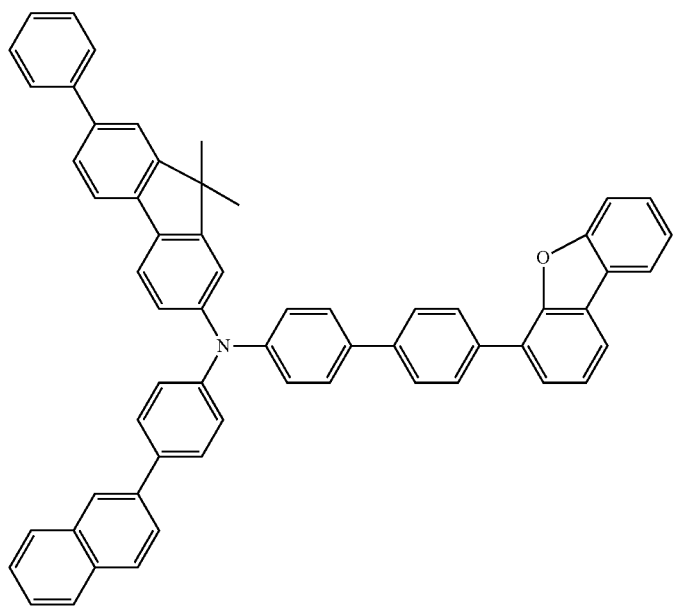

-continued
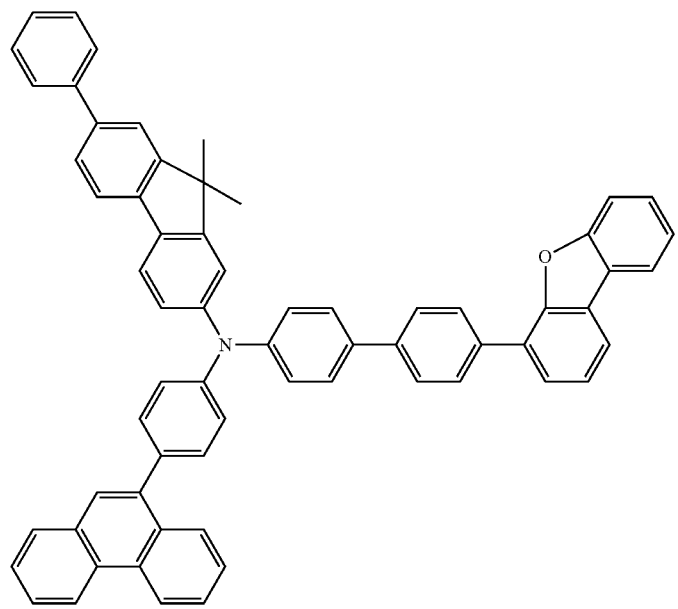
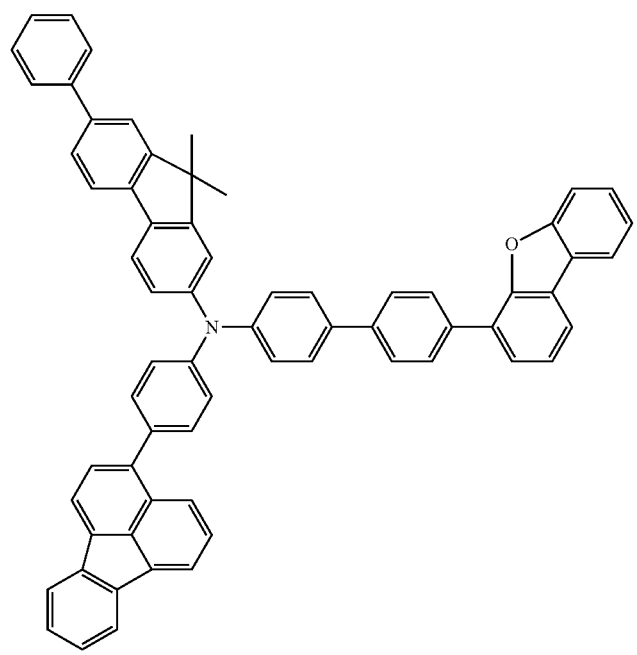

-continued
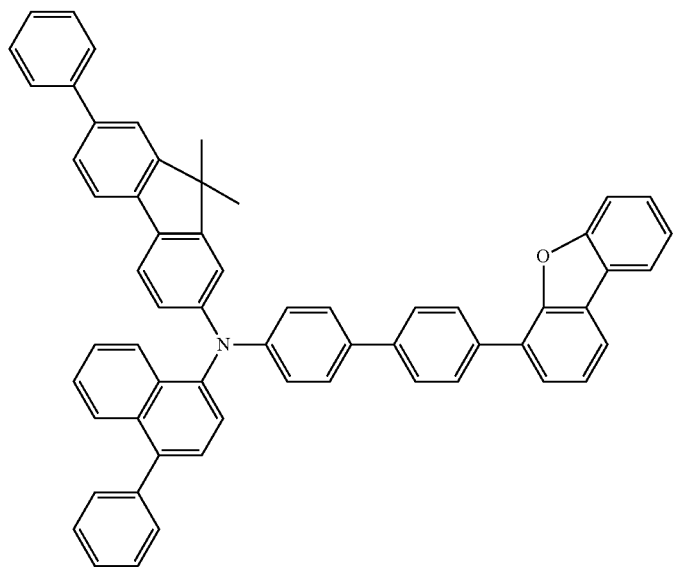
[Chem. 60]
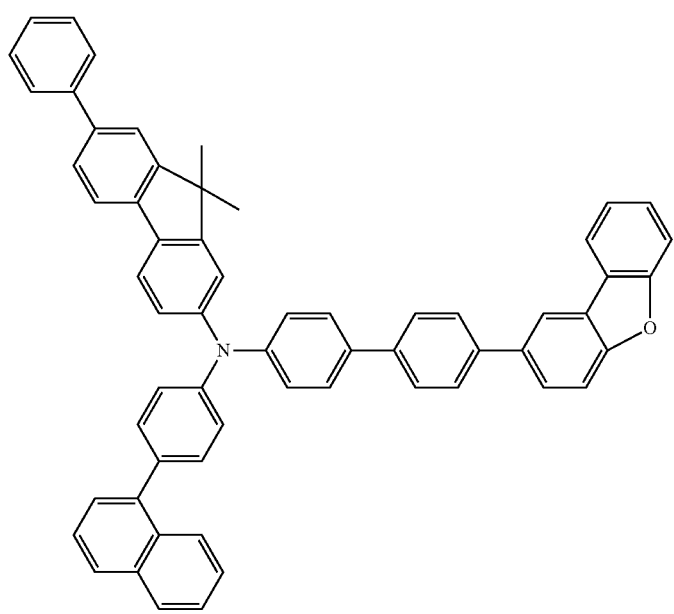

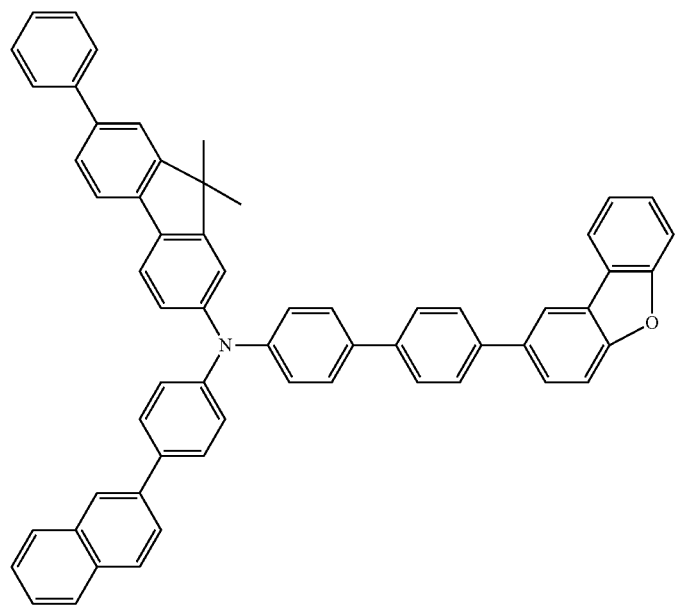
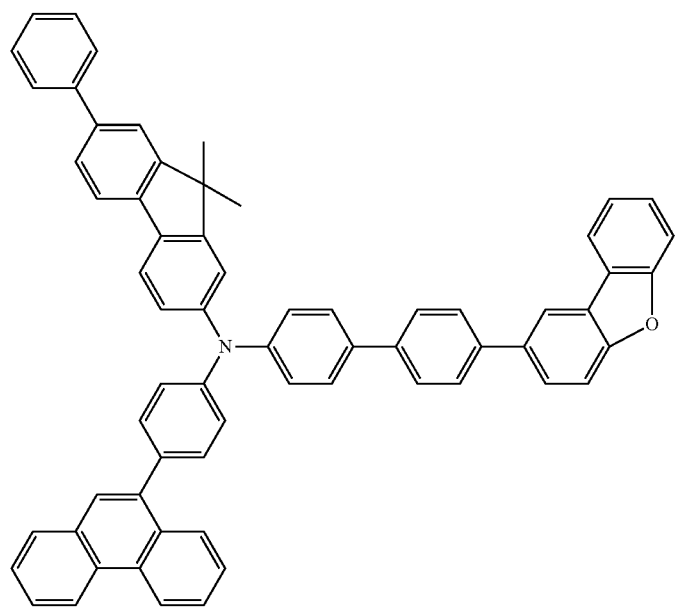

-continued
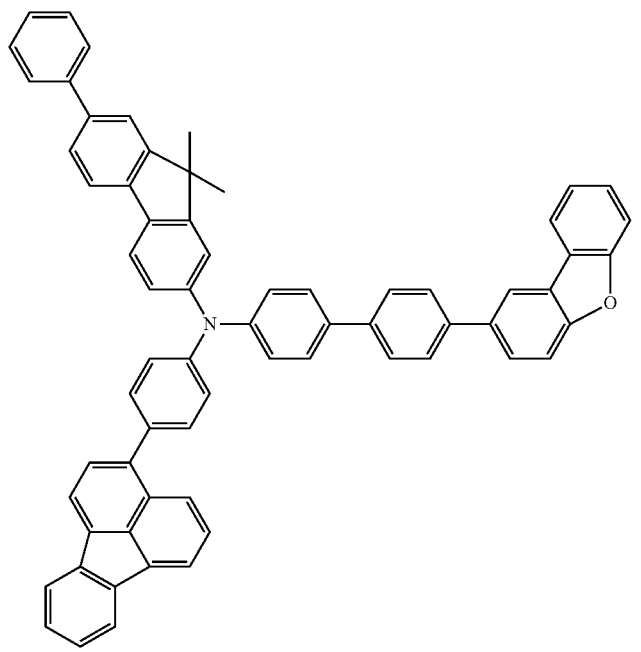
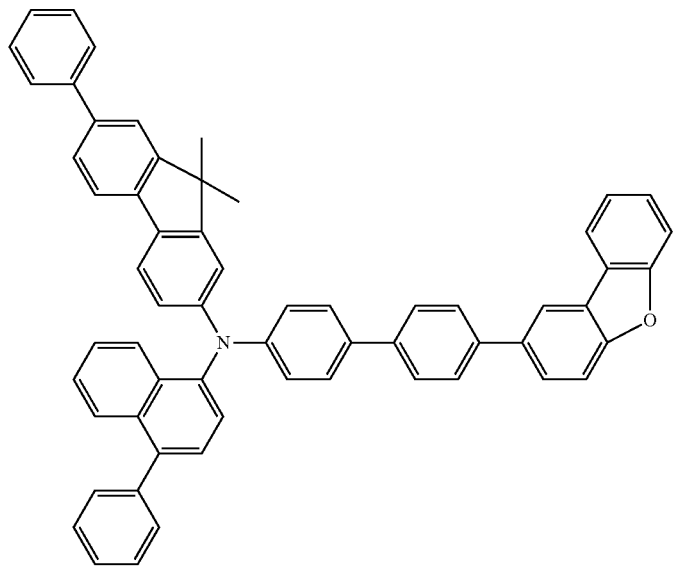
[Chem. 61]
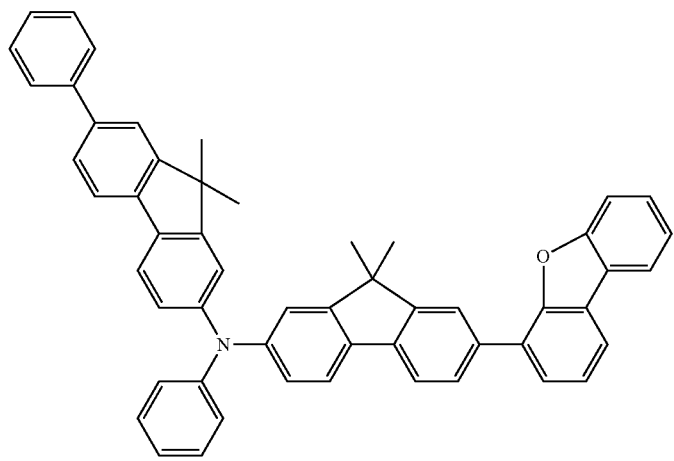

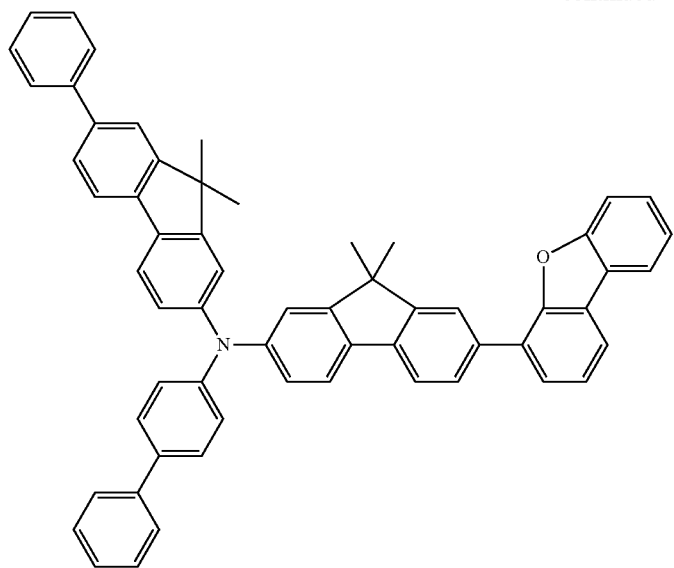
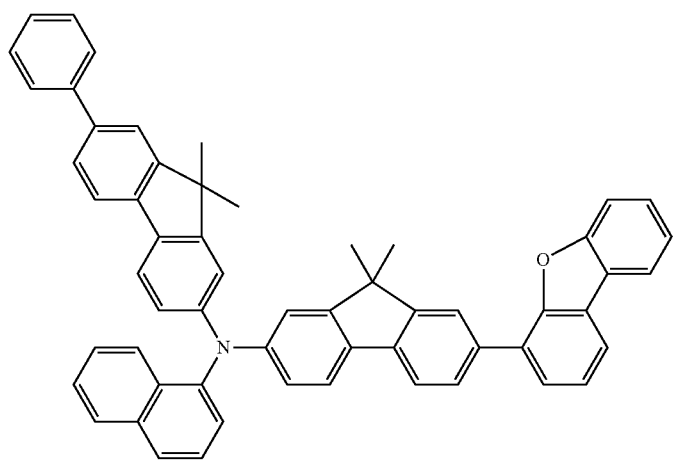
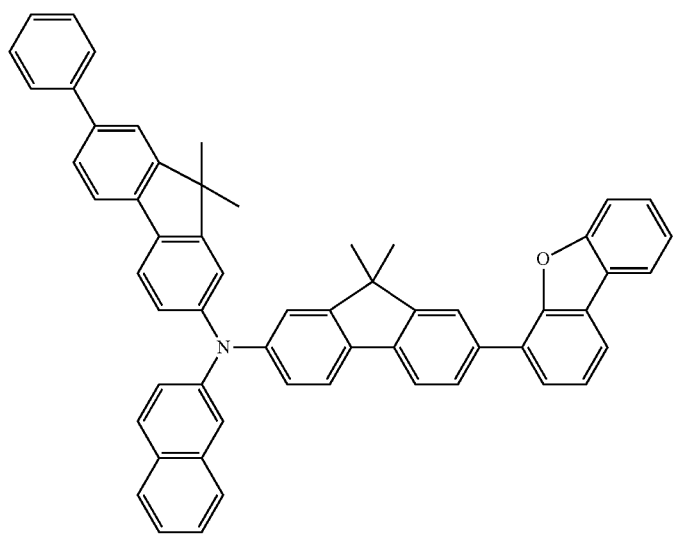

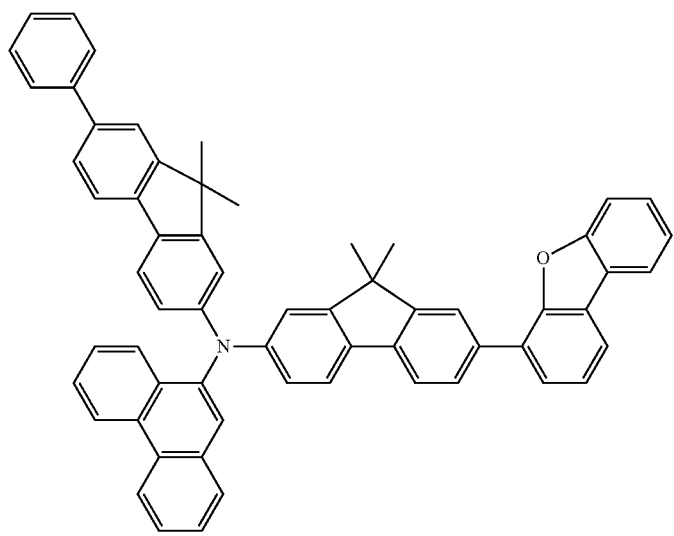
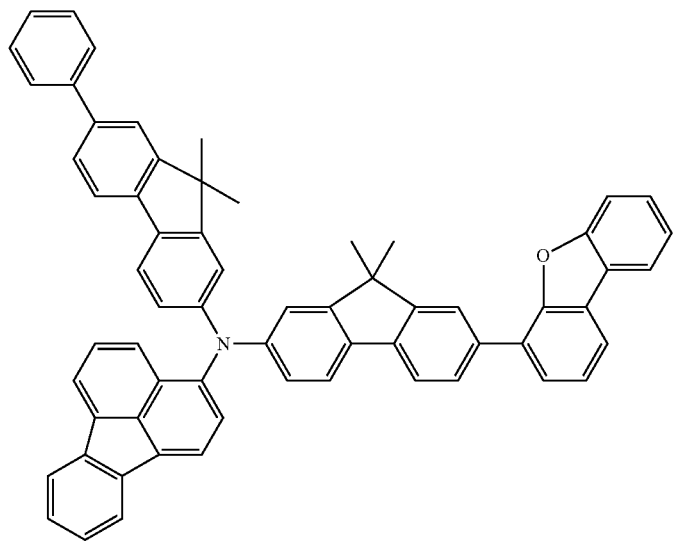
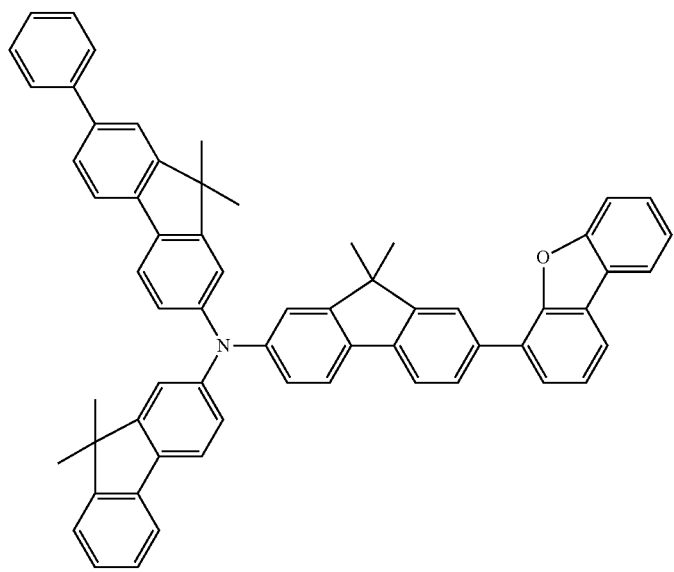

-continued
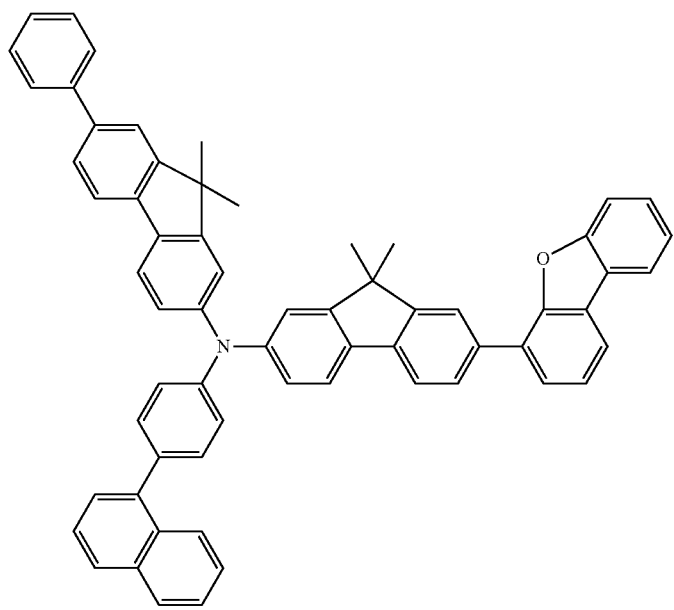
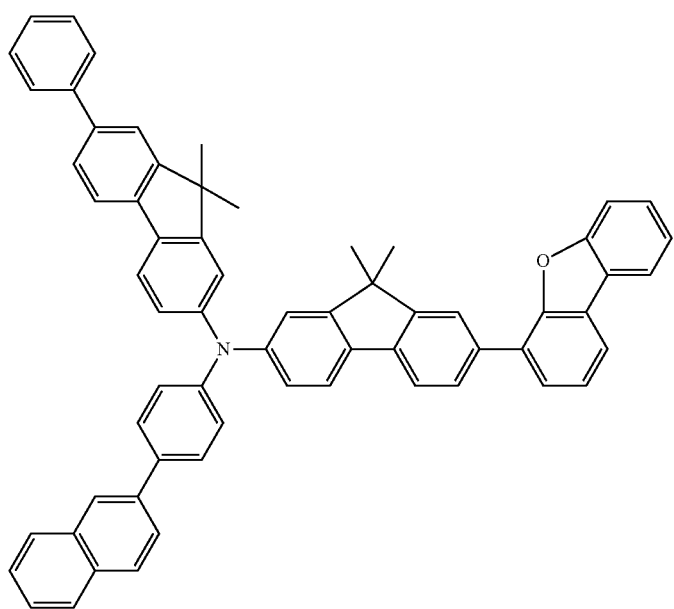

-continued
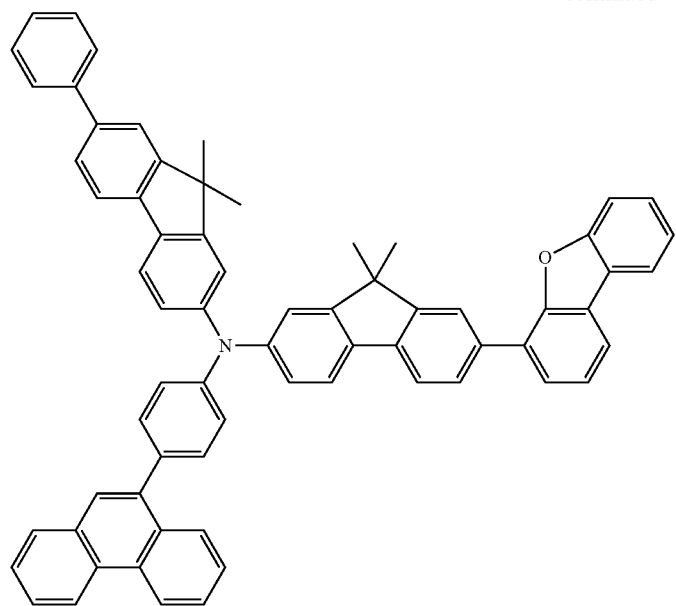
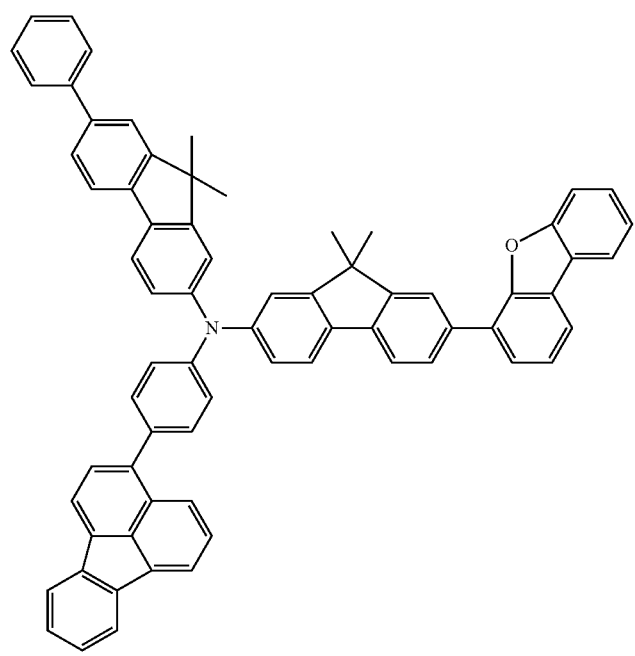

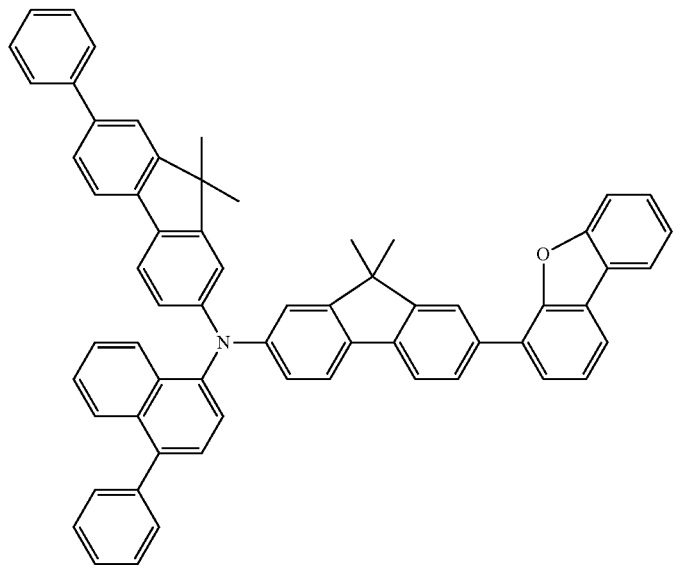
[Chem. 62]
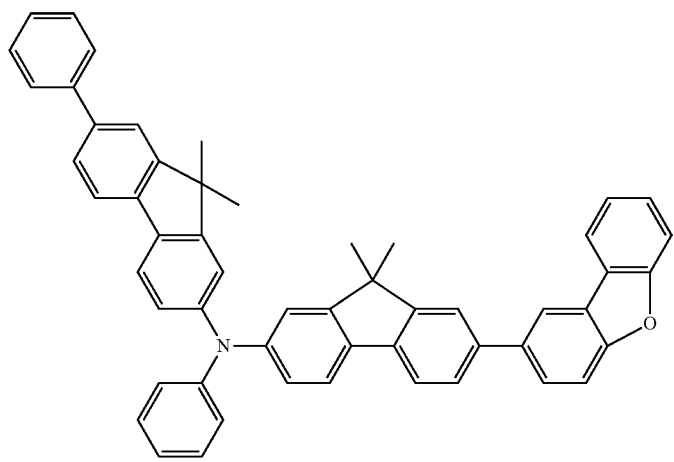
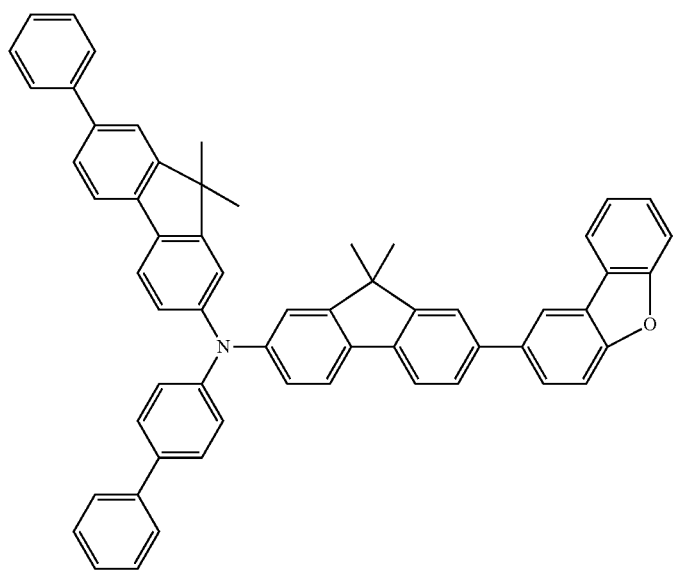

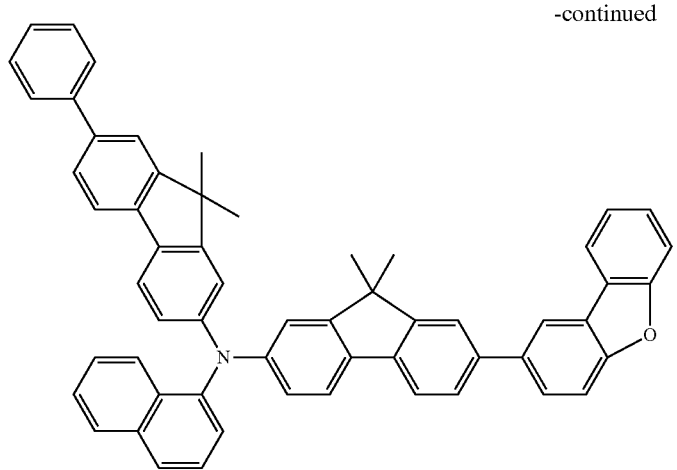
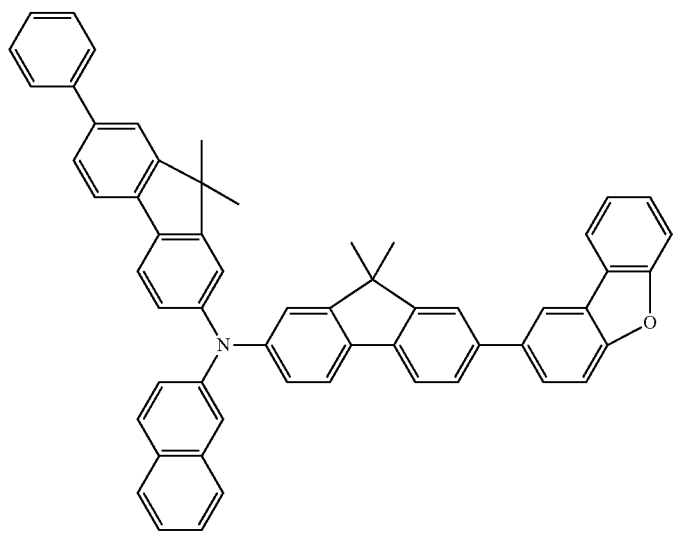
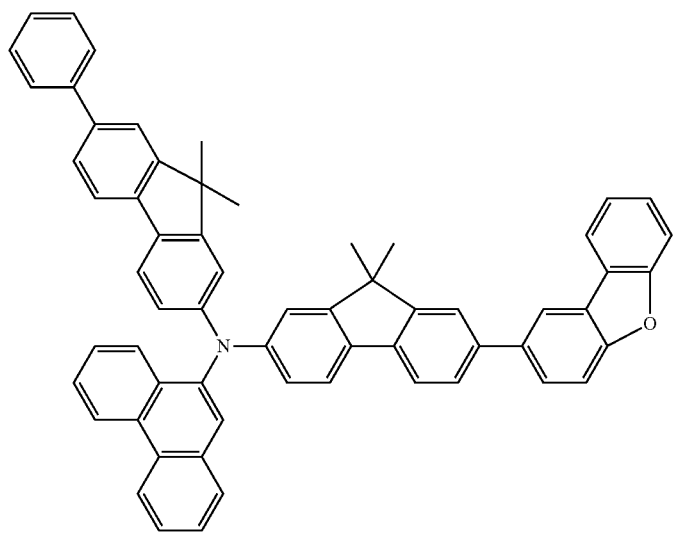

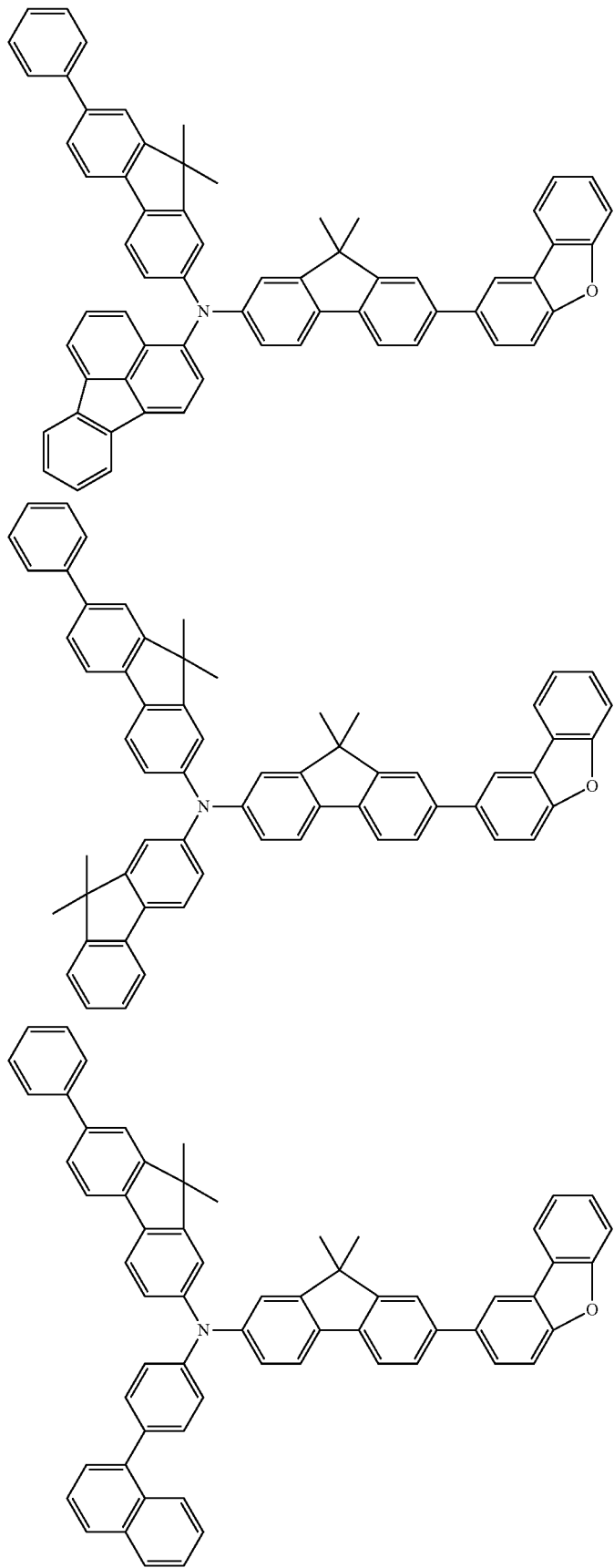

-continued
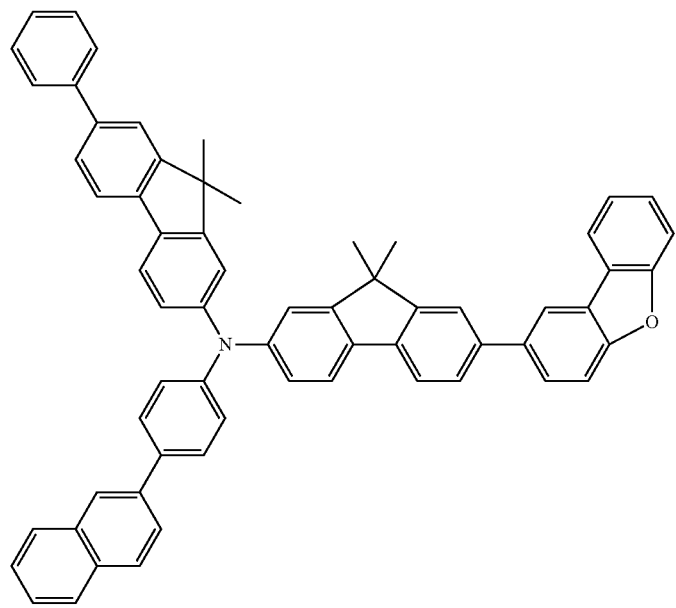
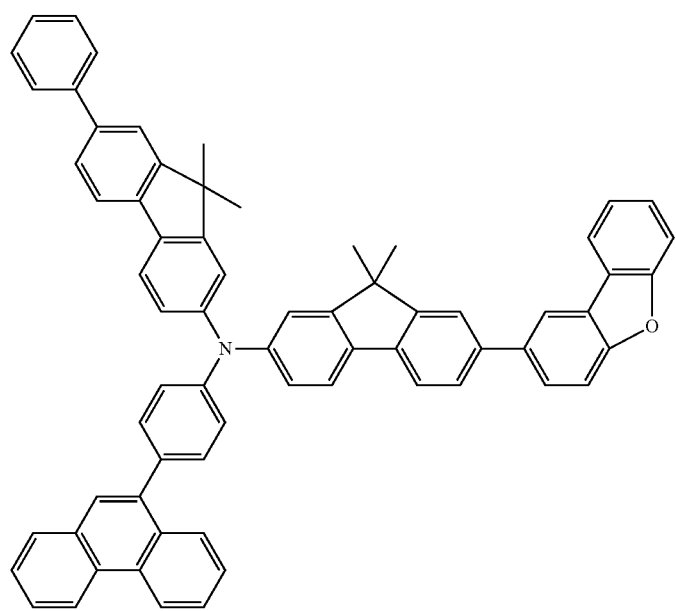

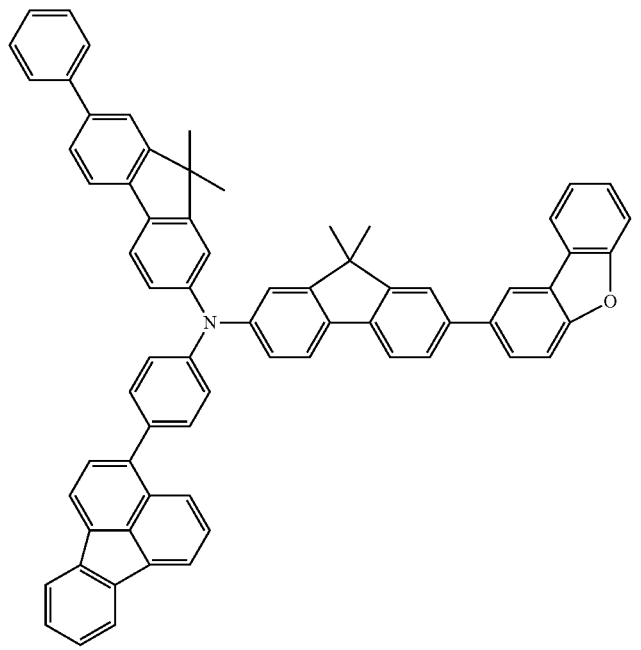
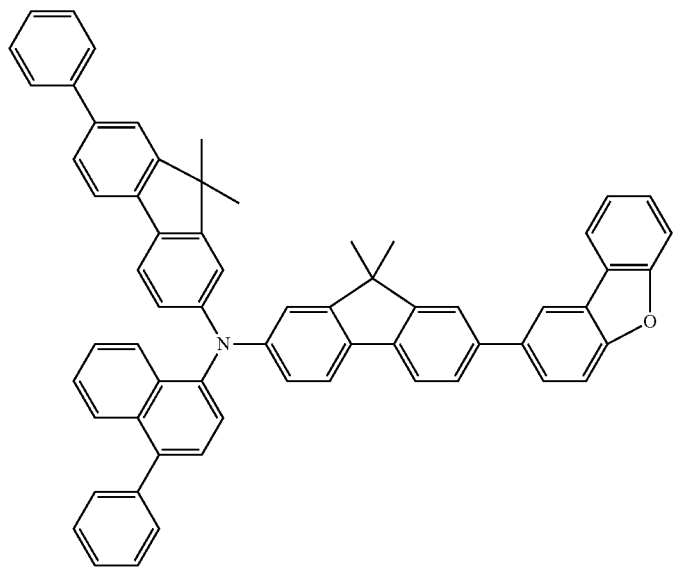
[Chem. 63]
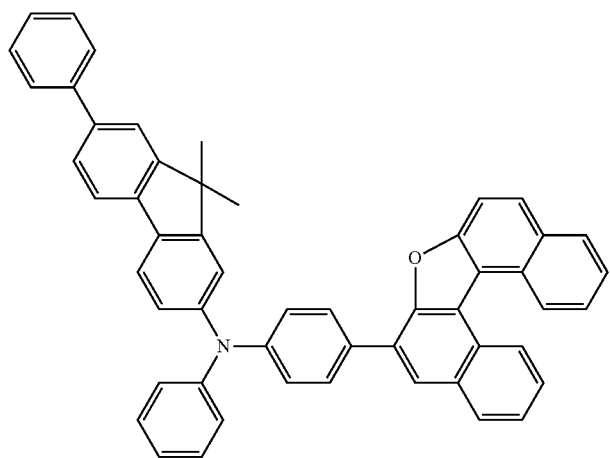

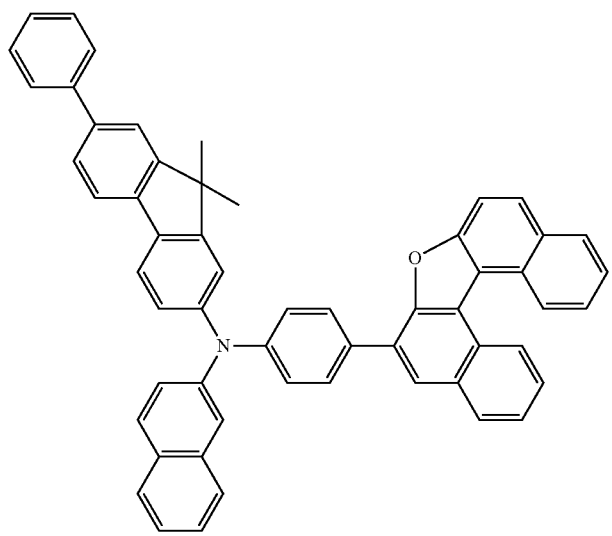
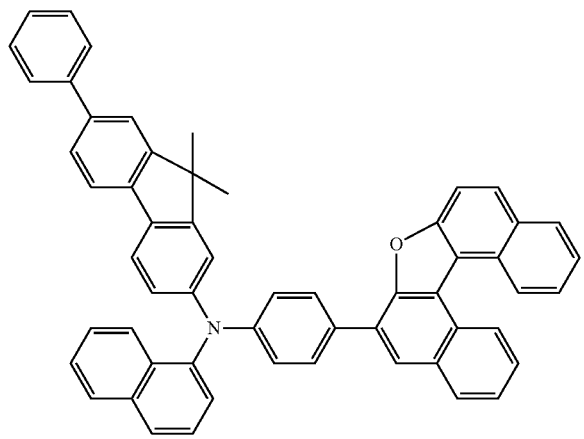
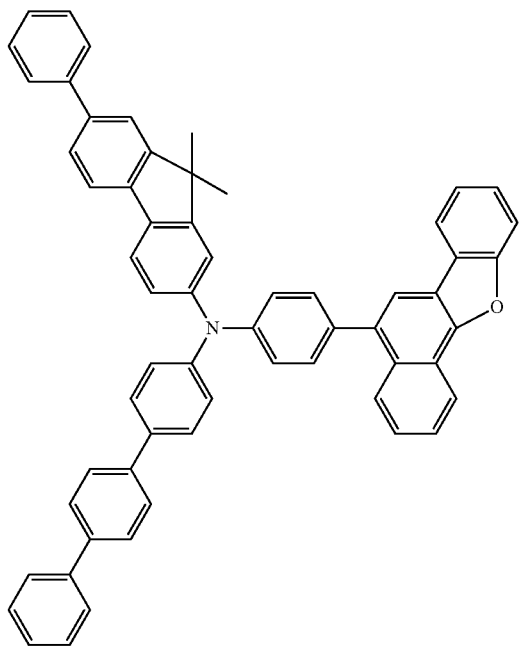
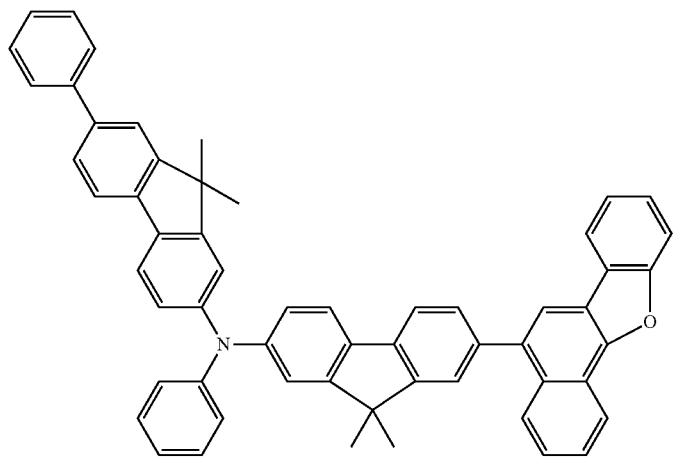

-continued
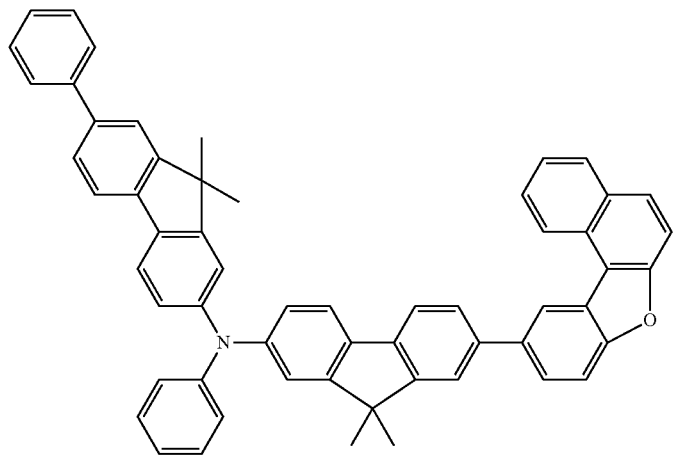
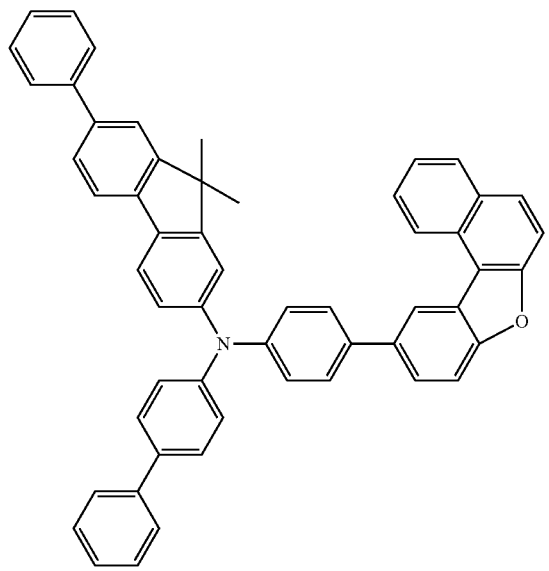
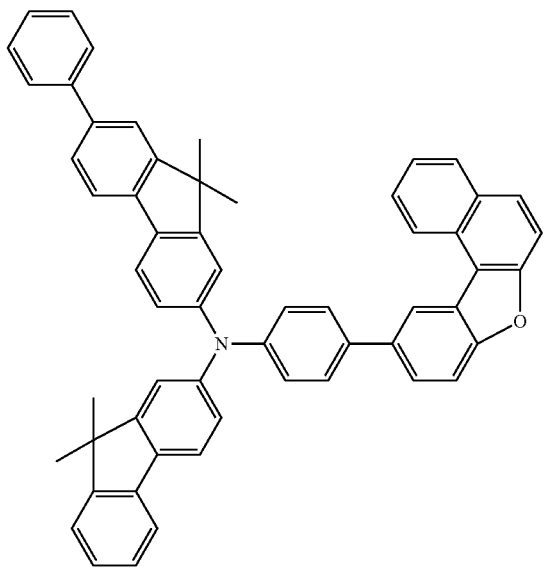
[Chem. 64]
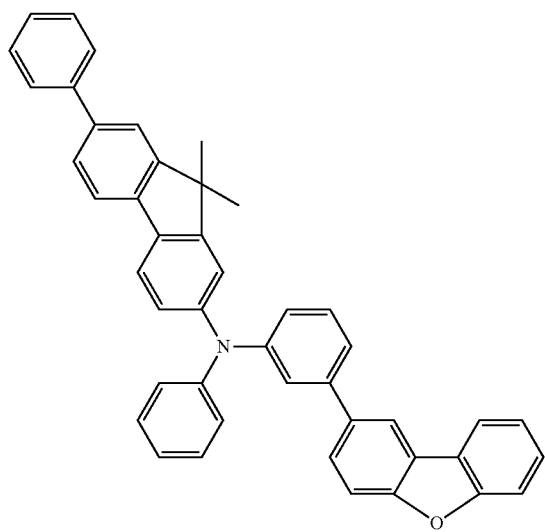
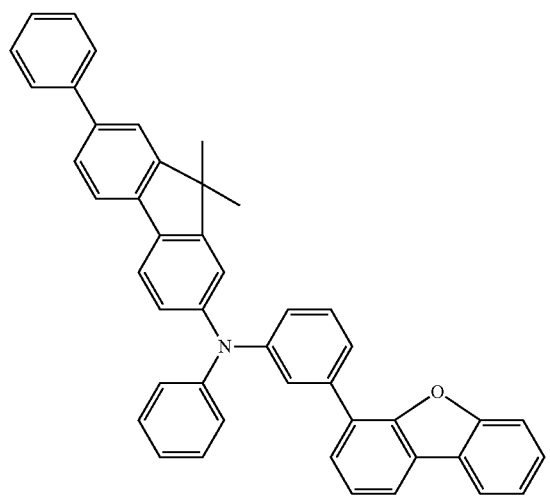

-continued
333
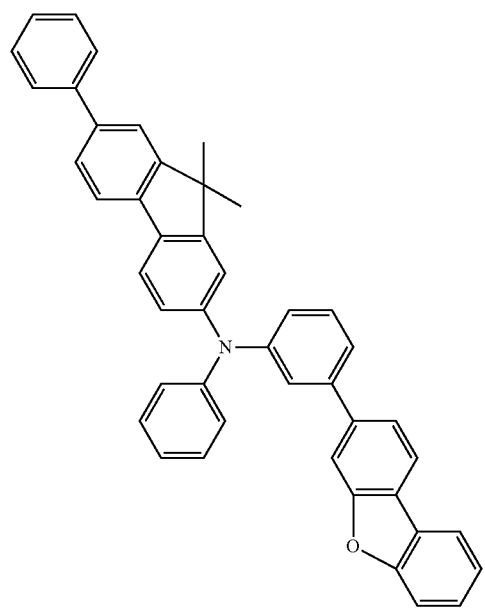
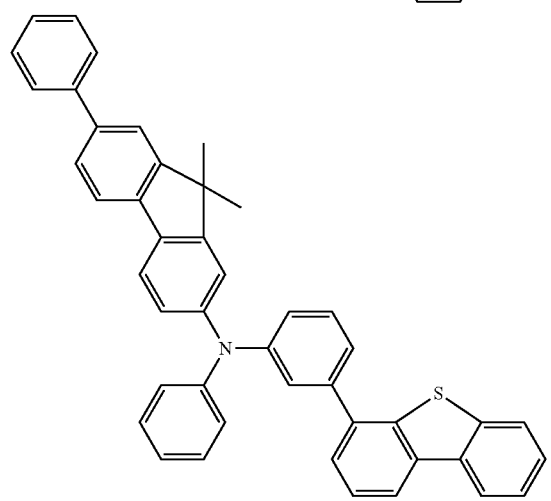
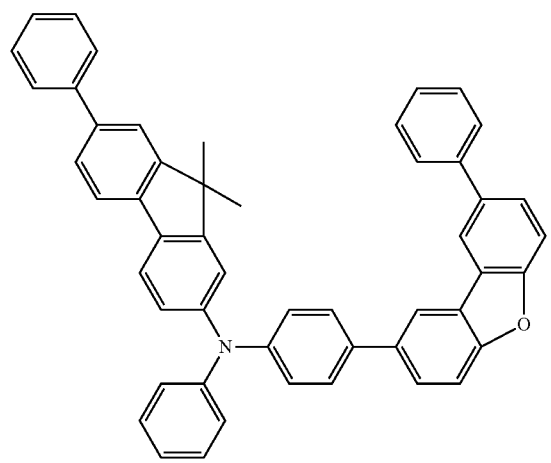
334
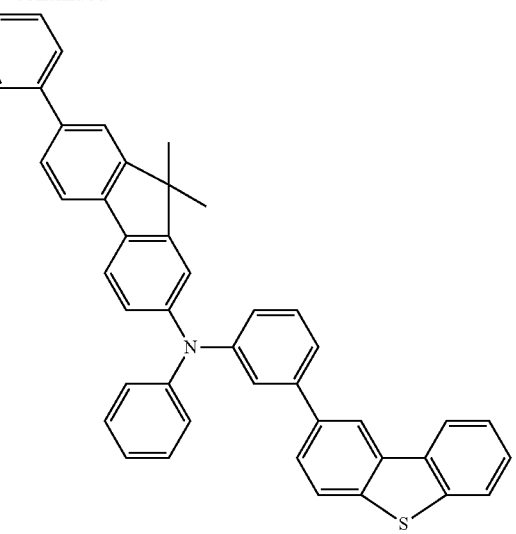
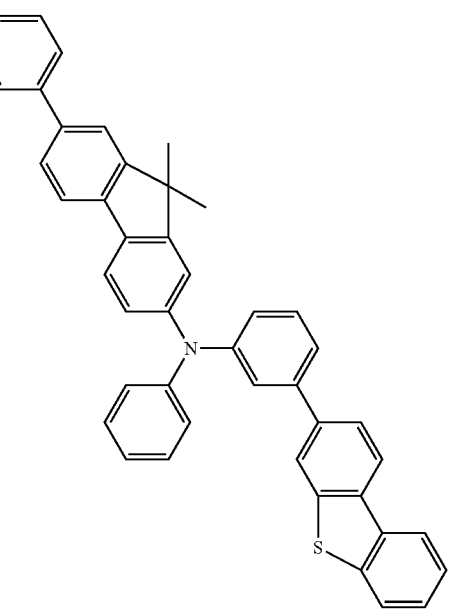
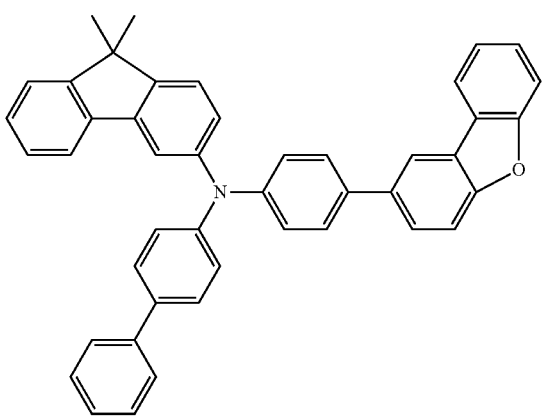

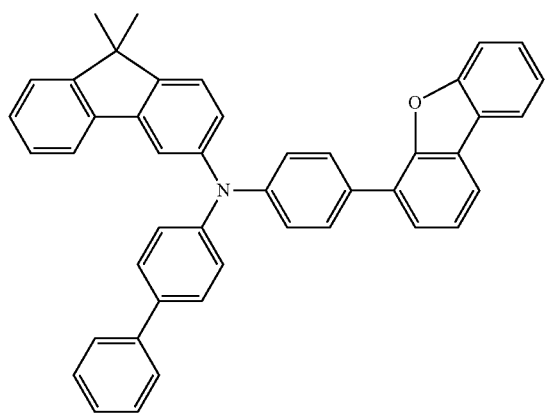
[Chem. 65]
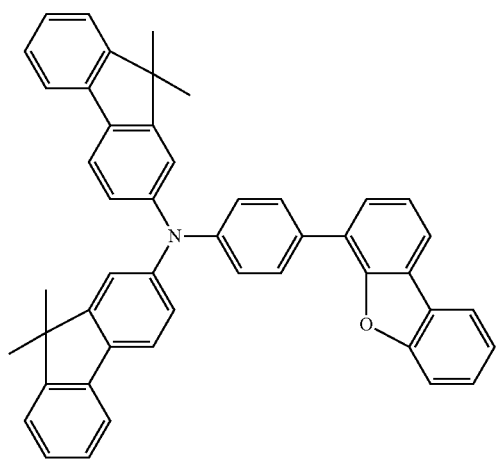
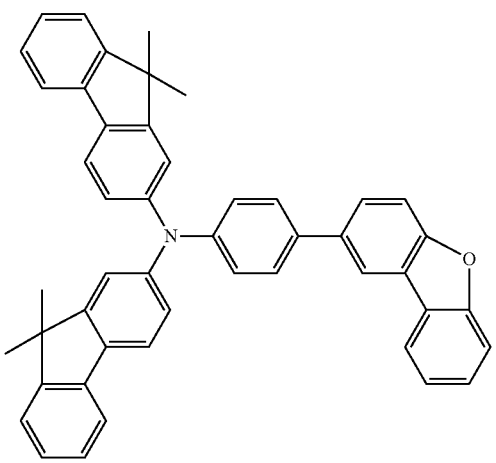
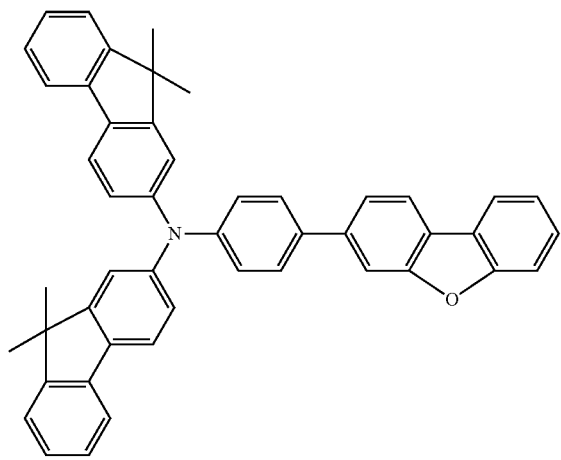
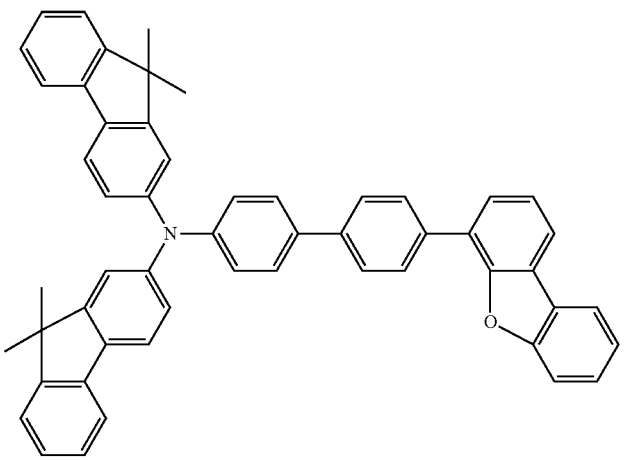

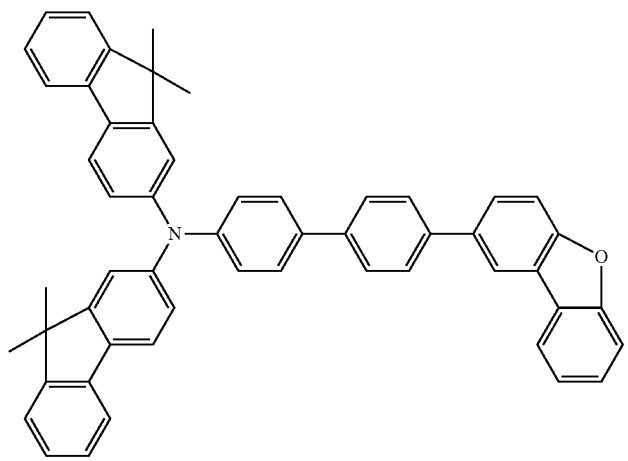
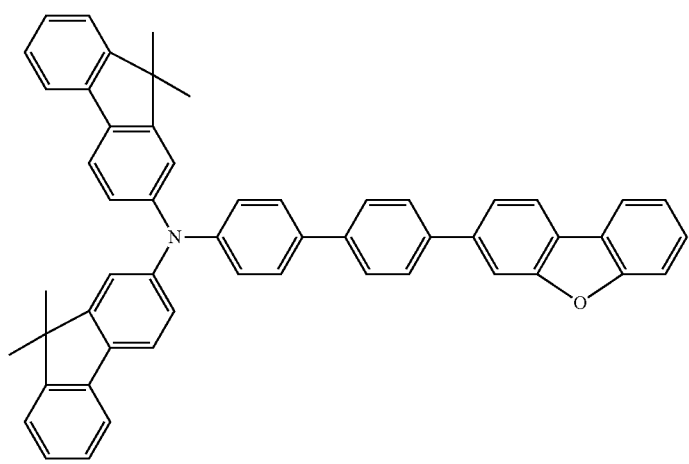
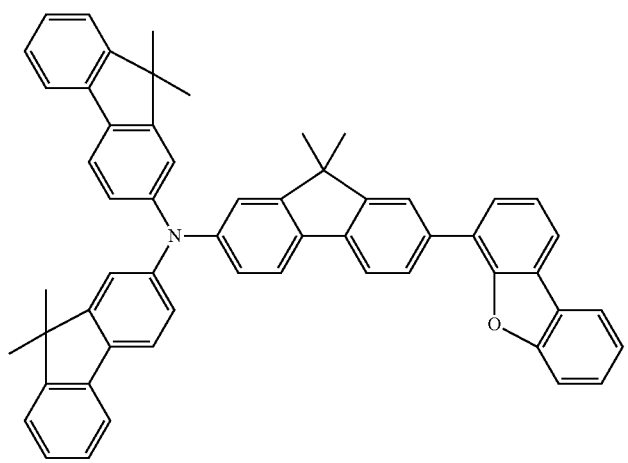

-continued
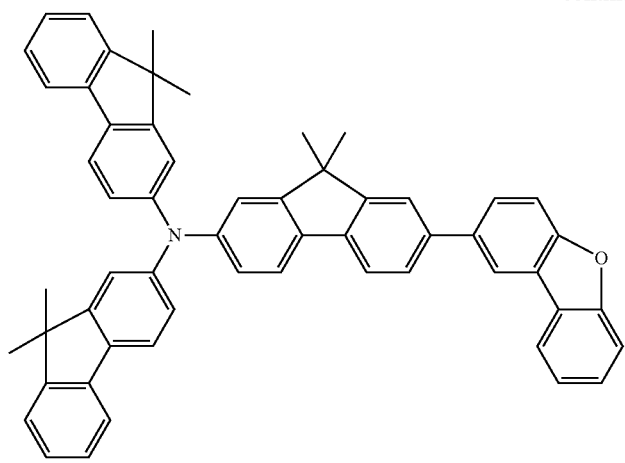
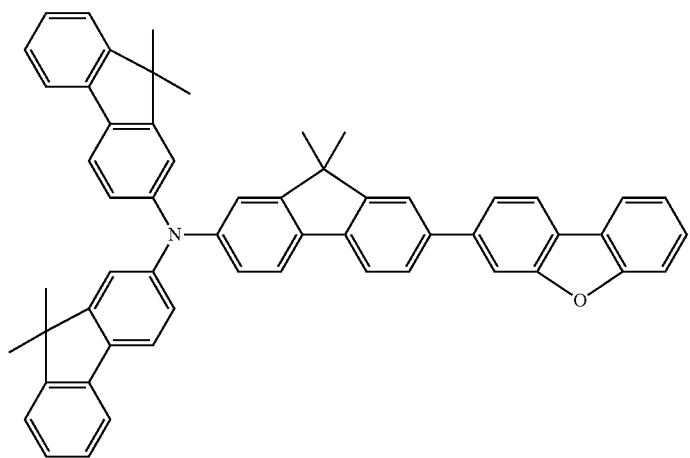
[Chem. 66]
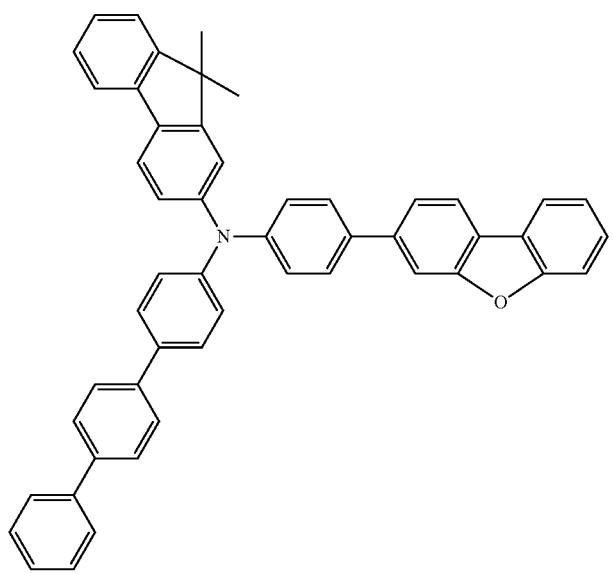

-continued
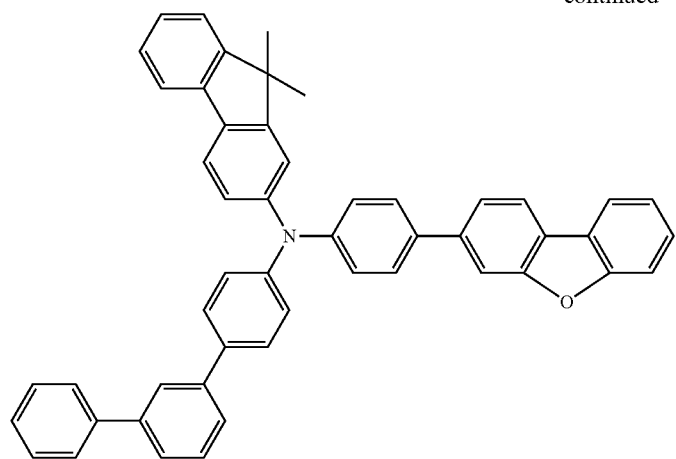
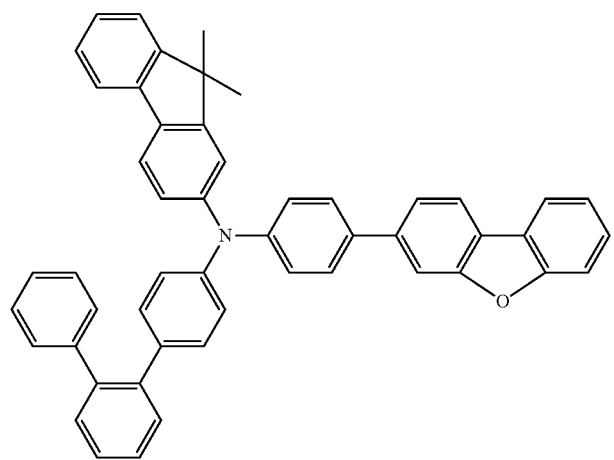
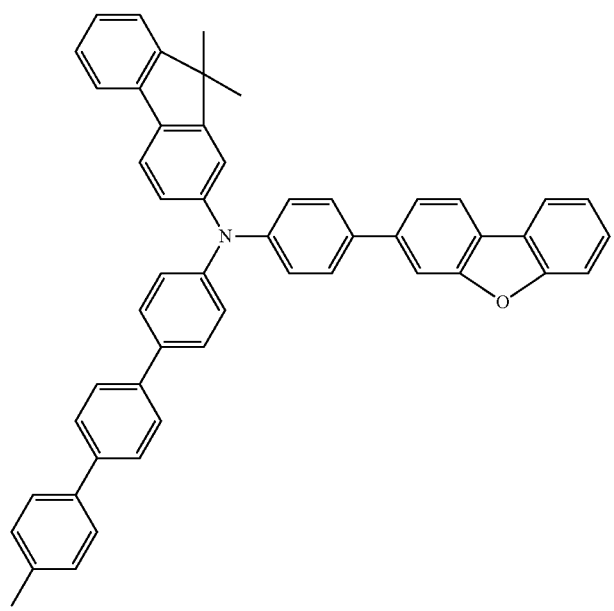

-continued
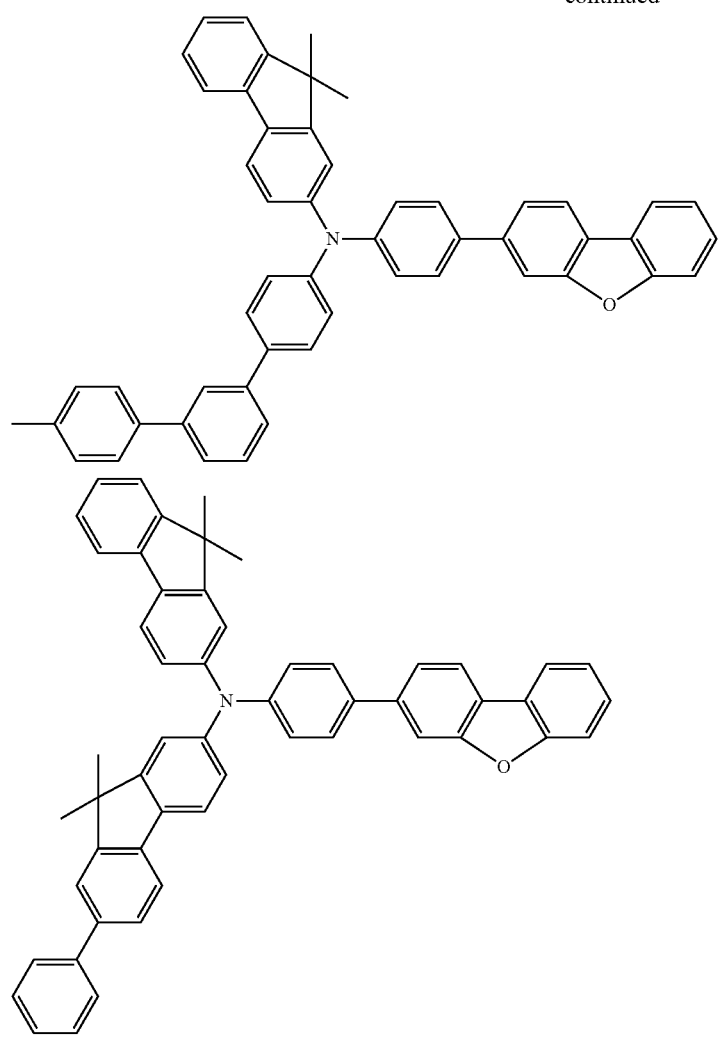
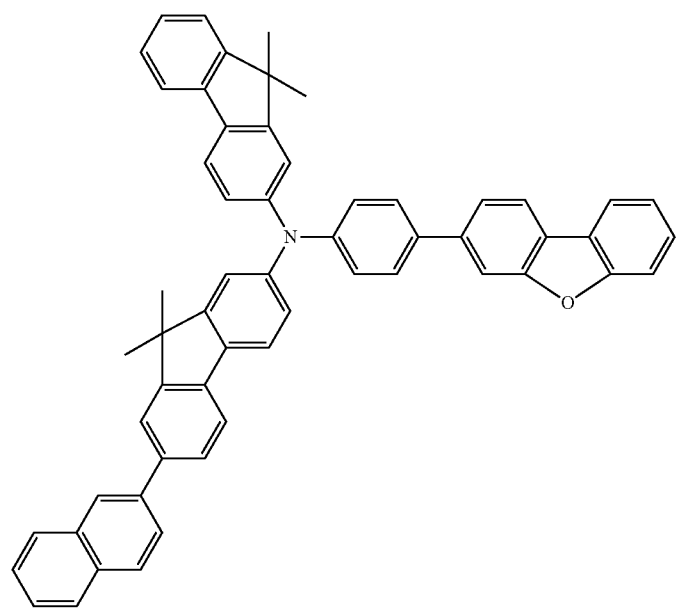

-continued
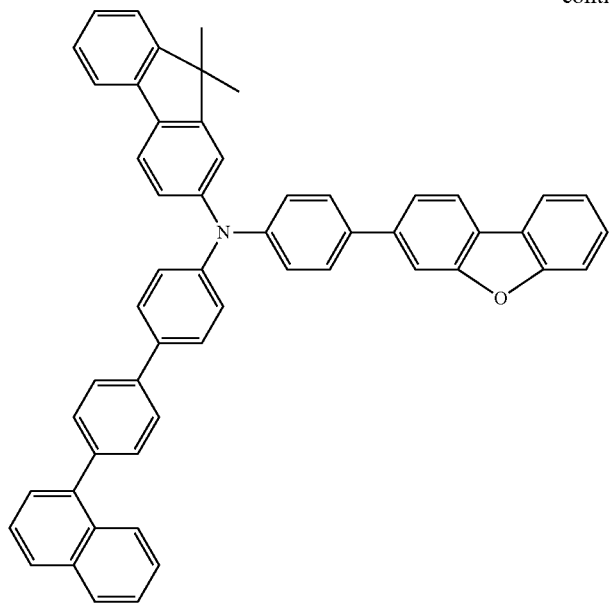
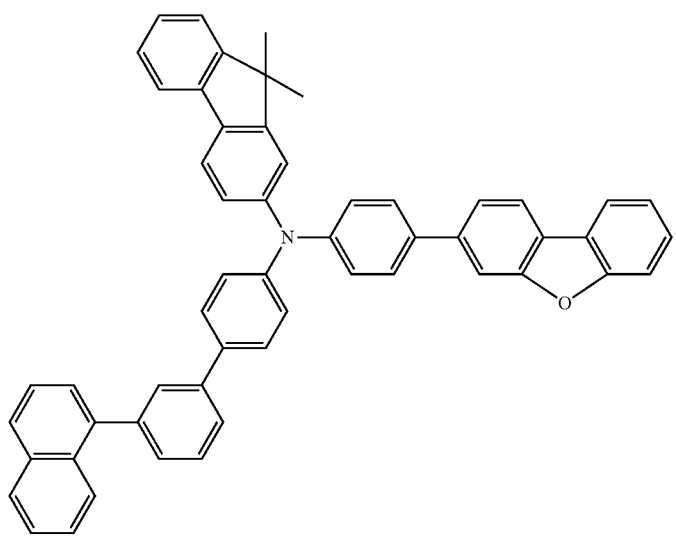
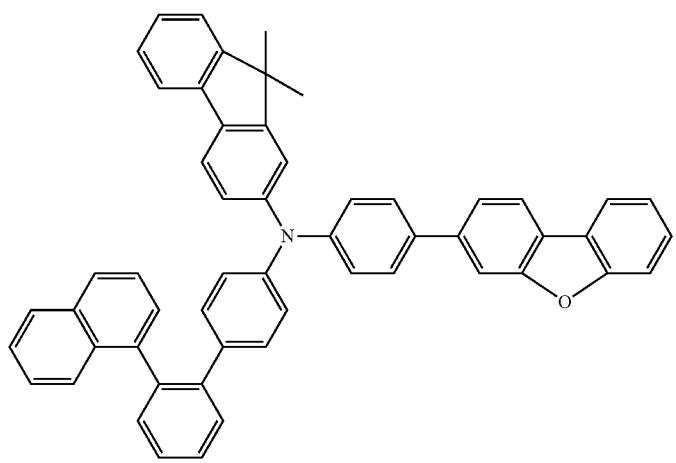

-continued
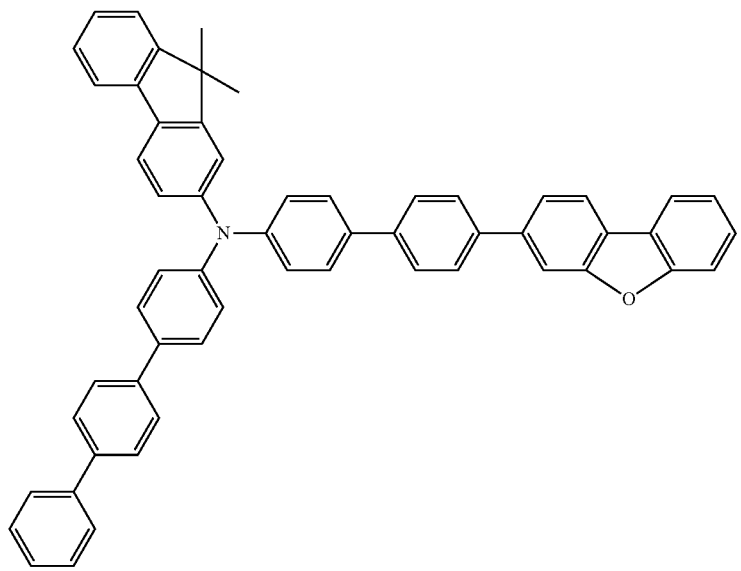
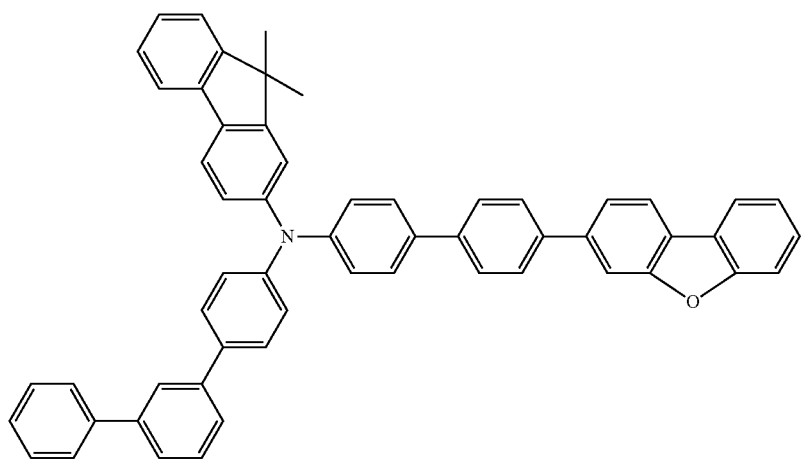
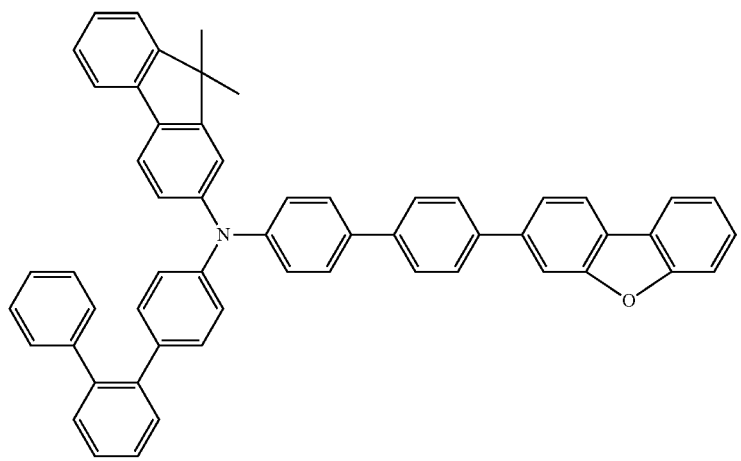

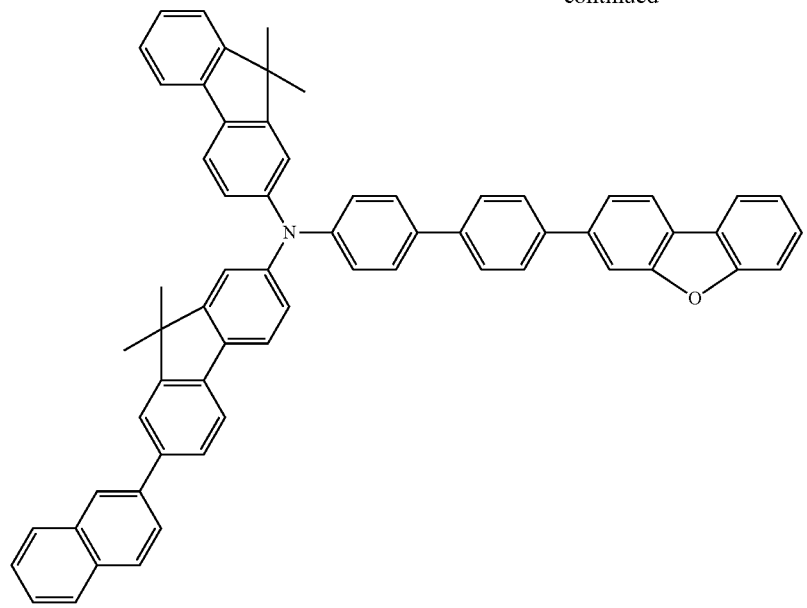
[Chem. 67]
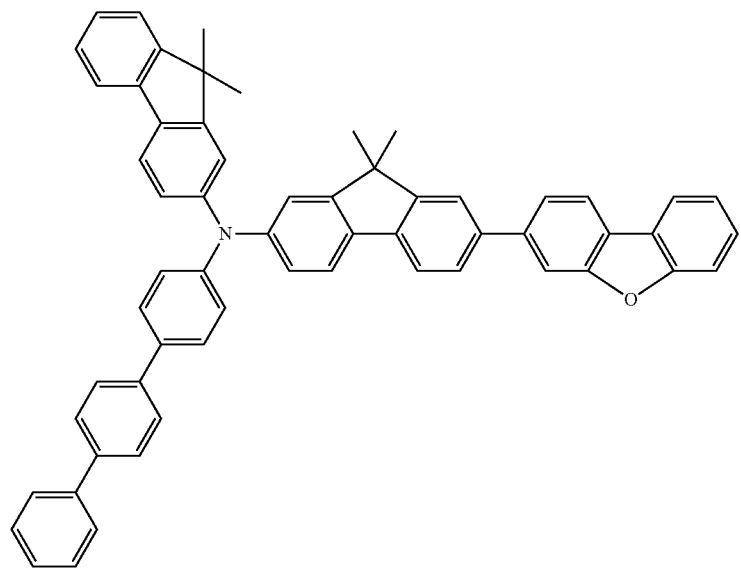
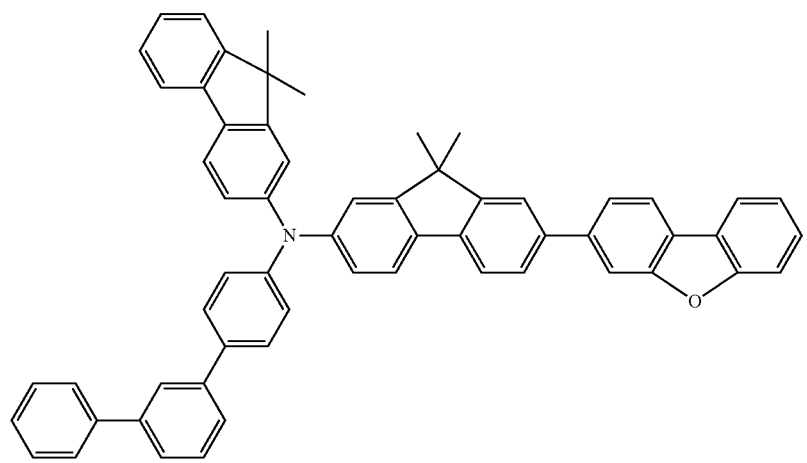

-continued
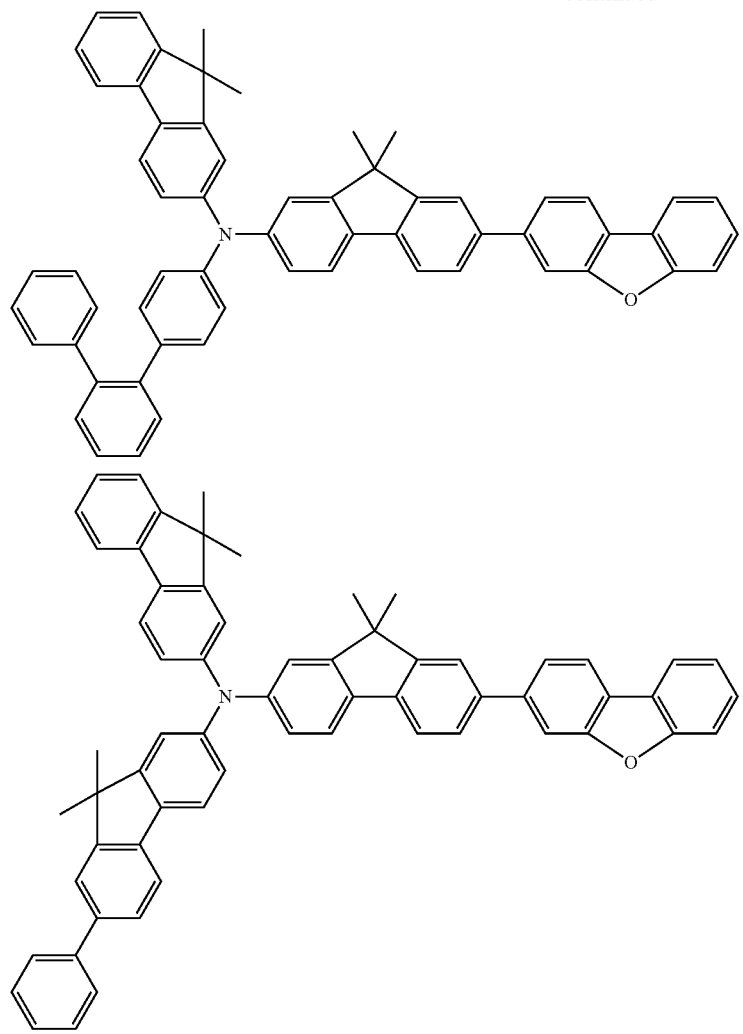
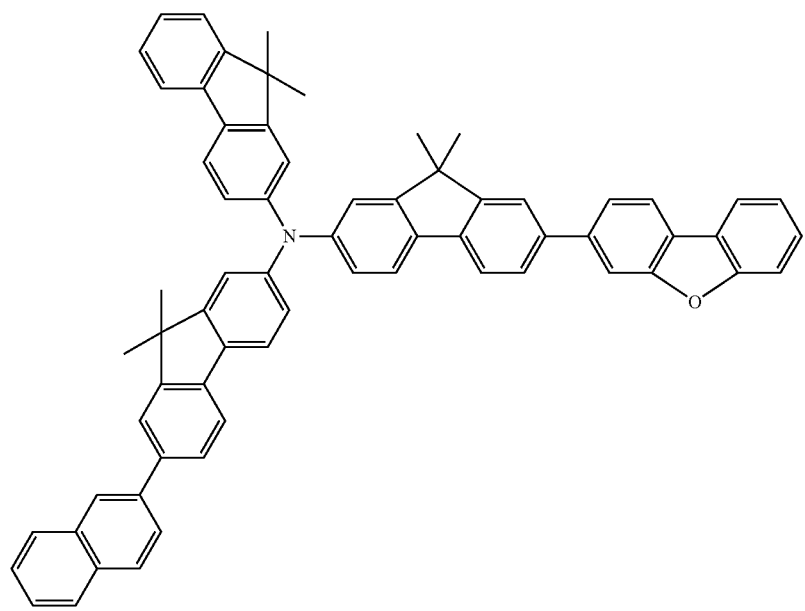

-continued
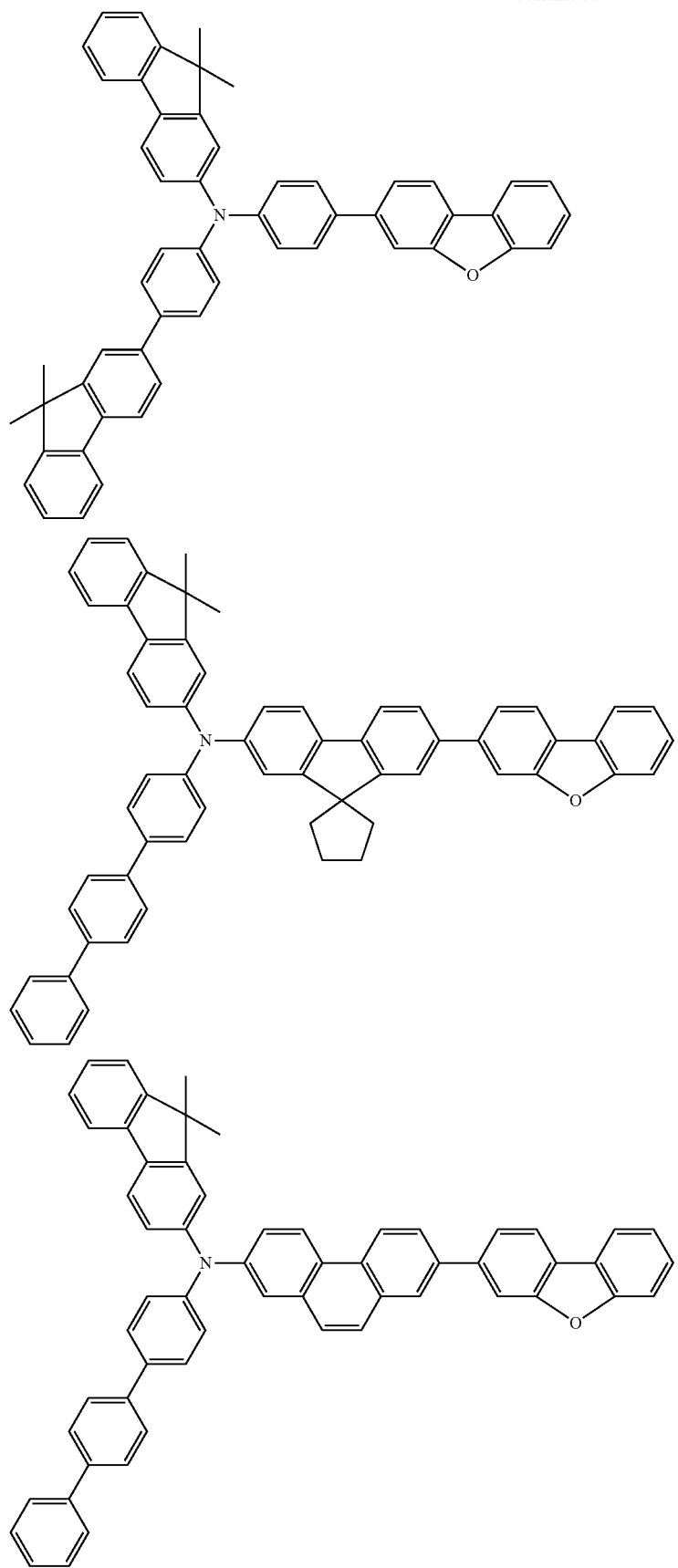

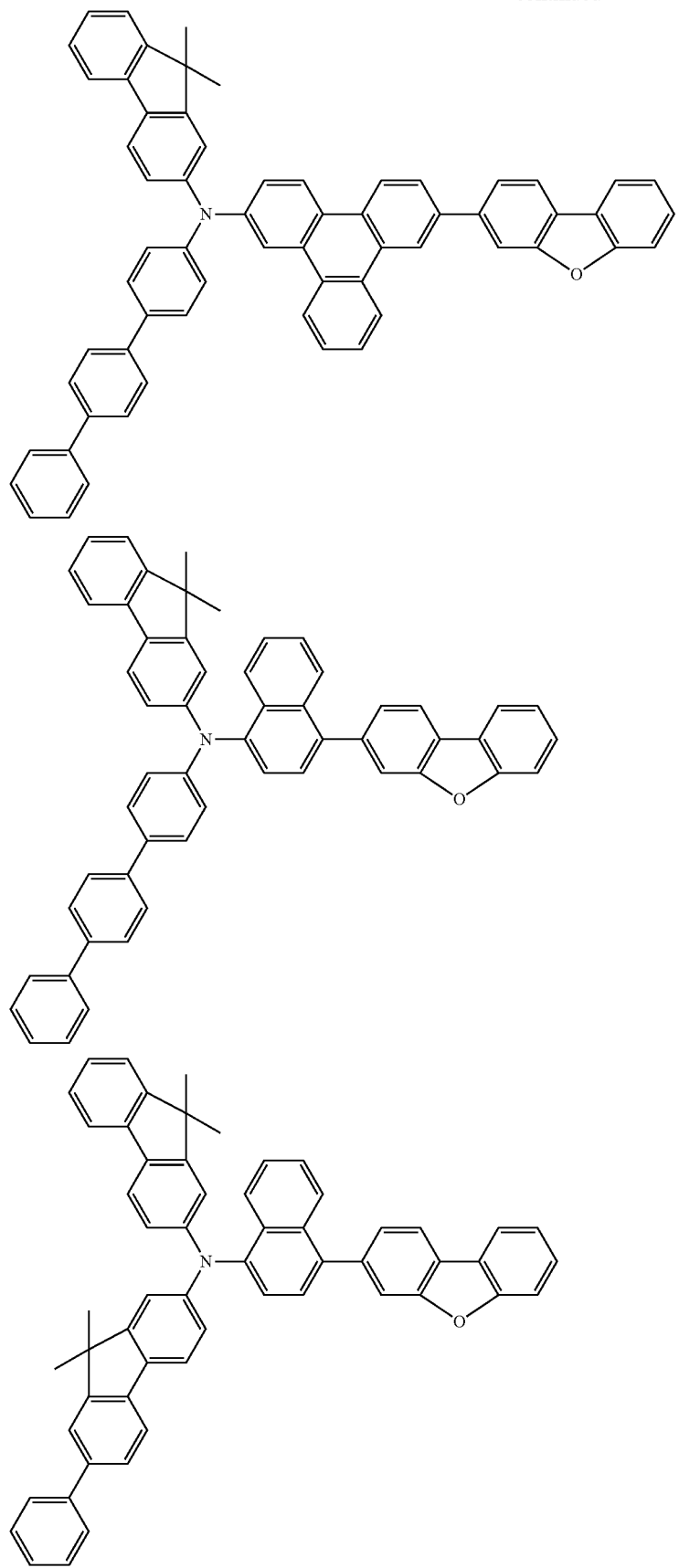

-continued
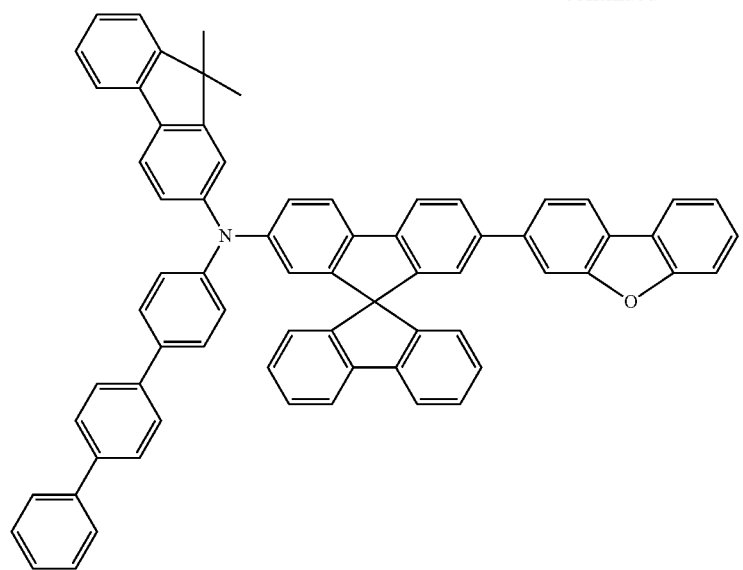
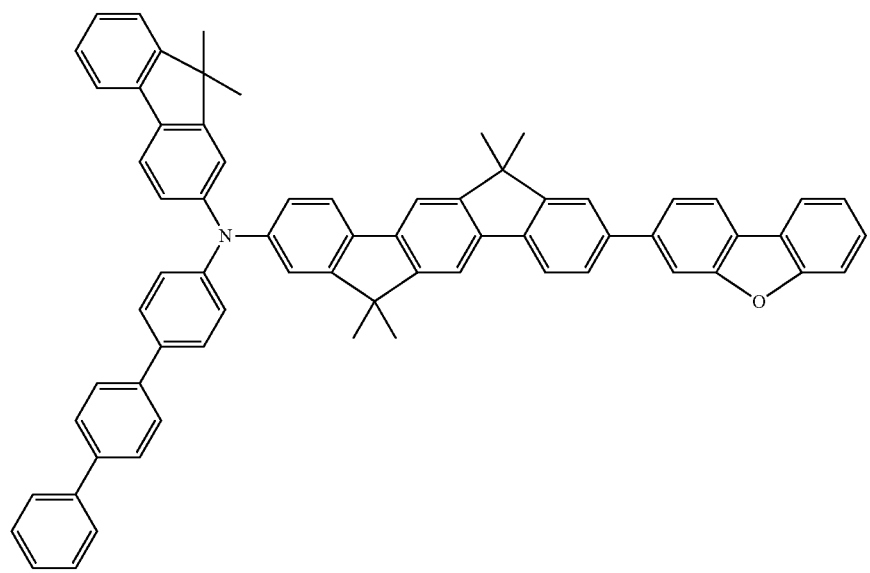
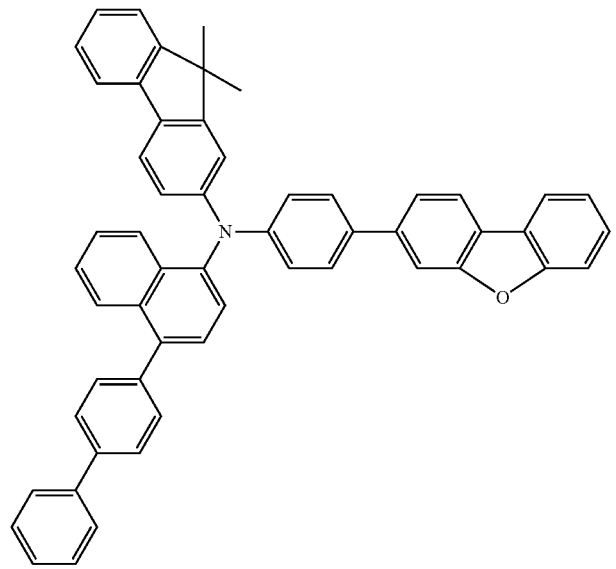

[Chem. 68]
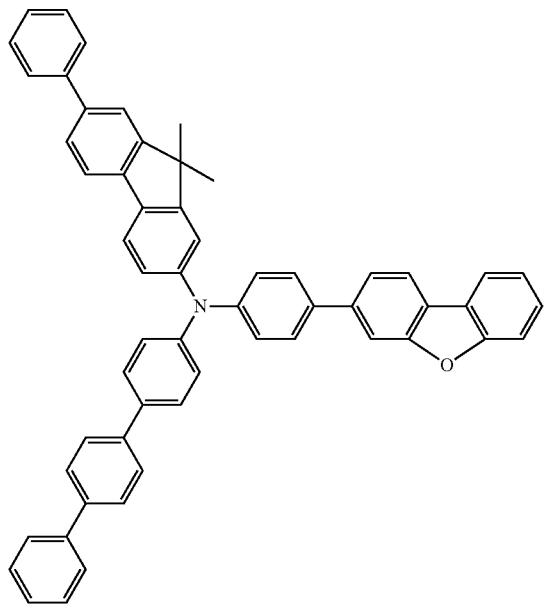
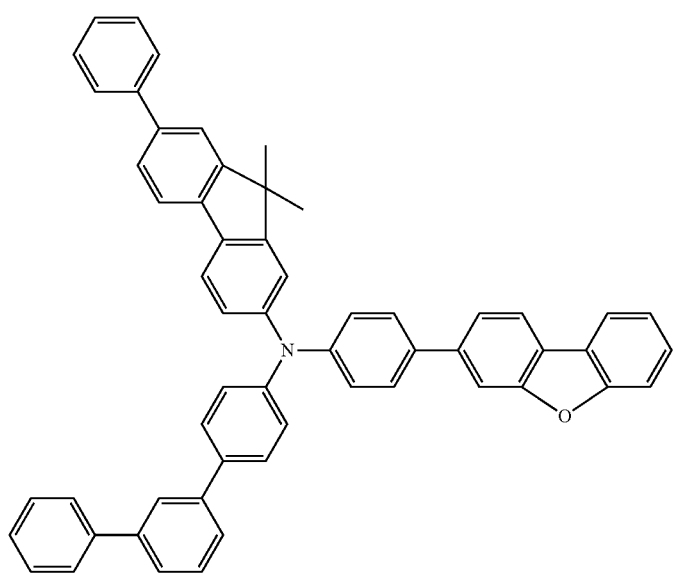

361
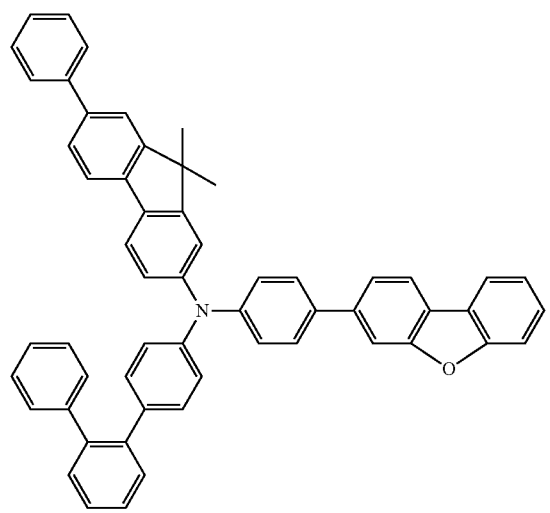
362
-continued
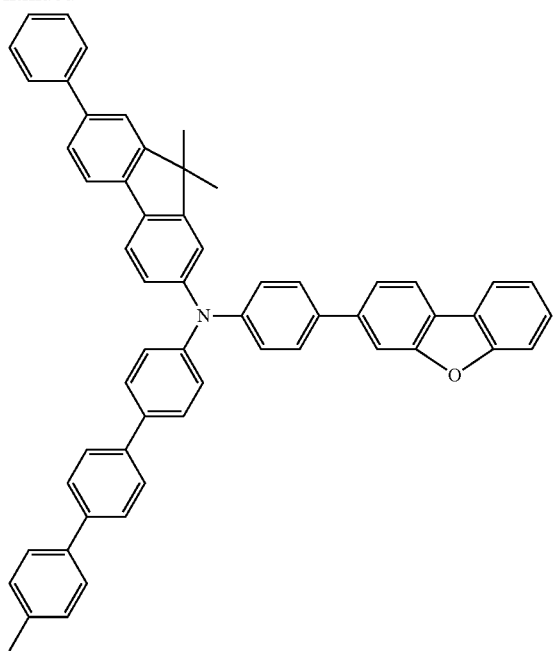
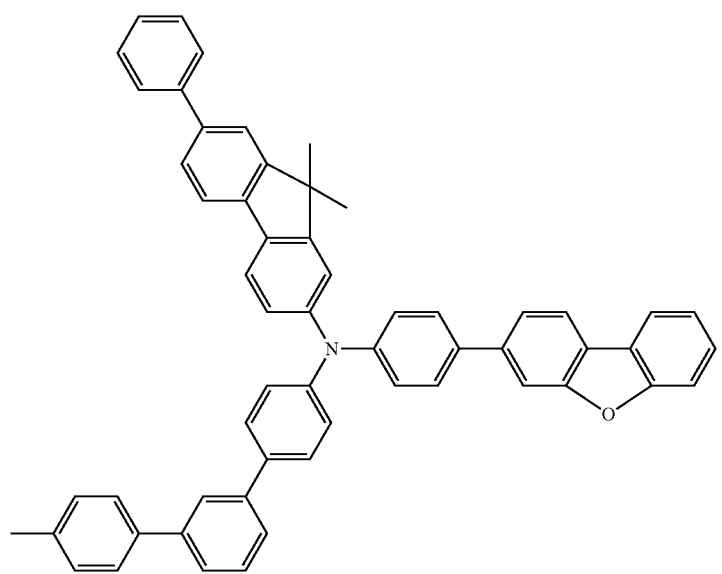

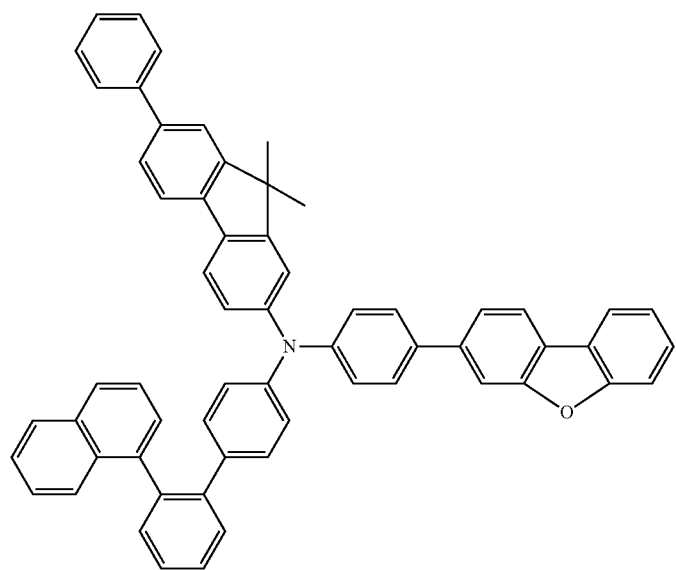
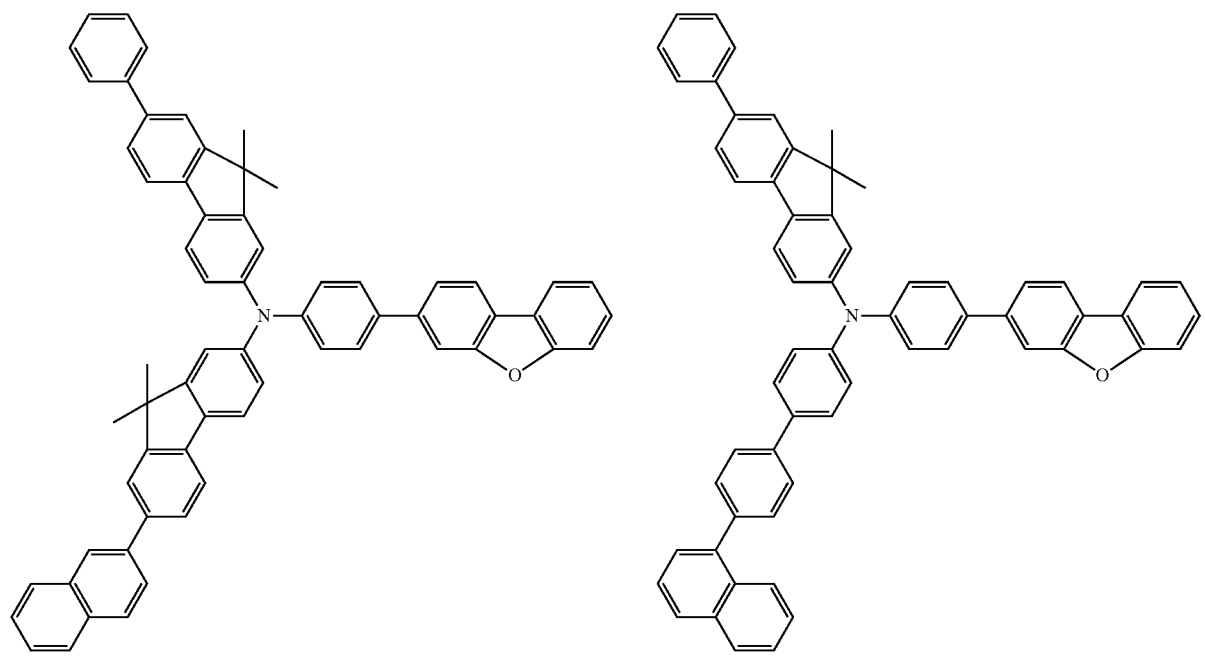

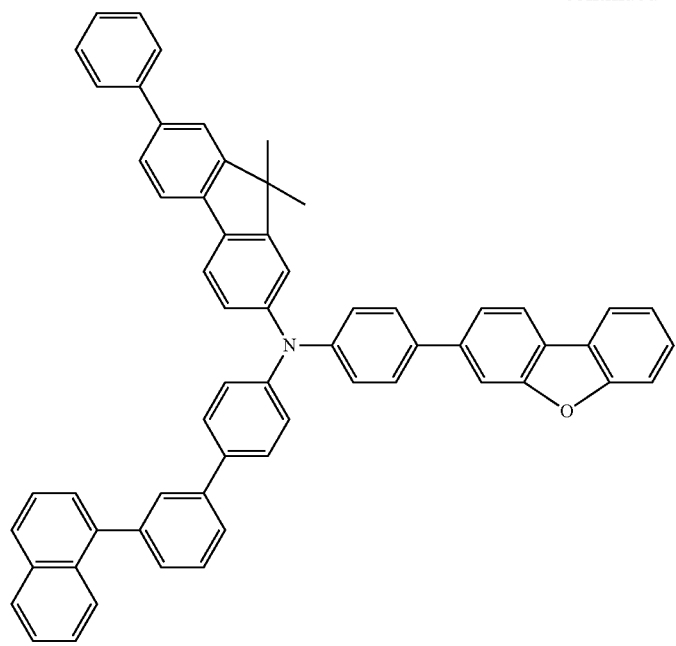
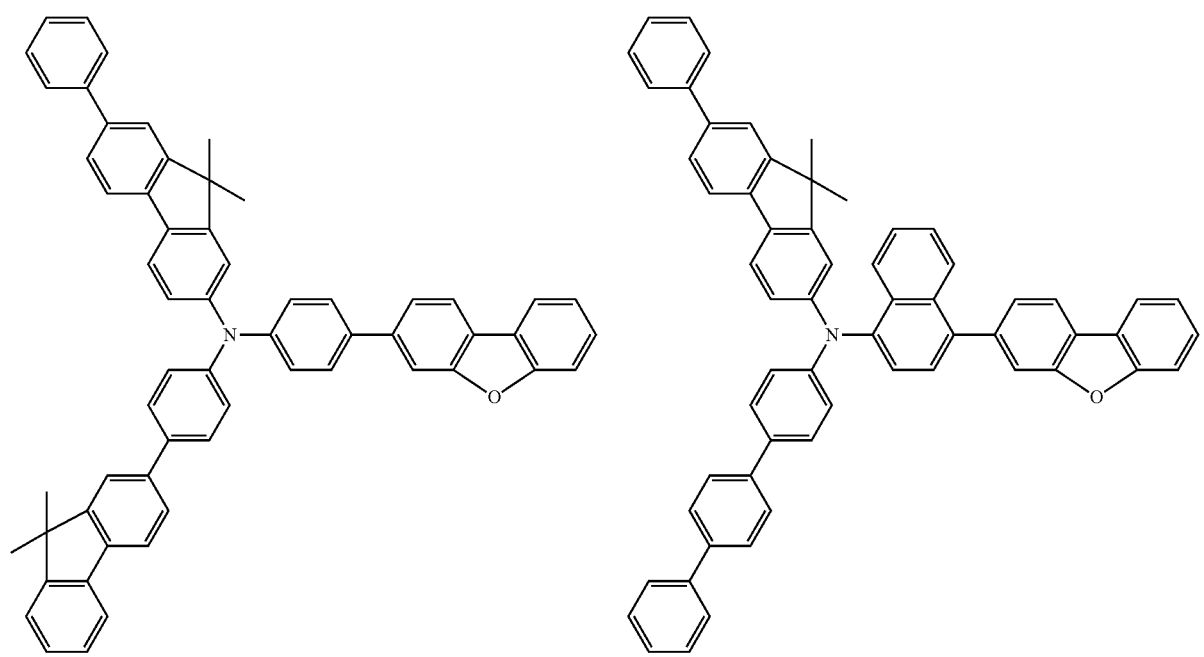

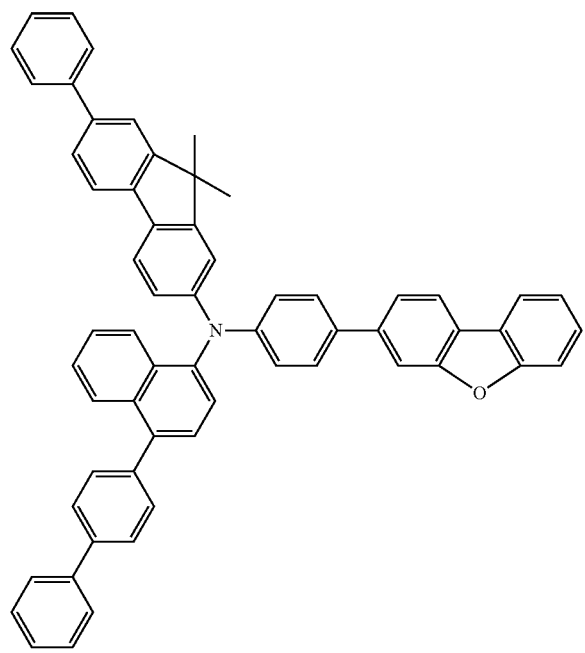
[Chem. 69]
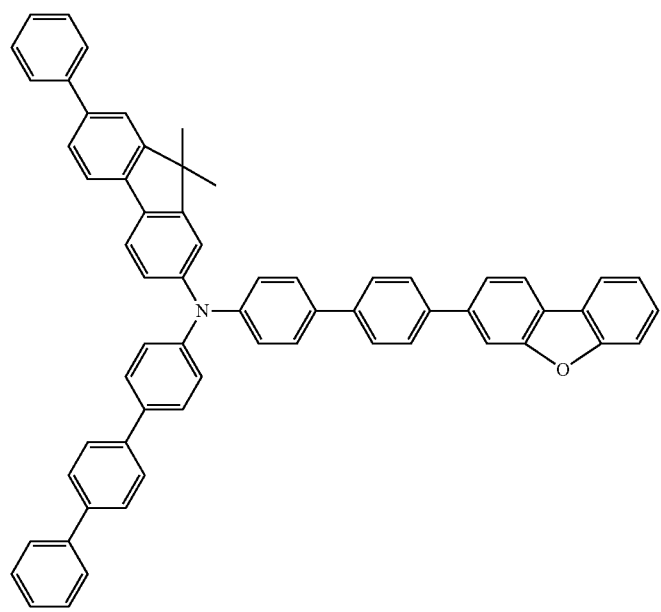

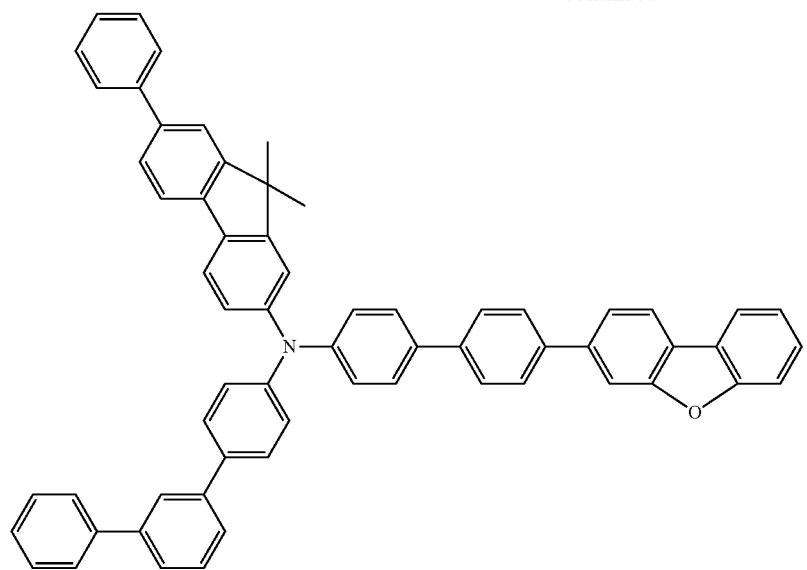
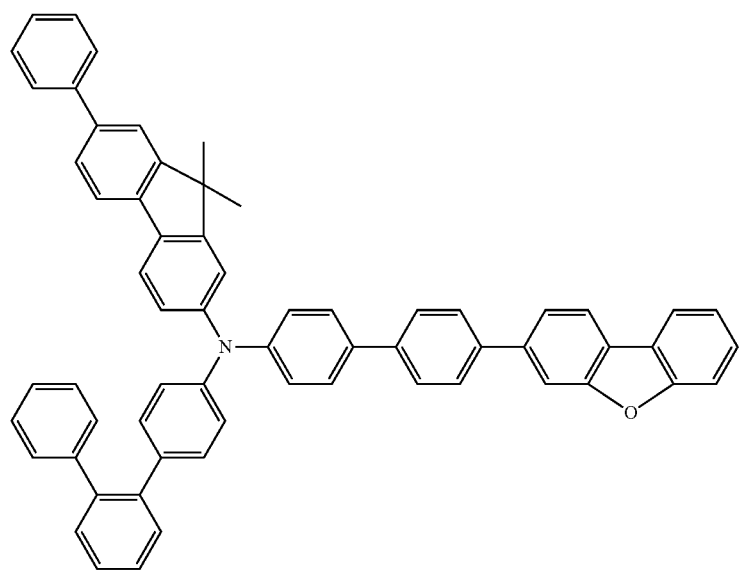

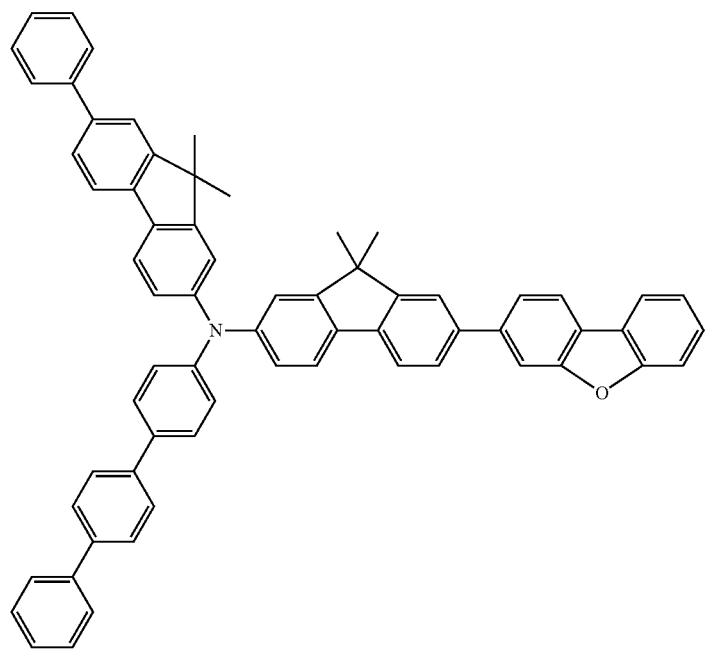
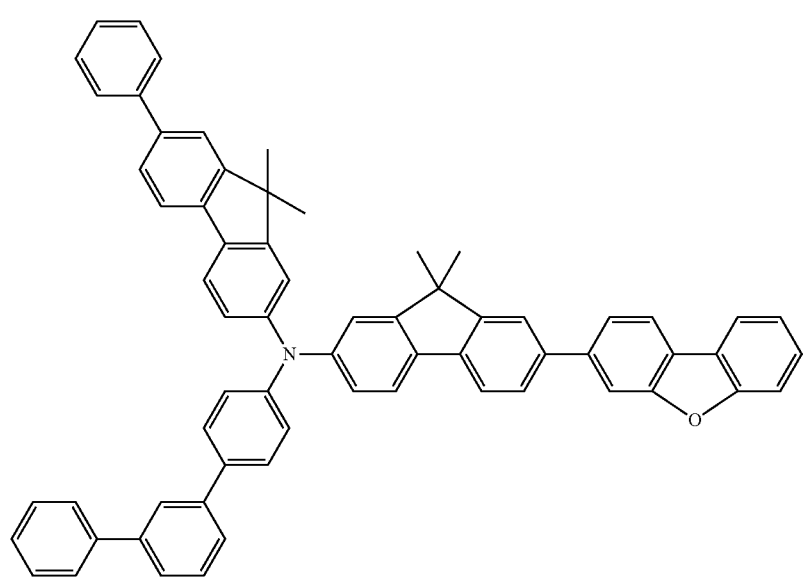

-continued
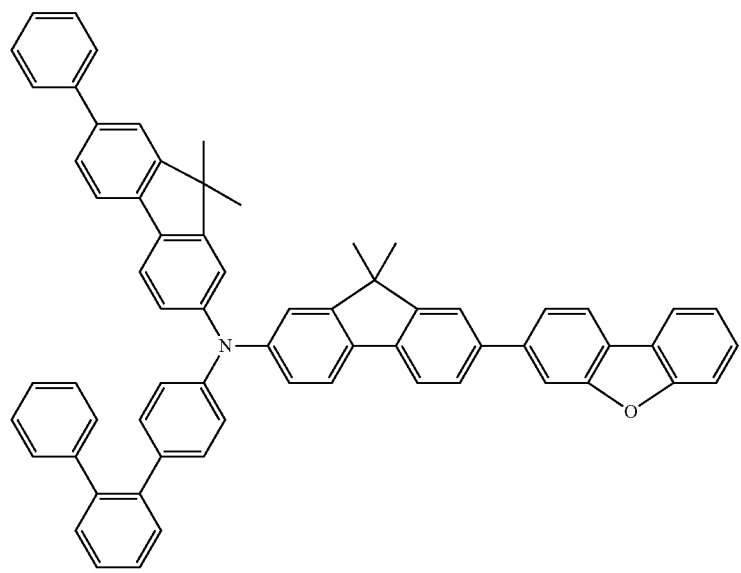
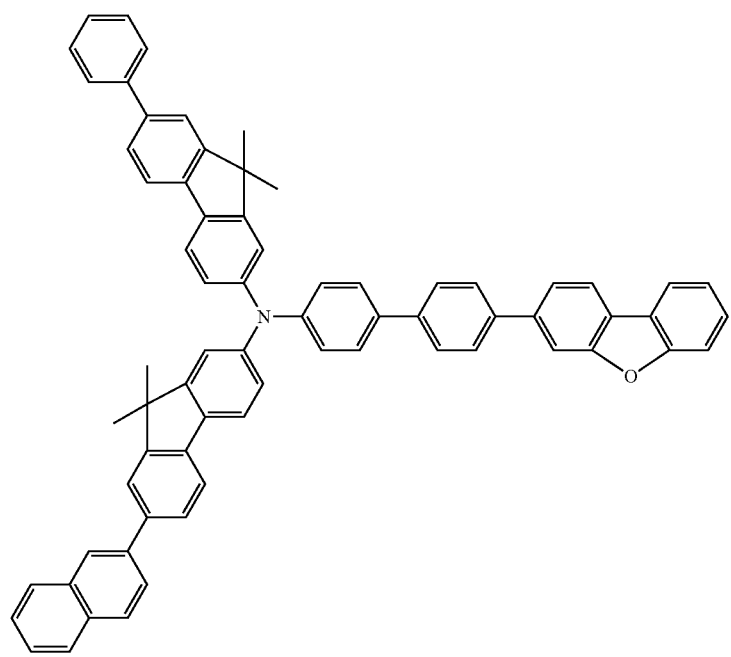

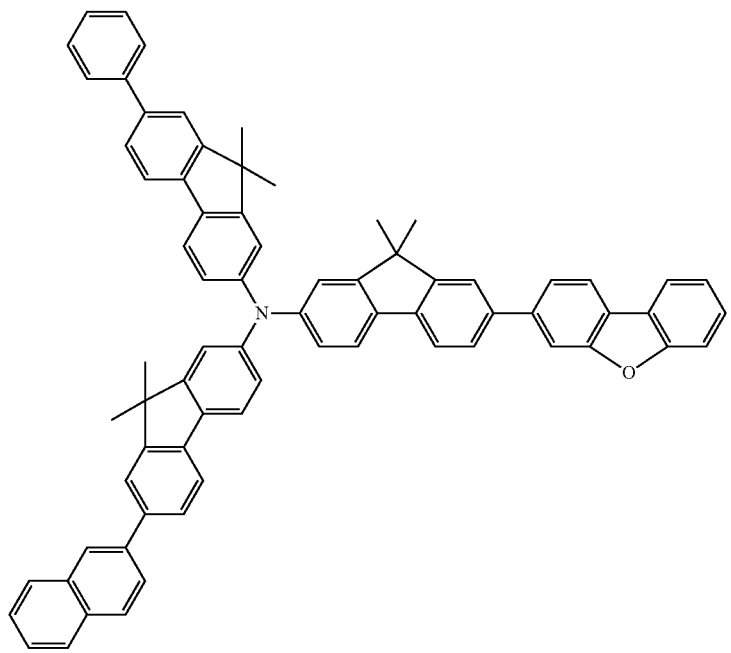
[Chem. 70]
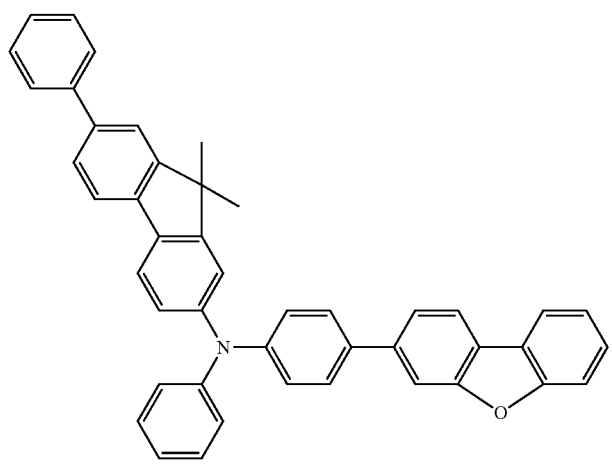
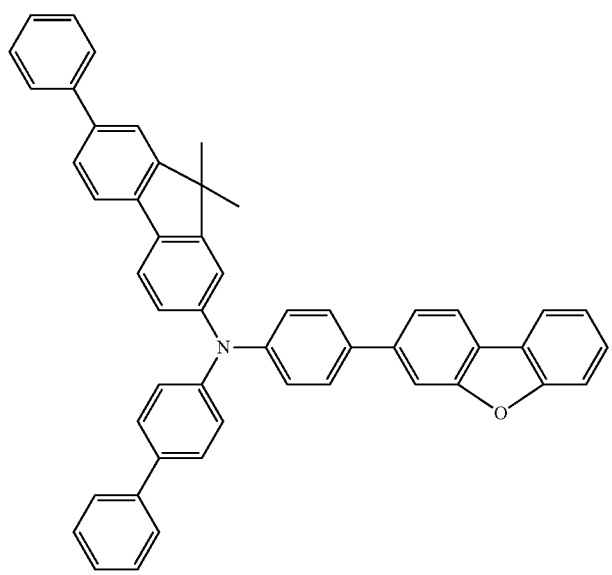

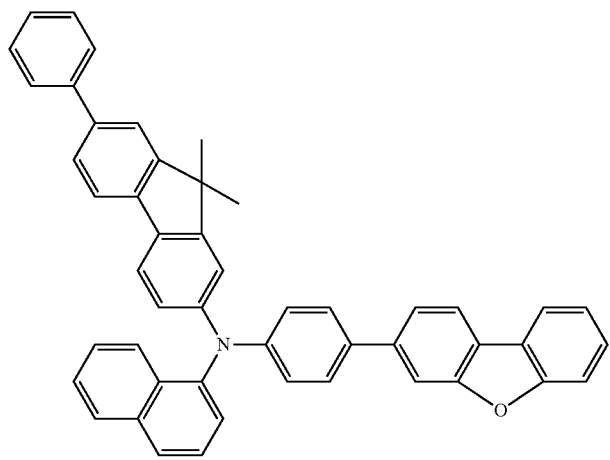
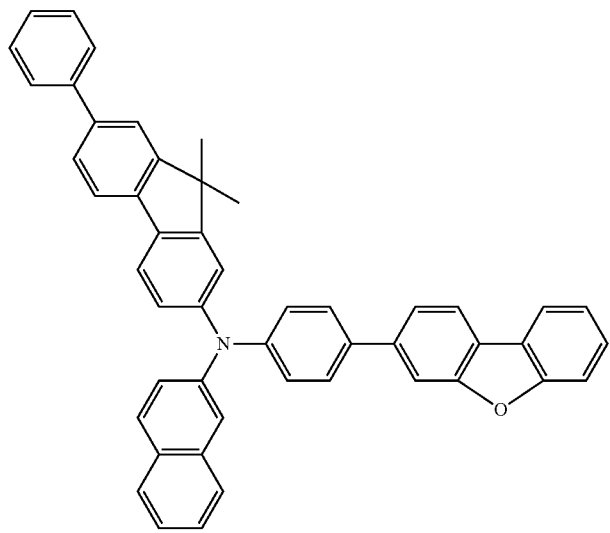
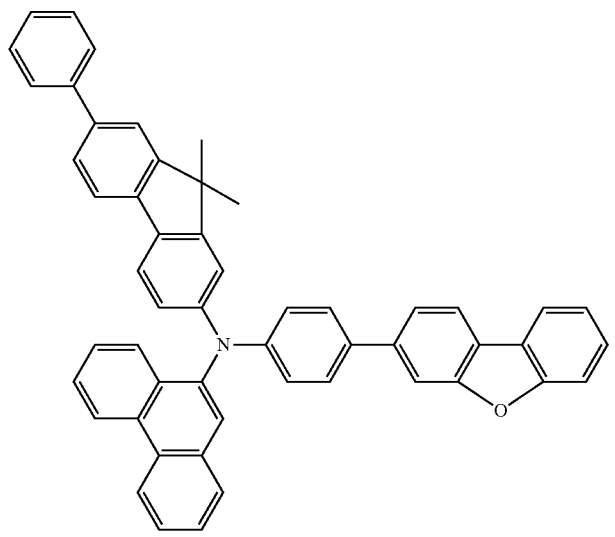

-continued
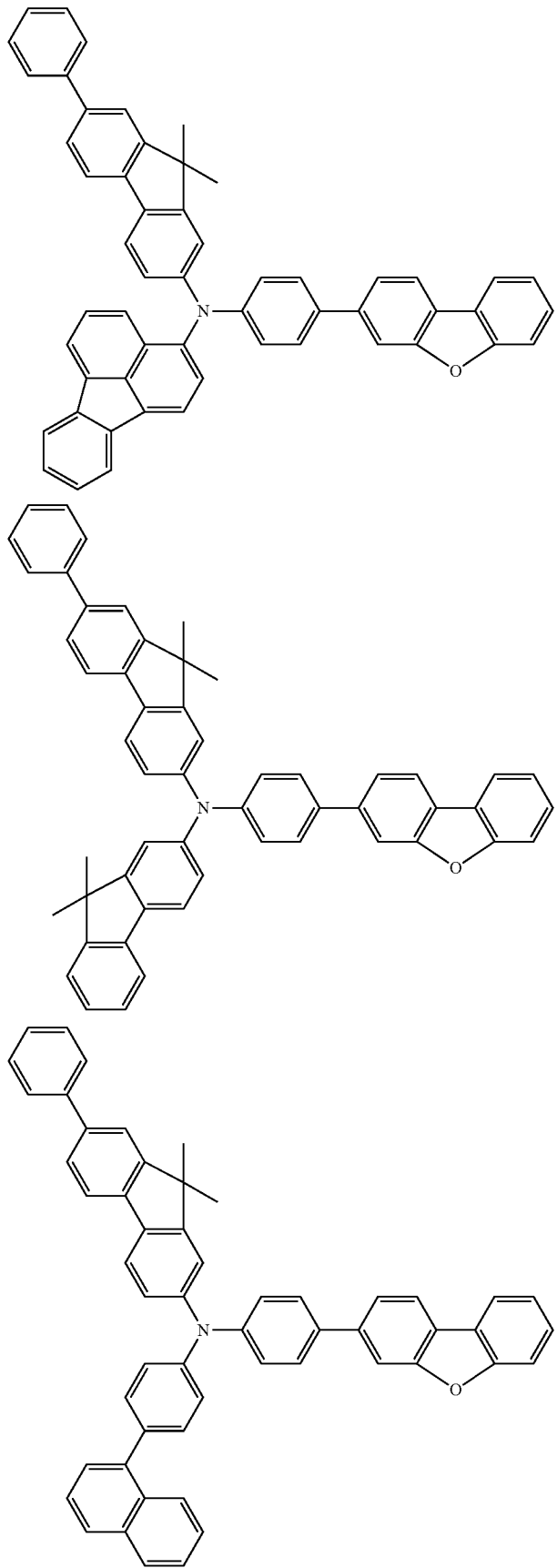

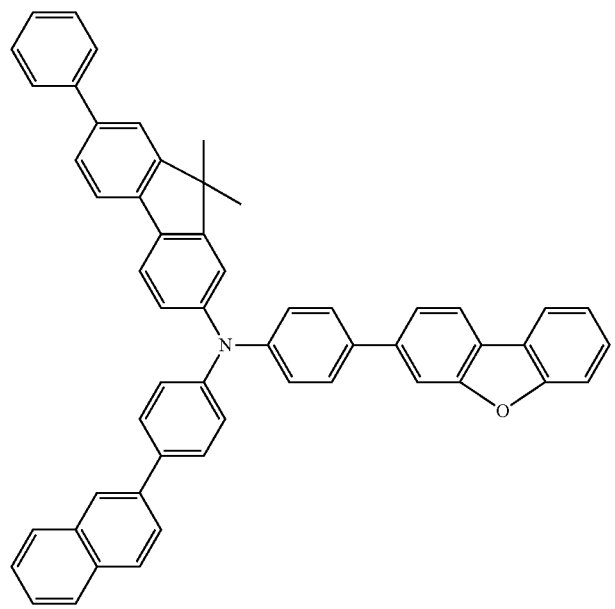
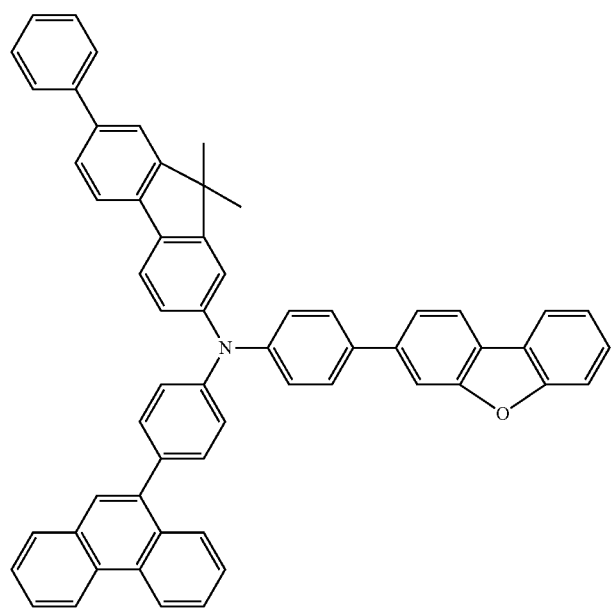

383 384
-continued
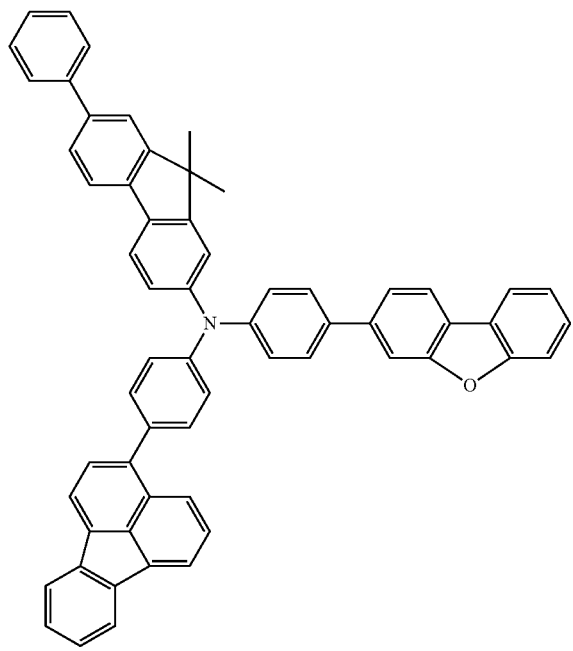
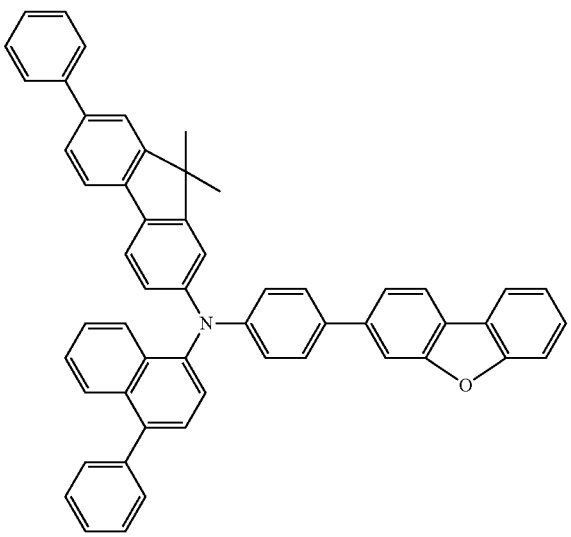
[Chem. 71]
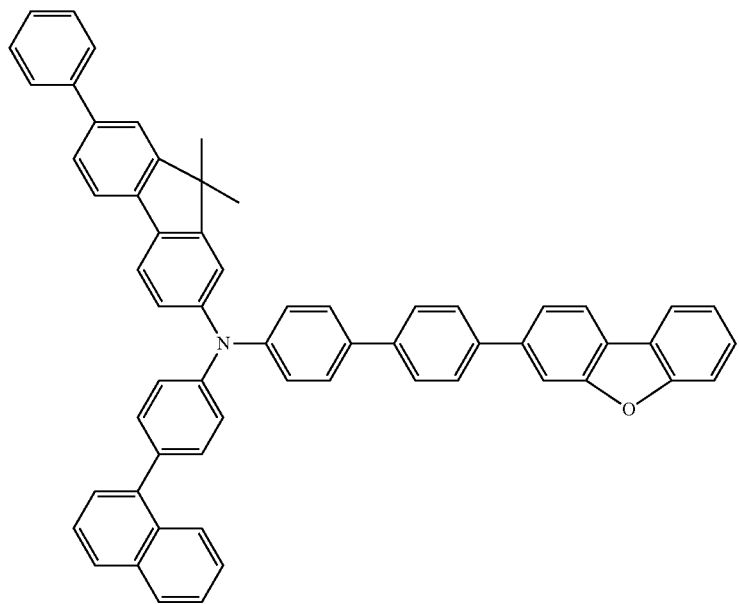

-continued
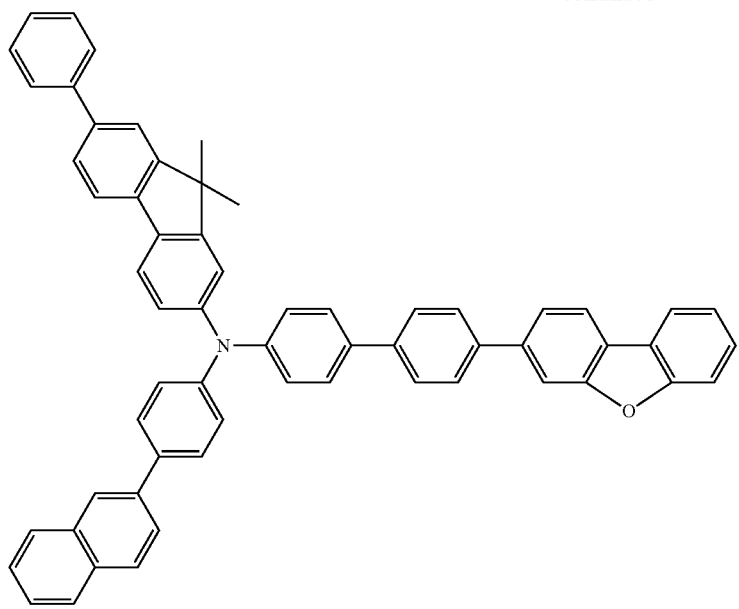
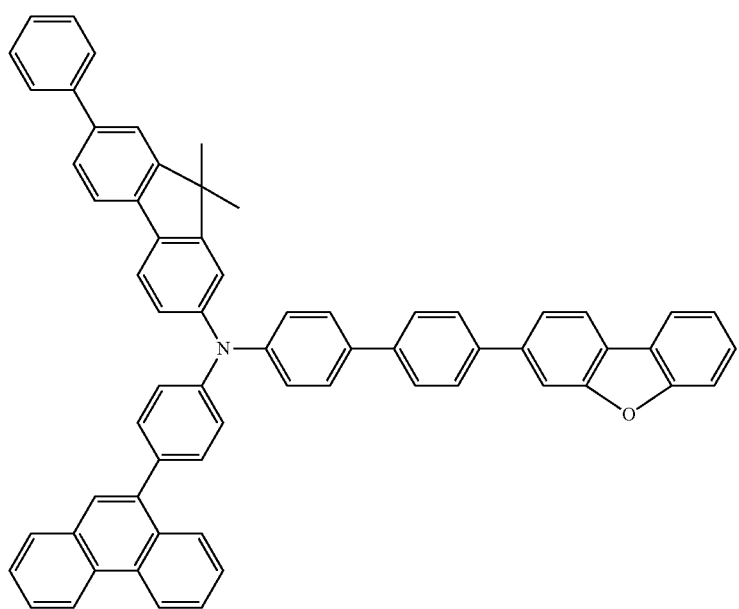

-continued
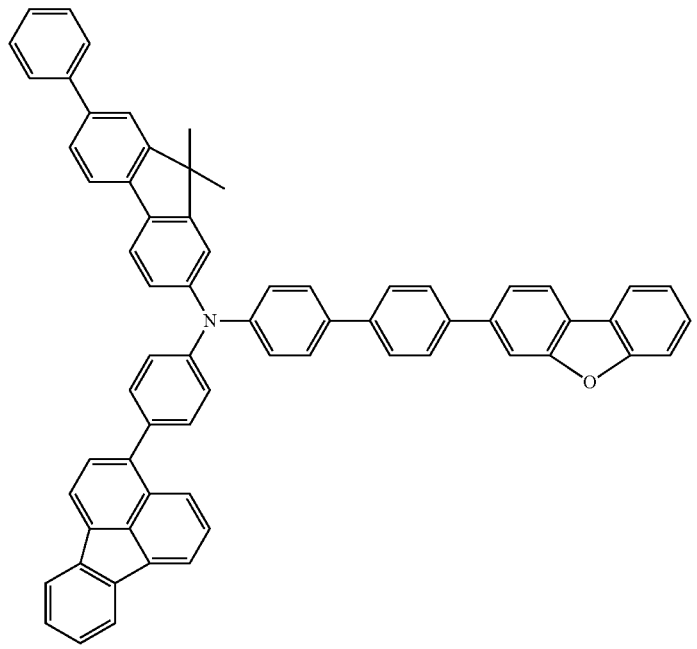
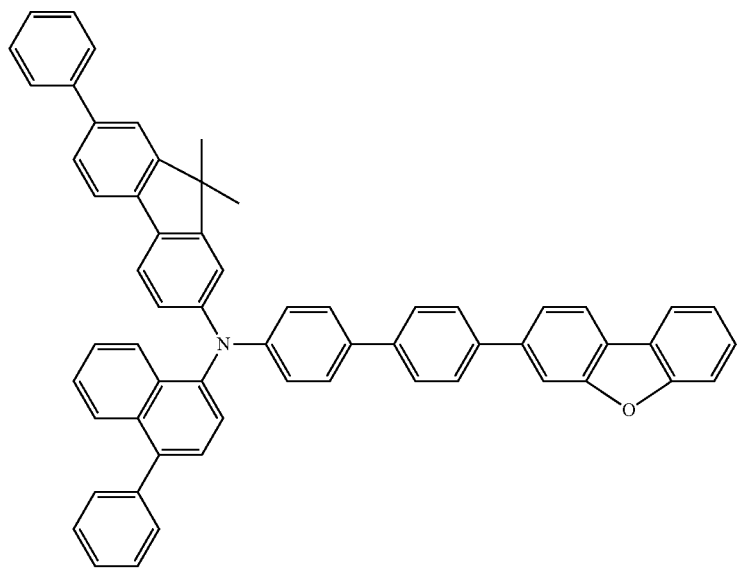
[Chem. 72]
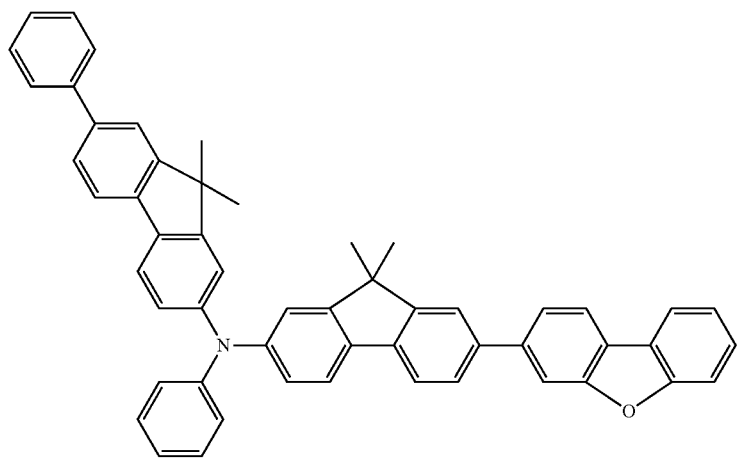

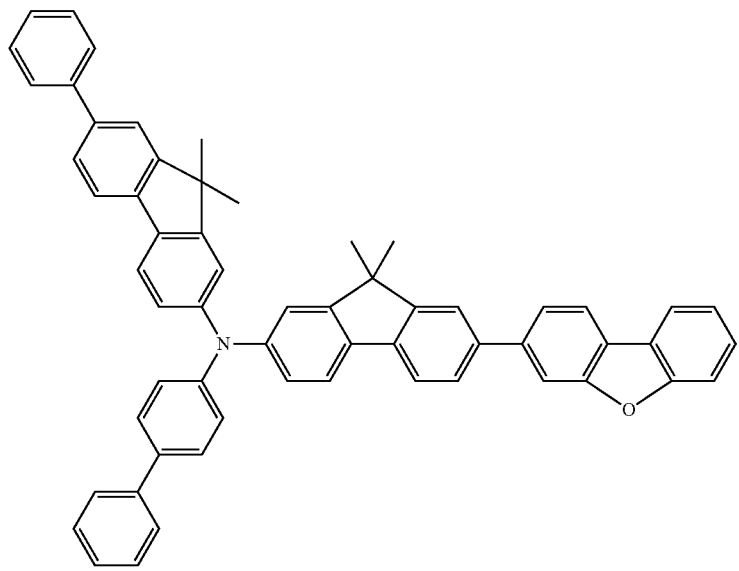
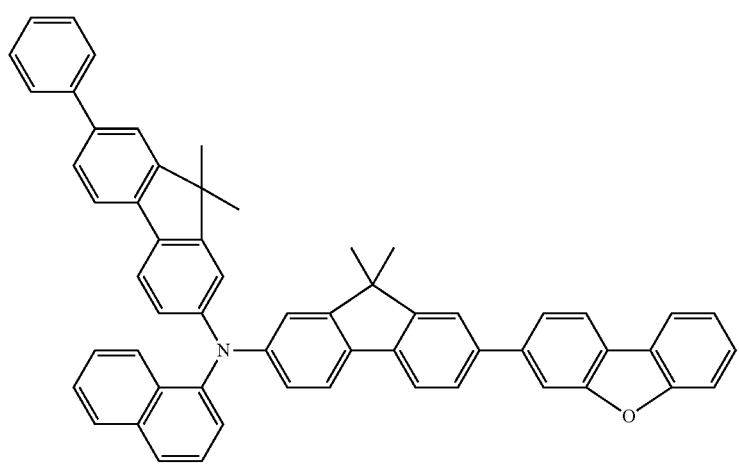
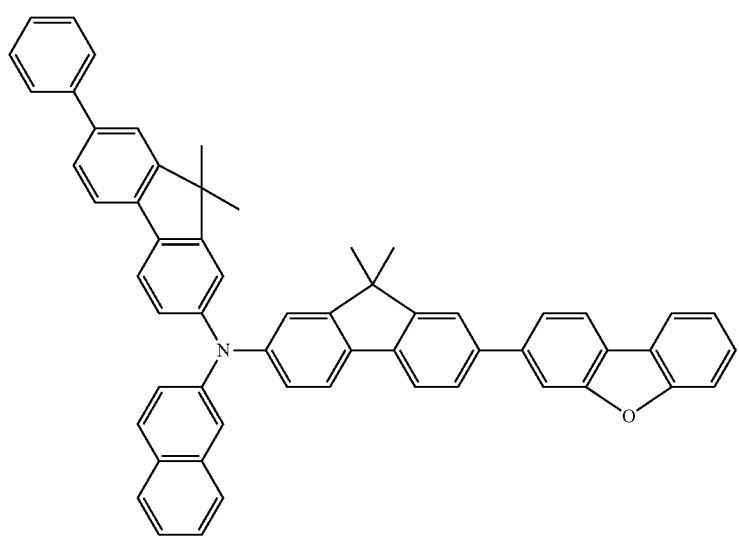

-continued
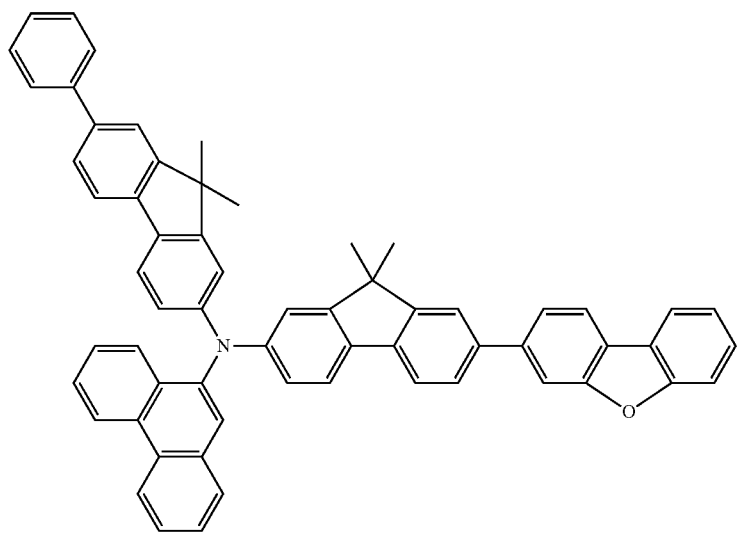
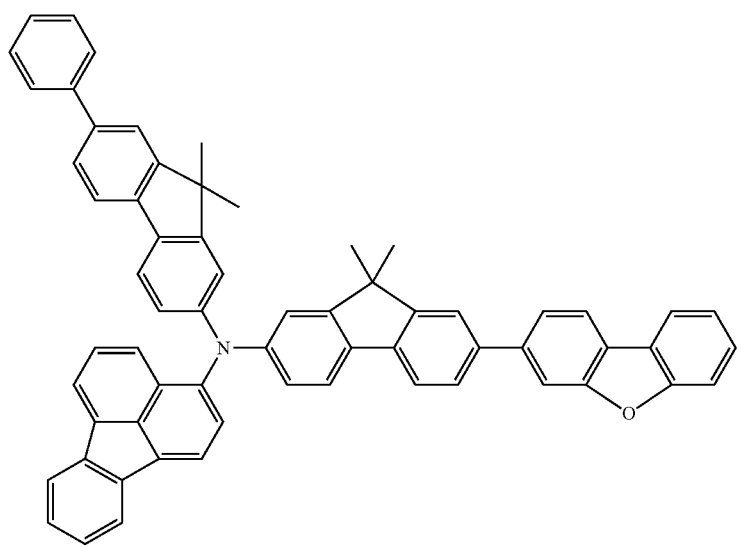
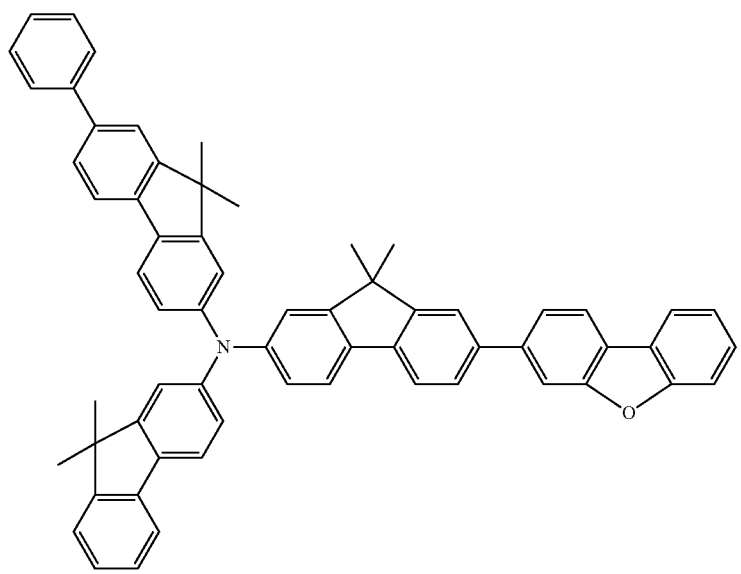

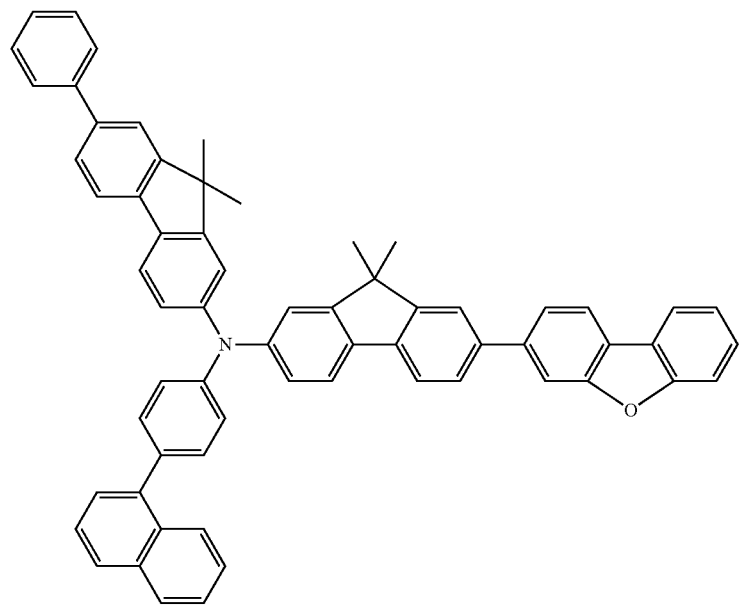
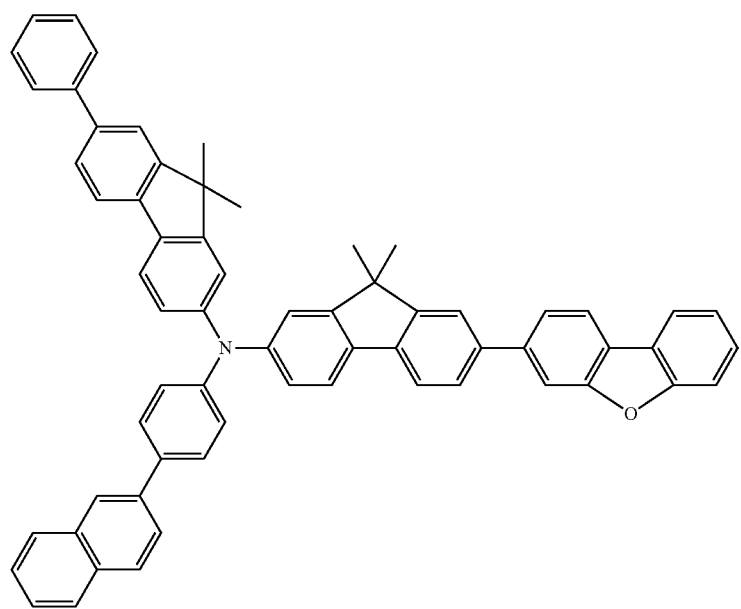

-continued
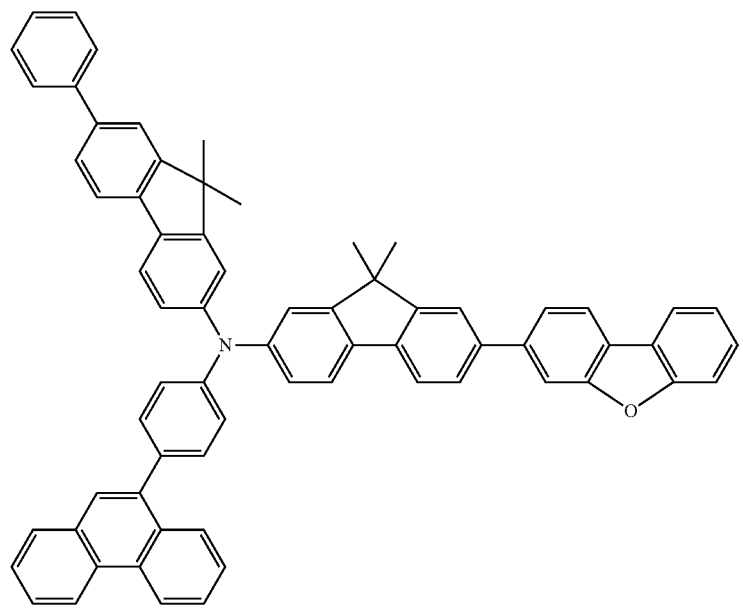
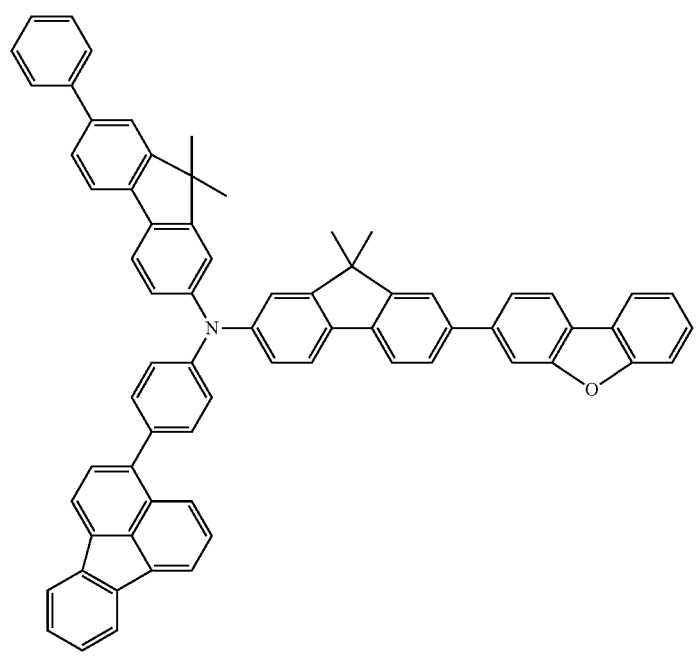

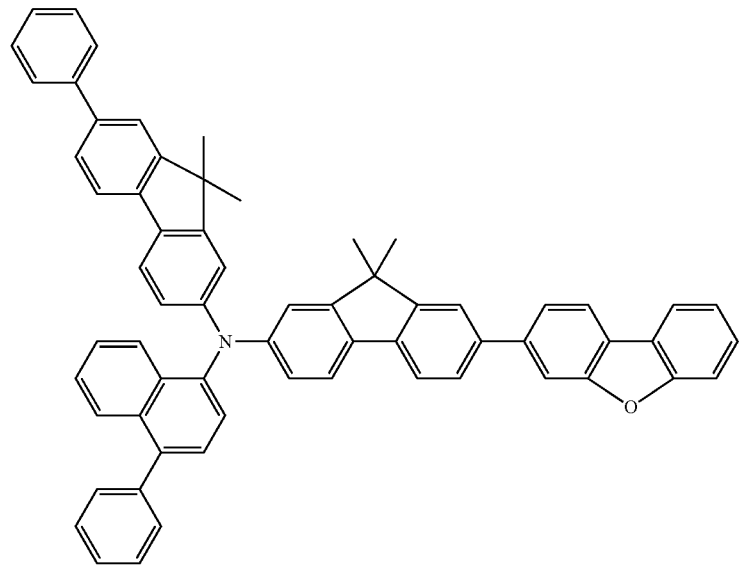
[Chem. 73]
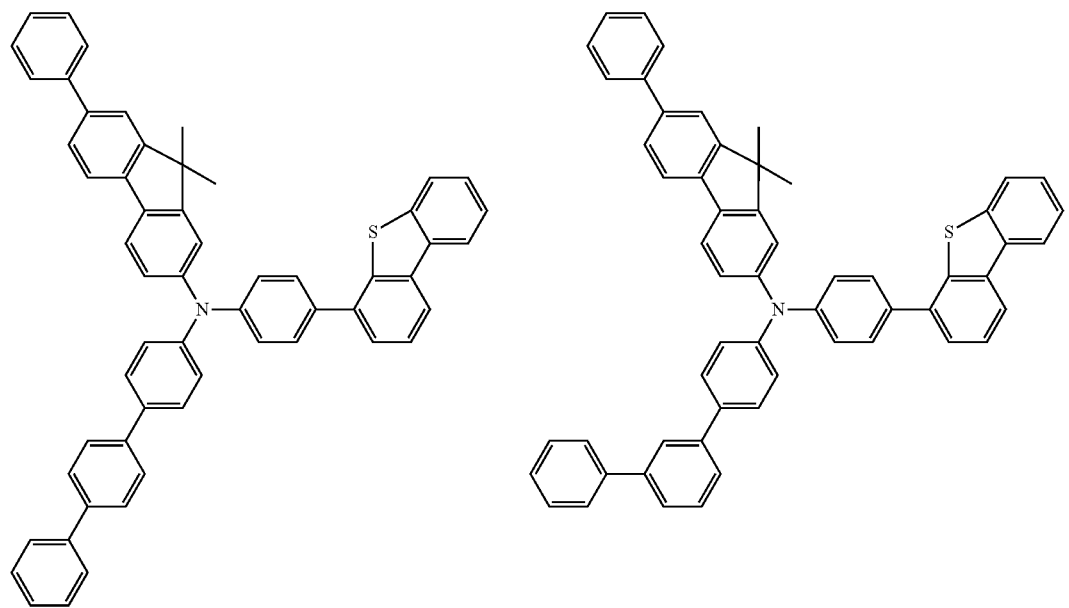

399
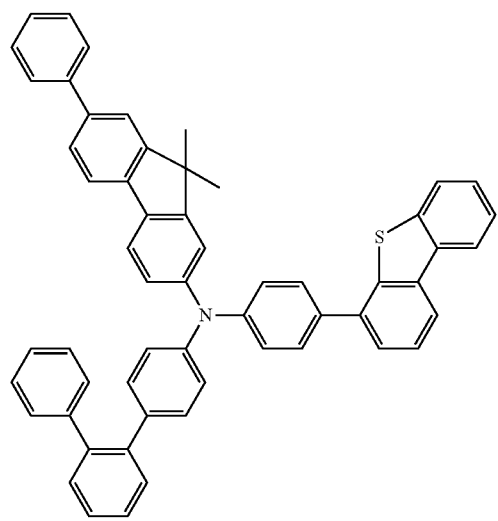
-continued
400
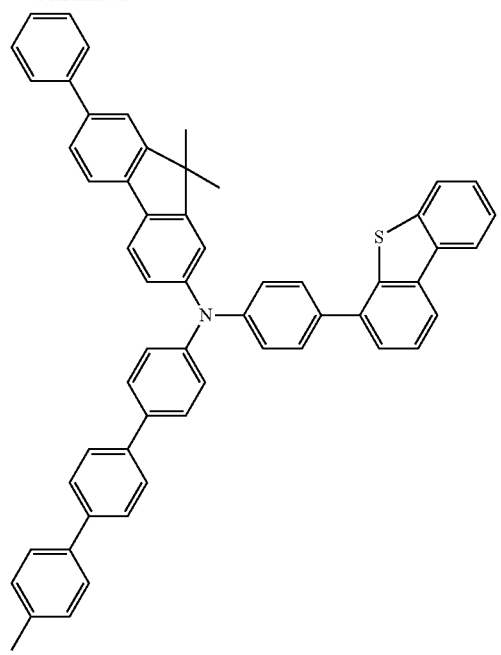
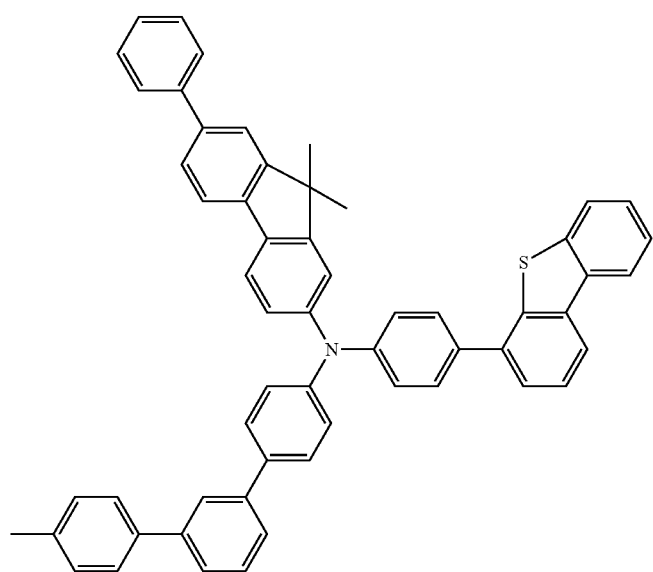

-continued
401
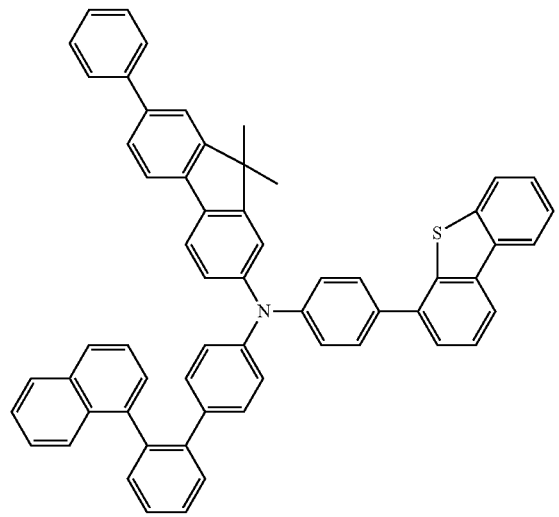
402
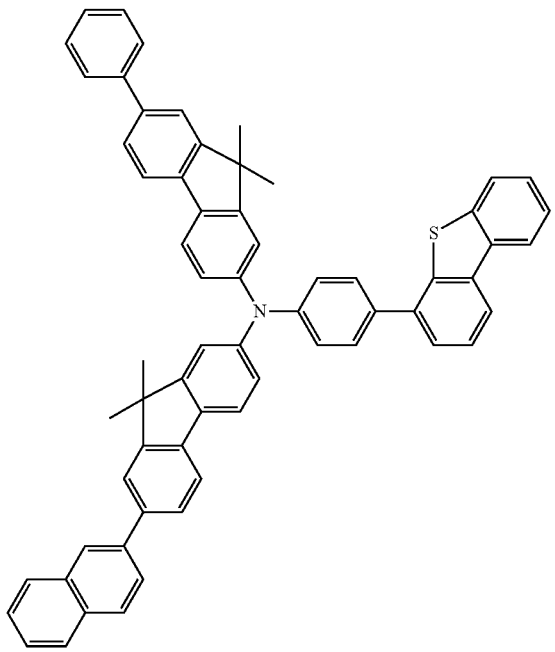
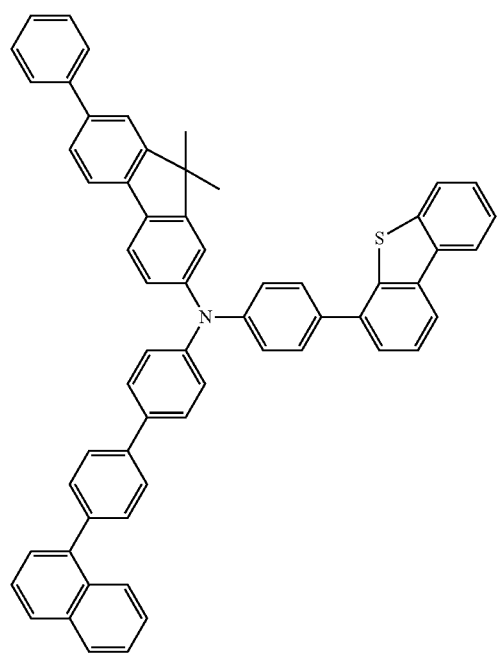
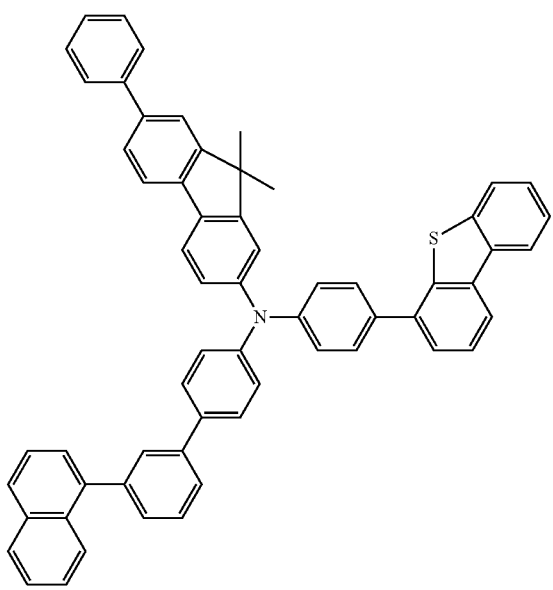

-continued
| 403 | 404 |
|---|---|
| 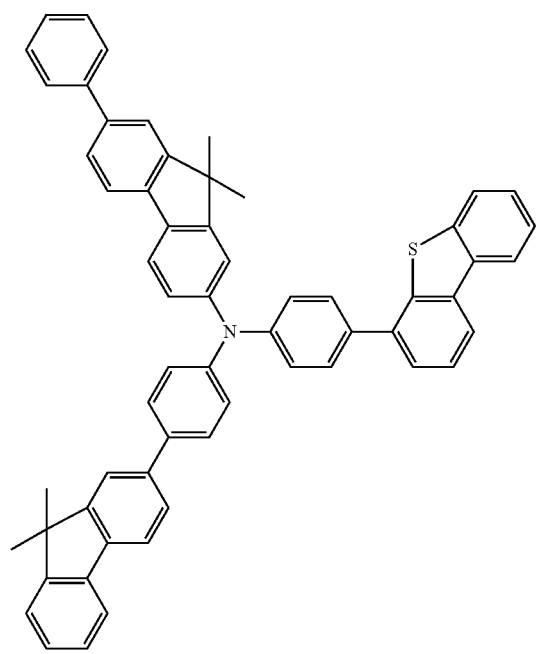 | 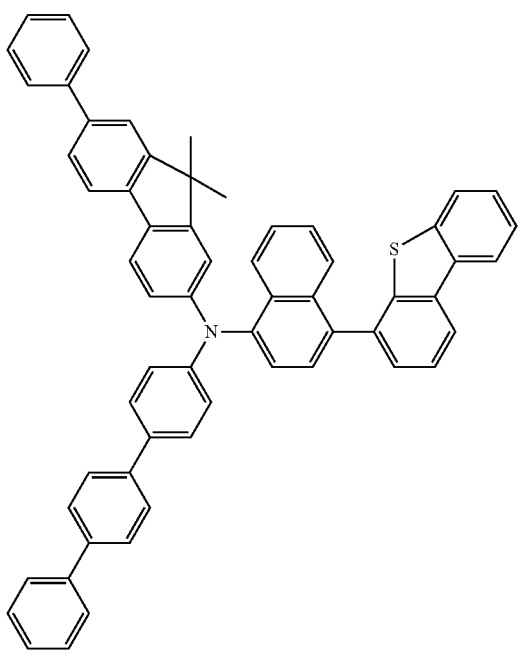 |
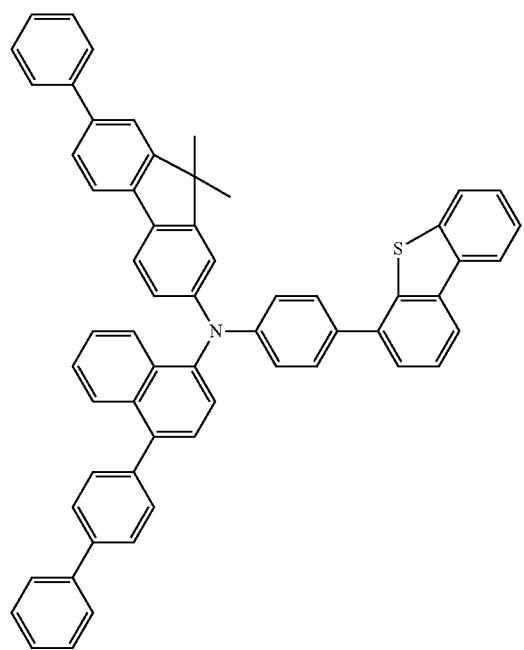

[Chem. 74]
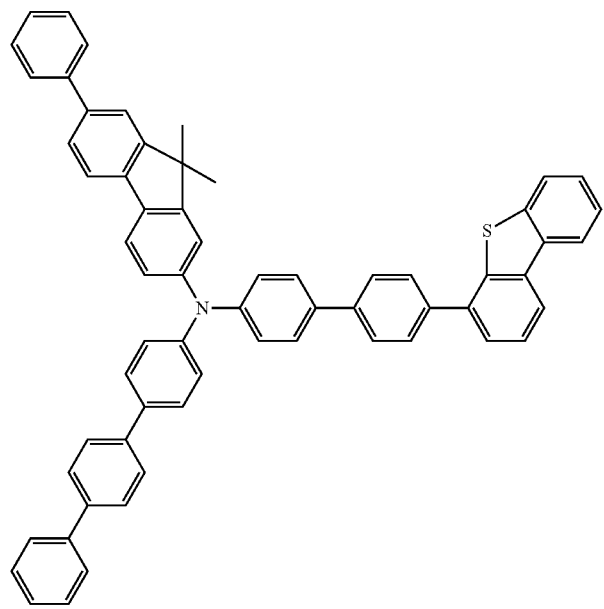
-continued
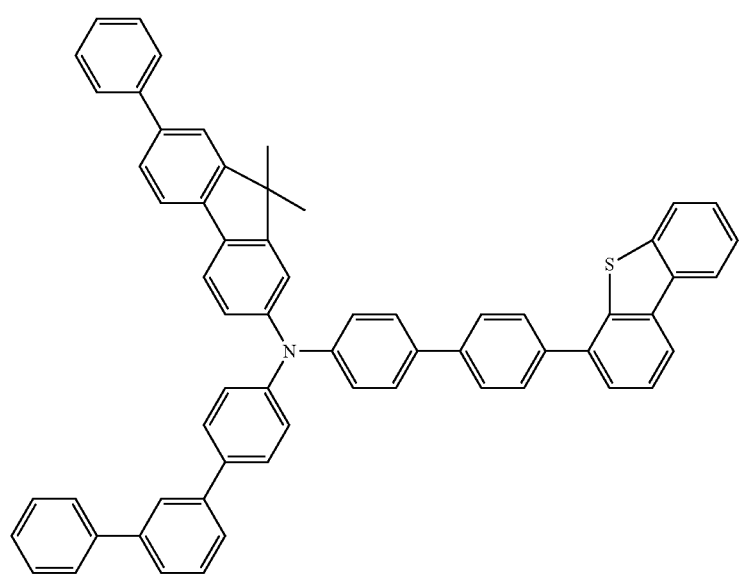

-continued
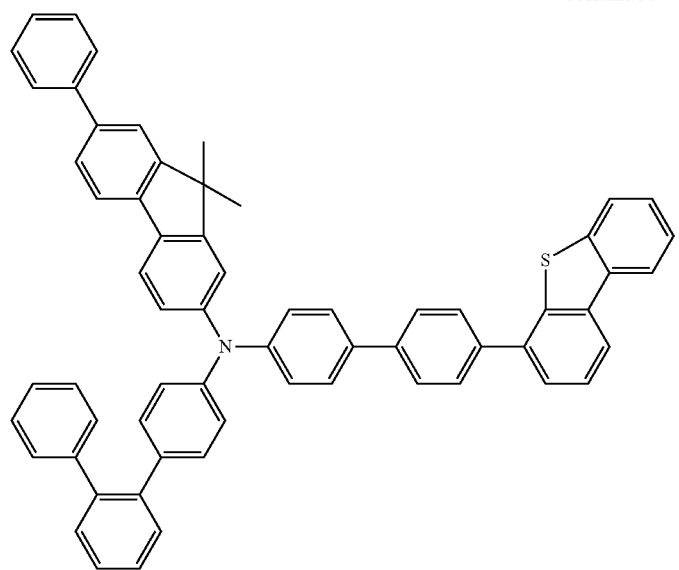
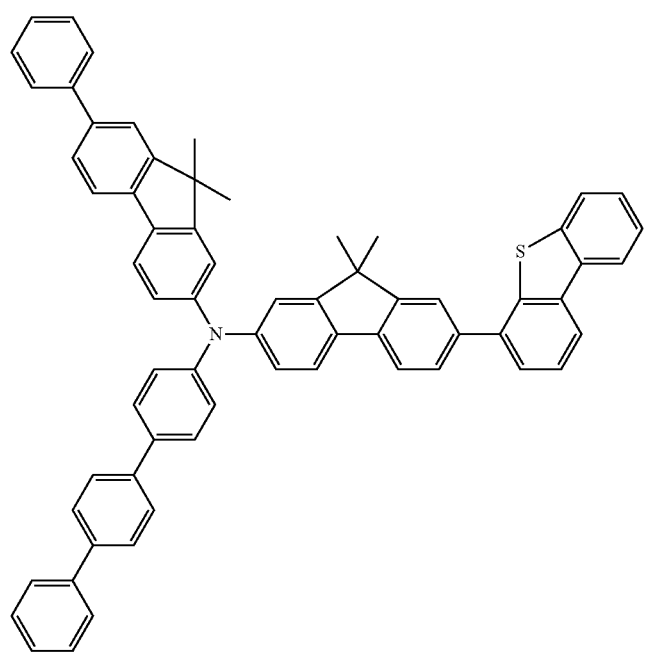

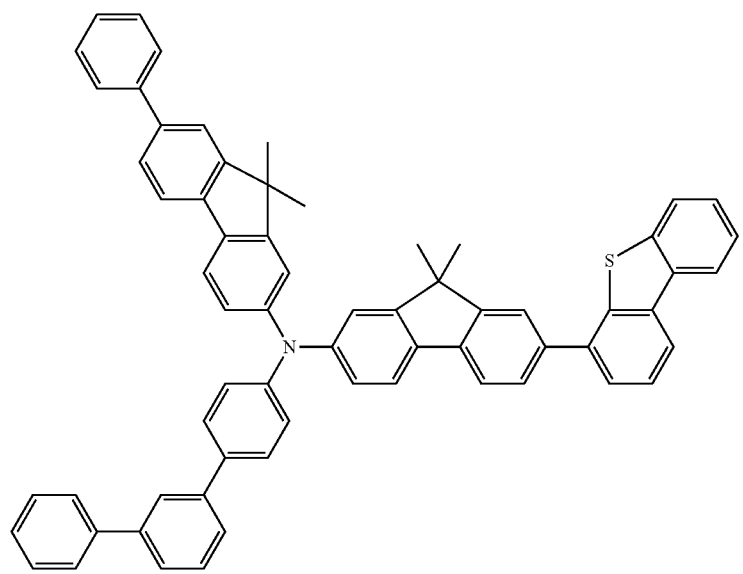
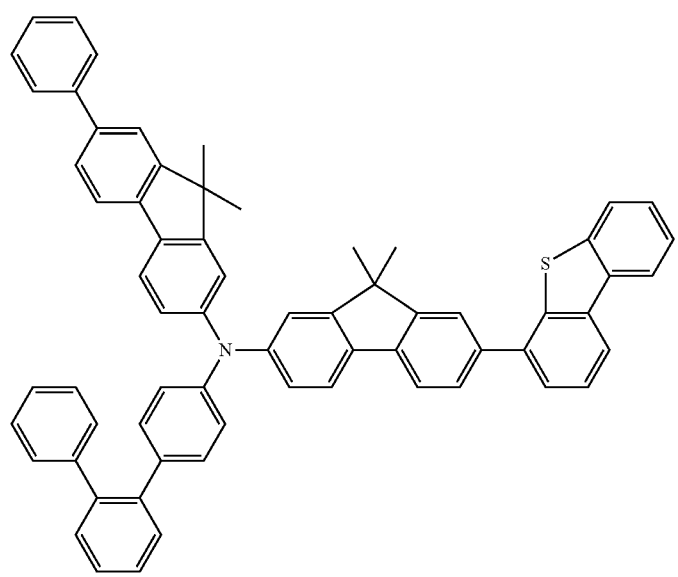

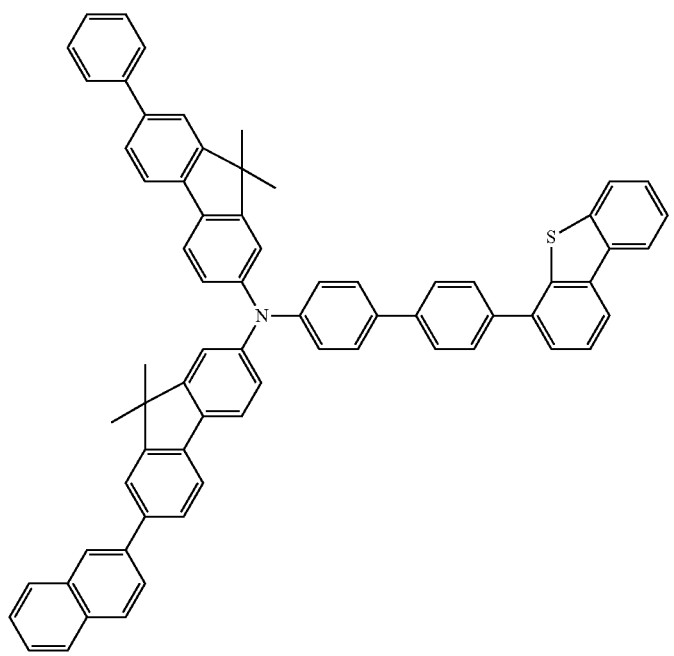
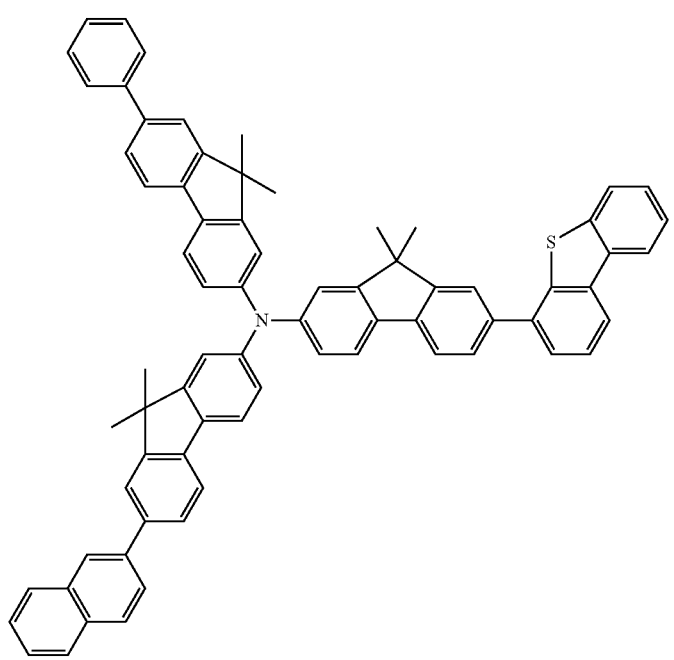

[Chem. 75]
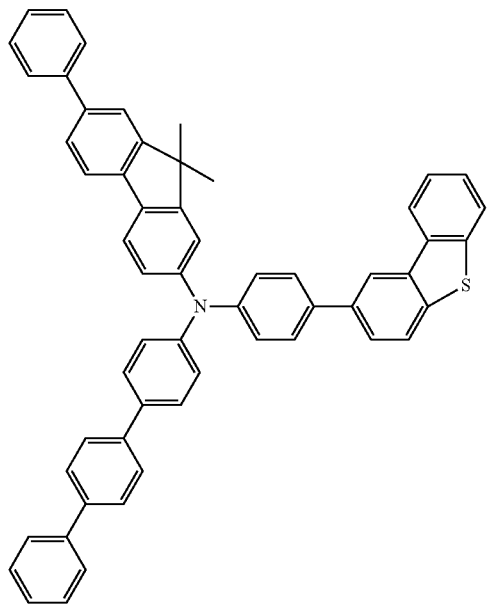
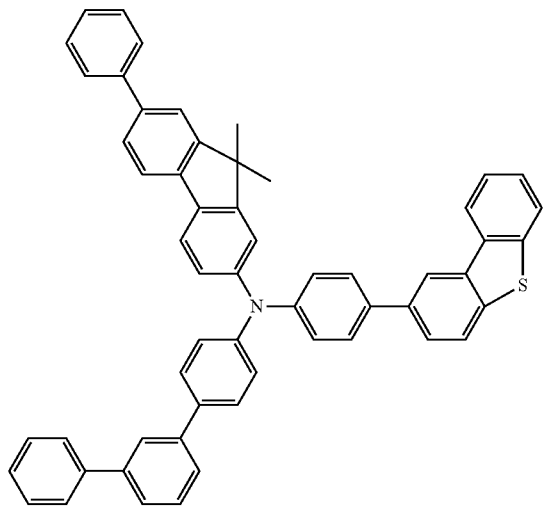
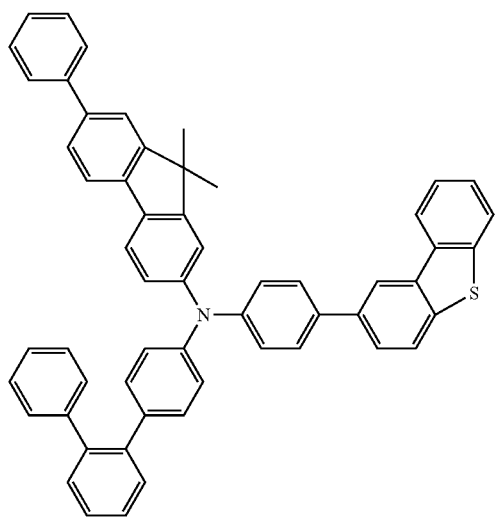
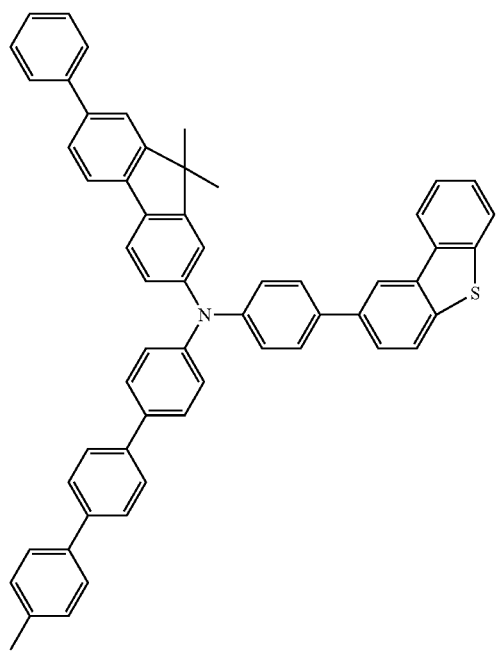

-continued
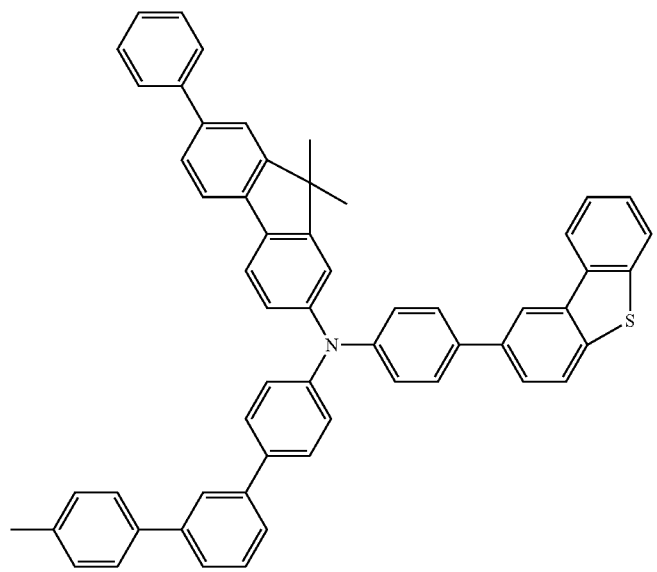
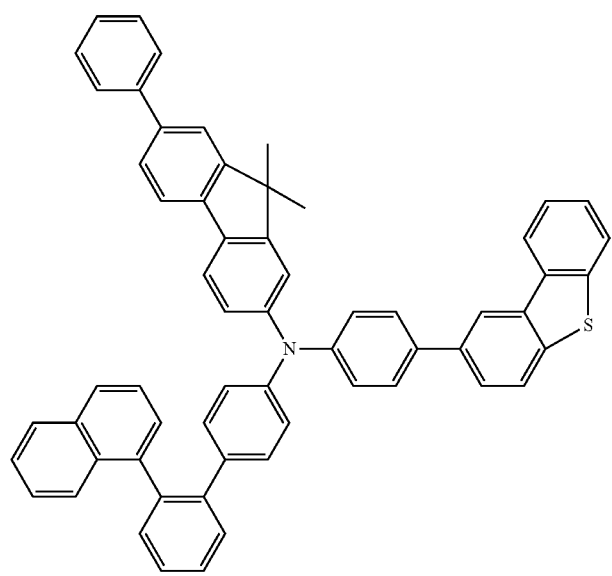

-continued
417
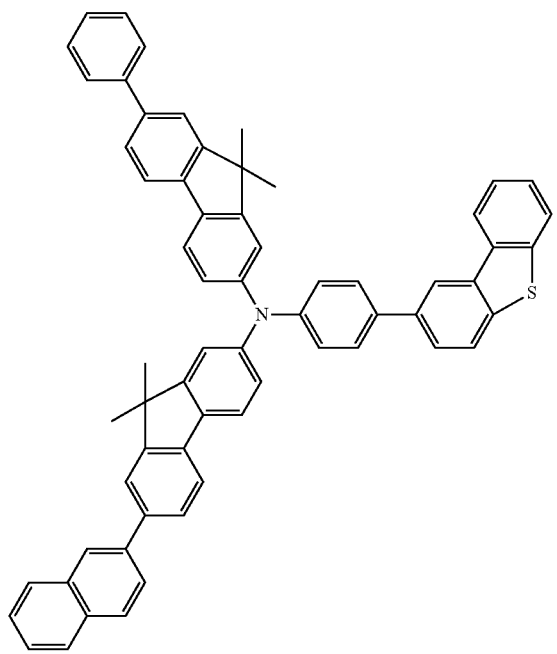
418
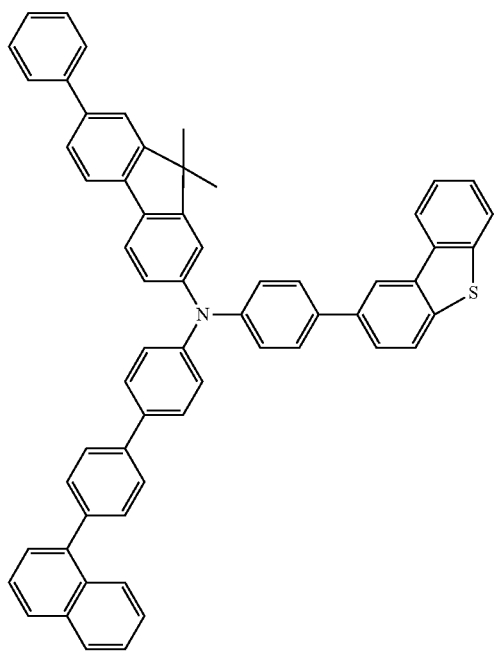
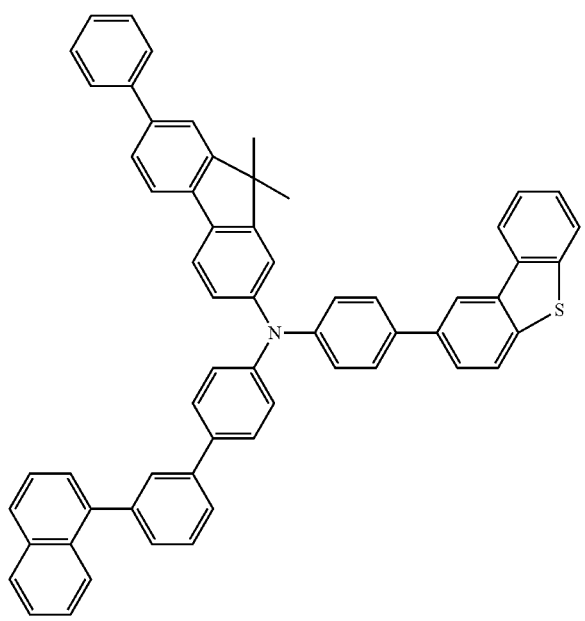
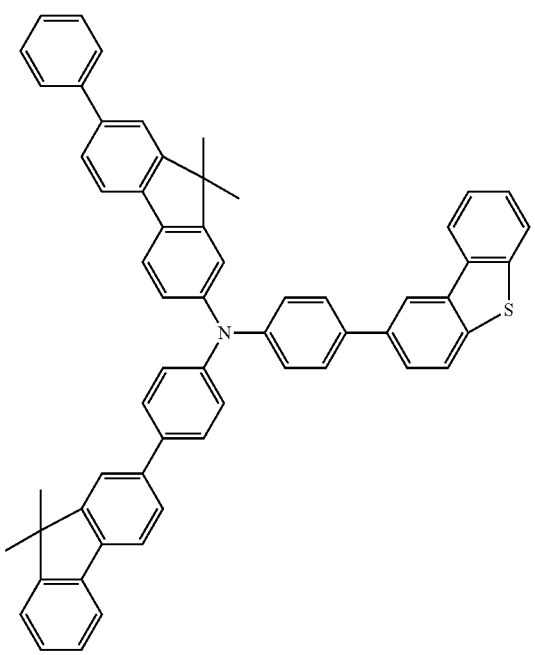

419
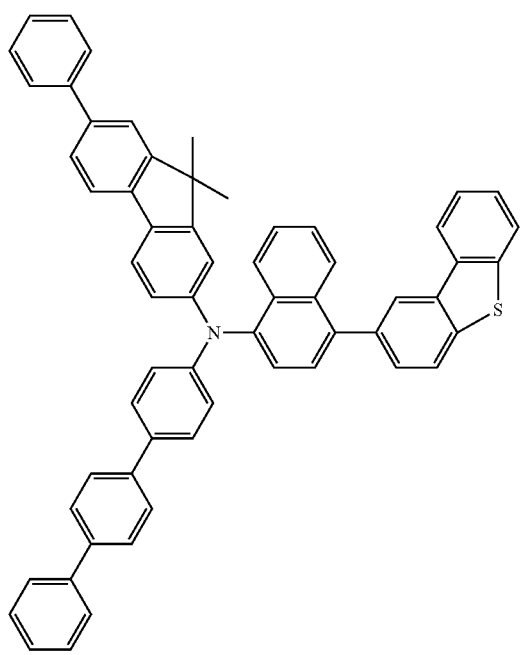
-continued
420
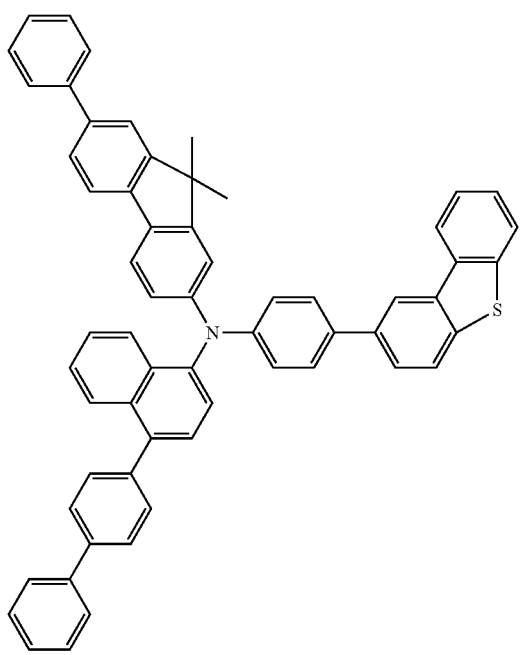
[Chem. 76]
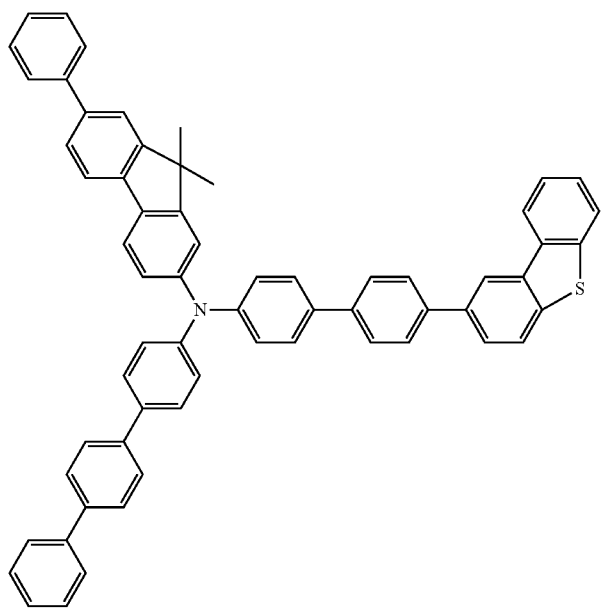

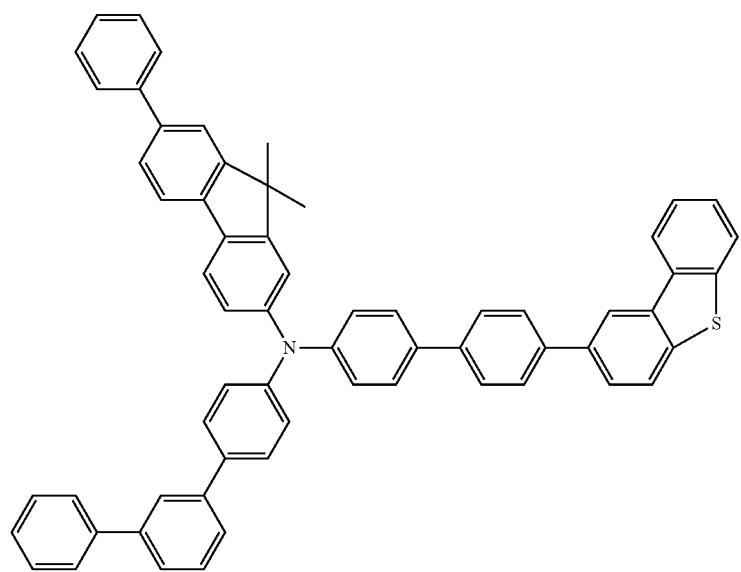
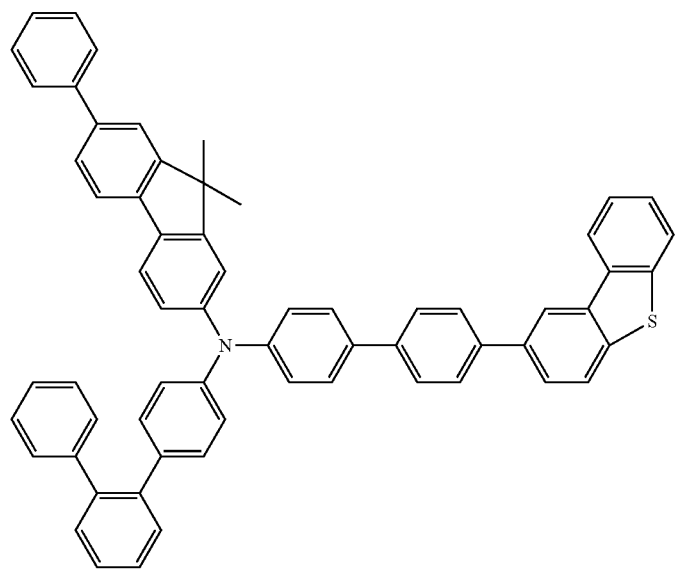

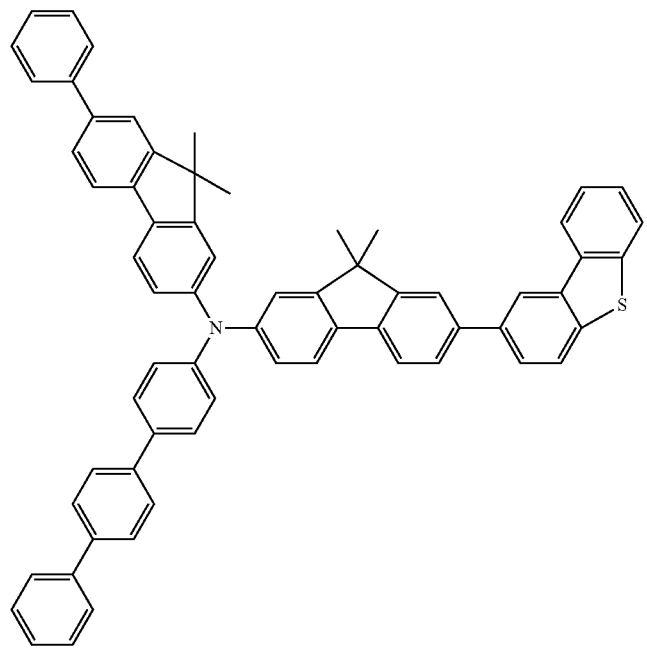
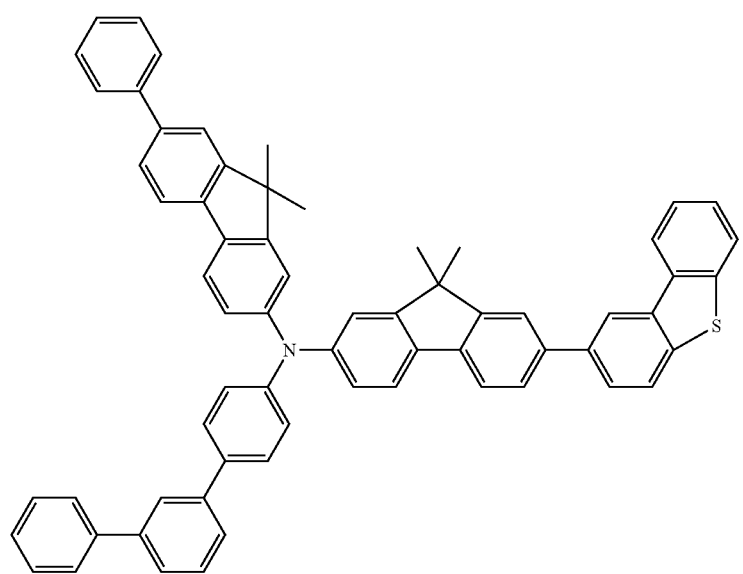

-continued
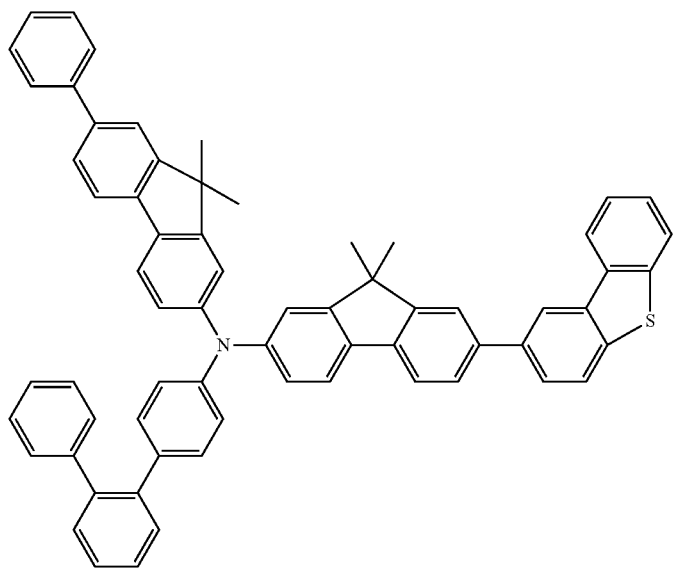
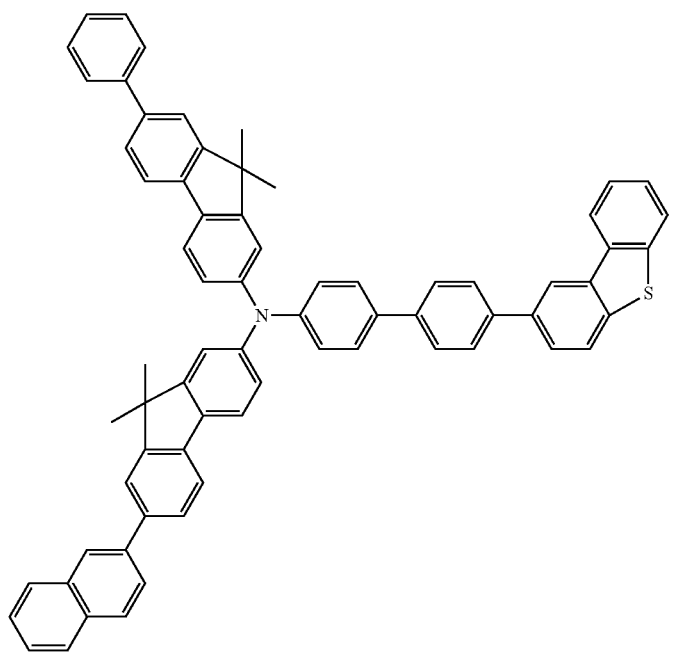

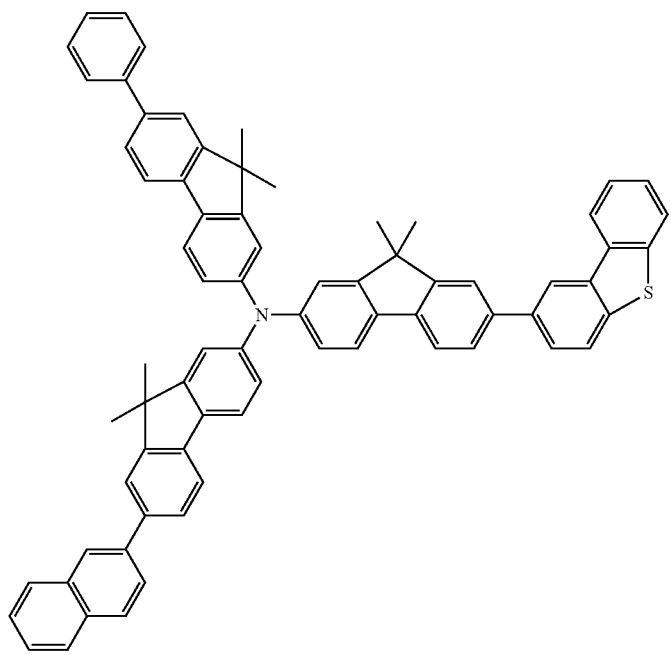
[Chem. 77]
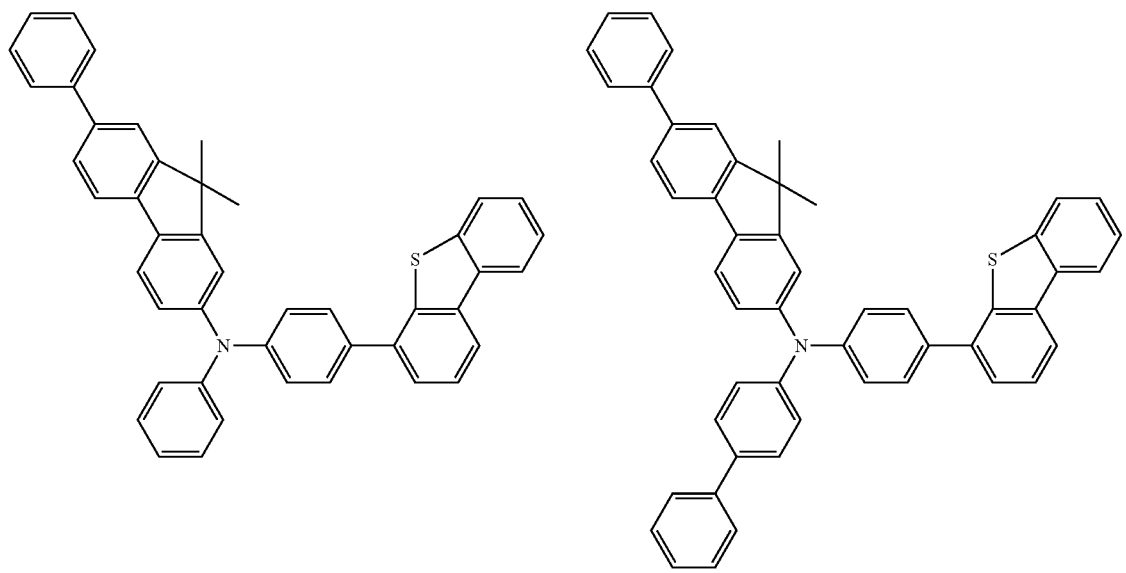

-continued
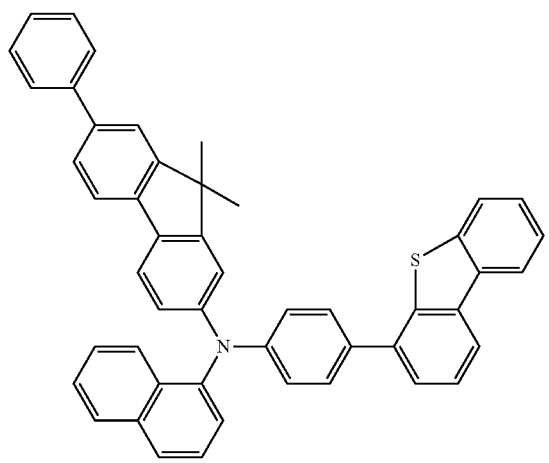
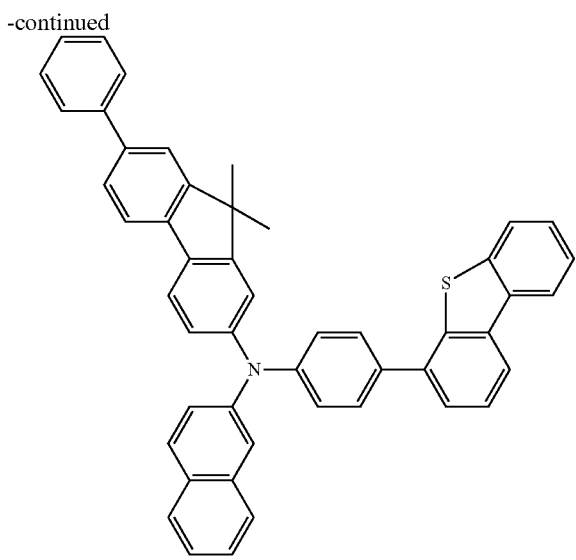
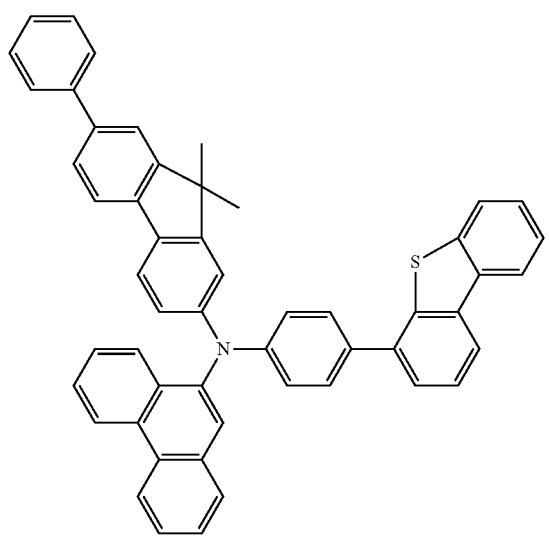
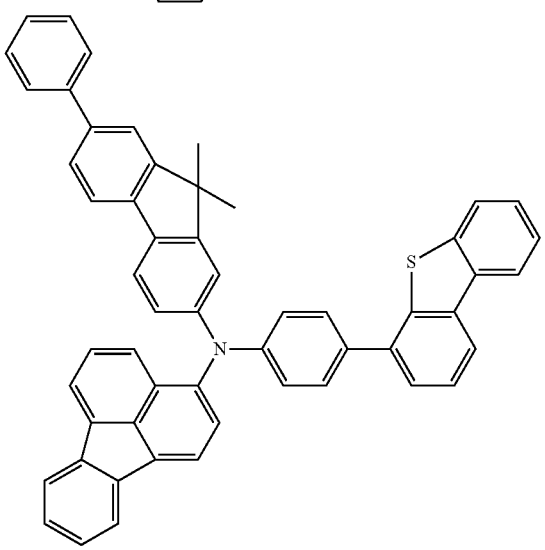
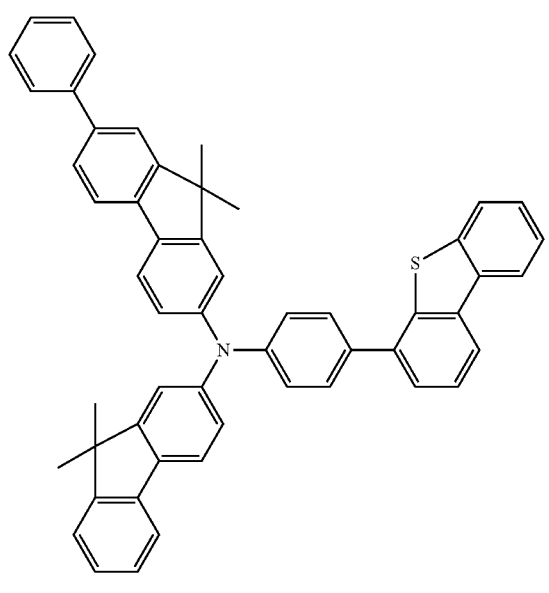
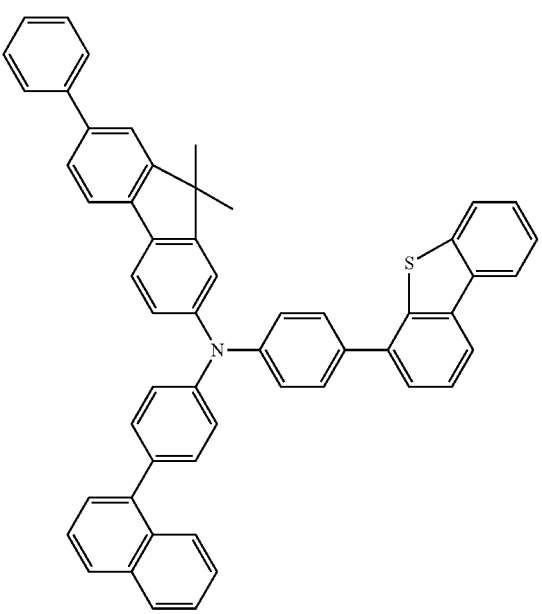

-continued
| 431 | 432 |
|---|---|
| 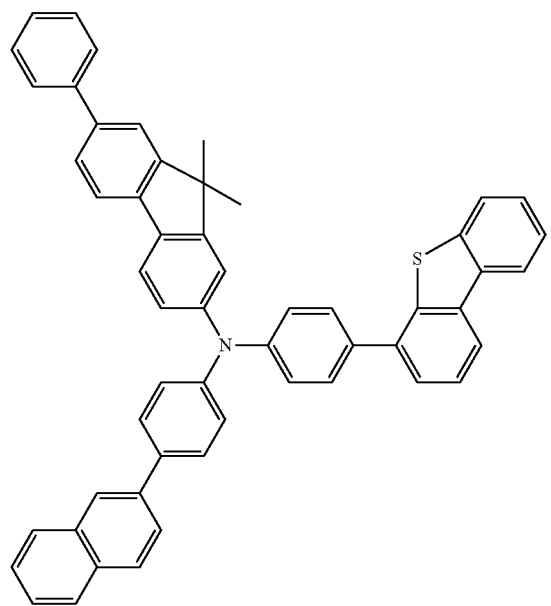 | 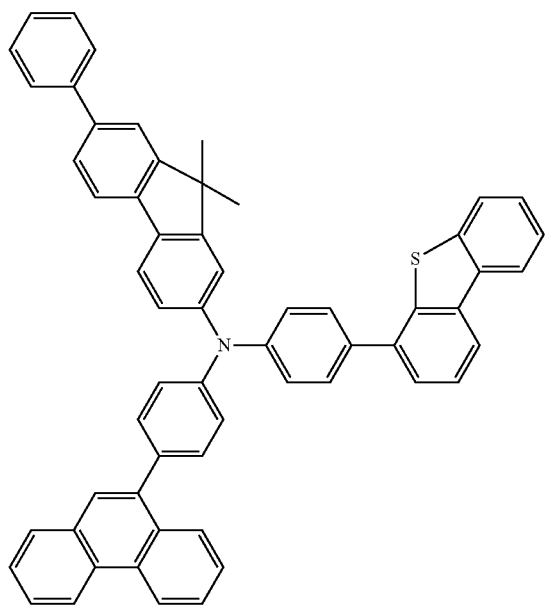 |
| 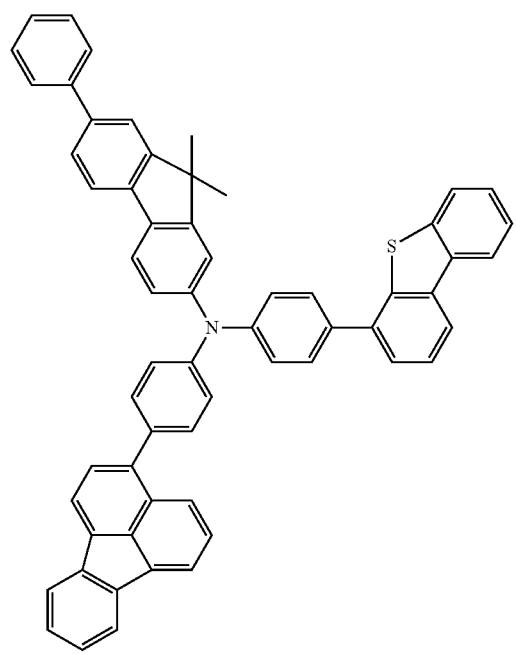 | |

[Chem. 78]
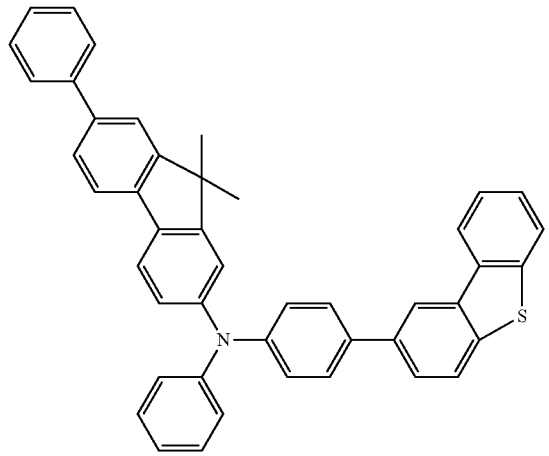
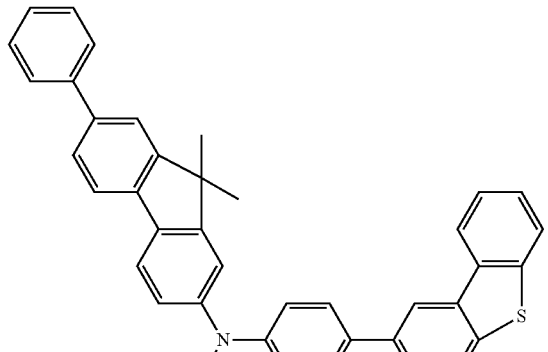
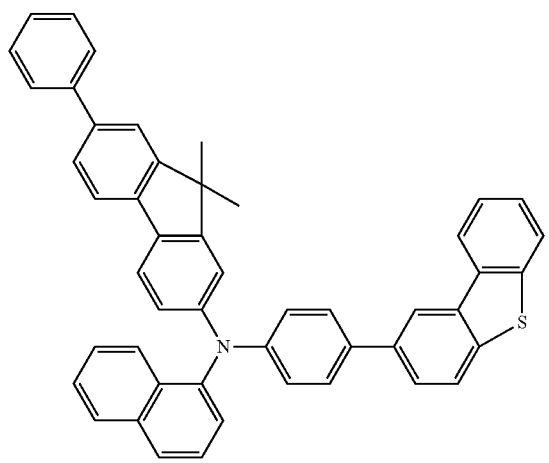
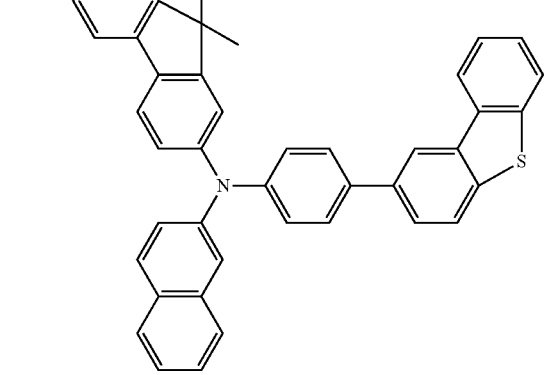
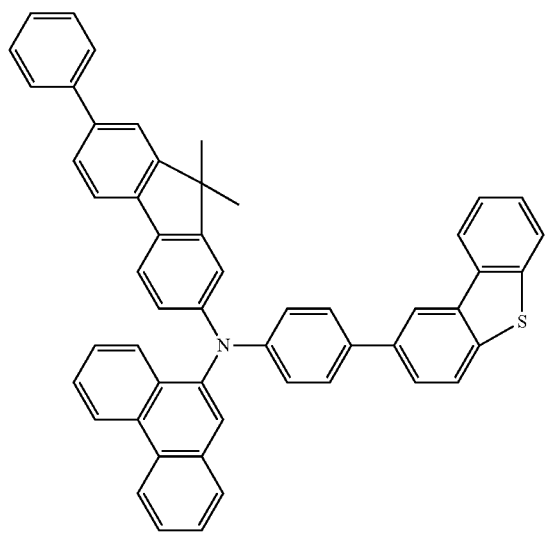
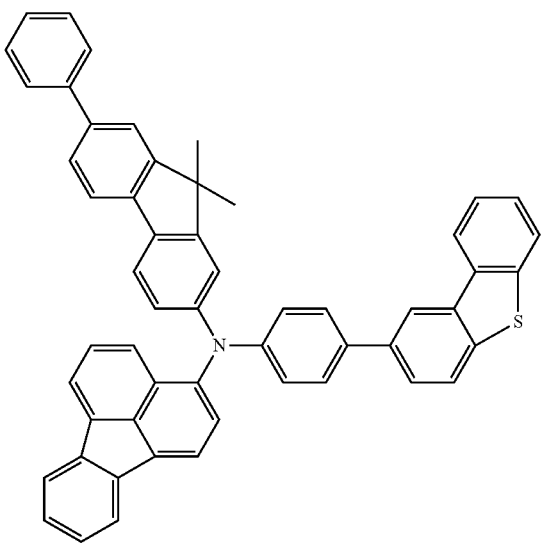

-continued
435
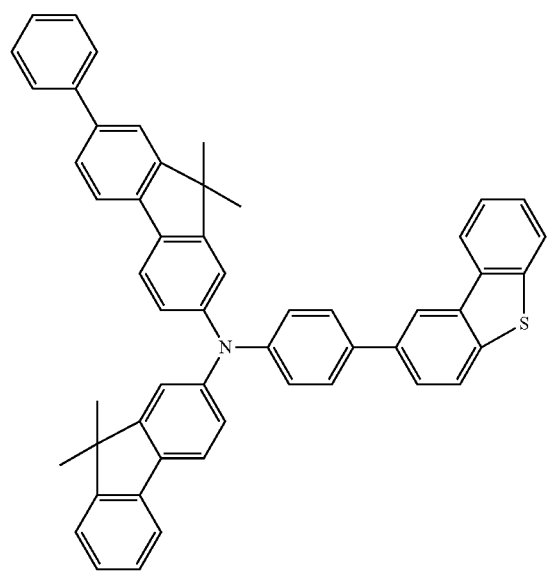
436
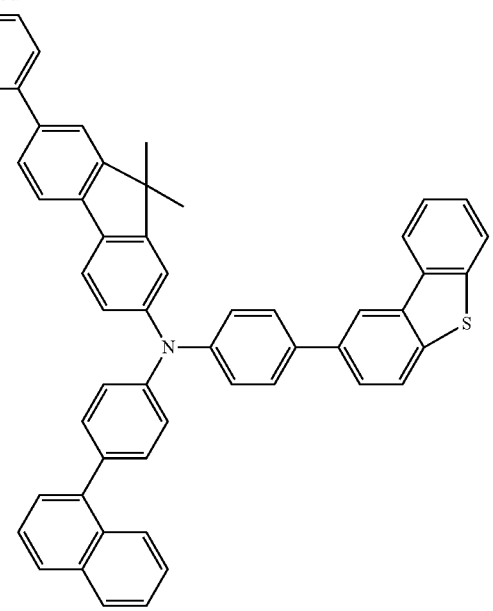
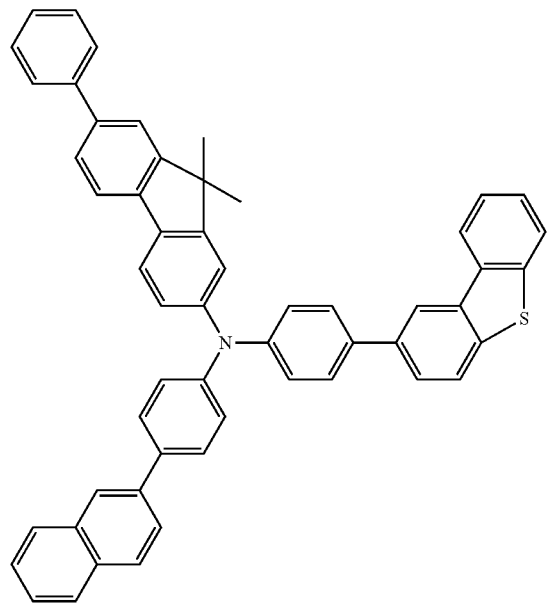
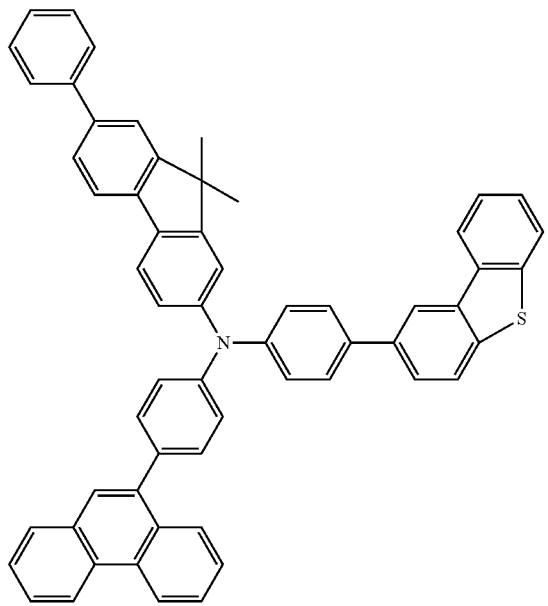

437
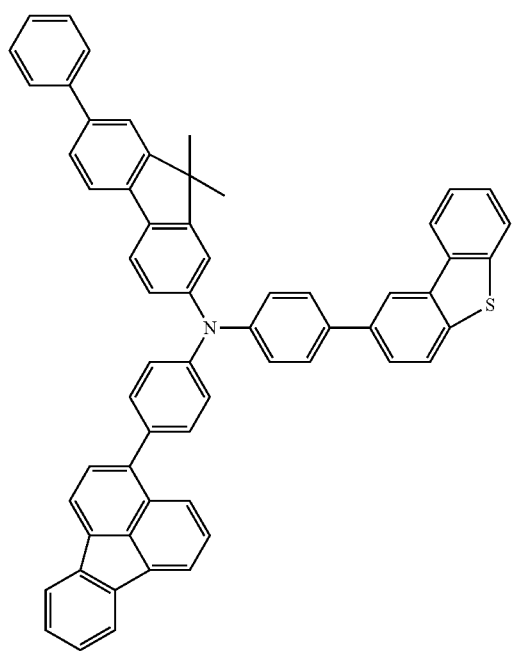
438
-continued
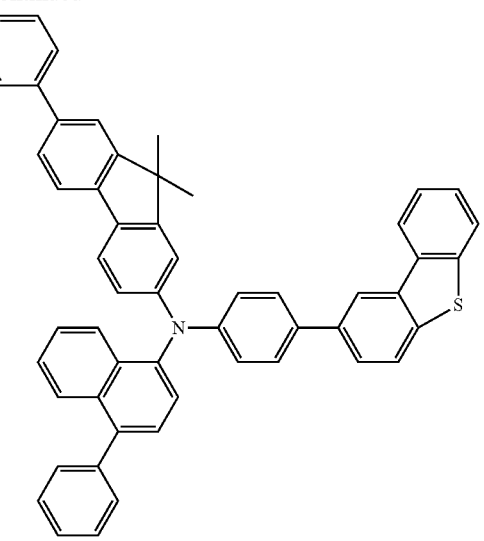
[Chem. 79]
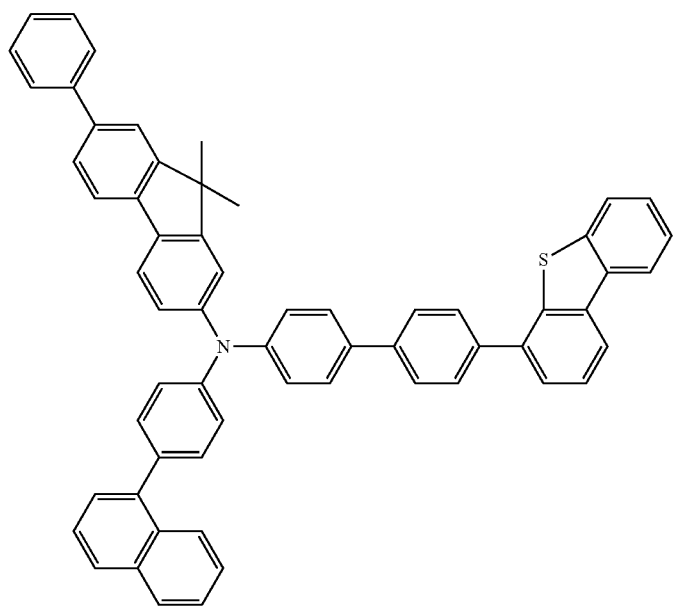

-continued
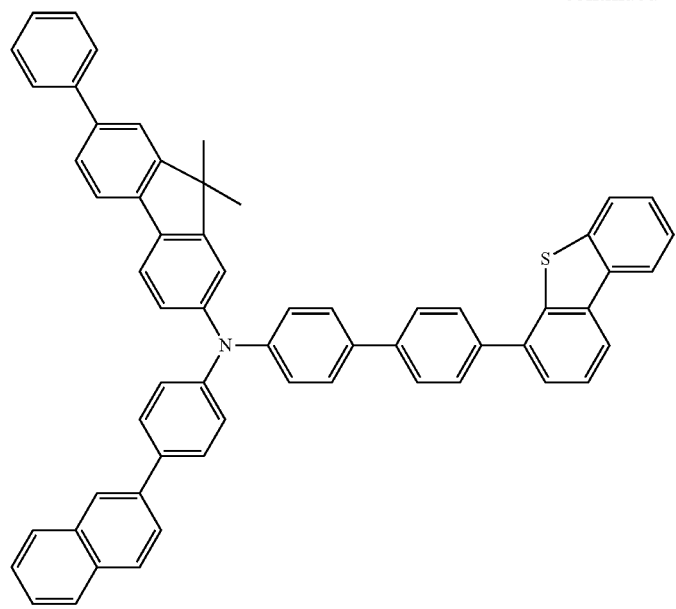
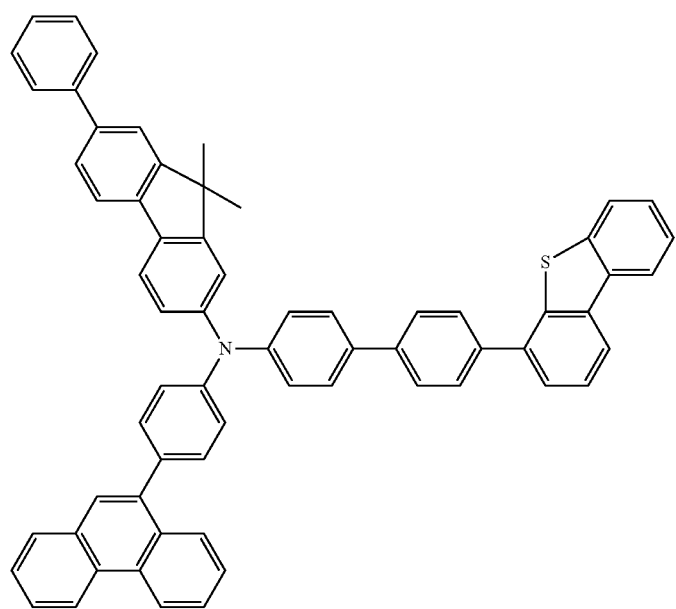

-continued
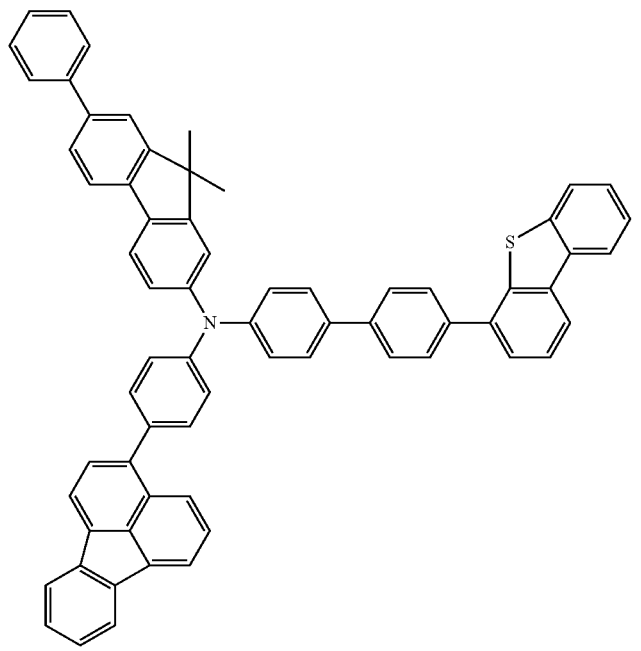
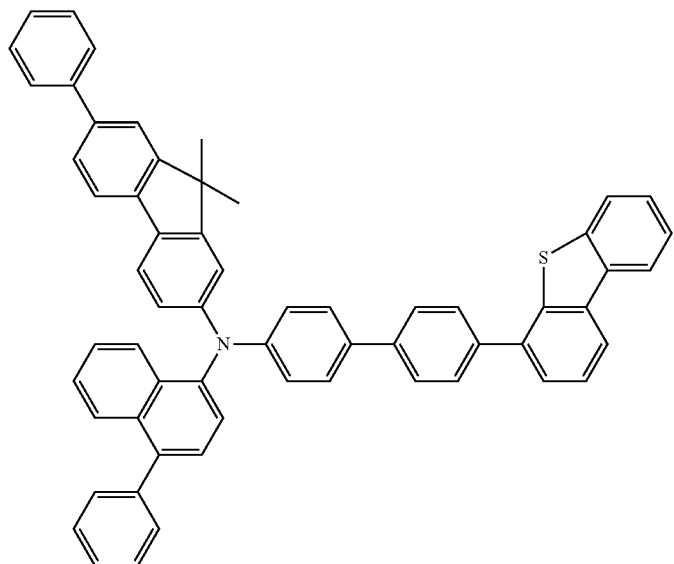
[Chem. 80]
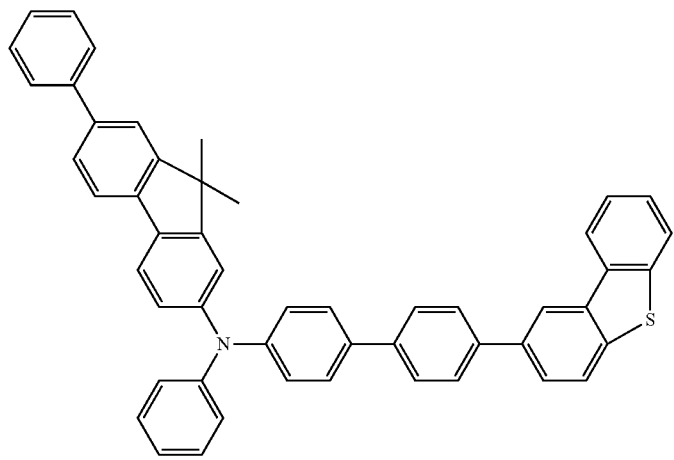

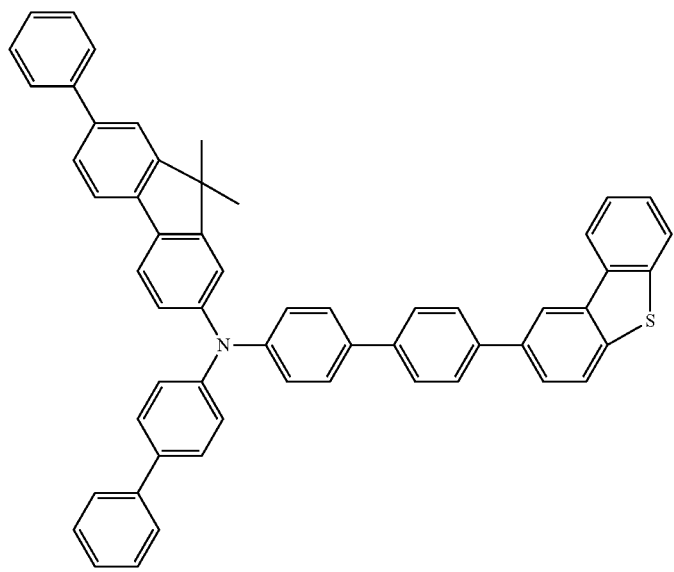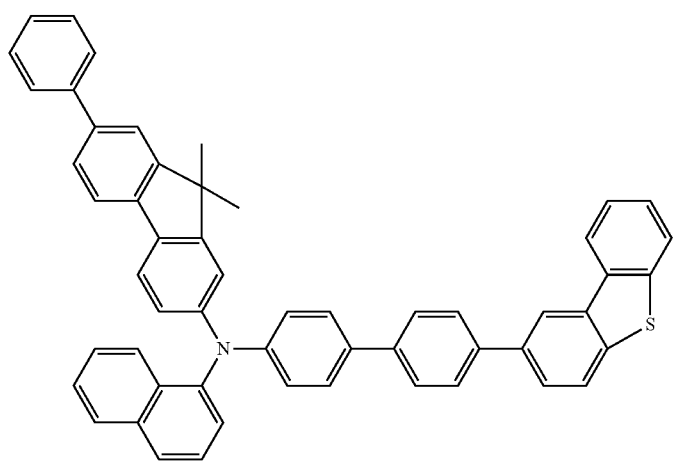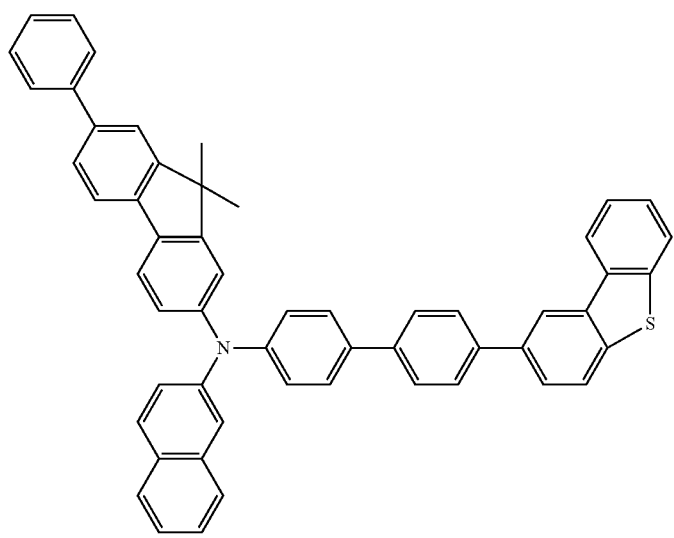

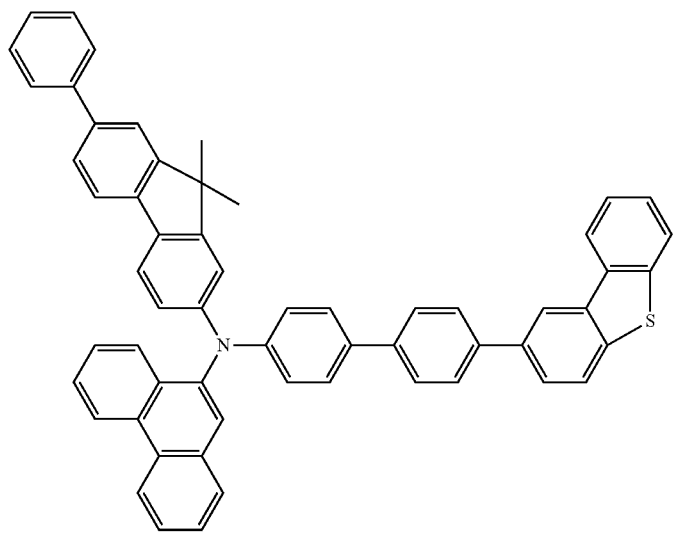
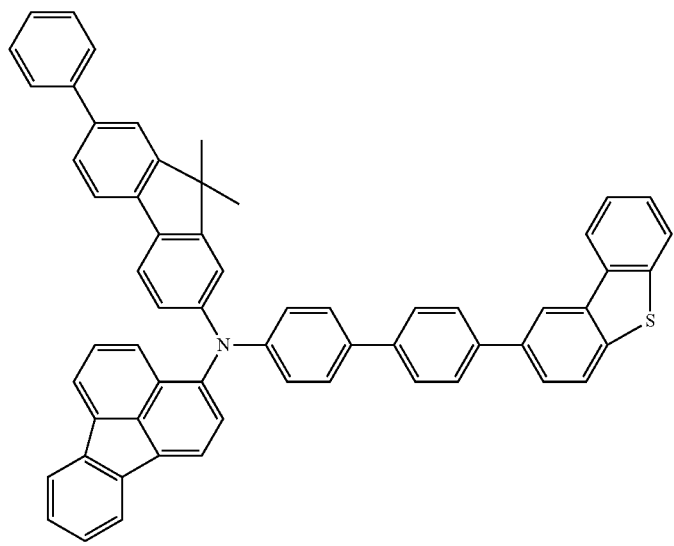
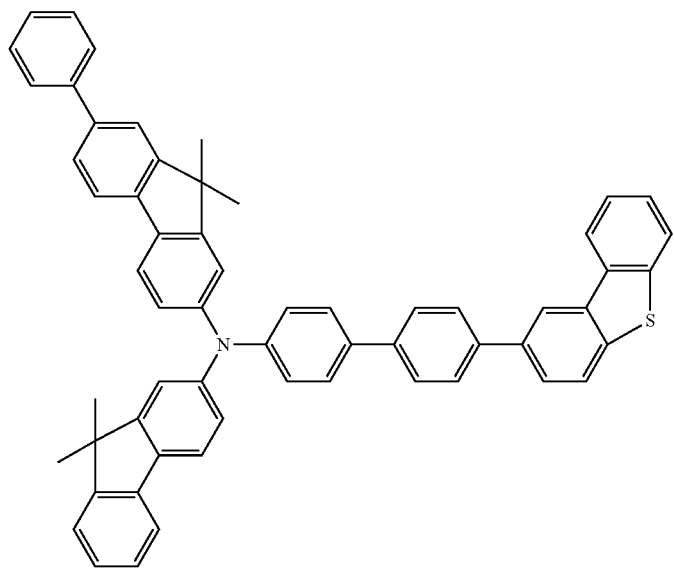

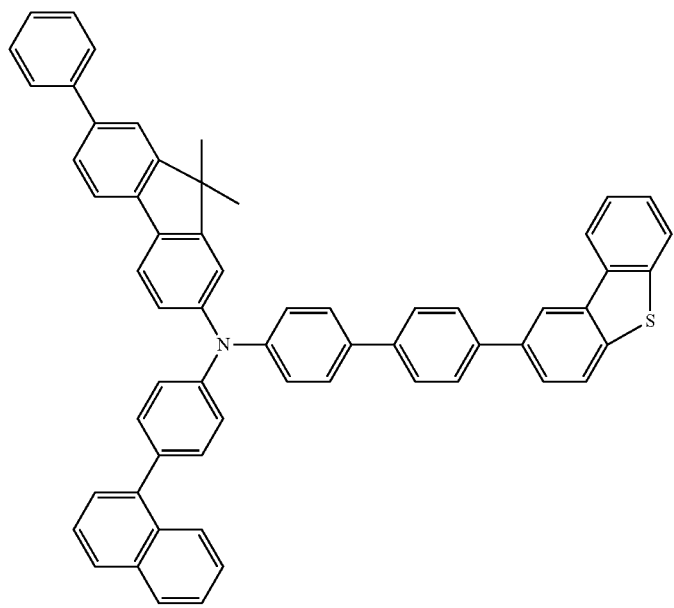
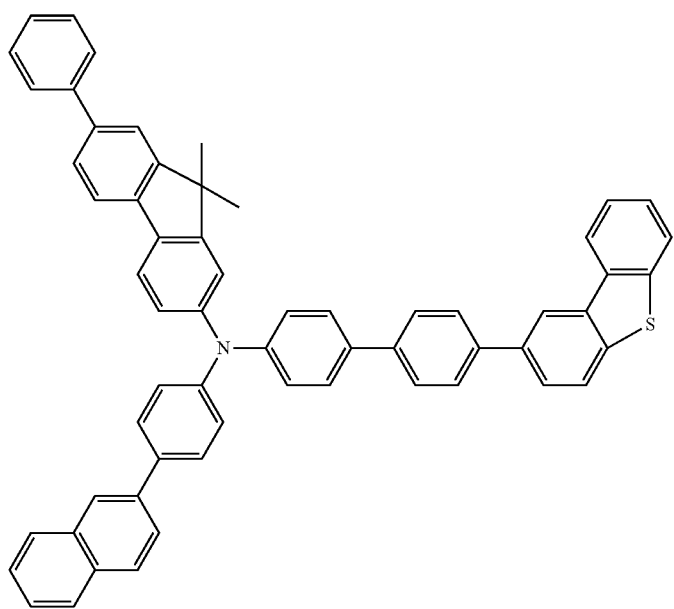

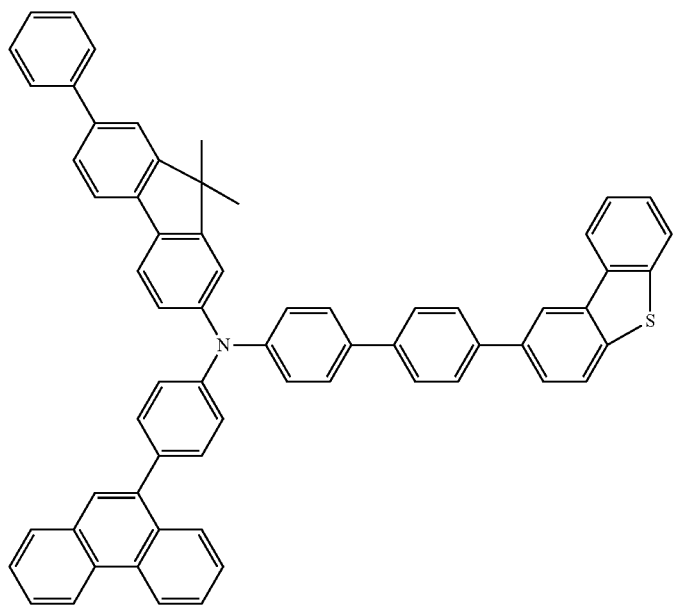
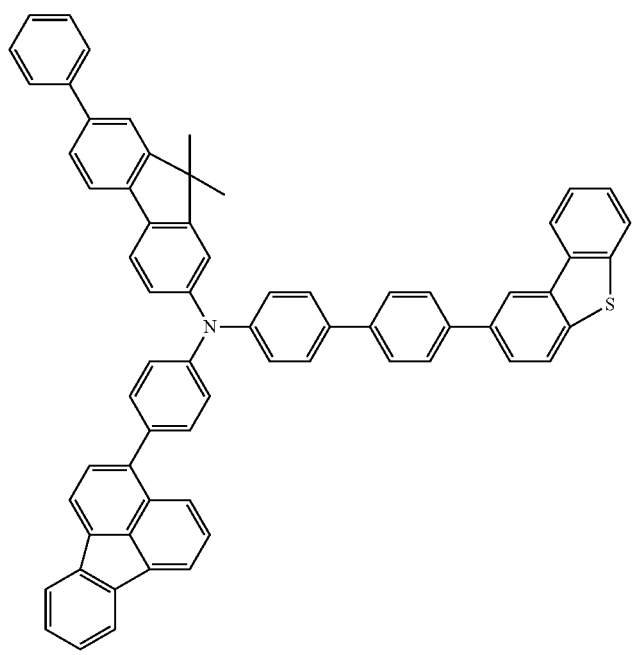

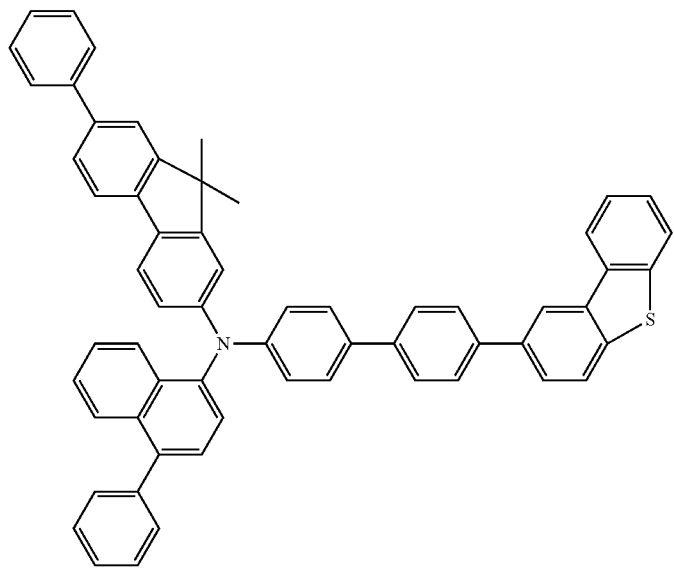
[Chem. 81]
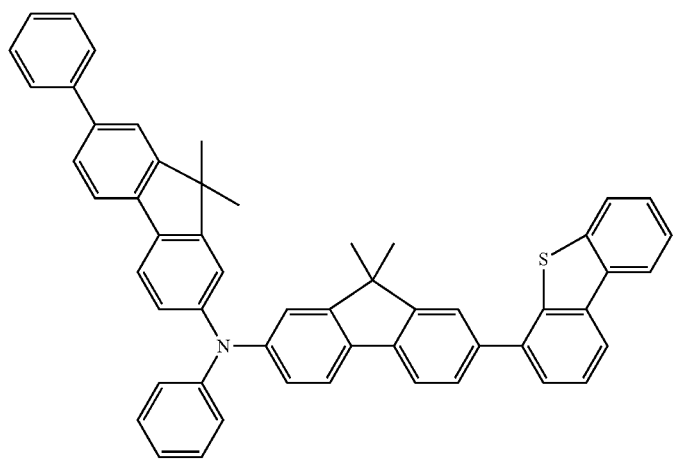
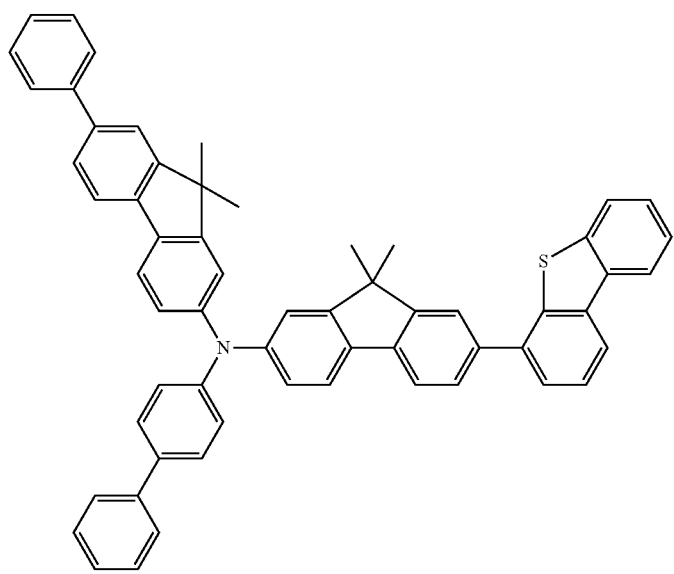

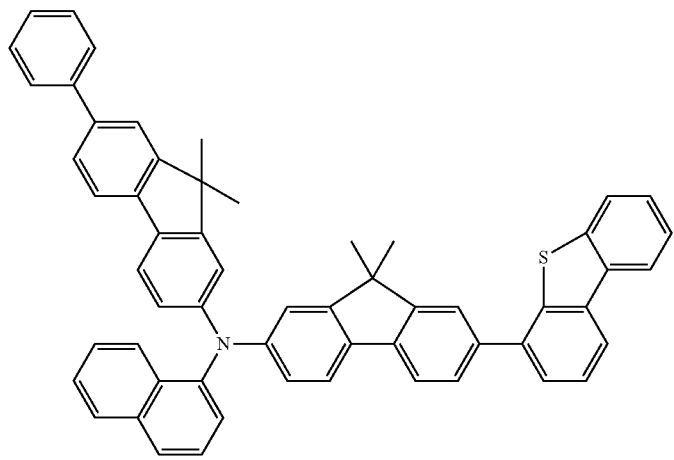
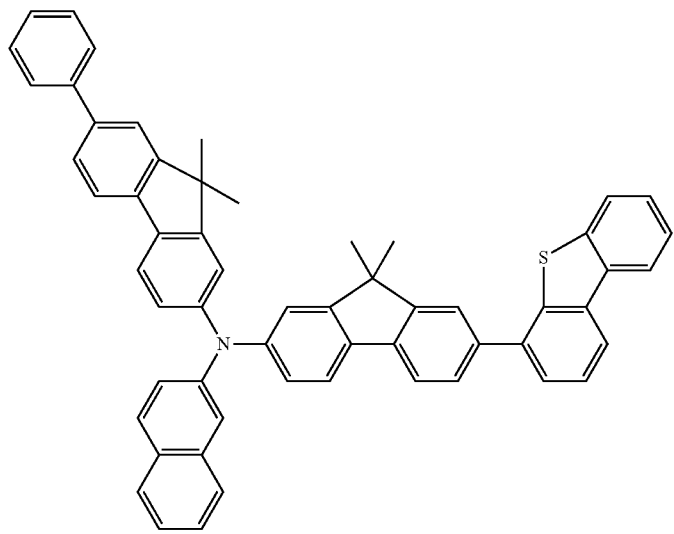
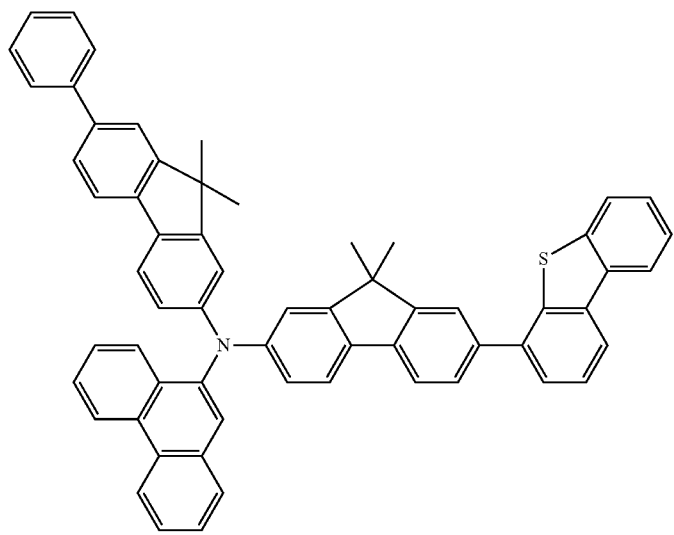

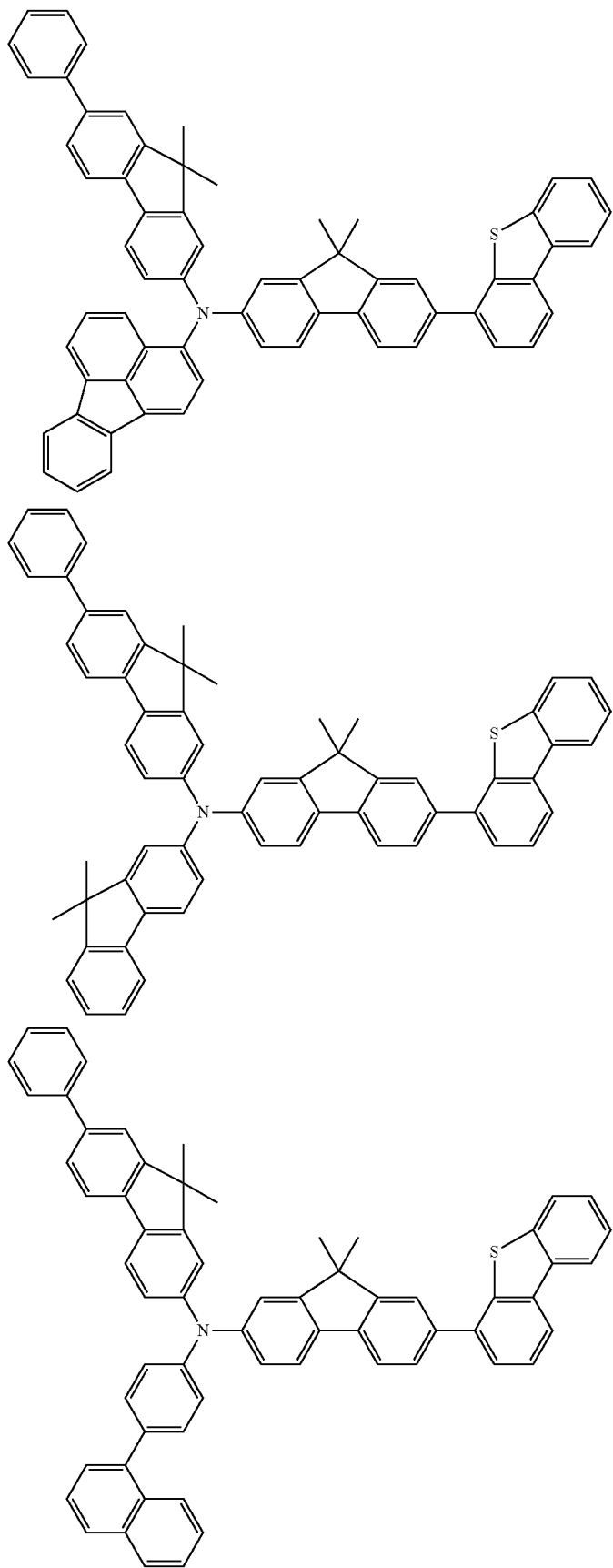

-continued
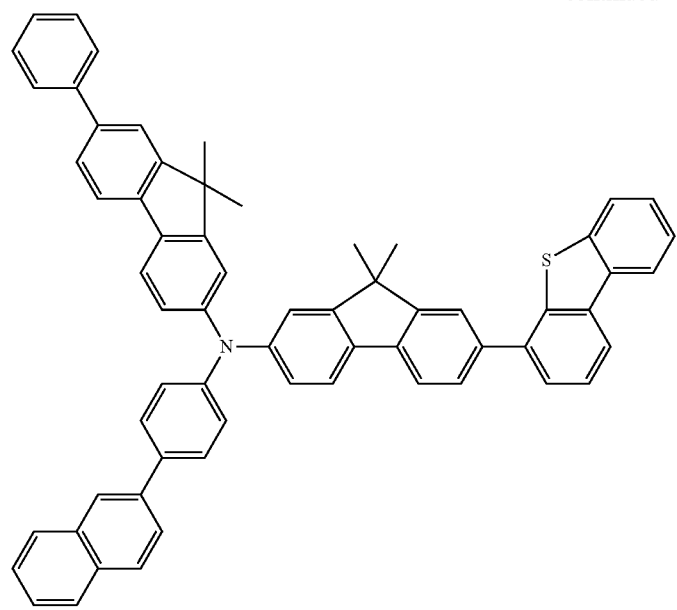
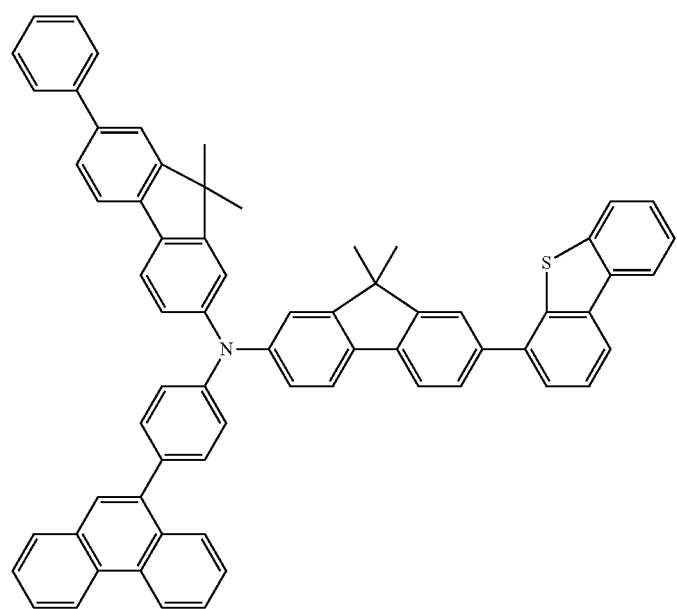

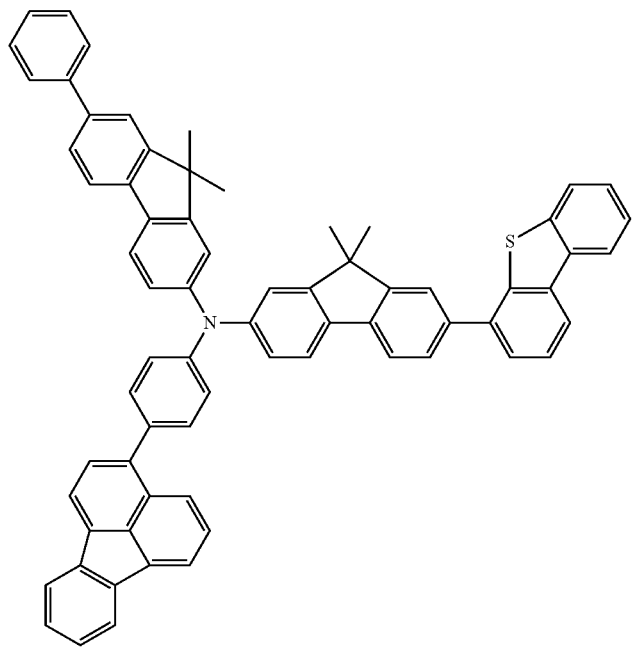
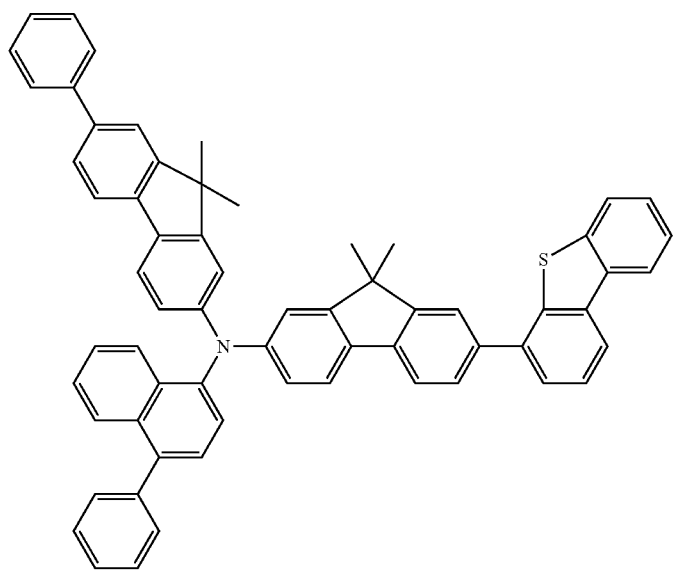
[Chem. 82]
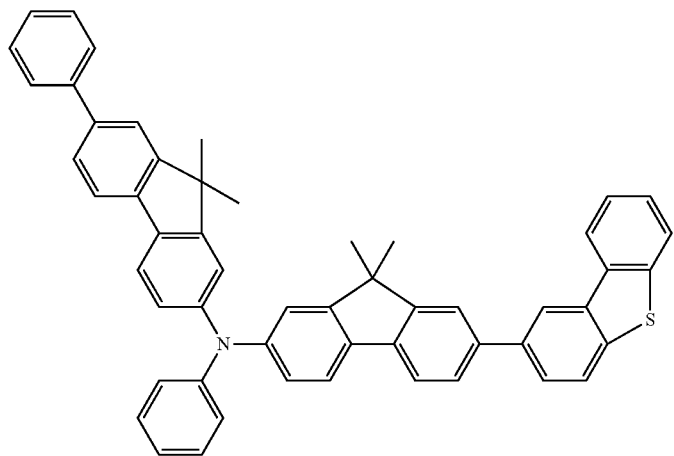

-continued
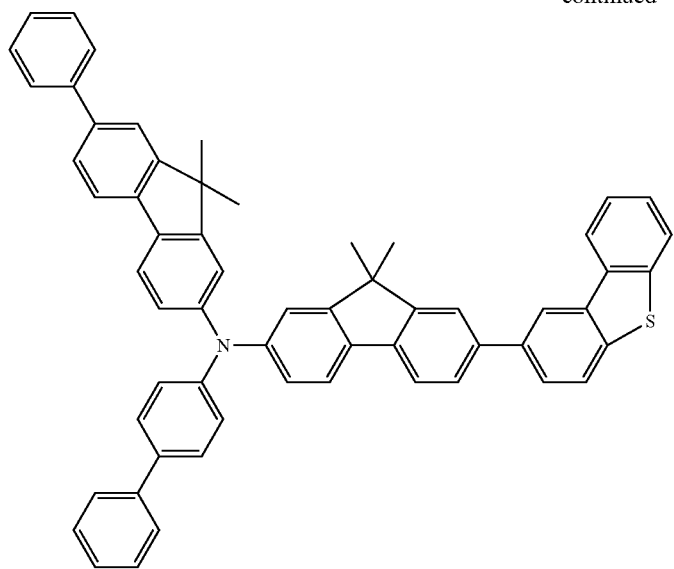
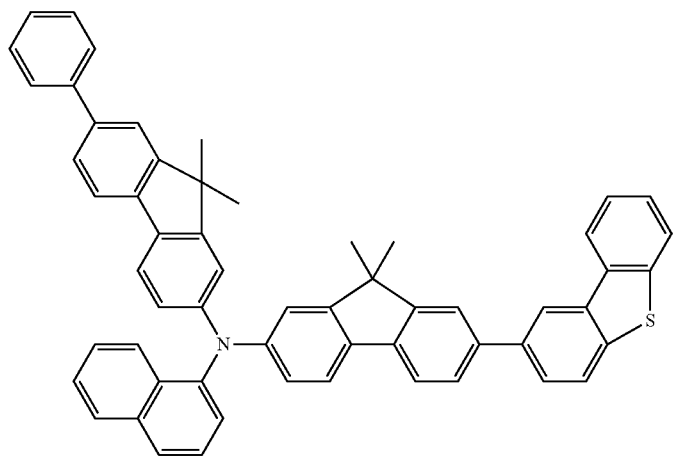
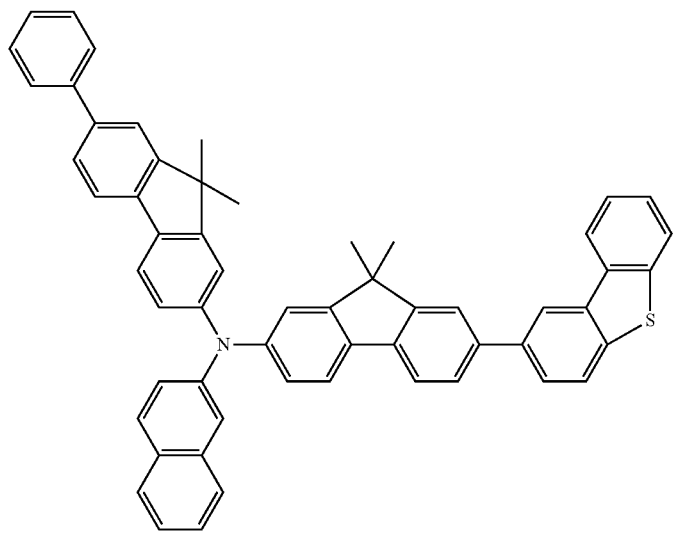

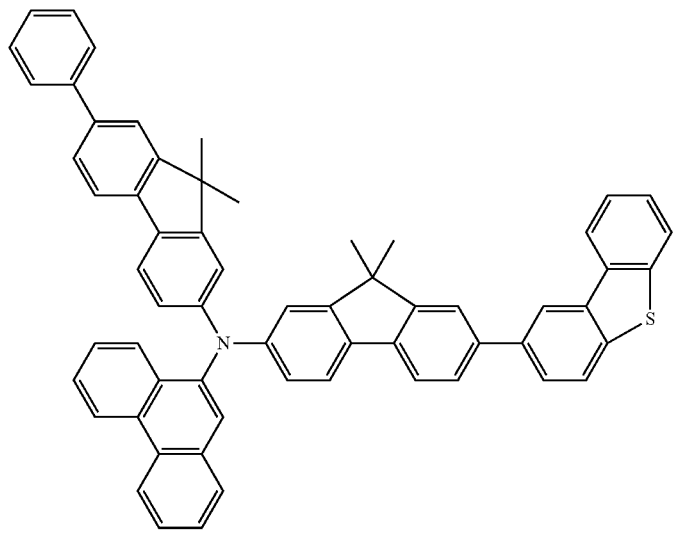
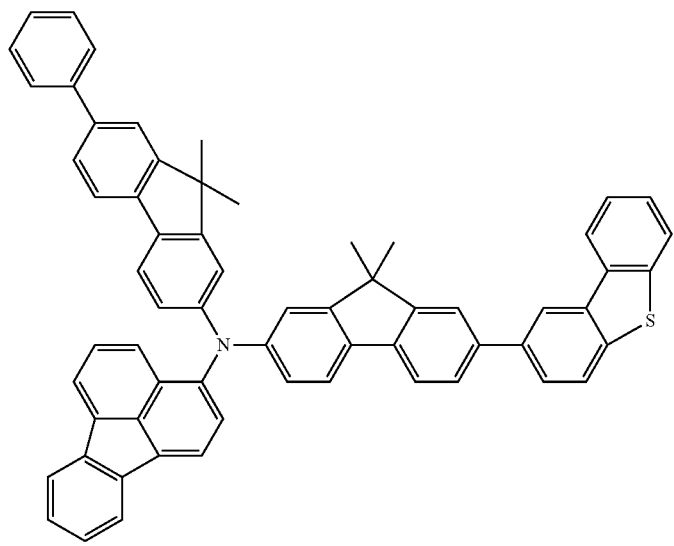
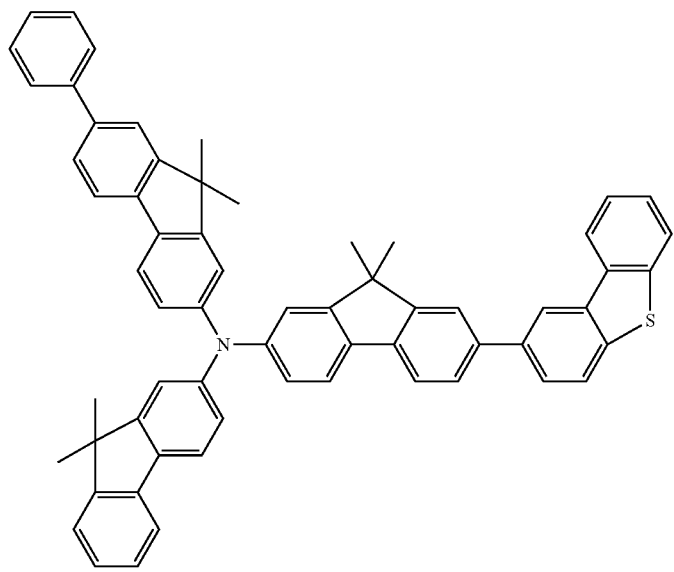

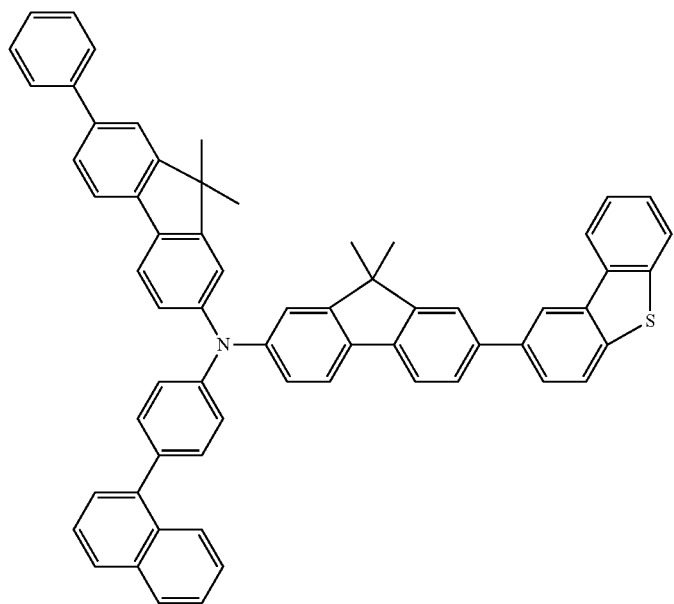
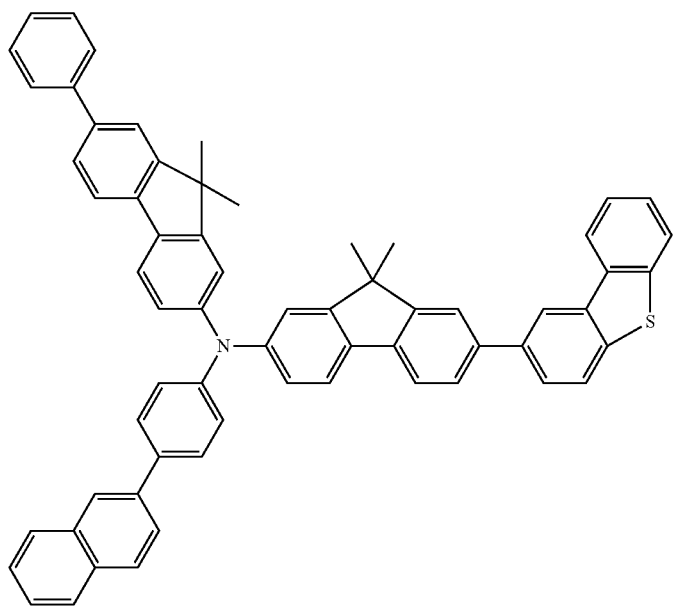

-continued
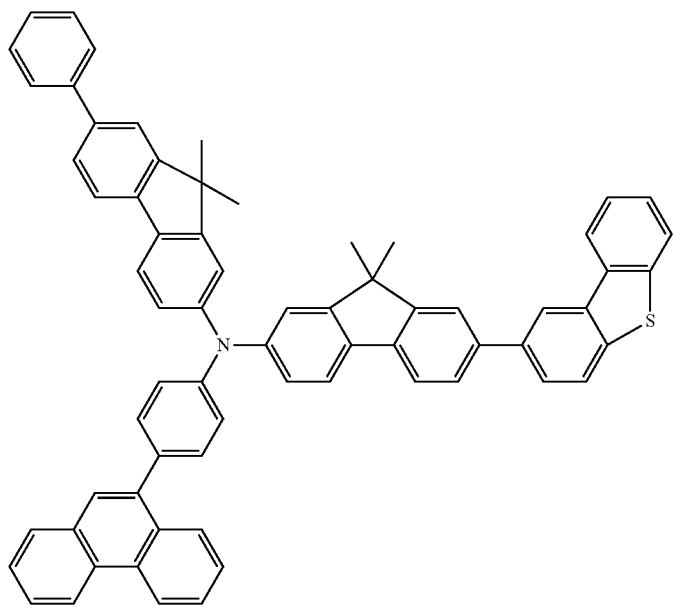
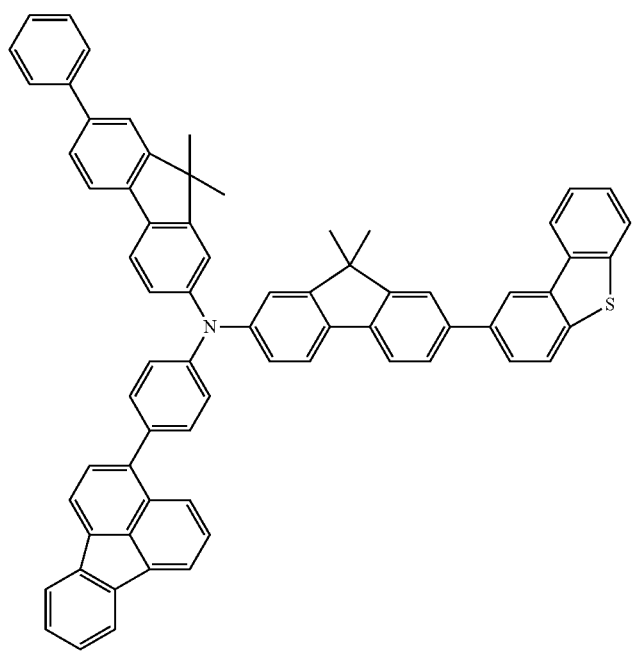

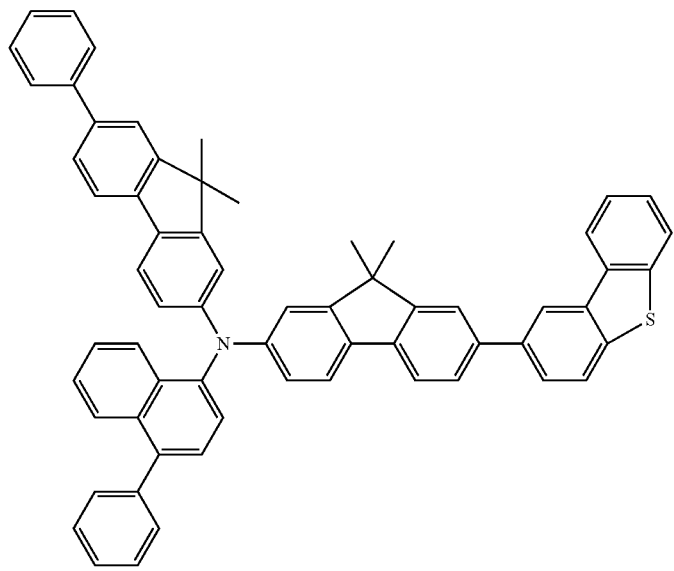
[Chem. 83]
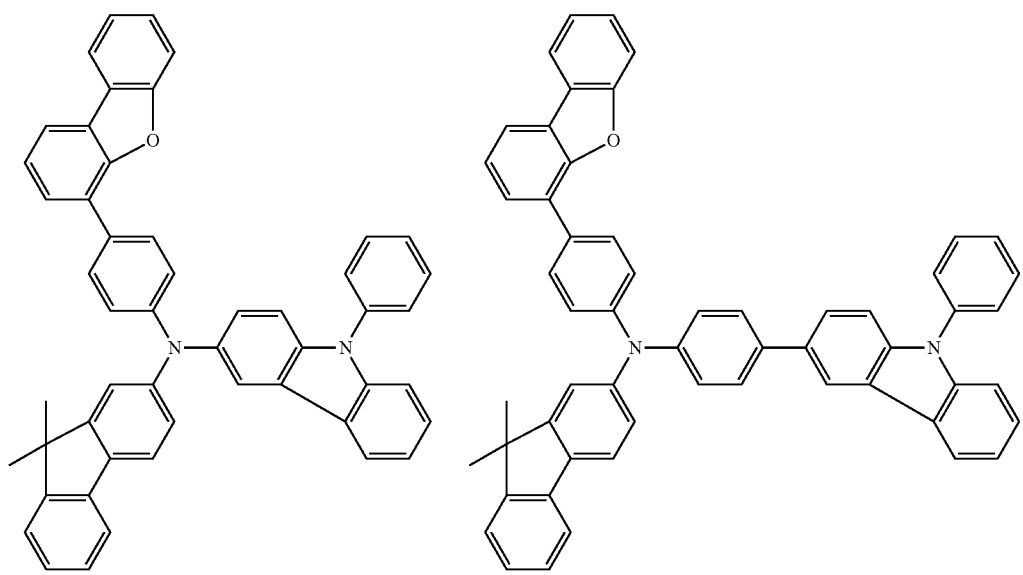

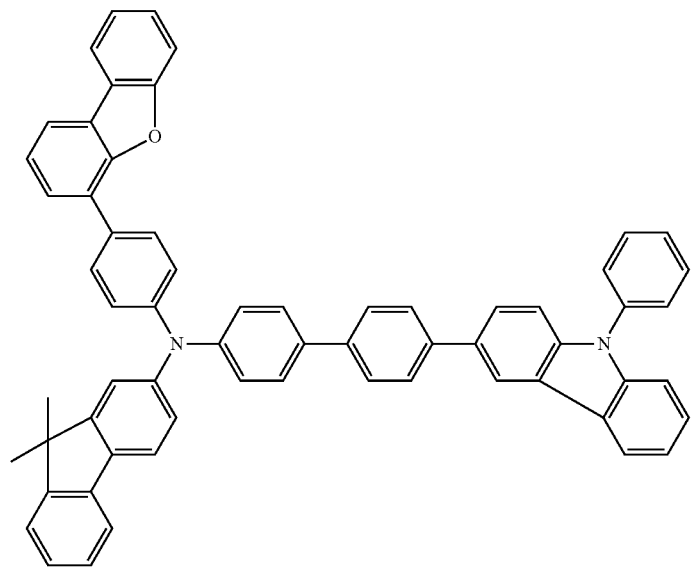
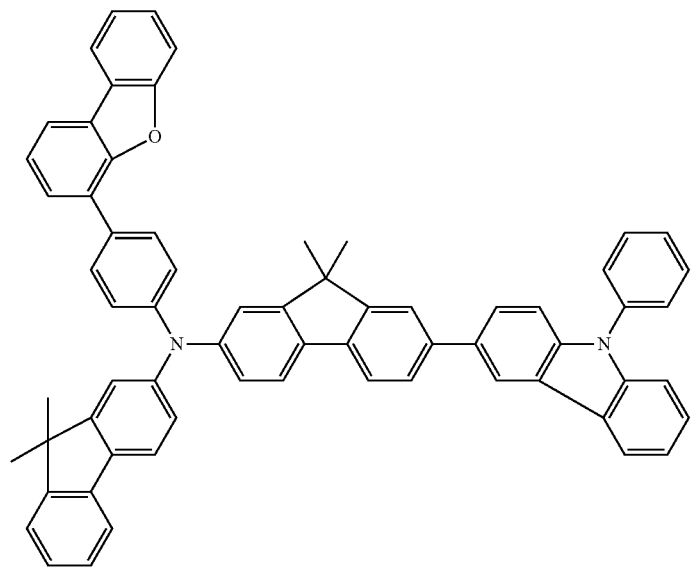
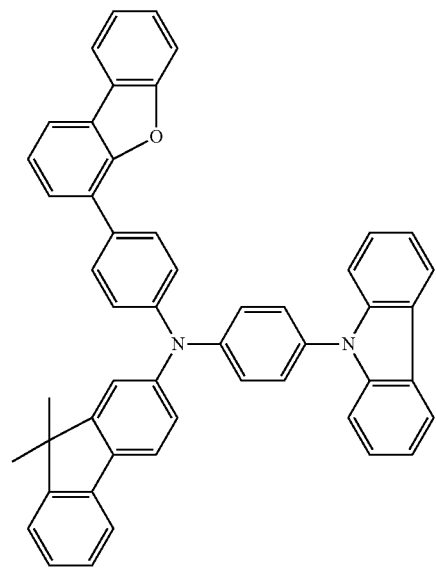
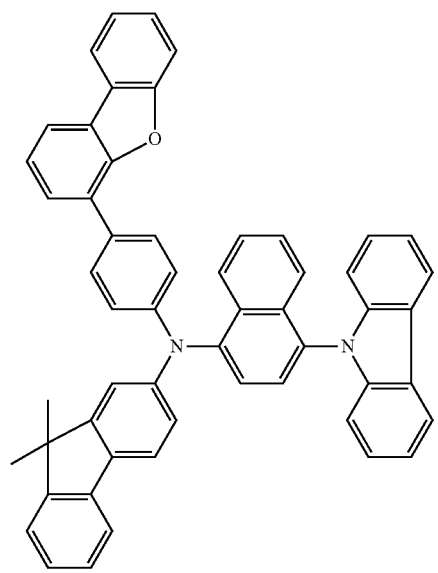
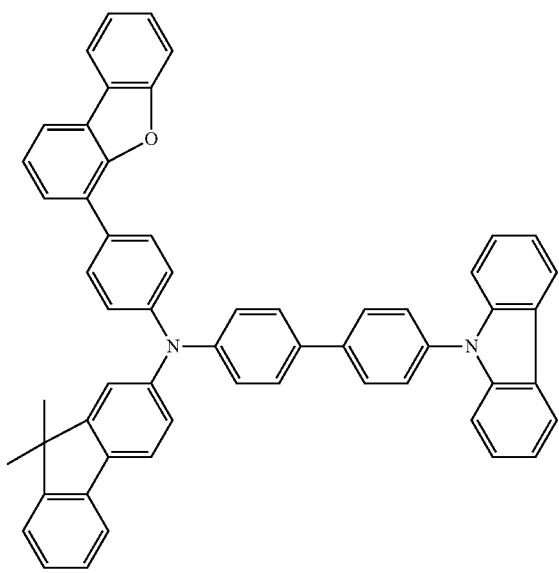

-continued
473
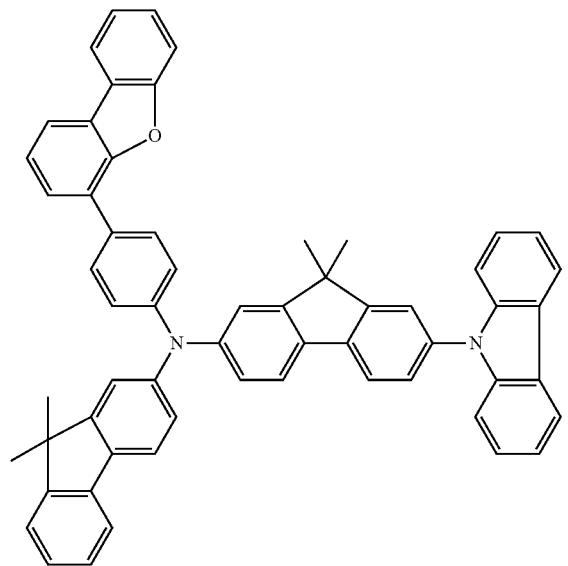
474
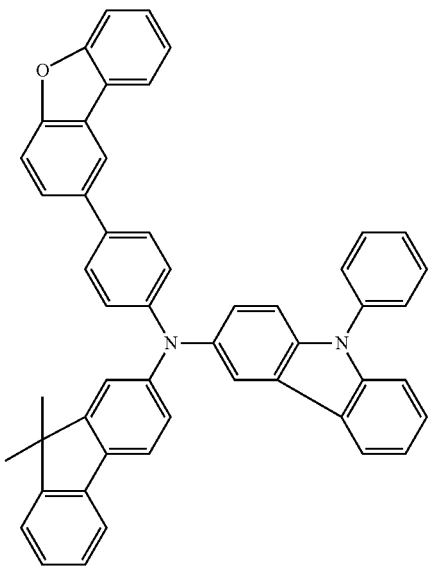
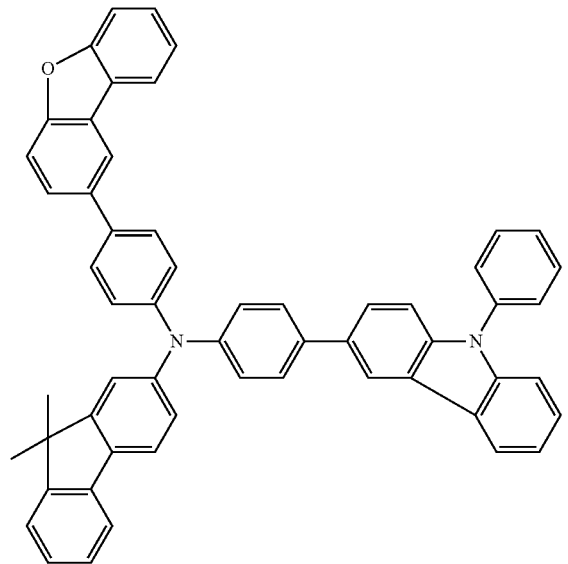
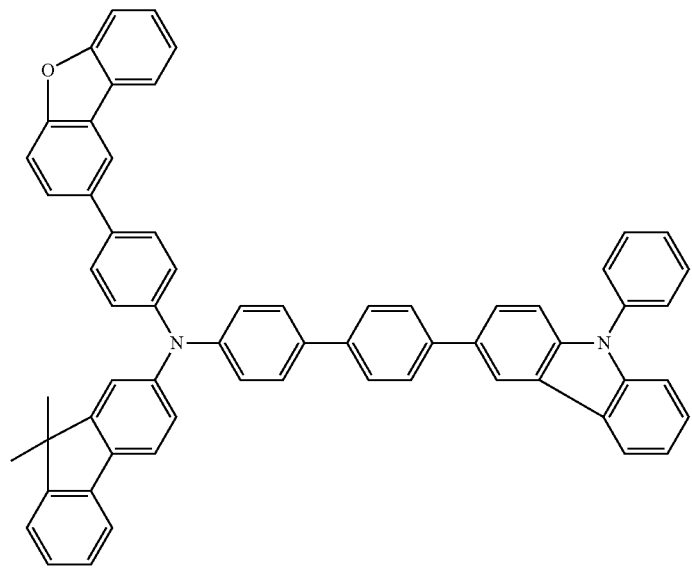

475
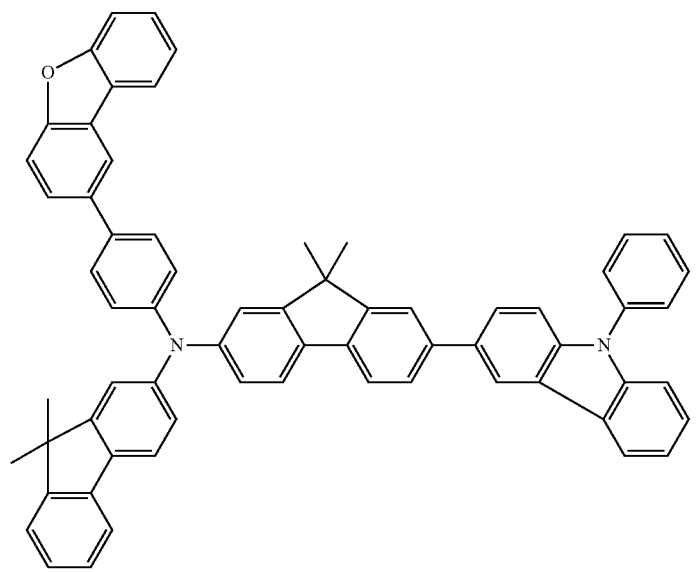
476
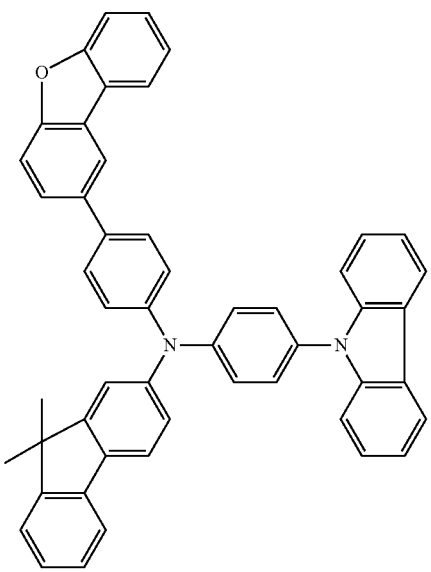
-continued
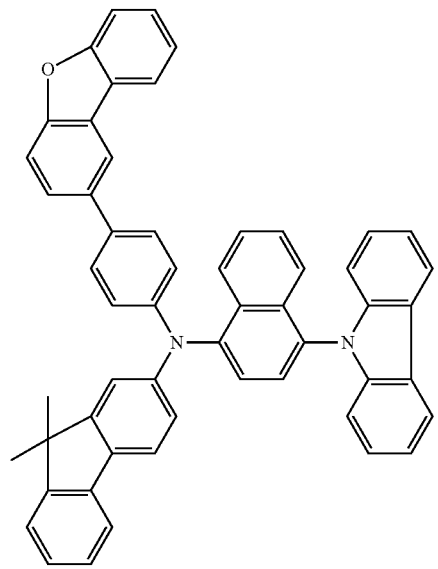
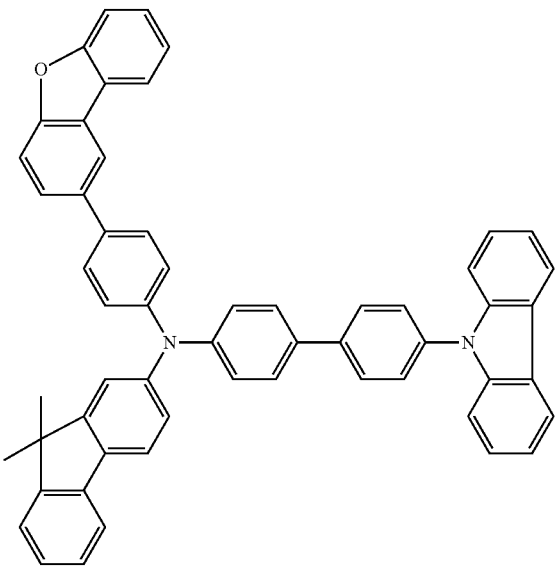
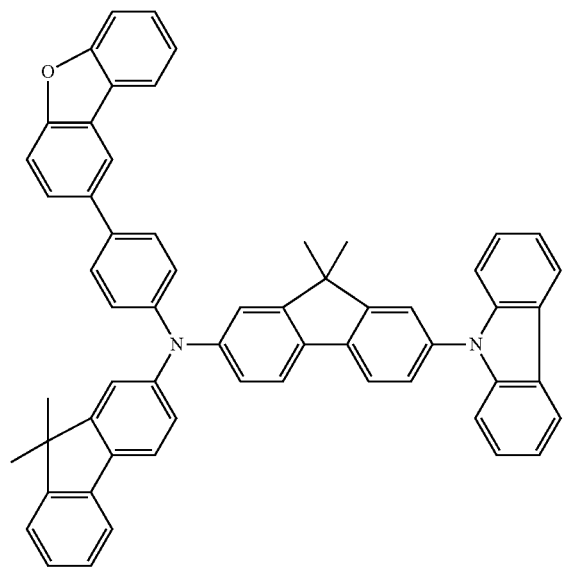

[Chem. 84]
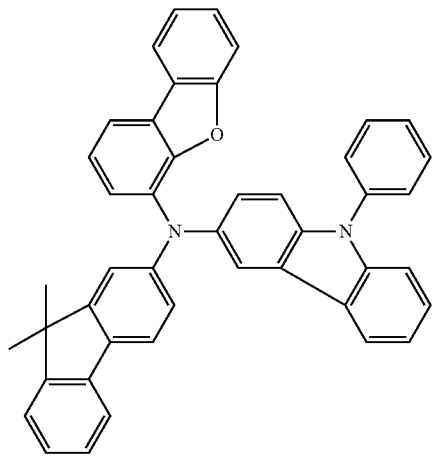
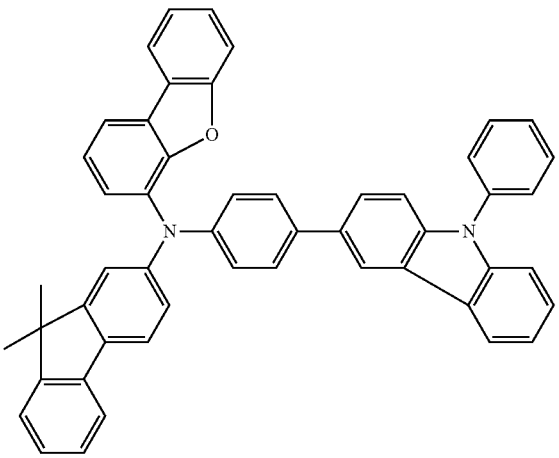
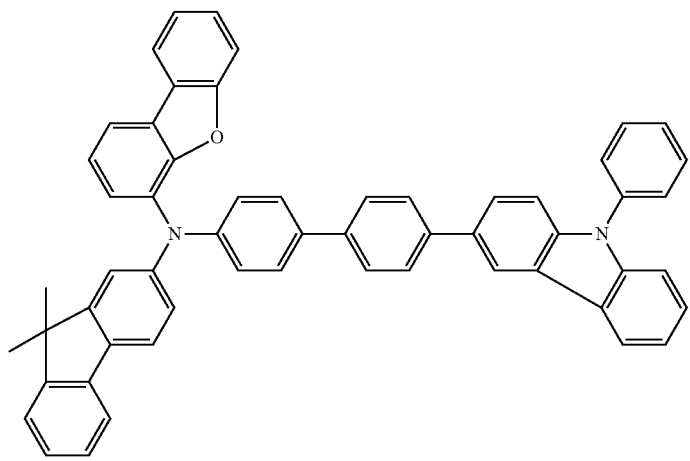
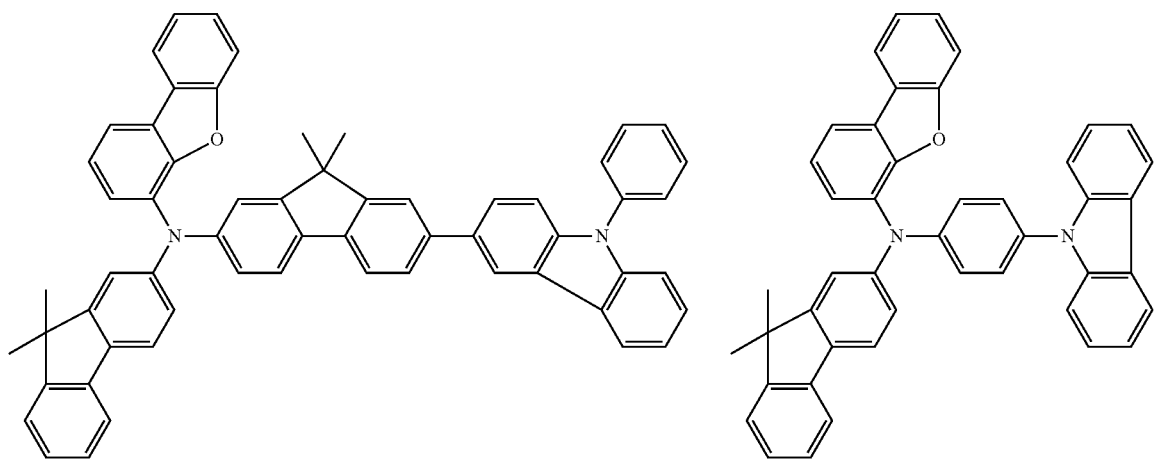

479
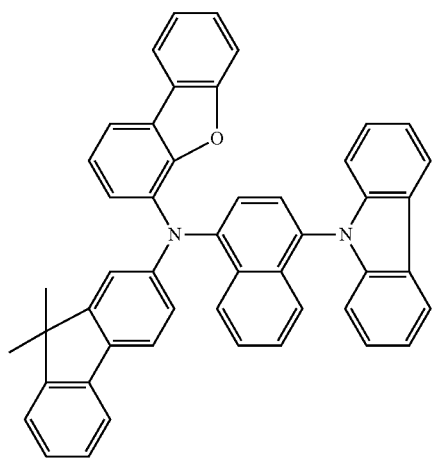
480
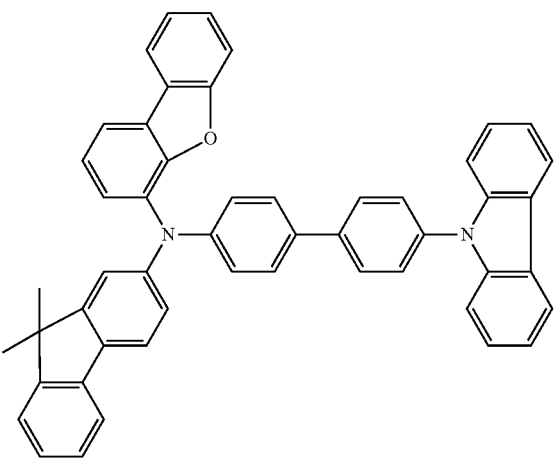
-continued
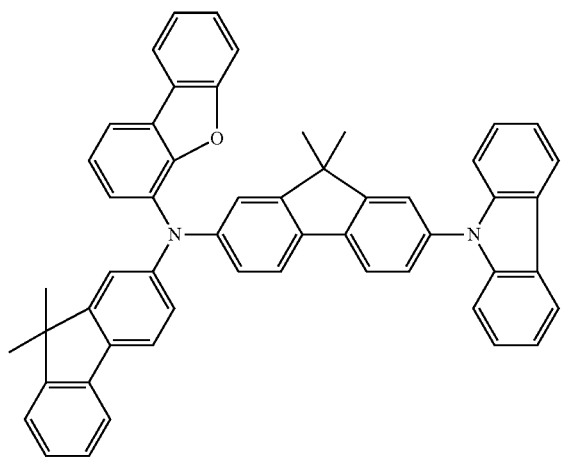
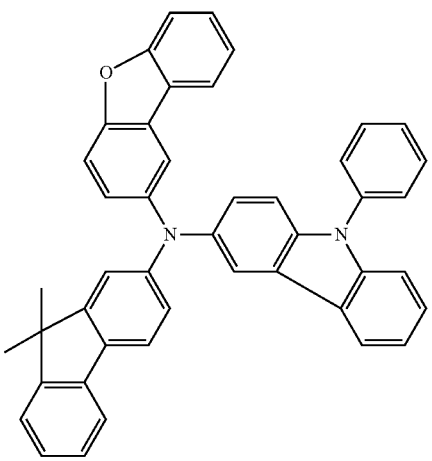
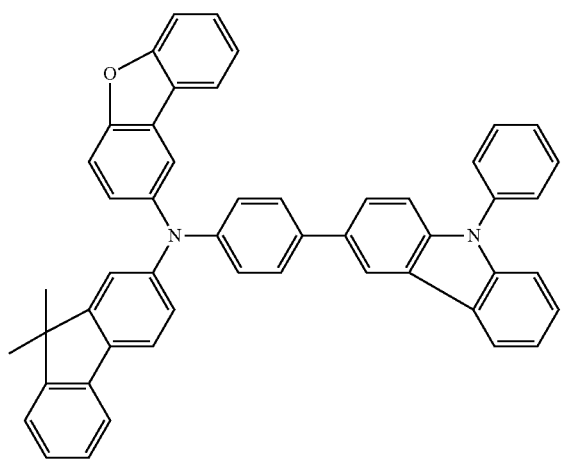

481
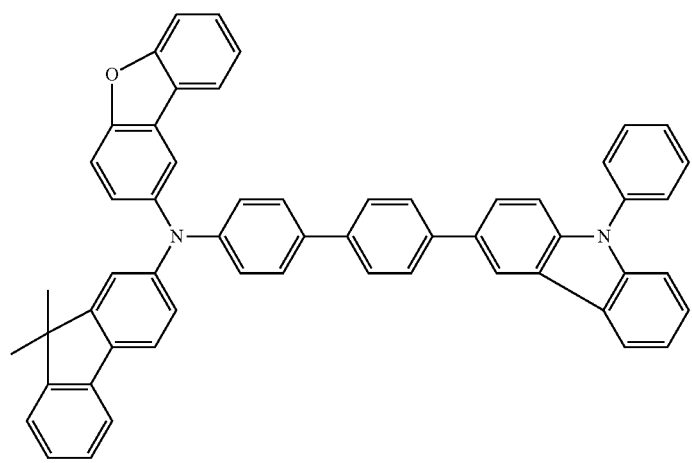
482
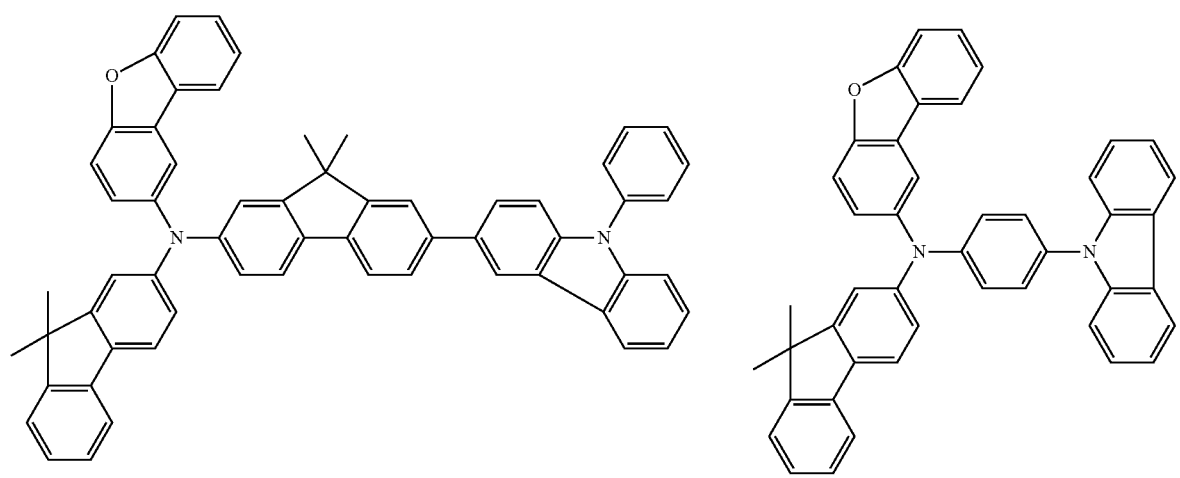
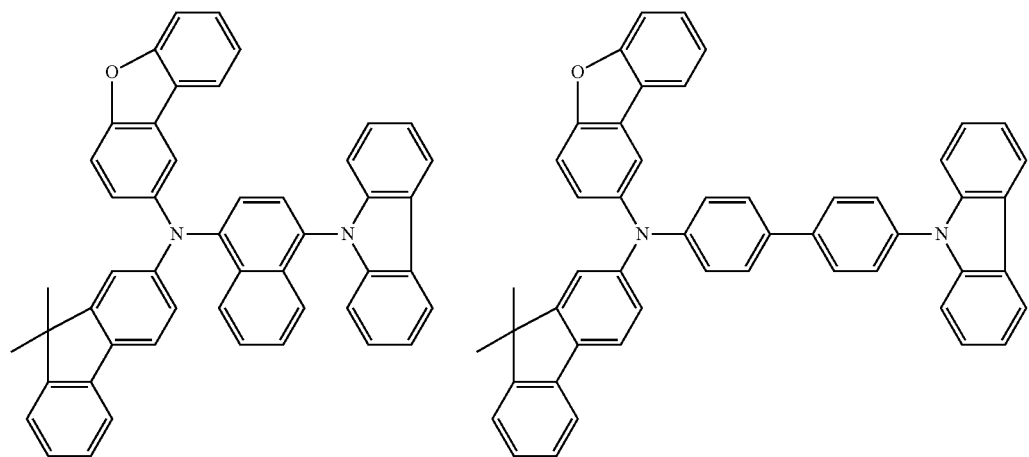

-continued
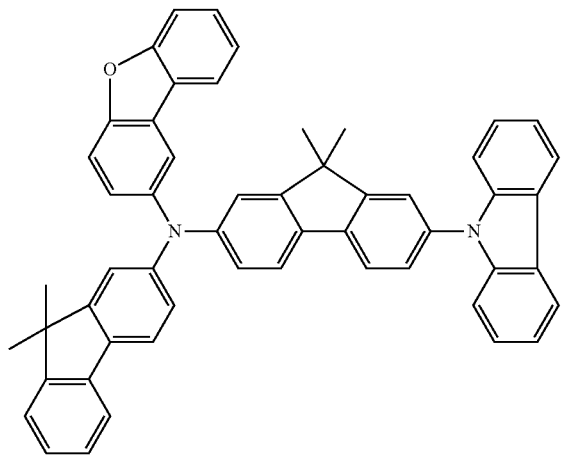
[Chem. 85]
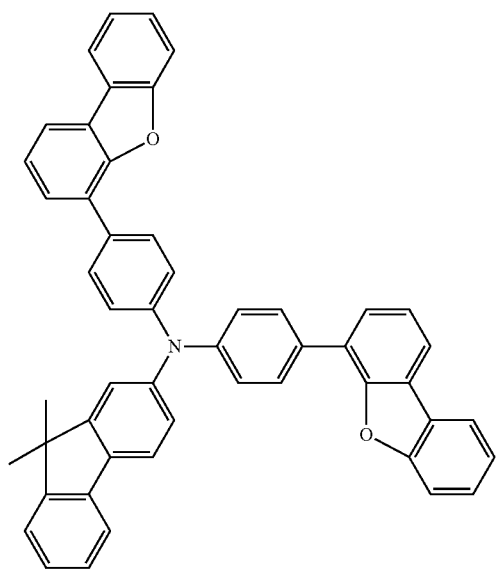
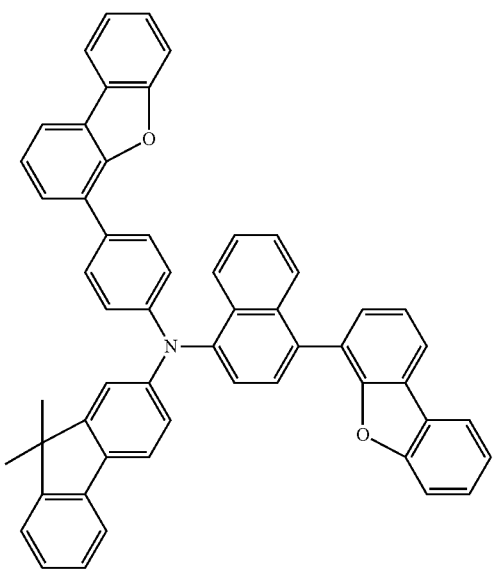
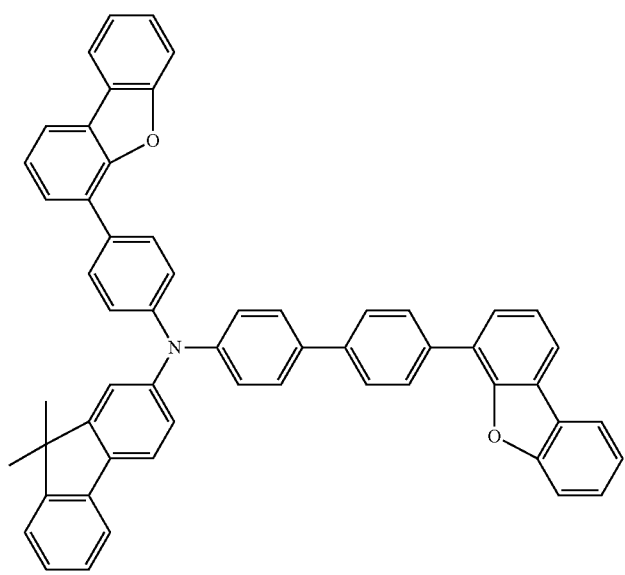

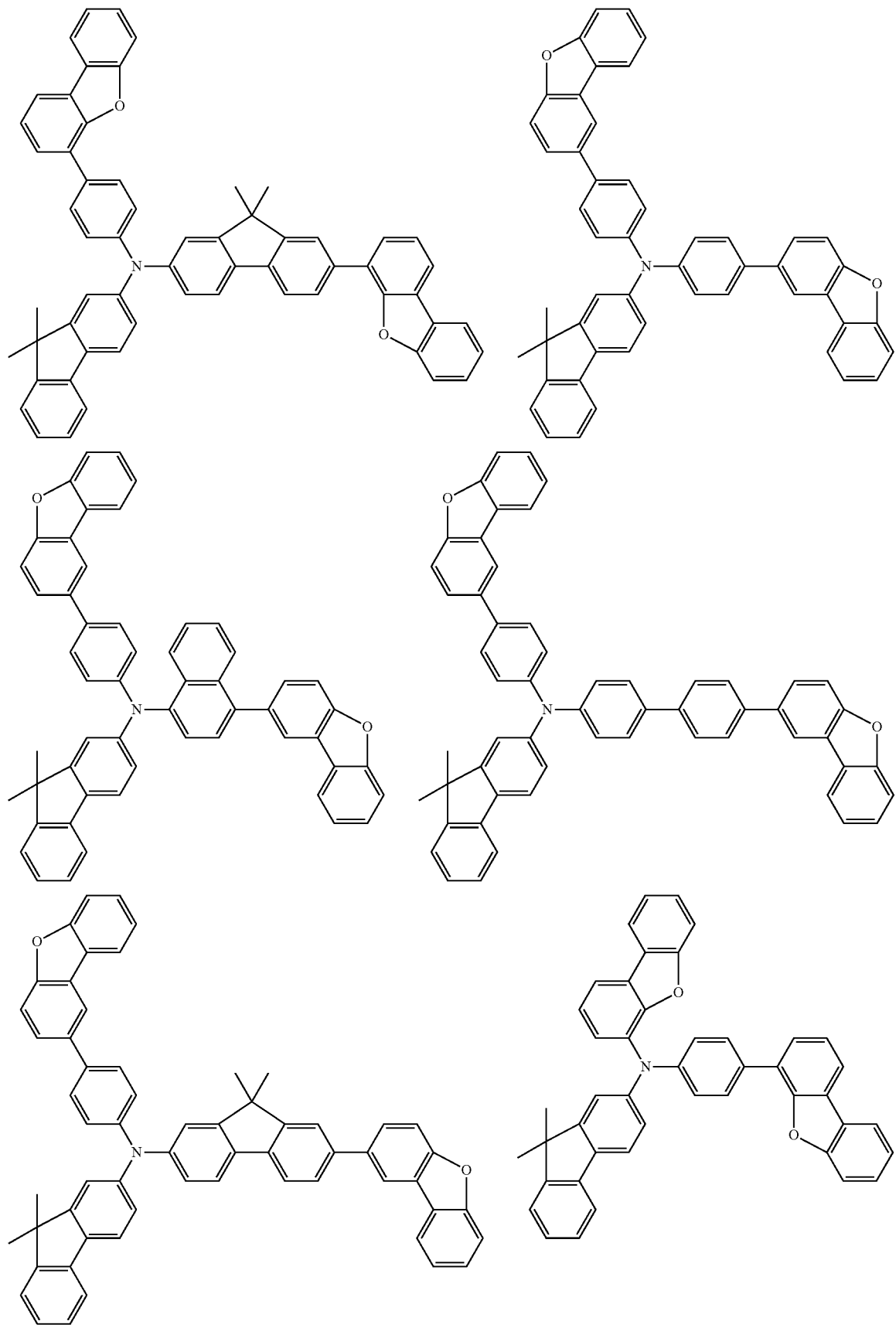

487
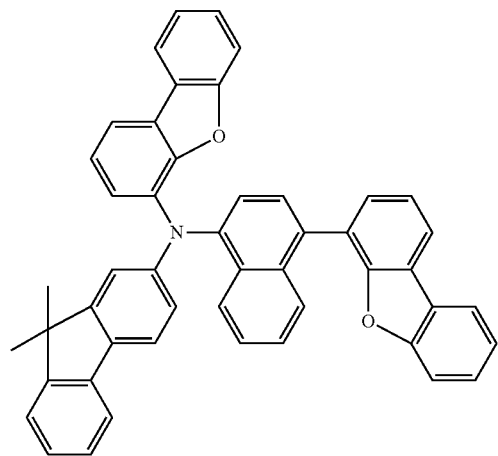
488
-continued
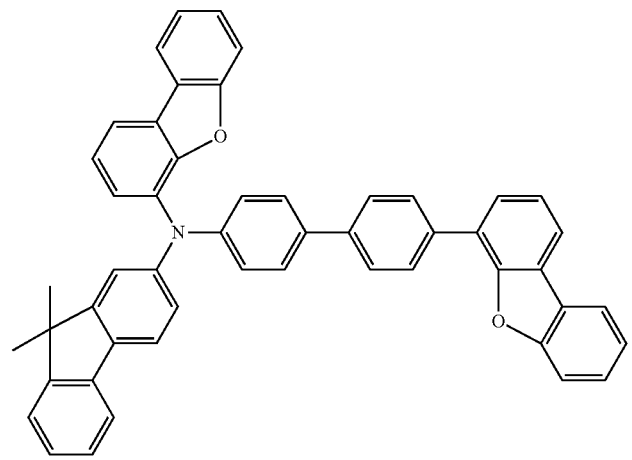
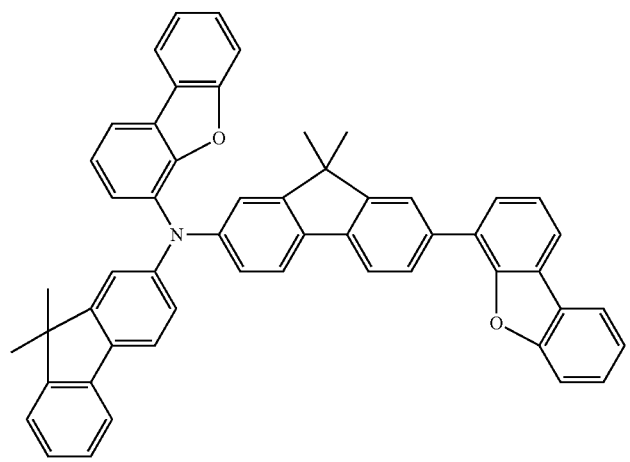
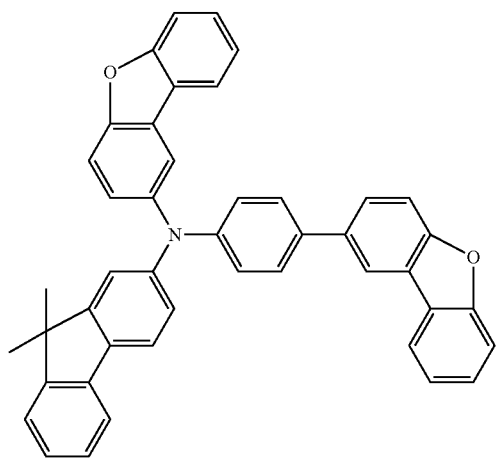
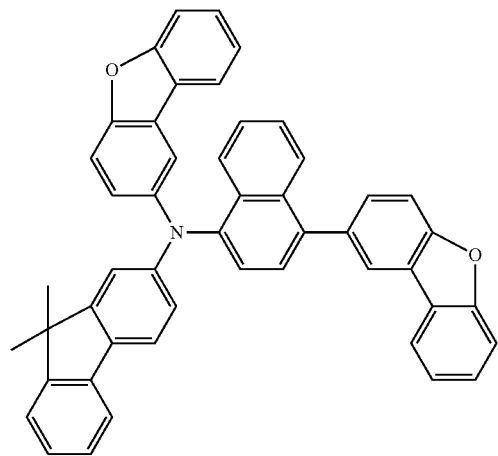
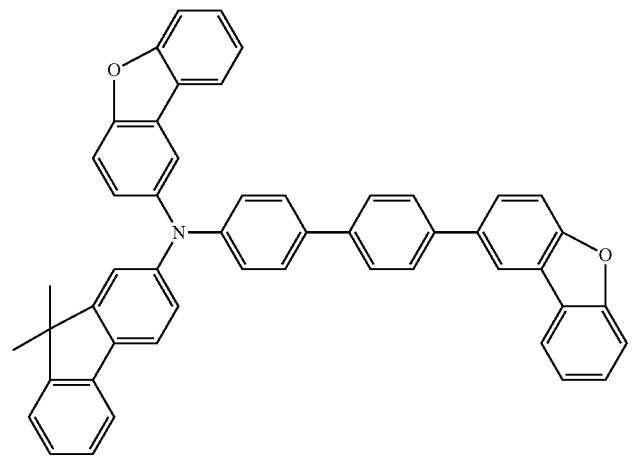

-continued
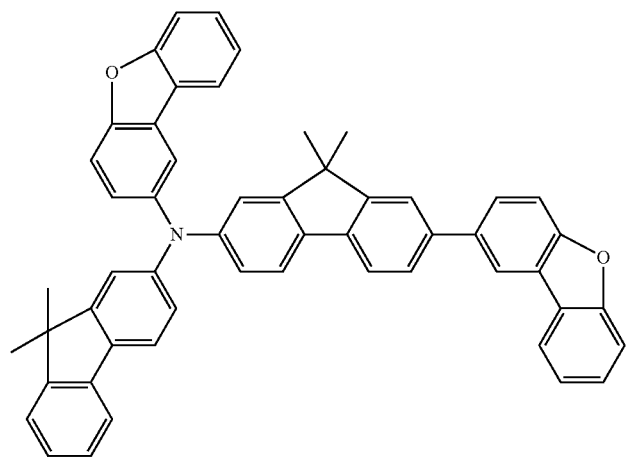
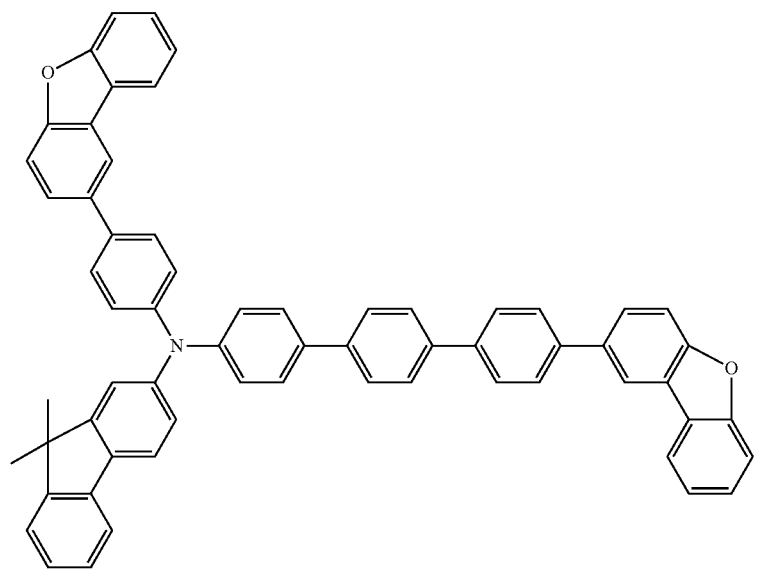
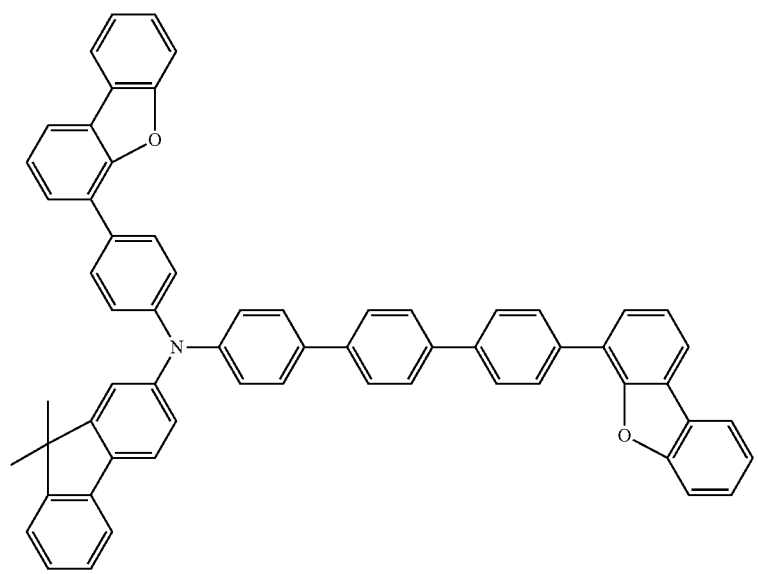

-continued
491
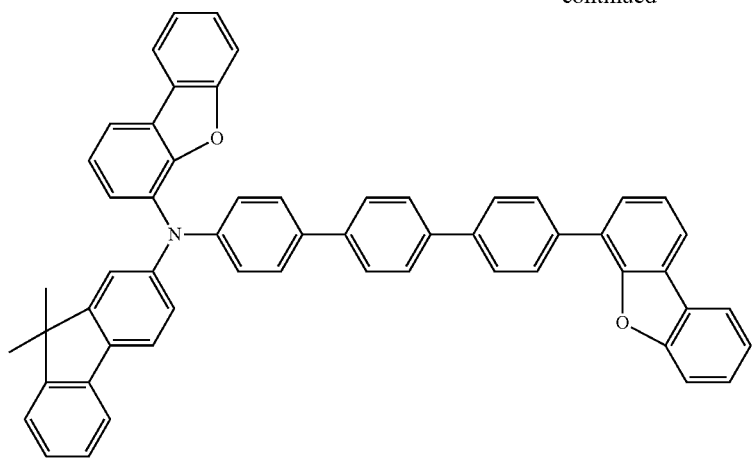
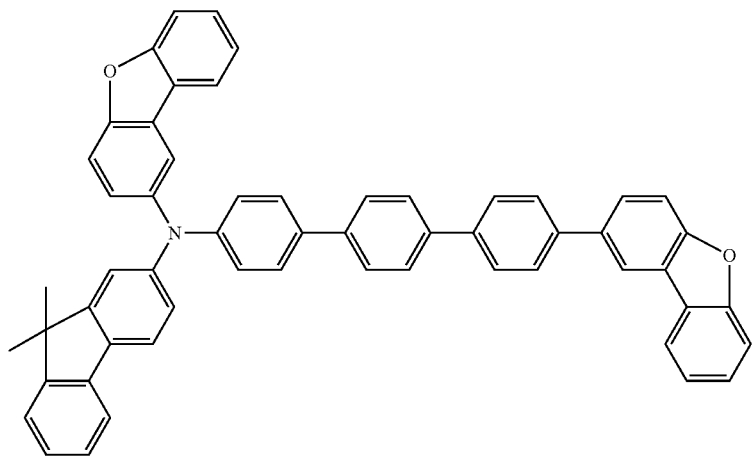
[Chem. 86]
492
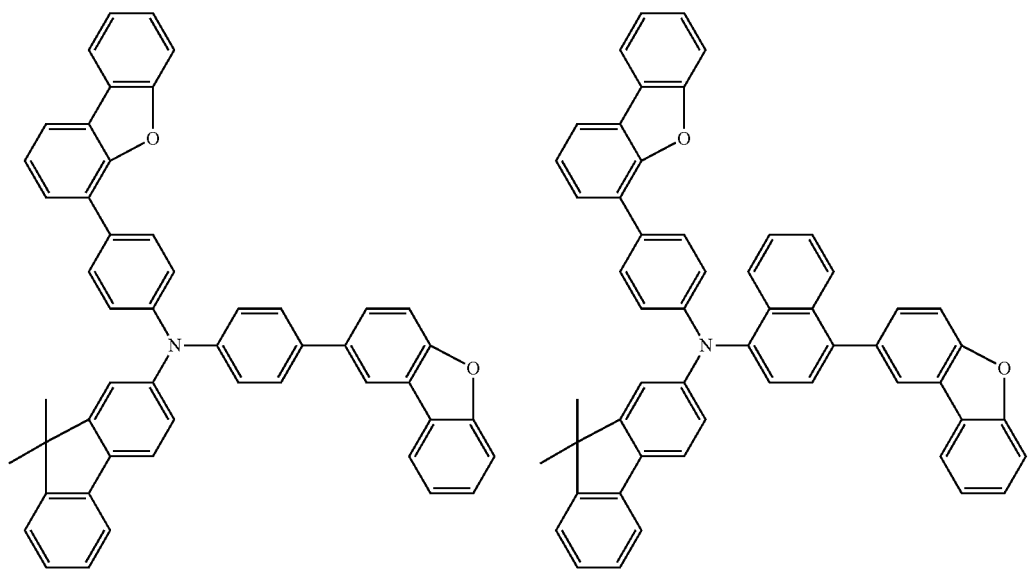

493
494
-continued
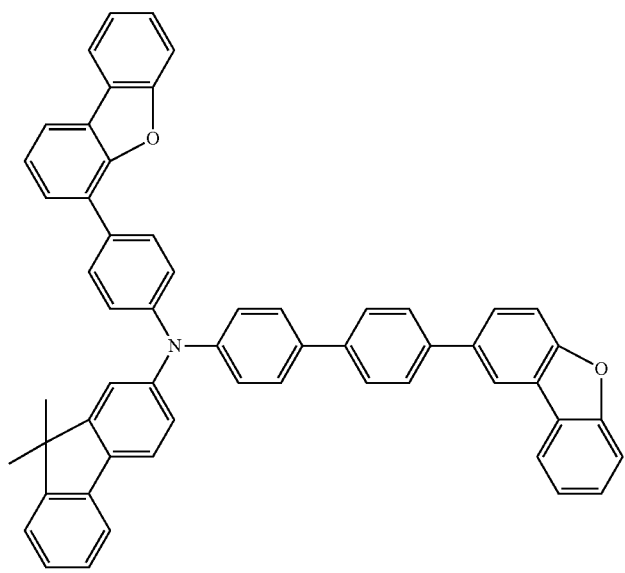
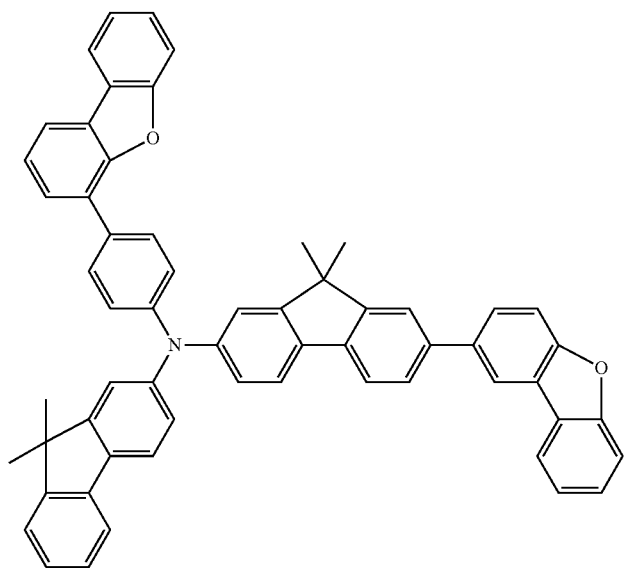
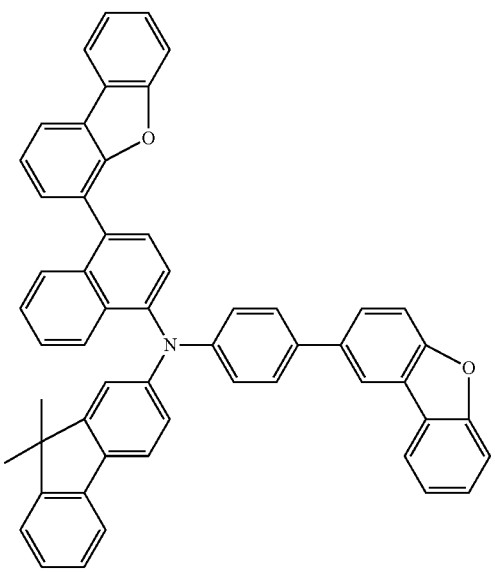

495 496
-continued
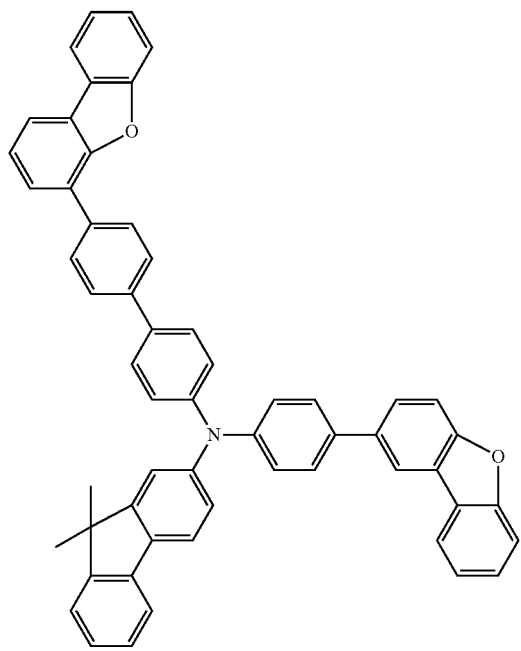
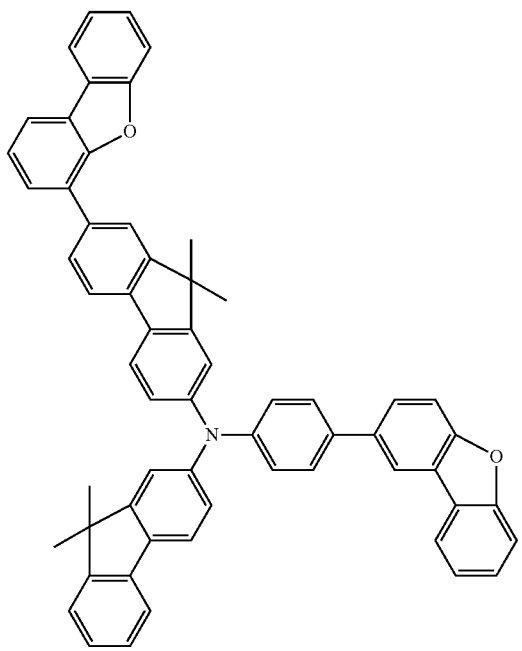
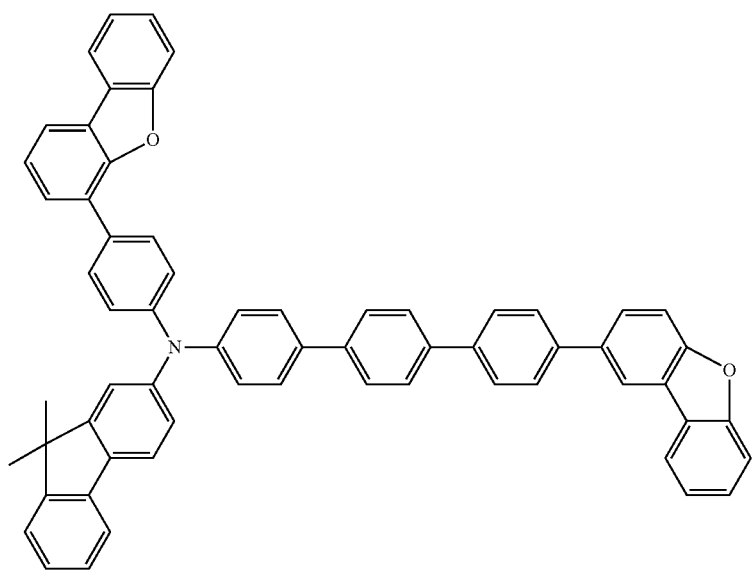

-continued
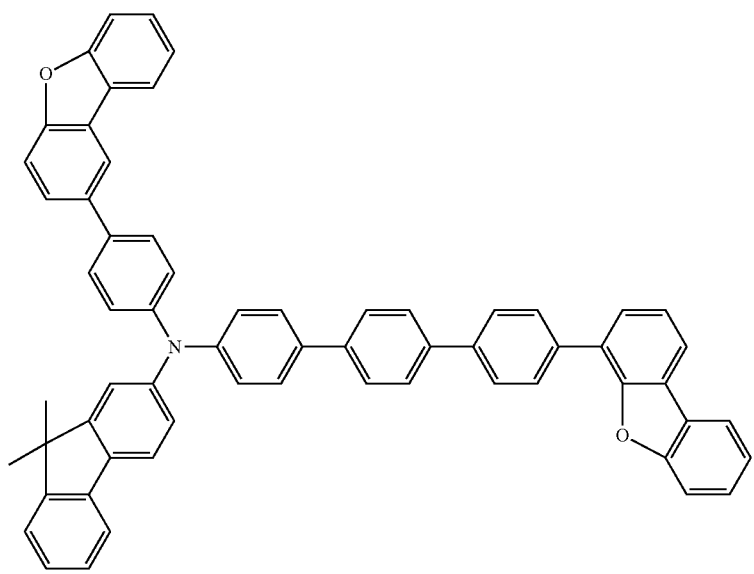
[Chem. 87]
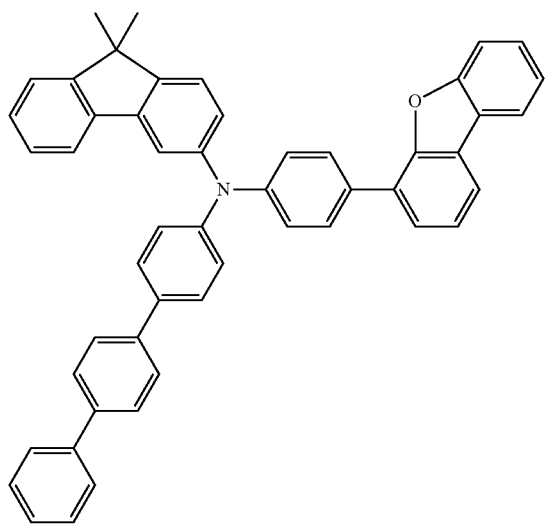
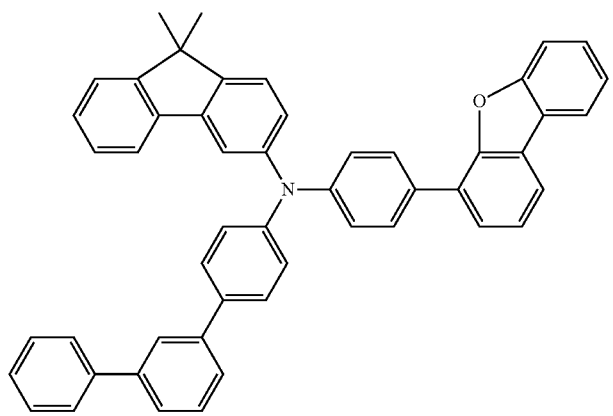
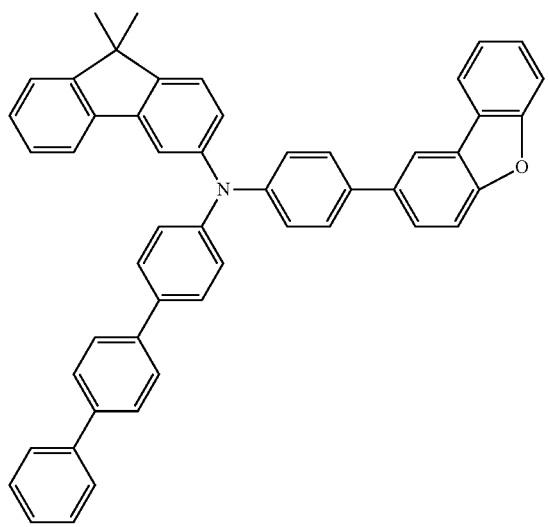
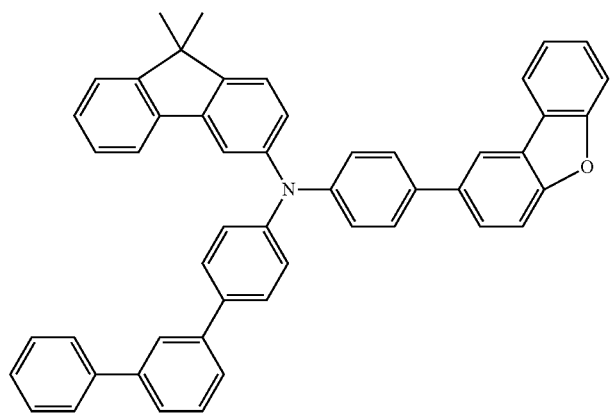

-continued
| 499 | 500 |
|---|---|
| 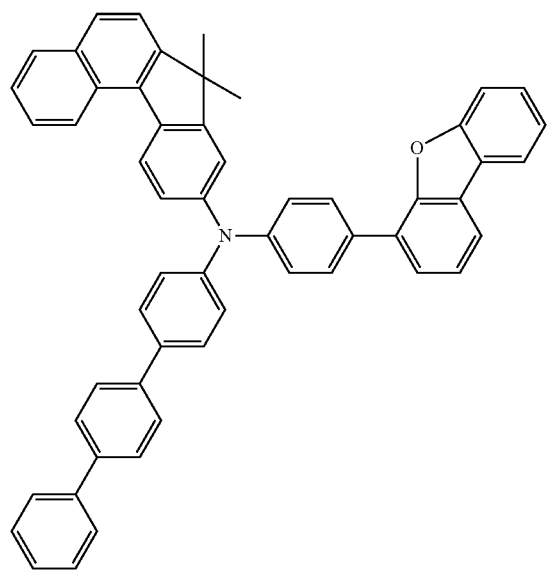 | 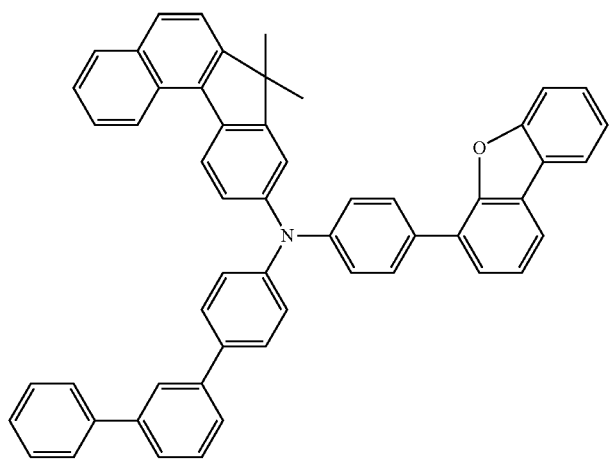 |
| 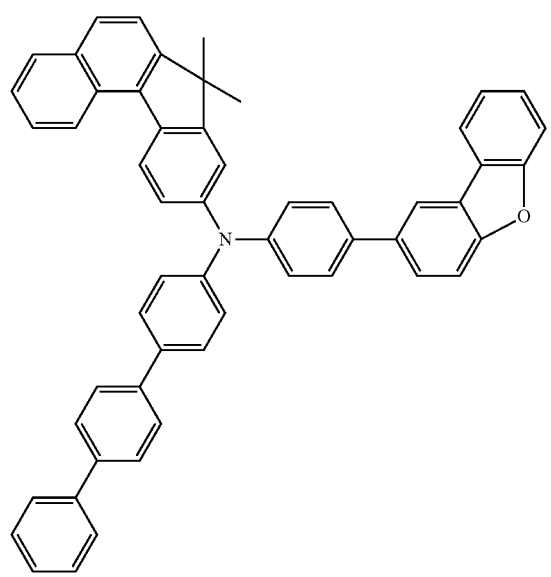 | 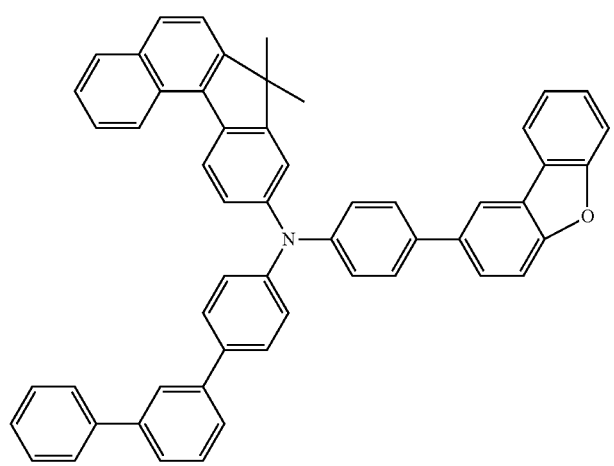 |

-continued
[Chem. 88]
501
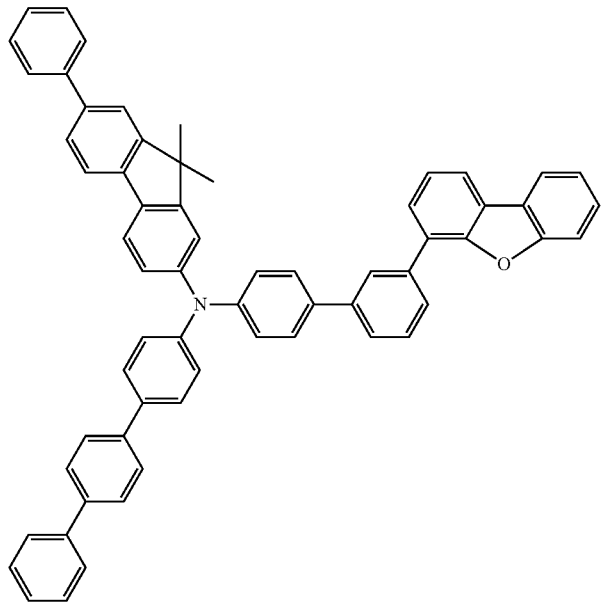
502
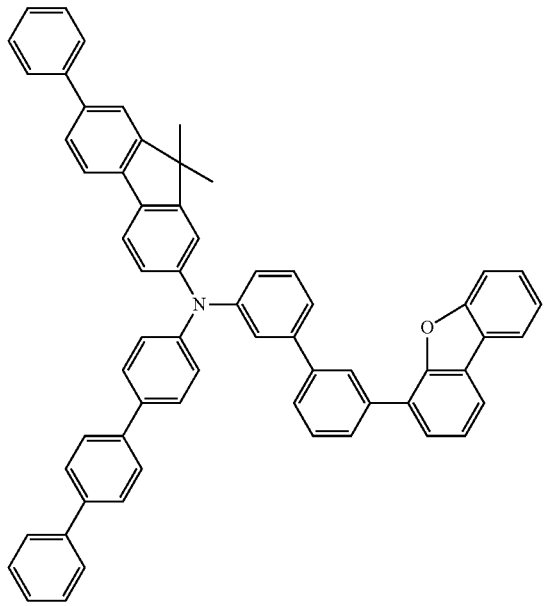
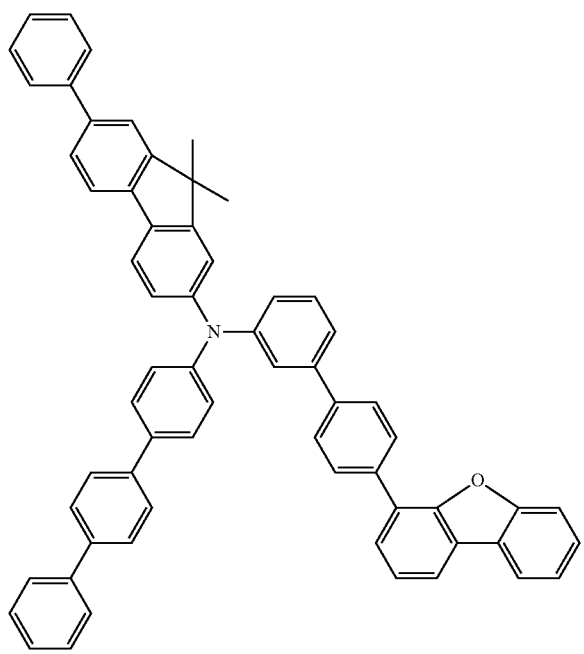

503
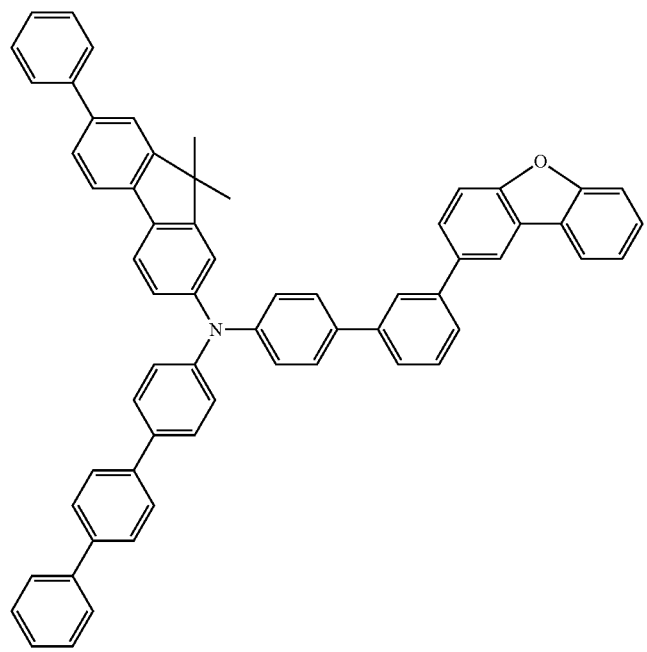
504
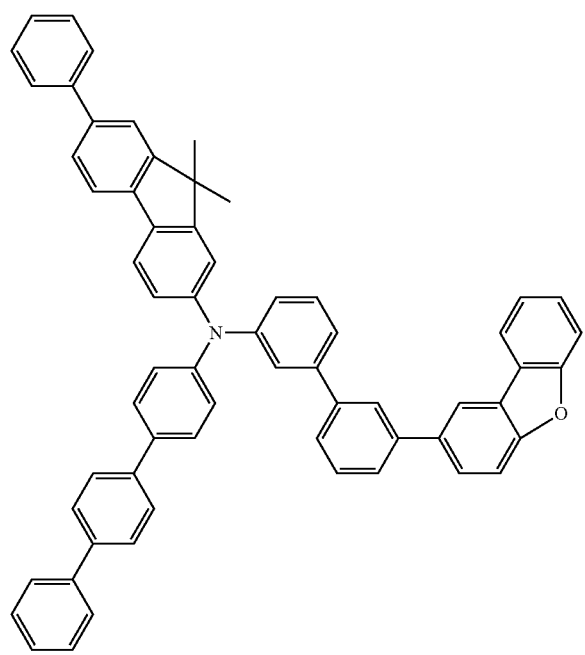

[Chem. 89]
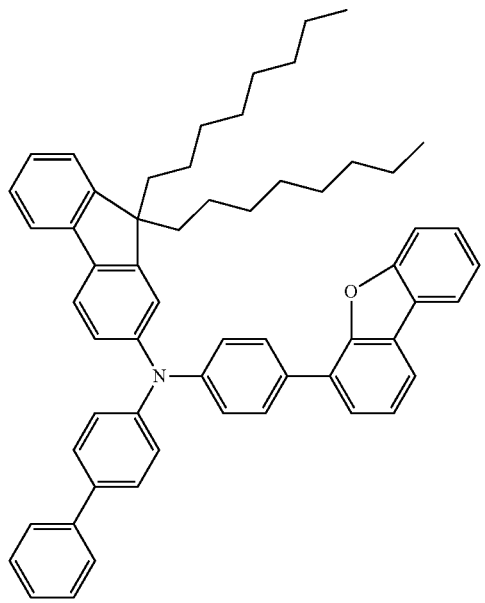
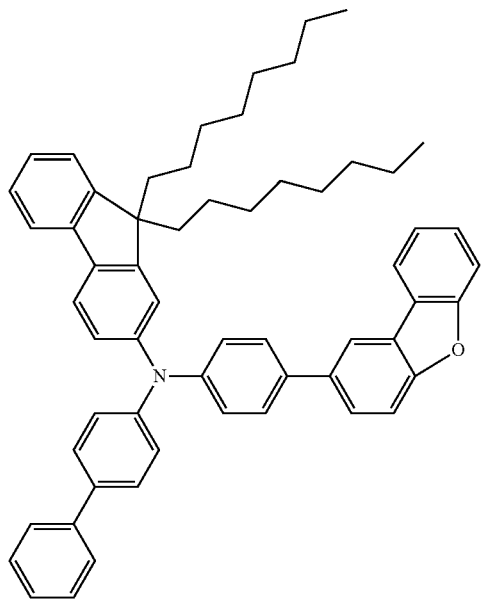
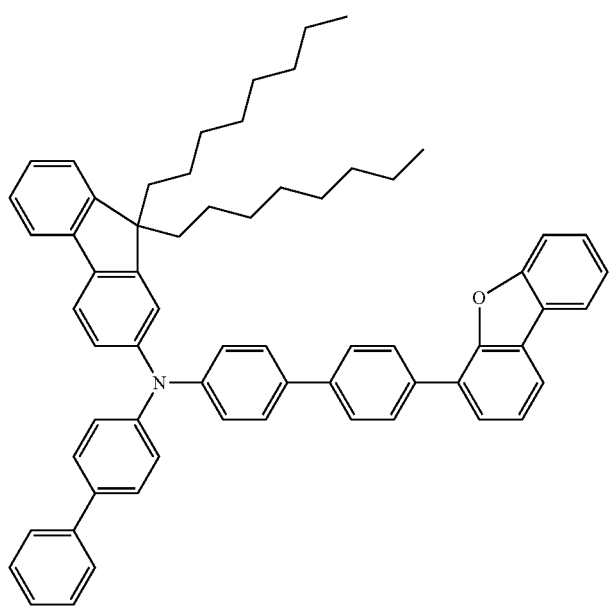 [SMILES: CCCCCCCCC1(CCCCCCCC)c2ccccc2-c2ccc(N(c3ccc(-c4ccccc4)cc3)c3ccc(-c4ccc(-c5ccc6oc7ccccc7c6c5)cc4)cc3)cc21]

-continued

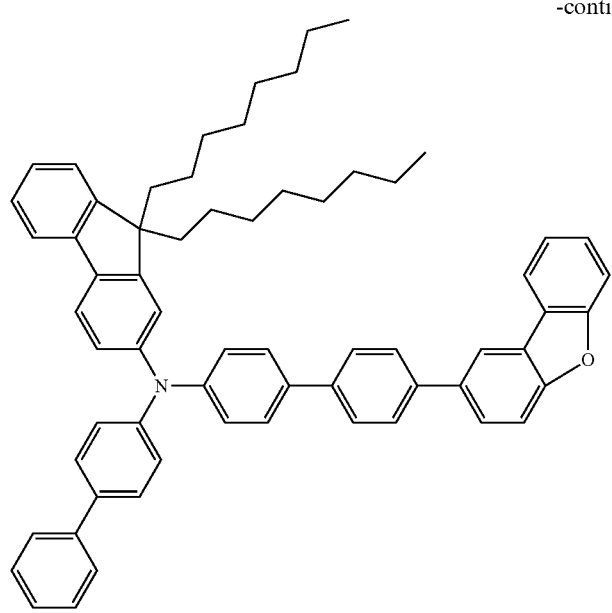

The aromatic amine derivative represented by the formula (I) of the present invention is useful as a material for an organic electroluminescence device.

It should be noted that a method of producing the aromatic amine derivative of the present invention is not particularly limited, and the derivative can be produced with reference to examples of the description by utilizing and applying a known method.

(Organic Electroluminescence Device)

Hereinafter, the structure of the organic EL device of the present invention is described.

Typical examples of the device structure of the organic EL device of the present invention may include, but not particularly limited to, the following structures (1) to (13). It should be noted that the device structure (8) is preferably used.

(1) Anode/light emitting layer/cathode
(2) Anode/hole injecting layer/light emitting layer/cathode
(3) Anode/light emitting layer/electron injecting layer/cathode
(4) Anode/hole injecting layer/light emitting layer/electron injecting layer/cathode
(5) Anode/organic semiconductor layer/light emitting layer/cathode
(6) Anode/organic semiconductor layer/electron barrier layer/light emitting layer/cathode
(7) Anode/organic semiconductor layer/light emitting layer/adhesion improving layer/cathode
(8) Anode/hole injecting layer/hole transporting layer/light emitting layer/(electron transporting layer/) electron injecting layer/cathode
(9) Anode/insulating layer/light emitting layer/insulating layer/cathode
(10) Anode/inorganic semiconductor layer/insulating layer/light emitting layer/insulating layer/cathode
(11) Anode/organic semiconductor layer/insulating layer/light emitting layer/insulating layer/cathode
(12) Anode/insulating layer/hole injecting layer/hole transporting layer/light emitting layer/insulating layer/cathode
(13) Anode/insulating layer/hole injecting layer/hole transporting layer/light emitting layer/(electron transporting layer/) electron injecting layer/cathode In addition, in the organic EL device of the present invention, the aromatic amine derivative of the present invention, which may be used in any one of the organic thin-film layers because the derivative hardly crystallizes, is preferably incorporated into the hole injecting layer or the hole transporting layer, more preferably incorporated into the hole transporting layer from the viewpoint of a reduction in the driving voltage of the organic EL device. The organic EL device using the aromatic amine derivative of the present invention not only is driven at a reduced voltage but also has high luminous efficiency and a long lifetime.

The content at which the aromatic amine derivative of the present invention is incorporated into one organic thin-film layer, preferably the hole injecting layer or the hole transporting layer is preferably 30 to 100 mol %, more preferably 50 to 100 mol %, still more preferably 80 to 100 mol %, particularly preferably substantially 100 mol % with respect to all components of the organic thin-film layer.

Hereinafter, each layer of the organic EL device of such a construction that the aromatic amine derivative of the present invention is incorporated into the hole transporting layer as a preferred embodiment is described.

(Substrate)

The organic EL device is generally prepared on a substrate having light-transmissive property. The substrate having light-transmissive property is the substrate which supports the organic EL device. It is preferred that the light-transmissive substrate have transmissive property which is a transmittance of light of 50% or more in the visible light region where the wavelength is 400 to 700 nm and still preferably be flat and smooth.

Examples of the light-transmissive substrate include a glass plate and a synthetic resin plate. In particular, examples of the glass plate include plates formed of soda-lime glass, glass containing barium and strontium, lead glass, aluminosilicate glass, borosilicate glass, barium borosilicate glass, and quartz. Further, examples of the synthetic resin plate include plates formed of a polycarbonate resin, an acrylic resin, a polyethylene terephthalate resin, a polyether sulfide resin, and a polysulfone resin.

(Anode)

The anode has a role in injecting holes to the hole transporting layer or the light emitting layer. It is effective that the anode has a work function of 4 eV or more (preferably 4.5 eV or more). A material for the anode used in the present invention is specifically exemplified by carbon, aluminum, vanadium, iron, cobalt, nickel, tungsten, silver, gold, platinum, palladium, and alloys thereof, metal oxides such as tin oxide and indium oxide used for an ITO substrate and an NESA substrate, and organic conductive resins such as polythiophene and polypyrrole.

The anode is obtained by forming a thin film with one of the materials for electrodes by, for example, a vapor deposition method or a sputtering method.

As described above, when light emitted from the light emitting layer is obtained through the anode, it is preferred that the anode have a transmittance of more than 10% with respect to the emitted light. It is also preferred that the sheet resistance of the anode be several hundred Ω/□ or less. The thickness of the anode is generally 10 nm to 1 μm, preferably 10 to 200 nm although the value varies depending on materials.

(Cathode)

As the cathode, a material such as a metal, an alloy, an electroconductive compound, or a mixture of those materials, which have a small work function (4 eV or less) and are used as electrode materials, is used. Specific examples of the electrode material to be used include, but not particularly limited to, magnesium, calcium, tin, lead, titanium, yttrium, lithium, ruthenium, manganese, aluminum, lithium fluoride, and alloys thereof. Representative examples of the alloys include, but not particularly limited to, magnesium/silver, magnesium/indium, and lithium/aluminum. A ratio of the alloy components is controlled by, for example, the temperature of a vapor deposition source, an atmosphere, and a degree of vacuum, and an appropriate ratio is selected for the ratio. The anode and the cathode may each be formed of a layer construction having two or more layers, as required.

The cathode can be obtained by forming a thin film of the electrode material described above in accordance with a method such as vapor deposition or sputtering.

Here, when light emitted from the light emitting layer is obtained through the cathode, it is preferred that the cathode have a transmittance of more than 10% with respect to the emitted light. It is also preferred that the sheet resistivity of the cathode be several hundred Ω/□ or less. In addition, the thickness of the cathode is generally 10 nm to 1 μm, preferably 50 nm to 200 nm.

(Insulating Layer)

In addition, in general, defects in pixels are liable to be formed in organic EL devices due to leak and short circuit because an electric field is applied to ultra-thin films. In order to prevent the formation of the defects, an insulating layer formed of a thin-film layer having insulating property may be inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. It should be noted that a mixture or a laminate of those materials may be used.

(Light Emitting Layer)

The light emitting layer of the organic EL device has a combination of the following functions (1) to (3).

(1) The injecting function: the function that allows holes to be injected from the anode or the hole injecting layer and electrons to be injected from the cathode or the electron injecting layer when an electric field is applied.

(2) The transporting function: the function of transporting injected charges (i.e., electrons and holes) by the force of the electric field.

(3) The light emitting function: the function of providing the field for recombination of electrons and holes and leading the recombination to the emission of light.

Although the ease with which a hole is injected and the ease with which an electron is injected may differ from each other, and transporting abilities represented by the mobilities of a hole and an electron may vary in extent, one of the charges is preferably transferred.

A host material or a doping material which can be used in the light emitting layer is not particularly limited, and examples thereof include condensed ring aromatic compounds and derivatives thereof, such as naphthalene, phananthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethynyl)anthracene, and 1,4-bis(9'-ethynylanthracenyl)benzene, organic metal complexes such as tris(8-quinolinolato)aluminum and bis-(2-methyl-8-quinolinolato)-4-(phenylphenolinato)aluminum, an arylamine derivative, a styrylamine derivative, a stilbene derivative, a coumarin derivative, a pyrane derivative, an oxazone derivative, a benzothiazole derivative, a benzoxazole derivative, a benzimidazole derivative, a pyrazine derivative, a cinnamate derivative, a diketopyrrolopyrrole derivative, an acridone derivative, and quinacridone derivative. Of those, an arylamine derivative, a styrylamine derivative are preferred, and a styrylamine derivative is more preferred.

An additional known light emitting material, doping material, hole injecting material, or electron injecting material as well as the aromatic amine derivative of the present invention can be used in the plurality of layers as required. Alternatively, the aromatic amine derivative of the present invention can be used as a doping material.

Reductions in the luminance and lifetime of the organic EL device due to quenching can be prevented by providing the organic thin-film layers with a multilayer structure. A light emitting material, a doping material, a hole injecting material, and an electron injecting material can be used in combination as required. In addition, the doping material enables the achievement of improvements in emission luminance and luminous efficiency, and of the emission of red or blue light.

In addition, each of the hole injecting layer, the light emitting layer, and the electron injecting layer may be formed of a layer construction having two or more layers. At that time, in the case of the hole injecting layer, a layer into which a hole is injected from an electrode is referred to as "hole injecting layer," and a layer that receives the hole from the hole injecting layer and transports the hole to the light emitting layer is referred to as "hole transporting layer." Similarly, in the case of the electron injecting layer, a layer into which an electron is injected from an electrode is referred to as "electron injecting layer," and a layer that receives the electron from the electron injecting layer and transports the electron to the light emitting layer is referred to as "electron transporting layer."

Each of those layers is selected and used in consideration of various factors such as the energy level of a material therefor, its heat resistance, and its adhesiveness with an organic layer or a metal electrode.

(Hole Injecting Layer and Hole Transporting Layer)

The hole injecting layer and the hole transporting layer are layers which help injection of holes into the light emitting layer and transports the holes to the light emitting region. The layers each exhibit a great mobility of holes and, in general, have an ionization energy as small as 5.7 eV or less. As such hole injecting layer and hole transporting layer, a material which transports holes to the light emitting layer under an electric field of a smaller strength is preferred. A material which exhibits, for example, a mobility of holes of $10^{-4}$ cm$^2$/V·sec or more under application of an electric field of $10^4$ to $10^6$ V/cm is preferred.

As described above, the aromatic amine derivative of the present invention is particularly preferably used in the hole transporting layer.

When the aromatic amine derivative of the present invention is used in the hole transporting layer, the aromatic amine derivative of the present invention may be used alone or as a mixture with any other material for forming the hole transporting layer.

The other material which can be used as a mixture with the aromatic amine derivative of the present invention for forming the hole transporting layer is not particularly limited as long as the material has the preferred property. The material can be arbitrarily selected from materials which are conventionally used as hole transporting materials in photoconductive materials and known materials which are used for hole transporting layers in organic EL devices. In the description, a material that has a hole transporting ability and can be used in a hole transporting zone is referred to as "hole transporting material."

Specific examples of the other material for a hole transporting layer than the aromatic amine derivative of the present invention include, but not particularly limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Of the hole injecting materials that can be used in the organic EL device of the present invention, more effective hole injecting materials are an aromatic tertiary amine derivative and a phthalocyanine derivative.

Examples of the aromatic tertiary amine derivative include, but not particularly limited to, triphenylamine, tritolylamine, tolyldiphenylamine, N,N'-diphenyl-N,N'-(3-methylphenyl)-1,1'-biphenylyl-4,4'-diamine, N,N,N',N'-(4-methylphenyl)-1,1'-phenyl-4,4'-diamine, N,N,N',N'-(4-methylphenyl)-1,1'-biphenylyl-4,4'-diamine, N,N'-diphenyl-N,N'-dinaphthyl-1,1'-biphenylyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, and an oligomer or a polymer having one of the aromatic tertiary amine skeletons.

Examples of the phthalocyanine (Pc) derivative include, but not limited to, phthalocyanine derivatives such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, and GaPc-O—GaPc, and naphthalocyanine derivatives. In addition, the organic EL device of the present invention preferably has formed therein a layer containing any such aromatic tertiary amine derivative and/or any such phthalocyanine derivative, for example, the hole transporting layer or the hole injecting layer between a light emitting layer and an anode.

A material for the hole injecting layer is not particularly limited as long as the material has the preferred properties. An arbitrary material selected from a material conventionally used as a hole injecting material in a photoconductive material and a known material used in the hole transporting layer of an organic EL device can be used. In the description, a material that has a hole injecting ability and can be used in a hole injection zone is referred to as "hole injecting material."

In particular, in the organic EL device of the present invention, a hexaazatriphenylene compound represented by the following formula (A) is preferably used as a hole injecting material.

[Chem. 90]

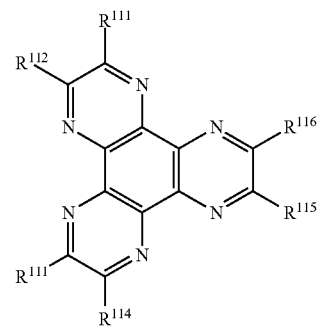

(A)

In the formula (A), R$^{111}$ to R$^{116}$ each independently represent a cyano group, —CONH$_2$, a carboxyl group, or —COOR$^{117}$ (where R$^{117}$ represents an alkyl group having 1 to 20 carbon atoms), or R$^{111}$ and R$^{112}$, R$^{113}$ and R$^{114}$, or R$^{115}$ and R$^{116}$ combine with each other to represent a group represented by —CO—O—CO—.

It should be noted that when R$^{111}$ to R$^{116}$ each represent a cyano group, —CONH$_2$, a carboxyl group, or —COOR$^{117}$, R$^{111}$ to R$^{116}$ preferably represent the same group. When R$^{111}$ and R$^{112}$, R$^{113}$ and R$^{114}$, or R$^{115}$ and R$^{116}$ combine with each other to represent a group represented by —CO—O—CO—, each of the pairs preferably represents a group represented by —CO—O—CO—.

(Electron Injecting Layer and Electron Transporting Layer)

Each of the electron injecting layer and the electron transporting layer is a layer which helps injection of electrons into the light emitting layer, transports the electrons to the light emitting region, and exhibits a great mobility of electrons. Further, the adhesion improving layer is an electron injecting layer including a material exhibiting particularly improved adhesion with the cathode.

In addition, it is known that, in an organic EL device, emitted light is reflected by an electrode (cathode in this case), and hence emitted light directly extracted from an anode and emitted light extracted via the reflection by the electrode interfere with each other. The thickness of an electron transporting layer is appropriately selected from the range of several nanometers to several micrometers in order that the interference effect may be effectively utilized. In particular, when the thickness of the electron transporting layer is large, an electron mobility is preferably at least $10^{-5}$ cm$^2$/V·s or more upon application of an electric field of $10^4$ to $10^6$ V/cm in order to avoid an increase in voltage.

Specific examples of the material to be used for the electron injecting layer include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the material is not particularly limited thereto. In addition, an electron-accepting substance can be added to the hole injecting material or an electron-donating substance can be added to the electron injecting material to thereby sensitize the hole injecting material or the electron injecting material, respectively.

In the organic EL device of the present invention, more effective electron injecting materials are a metal complex compound and a nitrogen-containing five-membered ring derivative.

Examples of the metal complex compound include, but not particularly limited to, 8-hydroxyquinolinatolithium, tris(8-hydroxyquinolinato)aluminum, bis(2-methyl-8-quinolinato)(1-naphtholato)aluminum.

Examples of the nitrogen-containing five-membered ring derivative preferably include, an oxazole derivative, a thiazole derivative, an oxadiazole derivative, a thiadiazole derivative, and a triazole derivative.

In the organic EL device of the present invention, the nitrogen-containing five-membered ring derivative is particularly preferably a benzimidazole derivative represented by any one of the following formulae (1) to (3).

[Chem. 91]

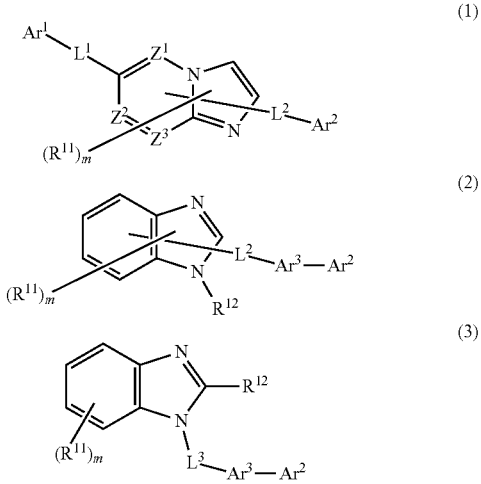

In the formulae (1) to (3), $Z^1$, $Z^2$, and $Z^3$ each independently represent a nitrogen atom or a carbon atom.

$R^{11}$ and $R^{12}$ each independently represent a substituted or unsubstituted aryl group having 6 to 60 carbon atoms, a substituted or unsubstituted heteroaryl group having 3 to 60 carbon atoms, an alkyl group having 1 to 20 carbon atoms, an alkyl group having 1 to 20 carbon atoms and substituted with a halogen atom, or an alkoxy group having 1 to 20 carbon atoms.

m represents an integer of 0 to 5, and when m represents an integer of 2 or more, a plurality of $R^{11}$'s may be identical to or different from each other. In addition, a plurality of $R^{11}$'s adjacent to each other may be bonded to each other to form a substituted or unsubstituted aromatic hydrocarbon ring. Examples of the substituted or unsubstituted aromatic hydrocarbon ring which the plurality of $R^{11}$'s adjacent to each other are bonded to each other to represent when m represents an integer of 2 or more include a benzene ring, a naphthalene ring, and an anthracene ring.

$Ar^1$ represents a substituted or unsubstituted aryl group having 6 to 60 carbon atoms, or a substituted or unsubstituted heteroaryl group having 3 to 60 carbon atoms.

$Ar^2$ represents a hydrogen atom, an alkyl group having 1 to 20 carbon atoms, an alkyl group having 1 to 20 carbon atoms and substituted with a halogen atom, an alkoxy group having 1 to 20 carbon atoms, a substituted or unsubstituted aryl group having 6 to 60 carbon atoms, or a substituted or unsubstituted heteroaryl group having 3 to 60 carbon atoms.

$Ar^3$ represents a substituted or unsubstituted arylene group having 6 to 60 carbon atoms, or a substituted or unsubstituted heteroarylene group having 3 to 60 carbon atoms.

$L^1$, $L^2$, and $L^3$ each independently represent a single bond, a substituted or unsubstituted arylene group having 6 to 60 carbon atoms, a substituted or unsubstituted heterofused ring group having 9 to 60 ring atoms, or a substituted or unsubstituted fluorenylene group.

In the organic EL device of the present invention, a light emitting material, a doping material, a hole injecting material, or an electron injecting material may be incorporated into the layer containing the aromatic amine derivative of the present invention.

In addition, the surface of the organic EL device obtained by the present invention can be provided with a protective layer, or the entirety of the device can be protected with silicone oil, a resin, or the like from the viewpoint of an improvement in the stability of the device against a temperature, a humidity, an atmosphere, or the like.

Any one of dry film forming methods such as vacuum deposition, sputtering, plasma, and ion plating, and wet film forming methods such as spin coating, dipping, and flow coating is applicable to the formation of each layer of the organic EL device of the present invention.

The thickness of each layer is not particularly limited, but may be set to an appropriate thickness as an organic EL device. An excessively large thickness requires an increased applied voltage for obtaining certain optical output, resulting in poor efficiency. An excessively small thickness causes a pin hole or the like, with the result that sufficient emission luminance cannot be obtained even when an electric field is applied. In general, the thickness is in the range of preferably 5 nm to 10 μm, or more preferably 10 nm to 0.2 μm.

In the case of a wet film forming method, a material of which each layer is formed is dissolved or dispersed into an appropriate solvent such as ethanol, chloroform, tetrahydrofuran, or dioxane, to thereby form a thin film. At that time, any one of the above solvents may be used.

An organic EL material-containing solution containing the aromatic amine derivative of the present invention as an organic EL material and a solvent can be used as a solution suitable for such wet film forming method. In addition, an appropriate resin or additive may be used in each of the organic thin-film layers for, for example, improving film formability or preventing a pin hole in the layer. Examples of the resin include: insulating resins such as polystyrene, polycarbonate, polyallylate, polyester, polyamide, polyurethane, polysulfone, polymethyl methacrylate, polymethyl acrylate, and cellulose, and copolymers thereof; photoconductive resins such as poly-N-vinylcarbazole and polysilane; and conductive resins such as polythiophene and polypyrrole. Examples of the additive include an antioxidant, a UV absorber, and a plasticizer.

EXAMPLES
Hereinafter, the present invention is specifically described by way of examples. However, the present invention is by no means limited by these examples.
It should be noted that the structures of intermediates synthesized in Synthesis Examples 1 to 23 below are as shown below.
[Chem. 92]
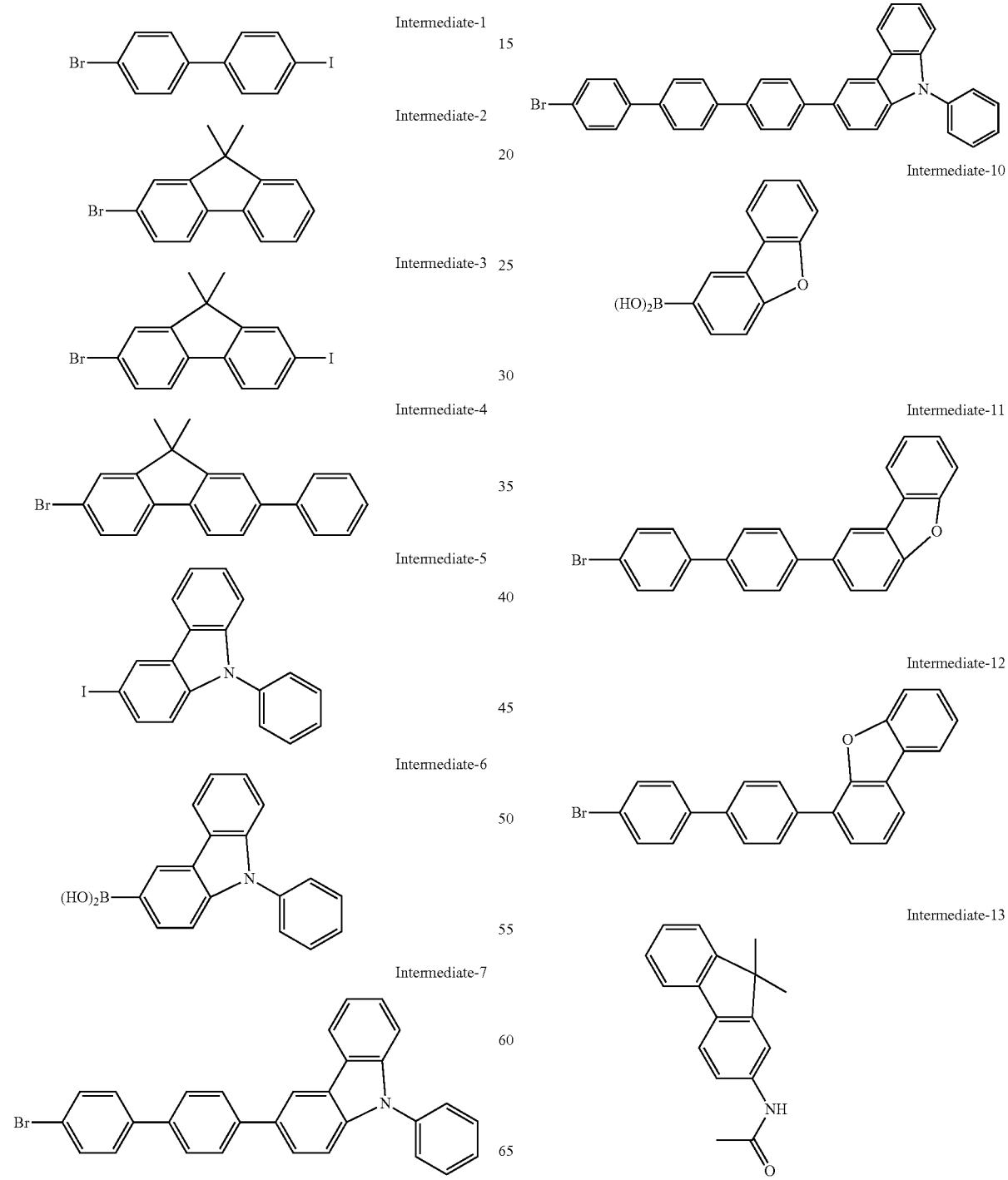

Intermediate-14
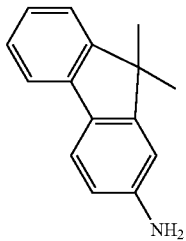
Intermediate-15
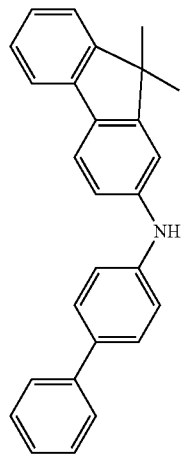
Intermediate-16
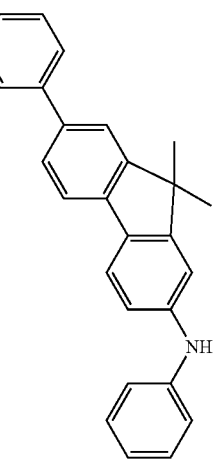
Intermediate-17
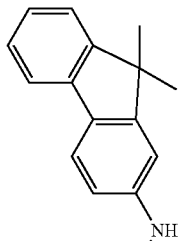
Intermediate-18
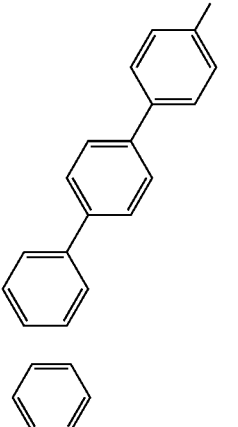
Intermediate-19
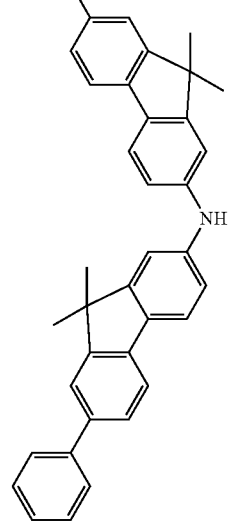
Intermediate-20
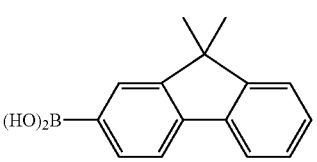
Intermediate-21
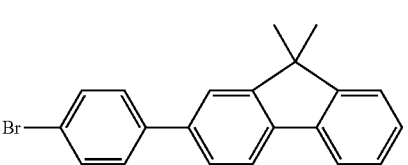

Intermediate-22

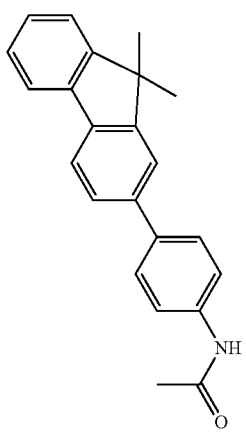

Intermediate-23

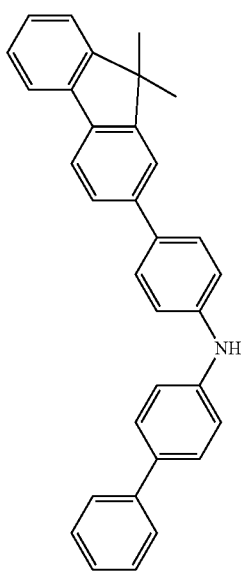

Synthesis Example 1 (Synthesis of Intermediate-1)

In a stream of argon, 47 g of 4-bromobiphenyl, 23 g of iodine, 9.4 g of periodic acid dihydrate, 42 ml of water, 360 ml of acetic acid, and 11 ml of sulfuric acid were loaded into a 1,000-ml three-necked flask, and the mixture was stirred at 65° C. for 30 minutes and was then subjected to a reaction at 90° C. for 6 hours. The reactant was poured into ice water, followed by filtering. The resultant was washed with water, and then washed with methanol, whereby 67 g of a white powder were obtained.

Main peaks having ratios m/z of 358 and 360 were obtained with respect to $C_{12}H_8BrI=359$ by a field desorption mass spectrometry (hereinafter, referred to as FD-MS) analysis, so the powder was identified as the intermediate-1.

Synthesis Example 2 (Synthesis of Intermediate-2)

Under an argon atmosphere, 12.5 g of 2-bromofluorene, 0.7 g of benzyltriethylammonium chloride, 60 ml of dimethyl sulfoxide, 8.0 g of sodium hydroxide, and 17 g of methyl iodide were loaded into a 200-ml three-necked flask, and then the mixture was subjected to a reaction for 18 hours.

After the completion of the reaction, water and ethyl acetate were added to perform separation and extraction. After that, the resultant was concentrated, and then the resultant coarse product was purified by silica gel chromatography (hexane). Thus, 12.4 g of a yellow oily substance were obtained. The substance was identified as the intermediate-2 by FD-MS analysis.

Synthesis Example 3 (Synthesis of Intermediate-3)

A reaction was performed in the same manner as in Synthesis Example 1 except that 2-bromo-9,9-dimethylfluorene was used instead of 4-bromobiphenyl. As a result, 61 g of a white powder were obtained. The powder was identified as the intermediate-3 by FD-MS analysis.

Synthesis Example 4 (Synthesis of Intermediate-4)

Under an argon atmosphere, 39.9 g of the intermediate-3, 12.8 g of phenylboronic acid, 2.31 g of tetrakis(triphenylphosphine)palladium, 300 ml of toluene, and 150 ml of an aqueous solution of sodium carbonate having a concentration of 2 M were loaded into a 1,000-ml three-necked flask, and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 27.3 g of a white crystal were obtained. The crystal was identified as the intermediate-4 by FD-MS analysis.

Synthesis Example 5 (Synthesis of Intermediate-5)

17.7 Grams of 9-phenylcarbazole, 6.03 g of potassium iodide, 7.78 g of potassium iodate, 5.9 ml of sulfuric acid, and ethanol were loaded into a 200-ml three-necked flask, and then the mixture was subjected to a reaction at 75° C. for 2 hours.

After the resultant had been cooled, water and ethyl acetate were added to perform separation and extraction. After that, the organic layer was washed with baking soda water and water, and was then concentrated. The resultant coarse product was purified by silica gel chromatography (toluene), and then the resultant solid was dried under reduced pressure. Thus, 21.8 g of a white solid were obtained. The solid was identified as the intermediate-5 by FD-MS analysis.

Synthesis Example 6 (Synthesis of Intermediate-6)

In a stream of argon, 13.1 g of the intermediate-5, dehydrated toluene, and dehydrated ether were loaded into a 300-ml three-necked flask, and then the mixture was cooled to −45° C. 25 Milliliters of a solution (1.58 M) of n-butyllithium in hexane were dropped to the mixture, and then the temperature was increased to −5° C. over 1 hour while the mixture was stirred. The mixture was cooled to −45° C. again, and then 25 ml of boronic acid triisopropyl ester were slowly dropped to the mixture. After that, the mixture was subjected to a reaction for 2 hours.

After the temperature of the resultant had been returned to room temperature, a 10% diluted hydrochloric acid solution was added to the resultant, and then the mixture was stirred so that an organic layer was extracted. After having been washed with a saturated salt solution, the organic layer was dried with anhydrous magnesium sulfate and separated by filtration. After that, the separated product was concentrated. The resultant solid was purified by silica gel chromatography (toluene), and then the resultant solid was washed with n-hexane and dried under reduced pressure. Thus, 7.10 g of a solid were obtained. The solid was identified as the intermediate-6 by FD-MS analysis.

Synthesis Example 7 (Synthesis of Intermediate-7)

Under an argon atmosphere, 35.9 g of the intermediate-1, 30.1 g of the intermediate-6, 2.31 g of tetrakis(triphenylphosphine)palladium, 300 ml of toluene, and 150 ml of an aqueous solution of sodium carbonate having a concentration of 2 M were loaded into a 1,000-ml three-necked flask, and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 24.2 g of a white crystal were obtained. The crystal was identified as the intermediate-7 by FD-MS analysis.

Synthesis Example 8 (Synthesis of Intermediate-8)

A reaction was performed in the same manner as in Synthesis Example 6 except that 16.8 g of the intermediate-7 were used instead of the intermediate-5. Thus, 10.1 g of a white powder were obtained. The powder was identified as the intermediate-8 by FD-MS analysis.

Synthesis Example 9 (Synthesis of Intermediate-9)

A reaction was performed in the same manner as in Synthesis Example 7 except that: 28.3 g of 4-iodobromobenzene were used instead of the intermediate-1; and 46.1 g of the intermediate-8 were used instead of the intermediate-6. Thus, 33 g of a white powder were obtained. The powder was identified as the intermediate-9 by FD-MS analysis.

Synthesis Example 10 (Synthesis of Intermediate-10)

Under a nitrogen atmosphere, 150 g of dibenzofuran and 1 l of acetic acid were loaded into a 300-ml three-necked flask, and then the contents were dissolved under heat. 188 Grams of bromine were added dropwise to the solution. After that, the mixture was stirred for 20 hours under air cooling. The precipitated crystal was separated by filtration, and was then sequentially washed with acetic acid and water. The washed crystal was dried under reduced pressure. The resultant crystal was purified by distillation under reduced pressure, and was then repeatedly recrystallized with methanol several times. Thus, 66.8 g of 2-bromodibenzofuran were obtained.

Under an argon atmosphere, 24.7 g of 2-bromodibenzofuran and 400 ml of anhydrous THF were loaded into a 1,000-ml three-necked flask, and then 63 ml of a solution of n-butyllithium in hexane having a concentration of 1.6 M were added to the mixture during the stirring of the mixture at −40° C. The reaction solution was stirred for 1 hour while being heated to 0° C. The reaction solution was cooled to −78° C. again, and then a solution of 26.0 g of trimethyl borate in 50 ml of dry THF was dropped to the solution. The reaction solution was stirred at room temperature for 5 hours.

200 Milliliters of 1N hydrochloric acid were added to the solution, and then the mixture was stirred for 1 hour. After that, the aqueous layer was removed. The organic layer was dried with magnesium sulfate, and then the solvent was removed by distillation under reduced pressure. The resultant solid was washed with toluene. Thus, 15.2 g of dibenzofuran-2-boronic acid were obtained.

Synthesis Example 11 (Synthesis of Intermediate-1)

A reaction was performed in the same manner as in Synthesis Example 7 except that 22.3 g of the intermediate-10 were used instead of the intermediate-6. Thus, 28.7 g of a white powder were obtained. The powder was identified as the intermediate-11 by FD-MS analysis.

Synthesis Example 12 (Synthesis of Intermediate-12)

A reaction was performed in the same manner as in Synthesis Example 7 except that 22.3 g of dibenzofuran-4-boronic acid were used instead of the intermediate-6. Thus, 31.9 g of a white powder were obtained. The powder was identified as the intermediate-12 by FD-MS analysis.

Synthesis Example 13 (Synthesis of Intermediate-13)

Under an argon atmosphere, 7.0 g of acetamide, 45.8 g of the intermediate-2, 6.8 g of copper(I) iodide, 6.3 g of N,N'-dimethylethylenediamine, 51 g of tripotassium phosphate, and 300 ml of xylene were loaded into a 500-ml three-necked flask, and then the mixture was subjected to a reaction at 140° C. for 36 hours. After having been cooled, the resultant was filtrated and washed with toluene. The washed product was further washed with water and methanol, and was then dried. Thus, 19 g of a pale yellow powder were obtained. The powder was identified as the intermediate-13 by FD-MS analysis.

Synthesis Example 14 (Synthesis of Intermediate-14)

31.0 Grams of the intermediate-13, 26 g of potassium hydroxide, 28 ml of ion-exchanged water, 39 ml of xylene, and 77 ml of ethanol were loaded into a 300-ml three-necked flask, and then the mixture was heated for 36 hours while being refluxed. After the completion of the reaction, the resultant was extracted with toluene and dried with magnesium sulfate. The dried product was concentrated under reduced pressure, and then the resultant coarse product was subjected to column purification. The purified product was recrystallized with toluene, and then the recrystallized product was taken by filtration. After that, the resultant was dried. Thus, 15.8 g of a white powder were obtained. The powder was identified as the intermediate-14 by FD-MS analysis.

Synthesis Example 15 (Synthesis of Intermediate-15)

A reaction was performed in the same manner as in Synthesis Examples 13 and 14 except that 15 g of the intermediate-13 were used instead of acetamide and 19.6 g of 4-bromobiphenyl were used instead of the intermediate-2 upon performance of Synthesis Examples 13 and 14 in the stated order. Thus, 13 g of a pale yellow powder were obtained. The powder was identified as the intermediate-15 by FD-MS analysis.

Synthesis Example 16 (Synthesis of Intermediate-16)

A reaction was performed in the same manner as in Synthesis Examples 13 and 14 except that 8.1 g of acetanilide were used instead of acetamide and 29.3 g of the intermediate-4 were used instead of the intermediate-2 upon performance of Synthesis Examples 13 and 14 in the stated order. Thus, 14 g of a pale yellow powder were obtained. The powder was identified as the intermediate-16 by FD-MS analysis.

Synthesis Example 17 (Synthesis of Intermediate-17)

A reaction was performed in the same manner as in Synthesis Examples 13 and 14 except that 15 g of the intermediate-13 were used instead of the acetamide upon performance of Synthesis Examples 13 and 14 in the stated order. Thus, 14.4 g of a pale yellow powder were obtained. The powder was identified as the intermediate-17 by FD-MS analysis.

Synthesis Example 18 ( Synthesis of Intermediate-18)

A reaction was performed in the same manner as in Synthesis Examples 13 and 14 except that 15 g of the intermediate-13 were used instead of acetamide and 26 g of 4-bromo-p-terphenyl were used instead of the intermediate-2 upon performance of Synthesis Examples 13 and 14 in the stated order. Thus, 15.5 g of a pale yellow powder were obtained. The powder was identified as the intermediate-18 by FD-MS analysis.

Synthesis Example 19 (Synthesis of Intermediate-19)

A reaction was performed in the same manner as in Synthesis Examples 13 and 14 except that 32 g of the intermediate-4 were used instead of the intermediate-2 upon performance of Synthesis Examples 13 and 14 in the stated order. Thus, 11 g of a pale yellow powder were obtained. The powder was identified as the intermediate-19 by FD-MS analysis.

Synthesis Example 20 (Synthesis of Intermediate-20)

A reaction was performed in the same manner as in Synthesis Example 6 except that 33 g of the intermediate-2 were used instead of the intermediate-5. Thus, 17 g of a white powder were obtained. The powder was identified as the intermediate-20 by FD-MS analysis.

Synthesis Example 21 (Synthesis of Intermediate-21)

A reaction was performed in the same manner as in Synthesis Example 9 except that 17 g of the intermediate-20 were used instead of the intermediate-8. Thus, 20 g of a white powder were obtained. The powder was identified as the intermediate-21 by ED-MS analysis.

Synthesis Example 22 (Synthesis of Intermediate-22)

A reaction was performed in the same manner as in Synthesis Example 13 except that 20 g of the intermediate-21 were used instead of the intermediate-2. Thus, 12 g of a pale yellow powder were obtained. The powder was identified as the intermediate-22 by FD-MS analysis.

Synthesis Example 23 (Synthesis of Intermediate-23)

A reaction was performed in the same manner as in Synthesis Examples 13 and 14 except that 12 g of the intermediate-22 were used instead of acetamide and 12.8 g of 4-bromobiphenyl were used instead of the intermediate-2 upon performance of Synthesis Examples 13 and 14 in the stated order. Thus, 10.4 g of a pale yellow powder were obtained. The powder was identified as the intermediate-23 by FD-MS analysis.

Shown below are the structures of the aromatic amine derivatives of the present invention produced in Examples-of-Synthesis 1 to 18 below.

[Chem. 93]

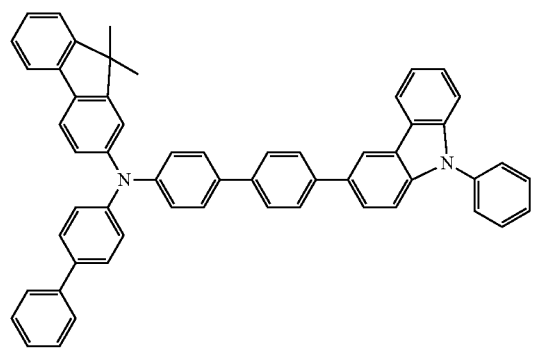

H-1

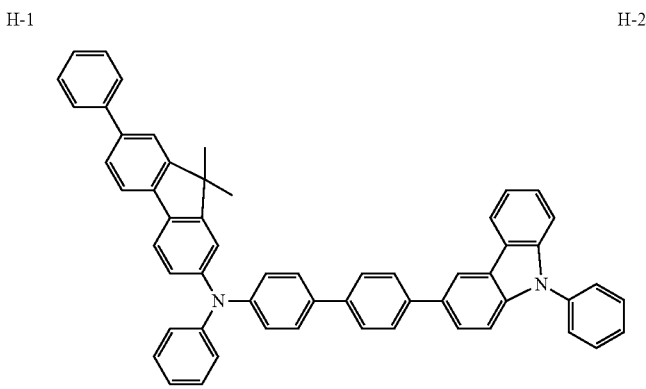

H-2

H-3
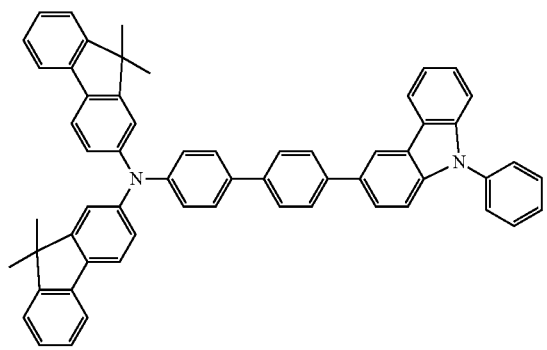
H-4
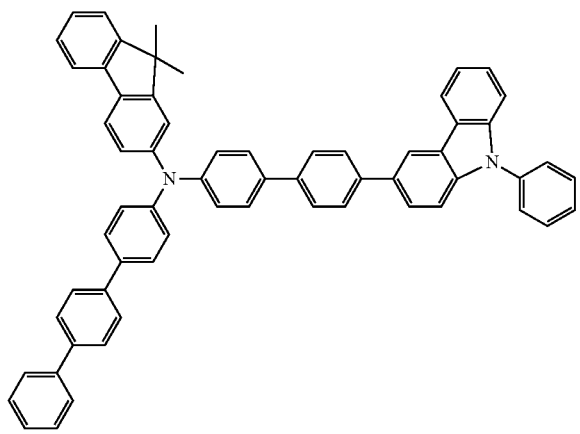
H-5
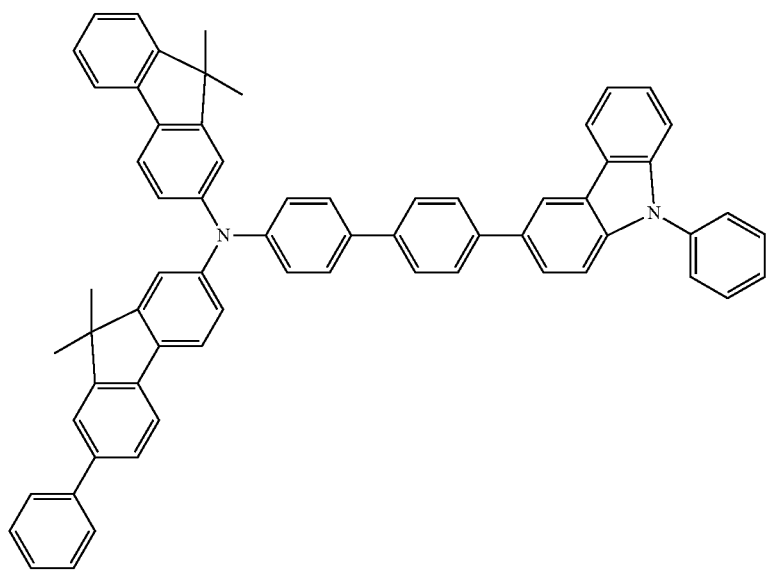
H-6
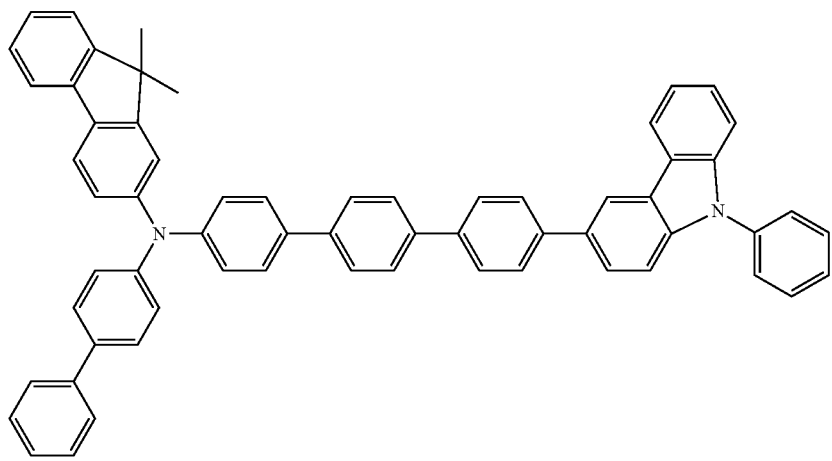

-continued
H-7
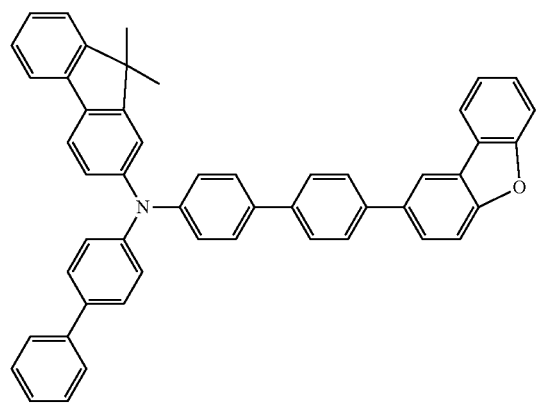
H-8
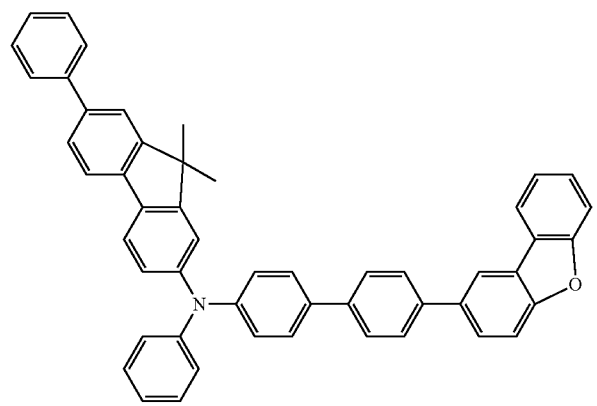
H-9
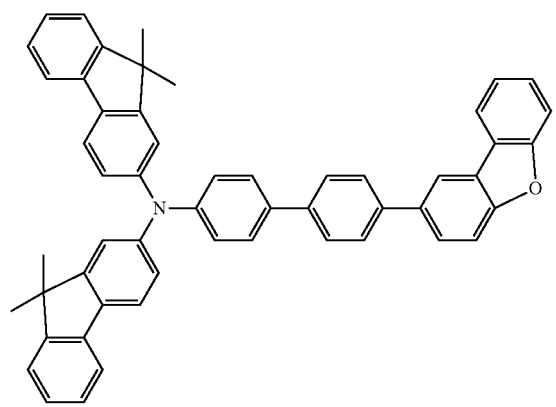
H-10
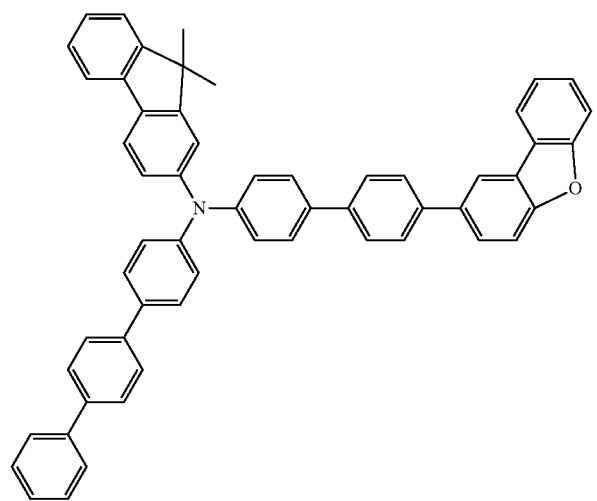
H-11
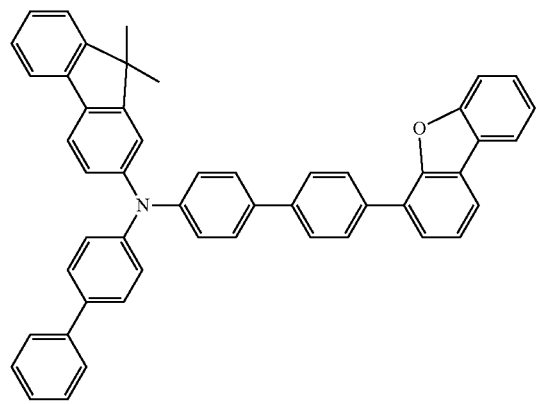
H-12
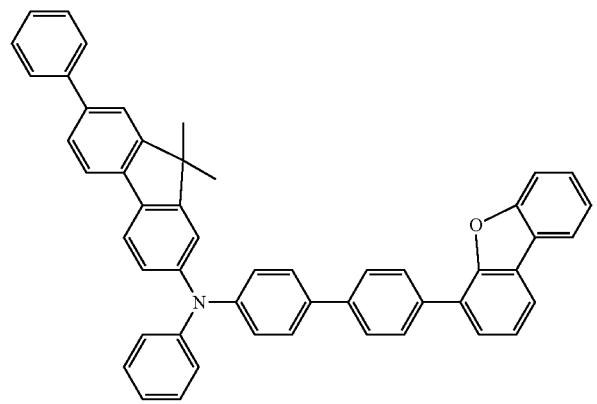

H-13
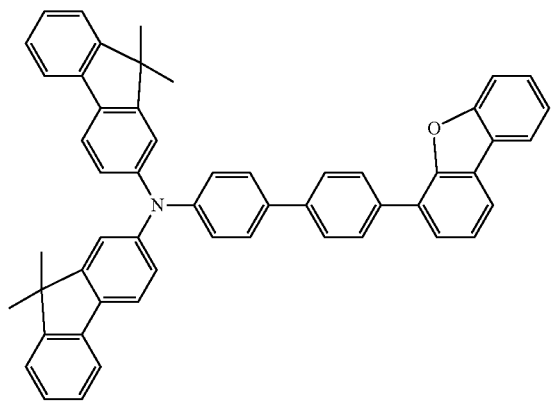
H-14
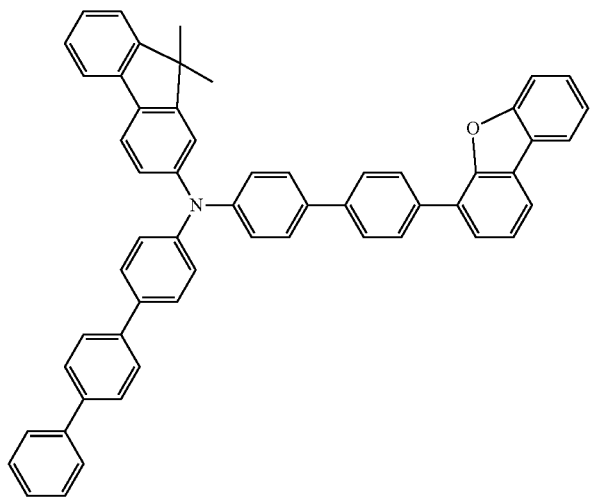
H-15
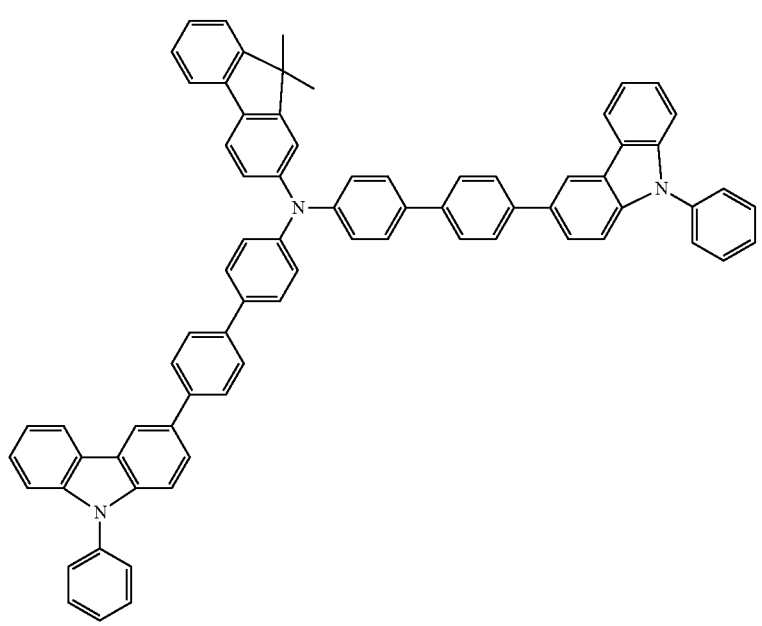

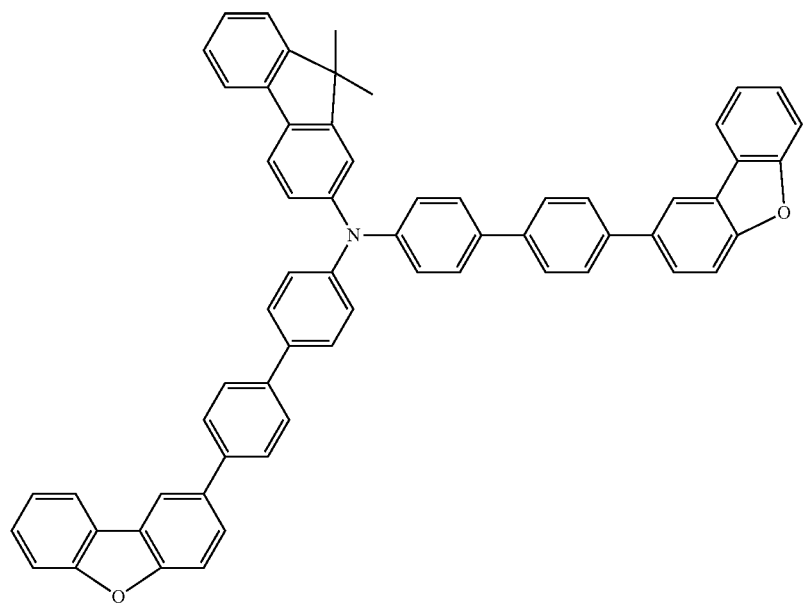
H-16
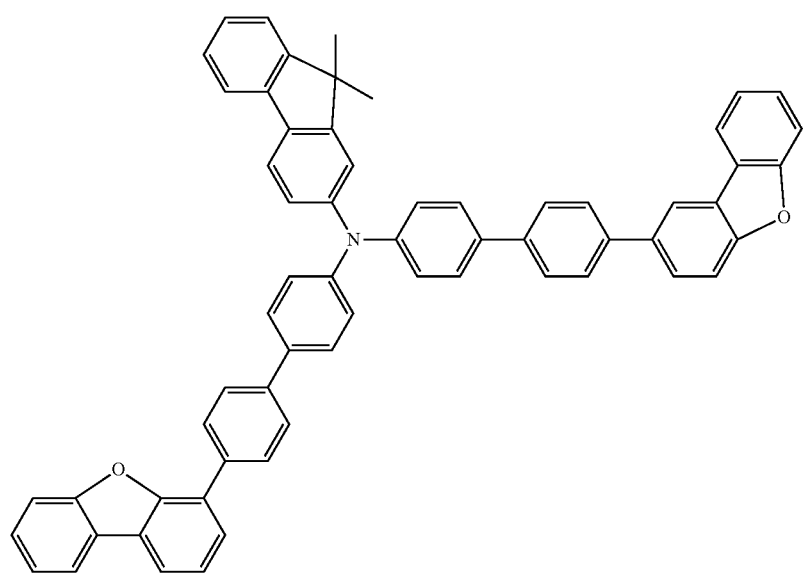
H-17

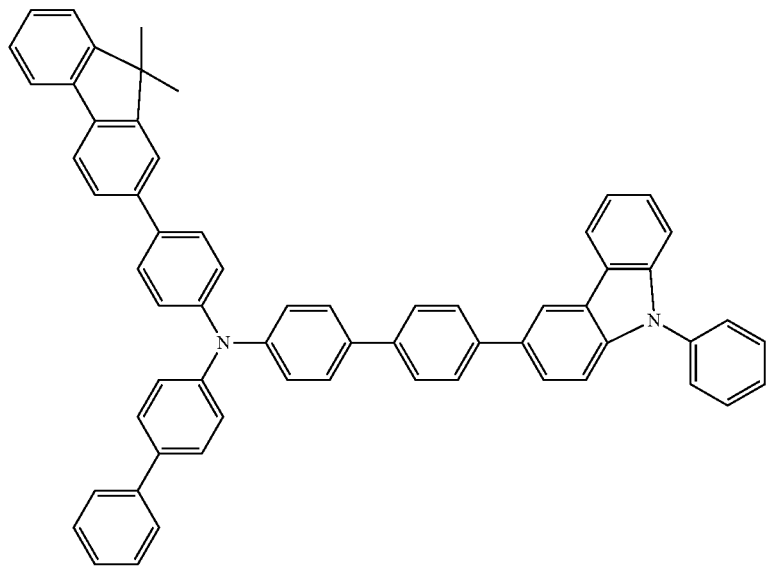

H-18

In addition, a method of measuring the hole mobility of each of the aromatic amine derivatives (H-1) to (H-18) of the present invention produced in the examples-of-synthesis below is described below.
(Measurement of Hole Mobility)

The hole mobility was measured by a time-of-flight method (TOF) Each of the aromatic amine derivatives (H-1) to (H-18) produced in Examples-of-Synthesis 1 to 18 below was formed into a film having a thickness of 2.5 to 3.0 μm on an ITO substrate, and Al was further provided as a counter electrode.

A voltage was applied between both the electrodes at an electric field intensity of 0.1 to 0.6 MV/cm, $N_2$ laser light (pulse width: 2 ns) was applied, and a generated current was measured with a storage oscilloscope (measuring frequency band: 300 MHz). The hole mobility was determined in accordance with an ordinary analysis method from a time τ at which the shoulder of a photocurrent appeared (time at which the photocurrent attenuated) with an equation "$\mu=d/(\tau \cdot E)$ (μ: the hole mobility, E: the electric field intensity, d: the thickness)."

Example-of-Synthesis 1 (Production of aromatic amine Derivative (H-1)

In a stream of argon, 9.5 g of the intermediate-7, 7.2 g of the intermediate-15, 2.6 g of t-butoxysodium, 92 mg of tris (dibenzylideneacetone)dipalladium, 42 mg of tri-t-butylphosphine, and 100 ml of dehydrated toluene were loaded into a 300-ml three-necked flask, and then the mixture was subjected to a reaction at 80° C. for 8 hours.

After having been cooled, the reaction product was poured into 500 ml of water, and then the mixture was subjected to celite filtration. The filtrate was extracted with toluene and dried with anhydrous magnesium sulfate. The dried product was concentrated under reduced pressure, and then the resultant coarse product was subjected to column purification. The purified product was recrystallized with toluene, and then the recrystallized product was taken by filtration. After that, the resultant was dried. Thus, 8.1 g of a pale yellow powder were obtained. The powder was identified as the aromatic amine derivative (H-1) by FD-MS analysis.

The hole mobility of the aromatic amine derivative (H-1) was measured by the method. Table 1 shows the result.

Example-of-Synthesis 2 (Production of Aromatic Amine Derivative (H-2)

A reaction was performed in the same manner as in Example-of-Synthesis 1 except that 7.2 g of the intermediate-16 were used instead of the intermediate-15. Thus, 7.8 g of a pale yellow powder were obtained. The powder was identified as the aromatic amine derivative (H-2) by FD-MS analysis.

The hole mobility of the aromatic amine derivative (H-2) was measured by the method. Table 1 shows the result.

Example-of-Synthesis 3 (Production of Aromatic Amine Derivative (H-3)

A reaction was performed in the same manner as in Example-of-Synthesis 1 except that 8.0 g of the intermediate-17 were used instead of the intermediate-15. Thus, 8.0 g of a pale yellow powder were obtained. The powder was identified as the aromatic amine derivative (H-3) by FD-MS analysis.

The hole mobility of the aromatic amine derivative (H-3) was measured by the method. Table 1 shows the result.

Example-of-Synthesis 4 (Production of Aromatic Amine Derivative (H-4)

A reaction was performed in the same manner as in Example-of-Synthesis 1 except that 8.8 g of the intermediate-18 were used instead of the intermediate-15. Thus, 6.8 g of a pale yellow powder were obtained. The powder was identified as the aromatic amine derivative (H-4) by FD-MS analysis.

The hole mobility of the aromatic amine derivative (H-4) was measured by the method. Table 1 shows the result.

Example-of-Synthesis 5 (Production of Aromatic Amine Derivative (H-5)

A reaction was performed in the same manner as in Example-of-Synthesis 1 except that 11.1 g of the intermediate-19 were used instead of the intermediate-15. Thus, 8.5 g of a pale yellow powder were obtained. The powder was identified as the aromatic amine derivative (H-5) by FD-MS analysis.

The hole mobility of the aromatic amine derivative (H-5) was measured by the method. Table 1 shows the result.

Example-of-Synthesis 6 (Production of Aromatic Amine Derivative (H-6)

A reaction was performed in the same manner as in Example-of-Synthesis 1 except that 11.0 g of the intermediate-9 were used instead of the intermediate-7. Thus, 8.3 g of a pale yellow powder were obtained. The powder was identified as the aromatic amine derivative (H-6) by FD-MS analysis.

The hole mobility of the aromatic amine derivative (H-6) was measured by the method. Table 1 shows the result.

Example-of-Synthesis 7 (Production of Aromatic Amine Derivative (H-7)

A reaction was performed in the same manner as in Example-of-Synthesis 1 except that 8.0 g of the intermediate-11 were used instead of the intermediate-7. Thus, 7.2 g of a pale yellow powder were obtained. The powder was identified as the aromatic amine derivative (H-7) by FD-MS analysis.

The hole mobility of the aromatic amine derivative (H-7) was measured by the method. Table 1 shows the result.

Example-of-Synthesis 8 (Production of Aromatic Amine Derivative (H-8)

A reaction was performed in the same manner as in Example-of-Synthesis 1 except that: 8.0 g of the intermediate-11 were used instead of the intermediate-7; and 7.2 g of the intermediate-16 were used instead of the intermediate-15. Thus, 7.2 g of a pale yellow powder were obtained. The powder was identified as the aromatic amine derivative (H-8) by FD-MS analysis.

The hole mobility of the aromatic amine derivative (H-8) was measured by the method. Table 1 shows the result.

Example-of-Synthesis 9 (Production of Aromatic Amine Derivative (H-9)

A reaction was performed in the same manner as in Example-of-Synthesis 1 except that: 8.0 g of the intermediate-11 were used instead of the intermediate-7; and 8.0 g of the intermediate-17 were used instead of the intermediate-15. Thus, 7.5 g of a pale yellow powder were obtained. The powder was identified as the aromatic amine derivative (H-9) by FD-MS analysis.

The hole mobility of the aromatic amine derivative (H-9) was measured by the method. Table 1 shows the result.

Example-of-Synthesis 10 (Production of Aromatic Amine Derivative (H-10)

A reaction was performed in the same manner as in Example-of-Synthesis 1 except that: 8.0 g of the intermediate-11 were used instead of the intermediate-7; and 8.8 g of the intermediate-18 were used instead of the intermediate-15. Thus, 6.3 g of a pale yellow powder were obtained. The powder was identified as the aromatic amine derivative (H-10) by FD-MS analysis.

The hole mobility of the aromatic amine derivative (H-10) was measured by the method. Table 1 shows the result.

Example-of-Synthesis 11 (Production of Aromatic Amine Derivative (H-11)

A reaction was performed in the same manner as in Example-of-Synthesis 1 except that 8.0 g of the intermediate-12 were used instead of the intermediate-7. Thus, 7.1 g of a pale yellow powder were obtained. The powder was identified as the aromatic amine derivative (H-11) by FD-MS analysis.

The hole mobility of the aromatic amine derivative (H-11) was measured by the method. Table 1 shows the result.

Example-of-Synthesis 12 (Production of Aromatic Amine Derivative (H-12)

A reaction was performed in the same manner as in Example-of-Synthesis 1 except that: 8.0 g of the intermediate-12 were used instead of the intermediate-7; and 7.2 g of the intermediate-16 were used instead of the intermediate-15. Thus, 7.1 g of a pale yellow powder were obtained. The powder was identified as the aromatic amine derivative (H-12) by FD-MS analysis.

The hole mobility of the aromatic amine derivative (H-12) was measured by the method. Table 1 shows the result.

Example-of-Synthesis 13 (Production of Aromatic Amine Derivative (H-13)

A reaction was performed in the same manner as in Example-of-Synthesis 1 except that: 8.0 g of the intermediate-12 were used instead of the intermediate-7; and 8.0 g of the intermediate-17 were used instead of the intermediate-15. Thus, 7.3 g of a pale yellow powder were obtained. The powder was identified as the aromatic amine derivative (H-13) by FD-MS analysis.

The hole mobility of the aromatic amine derivative (H-13) was measured by the method. Table 1 shows the result.

Example-of-Synthesis 14 (Production of Aromatic Amine Derivative (H-14)

A reaction was performed in the same manner as in Example-of-Synthesis 1 except that: 8.0 g of the intermediate-12 were used instead of the intermediate-7; and 8.8 g of the intermediate-18 were used instead of the intermediate-15. Thus, 6.1 g of a pale yellow powder were obtained. The powder was identified as the aromatic amine derivative (H-14) by FD-MS analysis.

The hole mobility of the aromatic amine derivative (H-14) was measured by the method. Table 1 shows the result.

Example-of-Synthesis 15 (Production of Aromatic Amine Derivative (H-15)

A reaction was performed in the same manner as in Example-of-Synthesis 1 except that 2.1 g of the intermediate-14 were used instead of the intermediate-15. Thus, 6.1 g of a pale yellow powder were obtained. The powder was identified as the aromatic amine derivative (H-15) by FD-MS analysis.

The hole mobility of the aromatic amine derivative (H-15) was measured by the method. Table 1 shows the result.

Example-of-Synthesis 16 (Production of Aromatic Amine Derivative (H-16)

A reaction was performed in the same manner as in Example-of-Synthesis 1 except that: 2.1 g of the intermediate-14 were used instead of the intermediate-15; and 8.0 g of the intermediate-11 were used instead of the intermediate-7. Thus, 7.0 g of a pale yellow powder were obtained. The powder was identified as the aromatic amine derivative (H-16) by FD-MS analysis.

The hole mobility of the aromatic amine derivative (H-16) was measured by the method. Table 1 shows the result.

Example-of-Synthesis 17 (Production of Aromatic Amine Derivative (H-17)

A reaction was performed in the same manner as in Example-of-Synthesis 1 except that: 2.1 g of the intermediate-14 were used instead of the intermediate-15; and 8.0 g of the intermediate-12 were used instead of the intermediate-7. Thus, 7.2 g of a pale yellow powder were obtained. The powder was identified as the aromatic amine derivative (H-17) by FD-MS analysis.

The hole mobility of the aromatic amine derivative (H-17) was measured by the method. Table 1 shows the result.

Example-of-Synthesis 18 (Production of Aromatic Amine Derivative (H-18)

A reaction was performed in the same manner as in Example-of-Synthesis 1 except that 8.8 g of the intermediate-23 were used instead of the intermediate-15. Thus, 7.5 g of a pale yellow powder were obtained. The powder was identified as the aromatic amine derivative (H-18) by FD-MS analysis.

The hole mobility of the aromatic amine derivative (H-18) was measured by the method. Table 1 shows the result.

TABLE 1

| Example-of-Synthesis | Hole transporting material | Hole mobility ($\times 10^{-4}$ cm$^2$/V·s) |
|---|---|---|
| 1 | H-1 | 6.5 |
| 2 | H-2 | 5.5 |
| 3 | H-3 | 5.6 |
| 4 | H-4 | 5.5 |
| 5 | H-5 | 5.6 |
| 6 | H-6 | 6.4 |
| 7 | H-7 | 7.6 |
| 8 | H-8 | 6.5 |
| 9 | H-9 | 7.2 |
| 10 | H-10 | 6.6 |
| 11 | H-11 | 7.5 |
| 12 | H-12 | 6.7 |
| 13 | H-13 | 7.0 |
| 14 | H-14 | 6.2 |
| 15 | H-15 | 6.7 |
| 16 | H-16 | 7.5 |
| 17 | H-17 | 7.2 |
| 18 | H-18 | 5.1 |

It was shown that the group of compounds of the present invention had sufficient hole mobilities in the measurement by the time-of-flight method (TOF) and were useful as hole transporting materials.

In addition, an organic EL device using, as a hole transporting material, an aromatic amine derivative produced by using any one of the following intermediates was produced, and the current efficiency and luminescent color of the organic EL device, and the half lifetime of its light emission when the device was driven with a DC constant current at an initial luminance of 5,000 cd/m$^2$ and room temperature were measured.

[Chem. 94]

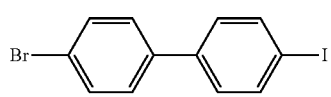

Intermediate-1'

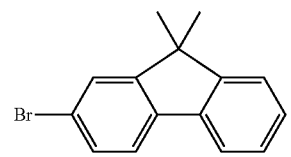

Intermediate-2'

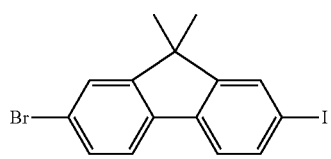

Intermediate-3'

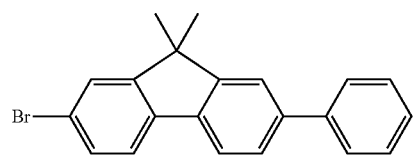

Intermediate-4'

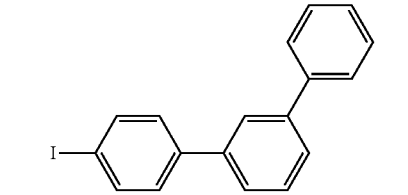

Intermediate-5'

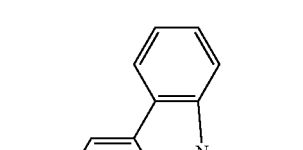

Intermediate-6'

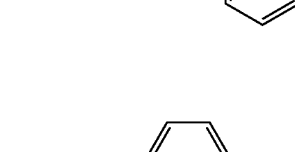

Intermediate-7'

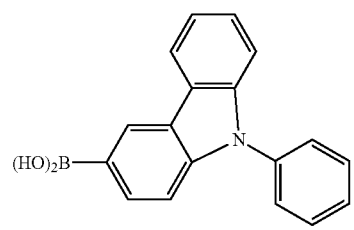

Intermediate-8'
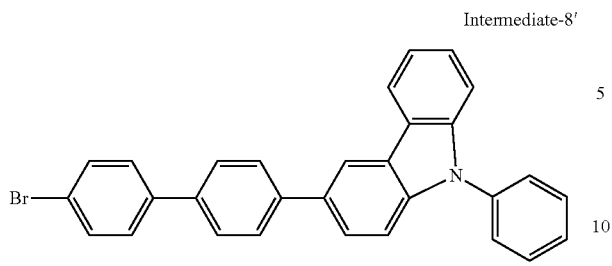
Intermediate-9'
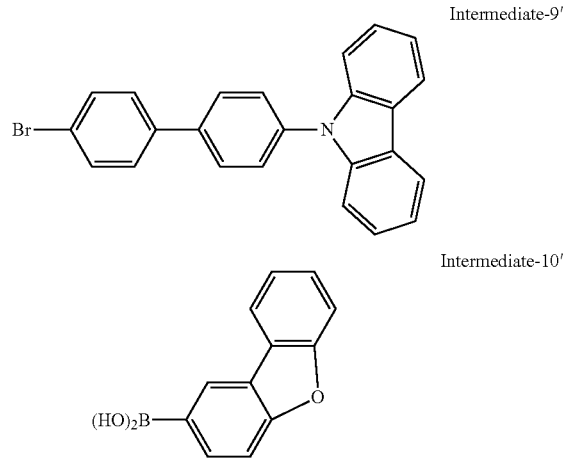
Intermediate-10'
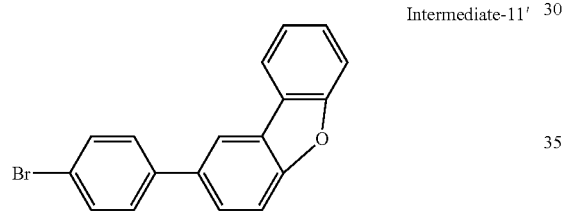
Intermediate-11'
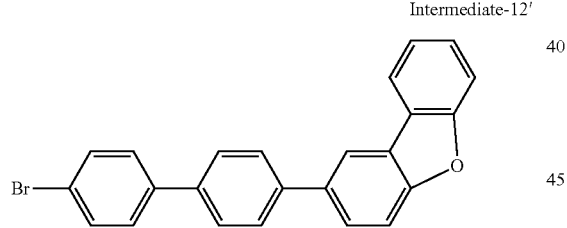
Intermediate-12'
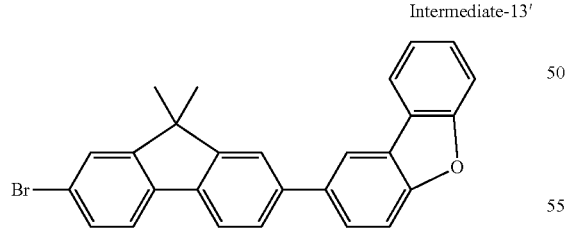
Intermediate-13'
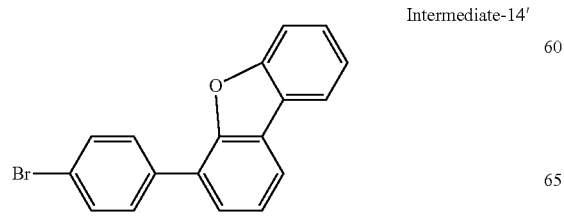
Intermediate-14'
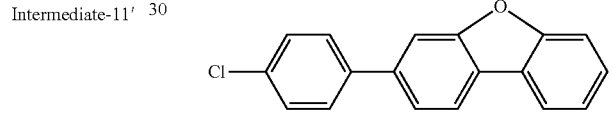
Intermediate-15'
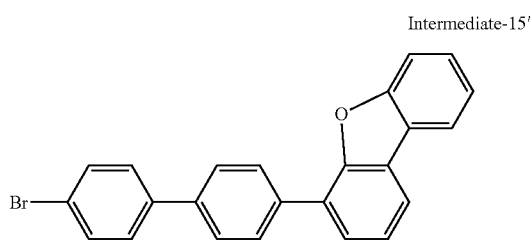
Intermediate-16'
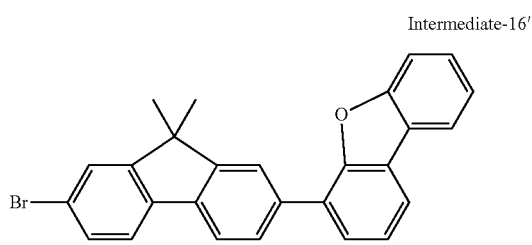
Intermediate-17'
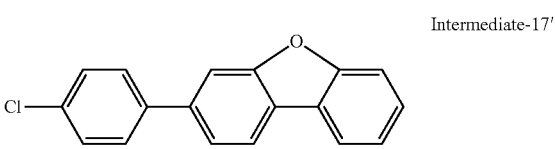
Intermediate-18'
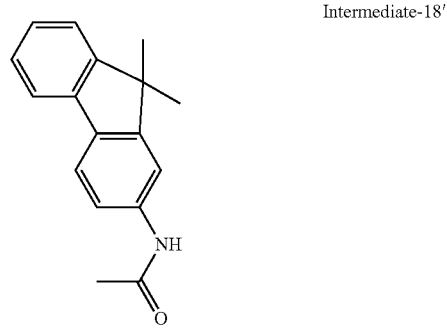
Intermediate-19'
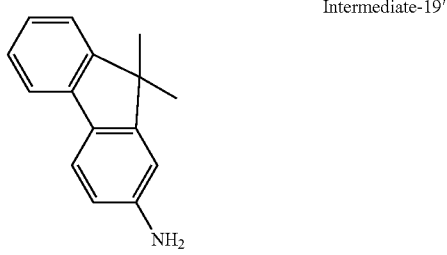

Intermediate-20'

Intermediate-21'

Intermediate-22'

Intermediate-23'

Intermediate-24'

Intermediate-25'

Intermediate-26'

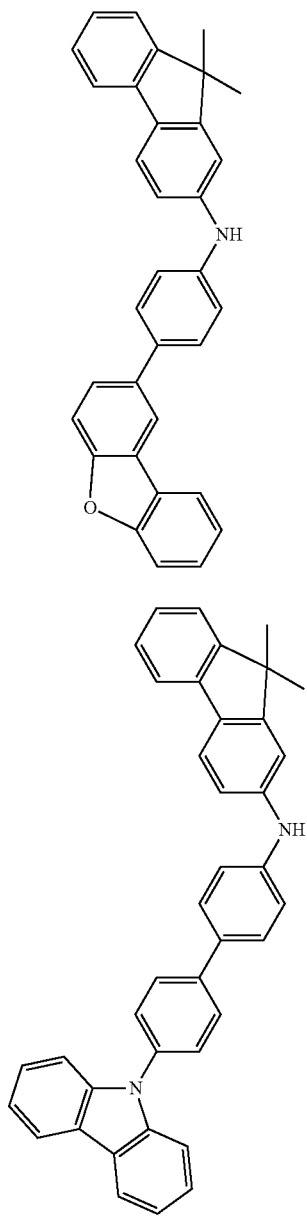

Intermediate-27'

Intermediate-28'

Intermediate-29'

Intermediate-30'

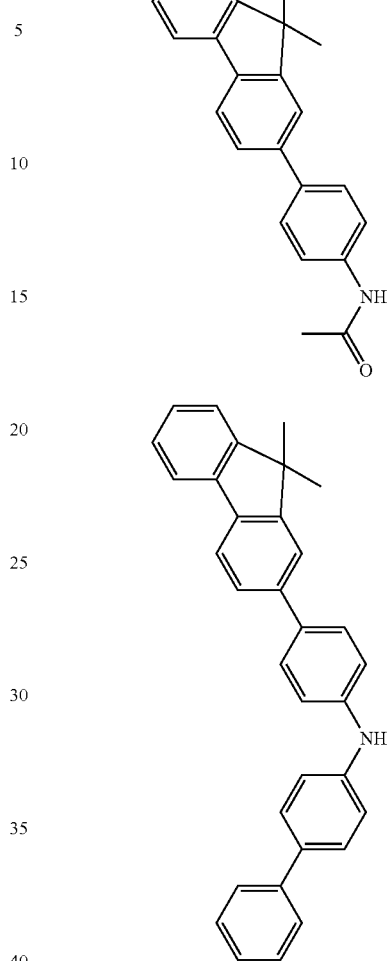

Intermediate-31'

Synthesis Example 24 (Synthesis of Intermediate-1')

Under an argon atmosphere, 47 g of 4-bromobiphenyl, 23 g of iodine, 9.4 g of periodic acid dihydrate, 42 ml of water, 360 ml of acetic acid, and 11 ml of sulfuric acid were loaded into a 1,000-ml three-necked flask, and the mixture was stirred at 65° C. for 30 minutes and was then subjected to a reaction at 90° C. for 6 hours. The reaction product was poured into ice water, followed by filtering. The resultant was washed with water, and then washed with methanol, whereby 67 g of a white powder were obtained.

Main peaks having ratios m/z of 358 and 360 were obtained with respect to $C_{12}H_8BrI=359$ by a field desorption mass spectrometry (hereinafter, referred to as FD-MS) analysis, so the powder was identified as the intermediate-1'.

Synthesis Example 25 (Synthesis of Intermediate-2')

Under an argon atmosphere, 12.5 g of 2-bromofluorene, 0.7 g of benzyltriethylammonium chloride, 60 ml of dimethyl sulfoxide, 8.0 g of sodium hydroxide, and 17 g of methyl iodide were loaded into a 200-ml three-necked flask, and then the mixture was subjected to a reaction for 18 hours.

After the completion of the reaction, water and ethyl acetate were added to perform separation and extraction.

After that, the resultant was concentrated, and then the resultant coarse product was purified by silica gel chromatography (hexane). Thus, 12.4 g of a yellow oily substance were obtained. The substance was identified as the intermediate-2' by FD-MS analysis.

Synthesis Example 26 (Synthesis of Intermediate-3')

A reaction was performed in the same manner as in Synthesis Example 24 except that 55 g of the intermediate-2' was used instead of 4-bromobiphenyl. As a result, 61 g of a white powder were obtained. The powder was identified as the intermediate-3' by FD-MS analysis.

Synthesis Example 27 (Synthesis of Intermediate-4')

Under an argon atmosphere, 39.9 g of the intermediate-3', 12.8 g of phenylboronic acid, 2.31 g of tetrakis(triphenylphosphine)palladium, 300 ml of toluene, and 150 ml of an aqueous solution of sodium carbonate having a concentration of 2 M were loaded into a 1,000-ml three-necked flask, and then the mixture was heated for 10 hours while being refluxed.

Immediately after the completion of the reaction, the resultant was filtered, and then the aqueous layer was removed. The organic layer was dried with sodium sulfate, and was then concentrated. The residue was purified by silica gel column chromatography. Thus, 27.3 g of a white crystal were obtained. The crystal was identified as the intermediate-4' by FD-MS analysis.

Synthesis Example 28 (Synthesis of Intermediate-5')

250 Grams of m-terphenyl, 50 g of hydroiodic acid dihydrate, 75 g of iodine, 750 ml of acetic acid, and 25 ml of concentrated sulfuric acid were loaded into a 2,000-ml three-necked flask, and then the mixture was subjected to a reaction at 70° C. for 3 hours. After the reaction, the resultant was poured into 5 l of methanol, and then the mixture was stirred for 1 hour. The resultant crystal, which had been taken from the mixture by filtration, was purified by means of column chromatography, and was then recrystallized with acetonitrile. Thus, 64 g of a white powder were obtained. The powder was identified as the intermediate-5' by FD-MS analysis.

Synthesis Example 29 (Synthesis of Intermediate-6')

17.7 Grams of 9-phenylcarbazole, 6.03 g of potassium iodide, 7.78 g of potassium iodate, 5.9 ml of sulfuric acid, and ethanol were loaded into a 200-ml three-necked flask, and then the mixture was subjected to a reaction at 75° C. for 2 hours.

After the resultant had been cooled, water and ethyl acetate were added to perform separation and extraction. After that, the organic layer was washed with baking soda water and water, and was then concentrated. The resultant coarse product was purified by silica gel chromatography (toluene), and then the resultant solid was dried under reduced pressure. Thus, 21.8 g of a white solid were obtained. The solid was identified as the intermediate-6' by FD-MS analysis.

Synthesis Example 30 (Synthesis of Intermediate-7')

Under an argon atmosphere, 13.1 g of the intermediate-6', dehydrated toluene, and dehydrated ether were loaded into a 300-ml three-necked flask, and then the mixture was cooled to −45° C. 25 Milliliters of a solution (1.58 M) of n-butyllithium in hexane were dropped to the mixture, and then the temperature was increased to −5° C. over 1 hour while the mixture was stirred. The mixture was cooled to −45° C. again, and then 25 ml of boronic acid triisopropyl ester were slowly dropped to the mixture. After that, the mixture was subjected to a reaction for 2 hours.

After the temperature of the resultant had been returned to room temperature, a 10% diluted hydrochloric acid solution was added to the resultant, and then the mixture was stirred so that an organic layer was extracted. After having been washed with a saturated salt solution, the organic layer was dried with anhydrous magnesium sulfate and separated by filtration. After that, the separated product was concentrated. The resultant solid was purified by silica gel chromatography (toluene), and then the resultant solid was washed with n-hexane and dried under reduced pressure. Thus, 7.10 g of a solid were obtained. The solid was identified as the intermediate-7' by FD-MS analysis.

Synthesis Example 31 (Synthesis of Intermediate-8')

Under an argon atmosphere, 28.3 g of 4-iodobromobenzene, 30.1 g of Intermediate-7', 2.31 g of tetrakis(triphenylphosphine)palladium, 300 ml of toluene, and 150 ml of an aqueous solution of sodium carbonate having a concentration of 2 M were loaded into a 1,000-ml three-necked flask, and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 20.2 g of a white crystal were obtained. The crystal was identified as the intermediate-8' by FD-MS analysis.

Synthesis Example 32 ( Synthesis of Intermediate-9')

Under an argon atmosphere, 36 g of Intermediate-1', 16.7 g of carbazole, 0.2 g of copper iodide (CuI), 42.4 g of tripotassium phosphate, 2 ml of trans-1,2-cyclohexanediamine, and 300 ml of 1,4-dioxane were loaded into a 1,000-ml three-necked flask, and then the mixture was stirred at 100° C. for 20 hours.

After the completion of the reaction, 300 ml of water were added to the resultant. After that, the mixture was subjected to liquid separation, and then the aqueous layer was removed. The organic layer was dried with sodium sulfate, and was then concentrated. The residue was purified by silica gel column chromatography. Thus, 23.1 g of a white crystal were obtained. The resultant was identified as the intermediate-9' by FD-MS analysis.

Synthesis Example 33 (Synthesis of Intermediate-10')

Under a nitrogen atmosphere, 150 g of dibenzofuran and 1 l of acetic acid were loaded into a 300-ml three-necked flask, and then the contents were dissolved under heat. 188 Grams of bromine were added dropwise to the solution. After that, the mixture was stirred for 20 hours under air cooling. The precipitated crystal was separated by filtration, and was then sequentially washed with acetic acid and water. The washed crystal was dried under reduced pressure. The resultant crystal was purified by distillation under reduced pressure, and was then repeatedly recrystallized with methanol several times. Thus, 66.8 g of 2-bromodibenzofuran were obtained.

Under an argon atmosphere, 24.7 g of 2-bromodibenzofuran and 400 ml of anhydrous THF were loaded into a 1,000-ml three-necked flask, and then 63 ml of a solution of n-butyllithium in hexane having a concentration of 1.6 M were added to the mixture during the stirring of the mixture at −40° C. The reaction solution was stirred for 1 hour while being heated to 0° C. The reaction solution was cooled to −78° C. again, and then a solution of 26.0 g of trimethyl borate in 50 ml of dry THF was dropped to the solution. The reaction solution was stirred at room temperature for 5 hours. 200 milliliters of 1N hydrochloric acid were added to the solution, and then the mixture was stirred for 1 hour. After that, the aqueous layer was removed. The organic layer was dried with magnesium sulfate, and then the solvent was removed by distillation under reduced pressure. The resultant solid was washed with toluene. Thus, 15.2 g of dibenzofuran-2-boronic acid were obtained.

Synthesis Example 34 (Synthesis of Intermediate-11')

A reaction was performed in the same manner as in Synthesis Example 31 except that 22.3 g of the intermediate-10' were used instead of the intermediate-7'. Thus, 19.4 g of a white powder were obtained. The powder was identified as the intermediate-1' by FD-MS analysis.

Synthesis Example 35 (Synthesis of Intermediate-12')

A reaction was performed in the same manner as in Synthesis Example 31 except that: 35.9 g of the Intermediate-1' were used instead of 4-iodobromobenzene; and 22.3 g of the intermediate-10' were used instead of the intermediate-7'. Thus, 28.7 g of a white powder were obtained. The powder was identified as the intermediate-12' by FD-MS analysis.

Synthesis Example 36 (Synthesis of Intermediate-13')

A reaction was performed in the same manner as in Synthesis Example 31 except that: 39.9 g of the Intermediate-3' were used instead of 4-iodobromobenzene; and 22.3 g of the intermediate-10' were used instead of the intermediate-7'. Thus, 28.6 g of a white powder were obtained. The powder was identified as the intermediate-13' by FD-MS analysis.

Synthesis Example 37 (Synthesis of Intermediate-14')

A reaction was performed in the same manner as in Synthesis Example 31 except that 22.3 g of dibenzofuran-4-boronic acid were used instead of the intermediate-7'. Thus, 25.9 g of a white powder were obtained. The powder was identified as the intermediate-14' by FD-MS analysis.

Synthesis Example 38 (Synthesis of Intermediate-15')

A reaction was performed in the same manner as in Synthesis Example 31 except that: 35.9 g of the intermediate-1' were used instead of 4-iodobromobenzene; and 22.3 g of dibenzofuran-4-boronic acid were used instead of the intermediate-7'. Thus, 31.9 g of a white powder were obtained. The powder was identified as the intermediate-15' by FD-MS analysis.

Synthesis Example 39 (Synthesis of Intermediate-16')

A reaction was performed in the same manner as in Synthesis Example 31 except that: 39.9 g of the intermediate-3' were used instead of 4-iodobromobenzene; and 22.3 g of dibenzofuran-4-boronic acid were used instead of the intermediate-7'. Thus, 35.7 g of a white powder were obtained. The powder was identified as the intermediate-16' by FD-MS analysis.

Synthesis Example 40 (Synthesis of Intermediate-17')

Under an argon atmosphere, 120.0 g of 1-bromo-3-fluoro-4-iodobenzene, 72.7 g of 2-methoxyphenyl boronic acid, and 9.2 g of tetrakis(triphenylphosphine)palladium, 1,000 ml of toluene, and 500 ml of an aqueous solution of sodium carbonate having a concentration of 2 M were loaded into a 2,000-ml three-necked flask, and then the mixture was heated for 10 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 89.6 g of a white crystal of 4-bromo-2-fluoro-2'-methoxybiphenyl were obtained.

Under an argon atmosphere, 89.6 g of 4-bromo-2-fluoro-2'-methoxybiphenyl and 900 ml of dichloromethane were loaded into a 2,000-ml three-necked flask, and then the mixture was stirred under ice cooling. 95.9 Grams of boron tribromide were added dropwise to the mixture, and then the whole was stirred at room temperature for 12 hours.

After the completion of the reaction, 200 ml of water were added to the resultant, and then the mixture was stirred for 1 hour. After that, the aqueous layer was removed. The organic layer was dried with magnesium sulfate, and was then concentrated. The residue was purified by silica gel column chromatography. Thus, 68.1 g of a white crystal of 4-bromo-2-fluoro-2'-hydroxybiphenyl were obtained.

68.1 Grams of 4-bromo-2-fluoro-2'-hydroxybiphenyl, 70.4 g of potassium carbonate, and 1,200 ml of N-methyl pyrrolidone were loaded into a 2,000-ml three-necked flask, and then the mixture was stirred at 180° C. for 3 hours.

After the completion of the reaction, water was added to the resultant, and then extraction with toluene was performed. The organic layer was dried with sodium sulfate, and was then concentrated. The residue was recrystallized from toluene so as to be purified. Thus, 44.2 g of a white crystal of 3-bromodibenzofuran were obtained.

Under an argon atmosphere, 34.2 g of 3-bromodibenzofuran, 26.0 g of 4-chlorophenyl boronic acid, 3.2 g of tetrakis(triphenylphosphine)palladium, 350 ml of toluene, and 170 ml of an aqueous solution of sodium carbonate having a concentration of 2 M were loaded into a 1,000-ml three-necked flask, and then the mixture was heated for 12 hours while being refluxed.

Immediately after the completion of the reaction, the resultant was filtrated, and then the aqueous layer was removed. The organic layer was dried with sodium sulfate, and was then concentrated. The residue was purified by silica gel column chromatography. Thus, 23.1 g of a white crystal were obtained. The crystal was identified as the intermediate-17' by FD-MS analysis.

Synthesis Example 41 (Synthesis of Intermediate-18')

Under an argon atmosphere, 7.0 g of acetamide, 45.8 g of the intermediate-2, 6.8 g of copper(I) iodide, 6.3 g of N,N'- dimethylethylenediamine, 51 g of tripotassium phosphate, and 300 ml of xylene were loaded into a 500-ml three-necked flask, and then the mixture was subjected to a reaction at 140° C. for 36 hours. After having been cooled, the resultant was filtrated and washed with toluene. The washed product was further washed with water and methanol, and was then dried. Thus, 19 g of a pale yellow powder were obtained. The powder was identified as the intermediate-18' by FD-MS analysis.

Synthesis Example 42 (Synthesis of Intermediate-19')

19.0 Grams of the intermediate-18', 26 g of potassium hydroxide, 28 ml of ion-exchanged water, 39 ml of xylene, and 77 ml of ethanol were loaded into a 300-ml three-necked flask, and then the mixture was heated for 36 hours while being refluxed. After the completion of the reaction, the resultant was extracted with toluene and dried with magnesium sulfate. The dried product was concentrated under reduced pressure, and then the resultant coarse product was subjected to column purification. The purified product was recrystallized with toluene, and then the recrystallized product was taken by filtration. After that, the resultant was dried. Thus, 15.8 g of the intermediate-19' were obtained as a white powder.

Synthesis Example 43 (Synthesis of Intermediate-20')

A reaction was performed in the same manner as in Synthesis Examples 41 and 42 except that 15 g of the intermediate-18' were used instead of acetamide and 26 g of 4-bromo-p-terphenyl were used instead of the intermediate-2' upon performance of Synthesis Examples 41 and 42 in the stated order. Thus, 15.5 g of a pale yellow powder were obtained. The powder was identified as the intermediate-20' by FD-MS analysis.

Synthesis Example 44 (Synthesis of Intermediate-21')

A reaction was performed in the same manner as in Synthesis Examples 41 and 42 except that 15 g of the intermediate-18' were used instead of acetamide and 29 g of intermediate-5' were used instead of the intermediate-2' upon performance of Synthesis Examples 41 and 42 in the stated order. Thus, 17.5 g of a pale yellow powder were obtained. The powder was identified as the intermediate-21' by FD-MS analysis.

Synthesis Example 45 (Synthesis of Intermediate-22')

A reaction was performed in the same manner as in Synthesis Examples 41 and 42 except that 15 g of the intermediate-18' were used instead of acetamide and 29 g of intermediate-4' were used instead of the intermediate-2' upon performance of Synthesis Examples 41 and 42 in the stated order. Thus, 18.5 g of a pale yellow powder were obtained. The powder was identified as the intermediate-22' by FD-MS analysis.

Synthesis Example 46 (Synthesis of Intermediate-23')

A reaction was performed in the same manner as in Synthesis Example 41 except that 29 g of the intermediate-4' were used instead of the intermediate-2'. Thus, 20.2 g of a pale yellow powder were obtained. The powder was identified as the intermediate-23' by FD-MS analysis.

Synthesis Example 47 (Synthesis of Intermediate-24')

A reaction was performed in the same manner as in Synthesis Examples 41 and 42 except that 20 g of the intermediate-23' were used instead of acetamide and 26 g of 4-bromo-p-terphenyl were used instead of the intermediate-2' upon performance of Synthesis Examples 41 and 42 in the stated order. Thus, 19.8 g of a pale yellow powder were obtained. The powder was identified as the intermediate-24' by FD-MS analysis.

Synthesis Example 48 (Synthesis of Intermediate-25')

A reaction was performed in the same manner as in Synthesis Examples 41 and 42 except that 15 g of the intermediate-18' were used instead of acetamide and 27 g of intermediate-14' were used instead of the intermediate-2' upon performance of Synthesis Examples 41 and 42 in the stated order. Thus, 17.3 g of a pale yellow powder were obtained. The powder was identified as the intermediate-25' by FD-MS analysis.

Synthesis Example 49 (Synthesis of Intermediate-26')

A reaction was performed in the same manner as in Synthesis Examples 41 and 42 except that 15 g of the intermediate-18' were used instead of acetamide and 27 g of intermediate-11' were used instead of the intermediate-2' upon performance of Synthesis Examples 41 and 42 in the stated order. Thus, 17.8 g of a pale yellow powder were obtained. The powder was identified as the intermediate-26' by FD-MS analysis.

Synthesis Example 50 (Synthesis of Intermediate-27')

A reaction was performed in the same manner as in Synthesis Examples 41 and 42 except that 15 g of the intermediate-18' were used instead of acetamide and 33 g of intermediate-9' were used instead of the intermediate-2' upon performance of Synthesis Examples 41 and 42 in the stated order. Thus, 20.3 g of a pale yellow powder were obtained. The powder was identified as the intermediate-27' by FD-MS analysis.

Synthesis Example 51 (Synthesis of Intermediate-28')

A reaction was performed in the same manner as in Synthesis Example 30 except that 33 g of the intermediate-2' were used instead of the intermediate-6'. Thus, 17 g of a white powder were obtained. The powder was identified as the intermediate-28' by EFD-MS analysis.

Synthesis Example 52 (Synthesis of Intermediate-29')

A reaction was performed in the same manner as in Synthesis Example 31 except that 17 g of the intermediate-28' were used instead of the intermediate-7'. Thus, 20 g of a white powder were obtained. The powder was identified as the intermediate-29' by FD-MS analysis.

Synthesis Example 53 (Synthesis of Intermediate-30')

A reaction was performed in the same manner as in Synthesis Example 41 except that 20 g of the intermediate-29' were used instead of the intermediate-2'. Thus, 12 g of a pale yellow powder were obtained. The powder was identified as the intermediate-30' by FD-MS analysis.

Synthesis Example 54 (Synthesis of Intermediate-31')

A reaction was performed in the same manner as in Synthesis Examples 41 and 42 except that 12 g of the intermediate-30' were used instead of acetamide and 12.8 g of 4-bromobiphenyl were used instead of the intermediate-2' upon performance of Synthesis Examples 41 and 42 in the stated order. Thus, 10.4 g of a pale yellow powder were obtained. The powder was identified as the intermediate-31' by FD-MS analysis.

Shown below are the structures of the aromatic amine derivatives of the present invention produced in Examples-of-Synthesis 19 to 50 below and the comparative compounds-1 and 2 used in Comparative Examples 1 and 2.

[Chem. 95]

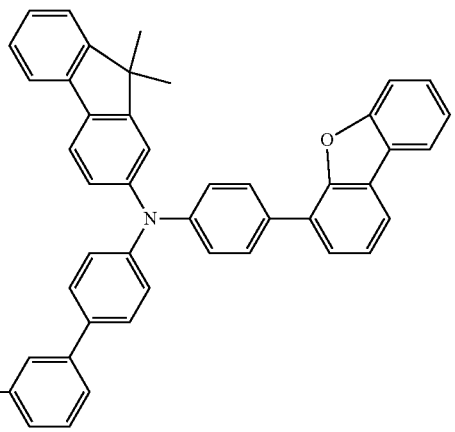

H-2'

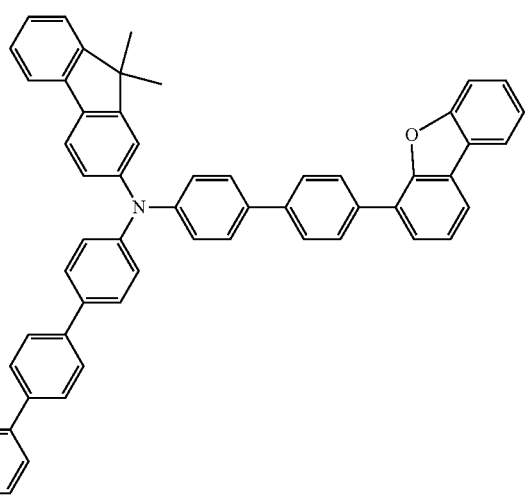

H-3'

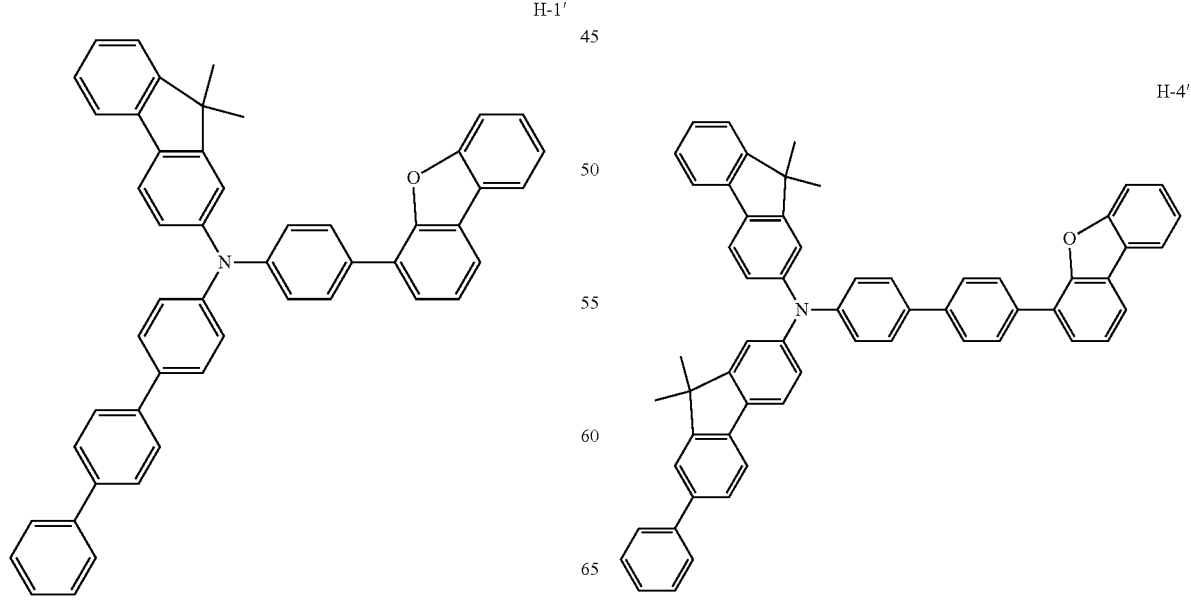

H-1'

H-4'

553
-continued
554
-continued
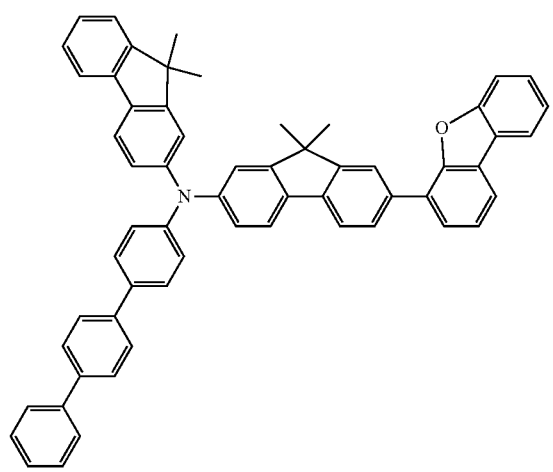
H-5'
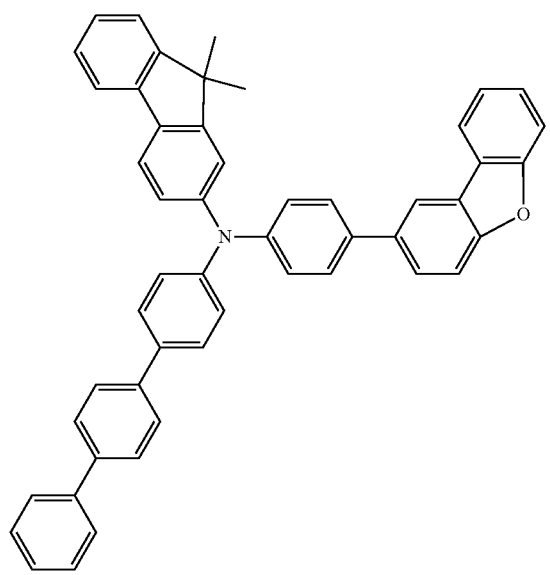
H-7'
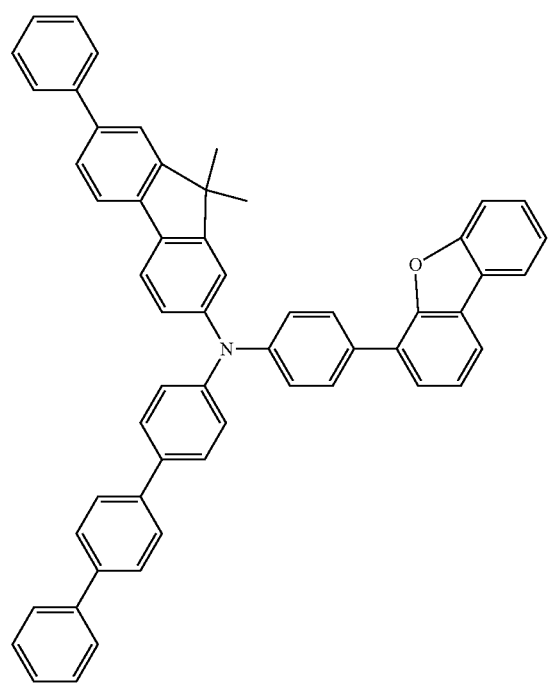
H-6'
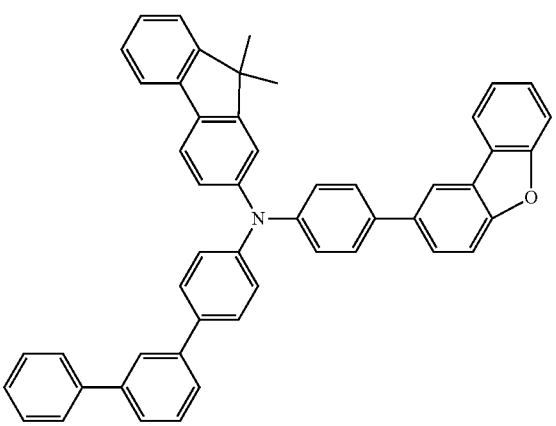
H-8'
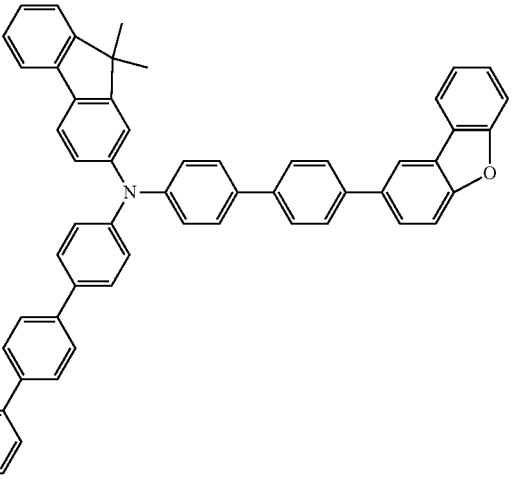
H-9'

H-10'
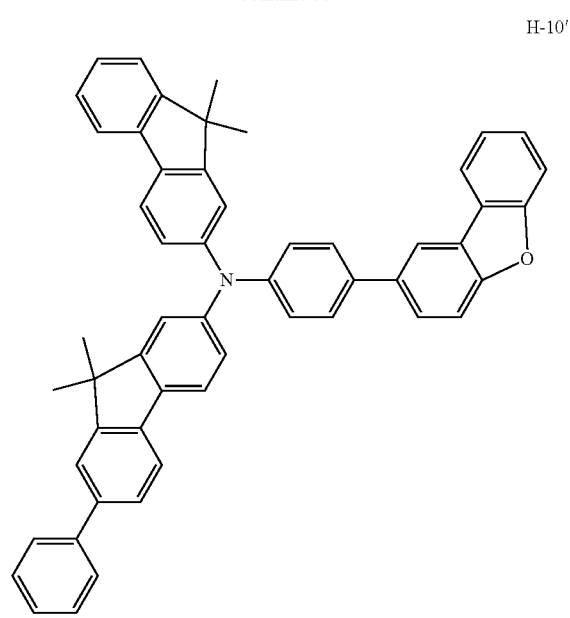
H-11'
H-12'
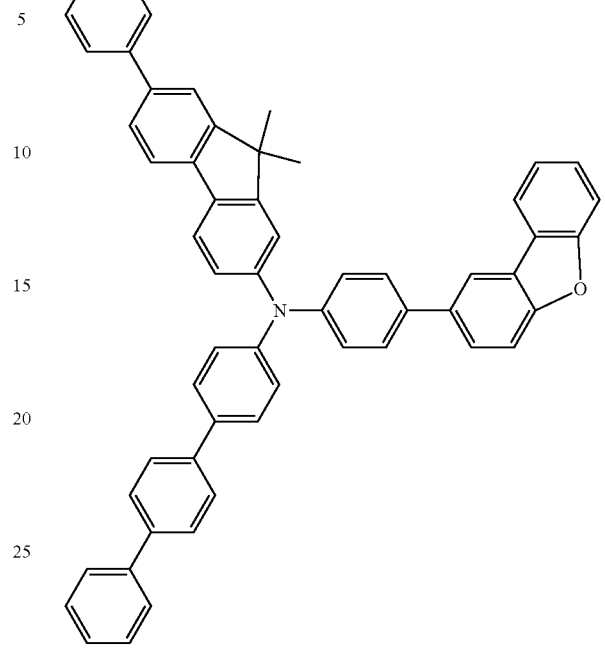
[Chem. 96]
H-13'
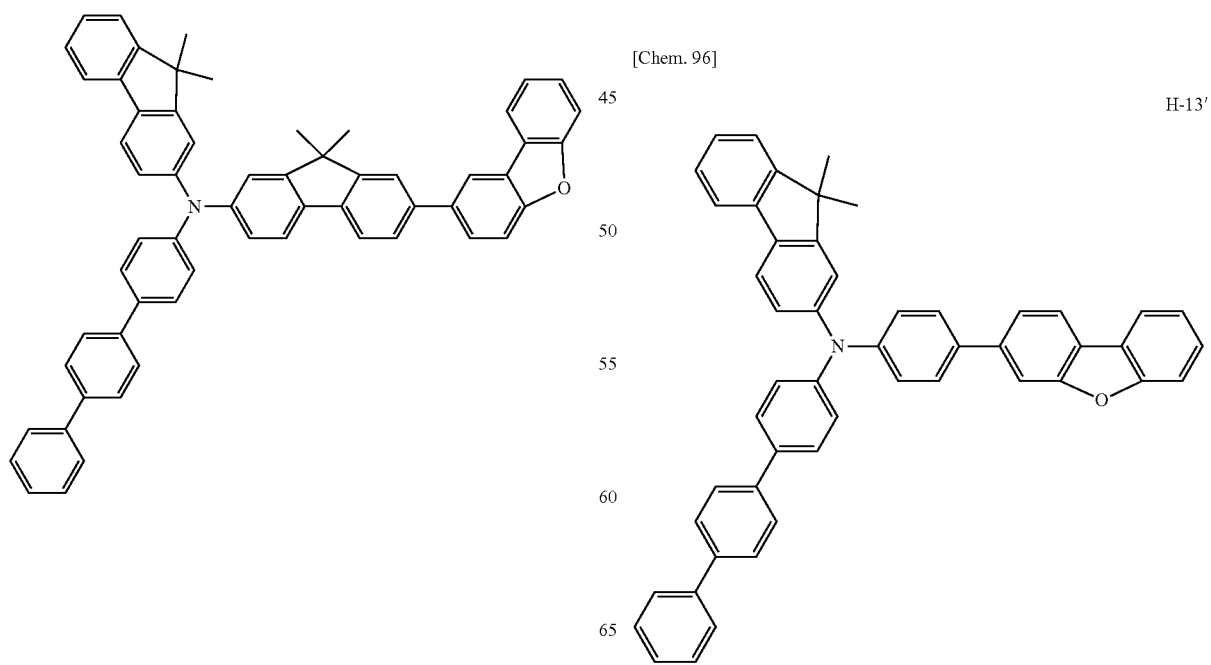

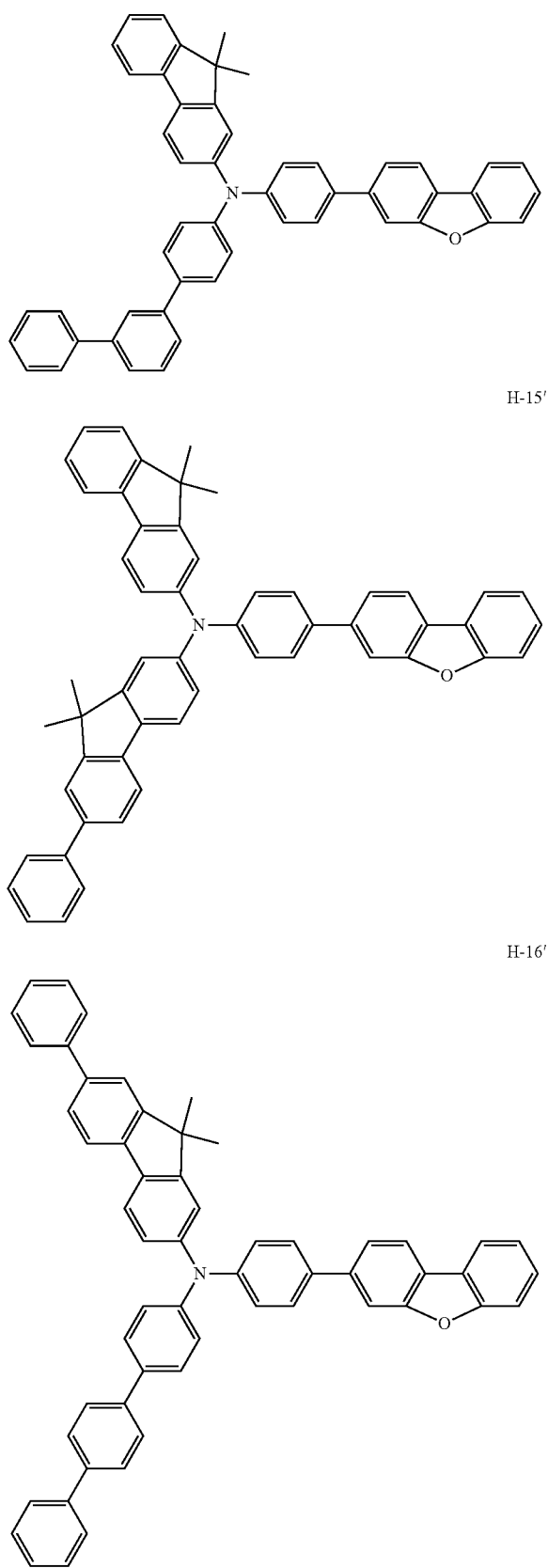
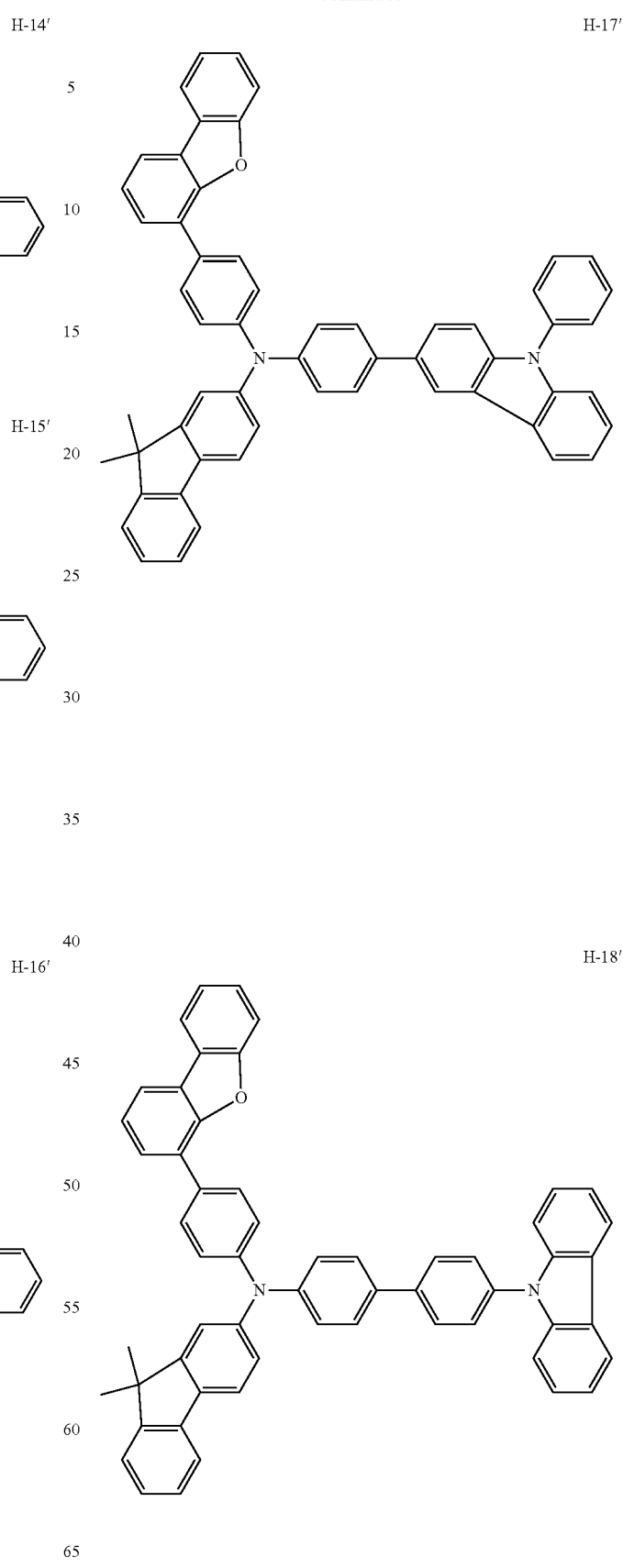

H-19'
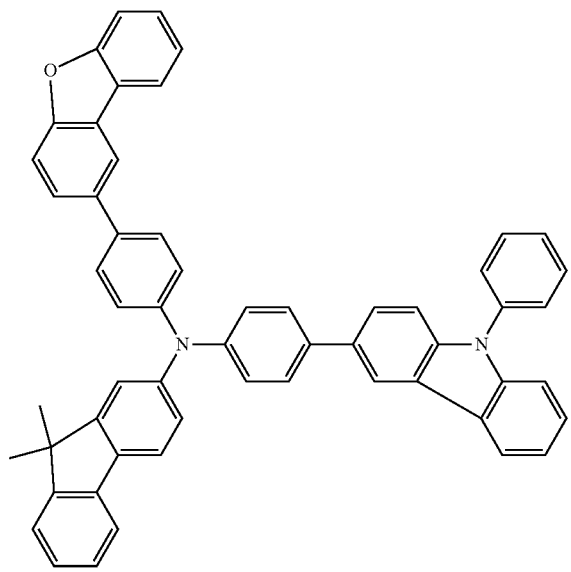
H-20'
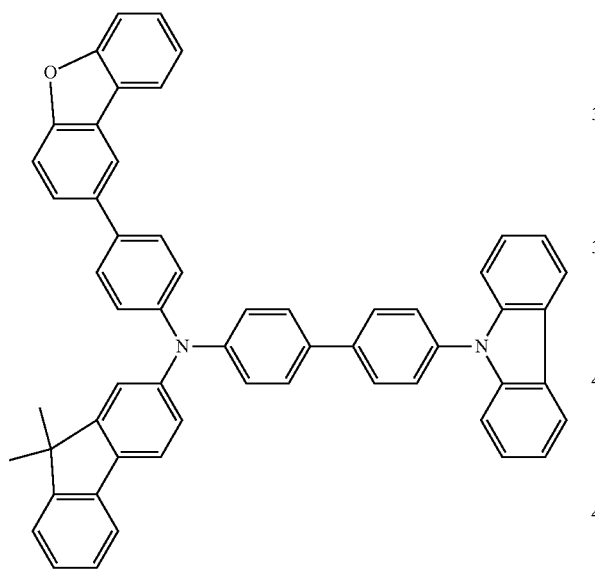
H-21'
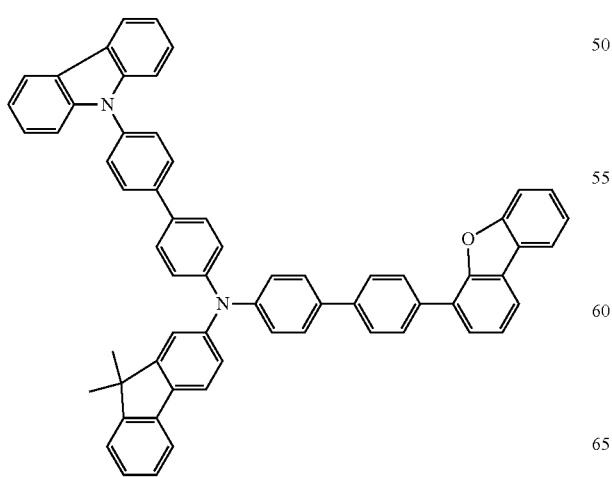
H-22'
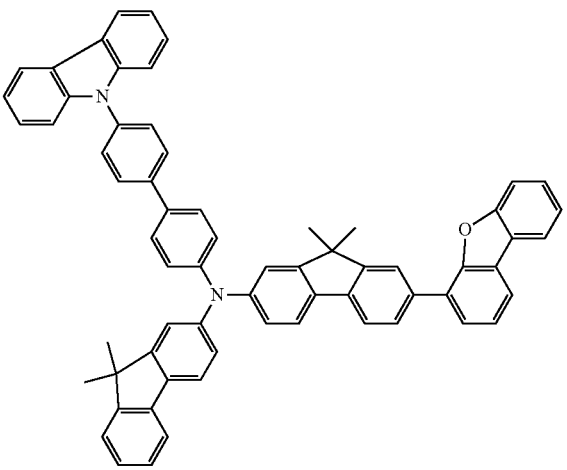
[Chem. 97]
H-23'
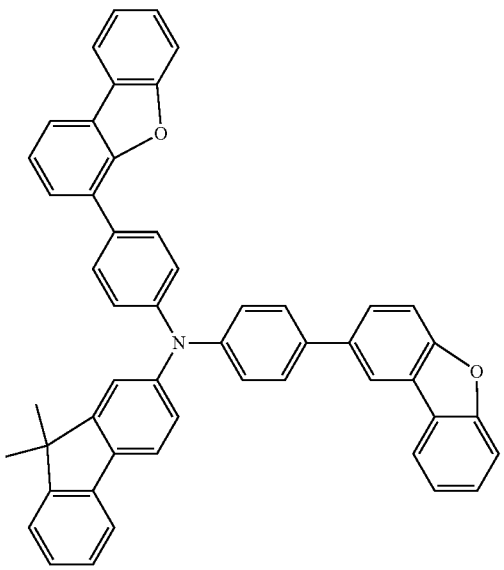

H-24'
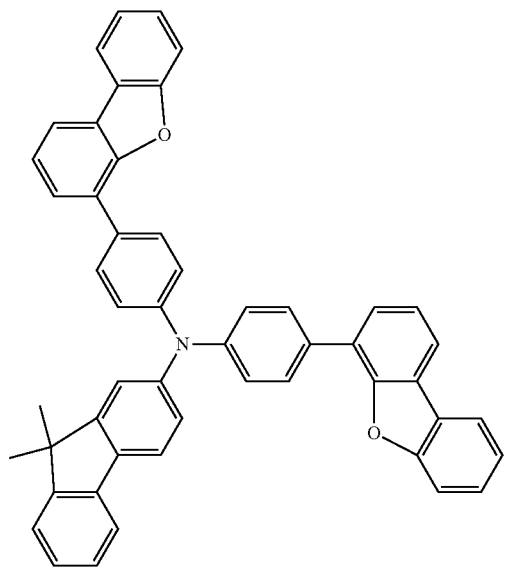
H-25'
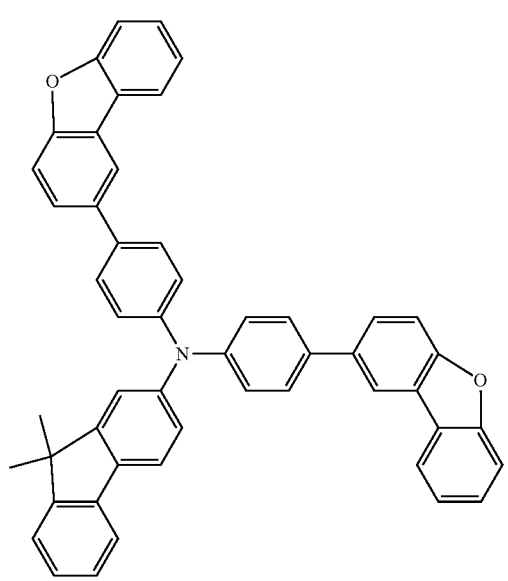
H-26'
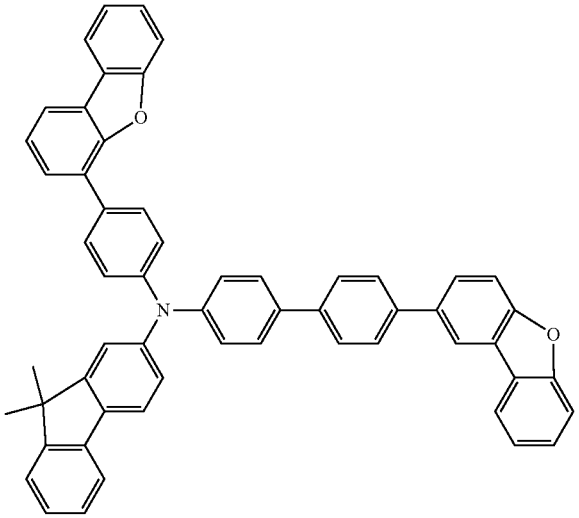
H-27'
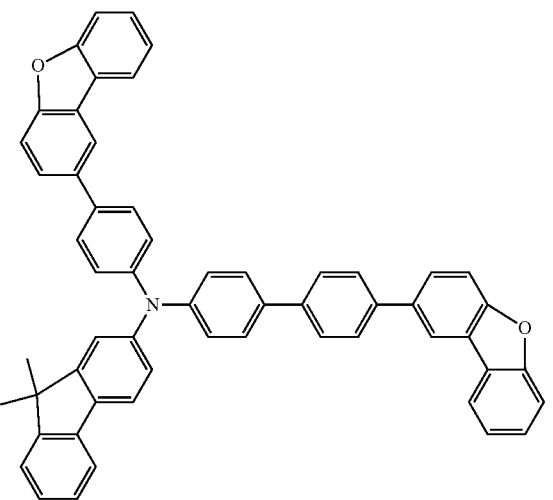
H-28'

563
-continued
H-29'
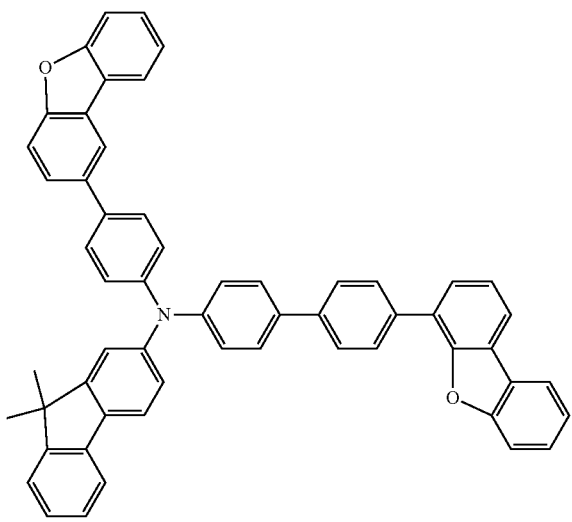
H-30'
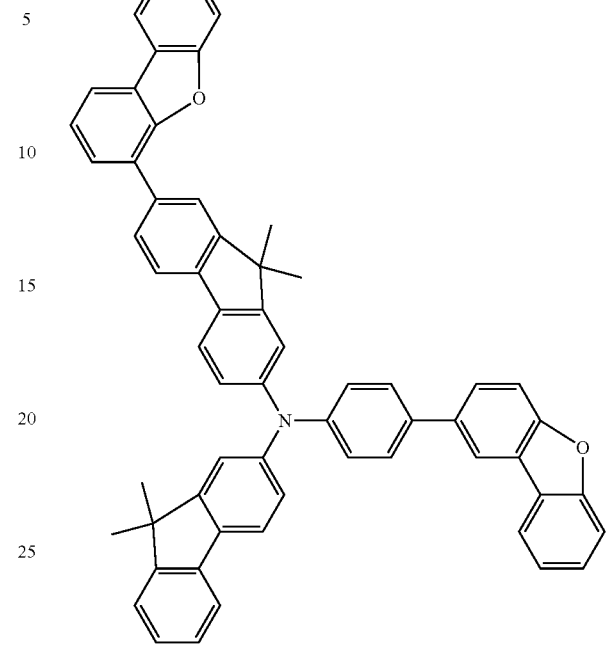
564
-continued
H-31'
H-32'
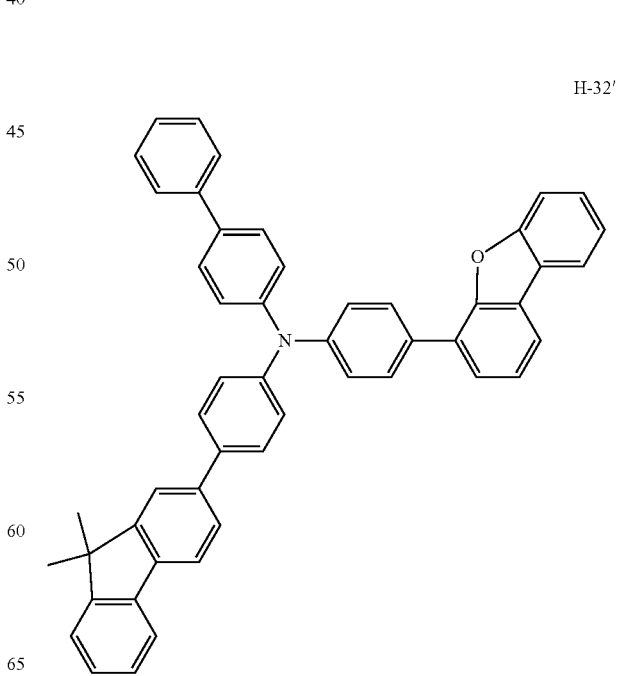

-continued

[Chem. 98]

Comparative compound-1

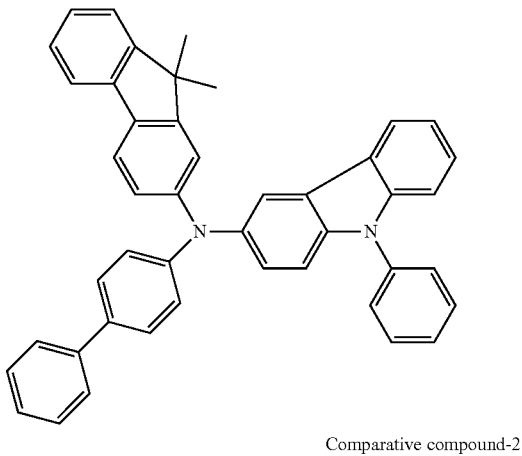

Comparative compound-2

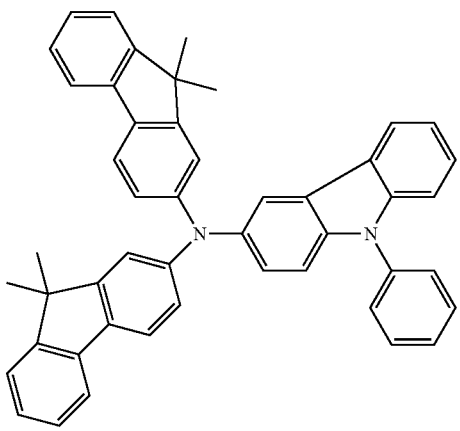

Example-of-Synthesis 19 (Production of Aromatic Amine derivative (H-1'))

In a stream of argon, 6.5 g of the intermediate-14', 8.8 g of the intermediate-20', 2.6 g of t-butoxy sodium, 92 mg of tris(dibenzylideneacetone)dipalladium, 42 mg of tri-t-butylphosphine, and 100 ml of dry toluene were loaded into a 300-ml three-necked flask, and then the mixture was subjected to a reaction at 80° C. for 8 hours.

After having been cooled, the reaction product was poured into 500 ml of water, and then the mixture was subjected to celite filtration. The filtrate was extracted with toluene, and was then dried with anhydrous magnesium sulfate. The dried product was concentrated under reduced pressure. The resultant coarse product was subjected to column purification, and was then recrystallized with toluene. The crystal was taken by filtration, and was then dried. As a result, 8.2 g of a pale yellow powder were obtained. The powder was identified as aromatic amine derivative (H-1') by FD-MS analysis.

Example-of-Synthesis 20 (Production of Aromatic Amine Derivative (H-2'))

A reaction was performed in the same manner as in Example-of-Synthesis 19 except that 8.8 g of the intermediate-21' were used instead of the intermediate-20'. Thus, 7.8 g of a pale yellow powder were obtained. The powder was identified as the aromatic amine derivative (H-2') by FD-MS analysis.

Example-of-Synthesis 21 (Production of Aromatic Amine Derivative (H-3'))

A reaction was performed in the same manner as in Example-of-Synthesis 19 except that 8.0 g of the intermediate-15' were used instead of the intermediate-14'. Thus, 9.2 g of a pale yellow powder were obtained. The powder was identified as the aromatic amine derivative (H-3') by FD-MS analysis.

Example-of-Synthesis 22 (Production of Aromatic Amine Derivative (H-4'))

A reaction was performed in the same manner as in Example-of-Synthesis 19 except that: 8.0 g of the intermediate-15' were used instead of the intermediate-14'; and 9.6 g of the intermediate-22' were used instead of the intermediate-20'. Thus, 9.4 g of a pale yellow powder were obtained. The powder was identified as the aromatic amine derivative (H-4') by FD-MS analysis.

Example-of-Synthesis 23 (Production of Aromatic Amine Derivative (H-5'))

A reaction was performed in the same manner as in Example-of-Synthesis 19 except that 8.8 g of the intermediate-16' were used instead of the intermediate-14'. Thus, 9.5 g of a pale yellow powder were obtained. The powder was identified as the aromatic amine derivative (H-5') by FD-MS analysis.

Example-of-Synthesis 24 (Production of Aromatic Amine Derivative (H-6'))

A reaction was performed in the same manner as in Example-of-Synthesis 19 except that 10.3 g of the intermediate-24' were used instead of the intermediate-20'. Thus, 8.3 g of a pale yellow powder were obtained. The powder was identified as the aromatic amine derivative (H-6') by FD-MS analysis.

Example-of-Synthesis 25 (Production of Aromatic Amine Derivative (H-7'))

A reaction was performed in the same manner as in Example-of-Synthesis 19 except that 6.5 g of the intermediate-11' were used instead of the intermediate-14'. Thus, 7.9 g of a pale yellow powder were obtained. The powder was identified as the aromatic amine derivative (H-7') by FD-MS analysis.

Example-of-Synthesis 26 (Production of Aromatic Amine Derivative (H-8'))

A reaction was performed in the same manner as in Example-of-Synthesis 19 except that: 6.5 g of the intermediate-11' were used instead of the intermediate-14'; and 8.8 g of the intermediate-21' were used instead of the intermediate-20'. Thus, 8.2 g of a pale yellow powder were obtained. The powder was identified as the aromatic amine derivative (H-8') by FD-MS analysis.

Example-of-Synthesis 27 (Production of Aromatic Amine Derivative (H-9'))

A reaction was performed in the same manner as in Example-of-Synthesis 19 except that 8.0 g of the intermediate-12' were used instead of the intermediate-14'. Thus, 8.9 g of a pale yellow powder were obtained. The powder was identified as the aromatic amine derivative (H-9') by FD-MS analysis.

Example-of-Synthesis 28 (Production of Aromatic Amine Derivative (H-10'))

A reaction was performed in the same manner as in Example-of-Synthesis 19 except that: 6.5 g of the intermediate-11' were used instead of the intermediate-14'; and 9.6 g of the intermediate-22' were used instead of the intermediate-20'. Thus, 9.3 g of a pale yellow powder were obtained. The powder was identified as the aromatic amine derivative (H-10') by FD-MS analysis.

Example-of-Synthesis 29 (Production of Aromatic Amine Derivative (H-11'))

A reaction was performed in the same manner as in Example-of-Synthesis 19 except that 8.8 g of the intermediate-13' were used instead of the intermediate-14'. Thus, 9.4 g of a pale yellow powder were obtained. The powder was identified as the aromatic amine derivative (H-1') by FD-MS analysis.

Example-of-Synthesis 30 (Production of Aromatic Amine Derivative (H-12'))

A reaction was performed in the same manner as in Example-of-Synthesis 19 except that: 6.5 g of the intermediate-11' were used instead of the intermediate-14'; and 10.3 g of the intermediate-24' were used instead of the intermediate-20'. Thus, 9.0 g of a pale yellow powder were obtained. The powder was identified as the aromatic amine derivative (H-12') by FD-MS analysis.

Example-of-Synthesis 31 (Production of Aromatic Amine Derivative (H-13'))

A reaction was performed in the same manner as in Example-of-Synthesis 19 except that 5.6 g of the intermediate-17' were used instead of the intermediate-14'. Thus, 8.3 g of a pale yellow powder were obtained. The powder was identified as the aromatic amine derivative (H-13') by FD-MS analysis.

Example-of-Synthesis 32 (Production of Aromatic Amine Derivative (H-14'))

A reaction was performed in the same manner as in Example-of-Synthesis 19 except that: 5.6 g of the intermediate-17' were used instead of the intermediate-14'; and 8.8 g of the intermediate-21' were used instead of the intermediate-20'. Thus, 8.1 g of a pale yellow powder were obtained. The powder was identified as the aromatic amine derivative (H-14') by FD-MS analysis.

Example-of-Synthesis 33 (Production of Aromatic Amine Derivative (H-15'))

A reaction was performed in the same manner as in Example-of-Synthesis 19 except that: 5.6 g of the intermediate-17' were used instead of the intermediate-14'; and 9.6 g of the intermediate-22' were used instead of the intermediate-20'. Thus, 9.7 g of a pale yellow powder were obtained. The powder was identified as the aromatic amine derivative (H-15') by FD-MS analysis.

Example-of-Synthesis 34 (Production of Aromatic Amine Derivative (H-16'))

A reaction was performed in the same manner as in Example-of-Synthesis 19 except that: 5.6 g of the intermediate-17' were used instead of the intermediate-14'; and 10.3 g of the intermediate-24' were used instead of the intermediate-20'. Thus, 9.5 g of a pale yellow powder were obtained. The powder was identified as the aromatic amine derivative (H-16') by FD-MS analysis.

Example-of-Synthesis 35 (Production of Aromatic Amine Derivative (H-17'))

A reaction was performed in the same manner as in Example-of-Synthesis 19 except that: 8.0 g of the intermediate-8' were used instead of the intermediate-14'; and 9.0 g of the intermediate-25' were used instead of the intermediate-20'. Thus, 9.2 g of a pale yellow powder were obtained. The powder was identified as the aromatic amine derivative (H-17') by FD-MS analysis.

Example-of-Synthesis 36 (Production of Aromatic Amine Derivative (H-18'))

A reaction was performed in the same manner as in Example-of-Synthesis 19 except that: 8.0 g of the intermediate-9' were used instead of the intermediate-14'; and 9.0 g of the intermediate-25' were used instead of the intermediate-20'. Thus, 8.8 g of a pale yellow powder were obtained. The powder was identified as the aromatic amine derivative (H-18') by FD-MS analysis.

Example-of-Synthesis 37 (Production of Aromatic Amine Derivative (H-19'))

A reaction was performed in the same manner as in Example-of-Synthesis 19 except that: 8.0 g of the intermediate-8' were used instead of the intermediate-14'; and 9.0 g of the intermediate-26' were used instead of the intermediate-20'. Thus, 9.0 g of a pale yellow powder were obtained. The powder was identified as the aromatic amine derivative (H-19') by FD-MS analysis.

Example-of-Synthesis 38 (Production of Aromatic Amine Derivative (H-20'))

A reaction was performed in the same manner as in Example-of-Synthesis 19 except that: 8.0 g of the intermediate-9' were used instead of the intermediate-14'; and 9.0 g of the intermediate-26' were used instead of the intermediate-20'. Thus, 9.7 g of a pale yellow powder were obtained. The powder was identified as the aromatic amine derivative (H-20') by FD-MS analysis.

Example-of-Synthesis 39 (Production of Aromatic Amine Derivative (H-21'))

A reaction was performed in the same manner as in Example-of-Synthesis 19 except that: 8.0 g of the intermediate-15' were used instead of the intermediate-14'; and 10.5 g of the intermediate-27' were used instead of the intermediate-20'. Thus, 10.5 g of a pale yellow powder were obtained. The powder was identified as the aromatic amine derivative (H-21') by FD-MS analysis.

Example-of-Synthesis 40 (Production of Aromatic Amine Derivative (H-22'))

A reaction was performed in the same manner as in Example-of-Synthesis 19 except that: 8.8 g of the intermediate-16' were used instead of the intermediate-14'; and 10.5 g of the intermediate-27' were used instead of the intermediate-20'. Thus, 9.5 g of a pale yellow powder were obtained. The powder was identified as the aromatic amine derivative (H-22') by FD-MS analysis.

Example-of-Synthesis 41 (Production of Aromatic Amine Derivative (H-23'))

A reaction was performed in the same manner as in Example-of-Synthesis 19 except that: 6.5 g of the intermediate-11' were used instead of the intermediate-14'; and 9.0 g of the intermediate-25' were used instead of the intermediate-20'. Thus, 8.3 g of a pale yellow powder were obtained. The powder was identified as the aromatic amine derivative (H-23') by FD-MS analysis.

Example-of-Synthesis 42 (Production of Aromatic Amine Derivative (H-24'))

A reaction was performed in the same manner as in Example-of-Synthesis 19 except that 9.0 g of the intermediate-25' were used instead of the intermediate-20'. Thus, 8.1 g of a pale yellow powder were obtained. The powder was identified as the aromatic amine derivative (H-24') by FD-MS analysis.

Example-of-Synthesis 43 (Production of Aromatic Amine Derivative (H-25'))

A reaction was performed in the same manner as in Example-of-Synthesis 19 except that: 6.5 g of the intermediate-11' were used instead of the intermediate-14'; and 9.0 g of the intermediate-26' were used instead of the intermediate-20'. Thus, 8.7 g of a pale yellow powder were obtained. The powder was identified as the aromatic amine derivative (H-25') by FD-MS analysis.

Example-of-Synthesis 44 (Production of Aromatic Amine Derivative (H-26'))

A reaction was performed in the same manner as in Example-of-Synthesis 19 except that: 8.0 g of the intermediate-12' were used instead of the intermediate-14'; and 9.0 g of the intermediate-25' were used instead of the intermediate-20'. Thus, 9.4 g of a pale yellow powder were obtained. The powder was identified as the aromatic amine derivative (H-26') by FD-MS analysis.

Example-of-Synthesis 45 (Production of Aromatic Amine Derivative (H-27'))

A reaction was performed in the same manner as in Example-of-Synthesis 19 except that: 8.0 g of the intermediate-15' were used instead of the intermediate-14'; and 9.0 g of the intermediate-25' were used instead of the intermediate-20'. Thus, 9.0 g of a pale yellow powder were obtained. The powder was identified as the aromatic amine derivative (H-27') by FD-MS analysis.

Example-of-Synthesis 46 (Production of Aromatic Amine Derivative (H-28'))

A reaction was performed in the same manner as in Example-of-Synthesis 19 except that: 8.0 g of the intermediate-12' were used instead of the intermediate-14'; and 9.0 g of the intermediate-26' were used instead of the intermediate-20'. Thus, 9.5 g of a pale yellow powder were obtained. The powder was identified as the aromatic amine derivative (H-28') by FD-MS analysis.

Example-of-Synthesis 47 (Production of Aromatic Amine Derivative (H-29'))

A reaction was performed in the same manner as in Example-of-Synthesis 19 except that: 8.0 g of the intermediate-15' were used instead of the intermediate-14'; and 9.0 g of the intermediate-26' were used instead of the intermediate-20'. Thus, 8.8 g of a pale yellow powder were obtained. The powder was identified as the aromatic amine derivative (H-29') by FD-MS analysis.

Example-of-Synthesis 48 (Production of Aromatic Amine Derivative (H-30'))

A reaction was performed in the same manner as in Example-of-Synthesis 19 except that: 8.8 g of the intermediate-13' were used instead of the intermediate-14'; and 9.0 g of the intermediate-25' were used instead of the intermediate-20'. Thus, 10.0 g of a pale yellow powder were obtained. The powder was identified as the aromatic amine derivative (H-30') by FD-MS analysis.

Example-of-Synthesis 49 (Production of Aromatic Amine Derivative (H-31'))

A reaction was performed in the same manner as in Example-of-Synthesis 19 except that: 8.8 g of the intermediate-16' were used instead of the intermediate-14'; and 9.0 g of the intermediate-26' were used instead of the intermediate-20'. Thus, 9.7 g of a pale yellow e (H-31') by FD-MSpowder were obtained. The powder was identified as the aromatic amine derivativ analysis.

Example-of-Synthesis 50 (Production of Aromatic Amine Derivative (H-32'))

A reaction was performed in the same manner as in Example-of-Synthesis 19 except that 8.8 g of the intermediate-31' were used instead of the intermediate-20'. Thus, 8.5 g of a pale yellow powder were obtained. The powder was identified as the aromatic amine derivative (H-32') by FD-MS analysis.

Example 1 (Production of Organic EL Device)

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes. After that, the substrate was subjected to UV ozone cleaning for 30 minutes.

The glass substrate with the transparent electrode line after the cleaning was mounted on a substrate holder of a vacuum vapor deposition device. First, the following compound H232 was deposited from vapor on the surface on the side where the transparent electrode line was formed so as to cover the transparent electrode. Then, the H232 film having a thickness of 60 nm was formed as the hole injecting layer. The aromatic amine derivative (H-1') obtained in Example-of-Synthesis 19 was deposited from vapor and formed into a hole transporting layer having a thickness of 20 nm on the H232 film. Further, the following compound EM1 was deposited from vapor and formed into a light emitting layer having a thickness of 40 nm. Simultaneously with this formation, the following amine compound D1 having a styryl group, as a light emitting molecule, was deposited from vapor in such a manner that a weight ratio between the compound EM1 and the amine compound D1 was 40:2.

The following Alq was formed into a film having a thickness of 10 nm on the resultant film. The film functions as an electron injecting layer. After that, Li serving as a reducing dopant (Li source: manufactured by SAES Getters) and the following Alq were subjected to co-vapor deposition. Thus, an Alq:Li film (having a thickness of 10 nm) was formed as an electron injecting layer (cathode). Metal Al was deposited from vapor onto the Alq:Li film to form a metal cathode. Thus, an organic EL device was formed.

The current efficiency of the resultant organic EL device was measured, and the luminescent color of the device was observed. It should be noted that a current efficiency at 10 mA/cm² was calculated by measuring a luminance by using a spectral radiance meter "CS1000" (manufactured by Konica Minolta Sensing, Inc.). Further, the half lifetime of its light emission when the device was driven with a DC constant current at an initial luminance of 5,000 cd/m² and room temperature was measured. Table 2 shows the results.

[Chem. 99]

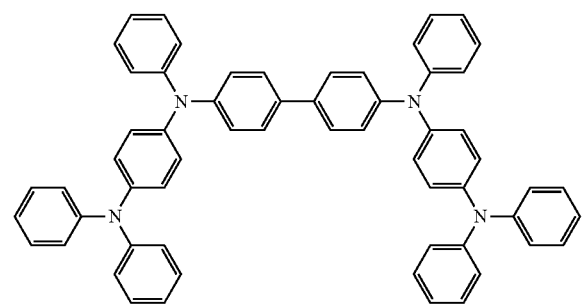

H232

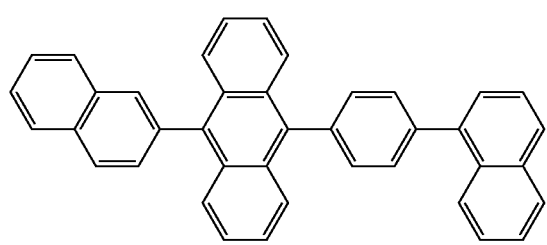

EM1

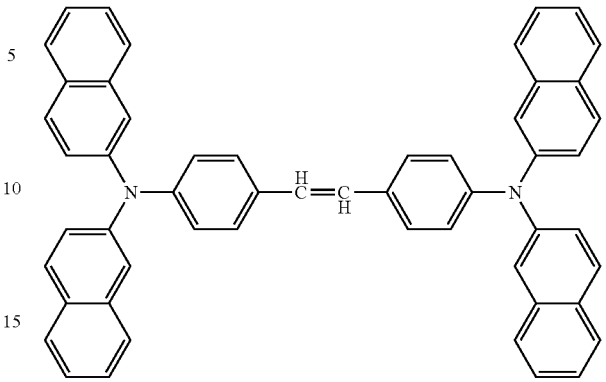

D1

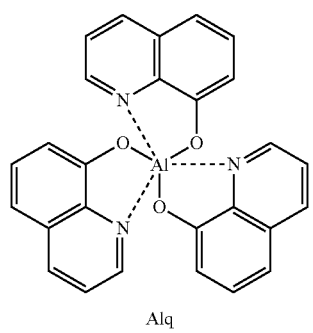

Alq

Examples 2 to 12 (Production of Organic EL Device)

Each organic EL device was produced in the same manner as in Example 1 except that the respective aromatic amine derivatives shown in Table 2 were used as hole transporting materials instead of the aromatic amine derivative (H-1').

In the same manner as in Example 1, the current efficiency of the resultant organic EL device was measured, the luminescent color of the device was observed, and the half lifetime of its light emission when the device was driven with a DC constant current at an initial luminance of 5,000 cd/m² and room temperature was measured. Table 2 shows the results.

Example 13(Production of Organic EL Device)

An organic EL device was produced in the same manner as in Example 1 except that the following arylamine compound D2 was used instead of the amine compound D1 having a styryl group.

In addition, in the same manner as in Example 1, the current efficiency of the resultant organic EL device was measured, the luminescent color of the device was observed, and the half lifetime of its light emission when the device was driven with a DC constant current at an initial luminance of 5,000 cd/m² and room temperature was measured. Table 2 shows the results.

[Chem. 100]

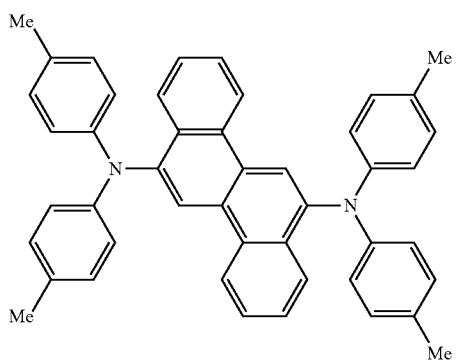

[Chem. 102]

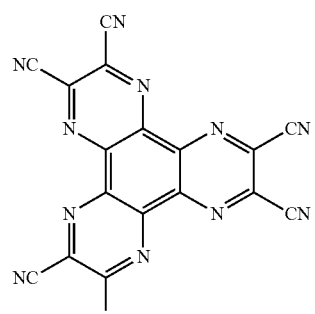

Acceptor compound (C-1)

Example 14 (Production of Organic EL Device)

An organic EL device was produced in the same manner as in Example 1 except that the following imidazole compound (ET1) was used as an electron transporting material instead of Alq.

In addition, in the same manner as in Example 1, the current efficiency of the resultant organic EL device was measured, the luminescent color of the device was observed, and the half lifetime of its light emission when the device was driven with a DC constant current at an initial luminance of 5,000 cd/m² and room temperature was measured. Table 2 shows the results.

[Chem. 101]

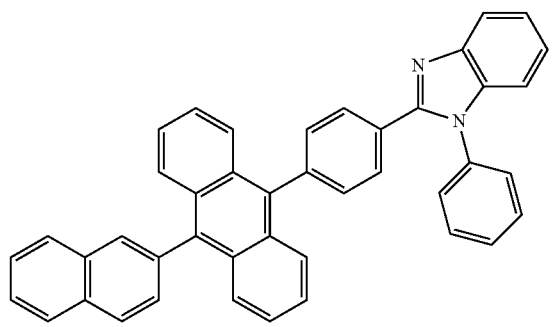

Imidazole compound (ET1)

Example 15 (Production of Organic EL Device)

An organic EL device was produced in the same manner as in Example 1 except that the following acceptor compound (C-1) was formed into a film having a thickness of 10 nm instead of H232, and then the aromatic amine derivative (H-1') was formed into a film having a thickness of 70 nm.

In addition, in the same manner as in Example 1, the current efficiency of the resultant organic EL device was measured, its luminescent color was observed, and the half lifetime of its light emission when the device was driven with a DC constant current at an initial luminance of 5,000 cd/m² and room temperature was measured. Table 2 shows the results.

Comparative Examples 1 and 2

Organic EL devices were each produced in the same manner as in Example 1 except that the comparative compound-1 or 2 shown in Table 2 was used as a hole transporting material instead of the compound H1.

In addition, in the same manner as in Example 1, the current efficiency of each of the resultant organic EL devices was measured, its luminescent color was observed, and the half lifetime of its light emission when the device was driven with a DC constant current at an initial luminance of 5,000 cd/m² and room temperature was measured. Table 2 shows the results.

Comparative Example 3

An organic EL device was produced in the same manner as in Example 13 except that the comparative compound-1 was used as a hole transporting material instead of the aromatic amine derivative (H-1').

In addition, in the same manner as in Example 1, the current efficiency of the resultant organic EL device was measured, its luminescent color was observed, and the half lifetime of its light emission when the device was driven with a DC constant current at an initial luminance of 5,000 cd/m² and room temperature was measured. Table 2 shows the results.

Comparative Example 4

An organic EL device was produced in the same manner as in Example 14 except that the comparative compound-1 was used as a hole transporting material instead of the aromatic amine derivative (H-1').

In addition, in the same manner as in Example 1, the current efficiency of the resultant organic EL device was measured, its luminescent color was observed, and the half lifetime of its light emission when the device was driven with a DC constant current at an initial luminance of 5,000 cd/m² and room temperature was measured. Table 2 shows the results.

Comparative Example 5

An organic EL device was produced in the same manner as in Example 15 except that the comparative compound-1 was used as a hole transporting material instead of the aromatic amine derivative (H-1').

In addition, in the same manner as in Example 1, the current efficiency of the resultant organic EL device was measured, its luminescent color was observed, and the half lifetime of its light emission when the device was driven with a DC constant current at an initial luminance of 5,000 cd/m² and room temperature was measured. Table 2 shows the results.

TABLE 2

|  |  | Hole transporting material | Luminescent color | Driving voltage (V) | Half lifetime (h) |
|---|---|---|---|---|---|
| Example | 1 | H-1' | blue | 7.1 | 400 |
|  | 2 | H-6' | blue | 7.0 | 410 |
|  | 3 | H-7' | blue | 6.8 | 350 |
|  | 4 | H-12' | blue | 6.8 | 360 |
|  | 5 | H-13' | blue | 6.7 | 350 |
|  | 6 | H-16' | blue | 6.7 | 360 |
|  | 7 | H-17' | blue | 6.8 | 380 |
|  | 8 | H-18' | blue | 6.9 | 400 |
|  | 9 | H-19' | blue | 6.6 | 330 |
|  | 10 | H-23' | blue | 6.8 | 350 |
|  | 11 | H-24' | blue | 7.0 | 400 |
|  | 12 | H-25' | blue | 6.7 | 310 |
|  | 13 | H-1' | blue | 7.2 | 390 |
|  | 14 | H-1' | blue | 6.8 | 380 |
|  | 15 | H-1' | blue | 6.8 | 320 |
| Comparative Example | 1 | Comparative compound-1 | blue | 7.8 | 160 |
|  | 2 | Comparative compound-2 | blue | 8.0 | 130 |
|  | 3 | Comparative compound-1 | blue | 7.9 | 130 |
|  | 4 | Comparative compound-1 | blue | 7.2 | 150 |
|  | 5 | Comparative compound-1 | blue | 7.2 | 90 |

As is apparent from the results of Table 2, an organic EL device using the aromatic amine derivative of the present invention is driven at a reduced voltage and has a long half lifetime as compared with an organic EL device using an aromatic amine derivative for comparison.

Industrial Applicability

The utilization of the aromatic amine derivative of the present invention as a material for an organic EL device (especially a hole transporting material) provides the following organic EL device. The organic EL device has high luminous efficiency and a long lifetime, and is driven at a reduced voltage. Accordingly, the organic EL device of the present invention can be utilized in, for example, flat luminous bodies such as the flat panel display of a wall television, light sources for the backlights, meters, and the like of a copying machine, a printer, and a liquid crystal display, display boards, and identification lamps.

In addition, the material of the present invention is useful not only in the field of an organic EL device but also in the fields of, for example, an electrophotographic photosensitive member, a photoelectric converter, a solar cell, and an image sensor.

What we claim is:
1. An aromatic amine derivative of formula (I):

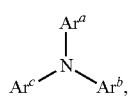

wherein: $Ar^a$ is of formula (II'):

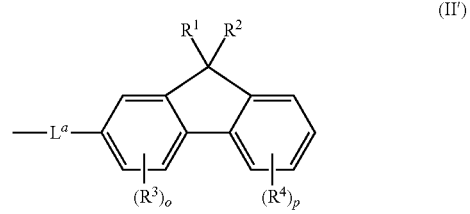

$L^a$ is a single bond;
$R^1$ and $R^2$ each are a linear or branched alkyl group having 1 to 10 carbon atoms, or an aryl group having 6 to 14 ring carbon atoms;
$R^3$ is an aryl group having 6 to 50 ring carbon atoms;
$R^4$ is a linear or branched alkyl group having 1 to 50 carbon atoms, a linear or branched alkenyl group having 3 to 50 carbon atoms, a cycloalkyl group having 3 to 50 ring carbon atoms, a triarylalkyl group having aryl groups each having 6 to 50 ring carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a halogen atom, or a cyano group,
such that a plurality of $R^3$'s or $R^4$'s are optionally adjacent to each other, or $R^3$ and $R^4$ may be bonded to each other to form a ring;
o is an integer of 0 to 3;
p is an integer of 0 to 4;
$Ar^b$ is of formula (III):

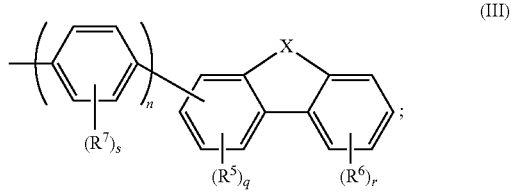

X is an oxygen atom;
$R^5$, $R^6$, and $R^7$ each independently are a linear or branched alkyl group having 1 to 50 carbon atoms, a linear or branched alkenyl group having 3 to 50 carbon atoms, a cycloalkyl group having 3 to 50 ring carbon atoms, an aryl group having 6 to 50 ring carbon atoms, a heteroaryl group having 6 to 50 ring atoms, a triarylalkyl group having aryl groups each having 6 to 50 ring carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a halogen atom, or a cyano group, such that a plurality of $R^5$'s, $R^6$'s, or $R^7$'s adjacent to each other, or $R^5$ and $R^6$ may be bonded to each other to form a ring;
n is an integer of 0 to 4;
when n is an integer of 2 to 4, $R^7$'s on different benzene rings may be identical to or different from each other, and respective $R^7$'s present on benzene rings adjacent to each other may be bonded to each other to form a ring;
q is an integer of 0 to 3;
r and s each independently are an integer of 0 to 4;
when n is an integer of 2 to 4, s's that specify the numbers of $R^7$'s on different benzene rings may have the same value or may have different values; and Ar$^c$ is a substituted or unsubstituted aryl group having 6 to 50 ring carbon atoms, or is of formula (III), wherein when said aryl group has a substituent, the substituent is selected from the group consisting of a linear or branched alkyl group having 1 to 50 carbon atoms, a cycloalkyl group having 3 to 50 carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a triarylalkyl group having aryl groups each having 6 to 50 ring carbon atoms, an aryl group having 6 to 50 ring carbon atoms, a halogen atom, and a cyano group.

2. The aromatic amine derivative of claim 1, wherein $R^1$ and $R^2$ each are a linear or branched alkyl group having 1 to 10 carbon atoms.

3. The aromatic amine derivative of claim 1, wherein $R^1$ and $R^2$ each are a methyl group.

4. The aromatic amine derivative of claim 1, wherein:
Ar$^b$ is of formula (III'):

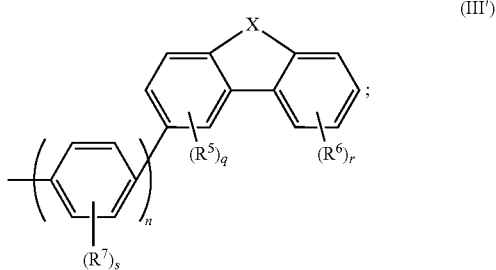

(III')

X is an oxygen atom;

$R^5$, $R^6$, and $R^7$ each independently are a linear or branched alkyl group having 1 to 50 carbon atoms, a linear or branched alkenyl group having 3 to 50 carbon atoms, a cycloalkyl group having 3 to 50 ring carbon atoms, an aryl group having 6 to 50 ring carbon atoms, a heteroaryl group having 6 to 50 ring atoms, a triarylalkyl group having aryl groups each having 6 to 50 ring carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a halogen atom, or a cyano group, such that a plurality of $R^5$'s, $R^6$'s, or $R^7$'s adjacent to each other, or $R^5$ and $R^6$ may be bonded to each other to form a ring;

n is an integer of 0 to 4;

when n is an integer of 2 to 4, $R^7$'s on different benzene rings may be identical to or different from each other, and respective $R^7$'s present on benzene rings adjacent to each other may be bonded to each other to form a ring;

q is an integer of 0 to 3;

r and s each independently are an integer of 0 to 4;

when n is an integer of 2 to 4, s's that specify the numbers of $R^7$'s on different benzene rings may have the same value or may have different values.

5. The aromatic amine derivative of claim 1, wherein Ar$^b$ is of any one of formulae (III-1) to (III-6):

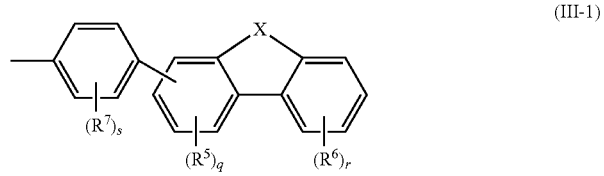

(III-1)

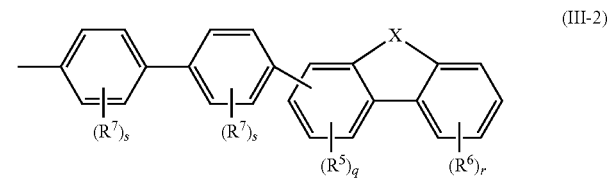

(III-2)

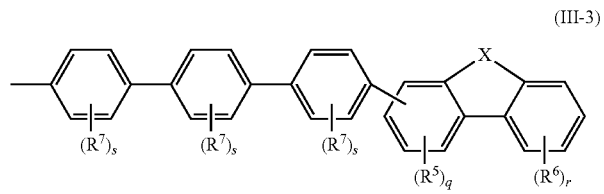

(III-3)

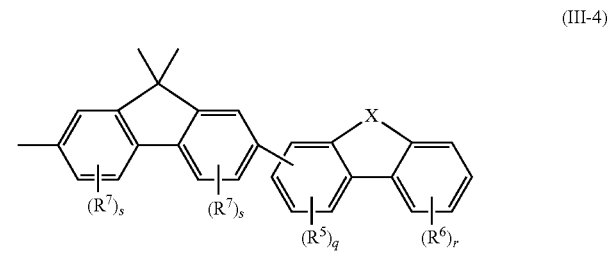

(III-4)

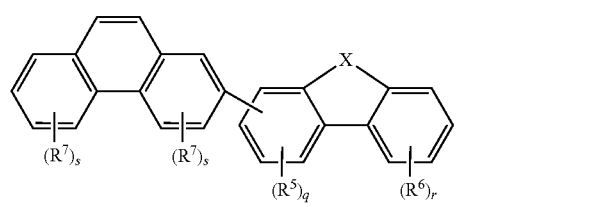

(III-5)

-continued

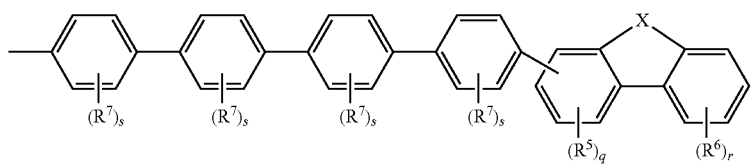
(III-6)

wherein
X is an oxygen atom;
$R^5$, $R^6$, and $R^7$ each independently are a linear or branched alkyl group having 1 to 50 carbon atoms, a linear or branched alkenyl group having 3 to 50 carbon atoms, a cycloalkyl group having 3 to 50 ring carbon atoms, an aryl group having 6 to 50 ring carbon atoms, a heteroaryl group having 6 to 50 ring atoms, a triarylalkyl group having aryl groups each having 6 to 50 ring carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a halogen atom, or a cyano group, such that a plurality of $R^5$'s, $R^6$'s, or $R^7$'s adjacent to each other, or $R^5$ and $R^6$ may be bonded to each other to form a ring;
q is an integer of 0 to 3;
r and s each independently are an integer of 0 to 4; and
wherein $R^7$'s or s's described in plurality may be identical to or different from each other.

6. The aromatic amine derivative of claim 1, wherein $Ar^b$ is of any one of formulae (III-2), (III-3), and (III-6):

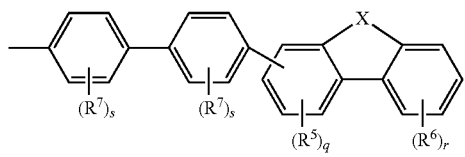
(III-2)

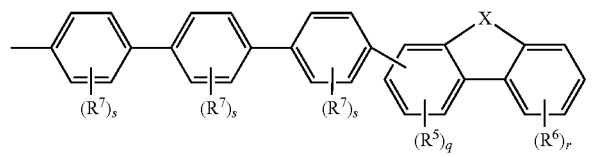
(III-3)

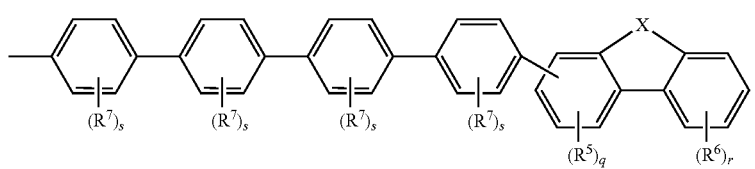
(III-6)

wherein
X is an oxygen atom;
$R^5$, $R^6$, and $R^7$ each independently are a linear or branched alkyl group having 1 to 50 carbon atoms, a linear or branched alkenyl group having 3 to 50 carbon atoms, a cycloalkyl group having 3 to 50 ring carbon atoms, an aryl group having 6 to 50 ring carbon atoms, a heteroaryl group having 6 to 50 ring atoms, a triarylalkyl group having aryl groups each having 6 to 50 ring carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a halogen atom, or a cyano group, such that a plurality of $R^5$'s, $R^6$'s, or $R^7$'s adjacent to each other, or $R^5$ and $R^6$ may be bonded to each other to form a ring;
q is an integer of 0 to 3;
r and s each independently are an integer of 0 to 4; and
wherein $R^7$'s or s's described in plurality may be identical to or different from each other.

7. The aromatic amine derivative of claim 1, wherein $Ar^c$ is of formula (IV):

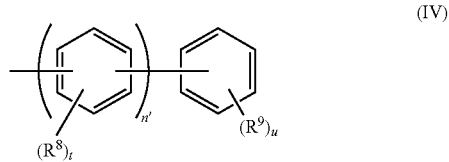
(IV)

wherein:
$R^8$ and $R^9$ each are a halogen atom, a linear or branched alkyl group having 1 to 50 carbon atoms, a linear or branched alkenyl group having 1 to 50 carbon atoms, or an aryl group having 6 to 50 ring carbon atoms, a plurality of $R^8$'s or $R^9$'s adjacent to each other, or $R^8$ and $R^9$ may be bonded to each other to form a ring, and an oxygen atom or a nitrogen atom may be present in the ring;
n' is an integer of 0 to 3;
t is an integer of 0 to 4;
u is an integer of 0 to 5, and
when n' is 2 or 3, $R^8$'s on different benzene rings may be identical to or different from each other.

8. The aromatic amine derivative of claim 7, wherein n' in formula (IV) is 2 or 3.

9. The aromatic amine derivative of claim 1, wherein $Ar^c$ is selected from the group consisting of a biphenylyl group, a terphenylyl group, a quaterphenylyl group, a naphthyl group, an anthryl group, a fluorenyl group, a phenanthryl group, and a dibenzofuranyl group.

10. The aromatic amine derivative of claim 1, wherein $Ar^c$ is a terphenylyl group or a quaterphenylyl group.

11. The aromatic amine derivative of claim 1, wherein $Ar^c$ is of formula (III).

12. The aromatic amine derivative of claim 11, wherein $Ar^c$ is of formula (III'):

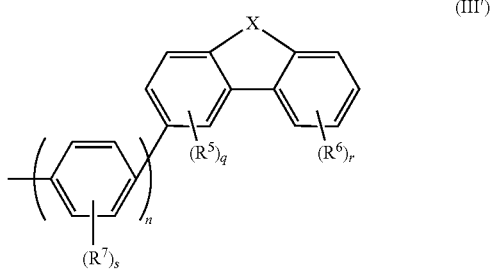

wherein:
X is an oxygen atom;
$R^5$, $R^6$, and $R^7$ each independently are a linear or branched alkyl group having 1 to 50 carbon atoms, a linear or branched alkenyl group having 3 to 50 carbon atoms, a cycloalkyl group having 3 to 50 ring carbon atoms, an aryl group having 6 to 50 ring carbon atoms, a heteroaryl group having 6 to 50 ring atoms, a triarylalkyl group having aryl groups each having 6 to 50 ring carbon atoms, a trialkylsilyl group having alkyl groups each having 1 to 50 carbon atoms, a triarylsilyl group having aryl groups each having 6 to 50 ring carbon atoms, an alkylarylsilyl group having an alkyl group having 1 to 50 carbon atoms and an aryl group having 6 to 50 ring carbon atoms, a halogen atom, or a cyano group, such that a plurality of $R^5$'s, $R^6$'s, or $R^7$'s adjacent to each other, or $R^5$ and $R^6$ may be bonded to each other to form a ring;
n is an integer of 0 to 4;
when n is an integer of 2 to 4, $R^7$'s on different benzene rings may be identical to or different from each other, and respective $R^7$'s present on benzene rings adjacent to each other may be bonded to each other to form a ring;
q is an integer of 0 to 3;
r and s each independently are an integer of 0 to 4;
when n is an integer of 2 to 4, s's that specify the numbers of $R^7$'s on different benzene rings may have the same value or may have different values.

13. An organic electroluminescence device, comprising an organic thin-film layer comprising a light emitting layer, wherein the organic thin-film layer is interposed between an anode and a cathode, and at least one layer of the organic thin-film layer comprisese the aromatic amine derivative of claim 1.

14. The organic electroluminescence device of claim 13, comprising a hole injecting layer or a hole transporting layer as the organic thin-film layer, wherein the aromatic amine derivative of claim 1 is incorporated into the hole injecting layer or the hole transporting layer.

15. The organic electroluminescence device of claim 13, wherein a styrylamine compound and an arylamine compound are incorporated into the light emitting layer.

16. The organic electroluminescence device of claim 13, comprising an electron transporting layer as the organic thin-film layer, wherein a nitrogen-containing heterocyclic derivative of any one of formulae (1) to (3) is incorporated into the electron transporting layer:

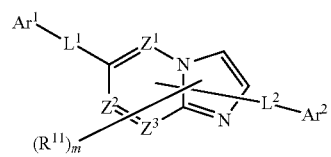

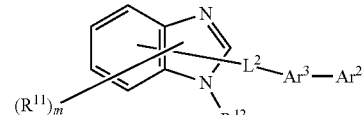

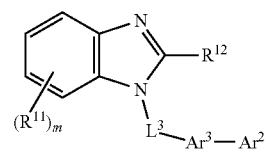

wherein:
$Z^1$, $Z^2$, and $Z^3$ each independently are a nitrogen atom or a carbon atom;
$R^{11}$ and $R^{12}$ each independently are a substituted or unsubstituted aryl group having 6 to 50 carbon atoms, a substituted or unsubstituted heteroaryl group having 3 to 50 carbon atoms, an alkyl group having 1 to 20 carbon atoms, an alkyl group having 1 to 20 carbon atoms and substituted with a halogen atom, or an alkoxy group having 1 to 20 carbon atoms;
m is an integer of 0 to 5, such that when m is an integer of 2 or more, a plurality of $R^{11}$'s may be identical to or different from each other, and a plurality of $R^{11}$'s adjacent to each other may be bonded to each other to form a substituted or unsubstituted aromatic hydrocarbon ring;
$Ar^1$ is a substituted or unsubstituted aryl group having 6 to 50 carbon atoms, or a substituted or unsubstituted heteroaryl group having 3 to 50 carbon atoms;
$Ar^2$ is a hydrogen atom, an alkyl group having 1 to 20 carbon atoms, an alkyl group having 1 to 20 carbon atoms and substituted with a halogen atom, an alkoxy group having 1 to 20 carbon atoms, a substituted or unsubstituted aryl group having 6 to 50 carbon atoms, or a substituted or unsubstituted heteroaryl group having 3 to 50 carbon atoms,
provided that one of $Ar^1$ and $Ar^2$ is a substituted or unsubstituted fused ring group having 10 to 50 carbon atoms, or a substituted or unsubstituted heterofused ring group having 9 to 50 ring atoms;
$Ar^3$ is a substituted or unsubstituted arylene group having 6 to 50 carbon atoms, or a substituted or unsubstituted heteroarylene group having 3 to 50 carbon atoms; and
$L^1$, $L^2$, and $L^3$ each independently are a single bond, a substituted or unsubstituted arylene group having 6 to 50 carbon atoms, a substituted or unsubstituted heterofused ring group having 9 to 50 ring atoms, or a substituted or unsubstituted fluorenylene group.

17. The organic electroluminescence device of claim 13, comprising at least a hole injecting layer as the organic thin-film layer, wherein a compound of formula (A) is incorporated into the hole injecting layer:

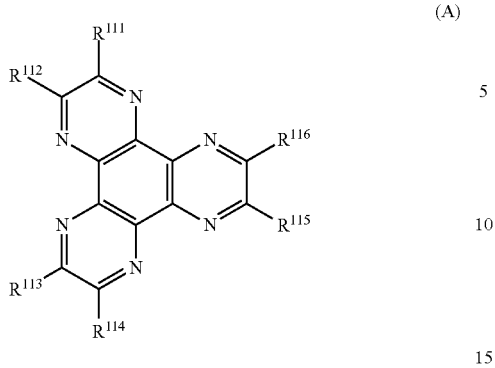
(A)
wherein:
$R^{111}$ to $R^{116}$ each independently are a cyano group, —$CONH_2$, a carboxyl group, or —$COOR^{117}$ and $R^{117}$ is an alkyl group having 1 to 20 carbon atoms, or $R^{111}$ and $R^{112}$, $R^{113}$ and $R^{114}$, or $R^{115}$ and $R^{116}$ combine with each other to are a group of —CO—O—CO—.
18. The organic electroluminescence device of claim 13, wherein the device emits bluish light.
\* \* \* \* \*